United States Patent
Nakao et al.

(10) Patent No.: US 6,710,054 B2
(45) Date of Patent: Mar. 23, 2004

(54) ARYL OR HETEROARYL FUSED IMIDAZOLE COMPOUNDS AS ANTI-INFLAMMATORY AND ANALGESIC AGENTS

(75) Inventors: Kazunari Nakao, Aichi-Ken (JP); Yoshiyuki Okumura, Aichi-Ken (JP); Miyako Matsumizu, Aichi-Ken (JP); Naomi Ueno, Aichi-Ken (JP); Yoshinobu Hashizume, Aichi-Ken (JP); Tomoki Kato, Aichi-Ken (JP); Akiyoshi Kawai, Aichi-Ken (JP); Yoriko Miyake, Aichi-Ken (JP); Seiji Nukui, Aichi-Ken (JP); Katsuhiro Shinjyo, Aichi-Ken (JP); Kana Taniguchi, Aichi-Ken (JP)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 09/977,621

(22) Filed: Oct. 15, 2001

(65) Prior Publication Data

US 2002/0107273 A1 Aug. 8, 2002

Related U.S. Application Data

(60) Provisional application No. 60/241,825, filed on Oct. 19, 2000.

(51) Int. Cl.[7] .............. A61K 31/437; C07D 471/04
(52) U.S. Cl. ................ 514/303; 546/118; 546/273.4; 548/302.1; 548/304.4; 548/309.7; 548/306.1; 514/338; 514/394; 514/393
(58) Field of Search ............... 546/118; 514/303

(56) References Cited

FOREIGN PATENT DOCUMENTS

| EP | 0405391 | 1/1991 | |
|---|---|---|---|
| GB | 2330307 | 4/1999 | |
| WO | WO 9947497 | 9/1999 | |
| WO | WO 0021532 | 4/2000 | |
| WO | WO 0021542 | 4/2000 | |
| WO | WO 0064880 | 11/2000 | ......... C07D/251/70 |
| WO | 0064888 | 11/2000 | |
| WO | 0250031 | 6/2002 | |
| WO | 0250032 | 6/2002 | |
| WO | 0250033 | 6/2002 | |

*Primary Examiner*—Laura L. Stockton
(74) *Attorney, Agent, or Firm*—Charles W. Ashbrook; David R. Kurlandsky

(57) ABSTRACT

This invention provides a compound of the formula (I):

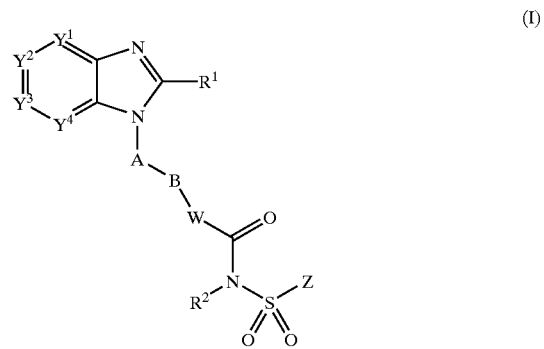

or the pharmaceutically acceptable salts thereof, wherein $Y^1$, $Y^2$, $Y^3$ and $Y^4$ are independently selected from N, CH, etc.; $R^1$ is H, $C_{1-8}$ alkyl, etc.; $Q^1$ is a 5–12 membered monocyclic or bicyclic aromatic ring optionally containing up to 4 heteroatoms selected from O, N, and S, etc.; A is 5–6 membered monocyclic aromatic ring optionally containing up to 3 heteroatoms selected form O, N and S, etc.; B is $C_{1-6}$ alkylene optionally substituted with an oxo group, etc.; W is NH, O, etc.; $R^2$ is H, $C_{1-4}$ alkyl, etc.; Z is a 5–12 membered monocyclic or bicyclic aromatic ring optionally containing up to 3 heteroatoms selected form O, N and S, etc.; L is halo, $C_{1-4}$ alkyl, etc.; m is 0, 1 or 2; $R^3$ and $R^4$ are independently selected from H and $C_{1-4}$ alkyl; $R^5$ is H, $C_{1-4}$ alkyl; etc.; $Q^2$ is a 5–12 membered monocyclic or bicyclic aromatic ring or tricyclic ring optionally containing up to 3 heteroatoms selected from O, N and S, etc. These compounds are useful for the treatment of medical conditions mediated by prostaglamndin such as pain, fever or inflammation, etc. This invention also provides a pharmaceutical composition comprising the above compound.

16 Claims, No Drawings

ARYL OR HETEROARYL FUSED IMIDAZOLE COMPOUNDS AS ANTI-INFLAMMATORY AND ANALGESIC AGENTS

This application claims priority under 35 U.S.C. §119(e) of U.S. application Ser. No. 60/241,825, filed Oct. 19, 2000.

TECHNICAL FIELD

This invention relates to aryl or heteroaryl fused imidazole compounds, or their pharmaceutically acceptable salts, pharmaceutical compositions containing them, and their medical uses. The compounds of this invention have activity as prostaglandin $E_2$ receptor antagonists, and these are useful in the treatment or alleviation of pain and inflammation and other inflammation-associated disorders, such as arthritis. treating or preventing disorders or medical conditions selected from pain, inflammatory diseases and the like.

BACKGROUND ART

Prostaglandins are mediators of pain, fever and other symptoms associated with inflammation. Especially prostaglandin $E_2$ ($PGE_2$) is the predominant elcosanoid detected in inflammation conditions. In addition, it is also involved in various physiological and/or pathological conditions and such as hyperalgesia, uterine contraction, digestive peristalsis, awakeness, suppression of gastric acidsecretion, blood pressure, platelet function, bone metabolism, angiogenesis or the like.

Four $PGE_2$ receptor subtypes ($EP_1$, $EP_2$, $EP_3$ and $EP_4$) displaying different pharmacological properties have been cloned. $EP_4$ subtype, a Gs-coupled receptor stimulates cAMP production, and is distributed in a wide variety of tissue suggesting major role in $PGE_2$-mediated biological events.

WO99/47497 discloses carboxylic acids and acylsulfonamides compounds as prostaglandin-receptor antagonists.

BRIEF DISCLOSURE OF THE INVENTION

The present invention provides a compound of the following formula:

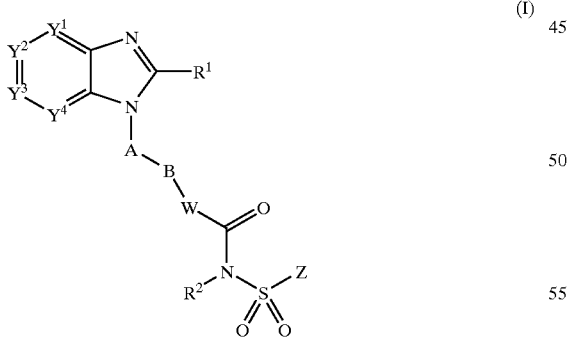

or the pharmaceutically acceptable salts thereof, wherein
$Y^1$, $Y^2$, $Y^3$ and $Y^4$ are independently selected from N, CH or C(L);

$R^1$ is H, $C_{1-8}$ alkyl, $C_{2-8}$ alkenyl, $C_{2-8}$ alkynyl, $C_{3-7}$ cycloalkyl, $C_{1-8}$ alkoxy, halo-substituted $C_{1-8}$ alkoxy, $C_{1-8}$ alkyl-S(O)m-, $Q^1$—, pyrrolidinyl, piperidyl, oxopyrrolidinyl, oxopiperidyl, amino, mono- or di-($C_{1-8}$ alkyl)amino, $C_{1-4}$alkyl-C(=O)—N($R^3$)— or $C_{1-4}$alkyl-S(O)m-N($R^3$)—, wherein said $C_{1-8}$ alkyl, $C_{2-8}$ alkenyl and $C_{2-8}$ alkynyl are optionally substituted with halo, $C_{1-3}$ alkyl, hydroxy, oxo, $C_{1-4}$ alkoxy-, $C_{1-4}$ alkyl-S(O)m-, $C_{3-7}$ cycloalkyl-, cyano, indanyl, 1,2,3,4-tetrahydronaphtyl, 1,2-dihydronaphtyl, pyrrolidinyl, piperidyl, oxopyrrolidinyl, oxopiperidyl, $Q^1$—, $Q^1$—C(=O)—, $Q^1$—O—, $Q^1$—S(O)m-, $Q^1$—$C_{1-4}$alkyl-O—, $Q^1$—$C_{1-4}$alkyl-S(O)m-, $Q^1$—$C_{1-4}$alkyl-C(O)—N($R^3$)—, $Q^1$—$C_{1-4}$alkyl-N($R^3$)— or $C_{1-4}$alkyl-C(O)—N($R^3$)—;

$Q^1$ is a 5–12 membered monocyclic or bicyclic aromatic ring optionally containing up to 4 heteroatoms selected from O, N and S, and is optionally substituted with halo, $C_{1-4}$ alkyl, halo-substituted $C_{1-4}$ alkyl, hydroxy, $C_{1-4}$ alkoxy, halo-substituted $C_{1-4}$ alkoxy, $C_{1-4}$ alkylthio, nitro, amino, mono- or di-($C_{1-4}$alkyl)amino, cyano, HO—$C_{1-4}$ alkyl, $C_{1-4}$ alkoxy-$C_{1-4}$alkyl, $C_{1-4}$ alkylsulfonyl, aminosulfonyl, $C_{1-4}$alkyl(=O)—, HO(O=)C—, $C_{1-4}$alkyl-O(O=)C—, $R^3$N($R^4$)C(=O)—, $C_{1-4}$ alkylsulfonylamino, $C_{3-7}$ cycloalkyl, $R^3$C(=O)N($R^4$)— or $NH_2$(HN=)C—;

A is a 5–6 membered monocyclic aromatic ring optionally containing up to 3 heteroatoms selected from O, N and S, wherein said 5–6 membered monocyclic aromatic ring is optionally substituted with up to 3 substituents selected from halo, $C_{1-4}$ alkyl, halo-substituted $C_{1-4}$ alkyl, hydroxy, $C_{1-4}$ alkoxy, halo-substituted $C_{1-4}$ alkoxy, $C_{1-4}$alkylthio, nitro, amino, mono- or di-($C_{1-4}$alkyl)amino, cyano, HO—$C_{1-4}$ alkyl, $C_{1-4}$ alkoxy-$C_{1-4}$ alkyl, $C_{-1-4}$ alkylsulfonyl, aminosulfonyl, acetyl, $R^3$N($R^4$)C(=O)—, HO(O=)C—, $C_{1-4}$alkyl-O(O=)C—, $C_{1-4}$ alkylsulfonylamino, $C_{3-7}$ cycloalkyl, $R^3$C(=O)N($R^4$)— and $NH_2$(HN=)C—;

B is halo-substituted $C_{1-6}$ alkylene, $C_{3-7}$ cycloalkylene, $C_{2-6}$ alkenylene, $C_{2-6}$ alkynylene, —O—$C_{1-5}$ alkylene, $C_{1-2}$ alkylene-O—$C_{1-2}$ alkylene or $C_{16}$ alkylene optionally substituted with an oxo group or $C_{1-3}$ alkyl;

W is NH, N—$C_{1-4}$ alkyl, O, S, N—$OR^5$ or a covalent bond;

$R^2$ is H, $C_{1-4}$ alkyl, OH or $C_{1-4}$ alkoxy;

Z is a 5–12 membered monocyclic or bicyclic aromatic ring optionally containing up to 3 heteroatoms selected from O, N and S, wherein said 5–12 membered monocyclic or bicyclic aromatic ring is optionally substituted with halo, $C_{1-4}$ alkyl, halo-substituted $C_{1-4}$ alkyl, $C_{1-4}$ alkenyl, $C_{1-4}$ alkynyl, hydroxy, $C_{1-4}$ alkoxy, halo-substituted $C_{1-4}$ alkoxy, $C_{1-4}$ alkylthio, nitro, amino, mono- or di-($C_{1-4}$ alkyl)amino, cyano, HO—$C_{1-4}$ alkyl, $C_{1-4}$ alkoxy-$C_{1-4}$alkyl, $C_{1-4}$ alkylsulfonyl, aminosulfonyl, $C_{1-4}$alkyl(=O)—, $R^3$C(=O)N($R^4$)—, HO(O=)C—, $C_{1-4}$alkyl-O(O=)C—, $C_{1-4}$ alkylsulfonylamino, $C_{3-7}$ cycloalkyl, $NH_2$(HN=)C—, $Q^2$—S(O)m-, $Q^2$—O—, $Q^2$—N($R^3$)— or $Q^2$—;

L is halo, $C_{1-4}$ alkyl, halo-substituted $C_{1-4}$ alkyl, hydroxy, $C_{1-4}$ alkoxy, halo-substituted $C_{1-4}$ alkoxy, $C_{1-4}$ alkylthio, nitro, amino, mono- or di-($C_{1-4}$ alkyl)amino, cyano, HO—$C_{1-4}$ alkyl, $C_{1-4}$ alkoxy-$C_{1-4}$alkyl, $C_{1-4}$ alkylsulfonyl, aminosulfonyl, $C_{1-4}$alkyl(=O)—, HO(O=)C—, $C_{1-4}$alkyl-O(O=)C—, $C_{1-4}$ alkylsulfonylamino, $C_{3-7}$ cycloalkyl, $R^3$C(=O)N($R^4$)—, $NH_2$(HN=)C—, $R^3$N($R^4$)C(=O)—, $R^3$N($R^4$)S(O)m-, $Q^2$—, $Q^2$—C(=O)—, $Q^2$—O—, $Q^2$—$C_{1-4}$ alkyl-O—, or two adjacent L groups are optionally joined together to form an alkylene chain having 3 or 4 members in which one or two (non-adjacent) carbon atoms are optionally replaced by oxygen atoms;

m is 0, 1 or 2;

$R^3$ and $R^4$ are independently selected from H and $C_{1-4}$ alkyl $R^5$ is H, $C_{1-4}$ alkyl, $C_{1-4}$ alkyl-(O=)C— or $C_{1-4}$ alkyl-O—(O=)C—; and $Q^2$ is a 5–12 membered monocyclic or bicyclic aromatic ring, or a 5–12 membered tricyclic ring optionally containing up to 3 heteroatoms selected from O, N and S, wherein said 5–12 membered monocyclic or bicyclic aromatic ring is optionally substituted with halo, $C_{1-4}$ alkyl, halo-substituted $C_{1-4}$ alkyl, $C_{1-4}$ alkenyl, $C_{1-4}$ alkynyl, hydroxy, $C_{1-4}$ alkoxy, halo-substituted $Cl_{1-4}$ alkoxy, $C_{1-4}$ alkylthio, nitro, amino, mono- or di-($C_{1-4}$ alkyl)amino, cyano, HO—$C_{1-4}$ alkyl, $C_{1-4}$ alkoxy-$C_{1-4}$ alkyl, $C_{1-4}$ alkylsulfonyl, aminosulfonyl, $C_{1-4}$alkyl-(O=)C—, $R^3(R^4)C(=O)N$—, HO(O=)C—, $C_{1-4}$ alkyl-O(O=)C—, $C_{1-4}$ alkylsulfonylamino, $C_{3-7}$ cycloalkyl, $C_{1-4}$ alkyl-C(=O)NH— or $NH_2(HN=)C$—.

The aryl or heteroaryl fused imidazole compounds of this invention have an antagonistic action towards prostaglandin and are thus useful in therapeutics, particularly for the treatment of a disorder or condition selected from the group consisting of pain, fever or inflammation associated with rheumatic fever, influenza or other viral infections, common cold, low back and neck pain, skeletal pain, post-partum pain, dysmenorrhea, headache, migraine, toothache, sprains and strains, myositis, neuralgia, fibromyalgia, synovitis, arthritis, including rheumatoid arthritis, degenerative joint diseases (osteoarthritis), gout and ankylosing sspondylitis, bursitits, burns including radiation and corrosive chemical injuries, sunburns, pain following surgical and dental procedures or bone fracture, immune and autoimmune diseases such as systemic lupus erythematosus; AIDS(acquired immuno deficiency syndrome), gastrointestinal cancers such as colon cancer ; cellular neoplastic transformations or metastic tumor growth; Diabetic retinopathy, tumor angiogenesis; prostanoid-induced smooth muscle contraction associated with dysmenorrhea, premature labor, allergic rhinitis, atopic dermatitis, asthma or eosinophil related disorders, Hyperimmunoglobulinaemia, Castleman's disease, myeloma; Alzheimer's disease, sleep disorders, endocrine disturbance; glaucoma; bone loss; osteoporosis; promotion of bone formation; Paget's disease: cytoprotection in peptic ulcers, gastritis, regional enteritis, ulcerative colitis, diverticulitis or other gastrointestinal lesions; GI bleeding and patients undergoing chemotherapy; coagulation disorders selected from hypoprothrombinemia, haemophilia and other bleeding problems; kidney disease; thrombosis; occlusive vascular disease; presurgery; and anti-coagulation, or the like in mammalian, especially humans.

The present invention provides a pharmaceutical composition for the treatment of a disorder or condition mediated by prostaglandin, in a mammalian including a human, which comprises administering to said subject a therapeutically effective amount of a compound of formula (I).

Further, the present invention also provides a pharmaceutical composition for the treatment of a disorder or condition selected from the group consisting of pain, fever or inflammation associated with rheumatic fever, influenza or other viral infections, common cold, low back and neck pain, skeletal pain, postpartum pain, dysmenorrhea, headache, migraine, toothache, sprains and strains, myositis, neuralgia, fibromyalgia, synovitis, arthritis, including rheumatoid arthritis, degenerative joint diseases (osteoarthritis), gout and ankylosing sspondylitis, bursitits, burns including radiation and corrosive chemical injuries, sunburns, pain following surgical and dental procedures, bone fracture, immune and autoimmune diseases such as systemic lupus erythematosus; AIDS(acquired immuno deficiency syndrome), gastrointestinal cancers such as colon cancer; cellular neoplastic transformations or metastic tumor growth;

Diabetic retinopathy, tumor angiogenesis; prostanoid-induced smooth muscle contraction associated with dysmenorrhea, premature labor, allergic rhinitis, atopic dermatitis, asthma or eosinophil related disorders, Hyperimmunoglobulinaemia, Castleman's disease, myeloma; Alzheimer's disease, sleep disorders, endocrine disturbance; glaucoma; bone loss; osteoporosis; promotion of bone formation;

Paget's disease: cytoprotection in peptic ulcers, gastritis, regional enteritis, ulcerative colitis, diverticulitis or other gastrointestinal lesions; GI bleeding and patients undergoing chemotherapy; coagulation disorders selected from hypoprothrombinemia, haemophilia and other bleeding problems; kidney disease;

thrombosis; occlusive vascular disease; presurgery; and anti-coagulation, or the like, which comprises a therapeutically effective amount of the aryl or heteroaryl fused imidazole compound of formula (I) or its pharmaceutically acceptable salt together with a pharmaceutically acceptable carrier.

Also, the present invention provides a method for the treatment of a disorder or condition mediated by prostaglandin, in a mammalian including a human, which comprises administering to said subject a therapeutically effective amount of a compound of formula (I).

Further, the present invention provides a method for the treatment of pain, fever or inflammation associated with rheumatic fever, influenza or other viral infections, common cold, low back and neck pain, skeletal pain, post-partum pain, dysmenorrhea, headache, migraine, toothache, sprains and strains, myositis, neuralgia, fibromyalgia, synovitis, arthritis, including rheumatoid arthritis, degenerative joint diseases (osteoarthritis), gout and ankylosing sspondylitis, bursitits, burns including radiation and corrosive chemical injuries, sunburns, pain following surgical and dental procedures, bone fracture, immune and autoimmune diseases such as systemic lupus erythematosus; AIDS, gastrointestinal cancers such as colon cancer; cellular neoplastic transformations or metastic tumor growth; Diabetic retinopathy, tumor angiogenesis; prostanoid-induced smooth muscle contraction associated with dysmenorrhea, premature labor, allergic rhinitis, atopic dermatitis, asthma or eosinophil related disorders, Hyperimmunoglobulinaemia, Castleman's disease, myeloma; Alzheimer's disease, sleep disorders, endocrine disturbance; glaucoma; bone loss; osteoporosis; promotion of bone formation; Paget's disease: cytoprotection in peptic ulcers, gastritis, regional enteritis, ulcerative colitis, diverticulitis or other gastrointestinal lesions; GI bleeding and patients undergoing chemotherapy; coagulation disorders selected from hypoprothrombinemia, haemophilia and other bleeding problems; kidney disease; thrombosis; occlusive vascular disease;

presurgery; and anti-coagulation or the like, in a mammalian subject, which comprises administering to said subject a therapeutically effective amount of a compound of formula (I).

Also, the present invention provides a pharmaceutical formulation comprising a compound of formula (I), a pharmaceutically acceptable carrier and, optionally, one or more other pharmacologically active ingredients.

Also, the present invention provides a pharmaceutical formulation comprising a compound of formula (I), a pharmaceutically acceptable carrier and, optionally, one or more other pharmacologically active ingredients selected from a COX-2 selective, COX-1 selective or non-selective NSAIDs (nonsteroidal anti-inflammatory drugs), opioids, anticonvulsants, antidepressants, local anesthetics, disease-modifying anti-rheumatoid drugs, or steroids.

Also, the present invention provides a compound of the following formula:

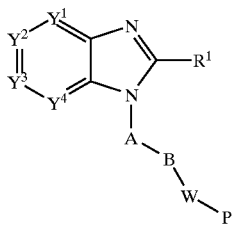

(II)

or salts thereof
   wherein $Y^1$, $Y^2$, $Y^3$ and $Y^4$ are independently selected from N, CH or C(L);
   $R^1$ is H, $C_{1-8}$ alkyl, $C_{2-8}$ alkenyl, $C_{2-8}$ alkynyl, $C_{3-7}$ cycloalkyl, $C_{1-8}$ alkoxy, halo substituted $C_{1-8}$ alkoxy, $C_{1-8}$ alkyl-S(O)m-, $Q^1$—, amino, mono- or di-($C_{1-8}$ alkyl)amino, $C_{1-4}$alkyl-C(=O)—N($R^3$)— or $C_{1-4}$alkyl-S(O)m-N($R^3$)—, wherein said $C_{1-8}$ alkyl, $C_{2-8}$ alkenyl and $C_{2-8}$ alkynyl are optionally substituted with halo, $C_{1-3}$ alkyl, $C_{1-4}$ alkoxy-, $C_{1-4}$ alkyl-S(O)m-, $C_{3-7}$ cycloalkyl-, cyano, indanyl, 1,2,3,4-tetrahydronaphtyl, 1,2-dihydronaphtyl, $Q^1$—, $Q^1$—C(=O)—, $Q^1$—O—, $Q^1$—S(O)m-, $Q^1$—$C_{1-4}$alkyl-O—, $Q^1$—$C_{1-4}$alkyl-S(O)m-, $Q^1$—$C_{1-4}$alkyl-C(O)—N($R^3$)— or $Q^1$—$C_{1-4}$alkyl-N($R^3$)—;
   $Q^1$ is a 5–12 membered monocyclic or bicyclic aromatic ring optionally containing up to 4 heteroatoms selected from O, N and S, and is optionally substituted with halo, $C_{1-4}$ alkyl, halo-substituted $C_{1-4}$ alkyl, hydroxy, $C_{1-4}$ alkoxy, halo-substituted $C_{1-4}$ alkoxy, $C_{1-4}$ alkylthio, nitro, amino, mono- or di-($C_{1-4}$alkyl)amino, cyano, HO—$C_{1-4}$ alkyl, $C_{1-4}$ alkoxy-$C_{1-4}$alkyl, $C_{1-4}$ alkylsulfonyl, aminosulfonyl, $C_{1-4}$alkyl(=O)—, HO(O=)C—, $C_{1-4}$alkyl-O(O=)C—, $R^3N(R^4)C$(=O)—, $C_{1-4}$ alkylsulfonylamino, $C_{3-7}$ cycloalkyl, $R^3C$(=O)N($R^4$)— or $NH_2$(HN=)C—;
   A is a benzene ring optionally substituted with up to 3 substituents or pyridine ring optionally substituted with up to 3 substituents, wherein said substituents selected from halo, $C_{1-4}$ alkyl, halo-substituted $C_{1-4}$ alkyl, hydroxy, $C_{1-4}$ alkoxy, halo-substituted $C_{1-4}$ alkoxy, $C_{1-4}$alkylthio, nitro, amino, mono- or di-($C_{1-4}$ alkyl) amino, cyano, HO—$C_{1-4}$ alkyl, $C_{1-4}$ alkoxy-$C_{1-4}$alkyl, $C_{1-4}$ alkylsulfonyl, aminosulfonyl, acetyl, $R^3N(R^4)C$(=O)—, HO(O=)C—, $C_{1-4}$alkyl-O(O=)C—, $C_{1-4}$ alkylsulfonylamino, $C_{3-7}$ cycloalkyl, $R^3C$(=O)N($R^4$)— and $NH_2$(HN=)C—;
   B is $C_{2-6}$ alkylene, $C_{3-7}$ cycloalkylene, $C_{2-6}$ alkenylene, or $C_{2-6}$ alkynylene optionally substituted with $C_{1-3}$ alkyl;
   W is NH or O;
   P is H, a protecting group, or $Q^3$—OC(=O)—;
   $Q^3$ is a 6–10 membered monocyclic or bicyclic aromatic ring optionally substituted with halo, $C_{1-4}$ alkyl, $C_{1-4}$ alkoxy, $C_{1-4}$ alkylthio, nitro, cyano, $C_{1-4}$ alkylsulfonyl, $C_{1-4}$alkyl(=O)—, HO(O=)C—, or $C_{1-4}$alkyl-O(O=)C—;

L is halo, $C_{1-4}$ alkyl, halo-substituted $C_{1-4}$ alkyl, hydroxy, $C_{1-4}$ alkoxy, halo-substituted $C_{1-4}$ alkoxy, $C_{1-4}$ alkylthio, nitro, amino, mono- or di-($C_{1-4}$ alkyl)amino, cyano, HO—$C_{1-4}$ alkyl, $C_{1-4}$ alkoxy-$C_{1-4}$alkyl, $C_{1-4}$ alkylsulfonyl, aminosulfonyl, $C_{1-4}$alkyl(=O)—, HO(O=)C—, $C_{1-4}$alkyl-O(O=)C—, $C_{1-4}$ alkylsulfonylamino, $C_{3-7}$ cycloalkyl, $R^3C$(=O)N($R^4$)—, $NH_2$(HN=)C—, $R^3N(R^4)C$(=O)— or $R^3N(R^4)S$(O)m-, or two adjacent L groups are optionally joined together to form an alkylene chain having 3 or 4 members in which one or two (non-adjacent) carbon atoms are optionally replaced by oxygen atoms;
   m is 0, 1 or 2; and
   $R^3$ and $R^4$ are independently selected from H and $C_{1-4}$ alkyl.

Also, the present invention provides a compound of the following formula:

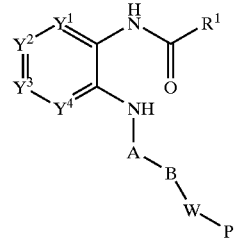

(III)

or salts thereof
   wherein $Y^1$, $Y^2$, $Y^3$ and $Y^4$ are independently selected from N, CH or C(L);
   $R^1$ is H, $C_{1-8}$ alkyl, $C_{2-8}$ alkenyl, $C_{2-8}$ alkynyl, $C_{3-7}$ cycloalkyl, $C_{1-8}$ alkoxy, halo-substituted $C_{1-8}$ alkoxy, $C_{1-8}$ alkyl-S(O)m-, $Q^1$—, amino, mono- or di-($C_{1-8}$ alkyl)amino, $C_{1-4}$alkyl-C(=O)—N($R^3$)— or $C_{1-4}$alkyl-S(O)m-N($R^3$)—, wherein said $C_{1-8}$ alkyl, $C_{2-8}$ alkenyl and $C_{2-8}$ alkynyl are optionally substituted with halo, $C_{1-3}$ alkyl, $C_{1-4}$ alkoxy-, $C_{1-4}$ alkyl-S(O)m-, $C_{3-7}$ cycloalkyl-, cyano, indanyl, 1,2,3,4-tetrahydronaphtyl, 1,2-dihydronaphtyl, $Q^1$—, $Q^1$—C(=O)—, $Q^1$—O—, $Q^1$—S(O)m-, $Q^1$—$C_{1-4}$alkyl-O—, $Q^1$—$C_{1-4}$alkyl-S(O)m-, $Q^1$—$C_{1-4}$alkyl-C(O)—N($R^3$)— or $Q^1$—$C_{1-4}$alkyl-N($R^3$)—;
   $Q^1$ is a 5–12 membered monocyclic or bicyclic aromatic ring optionally containing up to 4 heteroatoms selected from O, N and S, and is optionally substituted with halo, $C_{1-4}$ alkyl, halo-substituted $C_{1-4}$ alkyl, hydroxy, $C_{1-4}$ alkoxy, halo-substituted $C_{1-4}$ alkoxy, $C_{1-4}$ alkylthio, nitro, amino, mono- or di-($C_{1-4}$alkyl)amino, cyano, HO—$C_{1-4}$ alkyl, $C_{1-4}$ alkoxy-$C_{1-4}$alkyl, $C_{1-4}$ alkylsulfonyl, aminosulfonyl, $C_{1-4}$alkyl(=O)—, HO(O=)C—, $C_{1-4}$alkyl-O(O=)C—, $R^3N(R^4)C$(=O)—, $C_{1-4}$ alkylsulfonylamino, $C_{3-7}$ cycloalkyl, $R^3C$(=O)N($R^4$)— or $NH_2$(HN=)C—;
   A is a benzene ring optionally substituted with up to 3 substituents or pyridine ring optionally substituted with up to 3 substituents, wherein said substituents selected from halo, $C_{1-4}$ alkyl, halo-substituted $C_{1-4}$ alkyl, hydroxy, $C_{1-4}$ alkoxy, halo-substituted $C_{1-4}$ alkoxy, $C_{1-4}$alkylthio, nitro, amino, mono- or di-($C_{1-4}$ alkyl) amino, cyano, HO—$C_{1-4}$ alkyl, $C_{1-4}$ alkoxy-$C_{1-4}$alkyl, $C_{1-4}$ alkylsulfonyl, aminosulfonyl, acetyl, $R^3N(R^4)C$(=O)—, HO(O=)C—, $C_{1-4}$alkyl-O(O=)C—, $C_{1-4}$ alkylsulfonylamino, $C_{3-7}$ cycloalkyl, $R^3C$(=O)N($R^4$)— and $NH_2$(HN=)C—;

B is $C_{2-6}$ alkylene, $C_{3-7}$ cycloalkylene, $C_{2-6}$ alkenylene, or $C_{2-6}$ alkynylene optionally substituted with $C_{1-3}$ alkyl;

W is NH or O;

P is H, a protecting group, or Z—S(O)$_2$—N(R$^2$)—C(=O)—;

Z is a 5–12 membered monocyclic or bicyclic aromatic ring optionally containing up to 3 heteroatoms selected from O, N and S, wherein said 5–12 membered monocyclic or bicyclic aromatic ring is optionally substituted with halo, $C_{1-4}$ alkyl, halo-substituted $C_{1-4}$ alkyl, $C_{1-4}$ alkenyl, $C_{1-4}$ alkynyl, hydroxy, $C_{1-4}$ alkoxy, halo-substituted $C_{1-4}$ alkoxy, $C_{1-4}$ alkylthio, nitro, amino, mono- or di-($C_{1-4}$ alkyl)amino, cyano, HO—$C_{1-4}$ alkyl, $C_{1-4}$ alkoxy-$C_{1-4}$alkyl, $C_{1-4}$ alkylsulfonyl, aminosulfonyl, $C_{1-4}$alkyl(=O)—, R$^3$C(=O)N(R$^4$)—, HO(O=)C—, $C_{1-4}$alkyl-O(O=)C—, $C_{1-4}$ alkylsulfonylamino, $C_{3-7}$ cycloalkyl, NH$_2$(HN=)C—, Q$^2$—S(O)m-, Q$^2$—O—, Q$^2$—N(R$^3$)— or Q$^2$—;

L is halo, $C_{1-4}$ alkyl, halo-substituted $C_{1-4}$ alkyl, hydroxy, $C_{1-4}$ alkoxy, halo-substituted $C_{1-4}$ alkoxy, $C_{1-4}$ alkylthio, nitro, amino, mono- or di-($C_{1-4}$ alkyl)amino, cyano, HO—$C_{1-4}$ alkyl, $C_{1-4}$ alkoxy-$C_{1-4}$alkyl, $C_{1-4}$ alkylsulfonyl, aminosulfonyl, $C_{1-4}$alkyl(=O)—, HO(O=)C—, $C_{1-4}$alkyl-O(O=)C—, $C_{1-4}$ alkylsulfonylamino, $C_{3-7}$ cycloalkyl, R$^3$C(=O)N(R$^4$)—, NH$_2$(HN=)C—, R$^3$N(R$^4$)C(=O)— or R$^3$N(R$^4$)S(O)m-, or two adjacent L groups are optionally joined together to form an alkylene chain having 3 or 4 members in which one or two (non-adjacent) carbon atoms are optionally replaced by oxygen atoms;

m is 0, 1 or 2; and

R$^2$, R$^3$, and R$^4$ are independently selected from H and $C_{1-4}$ alkyl.

DETAILED DESCRIPTION OF THE INVENTION

The term "alkyl", as used herein, means a straight or branched saturated monovalent hydrocarbon radical including, but not limited to, methyl, ethyl, propyl, isopropyl, n-butyl, iso-butyl, sec-butyl, tert-butyl, neopentyl and the like.

The term "alkenyl", as used herein, means a hydrocarbon radical having at least one double bond including, but not limited to, ethenyl, propenyl, 1-butenyl, 2-butenyl and the like.

The term "alkynyl", as used herein, means a hydrocarbon radical having at least one triple bond including, but not limited to, ethynyl, propynyl, 1-butynyl, 2-butynyl and the like.

The term "halo", as used herein, refers to F, Cl, Br or I, preferably F or Cl.

The term "cycloalkyl", as used herein, means a saturated carbocyclic radical including, but not limited to, cyclopropyl, cyclobutyl, cyclohexyl, cycloheptyl, cyclooctyl, cyclononyl, cyclodecyl and the like.

The term "alkoxy", as used herein, means an O-alkyl group wherein "alkyl" is defined above.

The term "monocyclic aromatic ring", as used herein, means a monocyclic aromatic carbocyclic or heterocyclic ring (and containing 0–4 heteroatoms selected from O, N and S) including, but not limited to, phenyl, pyrazolyl, furyl, thienyl, oxazolyl, tetrazolyl, thiazolyl, imidazolyl, thiadiazolyl, pyridyl, pyrimidinyl, pyrrolyl, thiophenyl, pyrazinyl, pyridazinyl, isooxazolyl, isothiazolyl, triazolyl, furazanyl and the like.

The term "bicyclic aromatic ring", as used herein, means a monocyclic or bicyclic aromatic carbocyclic or heterocyclic ring (and containing 0–4 heteroatoms selected from O, N and S) including, but not limited to, naphthyl, benzofuranyl, isobenzofuranyl, benzothiophenyl, indolyl, isoindolyl, benzoxazolyl, benzothiazolyl, indazolyl, benzimidazolyl, quinolyl, isoquinolyl, cinnolinyl, phthalazinyl, quinazolinyl quinoxalinyl and the like.

The term "alkylene", as used herein, means saturated hydrocarbon (straight chain or branched) wherein a hydrogen atom is removed from each of the terminal carbons such as methylene, ethylene, propylene, butylene, pentylene, hexylene and the like.

The term "cycloalkylene", as used herein, means divalent cycloalkyl groups including, but not limited to, cyclopropylene, cyclobutylene, cyclopentylene, cyclohexylene and cycloheptylene and the like.

The term "alkenylene", as used herein, means a straight or branched hydrocarbon chain spacer radical having at least one double bond including, but not limited to, —CH=CH—, —CH=CHCH—, —CH=CHCH(CH$_3$)—, and the like.

The term "alkynylene", as used herein, means a straight or branched hydrocarbon chain spacer radical having at least one triple bond including, but not limited to, —C≡C—, —C—C≡CCH$_2$—, —C≡CCH(CH$_3$)—, and the like.

The term "tricyclic ring", as used herein, means a saturated carbocyclic radical including, but not limited to, adamantyl, tricyclo[5.2.1.0$^{2,6}$]decane, and the like.

The term "two adjacent L groups are optionally joined together to form an alkylene chain having 3 or 4 members in which one or two (non-adjacent) carbon atoms are optionally replaced by oxygen atoms", as used herein, means, but not limited to, —O—CH$_2$—O—, —CH$_2$—O—CH$_2$—, —O—CH$_2$CH$_2$—, —CH$_2$CH$_2$—O—, —O—CH$_2$CH$_2$—O—, —CH$_2$CH$_2$CH$_2$—O—, —O—CH$_2$CH$_2$CH$_2$—, —CH$_2$—O—CH$_2$CH$_2$—, —CH$_2$CH$_2$—O—CH$_2$—, and the like.

The term "aryl", as used herein, means aromatic radicals including, but not limited to, phenyl, naphthyl, tetrahydronaphthyl, indanyl, biphenyl and the like.

The term "protecting group", as used herein, means a hydroxy or amino protecting group which is selected from typical hydroxy or amino protecting groups described in Protective Groups in Organic Synthesis edited by T. W. Greene et al. (John Wiley & Sons, 1991);

The term "treating", as used herein, refers to reversing, alleviating, inhibiting the progress of, or preventing the disorder or condition to which such term applies, or one or more symptoms of such disorder or condition. The term "treatment" as used herein refers to the act of treating, as "treating" is defined immediately above.

In the compounds of formula (I),

Y$^1$, Y$^2$, Y$^3$, and Y$^4$ are preferably independently selected from N, CH and C(L);

L is halo, $C_{1-4}$ alkyl, halo-substituted $C_{1-4}$ alkyl, hydroxy, $C_{1-4}$ alkoxy, mono- or di-($C_{1-4}$ alkyl)amino, halo-substituted $C_{1-4}$ alkoxy, cyano, HO—$C_{1-4}$ alkyl, $C_{1-4}$ alkoxy-$C_{1-4}$ alkyl, $C_{1-4}$ alkylsulfonyl, aminosulfonyl, $C_{1-4}$ alkyl(=O)—, HO(O=)C—, $C_{1-4}$ alkyl-O(O=)C—, $C_{1-4}$ alkylsulfonylamino, $C_{3-7}$ cycloalkyl, R$^3$C(=O)N(R$^4$)—, R$^3$N(R$^4$)C(=O)—, R$^3$N(R$^4$)S(O)m-, Q$^2$—, Q$^2$—C(=O)—, Q$^2$—O—, Q$^2$—$C_{1-4}$alkyl-O—, or two adjacent L groups are optionally joined together to form an alkylene chain having 3 or 4 members in which one or two (non-adjacent) carbon atoms are optionally replaced by oxygen atoms;

m is 0 or 2;

$R^3$ and $R^4$ are independently selected from H and $C_{1-4}$ alkyl; and $Q^2$ is a 5–12 membered monocyclic or bicyclic aromatic ring, or a 8–12 membered tricyclic ring optionally containing up to 3 heteroatoms selected from O, N and S, wherein said 5–12 membered monocyclic or bicyclic aromatic ring is optionally substituted with halo, $C_{1-4}$ alkyl, halo-substituted $C_{1-4}$ alkyl, $C_{1-4}$ alkenyl, $C_{1-4}$ alkynyl, hydroxy, $C_{1-4}$ alkoxy, halo-substituted $C_{1-4}$ alkoxy, $C_{1-4}$ alkylthio, mono- or di-($C_{1-4}$ alkyl)amino, cyano, HO—$C_{1-4}$ alkyl, $C_{1-4}$ alkoxy-$C_{1-4}$ alkyl, $C_{1-4}$ alkylsulfonyl, aminosulfonyl, $C_{1-4}$ alkyl-(O=)C—, $R^3(R^4)C(=O)N$—, HO(O=)C—, $C_{1-4}$ alkyl-O(O=)C—, $C_{1-4}$ alkylsulfonylamino, $C_{3-7}$ cycloalkyl or $C_{1-4}$ alkyl-C(=O)NH—, more preferably $Y^1$, $Y^2$, $Y^3$, and $Y^4$ are independently selected from N, CH and C(L);

L is halo, $C_{1-4}$ alkyl, halo-substituted $C_{1-4}$ alkyl, hydroxy, $C_{1-4}$ alkoxy, mono- or di-($C_{1-4}$ alkyl)amino, halo-substituted $C_{1-4}$ alkoxy, cyano, HO—$C_{1-4}$ alkyl, $C_{1-4}$ alkylsulfonyl, aminosulfonyl, $C_{1-4}$ alkyl(=O)—, HO(O=)C—, $C_{1-4}$ alkyl-O(O=)C—, $C_{1-4}$ alkylsulfonylamino, $C_{3-7}$ cycloalkyl, $R^3C(=O)N(R^4)$—, $R^3N(R^4)C(=O)$—, $R^3N(R^4)S(O)m$-, $Q^2$—, $Q^2$—C(=O)—, $Q^2$—O—, $Q^2$—$C_{1-4}$alkyl-O—, or two adjacent L groups are optionally joined together to form an alkylene chain having 3 or 4 members in which one or two (non-adjacent) carbon atoms are optionally replaced by oxygen atoms;

m is 0 or 2;

$R^3$ and $R^4$ are independently selected from H and $C_{1-4}$ alkyl; and $Q^2$ is a 5 or 6 membered monocyclic aromatic ring, or a 8–12 membered tricyclic ring containing up to 3 heteroatoms selected from N and S, wherein said 5 or 6 membered monocyclic aromatic ring is optionally substituted with halo, more preferably $Y^1$, $Y^2$, $Y^3$, and $Y^4$ are independently selected from N, CH and C(L);

m is 0 or 2;

$R^3$ and $R^4$ are independently selected from H and $C_{1-4}$ alkyl; and $Q^2$ is 5 or 6 membered monocyclic aromatic ring or a 8–12 membered tricyclic ring optionally containing 1 sulfur atom wherein said 5 or 6 membered monocyclic aromatic ring is optionally substituted with halo, more preferably $Y^1$, $Y^2$, $Y^3$, and $Y^4$ are independently selected from N, CH and C(L);

L is halo, $C_{1-4}$ alkyl, halo-substituted $C_{1-4}$ alkyl, hydroxy, $C_{1-4}$ alkoxy, halo-substituted $C_{1-4}$ alkoxy, cyano, HO—$C_{1-4}$ alkyl, acetyl, $R^3N(R^4)C(=O)$—, $R^3N(R^4)S(O)m$-, $Q^2$—, $Q^2$—C(=O)—, $Q^2$—O—, $Q^2$—$C_{1-4}$alkyl-O—, or two adjacent L groups are joined together to form a methylenedioxy group;

$R^3$ and $R^4$ are independently selected from H and $C_{1-4}$ alkyl; and $Q^2$ is 5 or 6 membered monocyclic aromatic ring system, more preferably $Y^1$, $Y^2$, $Y^3$, and $Y^4$ are independently selected from N, CH and C—L;

L is chloro, methyl, trifuluoromethyl, hydroxy, methoxy, cyano, acetyl, —C(=O)NH$_2$, trifuluoromethyloxy, methanesulfonyl, or 1-hydroxy-1-methyl-ethyl, or two adjacent L groups are joined together to form a methylenedioxy group, more preferably $Y^1$, $Y^2$, $Y^3$ and $Y^4$ are selected from the group consisting of a) $Y^1$ and $Y^3$ are C(L), $Y^2$ is CH and $Y^4$ is N;
b) $Y^1$ is CH, $Y^2$ and $Y^3$ are C(L) and $Y^4$ is N;
c) $Y^1$, $Y^2$ and $Y^3$ are C(L) and $Y^4$ is N;
d) $Y^1$ and $Y^3$ are C(L), $Y^2$ is N and $Y^4$ is CH;
e) $Y^1$ is C(L) and $Y^2$, $Y^3$ and $Y^4$ are CH;
f) $Y^1$, $Y^3$ and $Y^4$ are CH, and $Y^2$ is C(L);
g) $Y^1$, $Y^2$ and $Y^3$ are CH, and $Y^4$ is C(L);
h) $Y^1$ and $Y^2$ are C(L), and $Y^3$ and $Y^4$ are CH;
i) $Y^1$ and $Y^3$ are C(L), and $Y^2$ and $Y^4$ are CH;
j) $Y^1$ and $Y^4$ are CH, and $Y^2$ and $Y^3$ are C(L);
k) $Y^1$ and $Y^2$ are CH, $Y^3$ is C(L) and $Y^4$ is N;
l) $Y^1$ and $Y^3$ are CH, $Y^2$ is C(L) and $Y^4$ is N;
m) $Y^1$, $Y^2$, $Y^3$ and $Y^4$ are CH;
n) $Y^1$ and $Y^2$ are C(L), $Y^3$ is CH and $Y^4$ is N;
o) $Y^1$, $Y^2$ and $Y^4$ are CH, and $Y^3$ is C(L);
p) $Y^1$ and $Y^2$ are C(L), $Y^3$ is N and $Y^4$ is CH;
q) $Y^1$ and $Y^3$ are C(L), and $Y^2$ and $Y^4$ are N;
r) $Y^1$ is C(L), $Y^2$ and $Y^3$ are CH, and $Y^4$ is N;
s) $Y^2$ is C(L), $Y^1$ and $Y^3$ are CH, and $Y^4$ is N; and
t) $Y^1$, $Y^2$ and $Y^3$ are C(L), and $Y^4$ is CH L is chloro, methyl, trifuluoromethyl, hydroxy, methoxy, cyano, acetyl, —C(=O)NH$_2$, trifuluoromethyloxy, methanesulfonyl, or 1-hydroxy-1-methyl-ethyl, or two adjacent L groups are joined together to form a methylenedioxy group, most preferably $Y^1$, $Y^2$, $Y^3$ and $Y^4$ are selected from the group consisting of a) $Y^1$ and $Y^3$ are C(L), $Y^2$ is CH and $Y^4$ is N;
b) $Y^1$ is CH, $Y^2$ and $Y^3$ are C(L) and $Y^4$ is N;
c) $Y^1$, $Y^2$ and $Y^3$ are C(L) and $Y^4$ is N;
d) $Y^1$ and $Y^3$ are C(L), $Y^2$ is N and $Y^4$ is CH;
e) $Y^1$ is C(L) and $Y^2$, $Y^3$ and $Y^4$ are CH;
f) $Y^1$, $Y^3$ and $Y^4$ are CH, and $Y^2$ is C(L);
g) $Y^1$, $Y^2$ and $Y^3$ are CH, and $Y^4$ is C(L);
h) $Y^1$ and $Y^2$ are C(L), and $Y^3$ and $Y^4$ are CH;
i) $Y^1$ and $Y^3$ are C(L), and $Y^2$ and $Y^4$ are CH;
j) $Y^1$ and $Y^4$ are CH, and $Y^2$ and $Y^3$ are C(L); and
k) $Y^1$, $Y^2$ and $Y^3$ are C(L), and $Y^4$ is CH L is chloro, methyl, trifuluoromethyl, hydroxy, methoxy, cyano, acetyl, —C(=O)NH$_2$, trifuluoromethyloxy, methanesulfonyl, or 1-hydroxy-1-methyl-ethyl, or two adjacent L groups are joined together to form a methylenedioxy group.

In the compounds of formula (I), $R^1$ is preferably H, $C_{1-8}$ alkyl, $C_{2-8}$ alkenyl, $C_{2-8}$ alkynyl, $C_{3-7}$ cycloalkyl, $C_{1-8}$ alkoxy, halo-substituted $C_{1-8}$ alkoxy, $C_{1-8}$ alkyl-S(O)m-, $Q^1$—, pyrrolidinyl, piperidyl, oxopyrrolidinyl, oxopiperidyl, amino, mono- or di-($C_{1-8}$ alkyl)amino, $C_{1-4}$alkyl-C(=O)—N($R^3$)— or $C_{1-4}$alkyl-S(O)m-N($R^3$)—, wherein said $C_{1-8}$ alkyl, $C_{2-8}$ alkenyl and $C_{2-8}$ alkynyl are optionally substituted with halo, $C_{1-3}$ alkyl, hydroxy, oxo, $C_{1-4}$ alkoxy-, $C_{1-4}$ alkyl-S(O)m-, $C_{3-7}$ cycloalkyl-, cyano, indanyl, 1,2,3,4-tetrahydronaphtyl, 1,2-dihydronaphtyl, pyrrolidinyl, piperidyl, oxopyrrolidinyl, oxopiperidyl, $Q^1$—, $Q^1$C(=O)—, $Q^1$—O—, $Q^1$—S(O)m, $Q^1$—$C_{1-4}$ alkyl-O—, $Q^1$—$C_{1-4}$ alkyl-S(O)m-, $Q^1$—$C_{1-4}$alkyl-C(O)—N($R^3$)—, $Q^1$—$C_{1-4}$alkyl-N($R^3$)— or $C_{1-4}$alkyl-C(O)—N($R^3$)—;

$Q^1$ is a 5–12 membered monocyclic or bicyclic aromatic ring optionally containing up to 4 heteroatoms selected from O, N and S, and is optionally substituted with halo, $C_{1-4}$ alkyl, halo-substituted $C_{1-4}$ alkyl, hydroxy, $C_{1-4}$ alkoxy, halo-substituted $C_{1-4}$ alkoxy, $C_{1-4}$ alkylthio, nitro, amino, mono- or di-($C_{1-4}$ alkyl)amino, cyano, HO—$C_{1-4}$ alkyl, $C_{1-4}$ alkoxy-$C_{1-4}$alkyl, $C_{1-4}$ alkylsulfonyl, aminosulfonyl, $C_{1-4}$ alkyl(=O)—, HO(O=)C—, $C_{1-4}$ alkyl-O(O)C—, $R^3N(R^4)C(=O)$—, $C_{1-4}$ alkylsulfonylamino, $C_{3-7}$ cycloalkyl, $R^3C(=O)N(R^4)$— or $NH_2(HN=)C$—;

m is 0 or 2; and $R^3$ is H or $C_{1-4}$ alkyl, more preferably $R^1$ is H, $C_{1-8}$ alkyl, $C_{2-8}$ alkenyl, $C_{2-8}$ alkynyl, $C_{3-7}$ cycloalkyl, $Q^1$—, pyrrolidinyl, piperidyl, oxopyrrolidinyl, oxopiperidyl, amino, mono- or di-($C_{1-8}$ alkyl)amino, wherein said $C_{1-8}$ alkyl is optionally substituted with halo, $C^{1-3}$ alkyl, hydroxy, oxo, $C_{1-4}$ alkoxy-, $C_{1-4}$ alkyl-S(O)m-, $C_{3-7}$ cycloalkyl-, cyano, indanyl, pyrrolidinyl, piperidyl, oxopyrrolidinyl, oxopiperidyl, $Q^1$—, $Q^1$—C(O)—, $Q^1$—O—, $Q^1$—S— or $Q^1$—$C_{1-4}$ alkyl-O—, or $C_{1-4}$alkyl-C(O)—N($R^3$)—;

$Q^1$ is a 5–12 membered monocyclic aromatic ring optionally containing up to 4 heteroatoms selected from N and S, and is optionally substituted with halo, $C_{1-4}$ alkyl, $C_{1-4}$ alkylsulfonyl and $C_{1-4}$ alkyl(=O)—; and m is 0 or 2, more preferably $R^1$ is H, $C_{1-8}$ alkyl, $C_{2-8}$ alkenyl, $C_{2-8}$ alkynyl, $C_{3-7}$ cycloalkyl, $Q^1$—, or mono- or di-($C_{1-8}$ alkyl)amino wherein said $C_{1-8}$ alkyl is optionally substituted with halo, $C_{1-3}$ alkyl, hydroxy, oxo, $C_{1-4}$ alkoxy-, $C_{1-4}$ alkyl-S(O)m-, $C_{3-7}$ cycloalkyl-, cyano, indanyl, pyrrolidinyl, piperidyl, oxopyrrolidinyl, oxopiperidyl, $Q^1$—, $Q^1$—C(=O)—, $Q^1$—O—, $Q^1$—S—, $Q^1$—$C_{1-4}$ alkyl-O—, or $C_{1-4}$alkyl-C(O)—N(H)—;

$Q^1$ is a 5 or 6 membered monocyclic aromatic ring optionally containing up to 4 heteroatoms selected from N and S; and m is 0 or 2, more preferably $R^1$ is $C_{1-5}$ alkyl, $C_{3-7}$ cycloalkyl, or $Q^1$—, mono- or di-($C_{1-8}$ alkyl)amino wherein said $C_{1-5}$ alkyl is optionally substituted with $C_{1-3}$ alkyl, hydroxy, oxo, pyrrolidinyl, piperidyl, oxopyrrolidinyl, oxopiperidyl, $Q^1$—, or $C_{1-4}$alkyl-C(O)—N(H)—; and $Q^1$ is 5–12 membered monocyclic aromatic ring system optionally containing up to 2 heteroatoms selected from N and S, more preferably $R^1$ is $C_{1-5}$ alkyl, mono- or di-($C_{1-8}$ alkyl)amino, pyrrolidinyl, or pyridyl optionally substituted with $C_{1-3}$ alkyl, hydroxy, oxo, 5 or 6 membered monocyclic aromatic ring, wherein said 5 or 6 membered monocyclic aromatic ring is containing 1 or 2 heteroatoms selected from N and S, or $C_{1-4}$alkyl-C(O)—N(H)—, most preferably $R^1$ is methyl, ethyl, n-propyl, isopropyl, n-butyl, isobutyl, neopentyl, thiazolylethyl methylamino, dimethylamino, pyrrolidinyl, pyridyl, or 1-acetylamino-1-methylethyl.

In the compounds of formula (I), $R^2$ is preferably H or $C_{1-4}$ alkyl, most preferably H.

In the compounds of formula (I),

A is preferably a 5–6 membered monocyclic aromatic ring optionally containing up to 2 heteroatoms selected from O, N, and S, wherein said 5–6 membered monocyclic aromatic ring is optionally substituted with up to 2 substituents selected from halo, $C_{1-4}$ alkyl, halo-substituted $C_{1-4}$ alkyl, hydroxy, $C_{1-4}$ alkoxy and halo-substituted $C_{1-4}$ alkoxy, more preferably 5–6 membered monocyclic aromatic ring optionally substituted with halo, $C_{1-4}$ alkyl or $C_{1-4}$ alkoxy, more preferably 5–6 membered monocyclic aromatic ring system optionally substituted with halo or $C_{1-4}$ alkyl, more preferably 5–6 membered monocyclic aromatic ring system, most preferably phenyl or pyridyl.

In the compounds of formula (I),

B is preferably $C_{3-7}$ cycloalkylene or $C_{1-6}$ alkylene optionally substituted with an oxo group or $C_{1-3}$ alkyl, more preferably $C_{1-3}$ alkylene optionally substituted with $C_{1-3}$ alkyl, more preferably $C_{1-2}$ alkylene optionally substituted with methyl, most preferably ethylene or propylene.

In the compounds of formula (I),

W is preferably NH, N—$C_{1-4}$ alkyl, O or N—OH, more preferably NH, N—$C_{1-2}$ alkyl or O, most preferably NH, N—$CH_3$ or O.

In the compounds of formula (I),

Z is preferably a 5–12 membered monocyclic or bicyclic aromatic ring optionally containing up to 3 heteroatoms selected from, N, O, and S, wherein said 5–12 membered monocyclic or bicyclic aromatic ring is optionally substituted with halo, $C_{1-4}$ alkyl, halo-substituted $C_{1-4}$ alkyl, $C_{1-4}$ alkenyl, hydroxy, $C_{1-4}$ alkoxy, nitro, amino, cyano, HO—$C_{1-4}$ alkyl, $C_{1-4}$ alkylsulfonyl, aminosulfonyl, $C_{1-4}$ alkyl(=O)—, $R^3C(=O)N(R^4)$—, HO(O=)C—, $C_{1-4}$ alkyl-O(O=)C—, $C_{1-4}$ alkylsulfonylamino, $C_{1-4}$ alkyl-C(=O)NH—, $Q^2$—S(O)m-, $Q^2$—O—, $Q^2$—N($R^3$)— or $Q^2$—;

m is 0 or 2;

$R^3$ and $R^4$ are independently selected from H and $C_{1-4}$ alkyl; and $Q^2$ is a 5–12 membered monocyclic or bicyclic aromatic ring, or a 8–12 membered tricyclic ring optionally containing up to 3 heteroatoms selected from O, N and S, wherein said 5–12 membered monocyclic or bicyclic aromatic ring is optionally substituted with halo, $C_{1-4}$ alkyl, halo-substituted $C_{1-4}$ alkyl, $C_{1-4}$ alkenyl, $C_{1-4}$ alkynyl, hydroxy, $C_{1-4}$ alkoxy, halo-substituted $C_{1-4}$ alkoxy, $C_{1-4}$ alkylthio, mono- or di-($C_{1-4}$ alkyl)amino, cyano, HO—$C_{1-4}$ alkyl, $C_{1-4}$ alkoxy-$C_{1-4}$ alkyl, $C_{1-4}$ alkylsulfonyl, aminosulfonyl, $C_{1\ 1-4}$ alkyl-(O=)C—, $R^3(R^4)C(=O)N$—, HO(O=)C—, $C_{1-4}$ alkyl-O(O=)C—, $C_{1-4}$ alkylsulfonylamino, $C_{3-7}$ cycloalkyl or $C_{1-4}$ alkyl-C(=O)NH—, more preferably Z is 5–12 membered monocyclic or bicyclic aromatic ring optionally containing up to 3 heteroatoms selected from, N and S, wherein said 5–12 membered monocyclic or bicyclic aromatic ring is optionally substituted with halo, $C_{1-4}$ alkyl, halo-substituted $C_{1-4}$ alkyl, $C_{1-4}$ alkenyl, $C_{1-4}$ alkoxy, nitro, amino, cyano, $R^3C(=O)N(R^4)$—, $C_{1-4}$ alkyl-O(O=)C—, $Q^2$—S(O)m-, $Q^2$—O—, $Q^2$—N($R^3$)— or $Q^2$—;

m is 0 or 2;

$R^3$ and $R^4$ are independently selected from H and $C_{1-4}$ alkyl; and $Q^2$ is a 5 or 6 membered monocyclic aromatic ring, or a 8–12 membered tricyclic ring containing up to 3 heteroatoms selected from N and S, wherein said 5 or 6 membered monocyclic aromatic ring is optionally substituted with halo, more preferably Z is 5–12 membered monocyclic or bicyclic aromatic ring optionally containing up to 3 heteroatoms selected from N and S, wherein said 5–12 membered monocyclic or bicyclic aromatic ring is optionally substituted with halo, $C_{1-4}$ alkyl, halo-substituted $C_{1-4}$ alkyl, $C_{1-4}$ alkenyl, $C_{1-4}$ alkoxy, nitro, amino, cyano, $R^3C(=O)N(R^4)$—, $C_{1-4}$ alkyl-O(O=)C—, $Q^2$—S(O)m-, $Q^2$—O—, $Q^2$—N($R^3$)— or $Q^2$—;

m is 0 or 2;

$R^3$ and $R^4$ are independently selected from H and $C_{1-4}$ alkyl; and $Q^2$ is 5 or 6 membered monocyclic aromatic ring or a 8–12 membered tricyclic ring optionally containing 1 sulfur atom wherein said 5 or 6 membered monocyclic aromatic ring is optionally substituted with halo, more preferably Z is 5–12 membered monocyclic or bicyclic aromatic ring optionally containing up to 3 heteroatoms selected from N and S, wherein said 5–12 membered monocyclic aromatic ring is optionally substituted with halo, $C_{1-4}$ alkyl, nitro, $R^3C(=O)N(R^4)$— or $Q^2$—;

$R^3$ and $R^4$ are independently selected from H and $C_{1-4}$ alkyl; and $Q^2$ is 5 or 6 membered monocyclic aromatic ring system, more preferably Z is 5–10 membered monocyclic or bicyclic aromatic ring optionally containing up to 3 heteroatoms selected from N and S, wherein said 5–10 membered monocyclic aromatic ring is optionally substituted with chloro, bromo, methyl, nitro, $CH_3C(=O)NH$—, $tBuC(=O)NH$— or phenyl, most preferably Z is phenyl, pyrazolyl, thiazolyl, thiadiazolyl, thienyl, naphthyl or benzothienyl, said phenyl, pyrazolyl, thiazolyl, thiadiazolyl and thienyl being optionally substituted with one to three substituents independently selected from chloro, bromo, methyl, acetylamino, pivaloylamino, nitro and phenyl.

A preferred group of compounds of the present invention includes compounds of formula (I) wherein $Y^1, Y^2, Y^3$, and $Y^4$ are independently selected from N, CH and C(L);

$R^1$ is H, $C_{1-8}$ alkyl, $C_{2-8}$ alkenyl, $C_{2-8}$ alkynyl, $C_{3-7}$ cycloalkyl, $C_{1-8}$ alkoxy, halo-substituted $C_{1-8}$ alkoxy, $C_{1-8}$ alkyl-S(O)m-, $Q^1$—, pyrrolidinyl, piperidyl, oxopyrrolidinyl, oxopiperidyl, amino, mono- or di-($C_{1-8}$ alkyl)amino, $C_{1-4}$alkyl-C(=O)—N($R^3$)— or $C_{1-4}$alkyl-S(O)m-N($R^3$)—, wherein said $C_{1-8}$ alkyl, $C_{2-8}$ alkenyl and $C_{2-8}$ alkynyl are optionally substituted with halo, $C_{1-3}$ alkyl, hydroxy, oxo, $C_{1-4}$ alkoxy-, $C_{1-4}$ alkyl-S(O)m-, $C_{3-7}$ cycloalkyl-, cyano, indanyl, 1,2,3,4-tetrahydronaphtyl, pyrrolidinyl, piperidyl, oxopyrrolidinyl, oxopiperidyl, $Q^1$—, $Q^1$—C(=O)—, $Q^1$—O—, $Q^1$—S(O)m-, $Q^1$—$C_{1-4}$ alkyl-O—, $Q^1$—$C_{1-4}$ alkyl-S(O)m-, $Q^1$—$C_{1-4}$alkyl-C(=O)—N($R^3$)—, or $C_{1-4}$alkyl-C(=O)—N($R^3$)—;

$Q^1$ is a 5–12 membered monocyclic or bicyclic aromatic ring optionally containing up to 4 heteroatoms selected from O, N and S, and is optionally substituted with halo, $C_{1-4}$ alkyl, halo-substituted $C_{1-4}$ alkyl, hydroxy, $C_{1-4}$ alkoxy, halo-substituted $C_{1-4}$ alkoxy, $C_{1-4}$ alkylthio, nitro, amino, mono- or di-($C_{1-4}$ alkyl)amino, cyano, HO—$C_{1-4}$ alkyl, $C_{1-4}$ alkoxy-$C_{1-4}$alkyl, $C_{1-4}$ alkylsulfonyl, aminosulfonyl, $C_{1-4}$ alkyl(=O)—, HO(O=)C—, $C_{1-4}$ alkyl-O(O)C—, $R^3N(R^4)C(=O)$—, $C_{1-4}$ alkylsulfonylamino, $C_{3-7}$ cycloalkyl, $R^3C(=O)N(R^4)$— or $NH_2(HN=)C$—;

A is a 5–6 membered monocyclic aromatic ring optionally containing up to 2 heteroatoms selected from O, N, and S, wherein said 5–6 membered monocyclic aromatic ring is optionally substituted with up to 2 substituents selected from halo, $C_{1-4}$ alkyl, halo-substituted $C_{1-4}$ alkyl, hydroxy, $C_{1-4}$ alkoxy and halo-substituted $C_{1-4}$ alkoxy;

B is $C_{3-7}$ cycloalkylene or $C_{1-6}$ alkylene optionally substituted with an oxo group or $C_{1-3}$ alkyl;

W is NH, N—$C_{1-4}$ alkyl, O or N—OH;

$R^2$ is H or $C_{1-4}$ alkyl;

Z is a 5–12 membered monocyclic or bicyclic aromatic ring optionally containing up to 3 heteroatoms selected from, N and S, wherein said 5–12 membered monocyclic or bicyclic aromatic ring is optionally substituted with halo, $C_{1-4}$ alkyl, halo-substituted $C_{1-4}$ alkyl, $C_{1-4}$ alkenyl, hydroxy, $C_{1-4}$ alkoxy, nitro, amino, cyano, HO—$C_{1-4}$ alkyl, $C_{1-4}$ alkylsulfonyl, aminosulfonyl, $C_{1-4}$ alkyl(=O)—, $R^3C(=O)N(R^4)$—, HO(O=)C—, $C_{1-4}$ alkyl-O(O=)C—, $C_{1-4}$ alkylsulfonylamino, $C_{1-4}$alkyl-C(=O)NH—, $Q^2$—S(O)m-, $Q^2$—O—, $Q^2$—N($R^3$)— or $Q^2$—;

L is halo, $C_{1-4}$ alkyl, halo-substituted $C_{1-4}$ alkyl, hydroxy, $C_{1-4}$ alkoxy, mono- or di-($C_{1-4}$ alkyl)amino, halo-substituted $C_{1-4}$ alkoxy, cyano, HO—$C_{1-4}$ alkyl, $C_{1-4}$ alkoxy-$C_{1-4}$ alkyl, $C_{1-4}$ alkylsulfonyl, aminosulfonyl, $C_{1-4}$ alkyl(=O)—, HO(O=)C—, $C_{1-4}$ alkyl-O(O=)C—, $C_{1-4}$ alkylsulfonylamino, $C_{3-7}$ cycloalkyl, $R^3C(=O)N(R^4)$—, $R^3N(R^4)C(=O)$—, $R^3N(R^4)S(O)m$-, $Q^2$—; $Q^2$—C(=O)—, $Q^2$—O—, $Q^2$—$C_{1-4}$alkyl-O—, or two adjacent L groups are optionally joined together to form an alkylene chain having 3 or 4 members in which one or two (non-adjacent) carbon atoms are optionally replaced by oxygen atoms;

m is 0 or 2;

$R^3$ and $R^4$ are independently selected from H and $C_{1-4}$ alkyl; and $Q^2$ is a 5–12 membered monocyclic or bicyclic aromatic ring, or a 8–12 membered tricyclic ring optionally containing up to 3 heteroatoms selected from O, N and S, wherein said 5–12 membered monocyclic or bicyclic aromatic ring is optionally substituted with halo, $C_{1-4}$ alkyl, halo-substituted $C_{1-4}$ alkyl, $C_{1-4}$ alkenyl, $C_{1-4}$ alkynyl, hydroxy, $C_{1-4}$ alkoxy, halo-substituted $C_{1-4}$ alkoxy, $C_{1-4}$ alkylthio, mono- or di-($C_{1-4}$ alkyl)amino, cyano, HO—$C_{1-4}$ alkyl, $C_{1-4}$ alkoxy-$C_{1-4}$ alkyl, $C_{1-4}$ alkylsulfonyl, aminosulfonyl, $C_{1-4}$ alkyl-(O=)C—, $R^3(R^4)C(=O)N$—, HO(O=)C—, $C_{1-4}$ alkyl-O(O=)C—, $C_{1-4}$ alkylsulfonylamino, $C_{3-7}$ cycloalkyl or $C_{1-4}$ alkyl-C(=O)NH—.

A further preferred group of compounds of the present invention includes compounds of formula (I) wherein $Y^1, Y^2, Y^3$, and $Y^4$ are independently selected from N, CH and C(L);

$R^1$ is H, $C_{1-8}$ alkyl, $C_{2-8}$ alkenyl, $C_{2-8}$ alkynyl, $C_{3-7}$ cycloalkyl, $Q^1$—, pyrrolidinyl, piperidyl, oxopyrrolidinyl, oxopiperidyl, amino, mono- or di-($C_{1-8}$ alkyl)amino, wherein said $C_{1-8}$ alkyl is optionally substituted with halo, $C^{1-3}$ alkyl, hydroxy, oxo, $C_{1-4}$ alkoxy-, $C_{1-4}$ alkyl-S(O)m-, $C_{3-7}$ cycloalkyl-, cyano, indanyl, pyrrolidinyl, piperidyl, oxopyrrolidinyl, oxopiperidyl, $Q^1$—, $Q^1$—C(O)—, $Q^1$—O—, $Q^1$—S—, $Q^1$—$C_{1-4}$ alkyl-O—, or $C_{1-4}$alkyl-C(O)—N($R^3$)—;

$Q^1$ is a 5–12 membered monocyclic aromatic ring optionally containing up to 4 heteroatoms selected from N and S, and is optionally substituted with halo, $C_{1-4}$ alkyl, $C_{1-4}$ alkylsulfonyl and $C_{1-4}$ alkyl(=O)—;

A is 5–6 membered monocyclic aromatic ring optionally substituted with halo, $C_{1-4}$ alkyl or $C_{1-4}$ alkoxy;

B is $C_{3-7}$ cycloalkylene or $C_{1-6}$ alkylene optionally substituted with an oxo group or $C_{1-3}$ alkyl;

W is NH, N—$C_{1-4}$ alkyl, O or N—OH;

$R^2$ is H or $C_{1-4}$ alkyl;

Z is 5–12 membered monocyclic or bicyclic aromatic ring optionally containing up to 3 heteroatoms selected from, N and S, wherein said 5–12 membered monocyclic or bicyclic aromatic ring is optionally substituted with halo, $C_{1-4}$ alkyl, halo-substituted $C_{1-4}$ alkyl, $C_{1-4}$ alkenyl, $C_{1-4}$ alkoxy, nitro, amino, cyano, $R^3C(=O)N$ ($R^4$)—, $C_{1-4}$ alkyl-O(O=)C—, $Q^2$—S(O)m-, $Q^2$—O—, $Q^2$—N($R^3$)— or $Q^2$—;

L is halo, $C_{1-4}$ alkyl, halo-substituted $C_{1-4}$ alkyl, hydroxy, $C_{1-4}$ alkoxy, halo-substituted $C_{1-4}$ alkoxy, mono- or di-($C_{1-4}$ alkyl)amino, cyano, HO—$C_{1-4}$ alkyl, $C_{1-4}$ alkylsulfonyl, aminosulfonyl, $C_{1-4}$ alkyl(=O)—, HO(O=)C—, $C_{1-4}$ alkyl-O(O=)C—, $C_{1-4}$ alkylsulfonylamino, $C_{3-7}$ cycloalkyl, $R^3$C(=O)N($R^4$)—, $R^3$N($R^4$)C(=O)—, $R^3$N($R^4$)S(O)m-, $Q^2$—, $Q^2$—C(=O)—, $Q^2$—O—, $Q^2$—$C_{1-4}$alkyl-O—, or two adjacent L groups are optionally joined together to form an alkylene chain having 3 or 4 members in which one or two (non-adjacent) carbon atoms are optionally replaced by oxygen atoms;

m is 0 or 2;

$R^3$ and $R^4$ are independently selected from H and $C_{1-4}$ alkyl; and $Q^2$ is a 5 or 6 membered monocyclic aromatic ring, or a 8–12 membered tricyclic ring containing up to 3 heteroatoms selected from N and S, wherein said 5 or 6 membered monocyclic aromatic ring is optionally substituted with halo.

A further preferred group of compounds of the present invention includes compounds of formula (I) wherein $Y^1$, $Y^2$, $Y^3$ and $Y^4$ are independently selected from N, CH and C(L);

$R^1$ is H, $C_{1-8}$ alkyl, $C_{2-8}$ alkenyl, $C_{2-8}$ alkynyl or $C_{3-7}$ cycloalkyl, wherein said $C_{1-8}$ alkyl is optionally substituted with halo, $C_{1-3}$ alkyl, hydroxy, oxo, $C_{1-4}$ alkoxy-, $C_{1-4}$ alkyl-S(O)m-, $C_{3-7}$ cycloalkyl-, cyano, indanyl, pyrrolidinyl, piperidyl, oxopyrrolidinyl, oxopiperidyl, $Q^1$—, $Q^1$—C(=O)—, $Q^1$—, $Q^1$—S—, $Q^1$—$C_{1-4}$ alkyl-O—, or $C_{1-4}$alkyl-C(O)—N($R^3$)—;

$Q^1$ is a 5 or 6 membered monocyclic aromatic ring optionally containing up to 4 heteroatoms selected from N and S;

A is 5–6 membered monocyclic aromatic ring system optionally substituted with halo or $C_{1-4}$ alkyl;

B is or $C_{3-7}$ cycloalkylene or $C_{1-6}$ alkylene optionally substituted with an oxo group or $C_{1-3}$ alkyl;

W is NH, N—$C_{1-4}$ alkyl, O or N—OH;

$R^2$ is H or $C_{1-4}$ alkyl;

Z is 5–12 membered monocyclic or bicyclic aromatic ring optionally containing up to 3 heteroatoms selected from N and S, wherein said 5–12 membered monocyclic or bicyclic aromatic ring is optionally substituted with halo, $C_{1-4}$ alkyl, halo-substituted $C_{1-4}$ alkyl, $C_{1-4}$ alkenyl, $C_{1-4}$ alkoxy, nitro, amino, cyano, $R^3$C(=O)N($R^4$)—, $C_{1-4}$ alkyl-O(O=)C—, $Q^2$—S(O)m-, $Q^2$—O—, $Q^2$—N($R^3$)— or $Q^2$—;

L is halo, $C_{1-4}$ alkyl, halo-substituted $C_{1-4}$ alkyl, hydroxy, $C_{1-4}$ alkoxy, halo-substituted $C_{1-4}$ alkoxy, cyano, HO—$C_{1-4}$ alkyl, $C_{1-4}$ alkylsulfonyl, aminosulfonyl, $C_{1-4}$ alkyl(=O), HO(O=)C—, $C_{1-4}$ alkyl-O(O=)C—, $C_{1-4}$ alkylsulfonylamino, $C_{3-7}$ cycloalkyl, $R^3$C(=O)N$R^4$—, $R^3$N($R^4$)C(=O)—, $R^3$N($R^4$)S(O)m-, $Q^2$—, $Q^2$—C(=O)—, $Q^2$—O—, $Q^2$—$C_{1-4}$alkyl-O—, or two adjacent L groups are optionally joined together to form an alkylene chain having 3 or 4 members in which one or two (non-adjacent) carbon atoms are optionally replaced by oxygen atoms;

m is 0 or 2;

$R^3$ and $R^4$ are independently selected from H and $C_{1-4}$ alkyl; and p1 $Q^2$ is 5 or 6 membered monocyclic aromatic ring or a 8–12 membered tricyclic ring optionally containing 1 sulfur atom wherein said 5 or 6 membered monocyclic aromatic ring is optionally substituted with halo.

A further preferred group of compounds of the present invention includes compounds of formula (I) wherein $Y^1$, $Y^2$, $Y^3$ and $Y^4$ are independently selected from N, CH and C(L);

$R^1$ is $C_{1-5}$ alkyl or $C_{3-7}$ cycloalkyl, wherein said $C_{1-5}$ alkyl is optionally substituted with $C_{1-3}$ alkyl, hydroxy, oxo, pyrrolidinyl, piperidyl, oxopyrrolidinyl, oxopiperidyl, $Q^1$—, or $C_{1-4}$alkyl-C(O)—N(H)—;

$Q^1$ is 5–12 membered monocyclic aromatic ring system optionally containing up to 2 heteroatoms selected from N and S, A is 5–6 membered monocyclic aromatic ring system;

B is $C_{1-3}$ alkylene optionally substituted with $C_{1-3}$ alkyl;

W is NH, N—$C_{1-2}$ alkyl or O;

$R^2$ is H;

Z is 5–12 membered monocyclic or bicyclic aromatic ring optionally containing up to 3 heteroatoms selected from N and S, wherein said 5–12 membered monocyclic aromatic ring is optionally substituted with halo, $C_{1-4}$ alkyl, nitro, $R^3$C(=O)N($R^4$)— or $Q^2$—;

L is halo, $C_{1-4}$ alkyl, halo-substituted $C_{1-4}$ alkyl, hydroxy, $C_{1-4}$ alkoxy, halo-substituted $C_{1-4}$ alkoxy, cyano, HO—$C_{1-4}$ alkyl, acetyl, $R^3$N($R^4$)C(=O)—, $R^3$N($R^4$)S(O)m-, $Q^2$—, $Q^2$—C(=O)—, or two adjacent L groups are joined together to form a methylenedioxy group;

$R^3$ and $R^4$ are independently selected from H and $C_{1-4}$ alkyl; and $Q^2$ is 5 or 6 membered monocyclic aromatic ring system.

A further preferred group of compounds of the present invention includes compounds of formula (I) wherein $Y^1$, $Y^2$, $Y^3$ and $Y^4$ are independently selected from N, CH and C—L;

$R^1$ is $C_{1-5}$ alkyl optionally substituted with $C_{1-3}$ alkyl, hydroxy, oxo, 5 or 6 membered monocyclic aromatic ring, wherein said 5 or 6 membered monocyclic aromatic ring is containing 1 or 2 heteroatoms selected from N and S, or $C_{1-4}$alkyl-C(O)—N($R^3$)—;

A is phenyl;

B is $C_{1-2}$ alkylene optionally substituted with methyl;

W is NH, N—$CH_3$ or O;

$R^2$ is H;

Z is 5–10 membered monocyclic or bicyclic aromatic ring optionally containing up to 3 heteroatoms selected from N and S, wherein said 5–10 membered monocyclic aromatic ring is optionally substituted with chloro, bromo, methyl, nitro, $CH_3$C(=O)NH—, tBuC(=O)NH— or phenyl; and L is chloro, methyl, trifuluoromethyl, hydroxy, methoxy, cyano, acetyl, —C(=O)$NH_2$, trifuluoromethyloxy, methanesulfonyl, or 1-hydroxy-1-methyl-ethyl, or two adjacent L groups are joined together to form a methylenedioxy group.

A further preferred group of compounds of the present invention includes compounds of formula (I) wherein $Y^1$, $Y^2$, $Y^3$ and $Y^4$ are independently selected from N, CH and C—L;

$R^1$ is methyl, ethyl, n-propyl, isopropyl, n-butyl, isobutyl, neopentyl, thiazolylethyl methylamino, dimethylamino, pyrrolidinyl, pyridyl, or 1-acetylamino-1-methylethyl;

A is phenyl;
B is ethylene or propylene;
W is NH, N—CH$_3$ or O;
R$^2$ is H;
Z is phenyl, pyrazolyl, thiazolyl, thiadiazolyl, thienyl, naphthyl or benzothienyl, said phenyl, pyrazolyl, thiazolyl, thiadiazolyl and thienyl being optionally substituted with one to three substituents independently selected from chloro, bromo, methyl, acetylamino, pivaloylamino, nitro and phenyl; and
L is chloro, methyl, trifuluoromethyl, hydroxy, methoxy, cyano, acetyl, —C(=O)NH$_2$, trifuluoromethyloxy, methanesulfonyl, or 1-hydroxy-1-methyl-ethyl, or two adjacent L groups are joined together to form a methylenedioxy group.

A further preferred group of compounds of the present invention includes compounds of formula (I) wherein
Y$^1$, Y$^2$, Y$^3$ and Y$^4$ are selected from the group consisting of
a) Y$^1$ and Y$^3$ are C(L), Y$^2$ is CH and Y$^4$ is N;
b) Y$^1$ is CH, Y$^2$ and Y$^3$ are C(L) and Y$^4$ is N;
c) Y$^1$, Y$^2$ and Y$^3$ are C(L) and Y$^4$ is N;
d) Y$^1$ and Y$^3$ are C(L), Y$^2$ is N and Y$^4$ is CH;
e) Y$^1$ is C(L) and Y$^2$, Y$^3$ and Y$^4$ are CH;
f) Y$^1$, Y$^3$ and Y$^4$ are CH, and Y$^2$ is C(L);
g) Y$^1$, Y$^2$ and Y$^3$ are CH, and Y$^4$ is C(L);
h) Y$^1$ and Y$^2$ are C(L), and Y$^3$ and Y$^4$ are CH;
i) Y$^1$ and Y$^3$ are C(L), and Y$^2$ and Y$^4$ are CH;
j) Y$^1$ and Y$^4$ are CH, and Y$^2$ and Y$^3$ are C(L);
k) Y$^1$ and Y$^2$ are CH, Y$^3$ is C(L) and Y$^4$ is N;
l) Y$^1$ and Y$^3$ are CH, Y$^2$ is C(L) and Y$^4$ is N;
m) Y$^1$, Y$^2$, Y$^3$ and Y$^4$ are CH;
n) Y$^1$ and Y$^2$ are C(L), Y$^3$ is CH and Y$^4$ is N;
o) Y$^1$, Y$^2$ and Y$^4$ are CH, and Y$^3$ is C(L);
p) Y$^1$ and Y$^2$ are C(L), Y$^3$ is N and Y$^4$ is CH;
q) Y$^1$ and Y$^3$ are C(L), and Y$^2$ and Y$^4$ are N;
r) Y$^1$ is C(L), Y$^2$ and Y$^3$ are CH, Y$^4$ is N; and
s) Y$^2$ is C(L), Y$^1$ and Y$^3$ are CH, and Y$^4$ is N;
R$^1$ is methyl, ethyl, n-propyl, isopropyl, n-butyl, isobutyl, neopentyl, thiazolylethyl methylamino, dimethylamino, pyrrolidinyl, pyridyl, or 1-acetylamino-1-methylethyl;
A is phenyl;
B is ethylene or propylene;
W is NH, N—CH$_3$ or O;
R$^2$ is H;
Z is phenyl, pyrazolyl, thiazolyl, thiadiazolyl, thienyl, naphthyl or benzothienyl, said phenyl, pyrazolyl, thiazolyl, thiadiazolyl and thienyl being optionally substituted with one to three substituents independently selected from chloro, bromo, methyl, acetylamino, pivaloylamino, nitro and phenyl; and
L is chloro, methyl, trifuluoromethyl, hydroxy, methoxy, cyano, acetyl, —C(=O)NH$_2$, trifuluoromethyloxy, methanesulfonyl, or 1-hydroxy-1-methyl-ethyl, or two adjacent L groups are joined together to form a methylenedioxy group.

A further preferred group of compounds of the present invention includes compounds of formula (I) wherein
Y$^1$, Y$^2$, Y$^3$ and Y$^4$ are selected from the group consisting of
a) Y$^1$ and Y$^3$ are C(L), Y$^2$ is CH and Y$^4$ is N;
b) Y$^1$ is CH, Y$^2$ and Y$^3$ are C(L) and Y$^4$ is N;
c) Y$^1$, Y$^2$ and Y$^3$ are C(L) and Y$^4$ is N;
d) Y$^1$ and Y$^3$ are C(L), Y$^2$ is N and Y$^4$ is CH;
e) Y$^1$ is C(L) and Y$^2$, Y$^3$ and Y$^4$ are CH;
f) Y$^1$, Y$^3$ and Y$^4$ are CH, and Y$^2$ is C(L);
g) Y$^1$, Y$^2$ and Y$^3$ are CH, and Y$^4$ is C(L);
h) Y$^1$ and Y$^2$ are C(L), and Y$^3$ and Y$^4$ are CH;
i) Y$^1$ and Y$^3$ are C(L), and Y$^2$ and Y$^4$ are CH; and
j) Y$^1$ and Y$^4$ are CH, and Y$^2$ and Y$^3$ are C(L);
R$^1$ is methyl, ethyl, n-propyl, isopropyl, n-butyl, isobutyl, neopentyl, thiazolylethyl methylamino, dimethylamino, pyrrolidinyl, pyridyl, or 1-acetylamino-1-methylethyl;
A is phenyl;
B is ethylene or propylene;
W is NH, N—CH$_3$ or O;
R$^2$ is H;
Z is phenyl, pyrazolyl, thiazolyl, thiadiazolyl, thienyl, naphthyl or benzothienyl, said phenyl, pyrazolyl, thiazolyl, thiadiazolyl and thienyl being optionally substituted with one to three substituents independently selected from chloro, bromo, methyl, acetylamino, pivaloylamino, nitro and phenyl; and
L is chloro, methyl, trifuluoromethyl, hydroxy, methoxy, cyano, acetyl, —C(=O)NH$_2$, trifuluoromethyloxy, methanesulfonyl, or 1-hydroxy-1-methyl-ethyl, or two adjacent L groups are joined together to form a methylenedioxy group.

Preferred individual compounds of this invention are following:

3-(4-{2-[({[(5-chloro-1,3-dimethyl-1h-pyrazol-4-yl)sulfonyl]amino}carbonyl)amino]ethyl}phenyl)-2-ethyl-5,7-dimethyl-3H-imidazo[4,5-b]pyridine;

3-(4-{2-[({[(2,4-dimethyl-1,3-thiazol-5-yl)sulfonyl]amino}carbonyl)amino]ethyl}phenyl)-2-ethyl-5,7-dimethyl-3H-imidazo[4,5-b]pyridine;

N-[5-({[({2-[4-(2-ethyl-5,7-dimethyl-3H-imidazo[4,5-b]pyridin-3-yl)phenyl]ethyl}amino)carbonyl]amino}sulfonyl)-1,3,4-thiadiazol-2-yl]acetamide;

6-ethyl-5-(4-{2-[({[(4-methylphenyl)sulfonyl]amino}carbonyl)amino]ethyl}phenyl)-5H-[1,3]dioxolo[4,5-f]benzimidazole;

6-chloro-5-cyano-2-ethyl-1-(4-{2-[({[(4-methylphenylsulfonyl]amino}carbonyl)amino]ethyl}phenyl)-1H-benzimidazole;

2-ethyl-5,7-dimethyl-3-(4-{2-[methyl({[(4-methylphenyl)sulfonyl]amino}carbonyl)amino]ethyl}phenyl)-3H-imidazo[4,5-b]pyridine;

2-ethyl-5,7-dimethyl-3-(4-{2-[({[(4-methylphenyl)sulfonyl]aminocarbonyl)amino]propyl}phenyl)-3H-imidazo[4,5-b]pyridine;

2-[4-(2-ethyl-5,7-dimethyl-3H-imidazo[4,5-b]pyridin-3-yl)phenyl]-1-methylethyl(4-methylphenyl)sulfonylcarbamate;

5,7-dimethyl-3-(4-{2-[({[(4-methylphenyl)sulfonyl]amino}carbonyl)amino]ethyl}phenyl)-2-propyl-3H-imidazo[4,5-b]pyridine;

2-isopropyl-5,7-dimethyl-3-(4-{2-[({[(4-methylphenyl)sulfonyl]amino}carbonyl)amino]ethyl}phenyl)-3H-imidazo[4,5-b]pyridine;

2-butyl-5,7-dimethyl-3-(4-{2-[({[(4-methylphenyl)sulfonyl]amino}carbonyl)amino]ethyl}phenyl)-3H-imidazo[4,5-b]pyridine;

2-isobutyl-5,7-dimethyl-3-(4-{2-[({[(4-methylphenyl)sulfonyl]amino}carbonyl)amino]ethyl}phenyl)-3H-imidazo[4,5-b]pyridine;

5,7-dimethyl-3-(4-{2-[({[(4-methylphenyl)sulfonyl]aminocarbonyl)amino]ethyl}phenyl)-2-neopentyl-3H-imidazo[4,5-b]pyridine;

5,7-dimethyl-3-(4-{2-[({[(4-methylphenyl)sulfonyl]amino}carbonyl)amino]ethyl}phenyl)-2-[2-(1,3-thiazol-2-yl)ethyl]-3H-imidazo[4,5-b]pyridine;

3-{4-[2-({[(4-biphenylsulfonyl)amino]carbonyl}amino)ethyl]phenyl}-2-ethyl-5,7-dimethyl-3H-imidazo[4,5-b]pyridine;

2-ethyl-5,7-dimethyl-3-{4-[2-({[(1-naphthylsulfonyl)amino]carbonyl}amino)ethyl]phenyl}-3H-imidazo[4,5-b]pyridine;

2-ethyl-5,7-dimethyl-3-{4-[2-({[(2-naphthylsulfonyl)amino]carbonyl}amino)ethyl]phenyl}-3H-imidazo[4,5-b]pyridine;

2-ethyl-5,7-dimethyl-3-(4-{2-[({[(2-thienyl)sulfonyl]amino}carbonyl)amino]ethyl}phenyl)-3H-imidazo[4,5-b]pyridine;

3-(4-{2-[({[(5-chloro-2-thienyl)sulfonyl]amino}carbonyl)amino]ethyl}phenyl)2-ethyl-5,7-dimethyl-3H-imidazo[4,5-b]pyridine;

3-(4-{2-[({[(4,5-dichloro-2-thienyl)sulfonyl]amino}carbonyl)amino]ethyl}phenyl)-2-ethyl-5,7-dimethyl-3H-imidazo[4,5-b]pyridine;

3-{4-[2-({[(1-benzothien-2-ylsulfonyl)amino]carbonyl}amino)ethyl]phenyl}-2-ethyl-5,7-dimethyl-3H-imidazo[4,5-b]pyridine;

3-(4-{2-[({[(2-chlorophenyl)sulfonyl]amino}carbonyl)amino]ethyl}phenyl)-2-ethyl-5,7-dimethyl-3H-imidazo[4,5-b]pyridine;

2-ethyl-5,6-dimethyl-3-(4-{2-[({[(4-methylphenyl)sulfonyl]amino}carbonyl)amino]ethyl}phenyl)-3H-imidazo[4,5-b]pyridine;

5,6-dichloro-2-ethyl-3-(4-{2-[({[(4-methylphenyl)sulfonyl]amino}carbonyl)amino]ethyl}phenyl)-3H-imidazo[4,5-b]pyridine;

5-chloro-2-ethyl-7-methyl-3-(4-{2-[({[(4-methylphenyl)sulfonyl]amino}carbonyl)amino]ethyl}phenyl)-3H-imidazo[4,5-b]pyridine;

6-cyano-2-ethyl-5,7-dimethyl-3-(4-{2-[({[(4-methylphenyl)sulfonyl]amino}carbonyl)amino]ethyl}phenyl)-3H-imidazo[4,5-b]pyridine;

2-ethyl-4,6-dimethyl-1-(4-{2-[({[(4-methylphenyl)sulfonyl]amino}carbonyl)amino]ethyl}phenyl)-1H-imidazo[4,5-c]pyridine;

4-methyl-2-ethyl-3-(4-{2-[({[(4-methylphenyl)sulfonyl]amino}carbonyl)amino]ethyl}phenyl)benzimidazole;

7-chloro-2-ethyl-3-(4-{2-[({[(4-methylphenyl)sulfonyl]amino}carbonyl)amino]ethyl}phenyl)benimidazole;

5-methoxy-2-ethyl-3-(4-{2-[({[(4-methylphenyl)sulfonyl]amino}carbonyl)amino]ethyl}phenyl)benzimidazole;

5-acetyl-2-ethyl-3-(4-{2-[({[(4-methylphenyl)sulfonyl]amino}carbonyl)amino]ethyl}phenyl)benzimidazole;

5-cyano-2-ethyl-1-(4-{2-[({[(4-methylphenyl)sulfonyl]amino}carbonyl)amino]ethyl}phenyl)-1H-benzimidazole;

2-ethyl-5-hydroxy-1-(4-{2-[({[(4-methylphenyl)sulfonyl]amino}carbonyl)amino]ethyl}phenyl)-1H-benzimidazole;

2-ethyl-4,5-dimethyl-1-(4-2-[({[(4-methylphenyl)sulfonyl]amino}carbonyl)amino]ethyl}phenyl)-1H-benzimidazole;

4,6-dimethyl-2-ethyl-3-(4-{2-[({[(4-methylphenyl)sulfonyl]amino}carbonyl)amino]ethyl}phenyl)benzimidazole;

5,6-dimethyl-1-(4-{2-[({[(4-methylphenyl)sulfonyl]amino}carbonyl)amino]ethyl}phenyl)-1H-benzimidazole;

5,6-dichloro-2-ethyl-1-(4-{2-[({[(4-methylphenyl)sulfonyl]amino}carbonyl)amino]ethyl}phenyl)-1H-benzimidazole;

2-[4-(5,6-dichloro-2-ethyl-1H-benzimidazol-1-yl)phenyl]ethyl-(4-methylphenyl)sulfonyl carbamate;

6-chloro-5-trifluoromethyl-1-(4-{2-[({[(4-methylphenyl)sulfonyl]amino}carbonyl)amino]ethyl}phenyl)-1H-benzimidazole;

4-(6-chloro-2-ethyl-5-trifluoromethyl-1H-benzimidazol-1-yl)phenethyl-(4-methylphenyl)sulfonyl carbamate;

5-chloro-6-methyl-1-(4-{2-[({[(4-methylphenyl)sulfonyl]amino}carbonyl)amino]ethyl}phenyl)-1H-benzimidazole;

6-chloro-2-ethyl-1-(4-{2-[({[(4-methylphenyl)sulfonyl]amino}carbonyl)amino]ethyl}phenyl)-1H-benzimidazole-5-carboxamide;

2-ethyl-3-{4-[2-({[({3-[hydroxy(oxido)amino]phenyl}sulfonyl)amino]carbonyl}amino)ethyl]phenyl}-5,7-dimethyl-3H-imidazo[4,5-b]pyridine;

3-(4-{2-[({[(4-chlorophenyl)sulfonyl]amino}carbonyl)amino]ethyl}phenyl)-2-ethyl-5,7-dimethyl-3H-imidazo[4,5-b]pyridine;

n-[4-({[({2-[4-(2-ethyl-5,7-dimethyl-3H-imidazo[4,5-b]pyridin-3-yl)phenyl]ethyl}amino)carbonyl]amino}sulfonyl)phenyl]-2,2-dimethylpropanamide;

3-(4-(2-[({[(2-chlorophenyl)sulfonyl]amino}carbonyl)amino]ethyl}phenyl)-2-ethyl-5,7-dimethyl-3H-imidazo[4,5-b]pyridine;

3-(4-(2-[({[(3-chlorophenyl)sulfonyl]amino}carbonyl)amino]ethyl}phenyl)-2-ethyl-5,7dimethyl-3H-imidazo[4,5-b]pyridine;

3-(4-{2-[({[(5-chloro-2-thienyl)sulfonyl]amino}carbonyl)amino]ethyl}phenyl)-2-ethyl-5,7-dimethyl-3H-imidazo[4,5-b]pyridine;

3-(4-{2-[({[(5-bromo-2-thienyl)sulfonyl]amino}carbonyl)amino]ethyl}phenyl)-2-ethyl-5,7-dimethyl-3H-imidazo[4,5-b]pyridine;

3-(4-{2-[({[(2-bromophenyl)sulfonyl]amino}carbonyl)amino]ethyl}phenyl)-2-ethyl-5,7-dimethyl-3H-imidazo[4,5-b]pyridine;

3-{4-[2-({[({4-chloro-3-nitrophenyl}sulfonyl)amino]carbonyl}amino)ethyl]phenyl}-2-ethyl-5,7-dimethyl-3H-imidazo[4,5-b]pyridine;

2-[4-(2-ethyl-4,6-dimethyl-1H-imidazo[4,5-c]pyridin-1-yl)phenyl]ethyl-(4-methylphenyl)sulfonyl carbamate;

2-(4-[5,7-dimethyl-2-(methylamino)-3H-imidazo[4,5-b]pyridin-3-yl]phenyl}ethyl-(4-methylphenyl)sulfonylcarbamate;

N-{[(2-{4-[5,7-dimethyl-2-(methylamino)-3H-imidazo[4,5-b]pyridin-3-yl]phenyl}ethyl)amino]carbonyl}-4-methylbenzenesulfonamide;

N-{[(2-{4-[2-ethyl-5-(1-hydroxy-1-methylethyl)-1H-benzimidazol-1-yl]phenyl}ethyl)amino]carbonyl}-4-methylbenzenesulfonamide;

2-ethyl-4,6-dimethyl-1-(4-2-[({[(4-methylphenyl)sulfonyl]amino}carbonyl)amino]ethyl}phenyl)-1H-benzimidazole-5-carboxamide;

2-{4-[6-chloro-2-ethyl-5-(trifluoromethyl)-1H-benzimidazol-1-yl]phenyl}ethyl-(2-chlorophenyl)sulfonylcarbamate;

2-{5-[6-chloro-2-ethyl-5-(trifluoromethyl)-1H-benzimidazol-1-yl]-2-pyridinyl}ethyl-4-methylphenyl) sulfonylcarbamate;

2-{4-[6-chloro-2-ethyl-5-(trifluoromethyl)-1H-benzimidazol-1-yl]phenyl}ethyl(5-methyl-2-pyridinyl) sulfonylcarbamate;

2-{4-[6-chloro-2-(1H-pyrazol-3-yl)-5-(trifluoromethyl)-1H-benzimidazol-1-yl]phenyl}ethyl(4-methylphenyl) sulfonylcarbamate;

2-{4-[6-chloro-2-(4-pyridinyl)-5-(trifluoromethyl)-1H-benzimidazol-1-yl]phenyl}ethyl(4-methylphenyl) sulfonylcarbamate;

2-{4-[5-(aminocarbonyl)-6-chloro-2-ethyl-1H-benzimidazol-1-yl]phenyl}phenyl}ethyl(4-methylphenyl)sulfonylcarbamate;

N-{[(2-{4-[6-chloro-2-ethyl-5-(methylsulfonyl)-1H-benzimidazol-1-yl]phenyl}ethyl)amino]carbonyl}-4-methylbenzenesulfonamide;

2-{4-[6-chloro-2-ethyl-5-(methylsulfonyl)-1H-benzimidazol-1-yl]phenyl}ethyl(4-methylphenyl) sulfonylcarbamate;

N-[({2-[4-(2-ethyl-5,7-dimethyl-3H-imidazo[4,5-b]pyridin-3-yl)phenyl]ethyl}amino)carbonyl]-2-thiophenesulfonamide;

2-[4-(4,6-dimethyl-2-phenyl-1H-imidazo[4,5-c]pyridin-1-yl)phenyl]ethyl(4-methylphenyl)sulfonylcarbamate;

2-[4-(2-butyl-4,6-dimethyl-1H-imidazo[4,5-c]pyridin-1-yl)phenyl]ethyl(4-methylphenyl)sulfonylcarbamate;

2-{4-[6-chloro-2-ethyl-5-(trifluoromethyl)-1H-benzimidazol-1-yl]phenyl}ethyl-(5-chloro-1,3-dimethyl-1H-pyrazol-4-yl)sulfonylcarbamate;

2-{4-[4,6-dimethyl-2-(3-phenylpropyl)-1H-imidazo[4,5-c]pyridin-1-yl]phenyl}ethyl-(4-methylphenyl) sulfonylcarbamate;

2-{4-[6-chloro-2-(2-pyridinyl)-5-(trifluoromethyl)-1H-benzimidazol-1-yl]phenyl}ethyl-(4-methylphenyl) sulfonylcarbamate;

(1S)-2-{4-[6-chloro-2-ethyl-5-(trifluoromethyl)-1H-benzimidazol-1-yl]phenyl}-1-methylethyl(4-methylphenyl)sulfonylcarbamate;

2-{6-[6-chloro-2-ethyl-5-(trifluoromethyl)-1H-benzimidazol-1-yl]-3-pyridinyl}ethyl-(4-methylphenyl)sulfonylcarbamate;

N-{[(2-{4-[6-chloro-2-(1-hydroxy-1-methylethyl)-5-(trifluoromethyl)-1H-benzimidazol-1-yl]phenyl}ethyl) amino]carbonyl}-4-methylbenzenesulfonamide;

N-([(2-{4-[5,7-dimethyl-2-(1H-pyrazol-3-yl)-3H-imidazo[4,5-b]pyridin-3-yl]phenyl}ethyl)amino] carbonyl}-4-methylbenzenesulfonamide;

2-{4-[2-(1,1-dimethylethyl)-4,6-dimethyl-1H-imidazo[4,5-c]pyridin-1-yl]phenyl}ethyl-(4-methylphenyl) sulfonylcarbamate;

2-{4-[2-[1-(acetylamino)-1-methylethyl]-6-chloro-5-(trifluoromethyl)-1H-benzimidazol-1-yl]phenyl}ethyl (4-methylphenyl)sulfonylcarbamate;

6-chloro-2-ethyl-1-(4-{2-[methyl({[(4-methylphenyl) sulfonyl]amino}carbonyl)amino]ethyl}phenyl)-1H-benzimidazole-5-carboxamide; and salts thereof.

Most preferred individual compounds of this invention are following:

6-ethyl-5-(4-{2-[({[(4-methylphenyl)sulfonyl] amino}carbonyl)amino]ethyl}phenyl)-5H-[1,3] dioxolo[4,5-f]benzimidazole;

6-chloro-5-cyano-2-ethyl-1-(4-{2-[({[(4-methylphenylsulfonyl]amino}carbonyl)amino] ethyl}phenyl)-1H-benzimidazole;

2-[4-(2-ethyl-5,7-dimethyl-3H-imidazo[4,5b]pyridin-3-yl)phenyl]-1-methylethyl-(4-methylphenyl) sulfonylcarbamate;

5,7-dimethyl-3-(4-{2-[({[(4-methylphenyl)sulfonyl] amino}carbonyl)amino]ethyl}phenyl)-2-[2-(1,3-thiazol-2-yl)ethyl]-3H-imidazo[4,5-b]pyridine;

2-ethyl-5,7-dimethyl-3-(4-{2-[({[(2-thienyl)sulfonyl] amino}carbonyl)amino]ethyl}phenyl)-3H-imidazo[4, 5-b]pyridine;

3-(4-{2-[({[(2-chlorophenyl)sulfonyl]amino}carbonyl) amino]ethyl}phenyl)-2-ethyl-5,7-dimethyl-3H-imidazo[4,5-b]pyridine;

2-ethyl-5,6-dimethyl-3-(4-{2-[({[(4-methylphenyl) sulfonyl]amino}carbonyl )amino]ethyl}phenyl)-3H-imidazo[4,5-b]pyridine;

5,6-dichloro-2-ethyl-3-(4-{2-[({[(4-methylphenyl) sulfonyl]amino}carbonyl)amino]ethyl}phenyl)-3H-imidazo[4,5-b]pyridine;

2-ethyl-4,6-dimethyl-1-(4-{2-[({[(4-methylphenyl) sulfonyl]amino}carbonyl)amino]ethyl}phenyl)-1H-imidazo[4,5-c]pyridine;

5-methoxy-2-ethyl-3-(4-{2-[({[(4-methylphenyl) sulfonyl]amino}carbonyl)amino]ethyl}phenyl) benzimidazole;

5-acetyl-2-ethyl-3-(4-{2-[({[(4-methylphenyl)sulfonyl] amino}carbonyl)amino]ethyl}phenyl)benzimidazole;

5-cyano-2-ethyl-1-(4-{2-[({[(4-methylphenyl)sulfonyl] amino}carbonyl)amino]ethyl}phenyl)-1H-benzimidazole;

2-ethyl-5-hydroxy-1-(4-{2-[({[(4-methylphenyl) sulfonyl]amino}carbonyl)amino]ethyl}phenyl)-1H-benzimidazole;

2-ethyl-4,5-dimethyl-1-(4-{2-[({[(4-methylphenyl) sulfonyl]aminocarbonyl)amino]ethyl}phenyl)-1H-benzimidazole;

4-(6-chloro-2-ethyl-5-trifluoromethyl-1H-benzimidazol-1-yl)phenethyl-(4-methylphenyl)sulfonylcarbamate; and 6-chloro-2-ethyl-1-(4-{2-[({[(4-methylphenyl)sulfonyl] amino}carbonyl)amino]ethyl}phenyl)-1H-benzimidazole-5-carboxamide;

2-[4-(2-ethyl-4,6-dimethyl-1H-imidazo[4,5-c]pyridin-1-yl)phenyl]ethyl(4-methylphenyl)sulfonylcarbamate;

2-{4-[5,7-dimethyl-2-(methylamino)-3H-imidazo[4,5-b]pyridin-3-yl]phenyl}ethyl-(4-methylphenyl) sulfonylcarbamate;

N-{[(2-(4-[5,7-dimethyl-2-(methylamino)-3H-imidazo[4, 5-b]pyridin-3-yl]phenyl}ethyl)amino]carbonyl}-4-methylbenzenesulfonamide;

N-{[(2-{4-[2-ethyl-5-(1-hydroxy-1-methylethyl)-1H-benzimidazol-1-yl]phenyl}ethyl)amino]carbonyl}-4-methylbenzenesulfonamide;

2-ethyl-4,6-dimethyl-1-(4-{2-[({[(4-methylphenyl) sulfonyl]amino}carbonyl)amino]ethyl}phenyl)-1H-benzimidazole-5-carboxamide;

2-{4-[6-chloro-2-ethyl-5-(trifluoromethyl)-1H-benzimidazol-1-yl]phenyl}ethyl (2-chlorophenyl) sulfonylcarbamate;

2-{5-[6-chloro-2-ethyl-5-(trifluoromethyl)-1H-benzimidazol-1-yl]-2-pyridinyl}ethyl-4-methylphenyl) sulfonylcarbamate;

2-{4-[6-chloro-2-ethyl-5-(trifluoromethyl)-1H-benzimidazol-1-yl]phenyl}ethyl-(5-methyl-2-pyridinyl)sulfonylcarbamate;

2-{4-[6-chloro-2-(1H-pyrazol-3-yl)-5-(trifluoromethyl)-1H-benzimidazol-1-yl]phenyl}ethyl-(4-methylphenyl) sulfonylcarbamate;

2-{4-[6-chloro-2-(4-pyridinyl)-5-(trifluoromethyl)-1H-benzimidazol-1-yl]phenyl}ethyl-(4-methylphenyl) sulfonylcarbamate;

2-{4-[5-(aminocarbonyl)-6-chloro-2-ethyl-1H-benzimidazol-1-yl]phenyl}ethyl-(4-methylphenyl) sulfonylcarbamate;

N-{[(2-{4-[6-chloro-2-ethyl-5-(methylsulfonyl)-1H-benzimidazol-1-yl]phenyl}ethyl)amino]carbonyl}-4-methylbenzenesulfonamide;

2-{4-[6-chloro-2-ethyl-5-(methylsulfonyl)-1H-benzimidazol-1-yl]phenyl}ethyl-(4-methylphenyl) sulfonylcarbamate;

N-[({2-[4-(2-ethyl-5,7-dimethyl-3H-imidazo[4,5-b]pyridin-3-yl)phenyl]ethyl}amino)carbonyl]-2-thiophenesulfonamide;

2-[4-(4,6-dimethyl-2-phenyl-1H-imidazo[4,5-c]pyridin-1-yl)phenyl]ethyl-(4-methylphenyl)sulfonylcarbamate;

2-[4-(2-butyl-4,6-dimethyl-1H-imidazo[4,5-c]pyridin-1-yl)phenyl]ethyl-(4-methylphenyl)sulfonylcarbamate;

2-(4-[6-chloro-2-ethyl-5-(trifluoromethyl)-1H-benzimidazol-1-yl]phenyl}ethyl-(5-chloro-1,3-dimethyl-1H-pyrazol-4-yl)sulfonylcarbamate;

2-{4-[4,6-dimethyl-2-(3-phenylpropyl)-1H-imidazo[4,5-c]pyridin-1-yl]phenyl}ethyl-(4-methylphenyl) sulfonylcarbamate;

2-{4-[6-chloro-2-(2-pyridinyl)-5-(trifluoromethyl)-1H-benzimidazol-1-yl]phenyl}ethyl-(4-methylphenyl) sulfonylcarbamate;

(1S)-2-{4-[6-chloro-2-ethyl-5-(trifluoromethyl)-1H-benzimidazol-1-yl]phenyl}-1-methylethyl-(4-methylphenyl)sulfonylcarbamate;

2-{6-[6-chloro-2-ethyl-5-(trifluoromethyl)-1H-benzimidazol-1-yl]-3-pyridinyl}ethyl-(4-methylphenyl)sulfonylcarbamate;

N-{[(2-{4-[6-chloro-2-(1-hydroxy-1-methylethyl)-5-(trifluoromethyl)-1H-benzimidazol-1-yl]phenyl}ethyl)amino]carbonyl}-4-methylbenzenesulfonamide;

N-{[(2-{4-[5,7-dimethyl-2-(1H-pyrazol-3-yl)-3H-imidazo[4,5-b]pyridin-3-yl]phenyl}ethyl)amino]carbonyl}-4-methylbenzenesulfonamide;

2-{4-[2-(1,1-dimethylethyl)-4,6-dimethyl-1H-imidazo[4,5-c]pyridin-1-yl]phenyl}ethyl-(4-methylphenyl) sulfonylcarbamate;

2-{4-[2-[1-(acetylamino)-1-methylethyl]-6-chloro-5-(trifluoromethyl)-1H-benzimidazol-1-yl]phenyl}ethyl (4-methylphenyl)sulfonylcarbamate;

6-chloro-2-ethyl-1-(4-{2-[methyl ({[(4-methylphenyl)sulfonyl]amino}carbonyl)amino]ethyl}phenyl)-1H-benzimidazole-5-carboxamide; and salts thereof.

General Synthesis

The following reaction Schemes illustrate the preparation of the compounds of the present invention. Unless otherwise indicated, $Y^1$ to $Y^4$, $R^1$ to $R^7$, A, B, W, Z, L, m, P, $Q^1$ and $Q^2$ in the reaction Schemes and discussion that follow are defined herein before.

The aryl or heteroaryl fused imidazole compounds of Formula (I) of this invention may be prepared by a variety of synthetic methods known to those skilled in the art.

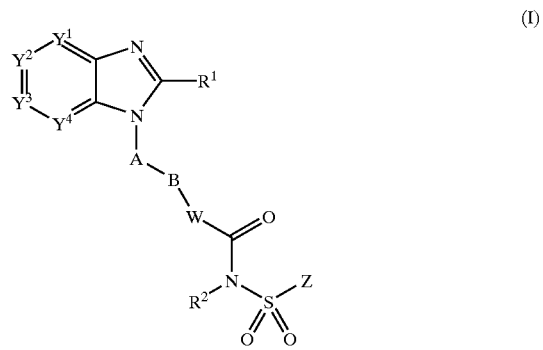

(I)

In a desired reaction step of the processes described hereafter, hydroxy or amino groups protection and removal of the hydroxy or amino protecting groups with reactants and reagents used may be carried out according to known procedures such as those described in Protective Groups in Organic Synthesis edited by T. W. Greene et al. (John Wiley & Sons, 1991). Typical hydroxy or amino protecting groups include benzyl, $C_2H_5O(C=O)-$, $CH_3(C=O)-$, t-butyldimethylsilyl(TBS), benzyloxycarbonyl represented as Z and t-But-O—C(=O) represented as t-Boc or Boc.

Reaction Scheme 1 illustrates a method for the preparation of the compound of formula (I) wherein A is phenyl, B is ethylene, W is $R^{1a}$-N wherein $R^{1a}$ is H or $C_{1-4}$ alkyl, and $R^{1b}$ is $C_{1-4}$ alkyl or aryl (hereinafter represented by Formula (Ia)).

Compound (Ia) may be prepared through the process comprising:

(a) coupling reaction of a compound of formula 1-1 with 4-aminophenethylalcohol wherein X is a leaving group such as halo, mesylate(OMs) or tosylate(OTs) to give a nitroaniline compound of formula 1-2;

(b) reduction of the resulting nitroaniline compound of formula 1-2 to give a diamine compound of formula 1-3;

(c) benzimidazole or imidazopyridine ring formation with the compound of formula 1-3 to give a compound of formula 1-4;

(d) hydrolysis of the compound of formula 1-4 to give a compound of formula 1-5; conversion of the hydroxy group of the compound 1–5 into a suitable leaving group such as halo, OMs or OTs to give a compound of formula 1-6;

(e) amination of the compound of formula 1-6 to give an amino compound of formula 1-7; and (f) sulfonylurea formation with the compound of formula 1-7 to give the compound of formula (Ia).

Scheme 1
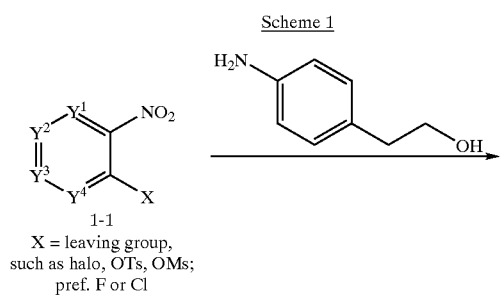
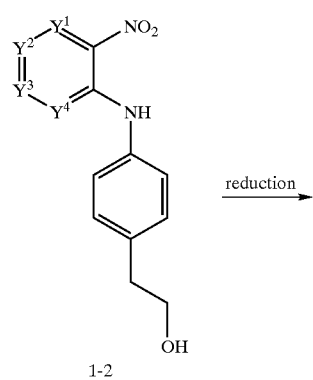
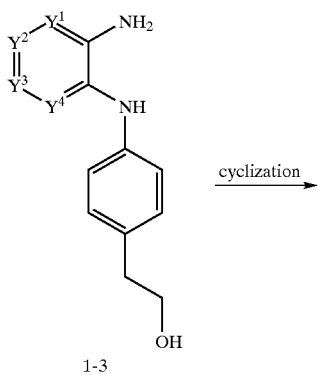
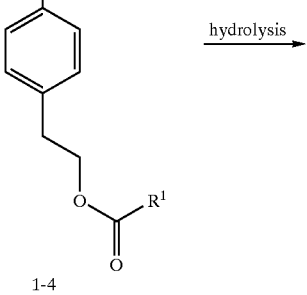
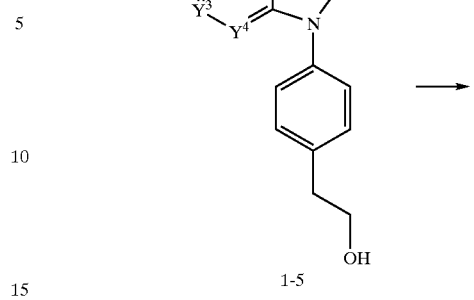
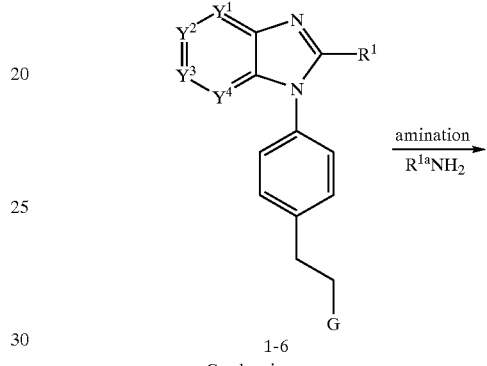
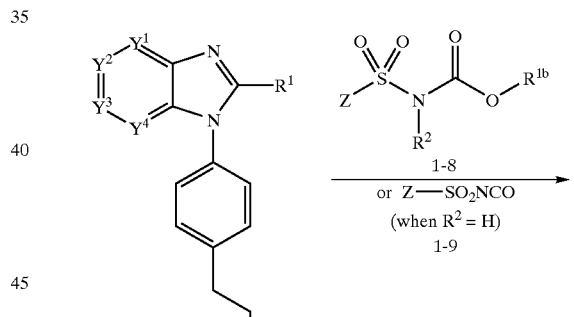

Each reaction step is described more specifically as follows:

(a)–(b) The coupling reaction (a) may be carried out in the absence of, or presence of a base in a reaction inert solvent or without solvent. A preferred base is selected from, for example, but not limited to, an alkali or alkaline earth metal hydroxide, alkoxide, carbonate, or hydride, such as sodium hydroxide, potassium hydroxide, sodium methoxide, sodium ethoxide, potassium tert-butoxide, sodium carbonate, potassium carbonate, potassium fluoride, sodium hydride or potassium hydride, or an amine such as triethylamine, tributylamine, diisopropylethylamine, 2,6-lutidine, pyridine or dimethylaminopyridine in the presence or absence of a reaction inert solvent. Preferred reaction inert solvents include, but are not limited to, benzene, toluene, xylene, o-dichlorobenzene, nitrobenzene, pyridine, dichloromethane, 1,2-dichloroethane, tetrahyrofuran, dimethylformamide (DMF), 1,4-dioxane, dimethylsulfoxide (DMSO) or mixtures thereof. Reaction temperatures are generally in the range of −100 to 250° C., preferably in the range of 0 to 150° C., but if necessary, lower or higher temperature can be employed. Reaction times are, in general, from 1 minute to a day, preferably from 20 minutes to 5 hours, however shorter or longer reaction times, if necessary, can be employed. Then the resulting compound of formula 1-2 may be extracted and subjected to reduction to give the compound of formula 1-3. The reduction may be carried out in the presence of a suitable reducing agent in a reaction inert solvent or without solvent. A preferred reducing agent is selected from, for example, but not limited to, $LiAlH_4$, $LiBH_4$, Fe, Sn or Zn. When a reducing reagent is Fe, Sn or Zn, if desired, the reaction is carried out under acidic conditions in the presence of water. Preferred reaction inert solvents include, but are not limited to, methanol, ethanol, diglyme, benzene, toluene, xylene, o-dichlorobenzene, dichloromethane, 1,2-dichloroethane, tetrahyrofuran, 1,4-dioxane, or mixtures thereof. Reaction temperatures are generally in the range of −100 to 250° C., preferably in the range of 0 to 150° C., but if necessary, lower or higher temperature can be employed. Reaction times are, in general, from 1 minute to a day, preferably from 20 minutes to 5 hours, however shorter or longer reaction times, if necessary, can be employed. The reduction may also be carried out under known hydrogenation conditions in the presence of a metal catalyst under hydrogen atmosphere or in the presence of hydrogen sources such as hydrazine or formic acid. If desired, the reaction is carried out under acidic conditions, for example, in the presence of hydrochloric acid or acetic acid. A preferred metal catalyst is selected from, for example, but not limited to, nickel catalysts such as Raney nickel, palladium catalysts such as Pd—C, platinum catalysts such as $PtO_2$, or ruthenium catalysts such as $RuCl_2(Ph_3P)_3$. Preferred reaction inert solvents include, but are not limited to, methanol, ethanol, ethyl acetate, THF or mixtures thereof. The reaction may be carried out at a temperature in the range from of −100 to 150° C., preferably in the range of 0° C. to 100° C., but if necessary, lower or higher temperature can be employed. Reaction times are, in general, from 1 minute to a day, preferably from 20 minutes to 5 hours, however shorter or longer reaction times, if necessary, can be employed.

(c) The compound of formula 1-3 may be cyclized to form a benzimidazole or imidazopyridine ring by any synthetic procedure applicable to structure-related compounds known to those skilled in the art (for example, see Grimmett, M. R. Imidazoles and Their Benzo Derivatives: (iii) Synthesis and Applications. In *Comprehensive Heterocyclic Chemistry*, Kevin T. Potts, Eds.; Pergamon Press Ltd.: Oxford, UK, 1984; Vol.5, pp457–498., Grimmett, M. R. Imidazoles. In *Comprehensive Heterocyclic Chemistry II*, Ichiro Shinkai, Eds.; Elsevier Science Ltd.: Oxford, UK, 1996; Vol.3, pp77–220., Townsend L. B; Wise D. S. Bicyclo 5–6 Systems: Three Heteroatoms 2:1. In *Comprehensive Heterocyclic Chemistry II*, Christopher A. Ramsden, Eds.; Elsevier Science Ltd.: Oxford, UK, 1996; Vol.7, pp283–349). For example, the compound of formula 1-3 is reacted with an appropriate cyclizing reagent to give the compound of formula 1-4 in a reaction inert solvent in the presence of, or absence of a coupling reagent. If desired, this reaction may be catalyzed by an acid such as para-toluenesulfonic acid or camphersulfonic acid. Suitable cyclizing reagents include, but are not limited to, a carboxylic acid, an amino carboxylic acid, an acid anhydride (e.g., acetic anhydride, isobutyric anhydride, benzoic anhydride, isonicotinic anhydride and the like) a formamidine (e.g., formamidine alkylate such as formamidine acetate), an alkyl carbonyl halide (e.g., a cycloalkyl carbonyl halide, bicyclic or bicyclic-heterocyclic-carbonyl halide, spirocarbocyclic- or spiro-heterocyclic-carbonyl halide), an aryl or an aryl alkyl carbonyl halide (e.g., phenylacetyl halide), an heteroaryl carboxylic acid (e.g., a piperidinyl carboxylic acid compound), trialkyl orthoformate (e.g., triethyl orthoformate), and the like. Suitable reaction inert solvents include, but are not limited to, benzene, toluene, xylene, o-dichlorobenzene, nitrobenzene, dichloromethane, 1,2-dichloroethane, tetrahyrofuran (THF), dimethylformamide (DMF), 1,4-dioxane, dimethylsulfoxide (DMSO) or mixtures thereof. Suitable coupling reagents are those typically used in peptide synthesis including, but are not limited to, dicyclohexylcarbodiimide (DCC), diisopropylcarbodiimide (DIPC), 1-ethyl-3-(3-dimethylaminopropyl)carbodiimide (WSC), benzotriazole-1-yloxy-tris(dimethylamino) phosphonium hexafluorophosphate (BOP), diphenylphosphorylazide (DPPA), or the like. The reaction may be carried out at a temperature in the range from of −100° C. to 250° C., preferably in the range of 0° C. to the reflux temperature, but if necessary, lower or higher temperature can be employed. Reaction times are, in general, from 1 minute to a few days, preferably from 30 minutes to 48 hours, however shorter or longer reaction times, if necessary, can be employed.

(d) The hydrolysis of the compound of formula 1-4 may be carried out by conventional procedures. The hydrolysis may be carried out by treatment with base. A preferred base is selected from, for example, but not limited to, an alkali or alkaline earth metal hydroxide, alkoxide, carbonate, or halide, such as sodium hydroxide, potassium hydroxide, sodium methoxide, sodium ethoxide, potassium tert-butoxide, sodium carbonate, potassium carbonate or lithium iodide, in the presence or absence of a reaction inert solvent. Preferred reaction inert solvents include, but are not limited to, water, methanol, ethanol, isopropanol, tetrahyrofuran (THF), benzene, toluene, xylene, o-dichlorobenzene, nitrobenzene, pyridine, dichloromethane, 1,2-dichloroethane, or mixtures thereof. Reaction temperatures are generally in the range of −100° C. to 250° C., preferably in the range of 0° C. to the reflux temperature, but if necessary, lower or higher temperature can be employed. Reaction times are, in general, from 1 minute to a day, preferably from 20 minutes to 5 hours, however shorter or longer reaction times, if necessary, can be employed.

(e)–(f) Step (e) and step (f) may be carried out under conditions known to those skilled in the art. For example, the hydroxy group of the compound of formula 1-5 may be converted to the halogen group using a halogenating agent in the presence or absence of a reaction inert solvent. Preferred halogenating agents include, but are not limited to, thionyl chloride, oxalyl chloride, para-toluenesulfonyl chloride, methanesulfonyl chloride, hydrogen halide such as hydrogen chloride or hydrogen bromide, phosphorus tri-halide such as phosphorus trichloride or phosphorus tribromide, phosphorus penta-halide such as phosphorus pentachloride, N-halo-succinimide such as N-chlorosuccinimide (NCS) or N-bromosuccinimide (NBS), phosphorus oxychloride, trimethylsilyl halide such as trimethylsilyl chloride or trimethylsilyl bromide, phosphorus reagents such as triphenyl phosphine, tributyl phosphine or triphenylphosphite in the presence of halogen source such as carbon tetrachloride, carbon tetrabromide, bromine, iodine, NBS or NCS. Preferred reaction inert solvents include, but are not limited to, tetrahyrofuran (THF), benzene, toluene, xylene, o-dichlorobenzene, nitrobenzene, pyridine, dichloromethane, 1,2-dichloroethane, carbon tetrachloride, carbon tetrabromide or mixtures thereof. Reaction temperatures are generally in the range of −100 to 250° C., preferably in the range of 0° C. to the reflux temperature, but if necessary, lower or higher temperature can be employed. Reaction times are, in general, from 1 minute to a day, preferably from 20 minutes to 5 hours, however shorter or longer reaction times, if necessary, can be employed. Alternatively, a hydroxy group of the compound of formula 1-5 may be converted to the sulfonate group using a sulfonating agent in the presence of, or absence of a base. Preferred sulfonating agents include, but are not limited to, para-toluenesulfonyl chloride, para-toluenesulfonic anhydride, methanesulfonyl chloride, methanesulfonic anhydride, trifluoromethanesulfonic anhydride, or the like in the presence of, or absence of a reaction-inert solvent. A preferred base is selected from, for example, but not limited to, an alkali or alkaline earth metal hydroxide, alkoxide, carbonate, halide or hydride, such as sodium hydroxide, potassium hydroxide, sodium methoxide, sodium ethoxide, potassium tert-butoxidie, sodium carbonate, potassium carbonate, potassium fluoride, sodium hydride or potassium hydride, or an amine such as triethylamine, tributylamine, diisopropylethylamine, pyridine or dimethylaminopyridine in the presence or absence of a reaction inert solvent. Preferred reaction inert solvents include, but are not limited to, benzene, toluene, xylene, o-dichlorobenzene, nitrobenzene, pyridine, dichloromethane, 1,2-dichloroethane, tetrahyrofuran, dimethylformamide (DMF), 1,4-dioxane, dimethylsulfoxide (DMSO) or mixtures thereof. Reaction temperatures are generally in the range of −100° C. to 250° C., preferably in the range of 0° C. to the reflux temperature, but if necessary, lower or higher temperature can be employed. Reaction times are, in general, from 1 minute to a day, preferably from 20 minutes to 5 hours, however shorter or longer reaction times, if necessary, can be employed. Then, the resulting compound of formula 1-6 may be subjected to the amination to give the compound of formula 1-7. For example, the compound of formula 1-6 is reacted with $R^{1a}$—$NH_2$ wherein $R^{1a}$ is as defined herein before. The reactants may be heated together in the absence or presence of a reaction inert solvent. Preferred reaction inert solvents include, but are not limited to, benzene, toluene, xylene, o-dichlorobenzene, nitrobenzene, pyridine, dichloromethane, 1,2-dichloroethane, or mixtures thereof. Preferably, the reaction conducted in the presence of base. A preferred base is selected from, for example, but not limited to, an alkali or alkaline earth metal hydroxide, alkoxide, carbonate, or hydride, such as sodium hydroxide, potassium hydroxide, sodium methoxide, sodium ethoxide, potassium tert-butoxide, sodium carbonate, potassium carbonate, sodium hydride or potassium hydride, or an amine such as triethylamine, tributylamine, diisopropylethylamine, pyridine or dimethylaminopyridine. Reaction temperatures are generally in the range of −100 to 250° C., preferably in the range of 0° C. to the reflux temperature, but if necessary, lower or higher temperature can be employed. Reaction times are, in general, from 1 minute to a day, preferably from 20 minutes to 5 hours, however shorter or longer reaction times, if necessary, can be employed.

(g) The compound of formula 1-7 may be treated with Z—$SO_2N(R^2)C(=O)O$—$R^{1b}$, wherein $R^{1b}$ is aryl or $C_{1-4}$ alkyl, or Z—$SO_2NCO$ to give the compound of formula (Ia). The reaction may be carried out in the absence or presence of a reaction inert solvent. Preferred reaction inert solvents include, but are not limited to, benzene, toluene, xylene, o-dichlorobenzene, nitrobenzene, pyridine, dichloromethane, 1,2-dichloroethane, or mixtures thereof. If desired, the reaction may be carried out in the presence of base, such as triethyl amine, diisopropylethylamine, or N-methylmorphorine. Reaction temperatures are generally in the range of −100 to 250° C., preferably in the range of 0° C. to the reflux temperature, but if necessary, lower or higher temperature can be employed. Reaction times are, in general, from 1 minute to a day, preferably from 20 minutes to 5 hours, however shorter or longer reaction times, if necessary, can be employed.

The compound of formula 1-2 may also be prepared by the Ullman reaction as shown in Scheme 1a. A compound of formula 1a-1 may be treated with a compound of formula 1a-2 in the absence or presence of a reaction inert solvent. Preferred reaction inert solvents include, but are not limited to, benzene, toluene, xylene, o-dichlorobenzene, nitrobenzene, pyridine, dimethylformamide (DMF), dimethoxyethane (DME) or mixtures thereof. Preferably, the reaction is conducted in the presence of metal catalyst. A preferred metal catalyst is selected from, for example, but not limited to, copper and nickel. Preferably, the reaction is conducted in the presence of base. A preferred base is selected from, for example, but not limited to, an alkali or alkaline earth metal hydroxide, alkoxide, carbonate, or hydride, such as sodium hydroxide, potassium hydroxide, sodium methoxide, sodium ethoxide, potassium tert-butoxide, sodium carbonate, potassium carbonate, sodium hydride or potassium hydride, or an amine such as triethylamine, tributylamine, diisopropylethylamine, pyridine or dimethylaminopyridine. Reaction temperatures are generally in the range of −100 to 250° C., preferably in the range of 0° C. to the reflux temperature, but if necessary, lower or higher temperature can be employed. Reaction times are, in general, from 1 minute to a day, preferably from 20 minutes to 5 hours, however shorter or longer reaction times, if necessary, can be employed.

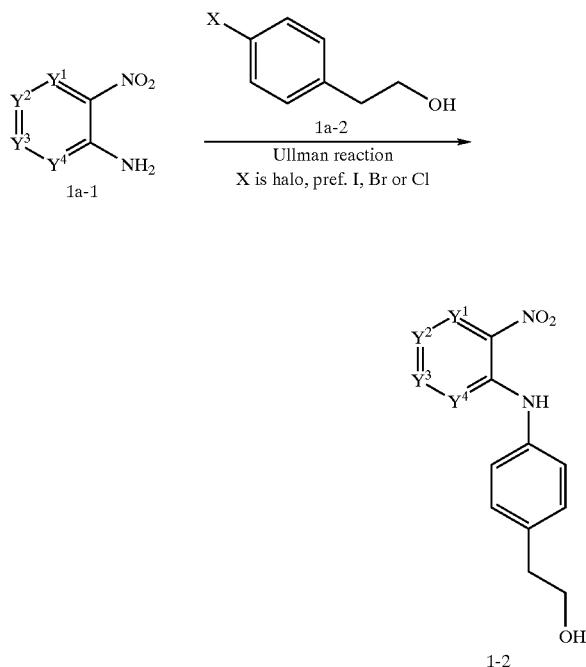

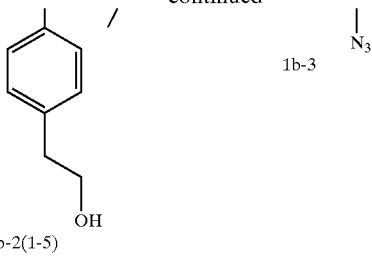

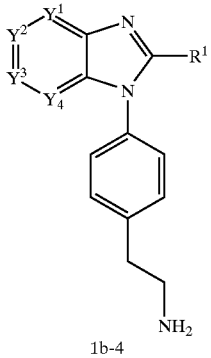

As shown in Scheme 1b, an intermediate compound of formula 1b-4 (1-7 wherein $R^{1a}$ is H) may be prepared through the process comprising:

(a) azide formation; and (b) reduction of the resulting azide compound of formula 1b-3 to give an amine compound of the formula 1b-4.

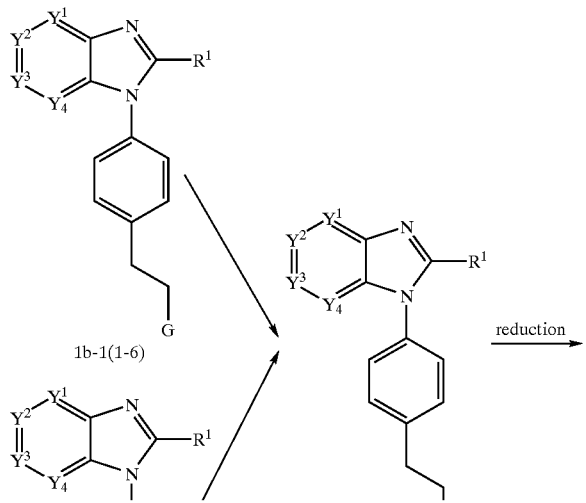

More specifically, the nucleophilic displacement with azide may be carried out by conventional procedures in the absence or presence of a reaction inert solvent. Preferred reaction inert solvents include, but are not limited to, benzene, toluene, xylene, o-dichlorobenzene, nitrobenzene, dichloromethane, 1,2-dichloroethane, dimethylformamide (DMF), dimethoxyethane (DME), hexamethylphosphoramide (HMPA) or mixtures thereof. Preferred azide agents are selected from, but are not limited to, sodium azide or lithium azide. Reaction temperatures are generally in the range of −100 to 250° C., preferably in the range of 0° C. to the reflux temperature, but if necessary, lower or higher temperature can be employed. Reaction times are, in general, from several minutes to a day, preferably from 20 minutes to 5 hours, however shorter or longer reaction times, if necessary, can be employed.

A compound of formula 1b-3 may also be prepared by the Mitsunobu reaction. The compound of formula 1b-2 may be treated with diphenylphosphoryl azide (DPPA) or $HN_3$ in the presence of dialkyl azodicarboxylate such as diethyl azodicarboxylate (DEAD) and phosphine reagent such as triphenylphosphine. Preferably, this reaction may be carried out in a reaction-inert solvent. Preferred reaction inert solvents include, but are not limited to, tetrahydrofuran (THF), diethyl ether, dimethylformamide (DMF), benzene, toluene, xylene, o-dichlorobenzene, nitrobenzene, dichloromethane, 1,2-dichloroethane, dimethoxyethane (DME), or mixtures thereof. The reduction may be carried out in the presence of a suitable reducing agent such as lithium aluminum hydride, sodium borohydride, triethyl phosphite, triphenylphosphine, zinc, dibutyl tinhydride or diboran in a reaction inert solvent selected form, but not limited to, THF, diethyl ether, methanol, ethanol. If desired, the reaction may be carried out under acidic conditions in the presence of hydrochloric acid or acetic acid. Reaction temperatures are generally in the range of −100 to 250° C., preferably in the range of 0° C. to the reflux temperature, but if necessary, lower or higher temperature can be employed. Reaction times are, in general, from 1 minute to a day, preferably from 20 minutes to 5 hours, however shorter or longer reaction times, if necessary, can be employed.

The reduction may also be carried out under known hydrogenation conditions in the presence of a metal catalyst such as Lindlar catalysts, Raney nickel catalysts, palladium catalysts or platinum catalysts (preferably Lindlar catalysts, palladium catalysts or platinum catalysts). This reaction may be carried out under hydrogen atmosphere in a reaction inert solvent such as methanol, ethanol, ethyl acetate or THF. Reaction temperatures are generally in the range of −100 to 250° C., preferably in the range of 0° C. to the reflux temperature, but if necessary, lower or higher temperature can be employed. Reaction times are, in general, from 1 minute to a day, preferably from 20 minutes to 5 hours, however shorter or longer reaction times, if necessary, can be employed.

As shown in Scheme 1c, an intermediate compound of formula 1c-5(1b-4) may also be prepared through the process comprising:

(a) coupling reaction of a compound of formula 1c-1(1-1), wherein X is a leaving group such as halo, mesylate and tosylate, with a 4-aminophenylacetonitrile to give a nitroaniline compound of formula 1c-2;

(b) chemoselective reduction of the resulting nitroaniline compound of formula 1c-2 to give a diamine compound of formula 1c-3;

(c) benzimidazole or imidazopyridine ring formation with the compound of formula 1c-3 to give a compound of formula 1c-4; and (d) reduction of the resulting compound of formula 1c-4 to give an amine compound of the formula 1c-5(1b-4).

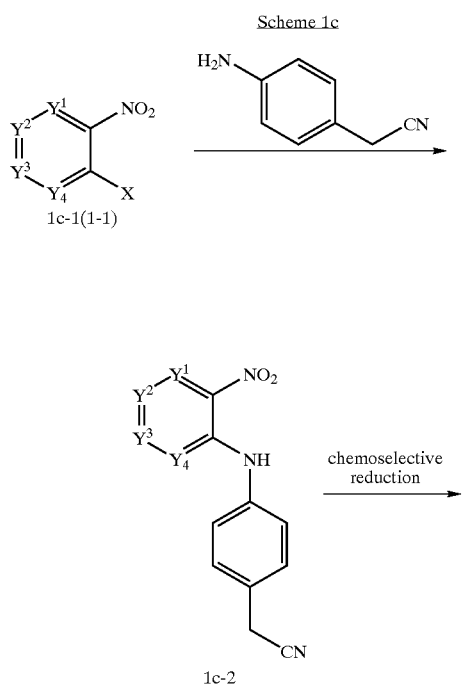

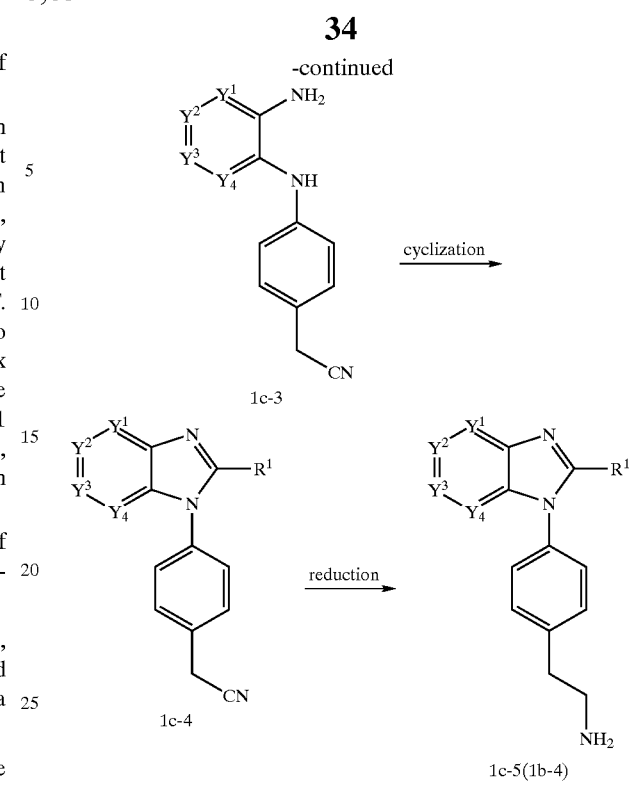

Each reaction step is described more specifically as follows.

(a)–(b) The coupling reaction (a) may be carried out in the absence of, or presence of a base in a reaction inert solvent or without solvent. A preferred base is selected from, for example, but not limited to, an alkali or alkaline earth metal hydroxide, alkoxide, carbonate or hydride, such as sodium hydroxide, potassium hydroxide, sodium methoxide, sodium ethoxide, potassium tert-butoxide, sodium carbonate, potassium carbonate, potassium fluoride, sodium hydride or potassium hydride, or an amine such as triethylamine, tributylamine, diisopropylethylamine, 2,6-lutidine, pyridine or dimethylaminopyridine in the presence or absence of a reaction inert solvent. Preferred reaction inert solvents include, but are not limited to, benzene, toluene, xylene, o-dichlorobenzene, nitrobenzene, pyridine, dichloromethane, 1,2-dichloroethane, tetrahyrofuran, dimethylformamide (DMF), 1,4-dioxane, dimethylsulfoxide (DMSO) or mixtures thereof. Reaction temperatures are generally in the range of −100 to 250° C., preferably in the range of 0 to 150° C., but if necessary, lower or higher temperature can be employed. Reaction times are, in general, from 1 minute to a day, preferably from 20 minutes to 5 hours, however shorter or longer reaction times, if necessary, can be employed.

Then the resulting compound of formula 1c-2 may be extracted and subjected to reduction to give the compound of formula 1c-3. The reduction may be carried out in the presence of a reducing agent in a reaction inert solvent or without solvent. A preferred reducing agent is selected from, for example, but not limited to, Fe, Sn or Zn. If desired, the reaction is carried out under acidic conditions in the presence of water. Preferred reaction inert solvents include, but are not limited to, methanol, ethanol, diglyme, benzene, toluene, xylene, o-dichlorobenzene, dichloromethane, 1,2-dichloroethane, tetrahyrofuran, 1,4-dioxane, or mixtures thereof. Reaction temperatures are generally in the range of −100 to 250° C., preferably in the range of 0 to 150° C., but if necessary, lower or higher temperature can be employed. Reaction times are, in general, from 1 minute to a day, preferably from 20 minutes to 5 hours, however shorter or longer reaction times, if necessary, can be employed.

(c) The compound of formula 1c-3 may be cyclized to form a benzimidazole or imidazopyridine ring by any synthetic procedure applicable to structure-related compounds known to those skilled in the art (for example, see Grimmett, M. R. Imidazoles and Their Benzo Derivatives: (iii) Synthesis and Applications. In *Comprehensive Heterocyclic Chemistry*, Kevin T. Potts, Eds.; Pergamon Press Ltd.: Oxford, UK, 1984; Vol.5, pp457–498., Grimmett, M. R. Imidazoles. In *Comprehensive Heterocyclic Chemistry II*, Ichiro Shinkai, Eds.; Elsevier Science Ltd.: Oxford, UK, 1996; Vol.3, pp77–220., Townsend L. B; Wise D. S. Bicyclo 5–6 Systems: Three Heteroatoms 2:1. In *Comprehensive Heterocyclic Chemistry II*, Christopher A. Ramsden, Eds.; Elsevier Science Ltd.: Oxford, UK, 1996; Vol.7, pp283–349). For example, the compound of formula 1c-3 is reacted with an appropriate cyclizing reagent to give the compound of formula 1c-4 in a reaction inert solvent in the presence of, or absence of a coupling reagent. If desired, this reaction may be catalyzed by an acid such as para-toluenesulfonic acid or camphersulfonic acid. Suitable cyclizing reagents include, but are not limited to, a carboxylic acid, an amino carboxylic acid, an acid anhydride (e.g., acetic anhydride, isobutyric anhydride, benzoic anhydride, isonicotinic anhydride and the like) a formamidine (e.g., formamidine alkylate such as formamidine acetate), an alkyl carbonyl halide (e.g., a cycloalkyl carbonyl halide, bicyclic or bicyclic-heterocyclic-carbonyl halide, spirocarbocyclic- or spiro-heterocyclic-carbonyl halide), an aryl or an aryl alkyl carbonyl halide (e.g., phenylacetyl halide), an heteroaryl carboxylic acid (e.g., a piperidinyl carboxylic acid compound), carbon disulfide, trialkyl orthoformate (e.g., triethyl orthoformate), and the like. Suitable reaction inert solvents include, but are not limited to, benzene, toluene, xylene, o-dichlorobenzene, nitrobenzene, dichloromethane, 1,2-dichloroethane, tetrahyrofuran (THF), dimethylformamide (DMF), 1,4-dioxane, dimethylsulfoxide (DMSO) or mixtures thereof. Suitable coupling reagents are those typically used in peptide synthesis including, but are not limited to, dicyclohexylcarbodiimide (DCC), diisopropylcarbodiimide (DIPC), 1-ethyl-3-(3-dimethylaminopropyl) carbodiimide (WSC), benzotriazole-1-yloxy-tris (dimethylamino)phosphonium hexafluorophosphate (BOP), diphenylphosphorylazide (DPPA), or the like. The reaction may be carried out at a temperature in the range from of −100 to 250° C., preferably in the range of 0° C. to the reflux temperature, but if necessary, lower or higher temperature can be employed. Reaction times are, in general, from 1 minute to a few days, preferably from 30 minutes to 48 hours, however shorter or longer reaction times, if necessary, can be employed.

The reduction of the compound of formula 1c-4 may be carried out in the presence of a suitable reducing agent such as diboran, boran-methyl sulfide complex, or lithium aluminum hydride in a reaction inert solvent selected form, but not limited to, THF or diethyl ether. Reaction temperatures are generally in the range of −100 to 250° C., preferably in the range of 0° C. to the reflux temperature, but if necessary, lower or higher temperature can be employed. Reaction times are, in general, from 1 minute to a day, preferably from 20 minutes to 5 hours, however shorter or longer reaction times, if necessary, can be employed.

The reduction of the compound of formula 1c-4 may also be carried out under known hydrogenation conditions such as in the presence of a metal catalyst such as Raney nickel catalysts, palladium catalysts or platinum catalysts under hydrogen atmosphere. This reaction may be carried out in a reaction inert solvent such as methanol, ethanol, chloroform or THF in the presence or absence of hydrogen chloride. If necessary, this reduction may be carried out under the adequate pressure in the range from about 0.5 to 10 kg/cm$^2$, preferably in the range from 1 to 6 kg/cm$^2$. Reaction temperatures are generally in the range of −100 to 250° C., preferably in the range of 0° C. to the reflux temperature, but if necessary, lower or higher temperature can be employed. Reaction times are, in general, from 1 minute to a day, preferably from 20 minutes to 5 hours, however shorter or longer reaction times, if necessary, can be employed.

The compound of formula (Ia) may also be prepared from the compound of formula 1d-1(1-7) through a carbamate compound of formula 1d-2, as depicted in Scheme 1d.

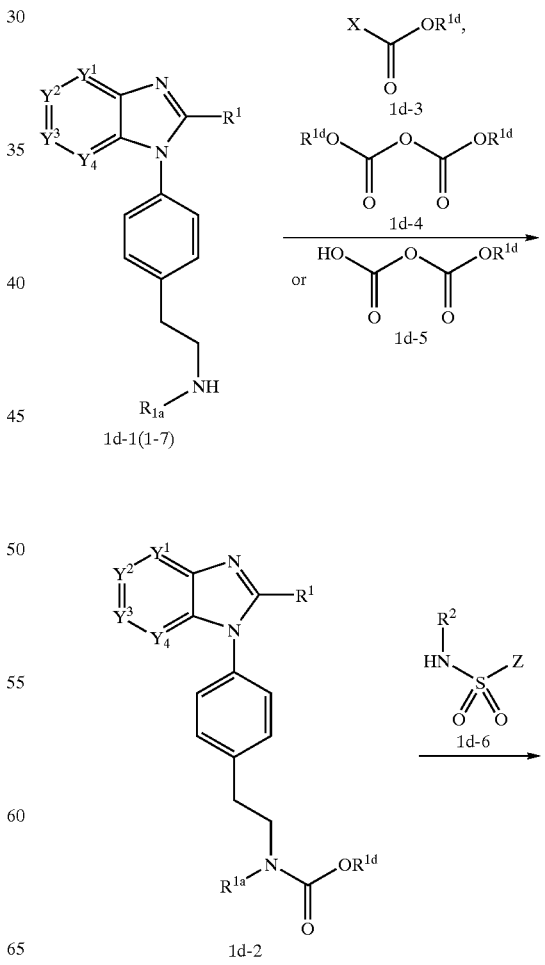

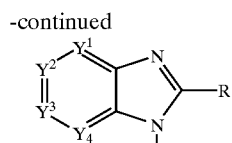

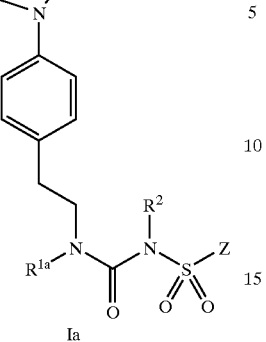

Ia

The compound of formula 1d-1(1-7) may be treated with the carbonating agents ($R^{1d}$ is aryl or $C_{1-4}$ alkyl) such as alkyl or aryl haloformate, dialkyl or diary dicarbonate or alkyl or aryl hydrogen dicarbonate in the presence or absence of a base. Suitable bases include, for example, an alkali or alkaline earth metal hydroxide, alkoxide, carbonate, halide or hydride, such as sodium hydroxide, potassium hydroxide, sodium methoxide, sodium ethoxide, potassium tert-butoxide, sodium carbonate, potassium carbonate, cesium carbonate, potassium fluoride, sodium hydride or potassium hydride, or an amine such as triethylamine, tributylamine, diisopropylethylamine, pyridine or dimethylaminopyridine in the presence or absence of a reaction inert solvent. Preferred reaction inert solvents include, but are not limited to, benzene, toluene, xylene, o-dichlorobenzene, nitrobenzene, pyridine, dichloromethane, 1,2-dichloroethane, tetrahyrofuran, dimethylformamide (DMF), 1,4-dioxane, dimethylsulfoxide (DMSO) or mixtures thereof. Reaction temperatures are generally in the range of −100 to 250° C., preferably in the range of 0 to 150° C., but if necessary, lower or higher temperature can be employed. Reaction times are, in general, from several minutes to a day, preferably from 20 minutes to 5 hours, however shorter or longer reaction times, if necessary, can be employed.

The resulting carbamate compound of formula 1d-2 may reacted with the sulfonamide compound in the presence of a base such as listed above in a reaction inert solvent as listed above (preferably DMF). Reaction temperatures are generally in the range of −100 to 250° C., preferably in the range of 0 to 150° C., but if necessary, lower or higher temperature can be employed. Reaction times are, in general, from 1 minute to a day, preferably from 20 minutes to 5 hours, however shorter or longer reaction times, if necessary, can be employed.

As shown in Scheme 1e, an intermediate compound of formula 1e-5 (1b-4) may also be prepared through the process comprising:
(a) coupling reaction of a compound of formula 1e-1 (1-1), wherein X is a leaving group such as halo, mesylate, tosylate, and triflate with a protected 4-aminophenylethylamine to give a nitroaniline compound of formula 1e-2;
(b) reduction of the resulting nitroaniline compound of formula 1e-2 to give a diamine compound of formula 1e-3;
(c) benzimidazole or imidazopyridine ring formation with the compound of formula 1e-3 to give a compound of formula 1e-4; and
(d) deprotection of the resulting compound of formula 1e-4 to give an amine compound of the formula 1e-5 (1b-4).

Scheme 1e

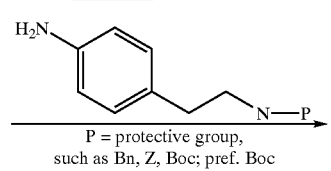

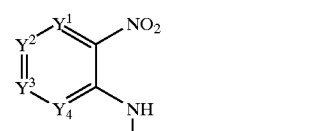

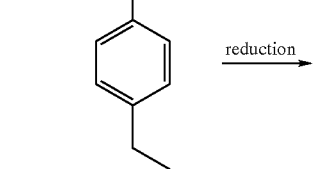

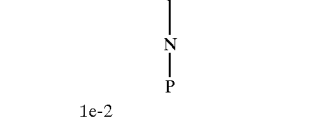

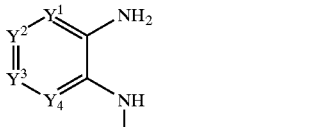

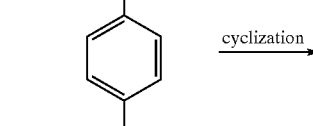

Each reaction step is described more specifically as follows.
(a)–(b) The coupling reaction (a) may be carried out in the absence of, or presence of a base in a reaction inert solvent. A preferred base is selected from, for example, but not limited to, an alkali or alkaline earth metal hydroxide, alkoxide, carbonate, or hydride, such as sodium hydroxide, potassium hydroxide, sodium methoxide, sodium ethoxide, potassium tert-butoxide, sodium carbonate, potassium carbonate, sodium hydride or potassium hydride, or an amine such as triethylamine, tributylamine, diisopropylethylamine, 2,6-lutidine, pyridine or dimethylaminopyridine in the presence of a reaction inert solvent. Preferred reaction inert solvents include, but are not limited to, benzene, toluene, xylene, o-dichlorobenzene, nitrobenzene, pyridine, dichloromethane, 1,2-dichloroethane, tetrahyrofuran, dimethylformamide (DMF), 1,4-dioxane, dimethylsulfoxide (DMSO) or mixtures thereof. Reaction temperatures are generally in the range of −100 to 250° C., preferably in the range of 0 to 150° C., but if necessary, lower or higher temperature can be employed. Reaction times are, in general, from 1 minute to a day, preferably from 20 minutes to 5 hours, however shorter or longer reaction times, if necessary, can be employed. Then the resulting compound of formula 1e-2 may be extracted and subjected to reduction to give the compound of formula 1e-3. The reduction may be carried out in the presence of a reducing agent in a reaction inert solvent. A preferred reducing agent is selected from, for example, but not limited to, Fe, Sn or Zn. If desired, the reaction is carried out under acidic conditions in the presence of water. Preferred reaction inert solvents include, but are not limited to, methanol, ethanol, diglyme, benzene, toluene, xylene, o-dichlorobenzene, dichloromethane, 1,2-dichloroethane, tetrahyrofuran, 1,4-dioxane, or mixtures thereof. Reaction temperatures are generally in the range of −100 to 250° C., preferably in the range of 0 to 150° C., but if necessary, lower or higher temperature can be employed. Reaction times are, in general, from 1 minute to a day, preferably from 20 minutes to 5 hours, however shorter or longer reaction times, if necessary, can be employed. The reduction may also be carried out under known hydrogenation conditions in the presence of a metal catalyst under hydrogen atmosphere or in the presence of hydrogen sources such as hydrazine or formic acid. If desired, the reaction is carried out under acidic conditions, for example, in the presence of hydrochloric acid or acetic acid. A preferred metal catalyst is selected from, for example, but not limited to, nickel catalysts such as Raney nickel, palladium catalysts such as Pd—C, platinum catalysts such as $PtO_2$, or ruthenium catalysts such as $RuCl_2$—$(Ph_3P)_3$. Preferred reaction inert solvents include, but are not limited to, methanol, ethanol, ethyl acetate, THF or mixtures thereof. The reaction may be carried out at a temperature in the range from of −100 to 150° C., preferably in the range of 0° C. to 100° C., but if necessary, lower or higher temperature can be employed. Reaction times are, in general, from 1 minute to a day, preferably from 20 minutes to 5 hours, however shorter or longer reaction times, if necessary, can be employed.

(c) The compound of formula 1e-3 may be cyclized to form a benzimidazole or imidazopyridine ring by any synthetic procedure applicable to structure-related compounds known to those skilled in the art (for example, see Grimmett, M. R. Imidazoles and Their Benzo Derivatives: (iii) Synthesis and Applications. In *Comprehensive Heterocyclic Chemistry*, Kevin T. Potts, Eds.; Pergamon Press Ltd.: Oxford, UK, 1984; Vol.5, pp457–498., Grimmett, M. R. Imidazoles. In *Comprehensive Heterocyclic Chemistry II*, Ichiro Shinkai, Eds.; Elsevier Science Ltd.: Oxford, UK, 1996; Vol.3, pp77–220., Townsend L. B; Wise D. S. Bicyclo 5–6 Systems: Three Heteroatoms 2:1. In *Comprehensive Heterocyclic Chemistry II*, Christopher A. Ramsden, Eds.; Elsevier Science Ltd.: Oxford, UK, 1996; Vol.7, pp283–349). For example, the compound of formula 1e-3 is reacted with an appropriate cyclizing reagent to give the compound of formula 1e-4 in a reaction inert solvent in the presence of, or absence of a coupling reagent. If desired, this reaction may be catalyzed by an acid such as para-toluenesulfonic acid or camphersulfonic acid. Suitable cyclizing reagents include, but are not limited to, a carboxylic acid, an amino carboxylic acid, an acid anhydride (e.g., acetic anhydride, isobutyric anhydride, benzoic anhydride, isonicotinic anhydride and the like) a formamidine (e.g., formamidine alkylate such as formamidine acetate), an alkyl carbonyl halide (e.g., a cycloalkyl carbonyl halide, bicyclic or bicyclic-heterocyclic-carbonyl halide, spirocarbocyclic- or spiro-heterocyclic-carbonyl halide), an aryl or an aryl alkyl carbonyl halide (e.g., phenylacethyl halide), an heteroaryl carboxylic acid (e.g., a piperidinyl carboxylic acid compound), carbon disulfide, trialkyl orthoformate (e.g., triethyl orthoformate), and the like. Suitable reaction inert solvents include, but are not limited to, benzene, toluene, xylene, o-dichlorobenzene, nitrobenzene, dichloromethane, 1,2-dichloroethane, tetrahyrofuran (THF), dimethylformamide (DMF), 1,4-dioxane, dimethylsulfoxide (DMSO) or mixtures thereof. Suitable coupling reagents are those typically used in peptide synthesis including, but are not limited to, dicyclohexylcarbodiimide (DCC), diisopropylcarbodiimide (DIPC), 1-ethyl-3-(3-dimethylaminopropyl) carbodiimide (WSC), benzotriazole-1-yloxy-tris (dimethylamino)phosphonium hexafluorophosphate (BOP), diphenylphosphorylazide (DPPA), or the like. The reaction may be carried out at a temperature in the range from of −100 to 250° C., preferably in the range of 0° C. to the reflux temperature, but if necessary, lower or higher temperature can be employed. Reaction times are, in general, from 1 minute to a few days, preferably from 30 minutes to 48 hours, however shorter or longer reaction times, if necessary, can be employed.

(d) The deprotection of the compound of formula 1e-4 may be carried out according to known procedures such as those described in Protective Groups in Organic Synthesis edited by T. W. Greene et al. (John Wiley & Sons, 1991). Typical amino protecting groups include benzyl represented as Bn, benzyloxycarbonyl represented as Cbz or Z and t-But-O—C(=O)— represented as t-Boc or Boc. In the case of Bn or Z protection, the removal of the amino protecting groups may be carried out under, for example, but not limited to, known hydrogenolysis conditions in the presence of a metal catalyst under hydrogen atmosphere or in the presence of hydrogen sources such as formic acid or ammonium formate in a reaction inert solvent. If desired, the reaction is carried out under acidic conditions, for example, in the presence of hydrochloric acid or acetic acid. A preferred metal catalyst is selected from, for example, but not limited to, palladium catalysts such as Pd—C. Preferred reaction inert solvents include, but are not limited to, methanol, ethanol, ethyl acetate, THF or mixtures thereof. The reaction may be carried out at a temperature in the range from of −100 to 150° C., preferably in the range of 0° C. to 100° C., but if necessary, lower or higher temperature can be employed. Reaction times are, in general, from 1 minute to a day, preferably from 20 minutes to 5 hours, however shorter or longer reaction times, if necessary, can be employed. In the case of Boc protection, the removal of the amino protecting groups may be carried out under, for example, but not limited to, known acid hydrolysis conditions in a reaction inert solvent or without solvent. If desired, the reaction is carried out under acidic conditions, for example, in the presence of hydrochloric acid or trifluoroacetic acid with a reaction inert scavenger of t-butyl cations. Preferred reaction inert scavenger of t-butyl cations include, but are not limited to, benzene, thiophenol, anisole, thioanisole, thiocresole, cresole, or dimethyl sulfide. Preferred reaction inert solvents include, but are not limited to, methanol, ethanol, ethyl acetate, dioxane or mixtures thereof. The reaction may be carried out at a temperature in the range from of −100 to 150° C., preferably in the range of 0° C. to 100° C., but if necessary, lower or higher temperature can be employed. Reaction times are, in general, from 1 minute to a day, preferably from 20 minutes to 5 hours, however shorter or longer reaction times, if necessary, can be employed.

Reaction Scheme 1f illustrates a method for the preparation of the compound of formula (I) wherein W is $R^{1a}$—N wherein $R^{1a}$ is H or $C_{1-4}$ alkyl, and $R^{1b}$ is $C_{1-4}$ alkyl or aryl (hereinafter represented by Formula (If)).

Compound (If) may be prepared through the process comprising:

(a) coupling reaction of a compound of formula 1f-1 with a compound of formula 1f-0 wherein X is a leaving group such as halo, mesylate(OMs) or tosylate(OTs) to give a nitroaniline compound of formula 1f-2;

(b) reduction of the resulting nitroaniline compound of formula 1f-2 to give a diamine compound of formula 1f-3;

(c) benzimidazole or imidazopyridine ring formation with the compound of formula 1f-3 to give a compound of formula 1f-4;

(d) hydrolysis of the compound of formula 1f-4 to give a compound of formula 1f-5; conversion of the hydroxy group of the compound 1f-5 into a suitable leaving group such as halo, OMs or OTs to give a compound of formula 1f-6;

(e) amination of the compound of formula 1f-6 to give an amino compound of formula 1f-7; and (f) sulfonylurea formation with the compound of formula 1f-7 to give the compound of formula (If).

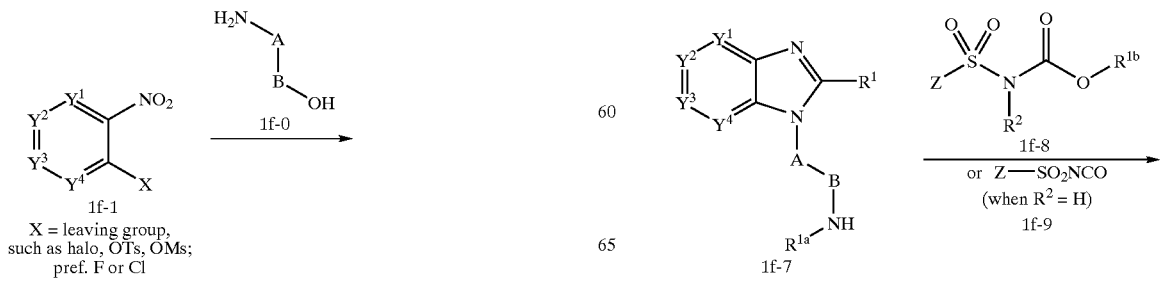

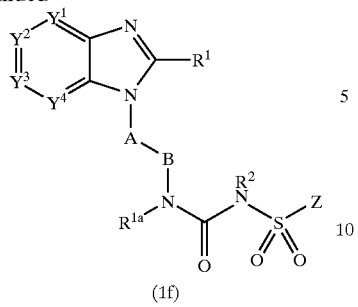

(1f)

Each reaction step is described more specifically as follows:

(a)–(b) The coupling reaction (a) may be carried out in the absence of, or presence of a base in a reaction inert solvent or without solvent. A preferred base is selected from, for example, but not limited to, an alkali or alkaline earth metal hydroxide, alkoxide, carbonate, halide or hydride, such as sodium hydroxide, potassium hydroxide, sodium methoxide, sodium ethoxide, potassium tert-butoxide, sodium carbonate, potassium carbonate, potassium fluoride, sodium hydride or potassium hydride, or an amine such as triethylamine, tributylamine, diisopropylethylamine, 2,6-lutidine, pyridine or dimethylaminopyridine in the presence or absence of a reaction inert solvent. Preferred reaction inert solvents include, but are not limited to, benzene, toluene, xylene, o-dichlorobenzene, nitrobenzene, pyridine, dichloromethane, 1,2-dichloroethane, tetrahyrofuran, dimethylformamide (DMF), 1,4-dioxane, dimethylsulfoxide (DMSO) or mixtures thereof. Reaction temperatures are generally in the range of –100 to 250° C., preferably in the range of 0 to 150° C., but if necessary, lower or higher temperature can be employed. Reaction times are, in general, from 1 minute to a day, preferably from 20 minutes to 5 hours, however shorter or longer reaction times, if necessary, can be employed. Then the resulting compound of formula 1f-2 may be extracted and subjected to reduction to give the compound of formula 1f-3. The reduction may be carried out in the presence of a suitable reducing agent in a reaction inert solvent or without solvent. A preferred reducing agent is selected from, for example, but not limited to, LiAlH$_4$, LiBH$_4$, Fe, Sn or Zn. When a reducing reagent is Fe, Sn or Zn, if desired, the reaction is carried out under acidic conditions in the presence of water. Preferred reaction inert solvents include, but are not limited to, methanol, ethanol, diglyme, benzene, toluene, xylene, o-dichlorobenzene, dichloromethane, 1,2-dichloroethane, tetrahyrofuran, 1,4-dioxane, or mixtures thereof. Reaction temperatures are generally in the range of –100 to 250° C., preferably in the range of 0 to 150° C., but if necessary, lower or higher temperature can be employed. Reaction times are, in general, from 1 minute to a day, preferably from 20 minutes to 5 hours, however shorter or longer reaction times, if necessary, can be employed. The reduction may also be carried out under known hydrogenation conditions in the presence of a metal catalyst under hydrogen atmosphere or in the presence of hydrogen sources such as hydrazine or formic acid. If desired, the reaction is carried out under acidic conditions, for example, in the presence of hydrochloric acid or acetic acid. A preferred metal catalyst is selected from, for example, but not limited to, nickel catalysts such as Raney nickel, palladium catalysts such as Pd—C, platinum catalysts such as PtO$_2$, or ruthenium catalysts such as RuCl$_2$(Ph$_3$P)$_3$. Preferred reaction inert solvents include, but are not limited to, methanol, ethanol, ethyl acetate, THF or mixtures thereof. The reaction may be carried out at a temperature in the range from of –100 to 150° C., preferably in the range of 0° C. to 100° C., but if necessary, lower or higher temperature can be employed. Reaction times are, in general, from 1 minute to a day, preferably from 20 minutes to 5 hours, however shorter or longer reaction times, if necessary, can be employed.

(c) The compound of formula 1f-3 may be cyclized to form a benzimidazole or imidazopyridine ring by any synthetic procedure applicable to structure-related compounds known to those skilled in the art (for example, see Grimmett, M. R. Imidazoles and Their Benzo Derivatives: (iii) Synthesis and Applications. In *Comprehensive Heterocyclic Chemistry*, Kevin T. Potts, Eds.; Pergamon Press Ltd.: Oxford, UK, 1984; Vol.5, pp457–498., Grimmett, M. R. Imidazoles. In *Comprehensive Heterocyclic Chemistry II*, Ichiro Shinkai, Eds.; Elsevier Science Ltd.: Oxford, UK, 1996; Vol.3, pp77–220., Townsend L. B; Wise D. S. Bicyclo 5–6 Systems: Three Heteroatoms 2:1. In *Comprehensive Heterocyclic Chemistry II*, Christopher A. Ramsden, Eds.; Elsevier Science Ltd.: Oxford, UK, 1996; Vol.7, pp283–349). For example, the compound of formula 1f-3 is reacted with an appropriate cyclizing reagent to give the compound of formula 1f-4 in a reaction inert solvent in the presence of, or absence of a coupling reagent. If desired, this reaction may be catalyzed by an acid such as para-toluenesulfonic acid or camphersulfonic acid. Suitable cyclizing reagents include, but are not limited to, a carboxylic acid, an amino carboxylic acid, an acid anhydride (e.g., acetic anhydride, isobutyric anhydride, benzoic anhydride, isonicotinic anhydride and the like) a formamidine (e.g., formamidine alkylate such as formamidine acetate), an alkyl carbonyl halide (e.g., a cycloalkyl carbonyl halide, bicyclic or bicyclic-heterocyclic-carbonyl halide, spirocarbocyclic- or spiro-heterocyclic-carbonyl halide), an aryl or an aryl alkyl carbonyl halide (e.g., phenylacethyl halide), an heteroaryl carboxylic acid (e.g., a piperidinyl carboxylic acid compound), trialkyl orthoformate (e.g., triethyl orthoformate), and the like. Suitable reaction inert solvents include, but are not limited to, benzene, toluene, xylene, o-dichlorobenzene, nitrobenzene, dichloromethane, 1,2-dichloroethane, tetrahyrofuran (THF), dimethylformamide (DMF), 1,4-dioxane, dimethylsulfoxide (DMSO) or mixtures thereof. Suitable coupling reagents are those typically used in peptide synthesis including, but are not limited to, dicyclohexylcarbodiimide (DCC), diisopropylcarbodiimide (DIPC), 1-ethyl-3-(3-dimethylaminopropyl) carbodiimide (WSC), benzotriazole-1-yloxy-tris (dimethylamino)phosphonium hexafluorophosphate (BOP), diphenylphosphorylazide (DPPA), or the like. The reaction may be carried out at a temperature in the range from of –100° C. to 250° C., preferably in the range of 0° C. to the reflux temperature, but if necessary, lower or higher temperature can be employed. Reaction times are, in general, from 1 minute to a few days, preferably from 30 minutes to 48 hours, however shorter or longer reaction times, if necessary, can be employed.

(d) The hydrolysis of the compound of formula 1f-4 may be carried out by conventional procedures. The hydrolysis may be carried out by treatment with base. A preferred base is selected from, for example, but not limited to, an alkali or alkaline earth metal hydroxide, alkoxide, carbonate, or halide, such as sodium hydroxide, potassium hydroxide, sodium methoxide, sodium ethoxide, potassium tert-butoxide, sodium carbonate, potassium carbonate or lithium iodide, in the presence or absence of a reaction inert solvent. Preferred reaction inert solvents include, but are not limited to, water, methanol, ethanol, isopropanol, tetrahyrofuran (THF), benzene, toluene, xylene, o-dichlorobenzene, nitrobenzene, pyridine, dichloromethane, 1,2-dichloroethane, or mixtures thereof. Reaction temperatures are generally in the range of −100° C. to 250° C., preferably in the range of 0° C. to the reflux temperature, but if necessary, lower or higher temperature can be employed. Reaction times are, in general, from 1 minute to a day, preferably from 20 minutes to 5 hours, however shorter or longer reaction times, if necessary, can be employed.

(e)–(f) Step (e) and step (f) may be carried out under conditions known to those skilled in the art. For example, the hydroxy group of the compound of formula 1f-5 may be converted to the halogen group using a halogenating agent in the presence or absence of a reaction inert solvent. Preferred halogenating agents include, but are not limited to, thionyl chloride, oxalyl chloride, para-toluenesulfonyl chloride, methanesulfonyl chloride, hydrogen halide such as hydrogen chloride or hydrogen bromide, phosphorus tri-halide such as phosphorus trichloride or phosphorus tribromide, phosphorus penta-halide such as phosphorus pentachloride, N-halo-succinimide such as N-chlorosuccinimide (NCS) or N-bromosuccinimide (NBS), phosphorus oxychloride, trimethylsilyl halide such as trimethylsilyl chloride or trimethylsilyl bromide, phosphorus reagents such as triphenyl phosphine, tributyl phosphine or triphenylphosphite in the presence of halogen source such as carbon tetrachloride, carbon tetrabromide, bromine, iodine, NBS or NCS. Preferred reaction inert solvents include, but are not limited to, tetrahyrofuran (THF), benzene, toluene, xylene, o-dichlorobenzene, nitrobenzene, pyridine, dichloromethane, 1,2-dichloroethane, carbon tetrachloride, carbon tetrabromide or mixtures thereof. Reaction temperatures are generally in the range of −100 to 250° C., preferably in the range of 0° C. to the reflux temperature, but if necessary, lower or higher temperature can be employed. Reaction times are, in general, from 1 minute to a day, preferably from 20 minutes to 5 hours, however shorter or longer reaction times, if necessary, can be employed. Alternatively, a hydroxy group of the compound of formula 1f-5 may be converted to the sulfonate group using a sulfonating agent in the presence of, or absence of a base. Preferred sulfonating agents include, but are not limited to, para-toluenesulfonyl chloride, para-toluenesulfonic anhydride, methanesulfonyl chloride, methanesulfonic anhydride, trifluoromethanesulfonic anhydride, or the like in the presence of, or absence of a reaction-inert solvent. A preferred base is selected from, for example, but not limited to, an alkali or alkaline earth metal hydroxide, alkoxide, carbonate, halide or hydride, such as sodium hydroxide, potassium hydroxide, sodium methoxide, sodium ethoxide, potassium tert-butoxide, sodium carbonate, potassium carbonate, potassium fluoride, sodium hydride or potassium hydride, or an amine such as triethylamine, tributylamine, diisopropylethylamine, pyridine or dimethylaminopyridine in the presence or absence of a reaction inert solvent. Preferred reaction inert solvents include, but are not limited to, benzene, toluene, xylene, o-dichlorobenzene, nitrobenzene, pyridine, dichloromethane, 1,2-dichloroethane, tetrahyrofuran, dimethylformamide (DMF), 1,4-dioxane, dimethylsulfoxide (DMSO) or mixtures thereof. Reaction temperatures are generally in the range of −100° C. to 250° C., preferably in the range of 0° C. to the reflux temperature, but if necessary, lower or higher temperature can be employed. Reaction times are, in general, from 1 minute to a day, preferably from 20 minutes to 5 hours, however shorter or longer reaction times, if necessary, can be employed. Then, the resulting compound of formula 1f-6 may be subjected to the amination to give the compound of formula 1f-7. For example, the compound of formula 1f-6 is reacted with $R^{1a}$—$NH_2$ wherein $R^{1a}$ is as defined herein before. The reactants may be heated together in the absence or presence of a reaction inert solvent. Preferred reaction inert solvents include, but are not limited to, benzene, toluene, xylene, o-dichlorobenzene, nitrobenzene, pyridine, dichloromethane, 1,2-dichloroethane, or mixtures thereof. Preferably, the reaction conducted in the presence of base. A preferred base is selected from, for example, but not limited to, an alkali or alkaline earth metal hydroxide, alkoxide, carbonate, or hydride, such as sodium hydroxide, potassium hydroxide, sodium methoxide, sodium ethoxide, potassium tert-butoxide, sodium carbonate, potassium carbonate, sodium hydride or potassium hydride, or an amine such as triethylamine, tributylamine, diisopropylethylamine, pyridine or dimethylaminopyridine. Reaction temperatures are generally in the range of −100 to 250° C., preferably in the range of 0° C. to the reflux temperature, but if necessary, lower or higher temperature can be employed. Reaction times are, in general, from 1 minute to a day, preferably from 20 minutes to 5 hours, however shorter or longer reaction times, if necessary, can be employed.

(g) The compound of formula 1f-7 may be treated with Z—$SO_2$N($R^2$)C(=O)O—$R^{1b}$, wherein $R^{1b}$ is aryl or $C_{1-4}$ alkyl, or Z—$SO_2$NCO to give the compound of formula (If). The reaction may be carried out in the absence or presence of a reaction inert solvent. Preferred reaction inert solvents include, but are not limited to, benzene, toluene, xylene, o-dichlorobenzene, nitrobenzene, pyridine, dichloromethane, 1,2-dichloroethane, or mixtures thereof. If desired, the reaction may be carried out in the presence of base, such as triethyl amine, diisopropylethylamine, or N-methylmorphorine. Reaction temperatures are generally in the range of −100 to 250° C., preferably in the range of 0° C. to the reflux temperature, but if necessary, lower or higher temperature can be employed. Reaction times are, in general, from 1 minute to a day, preferably from 20 minutes to 5 hours, however shorter or longer reaction times, if necessary, can be employed.

As described in scheme 2, the compound of formula (I), wherein A is phenyl, B is ethylene and W is NH (hereinafter represented by Formula (Ib)), may be prepared through the process comprising:

(a) coupling reaction of a compound of formula 2-1(1-1), wherein X is a leaving group such as halo, mesylate or tosylate with 2-(4-aminophenyl)propionic acid or ester (2-2) (when using ester derivative of 2-2, followed by hydrolysis) to give a nitroaniline compound of formula 2-3;

(b) Curutius rearrangement of the compound of formula 2-3 followed by treating with an alcohol or a phenol to give a carbamate compound of formula 2-5;

(c) sulfonylurea formation with compound of formula 2-5 to give a compound of formula 2-6;

(d) reduction of the resulting nitroaniline compound of formula 2-6 to give a diamine compound of formula 2-7; and (e) benzimidazole or imidazopyridine ring formation with the compound of formula 2-7 to give a compound of formula (Ib);

Each reaction step is described more specifically as follows.

(a) The compound of formula 2-3 may be prepared from the compound of 2-1(1-1) according to the similar procedure to that of described in Scheme 1.

(b) Curutius rearrangement of the compound of formula 2-3 may be carried out by conventional procedures. In a typical procedure, the rearrangement is carried out by treatment with DPPA in the presence of a base in a reaction inert solvent. Suitable bases include, for example, an amine such as triethylamine, tributylamine, diisopropylethylamine, pyridine or dimethylaminopyridine. Preferred reaction inert solvents include, but are not limited to, benzene, toluene, xylene, o-dichlorobenzene, nitrobenzene, tetrahyrofuran (THF), 1,4-dioxane, or mixtures thereof. Reaction temperatures are generally in the range of 0 to 250° C., preferably in the range of 25° C. to the reflux temperature, but if necessary, lower or higher temperature can be employed. Reaction times are, in general, from 1 minute to a day, preferably from 20 minutes to 5 hours, however shorter or longer reaction times, if necessary, can be employed.

The obtained isocyanate 2-4 may be treated with an alcohol or a phenol to give the compound of formula 2-5. Reaction temperatures are generally in the range of 0 to 250° C., preferably in the range of 25° C. to the reflux temperature, but if necessary, lower or higher temperature can be employed. Reaction times are, in general, from several minutes to a day, preferably from 20 minutes to 5 hours, however shorter or longer reaction times, if necessary, can be employed.

(c) Treatment of the obtained carbamate compound of formula 2-5 with sulfonamide in the presence or absence of a base may give the compound of formula 2-6. Suitable bases include, for example, an alkali or alkaline earth metal hydroxide, alkoxide, carbonate, halide or hydride, such as sodium hydroxide, potassium hydroxide, sodium methoxide, sodium ethoxide, potassium tert-butoxide, sodium carbonate, potassium carbonate, cesium carbonate, potassium fluoride, sodium hydride or potassium hydride in the presence or absence of a reaction inert solvent. Preferred reaction inert solvents include, but are not limited to, benzene, toluene, xylene, o-dichlorobenzene, nitrobenzene, dichloromethane, 1,2-dichloroethane, tetrahyrofuran, dimethylformamide (DMF), 1,4-dioxane, dimethylsulfoxide (DMSO) or mixtures thereof. Reaction temperatures are generally in the range of −100° C. to 250° C., preferably in the range of 0° C. to the reflux temperature, but if necessary, lower or higher temperature can be employed. Reaction times are, in general, from 1 minute to a day, preferably from 20 minutes to 5 hours, however shorter or longer reaction times, if necessary, can be employed.

(d) and (e) The reduction of the compound 2-6 and the following ring formation may be carried out in an analogous manner to those of described in Scheme 1 to give the compound of formula (Ib).

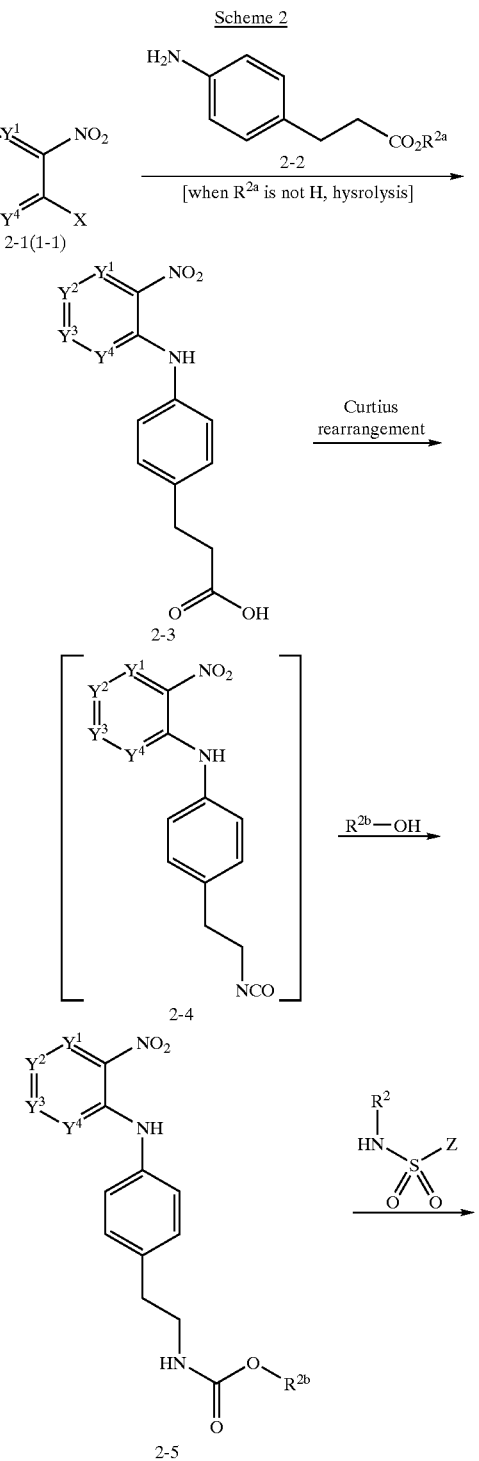

Scheme 2

-continued

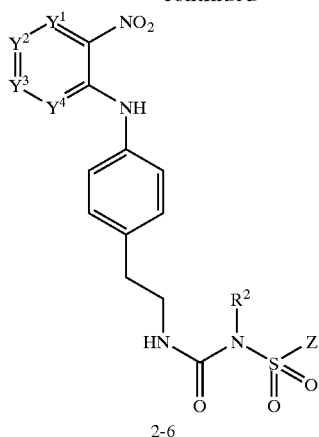

2-6

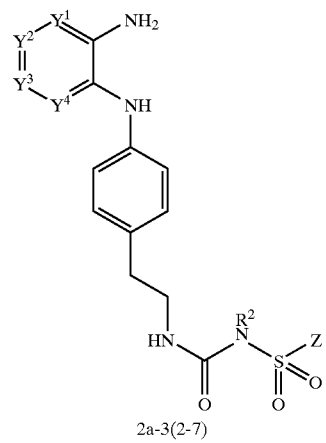

(Ib)

As shown in Scheme 2a, an intermediate compound of formula 2a-3 (2-7) may also be prepared through the procedure comprising (a) reduction of the above obtained compound 2a-1 (2-5) to give a diamine compound of formula 2a-2; and (b) sulfonylurea formation of the compound of formula 2a-2 may give a compound of formula 2a-3 (2-7).

The reduction of the compound of formula 2a-1 (2-5), and sulfonylurea formation with the obtained compound of formula 2a-2 may be carried out by the same procedure as described in scheme 1 and 1d.

As shown in scheme 2a, a carbamate compound of formula 2a-4 may be prepared from the compound of formula 2a-2 by the cyclization according to the same procedure as described in Scheme 1.

Scheme 2a

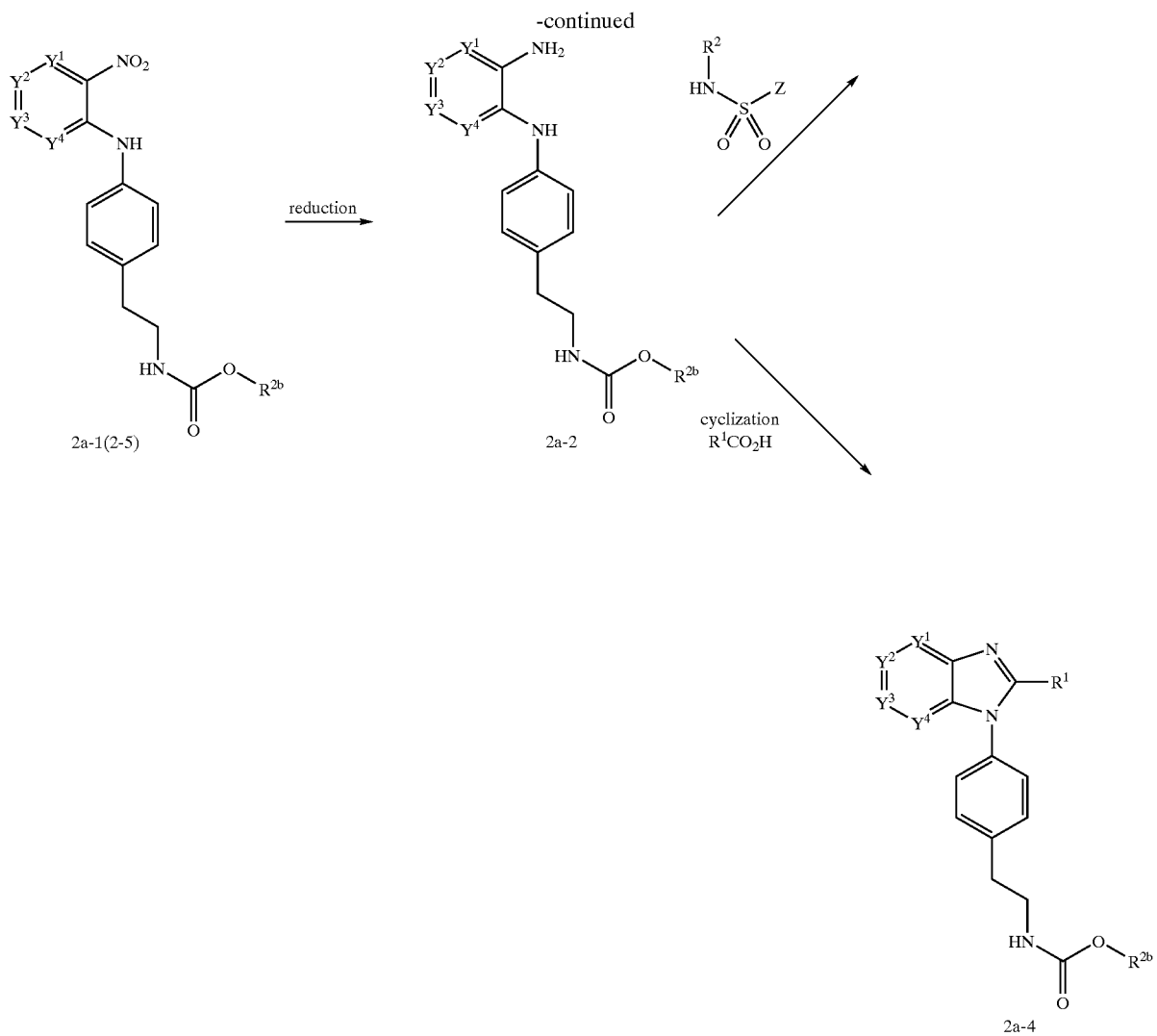

Alternatively, an intermediate compound of formula 2b-5 (2-5) may also be prepared from a carboxylic acid compound of formula 2b-1(2-3) by the methods illustrated in Scheme 2b. Path A in Scheme 2b illustrates a preparation procedure for a compound of formula 2b-5 (2-5) according to the Hoffman rearrangement (e.g., Wallis; Lane *Org React.* 1946, 3, 267–306). The amide compound of formula 2b-2 may be prepared by known methods (e.g., Org. Syn. Coll Vol 4, 513 (1963)). Hoffman rearrangement of the obtained carboxamide compound of formula 2b-2 may be carried out under the known conditions followed by treatment with an alcohol or a phenol under the same conditions described in Scheme 2 to afford the compound of formula 2b-5 (2-5). Path B in Scheme 2b illustrates a preparation procedure for the compound of formula 2b-5 (2-5) according to Lossen rearrangement (e.g., Bauer; Exner *Angew. Chem. Int Ed. Engl.* 1974, 13, 376–384). The O-acyl hydroxamic acid compound of formula 2b-3 may be prepared by known methods (e.g., Miller, Marvin J.; Mattingly, Phillip G.; Morrison, Marjorie A.; Kerwin, James F., *J.Amer.Chem.Soc.*, 1980, 102, 7026–7032). The carboxylic acid compound of formula 2b-1 (2-3) may be treated with hydroxamic acid derivative, usually O-acyl hydroxamic acid, in the presence of coupling agent such as dicyclohexylcarbodiimide (DCC), diisopropylcarbodiimide (DIPC), 1-ethyl-3-(3-dimethylaminopropyl)carbodiimide (WSC), benzotriazole-1-yloxy-tris(dimethylamino)phosphonium hexafluorophosphate (BOP), diphenylphosphorylazide (DPPA), or the like. This reaction may be carried out at from about 0° C. to the reflux temperature of the reaction mixture, preferably from about room temperature to the reflux temperature for about 1 minute to about 120 hours, preferably for from about 10 minutes to about 72 hours. Lossen rearrangement of the obtained O-acyl hydroxamic acid compound of formula 2b-3 may be carried out under the known conditions followed by treatment with an alcohol or a phenol under the same conditions described in Scheme 2 to afford the compound of formula 2b-5(2-5).

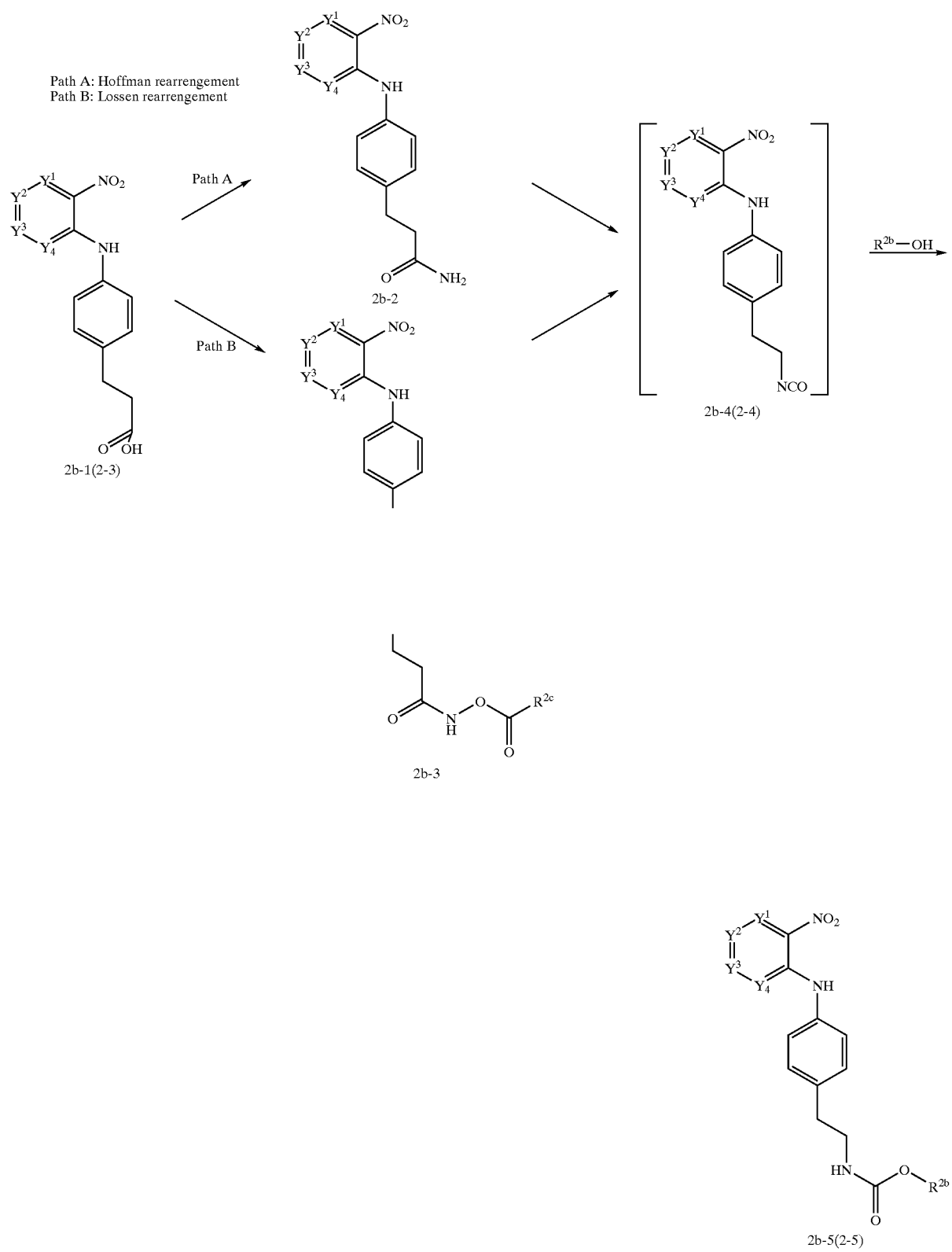
Scheme 2b

The compound of formula (Ia) may be prepared from the compound of formula (Ia1), wherein $R^2$ is H, by methods known to those skilled in the art as depicted in Scheme 3. The compound of formula (Ia1) may be treated with appropriate alkyl halides, $R^2$-halo in the presence of a base such as lithium diisopropyl amide (LDA), sodium hydride (NaH) or potassium t-butoxide in a reaction inert solvent such as THF or DMF at about 0° C. to 80° C. for 20 minutes to 24 hours.

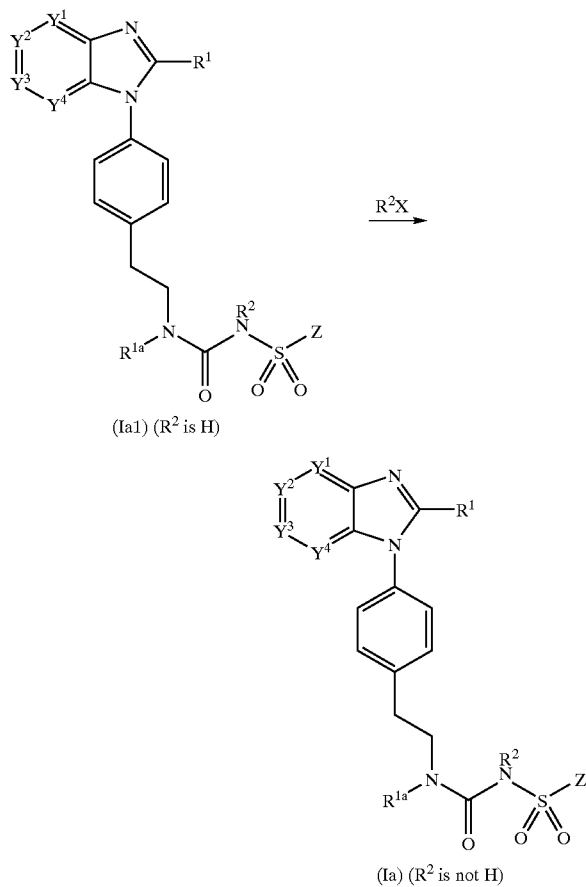

temperature, but if necessary, lower or higher temperature can be employed. Reaction times are, in general, from 1 minute to a day, preferably from 20 minutes to 5 hours, however shorter or longer reaction times, if necessary, can be employed.

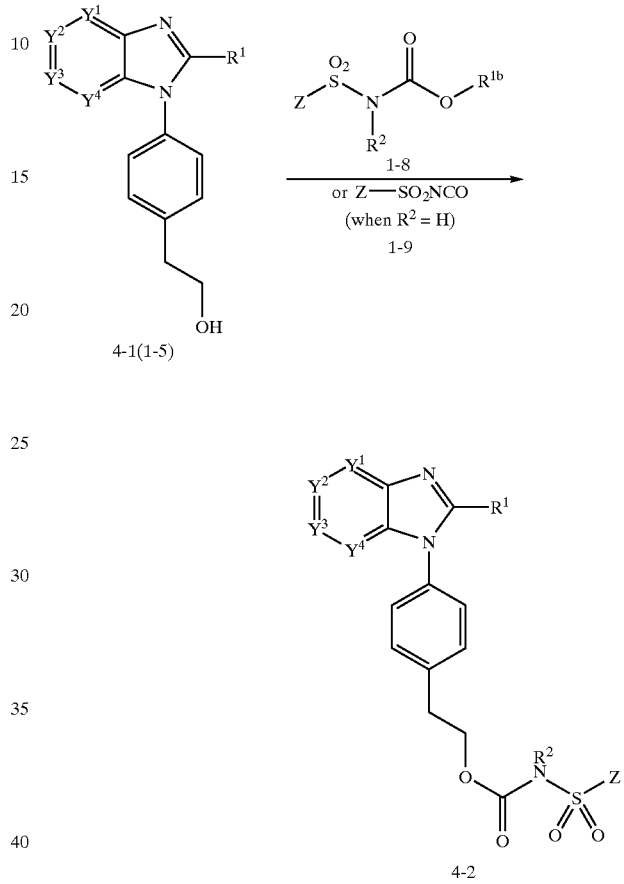

As depicted in Scheme 4, a carbamate compound of formula 4-2 may be prepared from a compound of formula 4-1(1-5) according to the same conditions described in Scheme 1. More specifically, the compound of formula 4-1 may be treated with $Z-SO_2N(R^2)C(=O)O-R^{1b}$ wherein $R^{1b}$ is aryl or $C_{1-4}$ alkyl or $Z-SO_2NCO$ to give the compound of formula (4-2). The reaction may be carried out in the absence or presence of a reaction inert solvent. Preferred reaction inert solvents include, but are not limited to, benzene, toluene, xylene, o-dichlorobenzene, nitrobenzene, pyridine, dichloromethane, 1,2-dichloroethane, or mixtures thereof. If desired, the reaction may be carried out in the presence of base, such as triethyl amine, diisopropylethylamine, or N-methylmorphorine. Reaction temperatures are generally in the range of –100° C. to 250° C., preferably in the range of 0° C. to the reflux As shown in Scheme 5, the compound of formula (I), wherein A is phenyl, B is ethylene and W is $N-OR^7$ (hereinafter represented by Formula (Id)) may be prepared through the process comprising:

(a) Mitsunobu reaction of a compound of formula 5-1 (1-5) to give a compound of formula 5-2;

(b) cleavage of the protecting group of the compound of formula 5-2 to give a hydroxyamine compound of formula 5-3; and (c) sulfonylurea formation with the compound of formula 5-3 to give a compound of formula (Id).

As shown in Scheme 4a, the compound of formula 4a-3 (4-2) may also be prepared by reacting a compound of formula 4a-1 with a substituted benzene compound of formula 4a-2 to give a 1-phenylbenzimidazole compound of formula 4a-3 (4-2); The compounds of formula 4a-1 may be synthesized by any of the known methods. The group $G^{19}$ of the compounds of formula 4a-2 is a selected from a suitable displaceable group, for example, fluoro, chloro, bromo, iodo, trifluoromethanesulfonyloxy, methanesulfonyloxy, p-toluenesulfonyloxy, or boronic acid group.

Scheme 4a

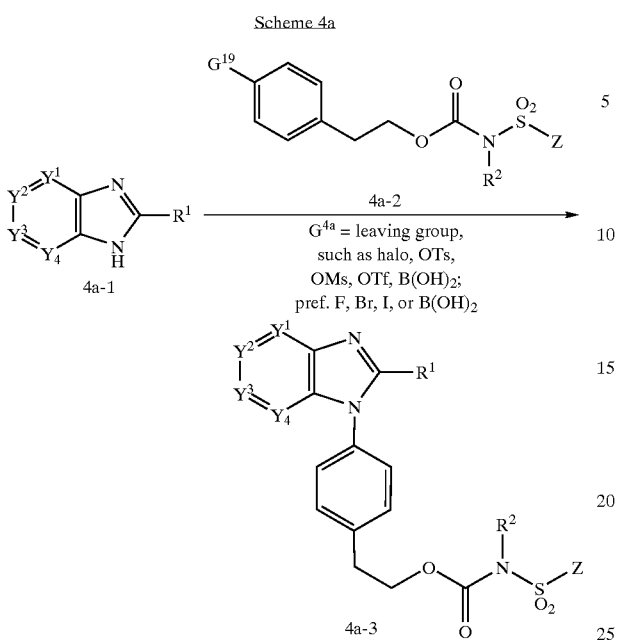

The coupling reaction may be carried out in the presence of a base in a reaction inert solvent. A preferred base is selected from, for example, but not limited to, an alkali or alkaline earth metal hydroxide, alkoxide, carbonate, or hydride, such as sodium hydroxide, potassium hydroxide, sodium methoxide, sodium ethoxide, potassium tert-butoxide, sodium carbonate, potassium carbonate, sodium hydride or potassium hydride, or an amine such as triethylamine, tributylamine, diisopropylethylamine, 2,6-lutidine, pyridine or dimethylaminopyridine. Preferred reaction inert solvents include, but are not limited to, benzene, toluene, xylene, o-dichlorobenzene, nitrobenzene, pyridine, dichloromethane, 1,2-dichloroethane, tetrahyrofuran, acetonitrile, dimethylformamide (DMF), 1,4-dioxane, dimethylsulfoxide (DMSO), 1,3-dimethyl-2-imidazolidinone, 1-methyl-2-pyrrolidinone, or mixtures thereof. Reaction temperatures are generally in the range of −100 to 250° C., preferably in the range of 0 to 150° C., but if necessary, lower or higher temperature can be employed. Reaction times are, in general, from 1 minute to several weeks, preferably from 20 minutes to 1 week, however shorter or longer reaction times, if necessary, can be employed. Conveniently, the compound of formula 4a-1 may be reacted with the compound of formula 4a-2 in the presence of a suitable catalyst to form the compound of formula 4a-3 (4-2) by any synthetic procedure applicable to structure-related compounds known to those skilled in the literature (e.g., Lam, P. Y. S.; Clark, C. G.; Saubern, S; Adams, J; Winters, M. P.; Chan, D. M. T.; Combs, A., *Tetrahedron Lett.*, 1998, 39, 2941–2944., Kiyomori, A.; Marcoux, J.; Buchwald, S. L., *Tetrahedron Left.*, 1999, 40, 2657–2660., Lam, P. Y. S.; Deudon, S.; Averill, K. M.; Li, R.; He, M. Y.; DeShong, P.; Clark, C. G., *J. Am. Chem. Soc.*, 2000, 122,7600–7601., Collman, J. P.; Zhong, M., *Org. Lett.*, 2000, 2, 1233–1236.). Preferred reaction catalyst is selected from, for example, but not limited to, tetrakis(triphenylphosphine)-palladium, bis(triphenylphosphine)palladium(II) chloride, copper(I), copper(I) acetate, copper(I) bromide, copper(I) chloride, copper(I) iodide, copper(I) oxide, copper(II) trifluoromethanesulfonate, copper(II) acetate, copper(II) bromide, copper(II) chloride, copper(II) iodide, copper(II) oxide, or copper(II) trifluoromethanesulfonate.

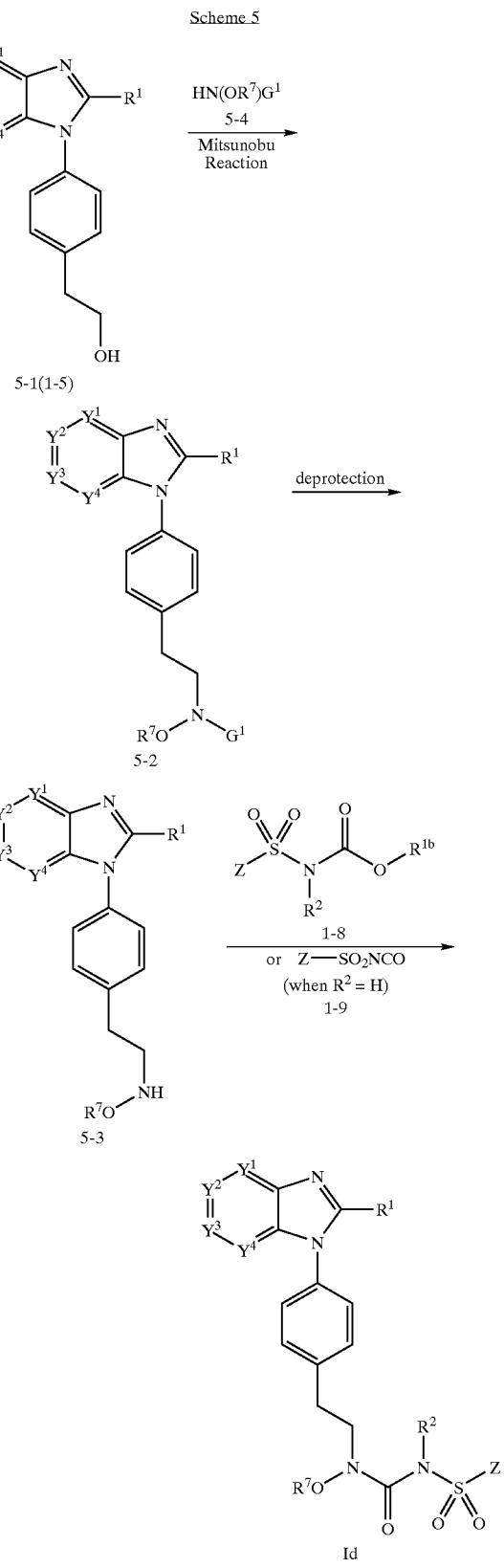

Each reaction step is described more specifically as follows.

(a) The compound of formula 5-2 may be prepared by the Mitsunobu reaction. The compound of formula 5-1 may be treated with HN(OR$^7$)G$^1$ wherein G$^1$ is H or a protecting group, preferably, G1 is a suitable protecting group, for example, methoxycarbonyl, ethoxycarbonyl, tert-butoxycarbonyl (Boc), benzyloxycarbonyl(Z), phenylsulfonyl, p-toluenesulfonyl, or the like, and R$^7$ is an alkyl (e.g., methyl or ethyl) or G$^2$ (G$^2$ is a suitable protecting group, for example, methoxycarbonyl, ethoxycarbonyl, tert-butoxycarbonyl (Boc), benzyloxycarbonyl(Z), phenylsulfonyl, p-toluenesulfonyl, trimethylsilyl, t-butyldimethylsilyl, or the like)). For example, the compound of formula 5-1 is reacted with [N,O-Bis-protectedhydroxylamine] (e.g., Baillie, L. C.; Batsanov, A.; Bearder, J. R.; Whiting, D. A. *J. Chem. Soc. Perkin Trans.* 1, 1998, 20, 3471.) in the presence of dialkyl azodicarboxylate such as diethyl azodicarboxylate (DEAD) and phosphine reagent such as triphenylphosphine. Preferably, this reaction may be carried out in a reaction-inert solvent. Preferred reaction inert solvents include, but are not limited to, tetrahydrofuran (THF), diethyl ether, dimethylformamide (DMF), benzene, toluene, xylene, o-dichlorobenzene, nitrobenzene, dichloromethane, 1,2-dichloroethane, dimethoxyethane (DME), or mixtures thereof. Reaction temperatures are generally in the range of −100° C. to 250° C., preferably in the range of 0° C. to the reflux temperature, but if necessary, lower or higher temperature can be employed. Reaction times are, in general, from 1 minute to a day, preferably from 20 minutes to 5 hours, however shorter or longer reaction times, if necessary, can be employed.

(b) Cleavage of the protecting group may be carried out by a number of standard procedures known to those skilled in the art (e.g., "Protection for the Hydroxy Group and the Amino Group", in *Protective Groups in Organic Synthesis*, 2nd Edition, T. W. Greene and P. G. M. Wuts, Ed., John Wiley and Sons, Inc. 1991, pp. 10–142, 309–405).

(c) sulfonylurea formation may be carried out according to the conditions illustrated in Scheme 1. Specifically, the compound of formula 5-3 may be treated with Z—SO$_2$N(R$^2$)C(=O)O—R$^{1b}$ wherein R$^{1b}$ is aryl or C$_{1-4}$,alkyl, or Z—SO$_2$NCO to give the compound of formula (Id). The reaction may be carried out in the absence or presence of a reaction inert solvent. Preferred reaction inert solvents include, but are not limited to, benzene, toluene, xylene, o-dichlorobenzene, nitrobenzene, pyridine, dichloromethane, 1,2-dichloroethane, or mixtures thereof. If desired, the reaction may be carried out in the presence of base, such as triethyl amine, diisopropylethylamine, or N-methylmorphorine. Reaction temperatures are generally in the range of −100° C. to 250° C., preferably in the range of 0° C. to the reflux temperature, but if necessary, lower or higher temperature can be employed. Reaction times are, in general, from 1 minute to a day, preferably from 20 minutes to 5 hours, however shorter or longer reaction times, if necessary, can be employed.

Reaction Scheme 6 illustrates a method for the preparation of the compound of formula (Ia), wherein at least one of Y$^1$, Y$^2$, Y$^3$ and Y$^4$ is C—CONH$_2$, A is phenyl, B is ethylene and W is R$^{1a}$—N (R$^{1a}$ is H or C$_{1-4}$ alkyl) (hereinafter represented by Formula (Ia$^2$)), and that of the compound of formula (Ia) wherein at least one of Y$^1$, Y$^2$, Y$^3$ and Y$^4$ is C—CO$_2$H, A is phenyl and B is ethylene and W is R$^{1a}$—N (R$^{1a}$ is H or C$_{1-4}$ alkyl) (hereinafter represented by Formula (Ia$^3$)). Compound (Ia$^3$) may be prepared through the process comprising:

(a) hydrolysis of a compound of formula 6-1 to give a compound of formula 6-2;

(b) conversion of the hydroxy group of the compound 6-2 into the leaving group such as halo, mesylate and tosylate to give a compound of formula 6-3;

(c) azide formation;

(d) reduction of the resulting azide compound followed by sulfonylurea formation to give the compound of formula (Ia$^2$); and (e) hydrolysis of the compound of formula (Ia$^2$) to give the compound of formula (Ia$^3$);

Each reaction step is described more specifically as follows:

(a) Intermediate 6-1 may be prepared by the methods illustrated in Scheme 1. The hydrolysis of the compound of formula 6-1 may be carried out by conventional procedures. The hydrolysis may be carried out by treatment with a peroxide such as hydrogen peroxide in the presence of a base such as sodium hydroxide, potassium hydroxide, lithium hydroxide or ammonium hydroxide in a suitable solvent such as aqueous methanol, dimethylsulfoxide and tetrahydrofuran. Reaction temperatures are generally in the range of −100° C. to 250° C., preferably in the range of 0° C. to the reflux temperature, but if necessary, lower or higher temperature can be employed. Reaction times are, in general, from 1 minute to a day, preferably from 20 minutes to 5 hours, however shorter or longer reaction times, if necessary, can be employed. The hydrolysis may also be carried out by treatment with a base such as sodium hydroxide, potassium hydroxide or lithium hydroxide, or an acid such as sulfuric acid in a suitable solvent such as aqueous methanol, aqueous ethanol, t-butanol or mixtures thereof. Reaction temperatures are generally in the range of −100° C. to 250° C., preferably in the range of 0° C. to the reflux temperature, but if necessary, lower or higher temperature can be employed. Reaction times are, in general, from several minutes to a day, preferably from 20 minutes to 5 hours, however shorter or longer reaction times, if necessary, can be employed.

(b) (c) and (d) Step (b), (c) and step (d) may be carried out according to the conditions illustrated in Scheme 1 and 1b.

(e) The hydrolysis of the compound of formula (Ia$^2$) may be carried out by conventional procedures. The hydrolysis may be carried out by treatment with a base such as sodium hydroxide, potassium hydroxide or lithium hydroxide, or an acid such as sulfuric acid or phosphoric acid in a suitable solvent such as aqueous methanol, ethanol ethylene glycol, water, tetrahydrofuran or mixtures thereof. Reaction temperatures are generally in the range of −100° C. to 250° C., preferably in the range of 0° C. to the reflux temperature, but if necessary, lower or higher temperature can be employed. Reaction times are, in general, from 1 minute to a day, preferably from 20 minutes to 5 hours, however shorter or longer reaction times, if necessary, can be employed.

Scheme 6

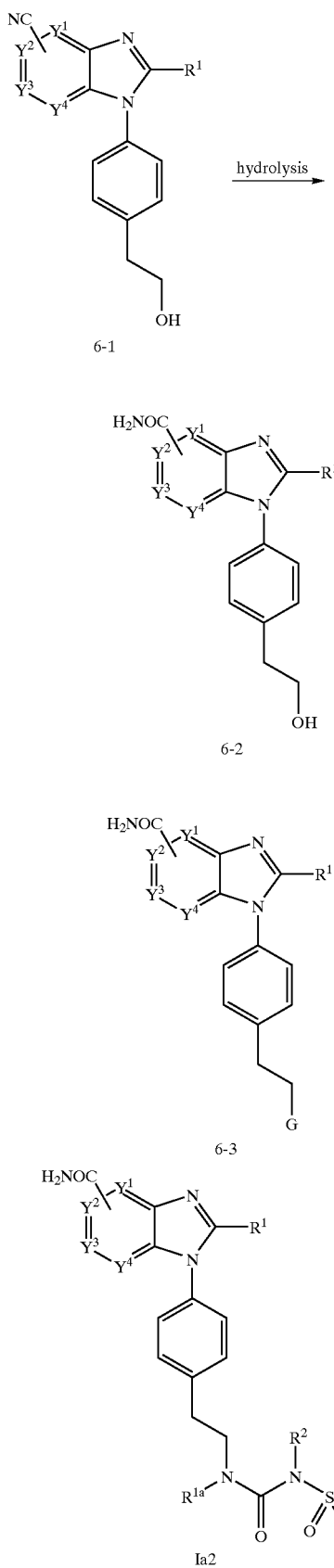

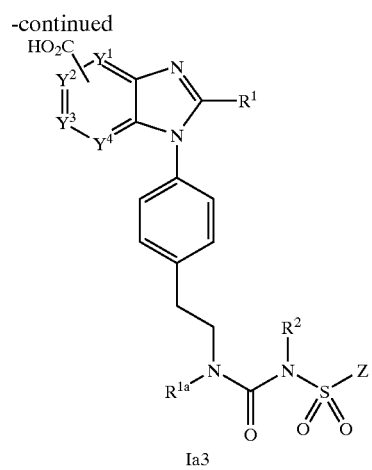

Reaction Scheme 7 illustrates an alternative method for the preparation of the compound of formula (Ia²). A compound of formula (Ia⁴) may be prepared by the methods illustrated in Scheme 1. Hydrolysis of the compound of formula (Ia⁴) may be carried out by treatment with a base such as sodium hydroxide, potassium hydroxide, lithium hydroxide or ammonium hydroxide in a suitable solvent such as aqueous methanol, dimethylsulfoxide and tetrahydrofuran. Reaction temperatures are generally in the range of −100° C. to 250° C., preferably in the range of 0° C. to the reflux temperature, but if necessary, lower or higher temperature can be employed. Reaction times are, in general, from 1 minute to a day, preferably from 20 minutes to 5 hours, however shorter or longer reaction times, if necessary, can be employed. The hydrolysis may also be carried out by treatment with a base such as sodium hydroxide, potassium hydroxide or lithium hydroxide, or an acid such as sulfuric acid in a suitable solvent such as aqueous methanol, aqueous ethanol, t-butanol or mixtures thereof. Reaction temperatures are generally in the range of −100° C. to 250° C., preferably in the range of 0° C. to the reflux temperature, but if necessary, lower or higher temperature can be employed. Reaction times are, in general, from 1 minute to a day, preferably from 20 minutes to 5 hours, however shorter or longer reaction times, if necessary, can be employed.

Scheme 7

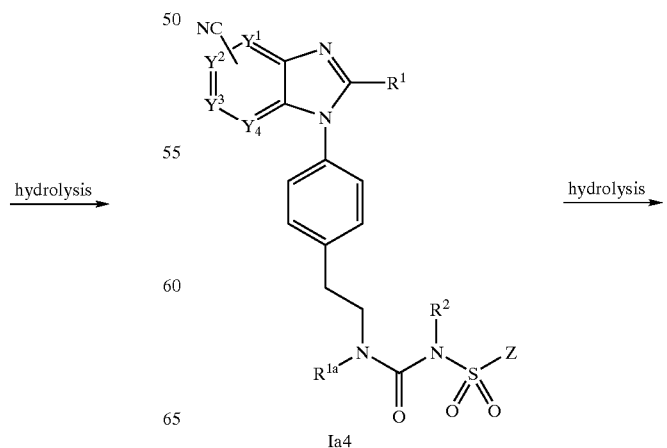

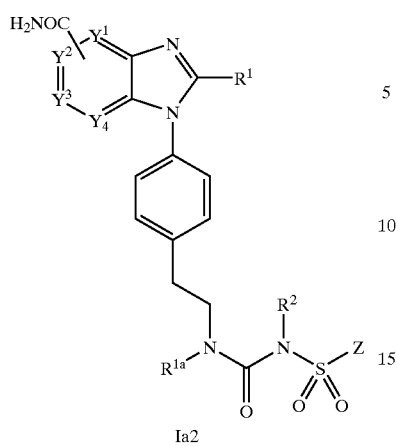

Ia2

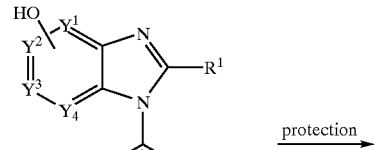

8-2

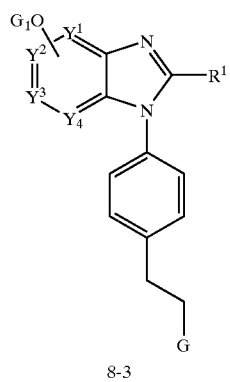

8-3

Reaction Scheme 8 illustrates a method for the preparation of the compound of formula (Ia) wherein at least one of $Y^1, Y^2, Y^3$ and $Y^4$ is C—$OG^1$ wherein $G^1$ is defined before, A is phenyl, B is ethylene and W is $R^{1a}$—N ($R^{1a}$ is H or $C_{1-4}$ alkyl), (hereinafter represented by Formula (Ia$^5$)) and that of the compound of formula (Ia) wherein at least one of $Y^1, Y^2, Y^3$ and $Y^4$ is C—OH, A is phenyl B is ethylene and W is $R^{1a}$—N ($R^{1a}$ is H or $C_{1-4}$ alkyl), (hereinafter represented by Formula (Ia$^6$)). Compound (Ia$^6$) may be prepared through the process comprising:

(a) dealkylation of a compound of formula 8-1 to give a compound of formula 8-2;

(b) protection of the hydroxy group of the compound 8-2 to give a compound of formula 8-3;

(c) preparation of the compound of formula (Ia$^5$); and (d) cleavage of the protecting group of the compound of formula (Ia$^5$) to give the compound of formula (Ia$^6$).

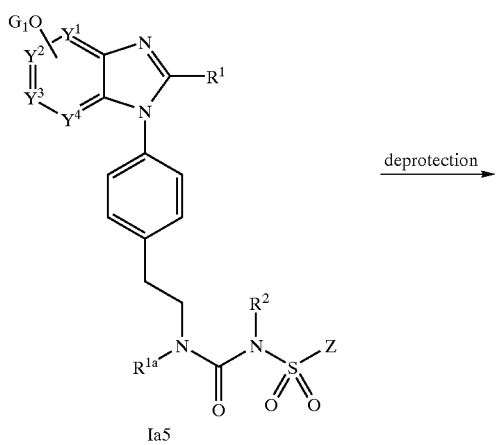

Ia5

Scheme 8

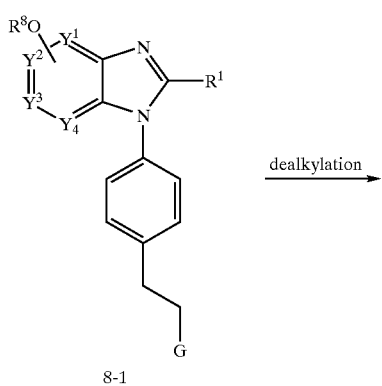

8-1

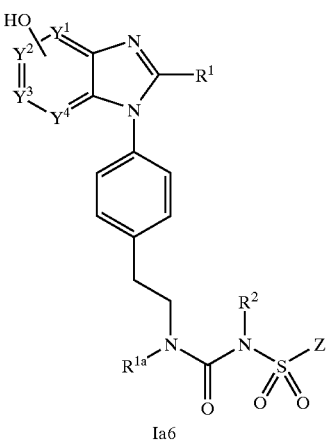

Ia6

Each reaction step is described more specifically as follows.

(a) Intermediate 8-1, wherein $R^8$ is C1–C4alkyl, may be prepared by the methods illustrated in Scheme 1. dealkylation of the compound of formula 8-1 may be carried out a number of standard procedures known to those skilled in the art (e.g., "Protection of Phenols", in *Protective Groups in Organic Synthesis*, 2nd Edition, T. W. Greene and P. G. M. Wuts, Ed., John Wiley and Sons, Inc. 1991, pp. 1-43-174). For example, the compound of formula 8-1 may be treated with a proton and/or Lewis acid such as hydrogen bromide or aluminum chloride in a suitable solvent such as water, acetic acid or dichloromethane. Reaction temperatures are generally in the range of –100° C. to 250° C., preferably in the range of 0° C. to the reflux temperature, but if necessary, lower or higher temperature can be employed. Reaction times are, in general, from 1 minute to a day, preferably from 20 minutes to 5 hours, however shorter or longer reaction times, if necessary, can be employed. The reaction may also carried out in the presence of a thioalkoxide such as sodium thiomethoxide, lithium thiomethoxide, sodium thioethoxide in the presence or absence of a reaction inert solvent such as DMSO, DMF or HMPA. Reaction temperatures are generally in the range of –100° C. to 250° C., preferably in the range of 0° C. to the reflux temperature, but if necessary, lower or higher temperature can be employed. Reaction times are, in general, from 1 minute to a day, preferably from 20 minutes to 5 hours, however shorter or longer reaction times, if necessary, can be employed.

(b) Protection of the compound of formula 8-2 may be carried out according to a number of standard procedures known to those skilled in the art (e.g., "Protection of Phenols", in *Protective Groups in Organic Synthesis*, 2nd Edition, T. W. Greene and P. G. M. Wuts, Ed., John Wiley and Sons, Inc. 1991, pp. 143–174).

(c) Preparation of the compound of formula ($Ia^5$) may be carried out according to the conditions illustrated in Scheme 1 and 1b.

(d) Cleavage of the protecting group may be carried out by a number of standard procedures known to those skilled in the art (e.g., "Protection of Phenols", in *Protective Groups in Organic Synthesis*, 2nd Edition, T. W. Greene and P. G. M. Wuts, Ed., John Wiley and Sons, Inc. 1991, pp. 143–174).

As depicted in Scheme 9, the compound of formula (Ia), wherein at least one of $Y^1$, $Y^2$, $Y^3$ and $Y^4$ is C—$SO_2NH_2$, A is phenyl, B is ethylene and W is $R^{1a}$—N ($R^{1a}$ is H or $C_{1-4}$alkyl), (hereinafter represented by Formula ($Ia^8$)) may be prepared from the compound of formula (Ia), wherein at least one of $Y^1$, $Y^2$, $Y^3$ and $Y^4$ is C—$SO_2NHtBu$, A is phenyl, B is ethylene and W is $R^{1a}$—N ($R^{1a}$ is H or $C_{1-4}$alkyl), (hereinafter represented by Formula ($Ia^7$)). The compound of formula ($Ia^7$) may be prepared by the methods illustrated in Scheme 1 and 1b. Cleavage of the protecting group may be carried out by a number of standard procedures known to those skilled in the art (e.g., Quan, Mimi L.; Ellis, Christopher D.; Liauw, Ann Y.; Alexander, Richard S.; Knabb, Robert M., et al., *J. Med. Chem.*, 1999, 42, 2760–2773).

Scheme 9

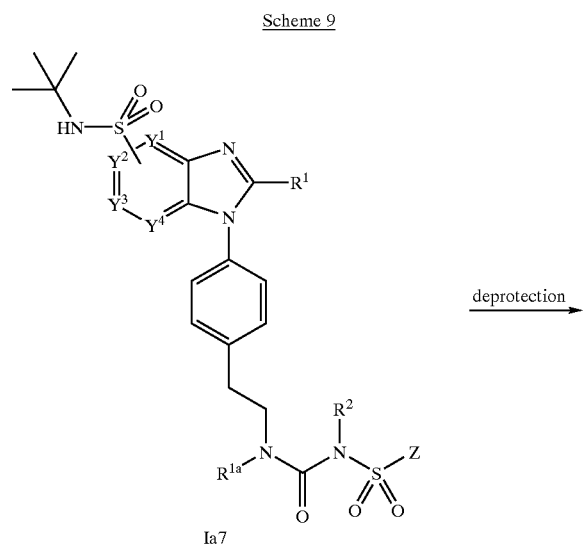

Ia7

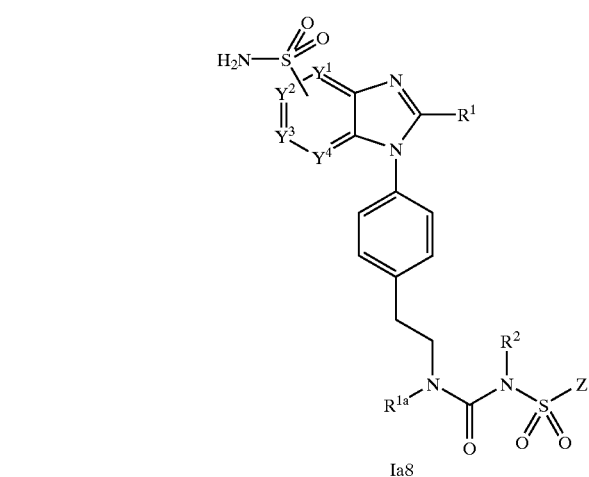

Ia8

Reaction Scheme 10 illustrates a method for the preparation of the compound formula (Ia) wherein at least one of $Y^1$, $Y^2$, $Y^3$ and $Y^4$ is C—$NHSO_2R^{10}$, A is phenyl, B is ethylene, $R^{10}$ is $C_1$–$C_4$ alkyl, W is $R^{1a}$—N ($R^{1a}$ is H or $C_{1-4}$alkyl), (hereinafter represented by Formula ($Ia^9$)).

Scheme 10

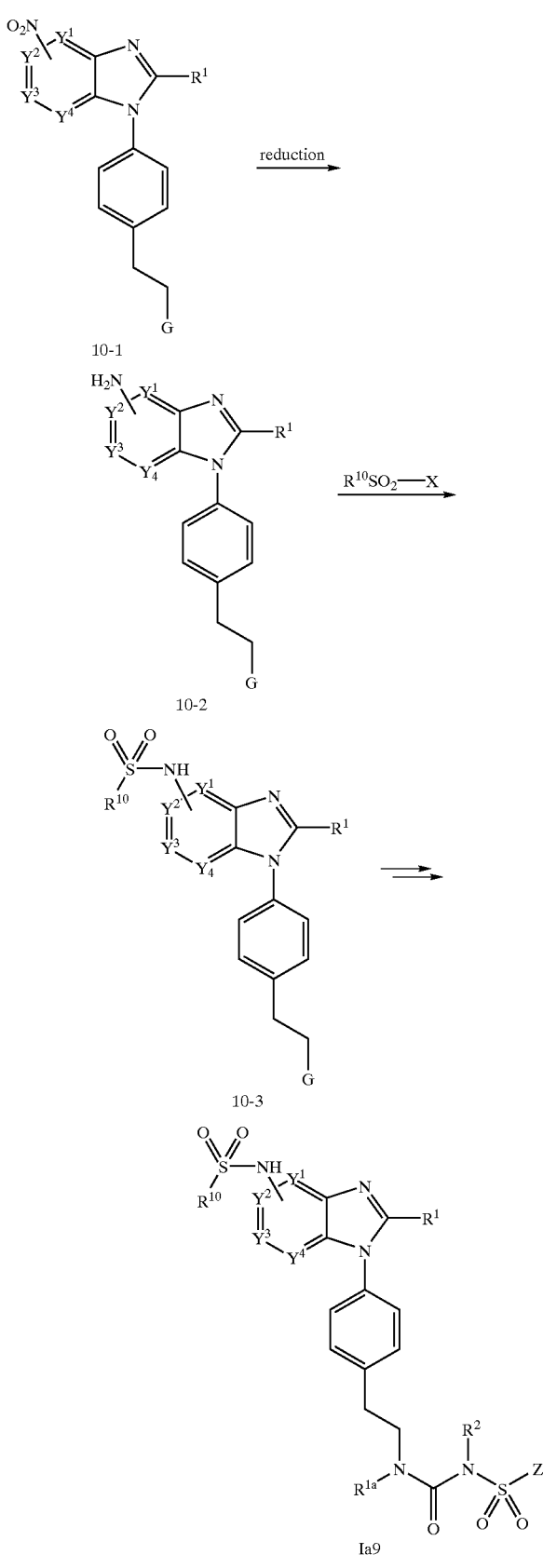

Compound (Ia$^9$) may be prepared through the process comprising:

(a) reduction of a compound of formula 10-1 to give a compound of formula 10-2;

(b) sulfonylation of the amino group of the compound 10-2 to give a compound of formula 10-3; and (c) formation of a compound of formula (Ia$^9$);

Each reaction step is described more specifically as follows.

(a) The intermediate 10-1 may be prepared by the methods illustrated in Scheme 1. Reduction of nitro group may be carried out according to the conditions illustrated in Scheme 1.

(b) Sulfonylation of the amino group of the compound 10-2 may be carried out by a number of standard procedures known to those skilled in the art (e.g., "Protection for the Hydroxy Group and the Amino Group", in *Protective Groups in Organic Synthesis*, 2nd Edition, T. W. Greene and P. G. M. Wuts, Ed., John Wiley and Sons, Inc. 1991, pp. 117–118, 379–384).

(c) Formation of the sulfonylurea compound of formula (Ia$^9$) may be carried out according to the conditions illustrated in Scheme 1 and 1b.

Reaction Scheme 11 illustrates a method for the preparation of the compound of formula (Ia) wherein at least one of $Y^1$, $Y^2$, $Y^3$ and $Y^4$ is C—NHC(=O)N(R$^3$)(R$^4$), A is phenyl, B is ethylene and W is R$^{1a}$—N (R1a is H or C1–4alkyl), (hereinafter represented by Formula (Ia$^{10}$)). Compound (Ia$^{10}$) may be prepared through the process comprising:

(a) urea formation with a compound of formula 11-1(10-2) to give a compound of formula 11-2; and (b) formation of a compound of formula (Ia$^{10}$);

Each reaction step is described more specifically as follows.

(a) The intermediate 11-1(10-2) as obtained in Scheme 10, may be treated with an isocyanate or cyanic acid (usually its salts) according to known procedures (e.g., Satchell and Satchell, *Chem. Soc. Rev.*, 1975, 4, 231–250). More specifically, this reaction may be carried out in a suitable reaction inert solvent such as dichloromethane, THF, benzene or toluene. Reaction temperatures are generally in the range of −100° C. to 250° C., preferably in the range of 0° C. to the reflux temperature, but if necessary, lower or higher temperature can be employed. Reaction times are, in general, from 1 minute to a day, preferably from 20 minutes to 5 hours, however shorter or longer reaction times, if necessary, can be employed.

(c) Formation of the sulfonylurea compound of formula (Ia$^{10}$) may be carried out according to the conditions illustrated in Scheme 1 and 1b.

Scheme 11

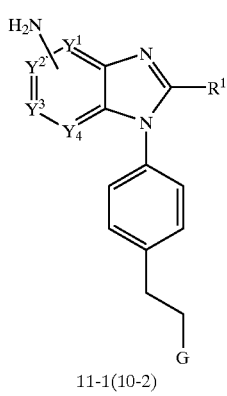

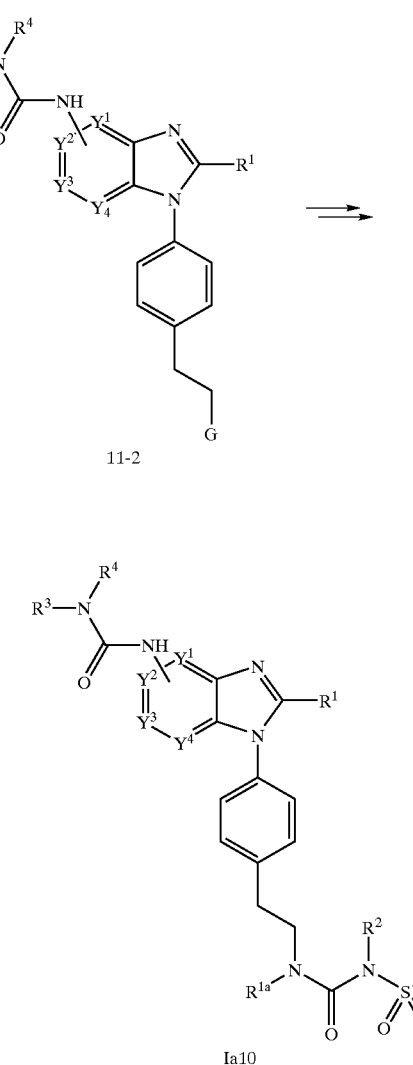

a reaction inert solvent such as methanol, ethanol, ethyl acetate or THF. If desired, the reaction is carried out under acidic conditions in the presence of an acid such as hydrogen chloride or acetic acid. Reaction temperatures are generally in the range of −100° C. to 250° C., preferably in the range of 0° C. to the reflux temperature, but if necessary, lower or higher temperature can be employed. Reaction times are, in general, from 1 minute to a day, preferably from 20 minutes to 5 hours, however shorter or longer reaction times, if necessary, can be employed.

Scheme 12

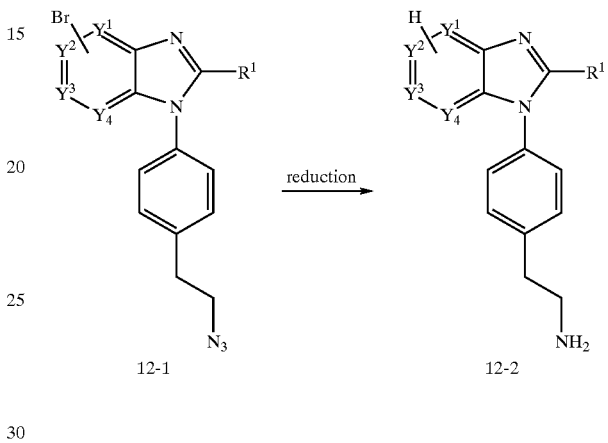

In addition, an intermediate compound 13-2 may be prepared by the methods illustrated in Scheme 13. Intermediate 13-1 may be prepared by the methods illustrated in Scheme 1. The reduction may also be carried out by the methods illustrated in Scheme 1.

Scheme 13

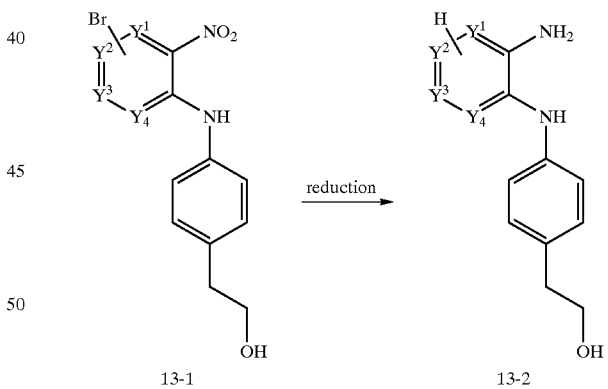

Intermediate compound 12-2 may be prepared by the methods illustrated in Scheme 12. Intermediate 12-1 may be prepared by the methods illustrated in Scheme 1 and Scheme 1b. The reduction may be carried out under known hydrogenation conditions such as in the presence of a metal catalyst such as palladium catalysts or platinum catalysts in the compound 14-2 may be carried out by a number of standard procedures known to those skilled in the art (e.g., "Protection for the Hydroxy Group and the Amino Group", in *Protective Groups in Organic Synthesis*, 2nd Edition, T. W. Greene and P. G. M. Wuts, Ed., John Wiley and Sons, Inc. 1991, pp. 117–118, 379–384).

An intermediate compound 14-3 may be prepared by the methods illustrated in Scheme 14. Intermediate 14-1 may be prepared by the methods illustrated in Scheme 1. Reduction of nitro group may be carried out according to the conditions illustrated in Scheme 1. Sulfonylation of the amino group of

Scheme 14

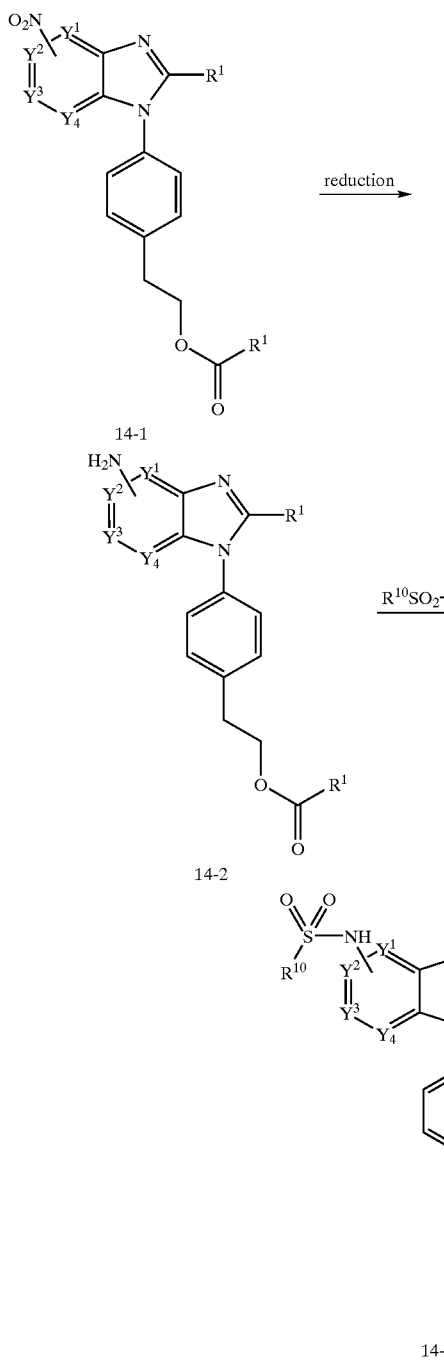

Intermediate compounds 15-6 and 15-7 may be prepared by the methods illustrated in Scheme 15. A compound of formula 15-1 may be treated with aqueous ammonia. Reaction temperatures are generally in the range of −100° C. to 250° C., preferably in the range of 0° C. to the reflux temperature, but if necessary, lower or higher temperature can be employed. Reaction times are, in general, from an hour to a week, preferably from 3 hours to 5 days, however shorter or longer reaction times, if necessary, can be employed. Thus, the obtained intermediate 15-2 may be treated with 1,3-diketone compound of formula 15-3, wherein $L^1$, $L^2$ and $L^3$ is independently selected from, but not limited to, halo, $C_{1-4}$alkyl, halo-substituted $C_{1-4}$ alkyl, $C_{1-4}$ alkoxy, halo-substituted $C_{1-4}$ alkoxy, nitro, cyano, $C_{1-4}$ alkoxy-$C_{1-4}$alkyl, acetyl, $C_{3-7}$ cycloalkyl, or two adjacent $L^1$, $L^2$ and $L^3$ groups may be joined together to form an alkylene chain having 3 or 4 members in which one or two (non-adjacent) carbon atoms may be replaced by oxygen atoms in the presence of a base such as pyridine, piperadine, imidazole, N,N-dimethylaminopyridine, $CH_3C(=O)ONa$ or $NaH_2PO_4$ and in the presence or absence of an acid such as acetic acid, hydrochloric aid or boric acid. Suitable reaction inert solvent includes water, dioxane, DMSO, DMF, p-toluene or ethanol. Reaction temperatures are generally in the range of −100° C. to 250° C., preferably in the range of 0° C. to the reflux temperature, but if necessary, lower or higher temperature can be employed. Reaction times are, in general, from an hour to a month, preferably from 6 hours to 14 days, however shorter or longer reaction times, if necessary, can be employed. Compounds 15-4 and 15-5 as obtained above may be treated with halogenating agent such as $POCl_3$, $SOCl_2$ or Vilsmeier complex (e.g., Laue T.; Plagens A., Eds.; NAMED ORGANIC REACTIONS, Wiley & Sons: New York, 1998, pp 258–262) in the presence or absence of a suitable reaction inert solvent such as dichloromethane, benzene or DMF to give compounds of formula 15-6 and/or 15-7. Reaction temperatures are generally in the range of −100° C. to 250° C. preferably in the range of 0° C. to the reflux temperature, but if necessary, lower or higher temperature can be employed. Reaction times are, in general, from 1 minute to a day, preferably from 20 minutes to 5 hours, however shorter or longer reaction times, if necessary, can be employed.

Scheme 15

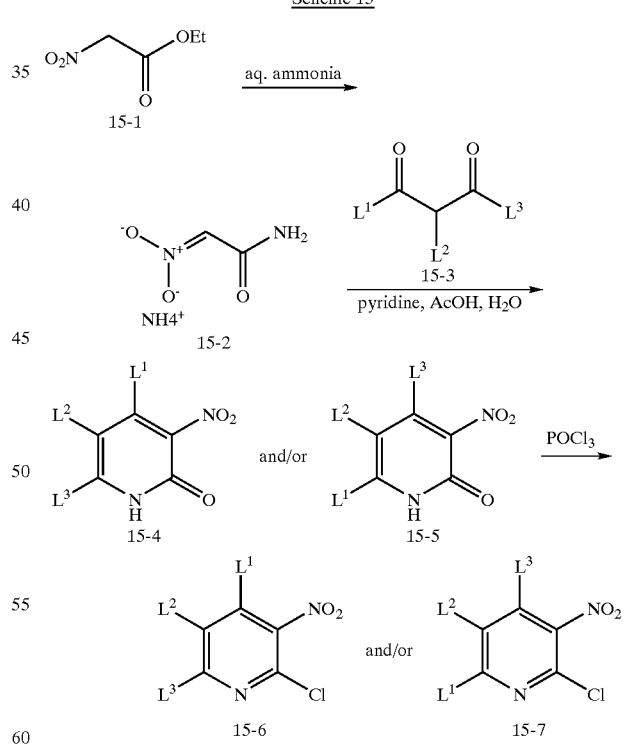

Reaction Scheme 16 illustrates a method for the preparation of the compound of formula (I) wherein $R^1$ is $NH_2$, A is phenyl, B is ethylene and W is NH (hereinafter represented by Formula ($Ia^{11}$)) and that of the compound of formula (I), wherein $R^1$ is $NHC(=O)R^{16}$ ($R^{16}$ is $C_{1-4}$ alkyl), A is phenyl, B is ethylene and W is NH (hereinafter represented by Formula (Ia$^{12}$)) and that of the compound of formula (I), wherein R$^1$ is NHS(O)$_2$R$^{16}$ (R$^{16}$ is C$_{1-4}$ alkyl), A is phenyl, B is ethylene and W is NH (hereinafter represented by Formula (Ia$^{13}$))

Compounds (Ia$^{11}$), (Ia$^{12}$) and (Ia$^{13}$) may be prepared through the process comprising:

(a) 2-amino-benzimidazole or 2-amino-imidazopyridine ring formation) with a compound of formula 16-1(2-7) to give the compound of formula (Ia$^{11}$);

(b) carbonylation of the compound of formula (Ia$^{11}$) to give the compound of formula (Ia$^{12}$); and (c) sulfonylation of the compound of formula (Ia$^{11}$) to give the compound of formula (Ia$^{13}$).

Each reaction step is described more specifically as follows.

(a) The compound 16-1(2-7) can be cyclized to form a benzimidazole or a imidazopyridine ring by reaction with an appropriate cyclizing agent to give the compound of formula (Ia$^{11}$) in a reaction inert solvent. Suitable cyclizing agents include cyanogen halide (e.g., cyanogen bromide), cyanamide, and guanidine-carbamate. Suitable solvents include tetrahydrofuran (THF), methanol, ethanol, acetonitrile, water, dimethylformamide and the like. This reaction may be carried out at about 0° C. to the reflux temperature of the reaction mixture, preferably at room temperature to the reflux temperature for about 1 minute to 120 hours, preferably 10 minutes to 72 hours.

(b) The compound of formula (Ia$^{11}$) may be reacted with an acylating agent such as alkylcarbonyl halide, acid anhydride in the presence of a base such as triethylamine or pyridine. Suitable reaction inert solvents include THF, DMF or benzene. The reaction may be carried out at about 0° C. to about reflux temperature for about 1 minute to 120 hours, preferably 10 minutes to 48 hours.

(c) The compound of formula (Ia$^{11}$) may also be reacted with an sulfonylating agent such as alkylsulfonyl halide, sulfonic acid anhydride in the presence of a base such as triethylamine or pyridine. Suitable reaction inert solvents include dichloromethane, THF, DMF or benzene. The reaction may be carried out at about 0° C. to about reflux temperature for about 1 minute to 120 hours, preferably 10 minutes to 48 hours.

Scheme 16

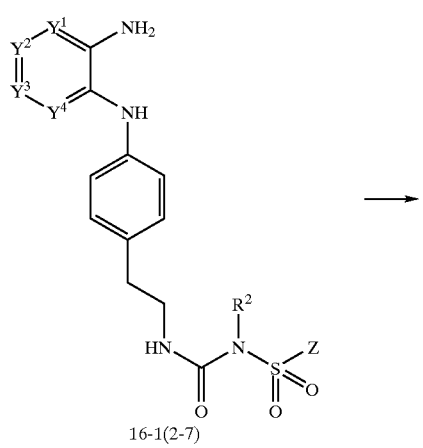

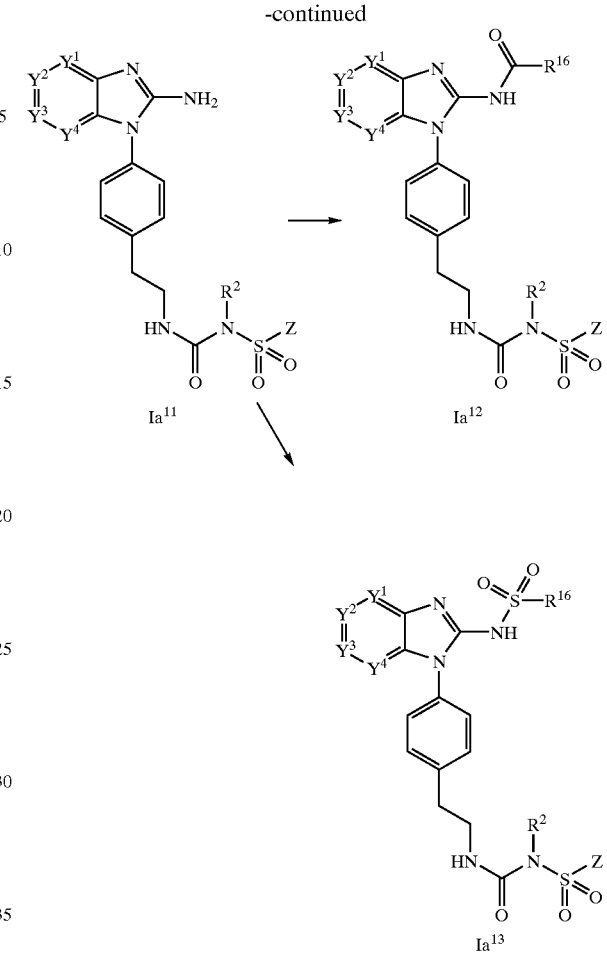

Reaction Scheme 17 illustrates a method for the preparation of the compound of formula (I) wherein R$^1$ is R$^{16}$NH (R$^{16}$ is C$_{1-8}$ alkyl), A is phenyl, B is ethylene and W is O or R$^{1a}$—N (R$^{1a}$ is H or C$_{1-4}$alkyl) (hereinafter represented by Formula (Ia$^{14}$)) and that of the compound of formula (I), wherein R$^1$ is (R$^{16}$)$_2$N (R$^{16}$ is C$_{1-8}$ alkyl), A is phenyl, B is ethylene and W is O or R$^{1a}$—N (R$^{1a}$ is H or C$_{1-4}$alkyl) (hereinafter represented by Formula (Ia$^{15}$)).

Compounds (Ia$^{14}$) and (Ia$^{15}$) may be prepared through the process comprising:

(a) 2-amino-benzimidazole or 2-amino-imidazopyridine ring formation with a compound of formula 17-1 to give a compound of formula (Ia$^{14}$); and (b) alkylation of the compound of formula (Ia$^{14}$) to give a compound of formula (Ia$^{15}$).

Each reaction step is described more specifically as follows.

(a) A compound of formula 17-1 may be subjected to a reaction with an isothiocyanate compound and a subsequent desulfurization under known conditions to give the compound of formula (Ia$^{14}$) (e.g., Y. Abe, H. Kayakiri, S. Satoh et al., *J. Med. Chem.* 1998, 41, 4062). For example, the first reaction may be carried out in a reaction inert solvent such as THF, acetonitrile or an alcohol (e.g., ethanol) at from about room temperature to about 100° C. from about 30 minutes to 48 hours. The cyclization may be carried out in the presence of an alkyl halide at from about 0° C. to reflux temperature from about 30 minutes to 48 hours.

(b) The compound of formula Ia[14] may be treated with appropriate alkyl halides in the presence of a base such as lithium diisopropyl amide (LDA), sodium hydride (NaH) or potassium t-butoxide in a reaction inert solvent such as hexamthylphosphorous triamide (HMPT), THF or DMF at about 0° C. to about 100° C. for about 5 minutes to about 48 hours.

Scheme 17

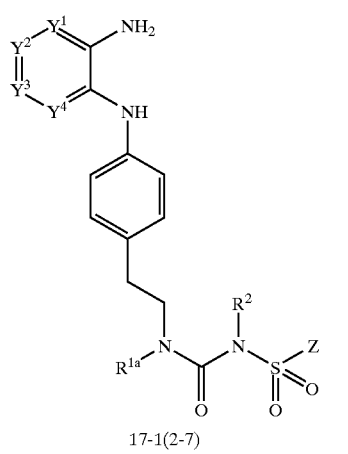

17-1(2-7)

MeNCS →

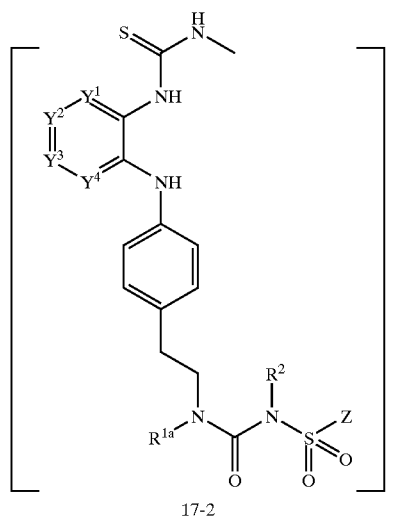

17-2

R[16]X →

-continued

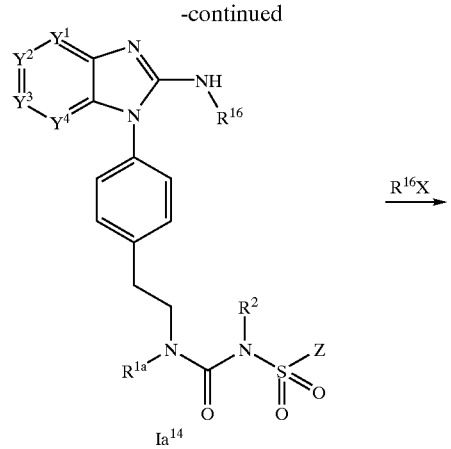

Ia[14]

R[16]X →

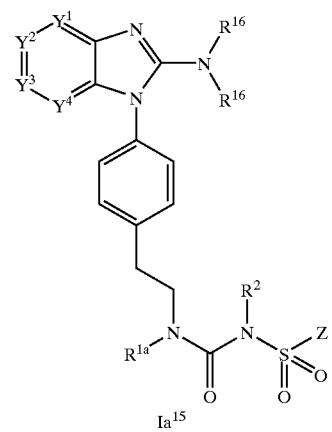

Ia[15]

Reaction Scheme 18 illustrates a method for the preparation of the compound of formula (I) wherein $R^1$ is $R^{18}S$ ($R^{18}$ is $C_{18}$ alkyl), A is phenyl, B is ethylene and W is O or $R^{1a}$—N ($R^{1a}$ is H or $C_{1-4}$alkyl) (hereinafter represented by Formula (Ia[17])).

Compound (Ia[17]) may be prepared through the process comprising:
 (a) 2-amino-benzimidazole or 2-amino-imidazopyridine ring formation with a compound of formula 18-1 to give a compound of formula (Ia[16]); and
 (b) alkylation of the compound of formula (Ia[16]) to give a compound of formula (Ia[17]).

Each reaction step is described more specifically as follows.
 (a) The compound of formula 18-1 may be subjected to a reaction with an thiocarbonyl reagent such as 1,1-thiocarbonylimidazole or di(2-pyridyl)thionocarbonate to give the compound of formula (Ia[16]) (e.g., Y. Abe, H. Kayakiri, S. Satoh et al., *J. Med. Chem.* 1998, 41, 4062). For example, the reaction may be carried out in a reaction inert solvent such as THF, acetonitrile, dichloromethane or an alcohol (e.g., ethanol) at from about room temperature to about 100° C. from about 30 minutes to 48 hours. The cyclization may be carried out in the presence of an alkyl halide at from about 0° C. to reflux temperature from about 30 minutes to 48 hours.
 (b) The compound of formula (Ia[16]) may be treated with appropriate alkyl halides in the presence of a base such as potassium carbonate, lithium diisopropyl amide (LDA), sodium hydride (NaH) or potassium t-butoxide in a reaction inert solvent such as hexamthylphosphorous triamide (HMPT), THF or DMF at about 0° C. to about 100° C. for about 5 minutes to about 48 hours.

Scheme 18

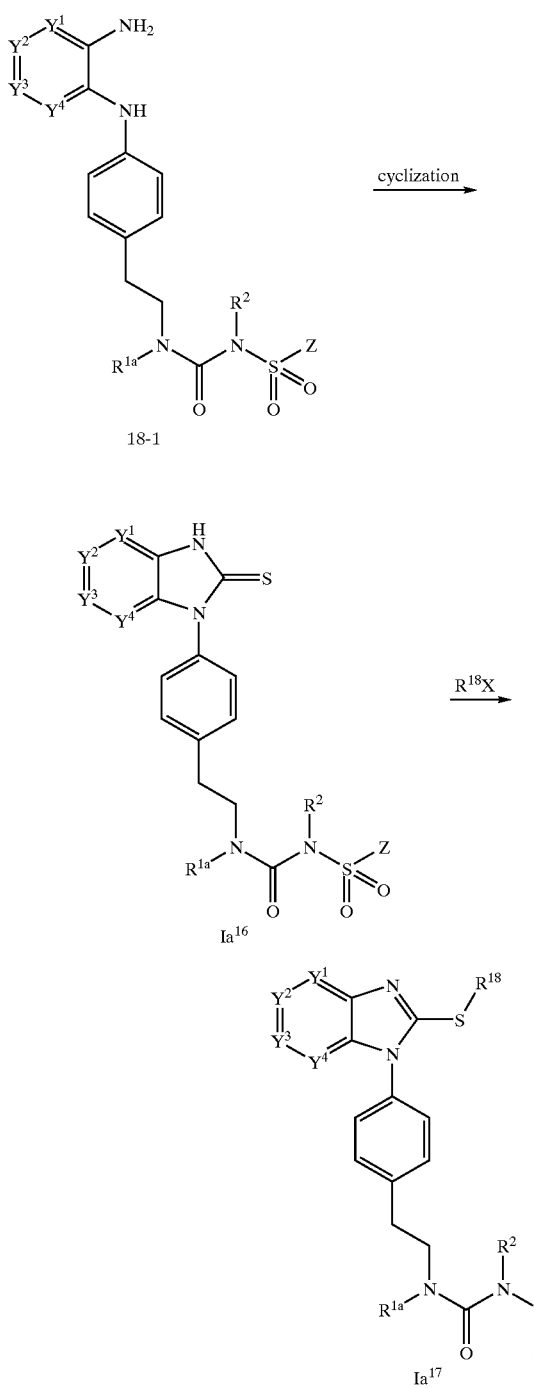

Scheme 19

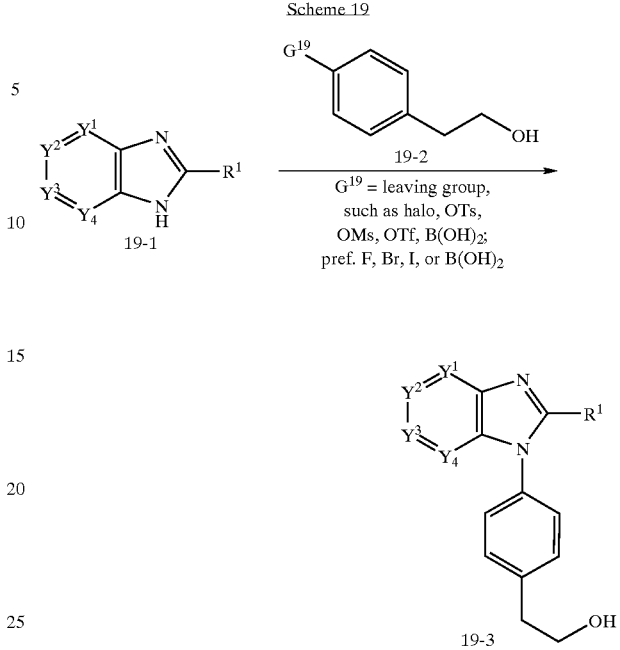

As shown in Scheme 19, the compound of formula 19-3 (1-5) may also be prepared by reacting a compound of formula 19-1 with a substituted benzene compound of formula 19-2 to give a 1-phenylbenzimidazole compound of formula 19-3; The compounds of formula 19-1 may be synthesized by any of the known methods. The group $G^{19}$ of the compounds of formula 19-2 is a selected from a suitable displaceable group, for example, fluoro, chloro, bromo, iodo, trifluoromethanesulfonyloxy, methanesulfonyloxy, p-toluenesulfonyloxy, or boronic acid group.

The coupling reaction may be carried out in the presence of a base in a reaction inert solvent. A preferred base is selected from, for example, but not limited to, an alkali or alkaline earth metal hydroxide, alkoxide, carbonate, or hydride, such as sodium hydroxide, potassium hydroxide, sodium methoxide, sodium ethoxide, potassium tert-butoxide, sodium carbonate, potassium carbonate, sodium hydride or potassium hydride, or an amine such as triethylamine, tributylamine, diisopropylethylamine, 2,6-lutidine, pyridine or dimethylaminopyridine. Preferred reaction inert solvents include, but are not limited to, benzene, toluene, xylene, o-dichlorobenzene, nitrobenzene, pyridine, dichloromethane, 1,2-dichloroethane, tetrahyrofuran, acetonitrile, dimethylformamide (DMF), 1,4-dioxane, dimethylsulfoxide (DMSO), 1,3-dimethyl-2-imidazolidinone, 1-methyl-2-pyrrolidinone or mixtures thereof. Reaction temperatures are generally in the range of −100 to 250° C., preferably in the range of 0 to 150° C., but if necessary, lower or higher temperature can be employed. Reaction times are, in general, from 1 minute to several weeks, preferably from 20 minutes to 1 week, however shorter or longer reaction times, if necessary, can be employed. Conveniently, the compound of formula 19-1 may be reacted with the compound of formula 19-2 in the presence of a suitable catalyst to form the compound of formula 19-3 by any synthetic procedure applicable to structure-related compounds known to those skilled in the literature (e.g., Lam, P. Y. S.; Clark, C. G.; Saubern, S; Adams, J; Winters, M. P.; Chan, D. M. T.; Combs, A., *Tetrahedron Lett.*, 1998, 39, 2941–2944., Kiyomori, A.; Marcoux, J.; Buchwald, S. L., *Tetrahedron Lett.*, 1999, 40, 2657–2660., Lam, P. Y. S.; Deudon, S.; Averill, K. M.; Li, R.; He, M. Y.; DeShong, P.; Clark, C. G., *J. Am. Chem. Soc.*, 2000, 122, 7600–7601., Collman, J. P.; Zhong, M., *Org. Lett.*, 2000, 2, 1233–1236.). Preferred reaction catalyst is selected from, for example, but not limited to, tetrakis(triphenylphosphine)-palladium, bis(triphenylphosphine)palladium(II) chloride, copper(I), copper(I) acetate, copper(I) bromide, copper(I) chloride, copper(I) iodide, copper(I) oxide, copper(I) trifluoromethanesulfonate, copper(II) acetate, copper(II) bromide, copper(II) chloride, copper(II) iodide, copper(II) oxide, or copper(II) trifluoromethanesulfonate.

As shown in Scheme 20, the compound of formula 1-5 or 1e-4 may also be prepared through the process comprising:
(a) acylation of a compound of formula 20-1;
(b) benzimidazole or imidazopyridine ring cyclization of a compound of formula 20-2 to give a compound of formula 20-3.

Scheme 20

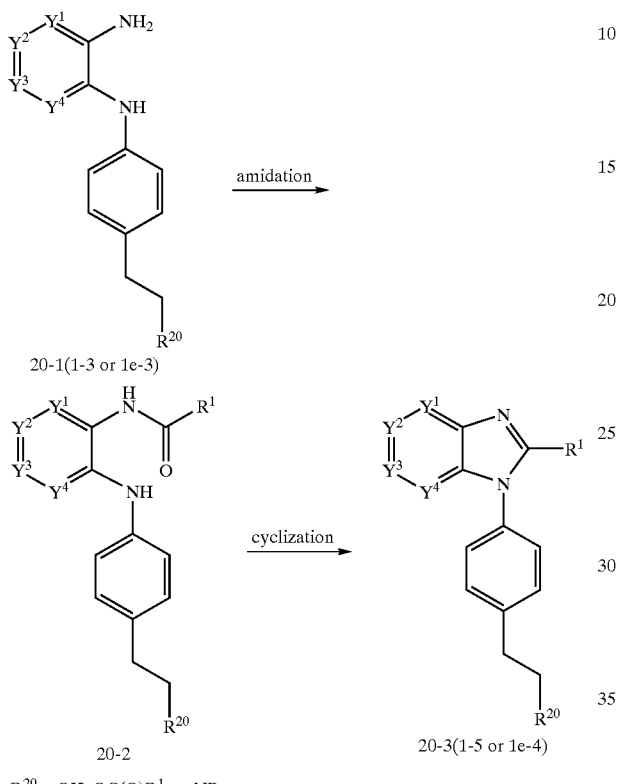

20-1 (1-3 or 1e-3)

20-2

20-3 (1-5 or 1e-4)

$R^{20}$ = OH, OC(O)$R^1$, or NP

Each reaction step is described more specifically as follows.
(a) A compound of formula 20-1 (1-3 or 1e-3) is reacted with an appropriate acylating reagent to give a compound of formula 20-2 in a reaction inert solvent in the presence of, or absence of a coupling reagent and/or additive. Suitable acylating reagents include, but are not limited to, a carboxylic acid, an amino carboxylic acid, an acid anhydride (e.g., acetic anhydride, isobutyric anhydride, benzoic anhydride, isonicotinic anhydride and the like) a formamidine (e.g., formamidine alkylate such as formamidine acetate), an alkyl carbonyl halide (e.g., a cycloalkyl carbonyl halide, bicyclic, heterocyclic, or bicyclic-heterocyclic-carbonyl halide, spirocarbocyclic- or spiro-heterocyclic-carbonyl halide), an aryl or an aryl alkyl carbonyl halide (e.g., phenylacethyl halide), an heteroaryl carboxylic acid (e.g., a piperidinyl carboxylic acid compound), trialkyl orthoformate (e.g., triethyl orthoformate), and the like. Suitable reaction inert solvents include, but are not limited to, benzene, toluene, xylene, o-dichlorobenzene, nitrobenzene, dichloromethane, 1,2-dichloroethane, tetrahyrofuran (THF), dimethylformamide (DMF), 1,4-dioxane, dimethylsulfoxide (DMSO) or mixtures thereof. Suitable coupling reagents are those typically used in peptide synthesis including, but are not limited to, dicyclohexylcarbodiimide (DCC), diisopropylcarbodiimide (DIPC), 1-ethyl-3-(3-dimethylaminopropyl)carbodiimide (WSC), benzotriazole-1-yloxy-tris(dimethylamino) phosphonium hexafluorophosphate (BOP), diphenylphosphorylazide (DPPA), N-[(1H-1,2,3-benzotriazol-1-yloxy)(dimethylamino)methylidene]-N-methylmethanaminium hexafluorophosphate (HBTU), tetramethylfluoroformamidinium hexafluorophosphate (TFFH), bromo[tri(1-pyrrolidinyl)]phosphonium hexafluorophosphate (PyBroP), bis(2-oxo-1,3-oxazolidin-3-yl)phosphinic chloride (BOP-Cl), (1H-1,2,3-benzotriazol-1-yloxy)[tri(1-pyrrolidinyl)]phosphonium hexafluorophosphate (PyBOP), or the like. Suitable additives include, but are not limited to, 1H-1,2,3-benzotriazol-1-ol (HOBt), 3H-[1,2,3]triazolo[4,5-b]pyridin-3-ol (HOAt), N,N-dimethyl-4-pyridinamine (DMAP), or the like. The reaction may be carried out at a temperature in the range from of −100° C. to 250° C., preferably in the range of 0° C. to the reflux temperature, but if necessary, lower or higher temperature can be employed. Reaction times are, in general, from 1 minute to a few days, preferably from 30 minutes to 48 hours, however shorter or longer reaction times, if necessary, can be employed.

(b) The resulting amide compound of formula 20-2 may also be cyclized to form a benzimidazole or imidazopyridine ring in the presence of a base (Bashir, M.; Kingston, D. G. I.; Carman, R. J.; Van Tassell, R. L.; Wilkins, T. D.,: Heterocycles, 1987, 26, 2877–2886.). A preferred base is selected from, for example, but not limited to, an alkali or alkaline earth metal hydroxide, alkoxide, or carbonate, such as sodium hydroxide, potassium hydroxide, lithium hydroxide, sodium methoxide, sodium ethoxide, potassium tert-butoxide, sodium carbonate, or potassium carbonate, in a reaction inert solvent. Preferred reaction inert solvents include, but are not limited to, water, methanol, ethanol, tetrahyrofuran (THF), benzene, toluene, xylene, dichloromethane, ethyleneglycol, or mixtures thereof. Reaction temperatures are generally in the range of −100 to 250° C., preferably in the range of 0 to 70° C., but if necessary, lower or higher temperature can be employed. Reaction times are, in general, from 1 hour to 5 days, preferably from 3 hours to 2 days, however shorter or longer reaction times, if necessary, can be employed.

As shown in Scheme 21, an intermediate compound of formula 21-2 (1-4 or 1e-4) may also be prepared.

Scheme 21

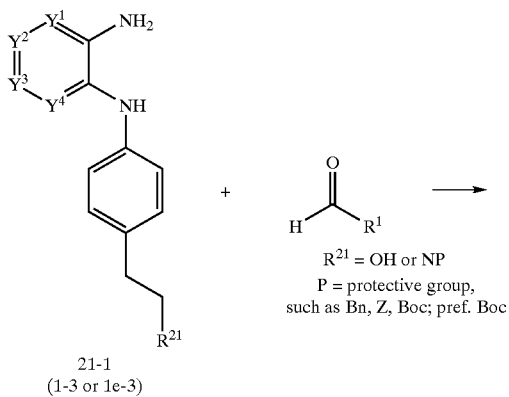

21-1
(1-3 or 1e-3)

$R^{21}$ = OH or NP
P = protective group, such as Bn, Z, Boc; pref. Boc

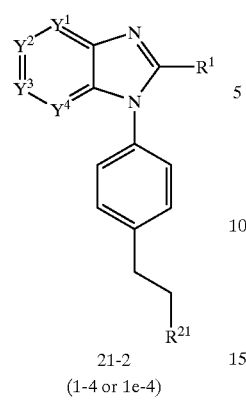

21-2
(1-4 or 1e-4)

The compound of formula 21-1 may be reacted with an appropriate aldehyde in a reaction inert solvent in the presence of, or absence of acid to produce an intermediate Shiff base. Succeedingly, the Shiff base can be oxidativery cyclized to form a benzimidazole or imidazopyridine ring by iodine, sulfur, cupric acetate, mercuric oxide, chloranil, active manganese dioxide, lead tetraacetate, nickel peroxide, barium permanganate, or the like. Suitable reaction inert solvents include, but are not limited to, methanol, ethanol, water, benzene, toluene, xylene, mesitylene, o-dichlorobenzene, nitrobenzene, dichloromethane, 1,2-dichloroethane, tetrahyrofuran (THF), dimethoxyethane (DME), 1,4-dioxane, dimethylsulfoxide (DMSO) or mixtures thereof. The reaction may be carried out at a temperature in the range from of −100 to 250° C., preferably in the range of 0° C. to the reflux temperature, but if necessary, lower or higher temperature can be employed. Reaction times are, in general, from 1 minute to a few days, preferably from 30 minutes to 48 hours, however shorter or longer reaction times, if necessary, can be employed.

Also, the aryl or heteroaryl fused imidazole comopounds of Formula (II) of this invention may be prepared by a variety of synthetic methods known to those skilled in the art.

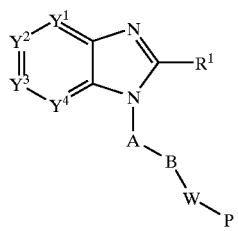

(II)

Reaction Scheme 22 illustrates a method for the preparation of the compound of formula (II).

Scheme 22

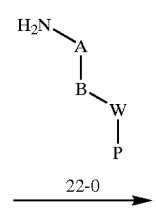

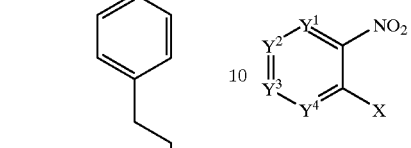

22-1

X = leaving group,
such as halo, OTs, OMs; pref. F or Cl

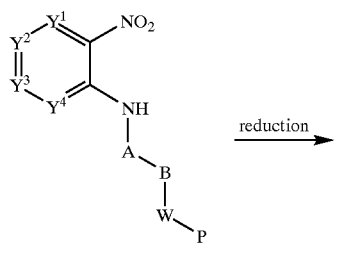

22-2

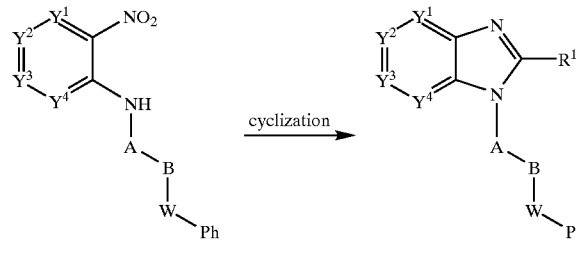

22-3          II

The compound of formula (II) may be prepared from the compound of 22-1(1-1) according to the similar procedure to that of described in Scheme 1.

Also, the aryl or heteroaryl comopounds of Formula (III) of this invention may be prepared by a variety of synthetic methods known to those skilled in the art.

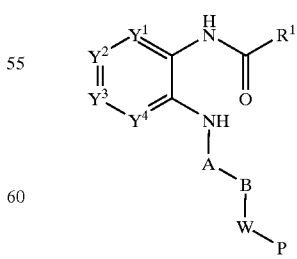

(III)

Reaction Scheme 23 illustrates a method for the preparation of the compound of formula (II).

Scheme 23

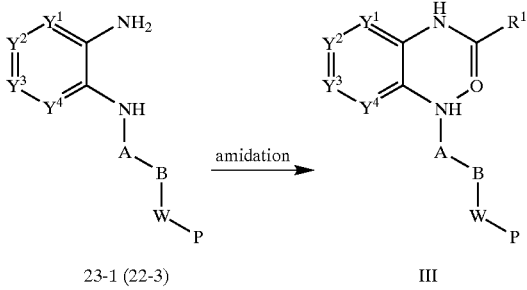

23-1 (22-3)        III

The compound of formula (III) may be prepared from the compound of 23-1(22-3) according to the similar procedure to that of described in Scheme 20.

In addition, the benzimidazole moiety of the compound of formula (I) which can be used herein may be prepared by known methods as shown in, for example: (1) Grimmett, M. R. Imidazoles and Their Benzo Derivatives: (iii) Synthesis and Applications. In *Comprehensive Heterocyclic Chemistry*, Kevin T. Potts, Eds.; Pergamon Press Ltd.: Oxford, UK, 1984; Vol.5, pp457–498; (2) Grimmett, M. R. Imidazoles. In *Comprehensive Heterocyclic Chemistry II*, Ichiro Shinkai, Eds.; Elsevier Science Ltd.: Oxford, UK, 1996; Vol.3, pp77–220.

The imidazopyridine moiety of the compound of formula (I) which can be used herein may be prepared by known methods as shown in, for example: Townsend L. B; Wise D. S. Bicyclo 5-6 Systems: Three Heteroatoms 2:1. In *Comprehensive Heterocyclic Chemistry II*, Christopher A. Ramsden, Eds.; Elsevier Science Ltd.: Oxford, UK, 1996; Vol.7, pp283–349.

The starting materials 1-1, 1-8, 1-9, 1a-2, 1d-3, 1d-4, 1d-5, 1d-6, 1f-0, 2-2, 5-4, 15-1, 15-3, 22-0 and the other reactants are known or commercially available compounds, or may be prepared according to known procedures for a person skilled in the art.

The subject invention also includes isotopically-labelled compounds, which are identical to those recited in formula (I), but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^3$H and $^{14}$C are incorporated, are useful in drug and/or substrate tissue distribution assay. Tritiated, i.e., $^3$H, and carbon-14, i.e., $^{14}$C, isotopes are particularly preferred for their ease of presentation and detectability. Further, substitution with heavier isotopes such as deutrium, i.e., $^2$H, can afford therapeutic advantage resulting from greater metabolic stability, for example increased in vivo half-life or reduced dosage requirement and, hence, may be preferred in some circumstances. Isotopically labelled compounds of formula (I) of this invention and prodrugs thereof can generally be prepared by carrying out the procedure disclosed in above-disclosed Schemes and/or Examples and Preparations below, by submitting a readily available isotopically labelled reagent for a non-isotopically labeled reagent.

The present invention includes salt forms of the compounds (I) as obtained Certain compounds of the present invention are capable of forming pharmaceutically acceptable non-toxic cations. Pharmaceutically acceptable non-toxic cations of compounds of formula (I) may be prepared by conventional techniques by, for example, contacting said compound with a stoichiometric amount of an appropriate alkali or alkaline earth metal (sodium, potassium, calcium and magnesium) hydroxide or alkoxide in water or an appropriate organic solvent such as ethanol, isopropanol, mixtures thereof, or the like.

The bases which are used to prepare the pharmaceutically acceptable base addition salts of the acidic compounds of this invention of formula (I) are those which form non-toxic base addition salts, i.e., salts containing pharmaceutically acceptable cations, such as adenine, arginine, cytosine, lysine, benethamine(i.e., N-benzyl-2-phenyletylamine), benzathine(i.e., N,N-dibenzylethylenediamine), choline, diolamine(i.e., diethanolamine), ethylenediamine, glucosamine, glycine, guanidine, guanine, meglumine(i.e., N-methylglucamine), nicotinamide, olamine(i.e., ethanolamine), ornithine, procaine, proline, pyridoxine, serine, tyrosine, valine and tromethamine(i.e., tris or tris (hydroxymethyl)aminomethane). The base addition salts can be prepared by conventional procedures.

Insofar as the certain compounds of this invention are basic compounds, they are capable of forming a wide variety of different salts with various inorganic and organic acids.

The acids which are used to prepare the pharmaceutically acceptable acid addition salts of the basic compounds of this invention of formula (I) are those which form non-toxic acid addition salts, i.e., salts containing pharmaceutically acceptable anions, such as the chloride, bromide, iodide, nitrate, sulfate or bisulfate, phosphate or acid phosphate, acetate, lactate, citrate or acid citrate, tartrate or bi-tartrate, succinate, malate, fumarate, gluconate, saccharate, benzoate, methanesulfonate, ethanesulfonate, benzenesulfonate, p-toluenesulfonate, adipate, aspartate camsylate, (i.e., 1,2-ethanedisulfontate), estolate(i.e., laurylsulfate), gluceptate(i.e., gluscoheptonate), gluconate, 3-hydroxy-2-naphthoate, xionofoate(i.e., 1-hydrroxy-2-naphthoate), isethionate,(i.e., 2-hydroxyethanesulfonate), mucate(i.e., galactarate), 2-naphsylate(i.e., naphthalenesulphonate, stearate, cholate, glucuronate, glutamate, hippurate, lactobionate, lysinate, maleate, mandelate, napadisylate, nicatinate, polygalacturonate, salicylate, sulphosalicylate, tannate, tryptophanate, borate, carbonate, oleate, phthalate and pamoate (i.e., 1,1'-methylene-bis-(2-hydroxy-3-naphthoate). The acid addition salts can be prepared by conventional procedures.

Also included within the scope of this invention are bioprecursors (also called pro-drugs) of the compounds of the formula (I). A bioprecursor of a compound of the formula (I) is a chemical derivative thereof which is readily converted back into the parent compound of the formula (I) in biological systems. In particular, a bioprecursor of a compound of the formula (I) is converted back to the parent compound of the formula (I) after the bioprecursor has been administered to, and absorbed by, a mammalian subject, e.g., a human subject. For example, it is possible to make a bioprecursor of the compounds of formula (I) in which one or both of L and W includes hydroxy groups by making an ester of the hydroxy group. When only one of L and W includes hydroxy group, only mono-ester are possible. When both L and W include hydroxy, mono- and di-esters (which can be the same or different) can be made. Typical esters are simple alkanoate esters, such as acetate, propionate, butyrate, etc. In addition, when L or W include a hydroxy group, bioprecursors can be made by converting the hydroxy group to an acyloxymethyl derivative (e.g., a pivaloyloxymethyl derivative) by reaction with an acyloxymethyl halide (e.g., pivaloyloxymethyl chloride).

When the compounds of the formula (I) of this invention may form solvates such as hydrates, such solvates are included within the scope of this invention.

Also, the compounds of formula (I) may be expected more effective therapeutic effects with being co-administered with a COX-2 selective NSAID.

Further, the present invention also encompasses a pharmaceutical composition for the treatment of inflammation, rheumatoid arthritis, pain, common cold, osteoarthritis, neuropathic pain, brain tumor, diuresis, or the like, which comprises a therapeutically effective amount of the aryl or heteroaryl fused imidazole compound of formula (I) and a COX-2 selective NSAID or their pharmaceutically acceptable salt together with a pharmaceutically acceptable carrier.

The compounds of the invention may advantageously be employed in combination with one or more other therapeutic ingredients selected from, a COX-2 selective, COX-1 selective or non-selective NSAIDs, opioids, anticonvulsants, antidepressants, local anesthetics, disease-modifying anti-rheumatoid drugs, or steroid.

The combination with a COX-2 selective NSAID is particularly favoured for use in the prophylaxis and treatment of pain and arthritis. Examples of a COX-2 selective NSAID are nimesulide, celecoxib, rofecoxib and valdecoxib.

The compounds of Formula (I) have been found to possess an activity as prostaglandin $E_2$ receptor antagonist, preferably as $EP_4$ receptor antagonist. Preferably, these compounds are useful as an analgesic, anti-inflammatory, diuretic, and the like, in mammalian subjects, especially humans in need of such agents. The affinity, antagonist activities and analgesic activity can be demonstrated by the following tests respectively.

METHOD FOR ASSESSING BIOLOGICAL ACTIVITIES

In vitro Assays
Rat EP Receptor Cell Membrane Binding Assay
Stable Expression of Rat EP1, 2, 3 and 4 Receptors in the Human Embryonic Kidney (HEK293) Cell Line The cDNA clones of rat EP1, 2, 3 and 4 receptors are obtained by polymerase chain reaction (PCR) from rat kidney or heart cDNA libraries (Clontech). Human embryonic kidney cells (HEK 293) are stably transfected with expression vectors for rat EP1, 2, 3 and 4 receptors in according to the method described in the article; the journal of biological chemistry vol.271 No.39, pp23642–23645.

Preparation of Membrane Fraction

The EP1, 2, 3 and 4 transfectant are grown in Dulbecco's modified Eagle's medium containing 10% fetal calf serum, 100 U/ml penicillin, 100 μg/ml streptomycin and 600 μg/ml G418 (selection medium) at 37° C. in a humidified atmosphere of 5% $CO_2$ in air. For the membrane preparation, cells are harvested with phosphate buffered saline (PBS) and centrifuged at 400×g for 5 min. The pellet is suspended with child (4° C.) PBS containing 1 mM Pefabloc (4-(2-aminoethyl)-benzenesulfonyl fluoride (AEBSF)), 10 □M Phosphoramidon, 1 □M Pepstatin A, 10 □M Elastatinal, 100 □M Antipain. Cells are lysed with ultrasonic cell disrupter for 20-sec sonication. Then cell mixtures are centrifuged at 45,000×g for 30 minutes. The pellet is resuspended in assay buffer (10 mM 2-morpholinoethanesulfonic acid (MES)-KOH, 1 mM etylenediamine tetraacetic acid (EDTA), 10 mM $MgCl_2$, pH 6.0), and protein concentration is determined by Bradford method (Bio-Rad assay). This membrane preparation is stored at −80° C. freezer until use for binding assay.

Binding Assay
Membrane Binding Assay

[$^3$H]-$PGE_2$ membrane binding assays are performed in the reaction mixture of 10 mM MES/KOH (pH6.0), 10 mM $MgCl_2$, 1 mM EDTA, 1 nM [$^3$H]-$PGE_2$ (Amersham TRK431, 164 Ci/mmol), 2~10 □g of protein from membrane fraction (rat EP1, 2, 3 and 4/HEK293 transfectant) and test compound (total volume is 0.1 ml in 96 well polypropylene plate). Incubation is conducted for 60 min at room temperature prior to separation of the bound and free radioligand by rapid filtration through glass fiber filters (Printed Filtermat B, 1205–404, glass fiber, double thickness, size 102×258 mm, Wallac inc., presoaked in 0.2% polyethylenimine). Filters are washed with assay buffer and the residual [$^3$H]-$PGE_2$ bound to the filter is determined by liquid scintillation counter (1205 Betaplate™). Specific binding is defined as the difference between total binding and nonspecific binding which is determined in the presence of 10 □M $PGE_2$.

cAMP Assay in Rat $EP_4$ Transfectant

HEK293 cells expressing rat $EP_4$ receptors (r$EP_4$ cells) are maintained in DMEM containing 10% FCS and 600 □g/ml geneticin. For harvesting r$EP_4$ cells, culture medium is aspirated and cells in 75 $cm^2$ flask are washed with 10 ml of phosphate buffered saline (PBS). Another 10 ml of PBS is added to the cells and incubated for 20 min at room temperature. Rat $EP_4$ cells are harvested by pipetting and centrifuged at 300 g for 4 min. Cells are resuspended in DMEM without neutral red at a density of $5×10^5$ cells/ml. The cells (70 □l) are mixed with 70 □l of DMEM (without neutral red) containing 2 mM IBMX (PDE inhibitor), 1 nM $PGE_2$ and test compounds in PCR-tubes, and incubated at 37° C. for 10 min. The reaction is stopped by heating at 100° C. for 10 min with thermal cycler. Concentration of cAMP in reaction mixtures is determined with SPA cAMP Kit (Amersham) according to the manufacture's instruction.

Reference: Eur.J.Pharmacol. 340 (1997) 227–241
In vivo Assays
Carrageenan Induced Mechanical Hyperalgesia in Rats Male 4-week-old SD rats (Japan SLC) were fasted over night. Hyperalgesia was induced by intraplantar injection of λ-carrageenin (0.1 ml of 1% w/v suspension in saline, Zushikagaku). The test compounds (1 ml of 0.1% methylcellulose/100 g body weight) were given per orally at 5.5 hours after the carrageenin injection. The mechanical pain threshold was measured by analgesy meter (Ugo Basile) at 4, 5, 6.5 and 7.5 hours after the carrageenin injection and the change of pain threshold was calculated.

Reference: Randall L. O. & Selitto I. J., Arch. Int. Pharmacodyn. 111, 409–419, 1957

Prostaglandin $E_2$($PGE_2$)-Induced Thermal Hyperalgesia in Rats

Male 4-week-old SD rats (Japan SLC) were fasted over night. Hyperalgesia was induced by intraplantar injection of 100 ng of PGE2 in 5% DMSO/saline(100 ul) into the right hindpaw of the rats. Animals were given orally or intravenously either vehicle (po: 0.1% methyl cellulose, iv: 10% DMSO/saline) or a test compound 15 or 5 min. prior to $PGE_2$ injection, respectively. Rats were placed in plastic cages of plantar test apparatus (Ugo Basile) and the mobile radiant heat source was focused on right hind paw of the rats. The thermal paw-withdrawal latency (sec.) was measured at 15 min after $PGE_2$ injection and the change in withdrawal threshold was calculated.

Reference: Hargreaves K. et al., Pain 32, 77–88, 1988.

Most of the compounds prepared in the working examples appearing hereafter demonstrate higher affinity for $EP_4$-receptors than for EP1, 2 and 3-receptors.

Some preferred compounds prepared in the working examples as described below were tested by the above method, and showed an $ED_{50}$ value under 60 mg/kg.

The aryl or heteroaryl fused imidazole compounds of formula (I) of this invention can be administered via either the oral, parenteral or topical routes to mammals. In general, these compounds are most desirably administered to humans in doses ranging from 0.1 mg to 3000 mg, preferably from 1 mg to 500 mg, which may be administered in a single dose or in divided doses throughout the day, although variations will necessarily occur depending upon the weight and condition of the subject being treated, the disease state being treated and the particular route of administration chosen. However, for example, a dosage level that is in the range of from 0.01 mg to 10 mg per kg of body weight per day is most desirably employed for treatment of pain associated with inflammation.

The compounds of the present invention may be administered alone or in combination with pharmaceutically acceptable carriers or diluents by either of the above routes previously indicated, and such administration can be carried out in single or multiple doses. More particularly, the novel therapeutic agents of the invention can be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various nontoxic organic solvents, etc. Moreover, oral-pharmaceutical compositions can be suitably sweetened and/or flavored. In general, the therapeutically-effective compounds of this invention are present in such dosage forms at concentration levels ranging 5% to 95% by weight.

For oral administration, tablets containing various excipients such as microcrystalline cellulose, sodium citrate, calcium carbonate, dipotassium phosphate and glycine may be employed along with various disintegrants such as starch and preferably corn, potato or tapioca starch, alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of a compound of the present invention in either sesame or peanut oil or in aqueous propylene glycol may be employed. The aqueous solutions should be suitably buffered (preferably pH>8) if necessary and the liquid diluent first rendered isotonic. These aqueous solutions are suitable for intravenous injection purposes. The oily solutions are suitable for intra-articular, intramuscular and subcutaneous injection purposes. The preparation of all these solutions under sterile conditions is readily accomplished by standard pharmaceutical techniques well known to those skilled in the art. Additionally, it is also possible to administer the compounds of the present invention topically when treating inflammatory conditions of the skin and this may preferably be done by way of creams, jellies, gels, pastes, ointments and the like, in accordance with standard pharmaceutical practice.

EXAMPLES

The invention is illustrated in the following non-limiting examples in which, unless stated otherwise: all operations were carried out at room or ambient temperature, that is, in the range of 18–25° C.; evaporation of solvent was carried out using a rotary evaporator under reduced pressure with a bath temperature of up to 60° C.; reactions were monitored by thin layer chromatography (TLC) and reaction times are given for illustration only; melting points (mp) given are uncorrected (polymorphism may result in different melting points); the structure and purity of all isolated compounds were assured by at least one of the following techniques: TLC (Merck silica gel 60 $F_{254}$ precoated TLC plates), mass spectrometry, nuclear magnetic resonance (NMR), infrared red absorption spectra (IR) or microanalysis. Yields are given for illustrative purposes only. Flash column chromatography was carried out using Merck silica gel 60 (230–400 mesh ASTM). Low-resolution mass spectral data (EI) were obtained on a Automass 120 (JEOL) mass spectrometer. Low-resolution mass spectral data (ESI) were obtained on a Quattro II (Micromass) mass spectrometer or a ZMD (Micromass). NMR data was determined at 270 MHz (JEOL JNM-LA 270 spectrometer) or 300 MHz (JEOL JNM-LA300 spectrometer) using deuterated chloroform (99.8% D) or dimethylsulfoxide (99.9% D) as solvent unless indicated otherwise, relative to tetramethylsilane (TMS) as internal standard in parts per million (ppm); conventional abbreviations used are: s=singlet, d=doublet, t=triplet, q=quartet, quint=quintet, m=multiplet, br.=broad, etc. IR spectra were measured by a Shimazu infrared spectrometer (IR-470). Chemical symbols have their usual meanings; bp (boiling point), mp (melting point), L (liter(s)), mL (milliliter(s)), g (gram(s)), mg (milligram(s)), mol (moles), mmol (millimoles), eq. (equivalent(s)), quant. (quantitative yield).

Example 1

2-ETHYL-5,7-DIMETHYL-3-(4-{2-[({[(4-METHYLPHENYL)SULFONYL]AMINO}CARBONYL)AMINO]ETHYL}PHENYL)-3H-IMIDAZO[4,5-b]PYRIDINE

Step 1. 4,6-Dimethyl-3-nitro-2(1H)-pyridinone

A mixture of ethyl nitroacetate (80.0 g, 601 mmol) in ammonium hydroxide (25% $NH_3$ in water, 400 mL) was stirred at room temperature for 3 days, and then the solution was concentrated by air-drying. The residue was dissolved in water (450 mL). To the solution was added 2,4-pentanedione (73.1 g, 730 mmol), pyridine (16.2 mL, 200 mmol) and acetic acid (11.4 mL, 200 mmol), and the mixture was stirred for an additional 7 days. The resulting precipitates were collected by filtration and dried under reduced pressure to give 35.0 g (35%) of the title compound as yellow solids: $^1$H-NMR (DMSO-$d_6$) δ 12.44 (1H, br.s), 6.06 (1H, s), 2.19 (3H, s), 2.13 (3H, s).

Step 2. 2-Chloro-4,6-dimethyl-3-nitropyridine

A mixture of 4,6-dimethyl-3-nitro-2(1H)-pyridinone (step 1, 10.0 g, 29.7 mmol) in phosphorus oxychloride (35 mL, 187.3 mmol) was stirred at 95° C. for 3 h, then cooled to 45° C. The excess amount of phosphorus oxychloride was removed by distillation under reduced pressure at 45° C. The residue was cooled to room temperature, and diluted with dichloromethane (75 mL). The resulting solution was cooled to 0° C., and 2N hydrochloric acid (50 mL) was added dropwise into the solution. The organic layer was separated, and washed with 2N hydrochloric acid (4×25 mL), 2N aqueous NaOH (2×50 mL) and brine (50 mL). The organic phase was dried ($MgSO_4$) and concentrated under reduced pressure to give 10.0 g (90%) of the title compound as white solids: $^1$H-NMR (CDCl$_3$) δ 7.07 (1H, s), 2.56 (3H, s), 2.35 (3H, s).

Step 3. 2-{4-[(4,6-Dimethyl-3-nitro-2-pyridinyl)amino]phenyl}ethanol

A mixture of 2-chloro-4,6-dimethyl-3-nitropyridine (step 2, 1.3 g, 7.0 mmol) and 4-aminophenylethyl alcohol (1.4 g, 10.2 mmol) was placed in a sealed tube and heated at 150°

C. for 3 h. The reaction mixture was cooled and purified by flash column chromatography on silica gel eluting with hexane/ethyl acetate (2:1) to afford 1.6 g (80%) of the title compound as orange solids: $^1$H-NMR (CDCl$_3$) δ 9.55 (1H, br.s), 7.57 (2H, d, J=8.4 Hz), 7.20 (2H, d, J=8.4 Hz), 6.52 (1H, s), 3.84 (2H, t, J=6.4 Hz), 2.85 (2H, t, J=6.4 Hz), 2.54 (3H, s).

Step 4. 2-{4-[(3-Amino-4,6-dimethyl-2-pyridinyl)amino] phenyl}ethanol

To a stirred solution of 2-{4-[(4,6-dimethyl-3-nitro-2-pyridinyl)amino]phenyl}ethanol (step 3, 1.6 g, 5.6 mmol) in ethyl acetate (15 mL) was added 10% Pd—C (160 mg). The mixture was stirred at room temperature for 6 h under hydrogen atmosphere. The palladium catalyst was removed by filtration and washed with ethanol (100 mL). The filtrate was concentrated under reduced pressure to afford 1.3 g (92%) of the title compound as pale yellow solids: $^1$H-NMR (CDCl$_3$) δ 7.10 (4H, s), 6.61 (1H, s), 3.81 (2H, t, J=6.4 Hz), 2.80 (2H, t, J=6.4 Hz), 2.36 (3H, s), 2.19 (3H, s).

Step 5. 2-[4-(2-Ethyl-5,7-dimethyl-3H-imidazo[4,5-b] pyridin-3-yl)phenyl]ethyl propionate To a stirred suspension of 2-{4-[(3-amino-4,6-dimethyl-2-pyridinyl)amino]phenyl}ethanol (step 4, 1.3 g, 5.1 mmol) in toluene (30 mL) was added dropwise propionyl chloride (990 mg, 10.7 mmol) at 0° C., and the reaction mixture was heated at reflux temperature for 2 h. After cooling, the mixture was poured into water (50 mL) and extracted with ethyl acetate (100 mL). The organic layer was washed with 2N aqueous NaOH (50 mL) and brine (50 mL), then dried (MgSO$_4$). Removal of solvent gave 1.8 g (quant.) of the title compound as brown solids: $^1$H-NMR (CDCl$_3$) δ 7.41 (2H, d, J=8.4 Hz), 7.33 (2H, d, J=8.4 Hz), 6.90 (1H, s), 4.37 (2H, t, J=6.9 Hz), 3.04 (2H, t, J=6.9 Hz), 2.82 (2H, q, J=7.6 Hz), 2.65 (3H, s), 2.52 (3H, s), 2.35 (2H, q, J=7.6 Hz), 1.27 (3H, t, J=7.6 Hz), 1.14 (3H, t, J=7.6 Hz).

Step 6. 2-[4-(2-Ethyl-5,7-dimethyl-3H-imidazo[4,5-b] pyridin-3-yl)phenyl]ethanol To a solution of 2-[4-(2-ethyl-5,7-dimethyl-3H-imidazo [4,5-b]pyridin-3-yl)phenyl]ethyl propionate (step 5, 1.75 g, 5.1 mmol) in methanol/THF (v/v, 1:1, 28 mL) was added 4N aqueous LiOH (4.6 mL, 18.4 mmol) and the resulting mixture was stirred at room temperature. After 3 h, the mixture was concentrated. The residue was dissolved in water (30 mL) and extracted with ethyl acetate (100 mL). The organic layer was washed with brine (50 mL), dried (MgSO$_4$), and concentrated. Purification by flash column chromatography on silica gel eluting with hexane/ethyl acetate (gradient elution from 2:1 to 0:1) to afford 1.3 g (86%) of the title compound as pale brown solids: $^1$H-NMR (CDCl$_3$) δ 7.40 (2H, d, J=8.4 Hz), 7.31 (2H, d, J=8.4 Hz), 6.91 (1H, s), 3.81–3.75 (2H, m), 3.47 (1H, br.s), 2.92 (2H, d, J=8.4 Hz), 2.81 (2H, q, J=7.6 Hz), 2.66 (3H, s), 2.51 (3H, s), 1.27 (3H, t, J=7.6 Hz).

Step 7. 3-[4-(2-Chloroethyl)phenyl]-2-ethyl-5,7-dimethyl-3H-imidazo[4,5-b]pyridine To a solution of 2-[4-(2-ethyl-5,7-dimethyl-3H-imidazo [4,5-b]pyridin-3-yl)phenyl]ethanol (step 6, 2.2 g, 7.4 mmol) in toluene (40 mL) was added thionyl chloride (2.0 mL, 23.6 mmol), and the resulting mixture was stirred at 80° C. for 3 h. The volatile components were removed under reduced pressure, and the residue was purified by flash column chromatography on silica gel eluting with hexane/ethyl acetate (gradient elution from 2:1 to 1:1) to afford 2.1 g (90%) of the title compound as white solids: $^1$H-NMR (CDCl$_3$) δ 7.41 (2H, d, J=8.4 Hz), 7.35 (2H, d, J=8.4 Hz), 6.90 (1H, s), 3.78 (2H, t, J=7.4 Hz), 3.15 (2H, t, J=7.4 Hz), 2.83 (2H, q, J=7.6 Hz), 2.71 (3H, s), 2.54 (3H, s), 1.28 (3H, t, J=7.6 Hz).

Step 8. 2-[4-(2-Ethyl-5,7-dimethyl-3H-imidazo[4,5-b] pyridin-3-yl)phenyl]ethyl azide To a stirred solution of 3-[4-(2-chloroethyl)phenyl]-2-ethyl-5,7-dimethyl-3H-imidazo[4,5-b]pyridine (step 7, 2.8 g, 9.0 mmol) and KI (1.5 g, 9.0 mmol) in DMF (50 mL) was added sodium azide (1.2 g, 18.0 mmol), and then the resulting mixture was stirred overnight at 100° C. The reaction mixture was poured into water (100 mL), and extracted with ethyl acetate (100 mL). The organic layer was washed with water (50 mL) and brine (50 mL), then dried (Na$_2$SO$_4$). After removal of solvent, the crude product was purified by flash column chromatography on silica gel eluting with hexane/ethyl acetate (1:1) to afford 2.35 g (85%) of the title compound as white solids: $^1$H-NMR (CDCl$_3$) δ 7.41 (2H, d, J=8.4 Hz), 7.35 (2H, d, J=8.4 Hz), 6.90 (1H, s), 3.59 (2H, t, J=7.1 Hz), 2.99 (2H, t, J=7.1 Hz), 2.83 (2H, q, J=7.6 Hz), 2.65 (3H, s), 2.52 (3H, s), 1.27 (3H, t, J=7.6 Hz).

Step 9. 2-[4-(2-Ethyl-5,7-dimethyl-3H-imidazo[4,5-b] pyridin-3-yl)phenyl]ethylamine To a solution of 2-[4-(2-ethyl-5,7-dimethyl-3H-imidazo [4,5-b]pyridin-3-yl)phenyl]ethyl azide (step 8. 2.35 g, 7.3 mmol) in methanol (50 mL) was added 10% Pd—C (200 mg). The resulting mixture was stirred for 4 h under hydrogen atmosphere. The mixture was filtered through a pad of Celite and the filtrate was concentrated. The residue was purified by flash column chromatography on silica gel eluting with dichloromethane/methanol/triethylamine (100:5:1) to afford 2.01 g (94%) of the title compound as white solids: $^1$H-NMR (CDCl$_3$) δ 7.39 (2H, d, J=8.4 Hz), 7.32 (2H, d, J=8.4 Hz), 6.90 (1H, s), 3.05 (2H, t, J=7.3 Hz), 2.88–2.78 (4H, m), 2.56 (3H, s), 2.51 (3H, s), 1.28 (3H, t, J=7.6 Hz).

Step 10. 2-Ethyl-5,7-dimethyl-3-(4-{2-[({[(4-methylphenyl)sulfonyl]amino}carbonyl)amino] ethyl}phenyl)-3H-imidazo[4,5-b]pyridine

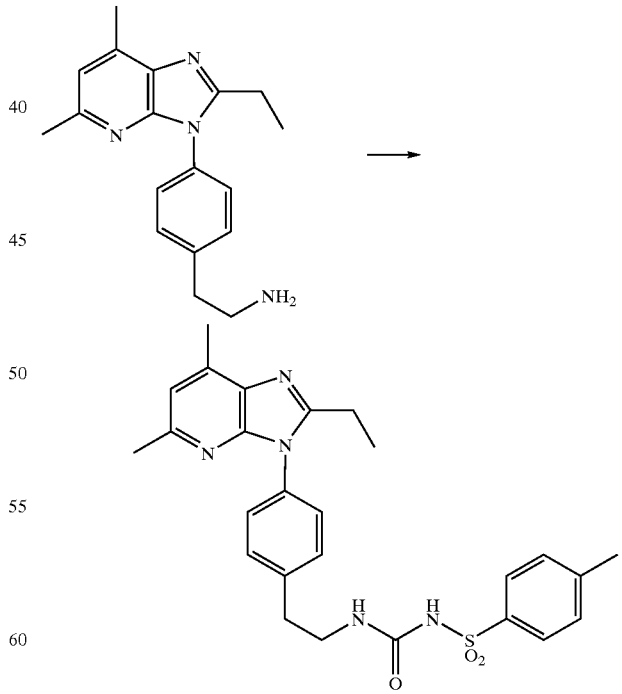

To a solution of 2-[4-(2-ethyl-5,7-dimethyl-3H-imidazo[4, 5-b]pyridin-3-yl)phenyl]ethylamine (step 9, 1.2 g, 4.0 mmol) in dichloromethane (15 mL) was added p-toluenesulfonyl isocyanate (805 mg, 4.0 mmol). The resulting mixture was stirred at room temperature for 3 h. After removal of solvent, the residue was purified by flash column chromatography on silica gel eluting with dichloromethane/methanol (20:1) to afford 1.10 g (56%) of the title compound as white solids: $^1$H-NMR (CDCl$_3$) δ 7.85 (2H, d, J=8.2 Hz), 7.32 (2H, d, J=8.2 Hz), 7.23 (2H, d, J=8.4 Hz), 7.16 (2H, d, J=8.4 Hz), 6.91 (1H, s), 6.12 (1H, br.s), 3.55–3.46 (2H, m), 2.85 (2H, t, J=6.3 Hz), 2.74–2.64 (5H, m), 2.42 (3H, s), 2.41 (3H, s), 1.21 (3H, t, J=7.6 Hz).

Example 2
2-ETHYL-5,7-DIMETHYL-3-(4-{2-[({[(4-METHYLPHENYL)SULFONYL]AMINO}CARBONYL)AMINO]ETHYL}PHENYL)-3H-IMIDAZO[4,5-b]PYRIDINE, SODIUM SALT To a solution of 2-ethyl-5,7-dimethyl-3-(4-{2-[({[(4-methylphenyl)sulfonyl]amino}carbonyl)amino]ethyl}phenyl)-3H-imidazo[4,5-b]pyridine (Example 1, 5.0 g, 10.2 mmol) in methanol (20 mL) was added 2N aqueous NaOH (5.1 mL, 10.2 mmol). The resulting mixture was stirred at room temperature for 5 min and concentrated. The residual solids were collected by filteration and dried under reduced pressure at 50° C. to afford the title compound as white solids: $^1$H-NMR (DMSO-d$_6$) δ 7.60 (2H, d, J=8.2 Hz), 7.31–7.39 (4H, m), 7.14 (2H, d, J=8.2 Hz), 6.96 (1H, s), 3.15 (2H, br.s), 2.66–2.75 (4H, m), 2.53 (3H, s), 2.40 (3H, s), 2.28 (3H, s), 1.20 (3H, t, J=7.6 Hz).

Example 3
2-[4-(2-ETHYL-5,7-DIMETHYL-3H-IMIDAZO[4,5-b]PYRIDINE-3-YL)PHENYL]ETHYL-(4-METHYLPHENYL)SULFONYLCARBAMATE To a solution of 2-[4-(2-ethyl-5,7-dimethyl-3H-imidazo[4,5-b]pyridin-3-yl)phenyl]ethanol (step 6 of Example 1, 300 mg, 1.0 mmol) in dichloromethane (10 mL) was added p-toluenesulfonyl isocyanate (237 mg, 1.2 mmol). The resulting mixture was stirred at room temperature overnight. After removal of solvent, the residual solids were recrystallized from ethyl acetate to afford 454 mg (92%) of the title compound as white solids: $^1$H-NMR (CDCl$_3$) δ 7.93 (2H, d, J=8.4 Hz), 7.33 (2H, d, J=8.4 Hz), 7.22 (4H, s), 6.92 (1H, s), 4.87 (1H, br.s), 4.35 (2H, t, J=6.6 Hz), 2.96 (2H, t, J=6.6 Hz), 2.78 (2H, q, J=7.7 Hz), 2.66 (3H, s), 2.50 (3H, s), 1.24 (3H, t, J=7.7 Hz).

Example 4
2-ETHYL-5,7-DIMETHYL-3-(4-{2-[({METHYL[(4-METHYLPHENYL)SULFONYL]AMINO}CARBONYL)AMINO]ETHYL}PHENYL)-3H-IMIDAZO[4,5-b]PYRIDINE To a stirred solution of 2-ethyl-5,7-dimethyl-3-(4-{2-[({[(4-methylphenyl)sulfonyl]amino}carbonyl)amino]ethyl}phenyl)-3H-imidazo[4,5-b]pyridine (Example 1, 200 mg, 0.41 mmol) in THF (10 mL) was added dropwise a solution of lithium diisopropylamide (LDA) (2.0 N in heptane/hexane/ethylbenzene, 0.8 mL, 1.6 mmol) with ice-cooling over a period of 10 min. After completion of the addition, the stirring was continued for an additional 20 min at the same temperature. To the resulting mixture was added dropwise MeI (0.5 mL) at 0° C., and stirred at room temperature for 15 h. The mixture was poured into a solution of phosphate buffer (100 mL) and extracted with dichloromethane (100 mL). The organic layer was washed with brine (50 mL), dried (Na$_2$SO$_4$), and concentrated. The residue was purified by flash chromatography on silica gel eluting with dichloromethane/methanol (10:1) to give 10 mg (5%) of the title compound as a colorless oil: $^1$H-NMR (CDCl$_3$) δ 7.64 (2H, d, J=8.3 Hz), 7.53–7.25 (7H, m), 6.89 (1H, s), 3.65–3.55 (2H, m), 3.14 (3H, s), 2.96 (2H, t, J=6.7 Hz), 2.82 (2H, q, J=7.6 Hz), 2.66 (3H, s), 2.50 (3H, s), 2.40 (3H, s), 1.25 (3H, t, J=7.6 Hz).

Example 5
2-ETHYL-5,7-DIMETHYL-3-(4-{2-[METHYL({[(4-METHYLPHENYL)SULFONYL]AMINO}CARBONYL)AMINO]ETHYL}PHENYL)-3H-IMIDAZO[4,5-b]PYRIDINE Step 1. N-{2-[4-(2-Ethyl-5,7-dimethyl-3H-imidazo[4,5-b]pyridin-3-yl)phenyl]ethyl}-N-methylamine A mixture of 3-[4-(2-chloroethyl)phenyl]-2-ethyl-5,7-dimethyl-3H-imidazo[4,5-b]pyridine (step 7 of Example 1, 627 mg, 9.0 mmol), a solution of methylamine (40% in methanol, 6 mL) and water (6 mL) was placed in a sealed tube and heated overnight at 130° C. The reaction mixture was partitioned between dichloromethane (50 mL) and water (50 mL). The organic phase was separated and the aqueous phase was extracted with dichloromethane (50 mL). The combined organic extracts were washed with brine (50 mL) and dried (Na$_2$SO$_4$). After removal of solvent, the crude product was purified by flash column chromatography on silica gel eluting with dichloromethane/methanol (5:1) to afford 523 mg (85%) of the title compound as white solids: $^1$H-NMR (CDCl$_3$) δ 7.41 (2H, d, J=8.3 Hz), 7.31 (2H, d, J=8.3 Hz), 6.90 (1H, s), 4.73 (1H, br.s), 2.93 (4H, s), 2.82 (2H, q, J=7.5 Hz), 2.65 (3H, s), 2.51 (3H, s), 2.49 (3H, s), 1.28 (3H, t, J=7.5 Hz).

Step 2. 2-Ethyl-5,7-dimethyl-3-(4-{2-[methyl({[(4-methylphenyl)sulfonyl]amino}carbonyl)amino]ethyl}phenyl)-3H-imidazo[4,5-b]pyridine To a solution of N-{2-[4-(2-ethyl-5,7-dimethyl-3H-imidazo[4,5-b]pyridin-3-yl)phenyl]ethyl}-N-methylamine (step 1, 523 mg, 1.7 mmol) in dichloromethane (10 mL) and triethylamine (2 mL) was added p-toluenesulfonyl isocyanate (400 mg, 2.0 mmol). The resulting reaction mixture was stirred at room temperature for 6 h. After removal of solvent, the residue was purified by flash column chromatography on silica gel eluting with dichloromethane/methanol (10:1) to afford 358 mg (42%) of the title compound as white solids: $^1$H-NMR (CDCl$_3$) δ 7.93 (2H, d, J=8.3 Hz), 7.31 (2H, d, J=8.4 Hz), 7.24 (2H, d, J=8.3 Hz), 7.14 (2H, d, J=8.4 Hz), 6.92 (1H, s), 3.66–3.49 (2H, m), 3.51 (3H, s), 2.93–2.70 (4H, m), 2.65 (3H, s), 2.50 (3H, s), 2.38 (3H, s), 1.24 (3H, t, J=7.2 Hz).

Example 6
2-ETHYL-5,7-DIMETHYL-3-(4-{2-[({[(4-METHYLPHENYL)SULFONYL]AMINO}CARBONYL)AMINO]PROPYL}PHENYL)-3H-IMIDAZO[4,5-b]PYRIDINE Step 1. 1-(4-Aminophenyl)-2-propanol A mixture of 1-(4-nitrophenyl)-2-propanol (Schadt, F. L.; et al. J.Am.Chem.Soc., 1978, 100, 228., 2.2 g, 12.3 mmol), iron powder (3.3 g, 59.1 mmol), ammonium chloride (370 mg, 6.9 mmol), ethanol (48 mL) and water (24 mL) was heated at reflux temperature for 2 h. The mixture was cooled and filtered through a pad of Celite. The filtrate was concentrated. The residue was diluted with ethyl acetate (200 mL) and washed with water (2×100 mL). The organic layer was dried (MgSO$_4$), and concentrated. Purification by flash column chromatography on silica gel eluting with hexane/ethyl acetate (1:1) to afford 1.45 g (78%) of the title compound as a yellow oil: $^1$H-NMR (CDCl$_3$) δ 7.00 (2H, d, J=8.6 Hz), 6.64 (2H, d, J=8.8 Hz), 3.99–3.89 (1H, m), 3.60 (2H, br s), 2.72–2.52 (2H, m), 1.22 (3H, d, J=6.2 Hz).

Step 2. 1-{4-[(4,6-Dimethyl-3-nitro-2-pyridinyl)amino]phenyl}-2-propanol

The title compound was prepared according to the procedure described in step 3 of Example 1 from 1-(4-aminophenyl)-2-propanol (step 1) and 2-chloro-4,6-dimethyl-3-nitropyridine (step 2 of Example 1).

$^1$H-NMR (CDCl$_3$) δ 9.59 (1H, br.s), 7.58 (2H, d, J=8.4 Hz), 7.20 (2H, d, J=8.4 Hz), 6.53 (1H, s), 4.13–4.01 (1H, m), 2.82–2.64 (2H, m), 2.55 (3H, s), 2.44 (3H, s), 1.25 (3H, d, J=6.2 Hz).

Step 3. 1-{4-[(3-Amino-4,6-dimethyl-2-pyridinyl)amino]phenyl}-2-propanol

A mixture of 1-{4-[(4,6-dimethyl-3-nitro-2-pyridinyl)amino]phenyl}-2-propanol (step 2, 500 mg, 1.66 mmol), iron powder (440 mg, 7.88 mmol), ammonium chloride (80 mg, 1.5 mmol) in ethanol/water (v/v, 31:8, 39 mL) was heated at reflux temperature for 2 h. The mixture was cooled and filtered through a pad of Celite. The filtrate was concentrated. The residue was diluted with dichloromethane (200 mL) and washed with water (2×100 mL). The organic layer was dried ($MgSO_4$), and concentrated. Removal of solvent gave 450 mg (quant.) of the title compound as brown solids: TLC Rf 0.10 (hexane/ethyl acetate=1:1).

Step 4. 2-[4-(2-Ethyl-5,7-dimethyl-3H-imidazo[4,5-b]pyridin-3-yl)phenyl]-1-methylethyl propionate The title compound was prepared according to the procedure described in step 5 of Example 1 from 1-{4-[(3-amino-4,6-dimethyl-2-pyridinyl)amino]phenyl}-2-propanol (step 3) and propionyl chloride.

TLC Rf=0.30 (hexane/ethyl acetate=1:1).

Step 5. 1-[4-(2-Ethyl-5,7-dimethyl-3H-imidazo[4,5-b]pyridin-3-yl)phenyl]-2-propanol The title compound was prepared according to the procedure described in step 6 of Example 1 from 2-[4-(2-ethyl-5,7-dimethyl-3H-imidazo[4,5-b]pyridin-3-yl)phenyl]-1-methyl propionate (step 4).

$^1$H-NMR ($CDCl_3$) δ 7.40 (2H, d, J=8.0 Hz), 7.33 (2H, d, J=8.0 Hz), 6.91 (1H, s), 4.16–4.07 (1H, m), 2.90–2.76 (4H, m), 2.66 (2H, s), 2.52 (3H, s), 1.32–1.22 (6H, m).

Step 6. 3-[4-(2-Chloropropyl)phenyl]-2-ethyl-5,7-dimethyl-3H-imidazo[4,5-b]pyridine The title compound was prepared according to the procedure described in step 7 of Example 1 from 1-[4-(2-ethyl-5,7-dimethyl-3H-imidazo[4,5-b]pyridin-3-yl)phenyl]-2-propanol (step 5).

TLC Rf=0.50 (hexane/ethyl acetate=1:1).

Step 7. 2-[4-(2-Ethyl-5,7-dimethyl-3H-imidazo[4,5-b]pyridin-3-yl)phenyl]-1-methylethyl azide The title compound was prepared according to the procedure described in step 8 of Example 1 from 3-[4-(2-chloropropyl)phenyl]-2-ethyl-5,7-dimethyl-3H-imidazo[4,5-b]pyridine (step 6).

$^1$H-NMR ($CDCl_3$) δ 7.40 (2H, d, J=8.4 Hz), 7.34 (2H, d, J=8.4 Hz), 6.91 (1H, s), 3.81–3.74 (1H, m), 2.95–2.79 (4H, m), 2.66 (3H, s), 2.52 (3H, s), 1.35 (3H, d, J=6.6 Hz), 1.27 (3H, t, J=7.5 Hz).

Step 8. 1-[4-(2-Ethyl-5,7-dimethyl-3H-imidazo[4,5-b]pyridin-3-yl)phenyl]-2-propanamine The title compound was prepared according to the procedure described in step 9 of Example 1 from 2-[4-(2-ethyl-5,7-dimethyl-3H-imidazo[4,5-b]pyridin-3-yl)phenyl]-1-methylethyl azide (step 7).

$^1$H-NMR ($CDCl_3$) δ 7.40–7.31 (4H, m), 6.90 (1H, s), 3.31–3.20 (1H, m), 2.87–2.77 (3H, m), 2.66–2.58 (4H, m), 2.52 (3H, s), 1.28 (3H, t, J=8.3 Hz), 1.19 (3H, d, J=6.8 Hz).

Step 9. 2-Ethyl-5,7-dimethyl-3-(4-{2-[({[(4-methylphenyl)sulfonyl]amino}carbonyl)amino]propyl}phenyl)-3H-imidazo[4,5-b]pyridine The title compound was prepared according to the procedure described in step 10 of Example 1 from 1-[4-(2-ethyl-5,7-dimethyl-3H-imidazo[4,5-b]pyridin-3-yl)phenyl]-2-propanamine (step 8).

mp 128° C.; MS (ESI) m/z 506.19 (M+H)$^+$; $^1$H-NMR ($CDCl_3$) δ 7.74 (2H, d, J=8.3 Hz), 7.30–7.19 (6H, m), 6.90 (1H, s), 4.08–4.02 (1H, m), 2.84–2.72 (4H, m), 2.65 (3H, s), 2.48 (3H, s), 2.32 (3H, s), 1.20–1.13 (6H, m).

Example 7
2-[4-(2-ETHYL-5,7-DIMETHYL-3H-IMIDAZO[4,5-b]PYRIDIN-3-YL)PHENYL]-1-METHYLETHYL (4-METHYLPHENYL)SULFONYLCARBAMATE The title compound was prepared according to the procedure described in Example 3 from 1-[4-(2-ethyl-5,7-dimethyl-3H-imidazo[4,5-b]pyridin-3-yl)phenyl]-2-propanol (step 5 of Example 6).

mp 108° C.; MS (ESI) m/z 507.18 (M+H)$^+$; $^1$H-NMR ($CDCl_3$) δ 7.91 (2H, d, J=8.4 Hz), 7.31 (2H, d, J=8.3 Hz), 7.23 (4H, s), 6.91 (1H, s), 5.10–5.04 (1H, m), 2.95–2.76 (4H, m), 2.65 (3H, s), 2.50 (3H, s), 2.41 (3H, s), 1.28–1.21 (6H, m).

Example 8
5,7-DIMETHYL-3-(4-{2-[({[(4-METHYLPHENYL)SULFONYL]AMINO}CARBONYL)AMINO]ETHYL}PHENYL)-2-PROPYL-3H-IMIDAZO[4,5-b]PYRIDINE Step 1. 2-[4-(5,7-Dimethyl-2-propyl-3H-imidazo[4, 5-b]pyridin-3-yl)phenyl]ethyl butyrate The title compound was prepared according to the procedure described in step 5 of Example 1 from 2-{4-[(3-amino-4,6-dimethyl-2-pyridinyl)amino]phenyl}ethanol (step 4 of Example 1) and butyryl chloride.

$^1$H-NMR ($CDCl_3$) δ 7.42 (2H, d, J=8.2 Hz), 7.32 (2H, d, J=8.2 Hz), 6.92 (1H, s), 4.39 (2H, t, J=6.4 Hz), 3.09 (2H, t, J=6.4 Hz), 2.77, (2H, t, J=7.7 Hz), 2.66 (3H, s), 2.52 (3H, s), 2.32 (2H, t, J=7.7 Hz), 1.81–1.58 (4H, m), 1.00–0.86 (6H, m).

Step 2. 2-[4-(5,7-Dimethyl-2-propyl-3H-imidazo[4,5-b]pyridin-3-yl)phenyl]ethanol The title compound was prepared according to the procedure described in step 6 of Example 1 from 2-[4-(5,7-dimethyl-2-propyl-3H-imidazo[4,5-b]pyridin-3-yl)phenyl]ethyl butyrate (step 1)

$^1$H-NMR ($CDCl_3$) δ 7.43 (2H, d, J=8.0 Hz), 7.32 (2H, d, J=8.0 Hz), 6.90 (1H, s), 4.00–3.89 (2H, m), 2.97 (2H, t, J=6.4 Hz), 2.78 (2H, t, J=7.8 Hz), 2.65 (3H, s), 2.51 (3H, s), 1.80–1.64 (2H, m), 0.92 (3H, t, J=7.4 Hz).

Step 3. 3-[4-(2-Chloroethyl)phenyl]-5,7-dimethyl-2-propyl-3H-imidazo[4,5-b]pyridine The title compound was prepared according to the procedure described in step 7 of Example 1 from 2-[4-(5,7-dimethyl-2-propyl-3H-imidazo[4,5-b]pyridin-3-yl)phenyl]ethanol (step 2).

MS (EI) m/z 327 (M$^+$).

Step 4. 2-[4-(5,7-Dimethyl-2-propyl-3H-imidazo[4,5-b]pyridin-3-yl)phenyl]ethyl azide The title compound was prepared according to the procedure described in step 8 of Example 1 from 3-[4-(2-chloroethyl)phenyl]-5,7-dimethyl-2-propyl-3H-imidazo[4,5-b]pyridine (step 3).

MS (EI) m/z 334 (M$^+$); $^1$H-NMR ($CDCl_3$) δ 7.42 (2H, d, J=8.4 Hz), 7.34 (2H, d, J=8.4 Hz), 6.91 (1H, s), 3.60 (2H, t, J=7.2 Hz), 3.00 (2H, t, J=7.2 Hz), 2.77 (2H, t, J=7.8 Hz), 2.65 (3H, s), 2.52 (3H, s), 1.75–1.62 (2H, m), 0.90 (3H, t, J=7.4 Hz).

Step 5. 2-[4-(5,7-Dimethyl-2-propyl-3H-imidazo[4,5-b]pyridin-3-yl)phenyl]ethylamine The title compound was prepared according to the procedure described in step 9 of Example 1 from 2-[4-(5,7-dimethyl-2-propyl-3H-imidazo[4,5-b]pyridin-3-yl)phenyl]ethyl azide (step 4).

$^1$H-NMR ($CDCl_3$) δ 7.42 (2H, d, J=8.3 Hz), 7.29 (2H, d, J=8.3 Hz), 6.88 (1H, s), 3.89 (2H, br.s), 3.18 (2H, t, J=6.8 Hz), 3.01 (2H, t, J=6.8 Hz), 2.75 (2H, t, J=7.5 Hz), 2.64 (3H, s), 2.48 (3H, s), 1.78–1.63 (2H, m), 0.90 (3H, t, J=7.3 Hz).

Step 6. 5,7-Dimethyl-3-(4-52-[({[(4-methylphenyl)sulfonyl]amino}carbonyl)amino]ethyl}phenyl)-2-propyl-3H-imidazo[4,5-b]pyridine The title compound was prepared according to the procedure described in step 10 of Example 1 from 2-[4-(5,7-dimethyl-2-propyl-3H-imidazo[4,5-b]pyridin-3-yl)phenyl] ethylamine (step 5).

$^1$H-NMR (CDCl$_3$) δ 7.86 (2H, d, J=8.3 Hz), 7.30 (2H, d, J=8.3 Hz), 7.23 (2H, d, J=8.3 Hz), 7.16 (2H, d, J=8.3 Hz), 6.90 (1H, s), 6.10 (1H, br.s), 3.58–3.46 (2H, m), 2.87 (2H, t, J=6.4 Hz), 2.71–2.59 (5H, m), 2.42 (3H, s), 2.40 (3H, s), 1.74–1.61 (2H, m), 0.89 (3H, t, J=7.0 Hz).

Example 9

2-ISOPROPYL-5,7-DIMETHYL-3-(4-{2-[({[(4-METHYLPHENYL)SULFONYL]AMINO}CARBONYL) AMINO]ETHYL}PHENYL)-3H-IMIDAZO[4,5-b] PYRIDINE

Step 1. 5-Bromo-4,6-dimethyl-3-nitro-2-pyridinol

To a solution of 5-bromo-4,6-dimethyl-3-nitro-2-pyridinylamine (Heitsch, H.; et al. *Bioorg. Med. Chem.* 1997, 5, 673., 2.0 g, 8.1 mmol) in trifluoroacetic acid/water (v/v, 2:1, 30 mL) was added sodium nitrite (1.1 g, 16 mmol) in small portions at room temperature, and then the reaction mixture was stirred overnight. The resulting precipitates were collected by filtration, washed with water, and dried under reduced pressure to give 2.2 g (quant.) of the title compound: $^1$H-NMR (CDCl$_3$) δ 2.53 (3H, s), 2.38 (3H, s).

Step 2. 3-Bromo-6-chloro-2,4-dimethyl-5-nitropyridine

The title compound was prepared according to the procedure described in step 2 of Example 1 from 5-bromo-4,6-dimethyl-3-nitro-2-pyridinol (step 1).

$^1$H-NMR (CDCl$_3$) δ 2.72 (3H, s), 2.41 (3H, s).

Step 3. 2-{4-[(5-Bromo-4,6-dimethyl-3-nitro-2-pyridinyl)amino]phenyl}ethanol

The title compound was prepared according to the procedure described in step 3 of Example 1 from 3-bromo-6-chloro-2,4-dimethyl-5-nitropyridine (step 2) and 4-aminophenylethyl alcohol.

$^1$H-NMR (CDCl$_3$) δ 8.66 (1H, br.s), 7.51 (2H, d, J=8.4 Hz), 7.22 (2H, d, J=8.4 Hz), 3.90–3.77 (2H, m), 2.88 (2H, t, J=6.5 Hz), 2.65 (3H, s), 2.59 (3H, s).

Step 4. 2-{4-[(3-Amino-5-bromo-4,6-dimethyl-2-pyridinyl)amino]phenyl}ethanol

The title compound was prepared according to the procedure described in step 4 of Example 1 from 2-{4-[(5-bromo-4,6-dimethyl-3-nitro-2-pyridinyl)amino] phenyl}ethanol (step 3).

$^1$H-NMR (CDCl$_3$) δ 7.12 (4H, s), 6.21 (1H, s), 3.38 (1H, br.s), 3.82 (2H, t, J=6.5 Hz), 2.80 (2H, t, J=6.5 Hz), 2.54 (3H, s), 2.38 (3H, s).

Step 5. 2-[4-(6-Bromo-2-isopropyl-5,7-dimethyl-3H-imidazo[4,5-b]pyridin-3-yl)phenyl]ethyl 2-methylpropanoate The title compound was prepared according to the procedure described in step 5 of Example 1 from 2-{4-[(3-amino-5-bromo-4,6-dimethyl-2-pyridinyl)amino] phenyl}ethanol (step 4) and isobutyryl chloride.

MS (EI) m/z 457 (M$^+$).

Step 6. 2-[4-(6-Bromo-2-isopropyl-5,7-dimethyl-3H-imidazo[4,5-b]pyridin-3-yl)phenyl]ethanol The title compound was prepared according to the procedure described in step 6 of Example 1 from 2-[4-(6-bromo-2-isopropyl-5,7-dimethyl-3H-imidazo[4,5-b] pyridin-3-yl)phenyl]ethyl 2-methylpropanoate (step 5).

$^1$H-NMR (CDCl$_3$) δ 7.45 (2H, d, J=8.3 Hz), 7.30 (2H, d, J=8.3 Hz), 3.96 (2H, t, J=7.3 Hz), 3.15–3.03 (1H, m), 2.97 (2H, t, J=7.3 Hz), 2.76 (3H, s), 2.67 (3H, s), 1.34 (6H, d, J=6.8 Hz).

Step 7. 6-Bromo-3-[4-(2-chloroethyl)phenyl]-2-isopropyl-5,7-dimethyl-3H-imidazo[4,5-b]pyridine The title compound was prepared according to the procedure described in step 7 Example 1 from 2-[4-(6-bromo-2-isopropyl-5,7-dimethyl-3H-imidazo[4,5-b]pyridin-3-yl) phenyl]ethanol (step 6).

$^1$H-NMR (CDCl$_3$) δ 7.43 (2H, d, J=8.3 Hz), 7.32 (2H, d, J=8.3 Hz), 3.81 (2H, t, J=7.3 Hz), 3.19 (2H, t, J=7.3 Hz), 3.15–3.02 (1H, m), 2.76 (3H, s), 2.66 (3H, s), 1.33 (6H, d, J=6.9 Hz).

Step 8. 2-[4-(6-Bromo-2-isopropyl-5,7-dimethyl-3H-imidazo[4,5-b]pyridin-3-yl)phenyl]ethyl azide The title compound was prepared according to the procedure described in step 8 Example 1 from 6-bromo-3-[4-(2-chloroethyl)phenyl]-2-isopropyl-5,7-dimethyl-3H-imidazo[4,5-b]pyridine (step 7).

MS (EI) m/z 412 (M$^+$); $^1$H-NMR (CDCl$_3$) δ 7.42 (2H, d, J=8.4 Hz), 7.30 (2H, d, J=8.4 Hz), 3.60 (2H, t, J=6.5 Hz), 3.16–3.02 (1H, m), 3.02 (2H, t, J=6.5 Hz), 2.77 (3H, s), 2.68 (3H, s), 1.33 (6H, d, J=6.9 Hz).

Step 9. [4-(2-Isopropyl-5,7-dimethyl-3H-imidazo[4,5-b] pyridin-3-yl)phenyl]ethylamine The title compound was prepared according to the procedure described in step 9 of Example 1 from 2-[4-(6-bromo-2-isopropyl-5,7-dimethyl-3H-imidazo[4,5-b] pyridin-3-yl)phenyl]ethyl azide (step 8).

H-NMR (CDCl$_3$) δ 7.49 (2H, d, J=8.3 Hz), 7.28 (2H, d, J=8.3 Hz), 6.93 (1H, s), 6.60 (2H, br.s), 3.32–3.00 (5H, m), 2.65 (3H, s), 2.48 (3H, s), 1.31 (6H, d, J=6.8 Hz).

Step 10. 2-Isopropyl-5,7-dimethyl-3-(4-{2-[({[(4-methylphenyl)sulfonyl]amino}carbonyl)amino] ethyl}phenyl)-3H-imidazo[4,5-b]pyridine The title compound was prepared according to the procedure described in step 10 of Example 1 from [4-(2-isopropyl-5,7-dimethyl-3H-imidazo[4,5-b]pyridin-3-yl) phenyl]ethylamine (step 9).

$^1$H-NMR (CDCl$_3$) δ 7.87 (2H, d, J=8.3 Hz), 7.31 (2H, d, J=8.3 Hz), 7.23 (2H, d, J=8.4 Hz), 7.17 (2H, d, J=8.4 Hz), 6.91 (1H, s), 6.08 (1H, br.s), 3.56–3.43 (2H, m), 3.02–2.89 (1H, m), 2.85 (2H, t, J=6.3 Hz), 2.67 (3H, s), 2.41 (6H, s), 1.26 (6H, d, J=6.8 Hz).

Example 10

2-ISOPROPYL-5,7-DIMETHYL-3-(4-{2-[({[(4-METHYLPHENYL)SULFONYL]AMINO}CARBONYL) AMINO]ETHYL}PHENYL)-3H-IMIDAZO[4,5-b] PYRIDINE, SODIUM SALT

The title compound was prepared according to the procedure described in Example 2 from 2-isopropyl-5,7-dimethyl-3-(4-{2-[({[(4-methylphenyl)sulfonyl] amino}carbonyl)amino]ethyl}phenyl)-3H-imidazo[4,5-b] pyridine (Example 9).

MS (ESI) m/z 506 (M+H)$^+$.

Example 11

2-BUTYL-5,7-DIMETHYL-3-(4-{2-[({[(4-METHYLPHENYL)SULFONYL]AMINO}CARBONYL) AMINO]ETHYL}PHENYL)-3H-IMIDAZO[4,5-b] PYRIDINE

Step 1. 2-[4-}6-Bromo-2-butyl-5,7-dimethyl-3H-imidazo[4, 5-b]pyridin-3-yl)phenylethyl pentanoate The title compound was prepared according to the procedure described in step 5 of Example 1 from 2-{4-[(3-amino-5-bromo-4,6-dimethyl-2-pyridinyl)amino] phenyl}ethanol (step 4 of Example 9) and pentanoyl chloride.

MS (EI) m/z 485 (M$^+$); $^1$H-NMR (CDCl$_3$) δ 7.42 (2H, d, J=8.3 Hz), 7.31 (2H, d, J=8.3 Hz), 4.37 (2H, t, J=6.9 Hz), 3.05 (2H, t, J=6.9 Hz), 2.79 (2H, t, J=7.7 Hz), 2.75 (3H, s), 2.67 (3H, s), 2.33 (2H, t, J=7.5 Hz), 1.75–1.54 (4H, m), 1.40–1.20 (4H, m), 0.91 (3H, t, J=7.3 Hz), 0.84 (3H, t, J=7.3 Hz).

Step 2. 2-[4-(6-Bromo-2-butyl-5,7-dimethyl-3H-imidazo[4,5-b]pyridin-3-yl)phenyl]ethanol The title compound was prepared according to the procedure described in step 6 of Example 1 from 2-[4-(6-bromo-2-butyl-5,7-dimethyl-3H-imidazo[4,5-b]pyridin-3-yl)phenyl]ethyl pentanoate (step 1).

MS (EI) m/z 401 (M$^+$).

Step 3. 6-Bromo-2-butyl-3-[4-(2-chloroethyl)phenyl]-5,7-dimethyl-3H-imidazo[4,5-b]pyridine The title compound was prepared according to the procedure described in step 7 Example 1 from 2-[4-(6-bromo-2-butyl-5,7-dimethyl-3H-imidazo[4,5-b]pyridin-3-yl)phenyl]ethanol (step 2).

MS (EI) m/z 419 (M$^+$).

Step 4. 2-[4-(6-Bromo-2-butyl-5,7-dimethyl-3H-imidazo[4,5-b]pyridin-3-yl)phenyl]ethyl azide The title compound was prepared according to the procedure described in step 8 Example 1 from 6-bromo-2-butyl-3-[4-(2-chloroethyl)phenyl]-5,7-dimethyl-3H-imidazo[4,5-b]pyridine step 3).

MS (EI) m/z 426 (M$^+$); $^1$H-NMR (CDCl$_3$) δ 7.43 (2H, d, J=8.4 Hz), 7.33 (2H, d, J=8.4 Hz), 3.61 (2H, t, J=7.2 Hz), 3.01 (2H, t, J=7.2 Hz), 2.79 (2H, t, J=7.9 Hz), 2.75 (3H, s), 2.67 (3H, s), 1.75–1.60 (2H, m), 1.36–1.20 (2H, m), 0.84 (3H, t, J=7.3 Hz).

Step 5. 2-[4-(2-Butyl-5,7-dimethyl-3H-imidazo[4,5-b]pyridin-3-yl)phenyl]ethylamine The title compound was prepared according to the procedure described in step 9 of Example 1 from 2-[4-(6-bromo-2-butyl-5,7-dimethyl-3H-imidazo[4,5-b]pyridin-3-yl)phenyl]ethyl azide (step 4).

$^1$H-NMR (CDCl$_3$) δ 7.59 (2H, d, J=8.3 Hz), 7.35 (2H, d, J=8.3 Hz), 6.90 (1H, s), 3.52–3.22 (4H, m), 3.01 (2H, br.s), 2.90 (2H, t, J=7.7 Hz), 2.74 (3H, s), 2.56 (3H, s), 1.79–1.62 (2H, m), 1.41–1.23 (2H, m), 0.84 (3H, t, J=7.5 Hz).

Step 6. 2-Butyl-5,7-dimethyl-3-(4-{2-[({[(4-methylphenyl)sulfonyl]amino}carbonyl)amino]ethyl}phenyl)-3H-imidazo[4,5-b]pyridine The title compound was prepared according to the procedure described in step 10 of Example 1 from 2-[4-(2-butyl-5,7-dimethyl-3H-imidazo[4,5-b]pyridin-3-yl)phenyl]ethylamine (step 5).

$^1$H-NMR (CDCl$_3$) δ 7.86 (2H, d, J=8.2 Hz), 7.31 (2H, d, J=8.2 Hz), 7.22 (2H, d, J=8.3 Hz), 7.14 (2H, d, J=8.3 Hz), 6.91 (1H, s), 6.09 (1H, br.s), 3.56–3.44 (2H, m), 2.84 (2H, t, J=6.4 Hz), 2.70–2.59 (5H, m), 2.42 (3H, s), 2.41 (3H, s), 1.69–1.43 (2H, m), 1.30–1.18 (2H, m), 0.80 (3H, t, J=7.3 Hz).

Example 12

2-BUTYL-5,7-DIMETHYL-3-(4-{2-[({[(4-METHYLPHENYL)SULFONYL]AMINO}CARBONYL)AMINO]ETHYL}PHENYL)-3H-IMIDAZO[4,5-b]PYRIDINE, SODIUM SALT

The title compound was prepared according to the procedure described in Example 2 from 2-butyl-5,7-dimethyl-3-(4-{2-[({[(4-methylphenyl)sulfonyl]amino}carbonyl)amino]ethyl}phenyl)-3H-imidazo[4,5-b]pyridine (Example 11).

MS (ESI) m/z 520 (M+H)$^+$.

Example 13

2-ISOBUTYL-5,7-DIMETHYL-3-(4-{2-[({[(4-METHYLPHENYL)SULFONYL]AMINO}CARBONYL)AMINO]ETHYL}PHENYL)-3H-IMIDAZO[4,5-b]PYRIDINE

Step 1. 2-[4-(2-Isobutyl-5,7-dimethyl-3H-imidazo[4,5-b]pyridin-3-yl)phenyl]ethyl 3-methylbutanoate The title compound was prepared according to the procedure described in step 5 of Example 1 from 2-{4-[(3-amino-4,6-dimethyl-2-pyridinyl)amino]phenyl}ethanol (step 4 of Example 1) and isovaleryl chloride.

MS (EI) m/z 407 (M$^+$).

Step 2. 2-[4-(2-2-Isobutyl-5,7-dimethyl-3H-imidazo[4,5-b]pyridin-3-yl)phenyl]ethanol The title compound was prepared according to the procedure described in step 6 of Example 1 from 2-[4-(2-isobutyl-5,7-dimethyl-3H-imidazo[4,5-b]pyridin-3-yl)phenyl]ethyl 3-methylbutanoate (step 1).

MS (EI) m/z 323 (M$^+$).

Step 3. 3-[4-(2-Chloroethyl)phenyl]-2-isobutyl-5,7-dimethyl-3H-imidazo[4,5-b]pyridine The title compound was prepared according to the procedure described in step 7 Example 1 from 2-[4-(2-isobutyl-5,7-dimethyl-3H-imidazo[4,5-b]pyridin-3-yl)phenyl]ethanol (step 2).

MS (EI) m/z 341 (M$^+$); $^1$H-NMR (CDCl$_3$) δ 7.41 (2H, d, J=8.2 Hz), 7.33 (2H, d, J=8.2 Hz), 6.90 (1H, s), 3.80 (2H, t, J=6.5 Hz), 3.18 (2H, t, J=6.5 Hz), 2.68 (2H, d, J=7.5 Hz), 2.66 (3H, s), 2.51 (3H, s), 2.14–1.96 (1H, m), 0.86 (6H, d, J=6.6 Hz).

Step 4. 2-[4-(2-isobutyl-5,7-dimethyl-3H-imidazo[4,5-b]pyridin-3-yl)phenyl]ethyl azide The title compound was prepared according to the procedure described in step 8 Example 1 from 3-[4-(2-chloroethyl)phenyl]-2-isobutyl-5,7-dimethyl-3H-imidazo[4,5-b]pyridine (step 3).

MS (EI) m/z 348 (M$^+$); $^1$H-NMR (CDCl$_3$) δ 7.42 (2H, d, J=8.4 Hz), 7.31 (2H, d, J=8.4 Hz), 6.91 (1H, s), 3.60 (2H, t, J=6.5 Hz), 3.00 (2H, t, J=6.5 Hz), 2.69 (2H, d, J=7.5 Hz), 2.65 (3H, s), 2.52 (3H, s), 2.08–1.98 (1H, m), 0.87 (6H, d, J=6.7 Hz).

Step 5. 2-[4-(2-2-Isobutyl-5,7-dimethyl-3H-imidazo[4,5-b]pyridin-3-yl)phenyl]ethylamine The title compound was prepared according to the procedure described in step 9 of Example 1 from 2-[4-(2-isobutyl-5,7-dimethyl-3H-imidazo[4,5-b]pyridin-3-yl)phenyl]ethyl azide (step 4).

$^1$H-NMR (CDCl$_3$) δ 7.40 (2H, d, J=8.3 Hz), 7.28 (2H, d, J=8.3 Hz), 6.91 (1H, s), 3.09 (2H, t, J=6.4 Hz), 2.93 (2H, t, J=6.4 Hz), 2.80 (2H, br.s), 2.68 (2H, d, J=7.5 Hz), 2.66 (3H, s), 2.53 (3H, s), 2.18–2.00 (1H, m), 0.88 (6H, d, J=6.8 Hz).

Step 6. 2-Isobutyl-5,7-dimethyl-3-(4-{2-[({[(4-methylphenyl)sulfonyl]amino}carbonyl)amino]ethyl}phenyl)-3H-imidazo[4,5-b]pyridine The title compound was prepared according to the procedure described in step 10 of Example 1 from 2-[4-(2-isobutyl-5,7-dimethyl-3H-imidazo[4,5-b]pyridin-3-yl)phenyl]ethylamine (step 5).

$^1$H-NMR (CDCl$_3$) δ 7.85 (2H, d, J=8.3 Hz), 7.28 (2H, d, J=8.3 Hz), 7.21 (2H, d, J=8.3 Hz), 7.12 (2H, d, J=8.3 Hz), 6.91 (1H, s), 6.14 (1H, br.s), 3.55–3.42 (2H, m), 2.82 (2H, t, J=6.3 Hz), 2.65 (3H, s), 2.53 (2H, d, J=7.3 Hz), 2.41 (3H, s), 2.39 (3H, s), 2.10–1.92 (1H, m) 0.81 (6H, d, J=6.6 Hz).

Example 14

2-ISOBUTYL-5,7-DIMETHYL-3-(4-{2-[({[(4-METHYLPHENYL)SULFONYL]AMINO}CARBONYL)AMINO]ETHYL}PHENYL)-3H-IMIDAZO[4,5-b]PYRIDINE, SODIUM SALT

The title compound was prepared according to the procedure described in Example 2 from 2-isobutyl-5,7-dimethyl-3-(4-{2-[({[(4-methylphenyl)sulfonyl]amino}carbonyl)amino]ethyl}phenyl)-3H-imidazo[4,5-b]pyridine (Example 13).

MS (ESI) m/z 520 (M+H)$^+$.

Example 15
5,7-DIMETHYL-3-(4-[2-[({[(4-METHYLPHENYL)SULFONYL]AMINO}CARBONYL)AMINO]ETHYL}PHENYL)-2-NEOPENTYL-3H-IMIDAZO[4,5-b]PYRIDINE Step 1. 2-[4-(2-Neopentyl-5,7-dimethyl-3H-imidazo[4,5-b]pyridin-3-yl)phenyl]ethyl 3,3-dimethylbutanoate The title compound was prepared according to the procedure described in step 5 of Example 1 from 2-{4-[(3-amino-4,6-dimethyl-2-pyridinyl)amino]phenyl}ethanol (step 4 of Example 1) and tert-butylacetyl chloride.

MS (EI) m/z 435 (M$^+$).

Step 2. 2-[4-(2-Neopentyl-5,7-dimethyl-3H-imidazo[4,5-b]pyridin-3-yl)phenyl]ethanol The title compound was prepared according to the procedure described in step 6 of Example 1 from 2-[4-(2-neopentyl-5,7-dimethyl-3H-imidazo[4,5-b]pyridin-3-yl)phenyl]ethyl 3,3-dimethylbutanoate (step 1).

MS (EI) m/z 337 (M$^+$).

Step 3. 3-[4-(2-Chloroethyl)phenyl]-2-neopentyl-5,7-dimethyl-3H-imidazo[4,5-b]pyridine The title compound was prepared according to the procedure described in step 7 Example 1 from 2-[4-(2-neopentyl-5,7-dimethyl-3H-imidazo[4,5-b]pyridin-3-yl)phenyl]ethanol (step 2).

$^1$H-NMR (CDCl$_3$) δ 7.41 (2H, d, J=8.2 Hz), 7.30 (2H, d, J=8.2 Hz), 6.89 (1H, s), 3.81 (2H, t, J=6.5 Hz), 3.18 (2H, t, J=6.5 Hz), 2.79 (2H, s), 2.66 (3H, s), 2.51 (3H, s), 0.89 (9H, s).

Step 4. 2-[4-(2-Neopentyl-5,7-dimethyl-3H-imidazo[4,5-b]pyridin-3-yl)phenyl]ethyl azide The title compound was prepared according to the procedure described in step 8 Example 1 from 3-[4-(2-chloroethyl)phenyl]-2-neopentyl-5,7-dimethyl-3H-imidazo[4,5-b]pyridine (step 3).

MS (EI) m/z 362 (M$^+$); $^1$H-NMR (CDCl$_3$) δ 7.42 (2H, d, J=8.3 Hz), 7.31 (2H, d, J=8.3 Hz), 6.91 (1H, s), 3.62 (2H, t, J=6.5 Hz), 3.02 (2H, t, J=6.5 Hz), 2.78 (2H, s), 2.68 (3H, s), 2.53 (3H, s), 0.88 (9H, s).

Step 5. 2-[4-(2-Neopentyl-5,7-dimethyl-3H-imidazo[4,5-b]pyridin-3-yl)phenyl]ethylamine The title compound was prepared according to the procedure described in step 9 of Example 1 from 2-[4-(2-neopentyl-5,7-dimethyl-3H-imidazo[4,5-b]pyridin-3-yl)phenyl]ethyl azide (step 4).

MS (EI) m/z 336 (M$^+$).

Step 6. 2-Neopentyl-5,7-dimethyl-3-(4-[2-[({[(4-methylphenyl)sulfonyl]amino}carbonyl)amino]ethyl}phenyl)-3H-imidazo[4,5-b]pyridine The title compound was prepared according to the procedure described in step 10 of Example 1 from 2-[4-(2-neopentyl-5,7-dimethyl-3H-imidazo[4,5-b]pyridin-3-yl)phenyl]ethylamine (step 5).

$^1$H-NMR (CDCl$_3$) δ 7.86 (2H, d, J=8.3 Hz), 7.31 (2H, d, J=8.3 Hz), 7.22 (2H, d, J=8.3 Hz), 7.14 (2H, d, J=8.3 Hz), 6.91 (1H, s), 6.18 (1H, br.s), 3.56–3.46 (2H, m), 2.85 (2H, t, J=6.4 Hz), 2.65 (3H, s), 2.60 (2H, s), 2.41 (3H, s), 2.40 (3H, s), 0.87 (9H, s).

Example 16
5,7-DIMETHYL-3-(4-{2-[({[(4-METHYLPHENYL)SULFONYL]AMINO}CARBONYL)AMINO]ETHYL}PHENYL)-2-NEOPENTYL-3H-IMIDAZO[4,5-b]PYRIDINE, SODIUM SALT The title compound was prepared according to the procedure described in Example 2 from 5,7-dimethyl-3-(4-{2-[({[(4-methylphenyl)sulfonyl]amino}carbonyl)amino]ethyl}phenyl)-2-neopentyl-3H-imidazo[4,5-b]pyridine (Example 15).

MS (ESI) m/z 534 (M+H)$^+$.

Example 17
5,7-DIMETHYL-3-(4-{2-[({[(4-METHYLPHENYL)SULFONYL]AMINO}CARBONYL)AMINO]ETHYL}PHENYL)-2-[2-(1,3-THIAZOL-2-YL)ETHYL]-3H-IMIDAZO[4,5-b]PYRIDINE Step 1. N-[4-(2-Chloroethyl)phenyl]-N-(4,6-dimethyl-3-nitro-2-pyridinyl)amine The title compound was prepared according to the procedure described in step 7 Example 1 from 2-{4-[(4,6-dimethyl-3-nitro-2-pyridinyl)amino]phenyl}ethanol (step 3 of Example 1).

$^1$H-NMR (CDCl$_3$) δ 9.46 (1H, br.s), 8.29 (1H, d, J=8.8 Hz), 7.42 (1H, d, J=1.7 Hz), 7.35 (2H, d, J=8.3 Hz), 7.22 (2H, d, J=8.3 Hz), 6.97 (1H, dd, J=8.8, 1.7 Hz), 3.77 (2H, t, J=7.2 Hz), 3.13 (2H, t, J=7.2 Hz).

Step 2. N$^2$-[4-(2-Chloroethyl)phenyl]-4,6-dimethyl-2,3-pyridinediamine

The title compound was prepared according to the procedure described in step 3 of Example 6 from N-[4-(2-chloroethyl)phenyl]-N-(4,6-dimethyl-3-nitro-2-pyridinyl)amine (step 1).

MS (EI) m/z 383 (M$^+$).

Step 3. 3-[4-(2-Chloroethyl)phenyl]-5,7-dimethyl-2-[2-(1,3-thiazol-2-yl)ethyl]-3H-imidazo[4,5-b]pyridine To a mixture of N$^2$-[4-(2-chloroethyl)phenyl]-4,6-dimethyl-2,3-pyridinediamine (step 2, 276 mg, 1.0 mmol) and 3-(1,3-thiazol-2-yl)propanoic acid (157 mg, 1.0 mmol) in dichloromethane (10 mL) was added 1-ethyl-3-(3-dimethylaminopropyl)carbodiimide, hydrochloride (WSC) (192 mg, 1.0 mmol) in one portion. The reaction mixture was stirred overnight at room temperature. The reaction mixture was concentrated under reduced pressure. The residue was suspended in toluene (20 mL) and heated at 150° C. for 5 h. The reaction mixture was poured into water (50 mL), the organic phase was separated, and the aqueous phase was extracted with ethyl acetate (100 mL). The combined organic phases were washed with brine (50 mL) and dried (Na$_2$SO$_4$). After removal of solvent, the crude product was purified by flash column chromatography on silica gel eluting with hexane/ethyl acetate (1:1) to afford 210 mg (53%) of the title compound: MS (EI) m/z 396 (M$^+$); $^1$H-NMR (CDCl$_3$) δ 7.63 (1H, d, J=3.4 Hz), 7.39 (2H, d, J=8.3 Hz), 7.28 (2H, d, J=8.3 Hz), 7.15 (1H, d, J=3.4 Hz), 6.93 (1H, s), (2H, t, J=7.4 Hz), 3.69–3.50 (2H, m), 3.39–3.20 (2H, m), 3.15 (2H, t, J=7.4 Hz), 2.66 (3H, s), 2.53 (3H, s).

Step 4. 2-(4-{5,7-Dimethyl-2-[2-(1,3-thiazol-2-yl)ethyl]-3H-imidazo[4,5-b]pyridin-3-yl}phenyl)ethyl azide The title compound was prepared according to the procedure described in step 8 Example 1 from 3-[4-(2-chloroethyl)phenyl]-5,7-dimethyl-2-[2-(1,3-thiazol-2-yl)ethyl]-3H-imidazo[4,5-b]pyridine (step 3).

MS (EI) m/z 403 (M$^+$); $^1$H-NMR (CDCl$_3$) δ 7.63 (1H, d, J=3.5 Hz), 7.38 (2H, d, J=8.4 Hz), 7.28 (2H, d, J=8.4 Hz), 7.15 (1H, d, J=3.5 Hz), 6.93 (1H, s), 3.63–3.54 (4H, m), 3.34–3.26 (2H, m), 2.98 (2H, t, J=7.4 Hz), 2.68 (3H, s), 2.53 (3H, s).

Step 5. 2-(4-{5,7-Dimethyl-2-[2-(1,3-thiazol-2-yl)ethyl]-3H-imidazole4,5-b]pyridin-3-yl}phenyl)ethylamine The title compound was prepared according to the procedure described in step 9 of Example 1 from 2-(4-{5,7-dimethyl-2-[2-(1,3-thiazol-2-yl)ethyl]-3H-imidazo[4,5-b]pyridin-3-yl}phenyl)ethyl azide (step 4).

MS (EI) m/z 377 (M$^+$).

Step 6. 5,7-Dimethyl-3-(4-{2-[({[(4-methylphenyl)sulfonyl]amino}carbonyl)amino]ethyl}phenyl)-2-[2-(1,3-thiazole-2-yl)ethyl]-3H-imidazo[4,5-b]pyridine The title compound was prepared according to the procedure described in step 10 of Example 1 from 2-(4-{5,7-dimethyl-2-[2-(1,3-thiazol-2-yl)ethyl]-3H-imidazo[4,5-b]pyridin-3-yl}phenyl)ethylamine (step 5).

MS (ESI) m/z 575 (M+H)+; ¹H-NMR (CDCl₃) δ 7.83 (2H, d, J=8.3 Hz), 7.61 (1H, d, J=3.5 Hz), 7.32 (2H, d, J=8.3 Hz), 7.19–7.15 (3H, m), 7.07 (2H, d, J=8.2 Hz), 6.91 (1H, s), 6.21 (1H, br.s), 3.52–3.40 (4H, m), 3.20–3.13 (2H, m), 2.81 (2H, t, J=6.1 Hz), 2.65 (3H, s), 2.44 (3H, s), 2.41 (3H, s).

Example 18
3-{4-[2-({[(4-BIPHENYLSULFONYL)AMINO]CARBONYL}AMINO)ETHYL]PHENYL}-2-ETHYL-5,7-DIMETHYL-3H-IMIDAZO[4,5-b]PYRIDINE
Step 1. Phenyl 2-[4-(2-ethyl-5,7-dimethyl-3H-imidazo[4,5-b]pyridin-3-yl)phenyl]ethylcarbamate To a stirred solution of 2-[4-(2-ethyl-5,7-dimethyl-3H-imidazo[4,5-b]pyridin-3-yl)phenyl]ethylamine (step 9 of Example 1, 1.55 g, 5.3 mmol) and triethylamine (0.80 mL, 5.8 mmol) in dichloromethane (26 mL) cooled in an ice bath was added dropwise phenyl chloroformate (0.69 mL, 5.5 mmol), and the mixture was stirred at ambient temperature. After 30 min, the reaction mixture was partitioned between saturated aqueous sodium bicarbonate (30 mL) and dichloromethane (30 mL). The organic layer was separated and the aqueous phase was extracted with dichloromethane (30 mL). The combined organic phases were dried (Na₂SO₄) and concentrated under reduced pressure. The residue was recrystallized from dichloromethane/hexane to give 1.90 g (87%) of the title compound as pale brown crystals: ¹H-NMR (CDCl₃) δ 7.43–7.11 (9H, m), 6.91 (1H, s), 5.50 (1H, br.s), 3.57 (2H, pseudo q, J=6.9 Hz), 2.98 (2H, t, J=6.9 Hz), 2.83 (2H, q, J=7.6 Hz), 2.66 (3H, s), 2.52 (3H, s), 1.28 (3H, t, J=7.6 Hz).
Step 2. 3-{4-[2-({[(4-Biphenylsulfonyl)amino]carbonyl}amino)ethyl]phenyl}-2-ethyl-5,7-dimethyl-3H-imidazo[4,5-b]pyridine To a stirred solution of 4-biphenylsulfonamide (Greenlee, W. J.; Walsh, T. F.; et al. Eur. Pat. Appl., EP 617001 (1994)., 56 mg, 0.24 mmol) in DMF (3 mL) was added NaH (60% oil dispersion, 20 mg, 0.5 mmol) at room temperature. After 5 min, phenyl 2-[4-(2-ethyl-5,7-dimethyl-3H-imidazo[4,5-b]pyridin-3-yl)phenyl]ethylcarbamate (step 1, 100 mg, 0.24 mmol) was added, and the mixture was stirred for an additional 1 h. The mixture was poured into water (50 mL) and extracted with diethyl ether (2×50 mL). The combined extracts were washed with water (50 mL), brine (50 mL) and dried (MgSO₄). Removal of solvent gave white oily solids. Purification by preparative TLC (ethyl acetate) gave 66 mg (50%) of the title compound as a colorless oil: MS (ESI) m/z 554 (M+H)+; ¹H-NMR (CDCl₃) δ□□8.06 (2H, d, J=8.6 Hz), 7.13 (2H, d, J=8.6 Hz), 7.60–7.53 (2H, m), 7.48–7.36 (3H, m), 7.21 (2H, d, J=8.4 Hz), 7.12 (2H, d, J=8.3 Hz), 6.92 (1H, s), 6.11 (1H, br.t, J=5.5 Hz), 3.54 (2H, dt, J=5.9, 6.0 Hz), 2.89 (2H, d, J=6.0 Hz), 2.64 (2H, q, J=7.5 Hz), 2.66 (3H, s), 2.40 (3H, t, J=7.5 Hz).

Example 19
2-ETHYL-5,7-DIMETHYL-3-{4-[2-({[(1-NAPHTHYLSULFONYL)AMINO]CARBONYL}AMINO)ETHYL]PHENYL}-3H-IMIDAZO[4,5-b]PYRIDINE The title compound was prepared according to the procedure described in step 2 of Example 18 from phenyl 2-[4-(2-ethyl-5,7-dimethyl-3H-imidazo[4,5-b]pyridin-3-yl)phenyl]ethylcarbamate (step 1 of Example 18) and 1-naphtylsulfonamide (Arnswald, M.; Neumann, W. P. Chem. Ber., 1991, 124, 1997; Khorgami, M. H. Synthesis, 1972, 574).

MS (ESI) m/z 528 (M+H)+; ¹H-NMR (CDCl₃) δ□8.52–8.48 (1H, m), 8.36 (1H, dd, J=1.1, 7.3 Hz), 8.11 (1H, d, 8.3 Hz), 8.00–7.94 (1H, m), 7.63–7.50 (3H, m), 7.20 (2H, d, J=8.4 Hz), 7.13 (2H, d, J=8.4 Hz), 6.94 (1H, s), 6.32 (1H, br.t, J=5,7 Hz), 3.50 (2H, dt, J=5.9, 6.0 Hz), 2.82 (2H, t, J=6.2 Hz), 2.68 (2H, q, J=7.5 Hz), 2.65 (3H, s), 2.41 (3H, s), 1.21 (3H, t, J=7.5 Hz).

Example 20
2-ETHYL-5,7-DIMETHYL-3-{4-[2-({[(2-NAPHTHYLSULFONYL)AMINO]CARBONYL}AMINO)ETHYL]PHENYL}-3H-IMIDAZO[4,5-b]PYRIDINE The title compound was prepared according to the procedure described in step 2 of Example 18 from phenyl 2-[4-(2-ethyl-5,7-dimethyl-3H-imidazo[4,5-b]pyridin-3-yl)phenyl]ethylcarbamate (step 1 of Example 18) and 2-naphtylsulfonamide.

MS (ESI) m/z 528 (M+H)+; ¹H-NMR (CDCl₃) δ 8.60 (1H, s), 8.01–7.84 (5H, m), 7.64–7.52 (2H, m), 7.20–7.08 (4H, m), 6.92 (1H, s), 6.20 (1H, t, J=5.6 Hz), 3.52–3.45 (2H, q, J=6.1 Hz), 2.84–2.80 (2H, t, J=6.3 Hz), 2.71–2.62 (2H, q, J=6.6 Hz), 2.66 (3H, s), 2.43 (3H, s), 1.22–1.16 (3H, t, J=6.6 Hz).

Example 21
2-ETHYL-5,7-DIMETHYL-3-(4-{2-[({[(2-THIENYL)SULFONYL]AMINO}CARBONYL)AMINO]ETHYL}PHENYL)-3H-IMIDAZO[4,5-b]PYRIDINE The title compound was prepared according to the procedure described in step 2 of Example 18 from phenyl 2-[4-(2-ethyl-5,7-dimethyl-3H-imidazo[4,5-b]pyridin-3-yl)phenyl]ethylcarbamate (step 1 of Example 18) and 2-thiophenesulfonamide (Huang, H. C.; Reinhard, E. J.; Reitz, D. B. Tetrahedron Lett., 1994, 35, 7201.; Graham, S. L.; Scholz, T. H. Synthesis, 1986, 1031).

¹H-NMR (CDCl₃) δ 8.01 (1H, s), 7.78 (1H, dd, J=1.3, 4.9 Hz), 7.63 (1H, dd, J=1.3, 4.9 Hz), 7.22 (2H, d, J=8.3 Hz), 7.14 (2H, d, J=8.3 Hz), 7.09 (1H, dd, J=3.8, 5.0 Hz), 6.92 (1H, s), 6.05 (1H, t, J=5.3 Hz), 3.53 (2H, q, J=6.2 Hz), 2.96 (3H, s), 2.88 (3H, s), 2.87 (2H, t, J=6.2 Hz), 2.67 (2H, q, J=7.5 Hz), 2.65 (3H, s), 2.43 (3H, s), 1.20 (3H, t, J=7.5 Hz).

Example 22
3-(4-{2-[({[(5-CHLORO-2-THIENYL)SULFONYL]AMINO}CARBONYL)AMINO]ETHYL}PHENYL)-2-ETHYL-5,7-DIMETHYL-3H-IMIDAZO[4,5-b]PYRIDINE The title compound was prepared according to the procedure described in step 2 of Example 18 from phenyl 2-[4-(2-ethyl-5,7-dimethyl-3H-imidazo[4,5-b]pyridin-3-yl)phenyl]ethylcarbamate (step 1 of Example 18) and 5-chloro-2-thiophenesulfonamide.

MS (ESI) m/z 518 (M+H)+; ¹H-NMR (CDCl₃) δ 7.99 (1H, s), 7.58–7.56 (1H, m), 7.23–7.15 (4H, m), 6.94–6.92 (1H, m), 6.04 (1H, br), 3.53–3.51 (2H, m), 2.87 (2H, m), 2.73–2.65 (2H, q, J=7.6 Hz), 2.65 (3H, s), 2.44 (3H, s), 1.21 (3H, t, J=7.6 Hz).

Example 23
3-(4-{2-[({[(4,5-DICHLORO-2-THIENYL)SULFONYL]AMINO}CARBONYL)AMINO]ETHYL}PHENYL)-2-ETHYL-5,7-DIMETHYL-3H-IMIDAZO[4,5-b]PYRIDINE The title compound was prepared according to the procedure described in step 2 of Example 18 from phenyl 2-[4-(2-ethyl-5,7-dimethyl-3H-imidazo[4,5-b]pyridin-3-yl)phenyl]ethylcarbamate (step 1 of Example 18) and 5,6-dichloro-2-thiophenesulfonamide.

MS (ESI) m/z 552 (M+H)+; ¹H-NMR (CDCl₃) δ 7.49 (1H, s), 7.27–7.14 (4H, m), 6.84 (1H, s), 3.47 (2H, br), 2.75 (2H, br), 2.69 (2H, q, J=7.6 Hz), 2.64 (3H, s), 2.38 (3H, s), 1.22 (3H, t, J=7.6 Hz).

Example 24
3-{4-[2-({[(1-BENZOTHIEN-2-YLSULFONYL)AMINO]CARBONYL}AMINO)ETHYL]PHENYL}-2-ETHYL-5,7-DIMETHYL-3H-IMIDAZO[4,5-b]PYRIDINE The title compound was prepared according to the procedure described in step 2 of Example 18 from phenyl 2-[4-(2-ethyl-5,7-dimethyl-3H-imidazo[4,5-b]pyridin-3-yl)phenyl]ethylcarbamate (step 1 of Example 18) and 1-benzothiophene-2-sulfonamide (Chern, J.; Leu, Y.; et al. *J. Med. Chem.*, 1997, 40, 2276.; Graham, S. L.; Shepard, K. L.; et al. *J. Med. Chem.*, 1989, 32, 2548).

mp 128.0–130.0° C.; MS (ESI) m/z 534 (M+H)$^+$; $^1$H-NMR (DMSO-d$_6$) δ 8.05–8.00 (3H, m), 7.50–7.42 (2H, m), 7.36 (2H, d, J=7.4 Hz), 7.32 (2H, d, J=7.4 Hz), 6.96 (1H, s), 6.61–6.56 (1H, m), 3.34–3.28 (2H, m), 2.80 (2H, t, J=6.6 Hz), 2.68 (2H, q, J=7.5 Hz), 2.54 (3H, s), 2.40 (3H, s), 1.19 (3H, t, J=7.5 Hz).

Example 25
3-(4-{2-[({[(2-CHLOROPHENYL)SULFONYL]AMINO}CARBONYL)AMINO]ETHYL}PHENYL)-2-ETHYL-5,7-DIMETHYL-3H-IMIDAZO[4,5-b]PYRIDINE The title compound was prepared according to the procedure described in step 10 of Example 1 from 2-[4-(2-ethyl-5,7-dimethyl-3H-imidazo[4,5-b]pyridin-3-yl)phenyl]ethylamine (step 9 of Example 1) and 2-chlorobenzenesulfonyl isocyanate.

MS (ESI) m/z 512 (M+H)$^+$; $^1$H-NMR (CDCl$_3$) δ 8.21–8.17 (1H, d, 7.7 Hz), 7.57–7.43 (3H, m), 7.32–7.22 (4H, m), 6.93 (s, 1H), 6.34 (1H, t, J=5.6 Hz), 3.56–3.49 (2H, q, J=6.3 Hz), 2.89–2.85 (2H, t, J=6.4 Hz), 2.80–2.71 (q, 2H, J=7.6 Hz), 2.67 (3H, s), 2.49 (3H, s), 1.28–1.22 (3H, t, J=7.6 Hz).

Example 26
2-ETHYL-5-METHYL-3-(4-{2-[({[(4-METHYLPHENYL)SULFONYL]AMINO}CARBONYL)AMINO]ETHYL}PHENYL)-3H-IMIDAZO[4,5-b]PYRIDINE Step 1. 2-{4-[(6-Methyl-3-nitro-2-pyridinyl)amino]phenyl}ethanol The title compound was prepared according to the procedure described in step 3 of Example 1 from 2-chloro-6-methyl-3-nitropyridine (Takayama, K.; Iwata, M.; Kono, N.; et al. Jpn. Kokai Tokkyo Koho, JP11292877 (1999).; Ding, C. Z.; Hunt, J. T.; Kim, S.; et al. PCT Int. Appl., WO 9730992 (1997)) and 4-aminophenylethyl alcohol.

$^1$H-NMR (CDCl$_3$) δ 8.24 (1H, d, J=9.1 Hz), 7.28–7.33 (4H, m), 6.65 (1H, d, J=9.2 Hz), 3.89 (2H, d, J=6.4 Hz), 2.89 (2H, d, J=6.4 Hz), 2.81 (3H, s).

Step 2. 2-{4-[(3-Amino-6-methyl-2-pyridinyl)amino]phenyl}ethanol

To a solution of 2-{4-[(6-methyl-3-nitro-2-pyridinyl)amino]phenyl}ethanol (step 1, 4.6 g, 16.9 mmol) in methanol (100 mL) was added 10% Pd—C (300 mg). The resulting mixture was stirred for 2 h under hydrogen atmosphere. The mixture was filtered through a pad of Celite and the filtrate was concentrated. The residue was purified by flash column chromatography eluting with hexane/ethyl acetate (gradient elution from 1:2 to 1:5) to afford 3.8 g (92%) of the title compound as yellow solids: $^1$H-NMR (CDCl$_3$) δ: 7.10–7.16 (4H, m), 6.91 (1H, d, J=8.4 Hz), 6.70 (1H, d, J=8.4 Hz), 6.19 (1H, s), 3.83 (2H, t, J=6.4 Hz), 2.81 (2H, t, J=6.4 Hz), 2.35 (3H, s).

Step 3. 2-[4-(2-Ethyl-5-methyl-3H-imidazo[4,5-b]pyridin-3-yl)phenyl]ethyl propionate The title compound was prepared according to the procedure described in step 5 of Example 1 from 2-{4-[(3-amino-6-methyl-2-pyridinyl)amino]phenyl}ethanol (step 2) and propionyl chloride.

MS (EI) m/z 337 (M$^+$).

Step 4. 2-[4-(2-Ethyl-5-methyl-3H-imidazo[4,5-b]pyridin-3-yl)phenyl]ethanol

The title compound was prepared according to the procedure described in step 6 of Example 1 from 2-[4-(2-ethyl-5-methyl-3H-imidazo[4,5-b]pyridin-3-yl)phenyl]ethyl propionate (step 3).

$^1$H-NMR (CDCl$_3$) δ 7.90 (1H, d, J=8.3 Hz), 7.43 (2H, d, J=8.2 Hz), 7.34 (2H, d, J=8.2 Hz), 7.07 (1H, d, J=8.3 Hz), 3.93 (2H, t, J=6.6 Hz), 2.97 (2H, t, J=6.6 Hz), 2.80 (2H, q, J=7.5 Hz), 2.56 (3H, s), 1.35 (3H, t, J=7.5 Hz).

Step 5. 2-[4-(2-Ethyl-5-methyl-3H-imidazo[4,5-b]pyridin-3-yl)phenyl]ethyl azide

A mixture of 2-[4-(2-ethyl-5-methyl-3H-imidazo[4,5-b]pyridin-3-yl)phenyl]ethanol (step 4, 217 mg, 0.77 mmol) in THF (20 mL) was added diethyl azodicarboxylate (DEAD) (0.3 mL, 1.5 mmol), triphenylphosphine (380 mg, 1.5 mmol) and diphenylphosphoryl azide (DPPA) (0.4 mL, 1.5 mmol). The mixture was stirred at room temperature for 4.5 h. After removal of solvent, the residue was purified by flash column chromatography on silica gel eluting with hexane/ethyl acetate (gladient elution from 1:1 to 1:2) to afford 70 mg (30%) of the title compound as a brown oil: $^1$H-NMR (CDCl$_3$) δ 7.90 (1H, d, J=8.1 Hz), 7.34–7.44 (4H, m), 7.08 (1H, d, J=8.1 Hz), 3.60 (2H, t, J=7.1 Hz), 3.00 (2H, t, J=7.1 Hz), 2.80 (2H, q, J=7.5 Hz), 2.57 (3H, s), 1.35 (3H, t, J=7.5 Hz).

Step 6. 2-[4-(2-Ethyl-5-methyl-3H-imidazo[4,5-b]pyridin-3-yl)phenyl]ethylamine

The title compound was prepared according to the procedure described in step 9 of Example 1 from 2-[4-(2-ethyl-5-methyl-3H-imidazo[4,5-b]pyridin-3-yl)phenyl]ethyl azide (step 5).

$^1$H-NMR (CDCl$_3$) δ 7.91 (1H, d, J=8.1 Hz), 7.42 (2H, d, J=8.3 Hz), 7.32 (2H, d, J=8.3 Hz), 7.06 (1H, d, J=8.1 Hz), 3.13 (2H, t, J=6.8 Hz), 2.95 (2H, t, J=6.8 Hz), 2.81 (2H, q, J=7.6 Hz), 2.55 (3H, s), 1.34 (3H, t, J=7.6 Hz).

Step 7. 2-Ethyl-5-methyl-3-(4-{2-[({[(4-methylphenyl)sulfonyl]amino}carbonyl)amino]ethyl}phenyl)-3H-imidazo[4,5-b]pyridine The title compound was prepared according to the procedure described in step 10 of Example 1 from 2-[4-(2-ethyl-5-methyl-3H-imidazo[4,5-b]pyridin-3-yl)phenyl]ethylamine (step 6).

MS (ESI) m/z 476 (M+H)$^+$; $^1$H-NMR (CDCl$_3$) δ 7.95 (1H, d, J=8.0 Hz), 7.84 (2H, d, J=8.2 Hz), 7.32 (2H, d, J=8.2 Hz), 7.25 (2H, d, J=8.2 Hz), 7.17 (2H, d, J=8.2 Hz), 7.10 (1H, d, J=8.0 Hz), 6.17 (1H, br.s), 3.52 (2H, t, J=6.6 Hz), 2.86 (2H, t, J=6.6 Hz), 2.69 (2H, q, J=7.5 Hz), 2.49 (3H, s), 2.41 (3H, s), 1.27 (3H, t, J=7.5 Hz).

Example 27
2-ETHYL-5-METHYL-3-(4-{2-[({[(4-METHYLPHENYL)SULFONYL]AMINO}CARBONYL)AMINO]ETHYL}PHENYL)-3H-IMIDAZO[4,5-b]PYRIDINE, SODIUM SALT The title compound was prepared according to the procedure described in Example 2 from 2-ethyl-5-methyl-3-(4-{2-[({[(4-methylphenyl)sulfonyl]amino}carbonyl)amino]ethyl}phenyl)-3H-imidazo[4,5-b]pyridine (Example 26).

$^1$H-NMR (DMSO-d$_6$) δ 7.91 (1H, d, J=7.9 Hz), 7.61 (2H, d, J=6.8 Hz), 7.36 (4H, s), 7.11–7.15 (3H, m), 2.67–2.75 (4H, m), 2.50 (2H, br.s), 2.45 (3H, s), 2.28 (3H, s), 1.21–1.24 (3H, m).

Example 28
2-ETHYL-5-METHOXY-3-(4-{2-[({[(4-METHYLPHENYL)SULFONYL]AMINO}CARBONYL)AMINO]ETHYL}PHENYL)-3H-IMIDAZO[4,5-b]PYRIDINE Step 1. 2-{4-[(6-Methoxy-3-nitro-2-pyridinyl)amino]phenyl}ethanol The title compound was prepared according to the procedure described in step 3 of Example 1 from 2-chloro-6-methoxy-3-nitropyridine and 4-aminophenylethyl alcohol.

$^1$H-NMR (CDCl$_3$) δ 10.59 (1H, br.s), 8.38 (1H, d, J=9.2 Hz), 7.59 (2H, d, J=8.3 Hz), 7.23 (2H), d, J=8.3 Hz), 6.20 (1H, d, J=9.2 Hz), 3.94 (3H, s), 3.87 (2H, t, J=6.6 Hz), 2.87 (2H, t, J=6.8 Hz).

Step 2. 2-{4-[(3-Amino-6-methoxy-2-pyridinyl)amino]phenyl}ethanol

A mixture of 2-{4-[(6-methoxy-3-nitro-2-pyridinyl)amino]phenyl}ethanol (step 1, 3.52 g, 12.17 mmol), iron powder (3.4 g, 60.84 mmol) and ammonium chloride (325 mg, 6.08 mmol) in ethanol/water (v/v, 2:1, 90 mL) was heated at reflux temperature for 1 h. After cooling, the catalyst was removed and the filtrate was concentrated. The residue was extracted with ethyl acetate (100 mL) and washed with water. The organic layer was dried (MgSO$_4$), and concentrated to give 3.41 g (quant.) of the title compound as a black oil: $^1$H-NMR (CDCl$_3$) δ7.48 (2H, d, J=8.4 Hz), 7.14 (2H, d, J=8.4 Hz), 7.04 (1H, d, J=8.2 Hz), 6.75 (1H, br.s), 6.13 (1H, d, J=8.2 Hz), 3.87 (3H, s), 3.83 (2H, t, J=6.6 Hz), 2.81 (2H, t, J=6.6 Hz).

Step 3. 2-[4-(2-Ethyl-5-methoxy-3H-imidazo[4,5-b]pyridin-3-yl)phenyl]ethyl propionate The title compound was prepared according to the procedure described in step 5 of Example 1 from 2-{4-[(3-amino-6-methoxy-2-pyridinyl)amino]phenyl}ethanol (step 2) and propionyl chloride.

TLC Rf=0.50 (hexane/ethyl acetate=2:1).

Step 4. 2-[4-(2-Ethyl-5-methoxy-3H-imidazo[4,5-b]pyridin-3-yl)phenyl]ethanol

The title compound was prepared according to the procedure described in step 6 of Example 1 from 2-[4-(2-ethyl-5-methoxy-3H-imidazo[4,5-b]pyridin-3-yl)phenyl]ethyl propionate (step 3).

$^1$H-NMR (CDCl$_3$) δ 7.91 (1H, d, J=8.6 Hz), 7.43 (2H, d, J=8.4 Hz), 7.35 (2H, d, J=8.4 Hz), 6.67 (1H, d, J=8.6 Hz), 3.98–3.88 (2H, m), 3.82 (3H, s), 2.99 (2H, t, J=6.4 Hz), 2.81 (2H, q, J=7.4 Hz), 1.34 (3H, t, J=7.4 Hz).

Step 5. 2-[4-(2-Ethyl-5-methoxy-3H-imidazo[4,5-b]pyridin-3-yl)phenyl]ethyl azide The title compound was prepared according to the procedure described in step 5 of Example 26 from 2-(4-(2-ethyl-5-methoxy-3H-imidazo[4,5-b]pyridin-3-yl)phenyl)ethanol (step 4).

TLC Rf=0.78 (hexane/ethyl acetate=1/1).

Step 6. 2-[4-(2-Ethyl-5-methoxy-3H-imidazo[4,5-b]pyridin-3-yl)phenyl]ethylamine

The title compound was prepared according to the procedure described in step 9 of Example 1 from 2-[4-(2-ethyl-5-methoxy-3H-imidazo[4,5-b]pyridin-3-yl)phenyl]ethyl azide (step 5).

$^1$H-NMR (CDCl$_3$) δ 7.92 (1H, d, J=8.6 Hz), 7.40–7.31 (4H, m), 6.67 (1H, d, J=8.6 Hz), 3.82 (3H, s), 3.13–3.10 (2H, m), 3.00–2.97 (2H, m), 2.80 (2H, q, J=7.6 Hz), 1.33 (3H, t, J=7.6 Hz).

Step 7. 2-Ethyl-5-methoxy-3-(4-{2-[({[(4-methylphenyl)sulfonyl]amino}carbonyl)amino]ethyl}phenyl)-3H-imidazo[4,5-b]pyridine The title compound was prepared according to the procedure described in step 10 of Example 1 from 2-[4-(2-ethyl-5-methoxy-3H-imidazo[4,5-b]pyridin-3-yl)phenyl]ethylamine (step 6).

$^1$H-NMR (CDCl$_3$) δ 7.95 (1H, d, J=8.7 Hz), 7.74 (2H, d, J=8.4 Hz), 7.34–7.27 (6H, m), 6.69 (1H, d, J=8.7 Hz), 6.55 (1H, m), 3.79 (3H, s), 3.60–3.53 (2H, m), 2.90 (2H, t, J=6.8 Hz), 2.77 (2H, q, J=7.4 Hz), 1.30 (3H, t, J=7.4 Hz).

Example 29
2-ETHYL-5-METHOXY-3-(4-{2-[({[(4-METHYLPHENYL)SULFONYL]AMINO}CARBONYL)AMINO]ETHYL}PHENYL)-3H-IMIDAZO[4,5-b]PYRIDINE, SODIUM SALT The title compound was prepared according to the procedure described in Example 2 from 2-ethyl-5-methoxy-3-(4-{2-[({[(4-methylphenyl)sulfonyl]amino}carbonyl)amino]ethyl}phenyl)-3H-imidazo[4,5-b]pyridine (Example 28).

$^1$H-NMR (DMSO-d$_6$) δ 7.94 (1H, d, J=8.4 Hz), 7.59 (2H, d, J=8.1 Hz), 7.41–7.34 (4H, m), 7.12 (2H, d, J=8.1 Hz), 6.68 (1H, d, J=8.4 Hz), 3.71 (3H, s), 3.14 (2H, m), 2.75–2.68 (4H, m), 2.27 (3H, s), 1.20 (3H, t, J=7.5 Hz); IR (KBr) α$_{max}$ 1597, 1518, 1489, 1425, 1389, 1261, 1130, 1086 cm$^{-1}$.

Example 30
6-CHLORO-2-ETHYL-3-(4-{2-[({[(4-METHYLPHENYL)SULFONYL]AMINO}CARBONYL)AMINO]ETHYL}PHENYL)-3H-IMIDAZO[4,5-b]PYRIDINE Step 1. 2-{4-[(5-Methyl-3-nitro-2-pyridinyl)amino]phenyl}ethanol The title compound was prepared according to the procedure described in step 3 of Example 1 from 2-chloro-5-methyl-3-nitropyridine and 4-aminophenylethyl alcohol.

$^1$H-NMR (CDCl$_3$) δ 9.96 (1H, br.s), 8.32–8.31 (2H, m), 7.55 (2H, d, J=8.3 Hz), 7.24 (2H, d, J=8.3 Hz), 3.85 (2H, m), 2.86 (2H, t, J=6.6 Hz), 2.32 (3H, s).

Step 2. 2-{4-[(3-Amino-5-methyl-2-pyridinyl)amino]phenyl}ethanol

The title compound was prepared according to the procedure described in step 2 of Example 28 from 2-{4-[(5-methyl-3-nitro-2-pyridinyl)amino]phenyl}ethanol (step 1).

$^1$H-NMR (CDCl$_3$) δ 7.59 (1H, m), 7.08–7.00 (4H, m), 6.80 (1H, m), 3.74 (2H, t, J=6.6 Hz), 2.74 (2H, t, J=6.6 Hz), 2.19 (3H, s).

Step 3. 2-[4-(2-Ethyl-6-methyl-3H-imidazo[4,5-b]pyridin-3-yl)phenyl]ethyl propionate The title compound was prepared according to the procedure described in step 5 of Example 1 from 2-{4-[(3-amino-5-methyl-2-pyridinyl)amino]phenyl}ethanol (step 2) and propionyl chloride.

TLC Rf=0.74 (dichloromethane/methanol=10:1).

Step 4. 2-[4-(2-Ethyl-6-methyl-3H-imidazo[4,5-b]pyridin-3-yl)phenyl]ethanol

The title compound was prepared according to the procedure described in step 6 of Example 1 from 2-[4-(2-ethyl-6-methyl-3H-imidazo[4,5-b]pyridin-3-yl)phenyl]ethyl propionate (step 3).

$^1$H-NMR (CDCl$_3$) δ 8.12 (1H, s), 7.84 (1H, s), 7.44 (2H, d, J=8.1 Hz), 7.33 (2H, d, J=8.1 Hz), 3.91–3.85 (2H, m), 2.96 (2H, t, J=6.7 Hz), 2.82 (2H, q, J=7.5 Hz), 2.46 (3H, s), 1.36 (3H, t, J=7.5 Hz).

Step 5. 2-[4-(2-Ethyl-6-methyl-3H-imidazo[4,5-b]pyridin-3-yl)phenyl]ethyl azide

The title compound was prepared according to the procedure described in step 5 Example 26 from 2-[4-(2-ethyl-6-methyl-3H-imidazo[4,5-b]pyridin-3-yl)phenyl]ethanol (step 4).

$^1$H-NMR (CDCl$_3$) δ 8.13 (1H, s), 7.84 (1H, s), 7.44 (2H, d, J=8.4 Hz), 7.36 (2H, d, J=8.4 Hz), 3.59 (2H, t, J=7.3 Hz), 3.00 (2H, t, J=7.3 Hz), 2.83 (2H, q, J=7.6 Hz), 2.46 (3H, s)1.36 (3H, t, J=7.6 Hz).

Step 4. 2-[4-(2-Ethyl-6-methyl-3H-imidazo[4,5-b]pyridin-3-yl)phenyl]ethylamine

The title compound was prepared according to the procedure described in step 9 of Example 1 from 2-[4-(2-ethyl-6-methyl-3H-imidazo[4,5-b]pyridin-3-yl)phenyl]ethyl azide (step 5).

$^1$H-NMR (CDCl$_3$) δ 8.12 (1H, s), 7.84 (1H, s), 7.42 (2H, d, J=8.4 Hz), 7.33 (2H, d, J=8.4 Hz), 3.07 (2H, t, J=6.8 Hz), 2.91–2.78 (4H, m), 2.46 (3H, s), 1.36 (3H, t, J=7.5 Hz).

Step 5. 2-Ethyl-6-methyl-3-(4-{2-[({[(4-methylphenyl)sulfonyl]amino}carbonyl)amino]ethyl}phenyl)-3H-imidazo[4,5-b]pyridine The reaction was carried out according to the procedure described in step 10 of Example 1 from 2-[4-(2-ethyl-6-methyl-3H-imidazo[4,5-b]pyridin-3-yl)phenyl]ethylamine (step 6).

$^1$H-NMR (CDCl$_3$) δ 8.04 (1H, d, J=1.8 Hz), 7.86–7.82 (3H, m), 7.33–7.21 (6H, m), 6.27 (1H, m), 3.52–3.49 (2H, m), 2.87 (2H, t, J=6.8 Hz), 2.76 (2H, q, J=7.6 Hz), 2.45 (3H, s), 2.41 (3H, s), 1.30 (3H, t, J=7.6 Hz).

Example 31

6-CHLORO-2-ETHYL-3-(4-{2-[({[(4-METHYLPHENYL)SULFONYL]AMINO}CARBONYL)AMINO]ETHYL}PHENYL)-3H-IMIDAZO[4,5-b]PYRIDINE, SODIUM SALT

The title compound was prepared according to the procedure described in Example 2 from 2-ethyl-6-methyl-3-(4-{2-[({[(4-methylphenyl)sulfonyl]amino}carbonyl)amino]ethyl}phenyl)-3H-imidazo[4,5-b]pyridine (Example 30).

$^1$H-NMR (DMSO-d$_6$) δ 8.04 (1H, m), 7.84 (1H, m), 7.60 (2H, d, J=8.1 Hz), 7.36 (4H, s), 7.12 (2H, d, J=8.1 Hz), 3.13 (2H, m), 2.78–2.71 (4H, m), 2.39 (3H, s), 2.27 (3H, s), 1.22 (3H, t, J=7.5 Hz); IR (KBr) α$_{max}$ 1601, 1518, 1423, 1375, 1283, 1250, 1128, 1084 cm$^{-1}$.

Example 32

6-CHLORO-2-ETHYL-3-(4-{2-[({[(4-METHYLPHENYL)SULFONYL]AMINO}CARBONYL)AMINO]ETHYL}PHENYL)-3H-IMIDAZO[4,5-b]PYRIDINE

Step 1. 2-{4-[(5-Chloro-3-nitro-2-pyridinyl)amino]phenyl}ethanol

The title compound was prepared according to the procedure described in step 3 of Example 1 from 2,5-dichloro-3-nitropyridine (Marfat, A.; Robinson, R. P. U.S. Pat. No. 5,811,432 (1998).; Haessig, R.; Siegrist, U. Eur. Pat. Appl., EP 483061 (1992).) and 4-aminophenylethyl alcohol.

$^1$H-NMR (CDCl$_3$) δ 10.00 (1H, br.s), 8.51–8.50 (1H, m), 8.41 (1H, d, J=2.4 Hz), 7.53 (2H, d, J=8.4 Hz), 7.27 (2H, d, J=8.4 Hz), 3.88–3.87 (2H, m), 2.88 (2H, t, J=6.6 Hz).

Step 2. 2-{4-[(3-Amino-5-chloro-2-pyridinyl)amino]phenyl}ethanol

The title compound was prepared according to the procedure described in step 2 of Example 28 from 2-{4-[(5-chloro-3-nitro-2-pyridinyl)amino]phenyl}ethanol (step 1).

$^1$H-NMR (CDCl$_3$) δ 7.73 (1H, d, J=2.2 Hz), 7.19–7.01 (4H, m), 6.97 (1H, d, J=2.2 Hz), 6.12 (1H, br.s), 3.81 (2H, t, J=6.4 Hz), 2.80 (2H, t, J=6.4 Hz).

Step 3. 2-[4-(6-Chloro-2-ethyl-3H-imidazo[4,5-b]pyridin-3-yl)phenyl]ethyl propionate The title compound was prepared according to the procedure described in step 5 of Example 1 from 2-{4-[(3-amino-5-chloro-2-pyridinyl)amino]phenyl}ethanol (step 2).

TLC Rf=0.43 (hexane/ethyl acetate=2:1).

Step 4. 2-[4-(6-Chloro-2-ethyl-3H-imidazo[4,5-b]pyridin-3-yl)phenyl]ethanol

The title compound was prepared according to the procedure described in step 6 of Example 1 from 2-[4-(6-chloro-2-ethyl-3H-imidazo[4,5-b]pyridin-3-yl)phenyl]ethyl propionate (step 3).

$^1$H-NMR (CDCl$_3$) δ 8.23 (1H, d, J=2.1 Hz), 8.01 (1H, d, J=2.1 Hz), 7.45 (2H, d, J=8.4 Hz), 7.31 (2H, d, J=8.4 Hz), 7.09 (1H, s), 3.92 (2H, t, J=6.4 Hz), 2.95 (2H, t, J=6.4 Hz), 2.83 (2H, q, J=7.4 Hz), 1.36 (3H, t, J=7.4 Hz).

Step 5. 2-[4-(6-Chloro-2-ethyl-3H-imidazo[4,5-b]pyridin-3-yl)phenyl]ethyl azide

The title compound was prepared according to the procedure described in step 5 of Example 26 from 2-[4-(6-chloro-2-ethyl-3H-imidazo[4,5-b]pyridin-3-yl)phenyl]ethanol (step 4).

$^1$H-NMR (CDCl$_3$) δ 8.25 (1H, d, J=2.2 Hz), 8.02 (1H, d, J=2.2 Hz), 7.46 (2H, d, J=8.3Hz), 7.35 (2H, d, J=8.3 Hz), 3.60 (2H, t, J=7.2 Hz), 3.00 (2H, t, J=7.2 Hz), 2.84 (2H, q, J=7.5 Hz), 1.37 (3H, t, J=7.5 Hz).

Step 6. 2-[4-(6-Chloro-2-ethyl-3H-imidazo[4,5-b]pyridin-3-yl)phenyl]ethylamine

The title compound was prepared according to the procedure described in step 9 of Example 1 from 2-[4-(6-chloro-2-ethyl-3H-imidazo[4,5-b]pyridin-3-yl)phenyl]ethyl azide (step 5).

$^1$H-NMR (CDCl$_3$) δ 8.22 (1H, d, J=2.1 Hz), 8.01 (1H, d, J=2.1 Hz), 7.45 (2H, d, J=8.2 Hz), 7.32 (2H, d, J=8.2 Hz), 3.13–3.08 (2H, m), 2.95–2.78 (4H, m), 1.36 (3H, t, J=7.6 Hz).

Step 7. 6-Chloro-2-ethyl-3-(4-{2-[({[(4-methylphenyl)sulfonyl]amino}carbonyl)amino]ethyl}phenyl)-3H-imidazo[4,5-b]pyridine The title compound was prepared according to the procedure described in step 10 of Example 1 from 2-[4-(6-chloro-2-ethyl-3H-imidazo[4,5-b]pyridin-3-yl)phenyl]ethylamine (step 6).

$^1$H-NMR (CDCl$_3$) δ 8.20 (1H, d, J=2.2 Hz), 8.03 (1H, d, J=2.2 Hz), 7.77 (2H, d, J=8.1 Hz), 7.38–7.27 (6H, m), 6.51–6.48 (1H, m), 3.57–3.50 (2H, m), 2.90 (2H, t, J=6.8 Hz), 2.81 (2H, t, J=7.5 Hz), 1.34 (3H, t, J=7.5 Hz).

Example 33

6-CHLORO-2-ETHYL-3-(4-{2-[({[(4-METHYLPHENYL)SULFONYL]AMINO}CARBONYL)AMINO]ETHYL}PHENYL)-3H-IMIDAZO[4,5-b]PYRIDINE, SODIUM SALT

The title compound was prepared according to the procedure described in Example 2 from 6-chloro-2-ethyl-3-(4-{2-[({[(4-methylphenyl)sulfonyl]amino}carbonyl)amino]ethyl}phenyl)-3H-imidazo[4,5-b]pyridine (Example 32).

$^1$H-NMR (DMSO-d$_6$) δ 8.24–8.21 (2H, m), 7.60 (2H, d, J=8.1 Hz), 7.42–7.34 (4H, m), 7.12 (2H, d, J=8.1 Hz), 3.13 (2H, m), 2.81–2.69 (4H, m), 2.27 (3H, s), 1.24 (3H, t, J=7.4 Hz), IR (KBr) α$_{max}$ 1597, 1516, 1421, 1375, 1246, 1128, 1084 cm$^{-1}$.

Example 34

2-ETHYL-5,6-DIMETHYL-3-(4-{2-[({[(4-METHYLPHENYL)SULFONYL]AMINO}CARBONYL)AMINO]ETHYL}PHENYL)-3H-IMIDAZO[4,5-b]PYRIDINE

Step 1. 2-{4-[(5,6-Dimethyl-3-nitro-2-pyridinyl)amino]phenyl}ethanol

A mixture of 2-chloro-5,6-dimethyl-3-nitropyridine (Godard, A.; Rocca, P.; Pomel, V.; et al. *J. Organomet. Chem.*, 1996, 517, 25.; Rocca, P.; Marsais, F.; Godard, A.; et al. *Tetrahedron Lett.*, 1993, 34, 2937., 3.3 g, 17.5 mmol), 4-aminophenylethyl alcohol (3.6 g, 26.3 mmol) and 2,6-lutidine (3.7 mL) in toluene (80 mL) was stirred under reflux temperature for 19 h. The mixture was diluted with ethyl acetate (100 mL) and washed with 1N aqueous NaOH (50 mL) and brine (50 mL). The organic layer was dried (Na$_2$SO$_4$), and concentrated. Purification by flash column chromatography on silica gel eluting with hexane/ethyl acetate (1:1) to afford 1.8 g (37%) of the title compound as orange solids: ¹H-NMR (CDCl₃) δ 8.24 (1H, br.s), 7.68 (2H, d, J=8.6 Hz), 7.24 (2H, d, J=8.6 Hz), 3.88 (2H, dt, J=6.1, 7.6 Hz), 2.88 (2H, t, J=7.6 Hz), 2.49 (3H, s), 2.26 (3H, s), 1.43 (1H, t, J=6.1 Hz).

Step 2. 2-{4-[(3-Amino-5,6-dimethyl-2-pyridinyl)amino]phenyl}ethanol

The title compound was prepared according to the procedure described in step 2 of Example 28 from 2-{4-[(5,6-dimethyl-3-nitro-2-pyridinyl)amino]phenyl}ethanol (step 1).

¹H-NMR (CDCl₃) δ 6.97 (2H, d, J=8.4 Hz), 6.92 (2H, d, J=8.4 Hz), 6.71 (1H, s), 6.22 (1H, br s), 3.67 (2H, t, J=6.8 Hz), 2.68 (2H, t, J=6.8 Hz), 2.29 (3H, s), 2.12 (3H, s).

Step 3 2-[4-(2-Ethyl-5,6-dimethyl-3H-imidazo[4,5-b]pyridin-3-yl)phenyl]ethyl propionate The title compound was prepared according to the procedure described in step 5 of Example 1 from 2-{4-[(3-amino-5,6-dimethyl-2-pyridinyl)amino]phenyl}ethanol (step 2) and propionyl chloride.

¹H-NMR (CDCl₃) δ 7.75 (1H, br.s), 7.42 (2H, d, J=8.6 Hz), 7.34 (2H, d, J=8.6 Hz), 4.37 (2H, t, J=6.6 Hz), 3.05 (2H, t, J=6.6 Hz), 2.80 (2H, q, J=7.6 Hz), 2.49 (3H, s), 2.38 (3H, s), 2.37–2.28 (2H, m), 1.34 (3H, t, J=7.6 Hz), 1.18 (3H, t, J=7.5 Hz).

Step 4. 2-[4-(2-Ethyl-5,6-dimethyl-3H-imidazo[4,5-b]pyridin-3-yl)phenyl]ethanol

The title compound was prepared according to the procedure described in step 6 of Example 1 from 2-[4-(2-ethyl-5,6-dimethyl-3H-imidazo[4,5-b]pyridin-3-yl)phenyl]ethyl propionate (step 3).

MS (ESI) m/z 296 (M+H)⁺; ¹H-NMR (CDCl₃) δ: 7.75 (1H, br.s), 7.43 (2H, d, J=8.6 Hz), 7.33 (2H, d, J=8.6 Hz), 3.92 (2H, br.t, J=6.6 Hz), 2.97 (2H, t, J=6.6 Hz), 2.80 (2H, q, J=7.6 Hz), 2.49 (3H, s), 2.38 (3H, s), 1.34 (3H, t, J=7.6 Hz).

Step 5. 3-[4-(2-Chloroethyl)phenyl]-2-ethyl-5,6-dimethyl-3H-imidazo[4,5-b]pyridine The title compound was prepared according to the procedure described in step 7 of Example 1 from 2-[4-(2-ethyl-5,6-dimethyl-3H-imidazo[4,5-b]pyridin-3-yl)phenyl]ethanol (step 4).

¹H-NMR (CDCl₃) δ 7.75 (1H, br.s), 7.43 (2H, d, J=8.6 Hz), 7.36 (2H, d, J=8.6 Hz), 3.80 (2H, t, J=7.3 Hz), 3.18 (2H, t, J=7.3 Hz), 2.81 (2H, q, J=7.6 Hz), 2.50 (3H, s), 2.38 (3H, s), 1.34 (3H, t, J=7.6 Hz).

Step 6. 2-[4-(2-Ethyl-5,6-dimethyl-3H-imidazo[4,5-b]pyridin-3-yl)phenyl]ethyl azide The title compound was prepared according to the procedure described in step 8 of Example 1 from 3-[4-(2-chloroethyl)phenyl]-2-ethyl-5,6-dimethyl-3H-imidazo[4,5-b]pyridine (step 5).

¹H-NMR (CDCl₃) δ 7.75 (1H, br.s), 7.42 (2H, d, J=8.4 Hz), 7.36 (2H, d, J=8.4 Hz), 3.60 (2H, t, J=7.3 Hz), 3.00 (2H, t, J=7.3 Hz), 2.80 (2H, q, J=7.6 Hz), 2.49 (3H, s), 2.38 (3H, s), 1.34 (3H, t, J=7.6 Hz).

Step 7. 2-[4-(2-Ethyl-5,6-dimethyl-3H-imidazo[4,5-b]pyriding-3-yl)phenyl]ethylamine The title compound was prepared according to the procedure described in step 9 of Example 1 from 2-[4-(2-ethyl-5,6-dimethyl-3H-imidazo[4,5-b]pyridin-3-yl)phenyl]ethyl azide (step 6).

¹H-NMR (CDCl₃) δ 7.76 (1H, br.s), 7.41 (2H, d, J=7.9 Hz), 7.33 (2H, d, J=7.9 Hz), 3.12 (2H, t, J=6.9 Hz), 2.95 (2H, t, J=6.9 Hz), 2.79 (2H, q, J=6.9 Hz), 2.47 (3H, s), 2.37 (3H, s), 1.33 (3H, t, J=6.9 Hz).

Step 8. 2-Ethyl-5,6-dimethyl-3-(4-{2-[({[(4-methylphenyl)sulfonyl]amino}carbonyl)amino]ethyl}phenyl)-3H-imidazo[4,5-b]pyridine The title compound was prepared according to the procedure described in step 10 of Example 1 from 2-[4-(2-ethyl-5,6-dimethyl-3H-imidazo[4,5-b]pyridin-3-yl)phenyl]ethylamine (step 7).

MS (ESI) m/z 492 (M+H)⁺; ¹H-NMR (CDCl₃) δ 7.87 (2H, d, J=8.2 Hz), 7.79 (1H, s), 7.31(2H, d, J=8.2 Hz), 7.23 (2H, d, J=8.1 Hz), 7.15 (2H, d, J=8.1 Hz), 6.24 (1H, m), 3.51 (2H, m), 2.85 (2H, t, J=6.1 Hz), 2.66 (2H, q, J=7.4 Hz), 2.39 (3H, s), 2.38 (3H, s), 2.36 (3H, s), 2.36 (3H, s), 1.25 (3H, t, J=7.4 Hz).

Example 35

2-ETHYL-5,6-DIMETHYL-3-(4-{2-[({[(4-METHYLPHENYL)SULFONYL]AMINO}CARBONYL)AMINO]ETHYL}PHENYL)-3H-IMIDAZO[4,5-b]PYRIDINE, SODIUM SALT

The title compound was prepared according to the procedure described in Example 2 from 2-ethyl-5,6-dimethyl-3-(4-{2-[({[(4-methylphenyl)sulfonyl]amino}carbonyl)amino]ethyl}phenyl)-3H-imidazo[4,5-b]pyridine (Example 34).

mp 156.0–158.5° C.; ¹H-NMR (DMSO-d₆) δ 7.58 (1H, s), 7.48 (2H, d, J=8.1 Hz), 7.19–7.13 (4H m), 6.98 (2H, d, J=8.1 Hz), 6.01 (1H, br.s), 3.15–2.98 (2H, m), 2.59–2.55 (2H, m), 2.50 (2H, q, J=7.6 Hz), 2.19 (3H, s), 2.13 (3H, s), 2.09 (3H, s), 1.01 (3H, t, J=7.6 Hz).

Example 36

2-[4-(2-ETHYL-5,6-DIMETHYL-3H-IMIDAZO[4,5-b]PYRIDIN-3-YL)PHENYL]ETHYL(4-METHYLPHENYL)SULFONYLCARBAMATE

The title compound was prepared according to the procedure described in Example 3 from 2-[4-(2-ethyl-5,6-dimethyl-3H-imidazo[4,5-b]pyridin-3-yl)phenyl]ethanol (step 4 of Example 34).

MS (ESI) m/z 493 (M+H)⁺; ¹H-NMR (DMSO-d₆) δ 7.94 (2H, d, J=8.4 Hz), 7.78 (1H, s), 7.33 (2H, d, J=8.1 Hz), 7.25–7.16 (4H, m), 4.35 (2H, t, J=6.6 Hz), 2.93 (2H, t, J=6.6 Hz), 2.73 (2H, q, J=7.4 Hz), 2.46 (3H, s), 2.43 (3H, s), 2.39 (3H, s), 1.28 (3H, t, J=7.4 Hz).

Example 37

5,6-DICHLORO-2-ETHYL-3-(4-{2-[({[(4-METHYLPHENYL)SULFONYL]AMINO}CARBONYL)AMINO]ETHYL}PHENYL)-3H-IMIDAZO[4,5-b]PYRIDINE

Step 1. 2-{4-[(5,6-Dichloro-3-nitro-2-pyridinyl)amino]phenyl}ethanol

The title compound was prepared according to the procedure described in step 1 of Example 34 from 3-nitro-2,5,6-trichloropyridine (Horn, U.; Mutterer, F.; Weis, C. D. *Helv. Chim. Acta.*, 1976, 59,190.) and 4-aminophenylethyl alcohol.

MS (EI) m/z 327 (M⁺); ¹H-NMR (CDCl₃) δ 10.11 (1H, br.s), 8.58 (1H, s), 7.57 (2H, d, J=8.4 Hz), 7.28 (2H, d, J=8.4 Hz), 3.93–3.86 (2H, m), 2.89 (2H, t, J=6.6 Hz).

Step 2. 2-{4-[(3-Amino-5,6-dichloro-2-pyridinyl)amino]phenyl}ethanol

The title compound was prepared according to the procedure described in step 2 of Example 28 from 2-{4-[(5,6-dichloro-3-nitro-2-pyridinyl)amino]phenyl}ethanol (step 1).

MS (EI) m/z 297 (M⁺).

Step 3 2-[4-(2-Ethyl-5,6-dichloro-3H-imidazo[4,5-b]pyridin-3-yl)phenyl]ethyl propionate The title compound was prepared according to the procedure described in step 5 of Example 1 from 2-{4-[(3-amino-5,6-dichloro-2-pyridinyl)amino]phenyl}ethanol (step 2) and propionyl chloride.

TLC Rf=0.63 (ethyl acetate/hexane=1:1).

Step 4. 2-[4-(2-Ethyl-5,6-dichloro-3H-imidazo[4,5-b]pyridin-3-yl)phenyl]ethanol

The title compound was prepared according to the procedure described in step 6 of Example 1 from 2-[4-(2-Ethyl- 5,6-dichloro-3H-imidazo[4,5-b]pyridin-3-yl)phenyl]ethyl propionate (Step 3).

MS (EI) m/z 335 (M$^+$); $^1$H-NMR (CDCl$_3$) δ 8.11 (1H, s), 7.46 (2H, d, J=8.1 Hz), 7.32 (2H, d, J=8.1 Hz), 3.97 (2H, t, J=6.2 Hz), 2.99 (2H, t, J=6.2 Hz), 2.82 (2H, q, J=7.5 Hz), 1.36 (3H, t, J=7.5 Hz).

Step 5. 3-[4-(2-Chloroethylphenyl]-2-ethyl-5,6-dichloro-3H-imidazo[4,5-b]pyridine The title compound was prepared according to the procedure described in step 7 of Example 1 from 2-[4-(2-ethyl-5,6-dichloro-3H-imidazo[4,5-b]pyridin-3-yl)phenyl]ethanol (step 4).

$^1$H-NMR (CDCl$_3$) δ 8.13 (1H, s), 7.45 (2H, d, J=8.1 Hz), 7.33 (2H, d, J=8.1 Hz), 3.80 (2H, t, J=7.2 Hz), 3.19 (2H, t, J=7.2 Hz), 2.82 (2H, q, J=7.5 Hz), 1.36 (3H, t, J=7.5 Hz.)

Step 6. 2-[4-(2-Ethyl-5,6-dichloro-3H-imidazo[4,5-b]pyridin-3-yl)phenyl]ethyl azide The title compound was prepared according to the procedure described in step 8 of Example 1 from 3-[4-(2-chloroethyl)phenyl]-2-ethyl-5,6-dichloro-3H-imidazo[4,5-b]pyridine (step 5).

MS (EI) m/z 360 (M$^+$); $^1$H-NMR (CDCl$_3$) δ 8.11 (1H, s), 7.44 (2H, d, J=8.4 Hz), 7.33 (2H, d, J=8.4 Hz), 3.61 (2H, t, J=7.2 Hz), 3.00 (2H, t, J=7.2 Hz), 2.81 (2H, q, J=7.5 Hz), 1.35 (3H, t, J=7.5 Hz).

Step 7. 2-[4-(2-Ethyl-5,6-dichloro-3H-imidazo[4,5-b]pyridin-3-yl)phenyl]ethylamine To a solution of 2-[4-(2-ethyl-5,6-dichloro-3H-imidazo[4,5-b]pyridin-3-yl)phenyl]ethyl azide (step 6, 69 mg, 0.2 mmol) in methanol (10 mL) was added Lindlar catalyst (5 mg). The resulting mixture was stirred for 6 h under hydrogen atmosphere. The mixture was filtered through a pad of Celite and the filtrate was concentrated. Purification by preparative TLC (dichloromethane/methanol=10:1) gave 60 mg (94%) of the title compound as colorless solids: MS (EI) m/z 334 (M$^+$); $^1$H-NMR (CDCl$_3$) δ 8.11 (1H, s), 7.43 (2H, d, J=8.3 Hz), 7.30 (2H, d, J=8.3 Hz), 3.11 (2H, t, J=6.6 Hz), 2.92 (2H, t, J=6.6 Hz), 2.81 (2H, J=7.5 Hz), 1.35 (3H, t, J=7.5 Hz).

Step 8. 5,6-Dichloro-2-ethyl-3-(4-{2-[({[(4-methylphenyl)sulfonyl]amino}carbonyl)amino]ethyl}phenyl)-3H-imidazo[4,5-b]pyridine The title compound was prepared according to the procedure described in step 10 of Example 1 from 2-[4-(2-ethyl-5,6-dichloro-3H-imidazo[4,5-b]pyridin-3-yl)phenyl]ethylamine (step 7).

mp 188.0–189.0° C.; MS (ESI) m/z 532 (M+H)$^+$; $^1$H-NMR (CDCl$_3$) δ 8.12 (1H, s), 7.77 (2H, d, J=8.4 Hz), 7.36–7.25 (6H, m), 6.49 (1H, br.t, J=5.9 Hz), 3.54 (2H, dt, J=5.9, 7.0 Hz), 2.90 (2H, t, J=7.0 Hz), 2.78 (2H, q, J=7.5 Hz), 2.41 (3H, s), 1.33 (3H, t, J=7.5 Hz).

Example 38
5-CHLORO-2-ETHYL-6-METHYL-3-(4-{2-[({[(4-METHYLPHENYL)SULFONYL]AMINO}CARBONYL) AMINO]ETHYL)PHENYL)-3H-IMIDAZO[4,5-b]PYRIDINE Step 1. 2-{4-[(6-Chloro-5-methyl-3-nitro-2-pyridinyl)amino]phenyl}ethanol The title compound was prepared according to the procedure described in step 1 of Example 34 from 2,6-dichloro-5-methyl-3-nitropyridine (Horn, U.; Mutterer, F.; Weis, C. D. Helv. Chim. Acta., 1976, 59, 190.) and 4-aminophenylethyl alcohol.

$^1$H-NMR (CDCl$_3$) δ 10.05 (1H, br.s), 8.34 (1H, s), 7.57 (2H, d, J=7.7 Hz), 7.24 (2H, d, J=7.7 Hz), 3.86 (2H, t, J=5.9 Hz), 2.87 (2H, t, J=5.9 Hz), 2.33 (3H, s).

Step 2. 2-{4-[(3-Amino-6-chloro-5-methyl-2-pyridinyl)amino]phenyl}ethanol

The title compound was prepared according to the procedure described in step 2 of Example 28 from 2-{4-[(6-chloro-5-methyl-3-nitro-2-pyridinyl)amino]phenyl}ethanol (step 1).

$^1$H-NMR (CDCl$_3$) δ 7.14–7.08 (4H, m), 6.86 (1H, s), 6.21 (1H, br.s), 3.79 (2H, t, J=6.4 Hz), 2.78 (2H, t, J=6.4 Hz), 2.33 (3H, s).

Step 3. 2-[4-(5-Chloro-2-ethyl-6-methyl-3H-imidazo[4,5-b]pyridin-3-yl)phenyl]ethyl propionate The title compound was prepared according to the procedure described in step 5 of Example 1 from 2-{4-[(3-amino-6-chloro-5-methyl-2-pyridinyl)amino]phenyl}ethanol (step 2) and propionyl chloride.

MS (EI) m/z 371 (M$^+$).

Step 4. 2-[4-(5-Chloro-2-ethyl-6-methyl-3H-imidazo[4,5-b]pyridin-3-yl)phenyl]ethanol The title compound was prepared according to the procedure described in step 6 of Example 1 from 2-[4-(5-chloro-2-ethyl-6-methyl-3H-imidazo[4,5-b]pyridin-3-yl)phenyl]ethyl propionate (step 3).

MS (EI) m/z 315 (M$^+$); $^1$H-NMR (CDCl$_3$) δ 7.87 (1H, s), 7.42 (2H, d, J=8.4 Hz), 7.29 (2H, d, J=8.4 Hz), 3.92 (2H, t, J=6.6 Hz), 2.96 (2H, t, J=6.6 Hz), 2.79 (2H, q, J=7.7 Hz), 2.47 (3H, s), 1.34 (3H, t, J=7.7 Hz).

Step 5. 3-[4-(2-Chloroethyl)phenyl]-5-chloro-2-ethyl-5-methyl-3H-imidazo[4,5-b]pyridine The title compound was prepared according to the procedure described in step 7 of Example 1 from 2-[4-(5-chloro-2-ethyl-6-methyl-3H-imidazo[4,5-b]pyridin-3-yl)phenyl]ethanol (step 4).

MS (EI) m/z 333 (M$^+$); $^1$H-NMR (CDCl$_3$) δ 7.88 (1H, s), 7.42 (2H, d, J=8.3 Hz), 7.33 (2H, d, J=8.3 Hz), 3.79 (2H, t, J=7.3 Hz), 3.17 (2H, t, J=7.3 Hz), 2.80 (2H, q, J=7.0 Hz), 2.48 (3H, s), 1.35 (3H, t, J=7.0 Hz).

Step 6. 2-[4-(5-Chloro-2-ethyl-6-methyl-3H-imidazo[4,5-b]pyridin-3-yl)phenyl]ethyl azide The title compound was prepared according to the procedure described in step 8 of Example 1 from 3-[4-(2-chloroethyl)phenyl]-5-chloro-2-ethyl-5-methyl-3H-imidazo[4,5-b]pyridine (step 5).

$^1$H-NMR (CDCl$_3$) δ 7.87 (1H, s), 7.42 (2H, d, J=8.4 Hz), 7.34 (2H, d, J=8.4 Hz), 3.59 (2H, t, J=7.1 Hz), 2.98 (2H, t, J=7.1 Hz), 2.81 (2H, q, J=7.6 Hz), 2.48 (3H, s), 1.35 (3H, t, J=7.6 Hz).

Step 7. 2-[4-(5-Chloro-2-ethyl-6-methyl-3H-imidazo[4,5-b]pyridin-3-yl)phenyl]ethylamine.

The title compound was prepared according to the procedure described in step 7 of Example 37 from 2-[4-(5-chloro-2-ethyl-6-methyl-3H-imidazo[4,5-b]pyridin-3-yl)phenyl]ethyl azide (step 6).

$^1$H-NMR (CDCl$_3$) δ: 7.88 (1H, s), 7.40 (2H, d, J=8.3 Hz), 7.31 (2H, d, J=8.3 Hz), 3.07 (2H, t, J=6.8 Hz), 2.87 (2H, t, J=6.8 Hz), 2.80 (2H, q, J=7.3 Hz), 2.48 (3H, s), 1.34 (3H, t, J=7.3 Hz).

Step 8. 5-Chloro-2-ethyl-6-methyl-3-(4-{2-[({[(4-methylphenyl)sulfonyl]amino}carbonyl)amino]ethyl}phenyl)-3H-imidazo[4,5-b]pyridine The title compound was prepared according to the procedure described in step 10 of Example 1 from 2-[4-(5-chloro-2-ethyl-6-methyl-3H-imidazo[4,5-b]pyridin-3-yl)phenyl]ethylamine (step 7).

mp 205–206° C.; MS (ESI) m/z 512 (M+H)$^+$; $^1$H-NMR (CDCl$_3$) δ 7.90 (1H, s), 7.79 (2H, d, J=8.3 Hz), 7.33–7.23 (6H, m), 6.46 (1H, br.s), 3.55–3.49 (2H, m), 2.88 (2H, t, J=6.8 Hz), 2.76 (2H, q, J=7.6 Hz), 2.48 (3H, s), 2.41 (3H, s), 1.31 (3H, t, J=7.6 Hz).

Example 39

5-CHLORO-2-ETHYL-7-METHYL-3-(4-{2-[({[(4-METHYLPHENYL)SULFONYL]AMINO}CARBONYL)AMINO]ETHYL}PHENYL)-3H-IMIDAZO[4,5-b]PYRIDINE

Step 1. 2{4-[(6-Chloro-4-methyl-3-nitro-2-pyridinyl)amino]phenyl}ethanol

The title compound was prepared according to the procedure described in step 1 of Example 34 from 2,6-dichloro-4-methyl-3-nitropyridine (Inubushi, A.; Kawano, E.; Shimada, Ke.; et al. PCT Int. Appl., WO 9802442 (1998)) and 4-aminophenylethyl alcohol.

$^1$H-NMR (CDCl$_3$) δ 9.56 (1H, s), 7.49 (2H, d, J=8.4 Hz), 7.22 (2H, d, J=8.4 Hz), 6.64 (1H, s), 3.84 (2H, t, J=6.4 Hz), 2.84 (2H, t, J=6.4 Hz), 2.55 (3H, s).

Step 2. 2-{4-[(3-Amino-6-chloro-4-methyl-2-pyridinyl)amino]phenyl}ethanol

The title compound was prepared according to the procedure described in step 2 of Example 28 from 2-{4-[(6-chloro-4-methyl-3-nitro-2-pyridinyl}amino]phenyl}ethanol (step 1).

MS (EI) m/z 277 (M$^+$).

Step 3. 2-[4-(5-Chloro-2-ethyl-7-methyl-3H-imidazo[4,5-b]pyridin-3-yl)phenyl]ethyl propionate The title compound was prepared according to the procedure described in step 5 of Example 1 from 2-{4-[(3-amino-6-chloro-4-methyl-2-pyridinyl)amino]phenyl}ethanol (step 2).

TLC Rf=0.46 (ethyl acetate/hexane=1:1).

Step 4. 2-[4-(5-Chloro-2-ethyl-7-methyl-3H-imidazo[4,5-b]pyridin-3-yl)phenyl]ethanol The title compound was prepared according to the procedure described in step 6 of Example 1 from 2-[4-(5-chloro-2-ethyl-7-methyl-3H-imidazo[4,5-b]pyridin-3-yl)phenyl]ethyl (step 3).

MS (EI) m/z 315 (M$^+$); $^1$H-NMR (CDCl$_3$) δ 7.43 (2H, d, J=8.4 Hz), 7.31 (2H, d, J=8.4 Hz), 7.07 (1H, s), 4.00–3.85 (2H, m), 2.97 (2H, t, J=6.6 Hz), 2.83 (2H, q, J=7.5 Hz), 2.68 (3H, s), 1.30 (3H, t, J=7.5 Hz).

Step 5. 3-[4-(2-Chloroethyl)phenyl]-5-chloro-2-ethyl-7-methyl-3H-imidazo[4,5-b]pyridine The title compound was prepared according to the procedure described in step 7 of Example 1 from 2-[4-(5-chloro-2-ethyl-7-methyl-3H-imidazo[4,5-b]pyridin-3-yl)phenyl]ethanol (step 4).

$^1$H-NMR (CDCl$_3$) δ 7.42 (2H, d, J=8.1 Hz), 7.33 (2H, d, J=8.1 Hz), 7.07 (1H, s), 3.79 (2H, t, J=7.3 Hz), 3.17 (2H, t, J=7.3 Hz), 2.83 (2H, q, J=7.5 Hz), 2.68 (3H, s), 1.30 (3H, t, J=7.5 Hz).

Step 6. 2-[4-(5-Chloro-2-ethyl-7-methyl-3H-imidazo[4,5-b]pyridin-3-yl)phenyl]ethyl azide The title compound was prepared according to the procedure described in step 8 of Example 1 from 3-[4-(2-chloroethyl)phenyl]-5-chloro-2-ethyl-7-methyl-3H-imidazo[4,5-b]pyridine (step 5).

$^1$H-NMR (CDCl$_3$) δ 7.42 (2H, d, J=8.6 Hz), 7.33 (2H, d, J=8.6 Hz), 7.07 (1H, s), 3.56 (2H, t, J=7.2 Hz), 2.99 (2H, t, J=7.2 Hz), 2.83 (2H, q, J=7.5 Hz), 2.68 (3H, s), 1.29 (3H, t, J=7.5 Hz.

Step 7. 2-[4-(5-Chloro-2-ethyl-7-methyl-3H-imidazo[4,5-b]pyridin-3-yl)phenyl]ethylamine.

To a stirred solution of 2-[4-(5-chloro-2-ethyl-7-methyl-3H-imidazo[4,5-b]pyridin-3-yl)phenyl]ethyl azide (step 6, 57 mg, 0.2 mmol) in THF (5 mL) was added triphenylphosphine (47 mg, 0.2 mmol) at room temperature. After completion of the addition, the stirring was continued for an additional 3 h at the same temperature. To the resulting mixture was added water (0.1 mL) at room temperature, and the reaction mixture was stirred at room temperature for 20 h. The mixture was concentrated to give colorless solids. Purification by preparative TLC (dichloromethane/methanol/triethylamine=10:1:1) gave 13 mg (25%) of the title compound as colorless solids: MS (EI) m/z 313 (M$^+$).

Step 8. 5-Chloro-2-ethyl-7-methyl-3-(4-{2-[({[(4-methylphenyl)sulfonyl]amino}carbonyl)amino]ethyl}phenyl)-3H-imidazo[4,5-b]pyridine The title compound was prepared according to the procedure described in step 10 of Example 1 from 2-[4-(5-chloro-2-ethyl-7-methyl-3H-imidazo[4,5-b]pyridin-3-yl)phenyl]ethylamine (step 7).

MS (ESI) m/z 512 (M+H)$^+$; $^1$H-NMR (CDCl$_3$) δ: 7.80 (2H, d, J=8.4 Hz), 7.34–7.23 (6H, m), 7.09 (1H, s), 6.37 (1H, br s), 3.56–3.52 (2H, m), 2.88 (2H, t, J=6.8 Hz), 2.77 (2H, q, J=7.5 Hz). 2.69 (3H, s), 2.42 (3H, s), 1.26 (3H, t, J=7.5 Hz).

Example 40

2-ETHYL-7-METHYL-3-(4-{2-[({[(4-METHYLPHENYL)SULFONYL]AMINO}CARBONYL)AMINO]ETHYL}PHENYL)-6-[(METHYLSULFONYL)AMINO[3H-IMIDAZO]4,5-b]PYRIDINE

Step 1.2-{4-[(4-Methyl-3,5-dinitro-2-pyridinyl)amino]phenyl}ethanol

The title compound was prepared according to the procedure described in step 3 of Example 1 from 2-chloro-4-methyl-3,5-dinitropyridine. (Czuba, Rocz.Chem., 1967, 41, 479) and 4-aminophenylethyl alcohol.

$^1$H-NMR (CDCl$_3$) δ 8.90 (1H, s), 8.50 (1H, br.s), 7.40 (2H, d, J=8.4 Hz), 7.23 (2H, d, J=8.4 Hz), 3.82 (2H, t, J=6.6 Hz), 2.84 (2H, t, J=6.6 Hz), 2.62 (3H, s).

Step 2. 2-{4-[(3-Amino-4-methyl-5-nitro-2-pyridinyl)amino]phenyl}ethanol

To a stirred solution of 2-{4-[(4-methyl-3,5-dinitro-2-pyridinyl)amino]phenyl}ethanol (step 1, 4.2 g, 13.1 mmol), triethylamine (9.6 mL, 68.9 mmol), 10% Pd—C (624 mg, 0.59 mmol) in acetonitrile (14 mL) was added dropwise a solution of formic acid (2.3 mL, 61.0 mmol) in acetonitrile (6.2 mL) at 0° C. over a period of 30 min. After stirring at room temperature for 5 h, the mixture was filtered through a pad of Celite, and the filtrate was concentrated. The residue was dissolved in dichloromethane (100 mL). The solution was washed with 1N aqueous NaOH (50 mL), brine (50 mL), dried (MgSO$_4$), and concentrated. Purification by flash column chromatography on silica gel eluting with hexane/ethyl acetate (gradient elution from 1:1 to 1:2) afforded 2.2 g (60%) of the title compound as red crystals: $^1$H-NMR (CDCl$_3$) δ8.42 (1H, s), 7.42 (2H, d, J=8.4 Hz), 7.21 (2H, d, J=8.4 Hz), 6.7 (1H, br s), 3.85 (2H, t, J=6.4 Hz), 2.86 (2H, t, J=6.6 Hz), 2.47 (3H, s).

Step 3. 2-[4-(2-Ethyl-7-methyl-6-nitro-3H-imidazo[4,5-b]pyridin-3-yl)phenyl]ethyl propionate The title compound was prepared according to the procedure described in step 5 of Example 1 from 2-{4-[(3-amino-4-methyl-5-nitro-2-pyridinyl)amino]phenyl}ethanol (step 2) and propionyl chloride.

$^1$H-NMR (CDCl$_3$) δ 9.03 (1H, s), 7.48 (2H, d, J=8.6 Hz), 7.33 (2H, d, J=8.4 Hz), 4.38 (2H, t, J=6.9 Hz), 3.07 (2H, t, J=6.9 Hz), 3.03 (3H, s), 2.87 (2H, q, J=7.6 Hz), 2.35 (2H, q, J=7.6 Hz), 1.35 (3H, t, J=7.4 Hz), 1.13 (3H, t, J=7.4 Hz).

Step 4. 2-[4-(6-Amino-2-ethyl-7-methyl-3H-imidazo[4,5-b]pyridin-3-yl)phenyl]ethyl propionate A suspension of 2-[4-(2-ethyl-7-methyl-6-nitro-3H-imidazo[4,5-b]pyridin-3-yl)phenyl]ethyl propionate (step 3, 2.5 g, 6.6 mmol), 10% Pd—C (250 mg, 0.23 mmol) in methanol (100 mL) was stirred under hydrogen atmosphere for 2 h. The suspension was filtered through a pad of Celite, and the filtrate was concentrated to afford 2.4 g (99%) of the title compound as a brown oil: $^1$H-NMR (CDCl$_3$) δ 7.82 (1H, s), 7.41 (2H, d, J=8.2 Hz), 7.32 (2H, d, J=8.4 Hz, 4.35 (2H, t, J=7.0 Hz), 3.51 (2H, br.s), 3.03 (2H, t, J=7.0 Hz), 2.82

(2H, q, J=7.5 Hz), 2.53 (3H, s), 2.35 (2H, q, J=7.5 Hz), 1.29 (3H, t, J=7.5 Hz), 1.44 (3H, t, J=7.5 Hz).

Step 5. 2-(4-{2-Ethyl-7-methyl-6-[(methylsulfonyl)amino]-3H-imidazo[4,5-b]pyridin-3-yl}phenyl)ethyl propionate To a stirred solution of 2-[4-(6-amino-2-ethyl-7-methyl-3H-imidazo[4,5-b]pyridin-3-yl)phenyl]ethyl propionate (step 4, 1.0 g, 3.0 mmol) and pyridine (280 mg, 3.5 mmol) in dichloromethane (18 mL) was added methanesulfonyl chloride (372 mg, 3.3 mmol) at 0° C., and the mixture was stirred at room temperature for 16 h. The reaction was quenched with water (10 mL), and the mixture was extracted with dichloromethane (50 mL). The organic layer was washed with brine (50 mL), dried (MgSO$_4$), and concentrated. Purification by flash column chromatography on silica gel eluting with ethyl acetate (gradient elution from 1:1 to 1:2) afforded 890 mg (70%) of the title compound as an amber oil; $^1$H-NMR (CDCl$_3$) δ 8.26 (1H, s), 7.43 (2H, d, J=8.4 Hz), 7.32 (2H, d, J=8.2 Hz), 7.00 (1H, br.s), 4.35 (2H, t, J=7.0 Hz), 3.03–3.01 (5H, m), 2.85 (2H, q, J=7.5 Hz), 2.75 (3H, s), 2.35 (2H, q, J=7.5 Hz), 1.30 (3H, t, J=7.5 Hz), 1.14 (3H, t, J=7.5 Hz).

Step 6. N-{2-Ethyl-3-[4-(2-hydroxyethyl)phenyl]-7-methyl-3H-imidazo[4,5-b]pyridin-6-yl}methanesulfonamide The title compound was prepared according to the procedure described in step 6 of Example 1 from 2-(4-{2-ethyl-7-methyl-6-[(methylsulfonyl)amino]-3H-imidazo[4,5-b]pyridin-3-yl}phenyl)ethyl propionate (step 5).

$^1$H-NMR (CDCl$_3$) δ 8.22 (1H, s), 7.46 (2H, d, J=8.2 Hz), 7.31 (2H, d, J=8.4 Hz), 6.52 (1H, br.s), 3.93 (2H, t, J=6.6 Hz), 3.03 (3H, s), 2.97 (2H, t, J=6.6 Hz), 2.85 (2H, q, J=7.6 Hz), 2.76 (3H, s), 1.32 (3H, t, J=7.4 Hz).

Step 7. N-{3-[4-(2-Chloroethyl)phenyl]-2-ethyl-7-methyl-3H-imidazo[4,5-b]pyridin-6-yl}methanesulfonamide The title compound was prepared according to the procedure described in step 7 of Example 1 from N-{2-ethyl-3-[4-(2-hydroxyethyl)phenyl]-7-methyl-3H-imidazo[4,5-b]pyridin-6-yl}methanesulfonamide (step 6).

TLC Rf=0.40 (ethyl acetate).

Step 8. N-{3-[4-(2-Azidoethyl)phenyl]-2-ethyl-7-methyl-3H-imidazo[4,5-b]pyridin-6-yl}methanesulfonamide The title compound was prepared according to the procedure described in step 8 of Example 1 from N-{3-[4-(2-chloroethyl)phenyl]-2-ethyl-7-methyl-3H-imidazo[4,5-b]pyridin-6-yl}methanesulfonamide (step 7).

$^1$H-NMR (CDCl$_3$) δ 8.26 (1H, s), 7.44 (2H, d, J=8.1 Hz), 7.34 (2H, d, J=8.1 Hz), 6.65 (1H, br.s), 3.59 (2H, t, J=7.0 Hz), 3.03 (3H, s), 2.99 (2H, t, J=7.1 Hz), 2.86 (2H q, J=7.4 Hz), 2.75 (3H, s), 1.31 (3H, t, J=7.5 Hz).

Step 9. N-{3-[4-(2-Aminoethyl)phenyl]-2-ethyl-7-methyl-3H-imidazo[4,5-b]pyridin-6yl}methanesulfonamide The title compound was prepared according to the procedure described in step 9 of Example 1 from N-{3-[4-(2-azidoethyl)phenyl]-2-ethyl-7-methyl-3H-imidazo[4,5-b]pyridin-6-yl}methanesulfonamide (step 8).

TLC Rf=0.05 (ethyl acetate).

Step 10. 2-Ethyl-7-methyl-3(4-{2-[({[(4-methylphenyl)sulfonyl]amino}carbonyl)amino]ethyl}phenyl)-6-[(methylsulfonyl)amino]-3H-imidazo[4,5-b]pyridine The title compound was prepared according to the procedure described in step 10 of Example 1 from N-{3-[4-(2-aminoethyl)phenyl]-2-ethyl-7-methyl-3H-imidazo[4,5-b]pyridin-6-yl}methanesulfonamide (step 9).

mp 166° C.; MS (ESI) m/z 571.25 (M+H)$^+$; $^1$H-NMR (CDCl$_3$) δ 8.16 (1H, s), 7.81 (2H, d, J=8.1 Hz), 7.31–7.18 (6H, m), 6.39 (1H, br.s), 3.48–3.46 (2H, m), 3.00 (3H, s), 2.82–2.71 (7H, m), 2.39 (3H, s), 1.26 (3H, t, J=7.2 Hz).

Example 41
6-CYANO-2-ETHYL-5,7-DIMETHYL-3-(4-{2-([{[(4-METHYLPHENYL)SULFONYL]AMINO}CARBONYL)AMINO]ETHYL}PHENYL)-3H-IMIDAZO[4,5-b]PYRIDINE Step 1, 6-Hydroxy-2,4-dimethylnicotinonitrile To a stirred solution of 6-amino-2,4-dimethylnicotinonitrile (Sato, K.; et al. *Bull.Chem.Soc.Jpn.*, 1969, 42, 2319., 22.4 g, 152 mmol) in 5% aqueous sulfuric acid (600 mL) was added dropwise a solution of sodium nitrite (25.2 g, 365 mmol) in water (100 mL) at 0° C., and the mixture was stirred at room temperature for 16 h. The resulting precipitate was collected by filtration to afford 10.2 g (45%) of the title compound: $^1$H-NMR (DMSO-d$_6$) δ 12.27 (1H, br.s), 6.17 (1H, s), 2.38 (3H, s), 2.20 (3H, s).

Step 2. 6-Hydroxy-2,4-dimethyl-5-nitronicotinonitrile

To a stirring mixture of nitric acid (fuming, 36 mL) and sulfuric acid (18 mL) was added 6-hydroxy-2,4-dimethylnicotinonitrile (step 1, 9.0 g, 60.8 mmol) in one portion, and the mixture was stirred at room temperature. After 1 h, the mixture was poured in water (100 mL) and neutralized with 2N aqueous NaOH. The resulting precipitates were collected by filtration to afford 3.2 g (27%) of the title compound: $^1$H-NMR (DMSO-d$_6$) δ 2.28 (3H, s), 2.11 (3H, s).

Step 3. 6-Chloro-2,4-dimethyl-5-nitronicotinonitrile

A mixture of 6-hydroxy-2,4-dimethyl-5-nitronicotinonitrile (step 2, 3.2 g, 16.6 mmol) and phosphorus oxychloride (20 mL) was stirred at 100° C. for 16 h. After cooling, the mixture was poured in water (100 mL). The resulting mixture was extracted with dichloromethane (3×100 mL). The organic layer was washed with brine (50 mL), dried (MgSO$_4$), and concentrated to afford 2.3 g (66%) of the title compound as brown solids: $^1$NMR (DMSO-d$_6$) δ 2.82 (3H, s), 2.52 (3H, s).

Step 4. 6-[4-(2-Hydroxyethyl)anilino]-2,4-dimethyl-5-nitronicotinonitrile

The title compound was prepared according to the procedure described in step 3 of Example 1 from 6-chloro-2, 4-dimethyl-5-nitronicotinonitrile (step 3) and 4-aminophenylethyl alcohol.

$^1$NMR (CDCl$_3$) δ 9.37 (1H, br.s), 7.51 (2H, d, J=8.4 Hz), 7.26 (2H, d, J=8.4 Hz), 3.89–3.87 (2H, m), 2.89 (2H, t, J=6.4 Hz), 2.72 (3H, s), 2.65 (3H, s), 1.46 (1H, t, J=5.8 Hz).

Step 5. 5-Amino-6-[4-(2-hydroxyethyl)anilino]-2,4-dimethylnicotinonitrile

The title compound was prepared according to the procedure described in step 4 of Example 1 from 6-[4-(2-hydroxyethyl)anilino]-2,4-dimethyl-5-nitronicotinonitrile (step 4).

$^1$NMR (CDCl$_3$) δ 7.49 (2H, d, J=8.6 Hz), 7.19 (2H, d, J=8.4 Hz), 6.98 (1H, br.s), 3.89–3.82 (2H, m), 3.11 (2H, br.s), 2.85 (2H, t, J=6.6 Hz), 2.58 (3H, s), 2.38 (3H, s), 2.38 (3H, s), 1.44 (1H, t, J=5.6 Hz).

Step 6. 2-[4-(6-Cyano-2-ethyl-5,7-dimethyl-3H-imidazo[4,5b]pyridin-3-yl)phenyl]ethyl propionate The title compound was prepared according to the procedure described in step 5 of Example 1 from 5-amino-6-[4-(2-hydroxyethyl)anilino]-2,4-dimethylnicotinonitrile (step 5) and propionyl chloride.

TLC Rf=0.4 (hexane/ethyl acetate=1:1).

Step 7. 2-Ethyl-3-[4-(2-hydroxyethyl)phenyl]-5,7-dimethyl-3H-imidazo[4,5-b]pyridine-6-carbonitrile The title compound was prepared according to the procedure described in step 6 of Example 1 from 2-[4-(6-cyano-2-ethyl-5,7-dimethyl-3H-imidazo[4,5-b]pyridin-3-yl)phenyl]ethyl propionate (step 6).

$^1$H-NMR (CDCl$_3$) δ 7.46 (2H, d, J=8.2 Hz), 7.31 (2H, d, J=8.2 Hz), 4.01–3.94 (2H, m), 3.49–3.47 (1H, m), 3.00 (2H, t, J=6.3 Hz), 2.86 (3H, s), 2.83 (2H, q, J=7.4 Hz), 2.74 (3H, s), 1.32 (3H, t, J=7.6 Hz).

Step 8. 3-[4-(2-Chloroethyl)phenyl]-2-ethyl-5,7-dimethyl-3H-imidazo[4,5-b]pyridine-6-carbonitrile The title compound was prepared according to the procedure described in step 7 of Example 1 from 2-ethyl-3-[4-(2-hydroxyethyl)phenyl]-5,7-dimethyl-3H-imidazo[4,5-b]pyridine-6-carbonitrile (step 7).

TLC Rf=0.8 (hexane/ethyl acetate=1:1).

Step 9. 3-[4-(2-Azidoethyl)phenyl]-2-ethyl-5,7-dimethyl-3H-imidazo[4,5-b]pyridine-6-carbonitrile The title compound was prepared according to the procedure described in step 8 of Example 1 from 3-[4-(2-chloroethyl)phenyl]-2-ethyl-5,7-dimethyl-3H-imidazo[4,5-b]pyridine-6-carbonitrile (step 8).

$^1$H-NMR (CDCl$_3$) δ 7.46 (2H, d, J=8.1 Hz), 7.33 (2H, d, J=8.2 Hz), 3.62 (2H, t, J=7.1 Hz), 3.02 (2H, t, J=7.1 Hz), 2.86 (3H, s), 2.82 (2H, q, J=7.6 Hz), 2.73 (3H, s), 1.31 (3H, t, J=7.6 Hz).

Step 10. 3-[4-(2-Aminoethyl)phenyl]-2-ethyl-5,7-dimethyl-3H-imidazo[4,5-b]pyridine-6-carbonitrile The title compound was prepared according to the procedure described in step 9 of Example 1 from 3-[4-(2-azidoethyl)phenyl]-2-ethyl-5,7-dimethyl-3H-imidazo[4,5-b]pyridine-6-carbonitrile (step 9).

TLC Rf=0.05 (hexane/ethyl acetate=1:1).

Step 11. 6-Cyano-2-ethyl-5,7-dimethyl-3-(4-{2-[({[(4-methylphenyl)sulfonyl]amino}carbonyl)amino]ethyl}phenyl)-3H-imidazo[4,5-b]pyridine The title compound was prepared according to the procedure described in step 10 of Example 1 from 3-[4-(2-aminoethyl)phenyl]-2-ethyl-5,7-dimethyl-3H-imidazo[4,5-b]pyridine-6-carbonitrile (step 10).

mp 133° C.; MS (ESI) m/z 517.12 (M+H)$^+$; $^1$H-NMR (CDCl$_3$) δ 7.78 (2H, d, J=8.1 Hz), 7.37–7.25 (6H, m), 6.46 (1H, br.s), 3.56–3.54 (2H, m), 2.92 (2H, t, J=7.0 Hz), 2.85 (3H, s), 2.76 (2H, q, J=6.0 Hz), 2.68 (3H, s), 2.41 (3H, s), 1.29 (3H, t, J=6.2 Hz).

Example 42

2-ETHYL-4,6-DIMETHYL-1-(4-{2-[({[(4-METHYLPHENYL)SULFONYL]AMINO}CARBONYL)AMINO]ETHYL}PHENYL)-1H-IMIDAZO[4,5-c]PYRIDINE

Step 1. 2-{4-[(2,6-Dimethyl-3-nitro-4-pyridinyl)amino]phenyl}ethanol

The title compound was prepared according to the procedure described in step 3 of Example 1 from 4-chloro-2,6-dimethyl-3-nitropyridine (Tanaka, A.; et al. *J. Med. Chem.*, 1999, 41, 4408.) and 4-aminophenylethyl alcohol.

$^1$H-NMR (CDCl$_3$) δ 8.74 (1H, br.s), 7.31 (2H, d, J=8.2 Hz), 7.18 (2H, d, J=8.2 Hz) s), 3.95–3.89 (2H, m), 2.91 (2H, t, J=6.6 Hz), 2.72 (3H, s), 2.36 (3H, s).

Step 2. 2-{4-[(3-Amino-2,6-dimethyl-4-pyridinyl)amino]phenyl}ethanol

The title compound was prepared according to the procedure described in step 4 of Example 1 from 2-{4-[(2,6-dimethyl-3-nitro-4-pyridinyl)amino]phenyl}ethanol (step 1).

$^1$H-NMR (CDCl$_3$) δ 7.19 (2H, d, J=8.4 Hz), 7.01 (2H, d, J=8.6 Hz), 6.76 (1H, s), 5.82 (1H, br.s), 3.87 (2H, t, J=6.4 Hz), 3.18 (2H, br.s), 2.85 (2H, t, J=6.4 Hz), 2.44 (3H, s, ) 2.35 (3H, s).

Step 3. 2-[4-(2-Ethyl-4,6-dimethyl-1H-imidazo[4,5-c]pyridin-1-yl)phenyl]ethyl propionate A mixture of 2-{4-[(3-amino-2,6-dimethyl-4-pyridinyl)amino]phenyl}ethanol (step 2, 2.4 g, 9.3 mmol), propionic anhydride (13 mL, 101 mmol) and propionic acid (13 mL, 174 mmol) was stirred at 120° C. for 16 h. After cooling, the mixture was diluted with 2N aqueous NaOH (150 mL) and extracted with dichloromethane (3×150 mL). The combined organic extracts were washed with brine (50 mL), dried (MgSO$_4$), and concentrated. Purification by flash column chromatography on silica gel eluting with dichloromethane/methanol (gradient elution from 20:1 to 10:1) afforded 2.3 g (69% ) of the title compound as a brown oil: $^1$H-NMR (CDCl$_3$) δ7.44 (2H, d, J=8.1 Hz), 7.27 (2H, d, J=8.2 Hz), 6.72 (1H, s), 4.38 (2H, t, J=6.9 Hz), 3.07 (2H, t, J=7.1 Hz), 2.88 (3H, s), 2.82 (2H, q, J=7.6 Hz), 2.56 (3H, s), 2.36 (2H, q, J=7.6 Hz), 1.29 (3H, t, J=7.6 Hz), 1.15 (3H, t, J=7.7 Hz).

Step 4. 2-[4-(2-Ethyl-4,6-dimethyl-1H-imidazo[4,5-c]pyridin-1-yl)phenyl]ethanol

The title compound was prepared according to the procedure described in step 6 of Example 1 from 2-[4-(2-ethyl-4,6-dimethyl-1H-imidazo[4,5-c]pyridin-1-yl)phenyl]ethyl propionate (step 3).

$^1$H-NMR (CDCl$_3$) δ 7.46 (2H, d, J=8.1 Hz), 7.26 (2H, d, J=8.1 Hz), 6.73 (1H, s), 4.00 (2H, t, J=6.6 Hz), 3.01 (2H, t, J=6.4 Hz), 2.88 (3H, s), 2.81 (2H, q, J=7.5 Hz), 2.54 (3H, s), 1.29 (3H, t, J=7.5 Hz).

Step 5. 1-[4-(2-Chloroethyl)phenyl]-2-ethyl-4,6-dimethyl-1H-imidazo[4,5-c]pyridine The title compound was prepared according to the procedure described in step 7 of Example 1 from 2-[4-(2-ethyl-4,6-dimethyl-1H-imidazo[4,5-c]pyridin-1-yl)phenyl]ethanol (step 4).

TLC Rf=0.1 (ethyl acetate).

Step 6. 1-[4-(2-Azidoethyl)phenyl]-2-ethyl-4,6-dimethyl-1H-imidazo[4,5-c]pyridine The title compound was prepared according to the procedure described in step 8 of Example 1 from 1-[4-(2-chloroethyl)phenyl]-2-ethyl-4,6-dimethyl-1H-imidazo[4,5-c]pyridine (step 5).

$^1$H-NMR (CDCl$_3$) δ 7.46 (2H, d, J=8.0 Hz), 7.29 (2H, d, J=7.7 Hz), 6.72 (1H, s), 3.62 (2H, t, J=6.9 Hz), 3.02 (2H, t, J=6.9 Hz), 2.88 (3H, s), 2.81 (2H, q, J=7.4 Hz), 2.56 (3H, s), 1.29 (3H, t, J=7.6 Hz).

Step 7. 2-[4-(2-Ethyl-4,6-dimethyl-1H-imidazo[4,5-c]pyridin-1-yl)phenyl]ethylamine The title compound was prepared according to the procedure described in step 9 of Example 1 from 1-[4-(2-azidoethyl)phenyl]-2-ethyl-4,6-dimethyl-1H-imidazo[4,5-c]pyridine (step 6).

$^1$H-NMR (CDCl$_3$) δ 7.42 (2H, d, J=8.2 Hz), 7.26 (2H, d, J=8.4 Hz), 6.73 (1H, s), 3.08 (2H, t, J=6.9 Hz), 2.90–2.78 (4H, m), 2.88 (3H, s), 2.56 (3H, s), 1.30 (3H, t, J=7.3 Hz).

Step 8. 2-Ethyl-4,6-dimethyl-1-(4-{2-[({[(4-methylphenyl)sulfonyl]amino}carbonyl)amino]ethyl}phenyl)-1H-imidazo[4,5-c]pyridine The title compound was prepared according to the procedure described in step 10 of Example 1 from 2-[4-(2-ethyl-4,6-dimethyl-1H-imidazo[4,5-c]pyridin-1-yl)phenyl]ethylamine (step 7).

mp 143° C.; MS (ESI) m/z 492.12 (M+H)$^+$; $^1$H-NMR (CDCl$_3$) δ 7.77 (2H, d, J=8.3 Hz), 7.38 (2H, d, J=8.4 Hz), 7.25 (2H, d, J=8.4 Hz), 7.20 (2H, d, J=8.4 Hz), 6.77 (1H, s), 3.58–3.51 (2H, m), 2.92 (2H, t, J=7.0 Hz), 2.89 (3H, s), 2.79 (2H, q, J=7.5 Hz), 2.53 (3H, s), 2.38 (3H, s), 1.28 (3H, t, J=7.5 Hz).

Example 43

2-ETHYL-1-(4-{2-[({[(4-METHYLPHENYL)SULFONYL]AMINO}CARBONYL)AMINO]ETHYL}PHENYL)-1H-BENZIMIDAZOLE

Step 1. 2-[4-(2-Nitroanilino)phenyl]ethanol

The title compound was prepared according to the procedure described in step 3 of Example 1 from 2-chloronitrobenzene and 4-aminophenylethyl alcohol.

$^1$H-NMR (CDCl$_3$) δ 9.47 (1H, s), 8.21 (1H, dd, J=1.5, 8.8 Hz), 7.40–7.16 (6H, m), 6.81–6.70 (1H, m), 3.91 (2H, t, J=6.5 Hz), 2.90 (2H, t, J=6.5 Hz).

Step 2. 2-[4-(2-Aminoanilino)phenyl]ethanol

The title compound was prepared according to the procedure described in step 4 of Example 1 from 2-[4-(2-nitroanilino)phenyl]ethanol (step 1).

$^1$H-NMR (CDCl$_3$) δ 7.15–6.96 (4H, m), 6.82–6.66 (4H, m), 5.14 (1H, s), 3.80 (2H, t, J=6.6 Hz), 3.75 (2H, br.s), 2.79 (2H, t, J=6.6 Hz).

Step 3. 2-[4-(2-Ethyl-1H-benzimidazol-1-yl)phenyl]ethyl propionate

The title compound was prepared according to the procedure described in step 5 of Example 1 from 2-[4-(2-aminoanilino)phenyl]ethanol (step 2) and propionyl chloride.

MS (EI) m/z 322 (M$^+$); $^1$H-NMR (CDCl$_3$) δ 7.79 (1H, d, J=7.7 Hz), 7.43 (2H, d, J=8.6 Hz) 7.34–7.06 (5H, m), 4.38 (2H, t, J=7.0 Hz), 3.07 (2H, t, J=7.0 Hz), 2.80 (2H, q, J=7.5 Hz), 2.36 (2H, q, J=7.6 Hz), 1.35 (3H, t, J=7.5 Hz), 1.15 (3H, t, J=7.6 Hz).

Step 4. 2-[4-(2-Ethyl-1H-benzimidazol-1-yl)phenyl]ethanol

The title compound was prepared according to the procedure described in step 6 of Example 1 from 2-[4-(2-ethyl-1H-benzimidazol-1-yl)phenyl]ethyl propionate (step 3).

$^1$H-NMR (CDCl$_3$) δ 7.81–7.75 (1H, m), 7.45 (2H, d, J=8.3 Hz), 7.31 (2H, d, J=8.3 Hz), 7.25–7.08 (3H, m), 3.98 (2H, t, J=6.5 Hz), 3.00 (2H, t, J=6.5 Hz), 2.80 (2H, q, J=7.5 Hz), 1.26 (3H, t, J=7.5 Hz).

Step 5. 2-[4-(2-Ethyl-1H-benzimidazol-1-yl)phenyl]ethyl azide

The title compound was prepared according to the procedure described in step 5 Example 26 from 2-[4-(2-ethyl-1H-benzimidazol-1-yl)phenyl]ethanol (step 4).

MS (EI) m/z 291 (M$^+$); $^1$H-NMR (CDCl$_3$) δ 7.81–7.76 (1H, m), 7.43 (2H, d, J=8.3 Hz) 7.40–7.06 (5H, m), 3.62 (2H, t, J=6.5 Hz), 3.04 (2H, t, J=6.5 Hz), 2.80 (2H, q, J=7.5 Hz), 1.27 (3H, t, J=7.5 Hz).

Step 6. 2-[4-(2-Ethyl-1H-benzimidazol-1-yl)phenyl]ethylamine

The title compound was prepared according to the procedure described in step 9 of Example 1 from 2-[4-(2-ethyl-1H-benzimidazol-1-yl)phenyl]ethyl azide (step 5).

$^1$H-NMR (CDCl$_3$) δ 7.80–7.74 (1H, m), 7.45–7.06 (7H, m), 3.06 (2H, t, J=6.5 Hz), 2.89 (2H, t, J=6.5 Hz), 2.76 (2H, q, J=7.5 Hz), 1.26 (3H, t, J=7.5 Hz).

Step 7. 2-Ethyl-1-(4-{2-[({[(4-methylphenyl)sulfonyl]amino}carbonyl)amino]ethyl}phenyl)-1H-benzimidazole The title compound was prepared according to the procedure described in step 10 of Example 1 from 2-[4-(2-ethyl-1H-benzimidazol-1-yl)phenyl]ethylamine (step 6).

$^1$H-NMR (CDCl$_3$) δ 7.75 (1H, d, J=8.8 Hz), 7.71 (2H, d, J=8.3 Hz), 7.39–7.14 (8H, m), 7.07 (1H, d, J=8.8 Hz), 6.68 (1H, br.s), 3.62–3.54 (2H, m), 2.94 (2H, t, J=6.3 Hz) 2.79 (2H, q, J=7.0 Hz), 2.41 (3H, s), 1.33 (3H, t, J=7.0 Hz).

Example 44
2-[4-(2-ETHYL-1H-BENZIMIDAZOL-1-YL)PHENYL] ETHYL (4-METHYLPHENYL) SULFONYLCARBAMATE The title compound was prepared according to the procedure described in Example 3 from 2-[4-(2-ethyl-1H-benzimidazol-1-yl)phenyl]ethanol (step 4 of Example 43).

$^1$H-NMR (CDCl$_3$) δ 7.93 (2H, d, J=8.3 Hz), 7.85–7.75 (2H, m), 7.40–7.15 (7H, m), 7.08 (1H, d, J=8.8 Hz), 4.77 (1H, br.s) 4.36 (2H, t, J=6.4 Hz), 3.00 (2H, t, J=6.4 Hz), 2.78 (2H, q, J=7.0 Hz), 2.44 (3H, s), 1.32 (3H, t, J=7.0 Hz).

Example 45
4-METHYL-2-ETHYL-3-(4-{2-[({[(4-METHYLPHENYL)SULFONYL]AMINO}CARBONYL)AMINO]ETHYL}PHENYL)-1H-BENZIMIDAZOLE Step 1. 2-[4-(3-Methyl-2-nitroanilino)phenyl]ethanol A mixture of 2-nitro-3-methylaniline (Newman, M. S.; Kannan R. *J. Org. Chem.*, 1976, 41, 3356., 1.9 g, 12.4 mmol), 4-bromophenylethyl alcohol (2.5 g, 12.4 mmol), K$_2$CO$_3$ (1.7 g, 12.4 mmol) and CuI (230 mg, 1.24 mmol) was placed in a sealed tube and heated at 200° C. for 2 h. After cooling, the mixture was poured into water (100 mL) and extracted with ethyl acetate (300 mL). The organic layer was washed with 2N aqueous NaOH (100 mL) and brine (100 mL), then dried (Na$_2$SO$_4$), and concentrated. Purification by flash column chromatography on silica gel eluting with hexane/ethyl acetate (1:1) to afford 700 mg (21%) of the title compound as an orange oil: $^1$H-NMR (CDCl$_3$) δ 7.77 (1H, br.s), 7.09–7.45 (6H, m), 6.69 (1H, d, J=6.3 Hz). 3.83 (2H, t, J=6.6 Hz), 2.82 (2H, t, J=6.6 Hz), 2.59 (3H, s).

Step 2. 2-[4-(2-Amino-3-methylanilino)phenyl]ethanol

The title compound was prepared according to the procedure described in step 2 of Example 26 from 2-[4-(3-methyl-2-nitroanilino)phenyl]ethanol (step 1).

$^1$H-NMR (CDCl$_3$) δ 7.02 (2H, d, J=8.2 Hz), 6.95 (1H, d, J=7.7 Hz), 6.91 (1H, d, J=7.0 Hz), 6.65 (1H, dd, J=7.0 Hz, 7.7 Hz), 6.62 (2H, d, J=8.2 Hz), 5.15 (1H, br.s), 3.75 (2H, t, J=6.6 Hz), 2.73 (2H, t, J=6.6 Hz), 2.19 (3H, s).

Step 3. 2-[4-(2-Ethyl-4-methyl-1H-benzimidazol-1-yl)phenyl]ethyl propionate

The title compound was prepared according to the procedure described in step 5 of Example 1 from 2-[4-(2-amino-3-methylanilino)phenyl]ethanol (step 2) and propionyl chloride.

TLC Rf=0.6 (hexane: ethyl acetate=1:1).

Step 4. 2-[4-(2-Ethyl-4-methyl-1H-benzimidazol-1-yl)phenyl]ethanol

The title compound was prepared according to the procedure described in step 6 of Example 1 from 2-[4-(2-ethyl-4-methyl-1H-benzimidazol-1-yl)phenyl]ethyl propionate (step 3).

$^1$H-NMR (CDCl$_3$) δ 7.41–7.43 (2H, m), 7.29 (2H, d, J=6.4 Hz), 7.07 (2H, d, J=6.4 Hz), 6.91–6.94 (1H, m), 3.97 (2H, t, J=6.6 Hz), 2.99 (2H, t, J=6.6 Hz), 2.84 (2H, q, J=7.5 Hz), 2.71 (3H, s), 1.27 (3H, t, J=7.5 Hz).

Step 5. 1-[4-(2-Chloroethyl)phenyl]-2-ethyl-4-methyl-1H-benzimidazole

The title compound was prepared according to the procedure described in step 7 of Example 1 from 2-[4-(2-ethyl-4-methyl-1H-benzimidazol-1-yl)phenyl]ethanol (step 4).

$^1$H-NMR (CDCl$_3$) δ 7.43 (2H, d, J=8.4 Hz), 7.30 (2H, d, J=8.4 Hz), 7.07–7.09 (2H, m), 6.90–6.95 (1H, m), 3.81 (2H, t, J=7.2 Hz), 3.19 (2H, t, J=7.2 Hz), 2.84 (2H, q, J=7.5 Hz), 2.72 (3H, s), 1.27 (3H, t, J=7.5 Hz).

Step 6. 2-[4-(2-Ethyl-4-methyl-1H-benzimidazol-1-yl)phenyl]ethyl azide

The title compound was prepared according to the procedure described in step 8 of Example 1 from 1-[4-(2-chloroethyl)phenyl]-2-ethyl-4-methyl-1H-benzimidazole (step 5).

$^1$H-NMR (CDCl$_3$) δ 7.43 (2H, d, J=8.0 Hz), 7.31 (2H, d, J=8.0 Hz), 7.05–7.09 (2H, m), 6.90–6.94 (1H, m), 3.61 (2H, t, J=7.0 Hz), 3.01 (2H, t, J=7.0 Hz), 2.84 (2H, q, J=7.5 Hz), 2.72 (3H, s), 1.27 (3H, t, J=7.5 Hz).

Step 7. 2-[4-(2-Ethyl-4-methyl-1H-benzimidazol-1-yl)phenyl]ethylamine

The title compound was prepared according to the procedure described in step 9 of Example 1 from 2-[4-(2-ethyl-4-methyl-1H-benzimidazol-1-yl)phenyl]ethyl azide (step 6).

$^1$H-NMR (CDCl$_3$) δ 7.40 (2H, d, J=8.3 Hz), 7.28 (2H, d, 8.3 Hz), 7.04–7.11 (2H, m) 6.86–6.95 (1H, m), 3.07 (2H, t,

J=6.6 Hz), 2.87 (2H, t, J=6.6 Hz), 2.84 (2H, q, J=7.5 Hz), 2.71 (3H, s), 1.27 (3H, t, J=7.5 Hz).

Step 8. 2-Ethyl-4-methyl-1-(4-{2-[({[(4-methylphenyl) sulfonyl]amino}carbonyl)amino]ethyl}phenyl)-1H-benzimidazole The title compound was prepared according to the procedure described in step 10 of Example 1 from 2-[4-(2-ethyl-4-methyl-1H-benzimidazol-1-yl)phenyl]ethylamine (step 7).

MS (ESI) m/z 477 (M+H)$^+$; $^1$H-NMR (DMSO-d$_6$) δ 7.65 (2H, d, J=7.7 Hz), 7.33–7.41 (4H, m), 7.15 (2H, d, J=7.7 Hz), 7.01–7.07 (2H, m), 6.86 (1H, d, J=6.8 Hz), 3.19 (2H, br.s), 2.68–2.74 (4H, m), 2.56 (3H, s), 2.28 (3H, s), 1.21 (3H, t, J=7.1 Hz); IR (KBr) α$_{max}$ 3390, 1602, 1519, 1429, 1230, 1130, 1085 cm$^{-1}$.

Example 46

4-METHYL-2-ETHYL-3-(4-{2-[({[(4-METHYLPHENYL)SULFONYL]AMINO}CARBONYL) AMINO]ETHYL}PHENYL)-1H-BENZIMIDAZOLE, SODIUM SALT

The title compound was prepared according to the procedure described in Example 2 from 2-ethyl-4-methyl-1-(4-{2-[({[(4-methylphenyl)sulfonyl]amino}carbonyl) amino] ethyl}phenyl)-1H-benzimidazole (Example 45).

$^1$H-NMR (DMSO-d$_6$) δ 7.65 (2H, d, J=7.7 Hz), 7.33–7.41 (4H, m), 7.15 (2H, d, J=7.7 Hz), 7.01–7.07 (2H, m), 6.86 (1H, d, J=6.8 Hz), 3.19 (2H, br.s), 2.68–2.74 (4H, m), 2.56 (3H, s), 2.28 (3H, s), 1.21 (3H, t, J=7.1 Hz); IR (KBr) α$_{max}$ 3390, 1602, 1519, 1429, 1230, 1130, 1085 cm$^{-1}$.

Example 47

2-ETHYL-5-METHYL-1-(4-{2-[({[(4-METHYLPHENYL)SULFONYL]AMINO}CARBONYL) AMINO]ETHYL}PHENYL)-1H-BENZIMIDAZOLE

Step 1. 2-[(4-Methyl-2-nitroanilino)phenyl]ethanol

The title compound was prepared according to the procedure described in step 1 Example 45 from 4-methyl-2-nitroaniline and 4-iodophenylethyl alcohol.

$^1$H-NMR (CDCl$_3$) δ 9.35 (1H, br.s), 8.00 (1H, s), 7.33–7.09 (6H, m), 3.91–3.89 (2H, m), 2.89 (2H, t, J=6.4 Hz), 2.30 (3H, s).

Step 2. 2-[(2-Amino-4-methylanilino)phenyl]ethanol

The title compound was prepared according to the procedure described in step 2 of Example 28 from 2-[(4-methyl-2-nitroanilino)phenyl]ethanol (step 1).

$^1$H-NMR (CDCl$_3$) δ 7.05 (2H, d, J=8.3 Hz), 6.98 (1H, d, J=7.7 Hz), 6.67–6.64 (3H, m), 6.58–6.55 (1H, m), 5.06 (1H, br.s), 3.80–3.78 (4H, m), 2.77 (2H, t, J=6.4 Hz), 2.28 (3H, s).

Step 3. 2-[4-(2-Ethyl-5-methyl-1H-benzimidazol-1-yl) phenyl]ethyl propionate

The title compound was prepared according to the procedure described in step 5 of Example 1from 2-[(2-amino-4-methylanilino)phenyl]ethanol (step 2) and propionyl chloride.

TLC Rf=0.33 (hexane/ethyl acetate=2:1).

Step 4. 2-[4-(2-Ethyl-5-methyl-1H-benzimidazol-1-yl) phenyl]ethanol

The title compound was prepared according to the procedure described in step 6 of Example 1 from 2-[4-(2-Ethyl-5-methyl-1H-benzimidazol-1-yl)phenyl]ethyl propionate (step 3).

$^1$H-NMR (CDCl$_3$) δ 7.55 (1H, s), 7.43 (2H, d, J=8.3 Hz), 7.28 (2H, d, J=8.3 Hz), 6.99–6.95 (2H, m), 3.99 (2H, t, J=6.6 Hz), 3.00 (2H, t, J=6.6 Hz), 2.77 (2H, q, J=7.7 Hz), 2.47 (3H, s), 1.32 (3H, t, J=7.7 Hz)

Step 5. 2-[4-(2-Ethyl-5-methyl-1H-benzimidazol-1-yl) phenyl]ethyl azide

The title compound was prepared according to the procedure described in step 5 of Example 26 from 2-[4-(2-ethyl-5-methyl-1H-benzimidazol-1-yl)phenyl]ethanol (step 4).

TLC Rf=0.74 (Hexane/ethyl acetate=1:1).

Step 6. 2-[4-(2-Ethyl-5-methyl-1H-benzimidazol-1-yl) phenyl]ethylamine

The title compound was prepared according to the procedure described in step 9 of Example 1 from 2-[4-(2-ethyl-5-methyl-1H-benzimidazol-1-yl)phenyl]ethyl azide (step 5).

$^1$H-NMR (CDCl$_3$) δ 7.55 (1H, s), 7.43 (2H, d, J=8.2 Hz), 7.29 (2H, d, J=8.2 Hz), 7.01–6.95 (2H, m), 4.85 (2H, br.s), 3.30–3.25 (2H, m), 3.16–3.11 (2H, m), 2.76 (2H, q, J=7.6 Hz), 2.45 (3H, s), 1.31 (3H, t, J=7.6 Hz).

Step 7. 2-Ethyl-5-methyl-1-(4-{2-[({[(4-methylphenyl) sulfonyl]amino}carbonyl)amino]ethyl}phenyl)-1H-benzimidazole The title compound was prepared according to the procedure described in step 10 of Example 1 from 2-[4-(2-ethyl-5-methyl-1H-benzimidazol-1-yl)phenyl]ethylamine (step 6).

$^1$H-NMR (DMSO-d$_6$) δ 7.76 (2H, d, J=8.4 Hz), 7.42–7.36 (6H, m), 7.00–6.91 (2H, m), 6.53–6.49 (1H, m), 3.29–3.24 (2H, m), 2.79–2.65 (4H, m), 2.40 (3H, s), 2.33 (3H, s), 1.20 (3H, t, J=7.4 Hz).

Example 48

2-ETHYL-5-METHYL-1-(4-{2-[({[(4-METHYLPHENYL)SULFONYL]AMINO}CARBONYL) AMINO]ETHYL}PHENYL)-1H-BENZIMIDAZOLE, SODIUM SALT

The title compound was prepared according to the procedure described in Example 2 from 2-ethyl-5-methyl-1-(4-{2-[({[(4-methylphenyl)sulfonyl]amino}carbonyl) amino}ethyl}phenyl)-1H-benzimidazole (Example 47).

$^1$H-NMR (DMSO-d$_6$) δ 7.60 (2H, d, J=7.7 Hz), 7.42–7.33 (5H, m), 7.13 (2H, d, J=7.7 Hz), 6.96 (2H, m), 3.16 (2H, m), 2.71–2.66 (4H, m), 2.39 (3H, s), 2.27 (3H, s), 1.20 (3H, t, J=7.5 Hz); IR (KBr) α$_{max}$ 1599, 1514, 1285, 1232, 1130, 1086 cm$^{-1}$.

Example 49

2-BUTYL-5-METHYL-1-(4-{2-[({[(4-METHYLPHENYL)SULFONYL]AMINO}CARBONYL) AMINO]BUTYL}PHENYL)-1H-BENZIMIDAZOLE

Step 1. 2-[4-(2-Butyl-5-methyl-1H-benzimidazol-1-yl) phenyl]ethyl Pentanoate

The title compound was prepared according to the procedure described in step 5 of Example 1 from 2-[(2-amino-4-methylanilino)phenyl]ethanol (step 2 of Example 47) and pentanoyl chloride.

$^1$H-NMR (CDCl$_3$) δ 7.56–7.55 (1H, m), 7.43–7.40 (2H, m), 7.29–7.26 (2H, m), 7.0–6.94 (2H, m), 4.38 (2H, t, J=6.9 Hz), 3.06 (2H, t, J=6.9 Hz), 2.75 (2H, t, J=7.4 Hz), 2.47 (3H, s), 2.33 (2H, t, J=7.4 Hz), 1.80–1.55 (4H, m), 1.41–1.23 (4H, m), 0.94–0.83 (6H, m).

Step 2. 2-[4-(2-Butyl-6-methyl-1H-benzimidazol-1-yl) phenyl]ethanol

The title compound was prepared according to the procedure described in step 6 of Example 1 from 2-[4-(2-butyl-6-methyl-1H-benzimidazol-1-yl)phenyl]ethyl pentanoate (step 1).

$^1$H-NMR (CDCl$_3$) δ 7.55 (1H, s), 7.44 (2H, d, J=8.2 Hz), 7.27 (2H, d, J=8.2 Hz), 7.02–6.95 (2H, m), 3.99 (2H, t, J=6.6 Hz), 3.01 (2H, t, J=6.6 Hz), 2.75 (2H, t, J=7.3 Hz), 2.47 (3H, s), 1.79–1.68 (2H, m), 1.36–1.23 (2H, m), 0.85 (3H, t, J=7.3 Hz).

Step 3. 2-[4-(2-Butyl-6-methyl-1H-benzimidazol-1-yl)phenyl]ethyl azide

The title compound was prepared according to the procedure described in step 5 of Example 26 from 2-[4-(2-butyl-6-methyl-1H-benzimidazol-1-yl)phenyl]ethanol (step 2).

$^1$H-NMR (CDCl$_3$) δ 7.56 (1H, s), 7.42 (2H, d, J=8.4 Hz), 7.29 (2H, d, J=8.4 Hz), 7.03–6.95 (2H, m), 3.61 (2H, t, J=6.9 Hz), 3.01 (2H, t, J=6.9 Hz), 2.75 (2H, t, J=7.3 Hz), 2.47 (3H, s), 1.80–1.68 (2H, m), 1.37–1.26 (2H, m), 0.85 (3H, t, J=7.3 Hz).

Step 3. 2-[4-(2-Butyl-6-methyl-1H-benzimidazol-1-yl)phenyl]ethylamine

The title compound was prepared according to the procedure described in step 9 of Example 1 from 2-[4-(2-butyl-6-methyl-1H-benzimidazol-1-yl)phenyl]ethyl azide (step 2).

$^1$H-NMR (CDCl$_3$) δ 7.55 (1H, s), 7.40 (2H, d, J=8.3 Hz), 7.26 (2H, d, J=8.3 Hz), 7.0–6.94 (2H, m), 3.15 (2H, t, J=7.3 Hz), 2.98 (2H, t, J=7.3 Hz), 2.74 (2H, t, J=7.7 Hz), 2.46 (3H, s), 1.77–1.67 (2H, m), 1.35–1.28 (2H, m), 0.84 (3H, t, J=7.7 Hz).

Step 4. 2-Butyl-5-methyl-1-(4-{2-[({[(4-methylphenyl)sulfonyl]amino}carbonyl)amino]ethyl}phenyl)-1H-benzimidazole The title compound was prepared according to the procedure described in step 10 of Example 1 from 2-[4-(2-butyl-6-methyl-1H-benzimidazol-1-yl)phenyl]ethylamine (step 3).

$^1$H-NMR (CDCl$_3$) δ 7.76 (2H, d, J=8.2 Hz), 7.54 (1H, m), 7.31–7.21 (6H, m), 7.03–6.95 (2H, m), 6.67–6.63 (1H, m), 3.61–3.54 (2H, m), 2.91 (2H, t, J=7.1 Hz), 2.73 (2H, t, J=7.3 Hz), 2.47 (3H, s), 2.40 (3H, s), 1.76–1.65 (2H, m), 1.36–1.28 (2H, m), 0.83 (3H, t, J=7.3 Hz)

Example 50

2-BUTYL-5-METHYL-1-(4-{2-[({[(4-METHYLPHENYL)SULFONYL]AMINO}CARBONYL)AMINO]BUTYL}PHENYL)-1H-BENZIMIDAZOLE, SODIUM SALT

The title compound was prepared according to the procedure described in Example 2 from 2-butyl-5-methyl-1-(4-{2-[({[(4-methylphenyl)sulfonyl]amino}carbonyl)amino]ethyl}phenyl)-1H-benzimidazole (Example 49).

mp 130–140° C.; $^1$H-NMR (DMSO-d$_6$) δ 7.59 (2H, d, J=7.8 Hz), 7.40–7.31 (5H, m), 7.11 (2H, d, J=7.8 Hz), 6.98–6.92 (2H, m), 3.15 (2H, m), 2.71–2.66 (4H, m), 2.39 (3H, s), 2.26 (3H, s), 1.67–1.57 (2H, m), 1.31–1.21 (2H, m), 0.79 (3H, t, J=7.5 Hz); IR (KBr) α$_{max}$ 1599, 1514, 1400, 1130, 1086 cm$^{-1}$.

Example 51

6-METHYL-2-ETHYL-3-(4-{2-[({[(4-METHYLPHENYL)SULFONYL]AMINO}CARBONYL)AMINO]ETHYL}PHENYL)-1H-BENZIMIDAZOLE

Step 1. 2-[4-(5-Methyl-2-nitroanilino)phenyl]ethanol

The title compound was prepared according to the procedure described in step 3 of Example 1 from 2-fuluoro-4-methylnitrobenzene and 4-aminophenylethyl alcohol.

$^1$H-NMR (CDCl$_3$) δ 9.51 (1H, br.s), 8.10 (1H, d, J=8.8 Hz), 7.20–7.31 (4H, m), 6.98 (1H, s), 6.58 (1H, d, J=8.4 Hz), 3.91 (2H, t, J=6.4 Hz), 2.89 (t, J=6.4 Hz), 2.27 (3H, s).

Step 2. 2-[4-(2-Amino-5-methanilino)phenyl]ethanol

The title compound was prepared according to the procedure described in step 2 of Example 26 from 2-[4-(5-methyl-2-nitroanilino)phenyl]ethanol (step 1).

$^1$H-NMR (CDCl$_3$) δ 7.07 (2H, d, J=8.3 Hz), 6.93 (1H, s), 6.81 (1H, d, J=8.1 Hz), 6.70–6.72 (3H, m), 3.81 (2H, t, J=6.4 Hz), 3.61 (2H, br.s), 2.78 (2H, t, J=6.4 Hz), 2.22 (3H, s).

Step 3. 2-[4-(2-Ethyl-6-methyl-1H-benzimidazol-1-yl)phenyl]ethyl propionate

The title compound was prepared according to the procedure described in step 5 of Example 1 from 2-[4-(2-Amino-5-methylanilino)phenyl]ethanol (step 2) and propionyl chloride.

$^1$H-NMR (CDCl$_3$) δ 7.64 (1H, d, J=8.3 Hz), 7.42 (2H, d, J=8.0 Hz), 7.28 (2H, d, J=8.0 Hz), 7.08 (1H, d, J=8.3 Hz), 6.87 (1H, s), 4.38 (2H, t, J=6.9 Hz), 3.06 (2H, t, J=6.9 Hz), 2.76 (2H, q, J=7.5 Hz), 2.41 (3H, s), 2.36 (2H, q, J=7.7 Hz), 1.35 (3H, t, J=7.5 Hz), 1.15 (3H, t, J=7.7 Hz).

Step 4. 2-[4-(2-Ethyl-6-methyl-1H-benzimidazol-1-yl)phenyl]ethanol

The title compound was prepared according to the procedure described in 6 of Example 1 from 2-[4-(2-ethyl-6-methyl-1H-benzimidazol-1-yl)phenyl]ethyl propionate (step 3).

$^1$H-NMR (CDCl$_3$) δ 7.64 (1H, d, J=8.1 Hz), 7.45 (2H, d, J=8.1 Hz), 7.19–7.30 (2H, m), 7.08 (1H, d, J=8.1 Hz), 6.88 (1H, s), 3.99 (2H, t, J=6.6 Hz), 3.00 (2H, t, J=6.6 Hz), 2.77 (2H, q, J=7.6 Hz), 2.40 (3H, s), 1.33 (3H, t, J=7.6 Hz).

Step 5. 1-[4-(2-Chloroethyl)phenyl]-2-ethyl-6-methyl-1H-benzimidazole

The title compound was prepared according to the procedure described in step 7 of Example 1 from 2-[4-(2-ethyl-6-methyl-1H-benzimidazol-1-yl)phenyl]ethanol (step 4).

$^1$H-NMR (CDCl$_3$) δ 7.65 (1H, d, J=8.2 Hz), 7.43 (2H, d, J=8.2 Hz), 7.31 (2H, d, J=8.2 Hz), 7.07 (1H, d, J=8.2 Hz), 6.88 (1H, s), 3.82 (2H, t, J=7.0 Hz), 3.19 (2H, t, 7.0 Hz) 2.77 (2H, q, J=7.6 Hz), 2.41 (3H, s), 1.33 (3H, t, J=7.6 Hz).

Step 6. 2-[4-(2-Ethyl-6-methyl-1H-benzimidazol-1-yl)phenyl]ethyl azide

The title compound was prepared according to the procedure described in step 8 of Example 1 from 1-[4-(2-chloroethyl)phenyl]-2-ethyl-6-methyl-1H-benzimidazole (step 5).

$^1$H-NMR (CDCl$_3$) δ 7.64 (1H, d, J=8.2 Hz), 7.43 (2H, d, J=8.2 Hz), 7.31 (2H, d, J=8.2 Hz), 7.08 (1H, d, J=8.2 Hz), 6.87 (1H, s), 3.62 (2H, t, J=7.0 Hz), 3.01 (2H, t, J=7.0 Hz), 2.77 (2H, q, J=7.6 Hz), 2.37 (3H, s), 1.33 (3H, t, J=7.6 Hz).

Step 7. 2-[4-(2-Ethyl-6-methyl-1H-benzimidazol-1-yl)phenyl]ethylamine

The title compound was prepared according to the procedure described in step 9 of Example 1 from 2-[4-(2-ethyl-6-methyl-1H-benzimidazol-1-yl)phenyl]ethyl azide (step 6).

$^1$H-NMR (CDCl$_3$) δ 7.64 (1H, d, J=8.3 Hz), 7.40 (2H, d, J=8.2 Hz), 7.28 (2H, d, J=8.2 Hz), 7.07 (1H, d, J=8.3 Hz), 6.88 (1H, s), 3.07 (2H, br.s), 2.87 (2H, t, J=6.8 Hz), 2.76 (2H, q, J=7.6 Hz), 2.40 (3H, s), 1.33 (3H, t, J=7.6 Hz).

Step 8. 6-Methyl-2-Ethyl-3-(4-{2-[({[(4-methylphenyl)sulfonyl]amino}carbonyl)amino]ethyl}phenyl)-1H-benzimidazole The title compound was prepared according to the procedure described in step 10 of Example 1 from 2-[4-(2-ethyl-6-methyl-1H-benzimidazol-1-yl)phenyl]ethylamine (step 7).

$^1$H-NMR (CDCl$_3$) δ 7.73 (2H, d, J=8.3 Hz), 7.66 (1H, d, J=8.0 Hz), 7.27–7.38 (6H, m), 7.09 (1H, d, J=8.0 Hz), 6.88 (1H, s), 3.59–3.63 (2H, m), 2.95 (2H, t, J=6.6 Hz), 2.77 (2H, q, J=7.5 Hz), 2.41 (3H, s), 2.39 (3H, s), 1.33 (3H, t, J=7.5 Hz).

Example 52

6-METHYL-2-ETHYL-3-(4-{2-[({[(4-METHYL PHENYL)SULFONYL]AMINO}CARBONYL)AMINO]ETHYL}PHENYL)-1H-BENZIMIDAZOLE, SODIUM SALT

The title compound was prepared according to the procedure described in Example 2 from 6-methyl-2-ethyl-3-(4-{2-[({[(4-methyl phenyl)sulfonyl]amino}carbonyl)amino]ethyl}phenyl)-1H-benzimidazole (Example 51).

mp 151–165° C.; $^1$H-NMR (DMSO-d$_6$) δ 7.64 (2H, d, J=8.0 Hz), 7.51 (1H, d, J=8.2 Hz), 7.33–7.42 (4H, m), 7.15

(2H, d, J=8.0 Hz), 7.02 (1H, dd, J=1.4 Hz, 8.2 Hz), 6.87 (1H, s) 3.18 (2H, br.s), 2.65–2.78 (4H, m), 2.34 (3H, s), 2.78 (3H, s), 1.21 (3H, t, J=7.6 Hz).

Example 53
7-METHYL-2-ETHYL-3-(4-{2-[({[(4-METHYLPHENYL)SULFONYL]AMINO}CARBONYL)AMINO]ETHYL}PHENYL)-1H-BENZIMIDAZOLE Step 1. 2-[4-(2-Methyl-6-nitroanilino)phenyl]ethanol The title compound was prepared according to the procedure described in step 1 Example 45 from 6-methyl-2-nitroaniline and 4-bromophenylethyl alcohol.

$^1$H-NMR (CDCl$_3$) δ 8.28 (1H, br.s), 7.96 (1H, d, J=8.4 Hz), 7.39–7.44 (1H, m), 7.02–7.12 (3H, m), 6.72 (2H, d, J=8.4 Hz), 3.82 (2H, t, J=6.5 Hz), 2.81 (2H, t, J=6.5 Hz), 2.08 (3H, s).

Step 2. 2-[4-(2-Amino-6-methylanilino)phenyl]ethanol

The title compound was prepared according to the procedure described in step 2 of Example 26 from 2-[4-(2-methyl-6-nitroanilino)phenyl]ethanol (step 1).

$^1$H-NMR (CDCl$_3$) δ 6.97–7.03 (3H, m), 6.66 (2H, d, J=7.6 Hz), 6.52 (2H, d, J=7.6 Hz), 4.97 (1H, br.s), 3.86 (2H, br.s), 3.79 (2H, t, J=6.4 Hz), 2.76 (2H, t, J=6.4 Hz), 2.16 (3H, s).

Step 3. 2-[4-(2-Ethyl-7-methyl-1H-benzimidazol-1-yl)phenyl]ethyl propionate

The title compound was prepared according to the procedure described in step 5 of Example 1 from 2-[4-(2-amino-6-methylanilino)phenyl]ethanol (step 2) and propionyl chloride.

TLC Rf=0.6 (hexane:ethyl acetate=1:1).

Step 4. 2-[4-(2-Ethyl-7-methyl-1-H-benzimidazol-1-yl)phenyl]ethanol

The title compound was prepared according to the procedure described in step 6 of Example 1 from 2-[4-(2-ethyl-7-methyl-1H-benzimidazol-1-yl)phenyl]ethyl propionate (step 3).

$^1$H-NMR (CDCl$_3$) δ 7.63 (1H, d, J=8.0 Hz), 7.38–7.41 (2H, m), 7.26–7.31 (2H, m), 7.14 (1H, dd, J=7.4 Hz, 8.0 Hz), 6.91 (1H, d, J=7.4 Hz), 3.98 (2H, t, J=6.6 Hz), 3.01 (2H, t, J=66 Hz), 2.63 (2H, q, J=7.5 Hz), 1.89 (3H, s), 1.31 (3H, t, J=7.5 Hz).

Step 5. 1-[4-(2-Chloroethyl)phenyl]-2-ethyl-7-methyl-1H-benzimidazole

The title compound was prepared according to the procedure described in step 7 of Example 1 from 2-[4-(2-ethyl-7-methyl-1H-benzimidazol-1-yl)phenyl]ethanol (step 4).

$^1$H-NMR (CDCl$_3$) δ 7.64 (1H, d, J=8.1 Hz), 7.26–7.39 (4H, m), 7.14 (1H, dd, J=7.4 Hz, 8.1 Hz), 6.91 (1H, d, J=7.4 Hz), 3.81 (2H, t, J=7.2 Hz), 3.19 (2H, d, J=7.2 Hz), 2.63 (2H, q, J=7.6 Hz), 1.88 (3H, s), 1.32 (3H, t, J=7.6 Hz).

Step 6. 2-[4-(2-Ethyl-7-methyl-1H-benzimidazol-1-yl)phenyl]ethyl azide

The title compound was prepared according to the procedure described in step 8 of Example 1 from 1-[4-(2-chloroethyl)phenyl]-2-ethyl-7-methyl-1H-benzimidazole (step 5).

$^1$H-NMR (CDCl$_3$) δ 7.64 (1H, d, J=7.4 Hz), 7.39 (2H, d, J=8.0 Hz), 7.31 (2H, d, J=8.0 Hz), 7.14 (1H, dd, J=7.4 Hz, 8.1 Hz), 6.91 (1H, d, J=8.1 Hz), 3.61 (2H, t, J=6.8 Hz), 3.02 (2H, t, J=6.8 Hz), 2.63 (2H, q, J=7.6 Hz), 1.89 (3H, s), 1.31 (3H, t, J=7.5 Hz).

Step 7. 2-[4-(2-Ethyl-7-methyl-1H-benzimidazol-1-yl)phenyl]ethylamine

The title compound was prepared according to the procedure described in step 9 of Example 1 from 2-[4-(2-ethyl-7-methyl-1H-benzimidazol-1-yl)phenyl]ethyl azide (step 6).

$^1$H-NMR (CDCl$_3$) δ 7.64 (1H, d, J=7.9 Hz), 7.36 (2H, d, J=8.2 Hz), 7.28 (2H, d, J=8.2 Hz), 7.14 (1H, dd, J=7.5 Hz, 7.9 Hz), 6.91 (1H, d, J=7.5 Hz), 3.06 (2H, t, J=6.8 Hz), 2.87 (2H, t, J=6.8 Hz), 2.63 (2H, q, J=7.5 Hz), 1.89 (3H, s), 1.32 (3H, t, J=7.5 Hz).

Step 8. 2-Ethyl-7-methyl-1-(4-{2-[({[(4-methylphenyl)sulfonyl]amino}carbonyl)amino]ethyl]phenyl)-1H-benzimidazole The title compound was prepared according to the procedure described in step 10 of Example 1 from 2-[4-(2-ethyl-7-methyl-1H-benzimidazol-1-yl)phenyl]ethylamine (step 7).

MS (ESI) m/z 477 (M+H)$^+$, $^1$H-NMR (CDCl$_3$) δ 7.75 (2H, d, J=8.3 Hz), 7.62 (1H, d, J=7.9 Hz), 7.28–7.33 (5H, m), 7.14 (2H, d, J=7.6 Hz), 6.91 (1H, d, J=7.9 Hz), 6.72 (1H, br.s), 3.58 (2H, d, J=6.8 Hz), 2.93 (2H, t, J=6.8 Hz), 2.62 (2H, q, J=7.6 Hz), 2.41 (3H, s), 1.86 (3H, s) 1.29 (3H, t, J=7.6 Hz).

Example 54
7-METHYL-2-ETHYL-3-(4-{2-[({[(4-METHYLPHENYL)SULFONYL]AMINO}CARBONYL)AMINO]ETHYL}PHENYL)-1H-BENZIMIDAZOLE, SODIUM SALT The title compound was prepared according to the procedure described in Example 2 from 2-ethyl-7-methyl-1-(4-{2-[({[(4-methylphenyl)sulfonyl]amino}carbonyl)amino]ethyl}phenyl)-1H-benzimidazole (Example 53).

$^1$H-NMR (DMSO-d$_6$) δ 7.63 (2H, d, J=7.4 Hz), 7.47 (1H, d, J=8.1 Hz), 7.36 (4H, s), 7.15 (2H, d, J=7.7 Hz), 7.06 (1H, dd, J=7.2 Hz, 8.1 Hz), 6.87 (1H, d, J=7.2 Hz), 5.99 (1H, br.s), 3.16 (2H, br.s), 2.76 (2H, br.s), 2.52 (2H, q, J=7.6 Hz), 2.28 (3H, s), 1.82 (3H, s), 1.19 (3H, t, J=7.6 Hz); IR (KBr) α$_{max}$ 3400, 1610, 1525, 1290, 1132, 1095, 820, 751 cm$^{-1}$.

Example 55
4-CHLORO-2-ETHYL-3-(4-{2-[({[(4-METHYLPHENYL)SULFONYL]AMINO}CARBONYL)AMINO]ETHYL}PHENYL)-1H-BENZIMIDAZOLE Step 1. 2-[4-(3-Chloro-2-nitroanilino)phenyl]ethanol A mixture of 2,6-dichloronitrobenzene (Norman, M. H.; Chen, N.; et al. PCT Int. Appl, WO 9940091 (1999)., Spada, A. P.; Fink, C. A.; Myers, M. R. PCT Int. Appl, WO 9205177 (1992)., 6.3 g, 32.8 mmol), 4-aminophenylethyl alcohol (4.9 g, 36 mmol) and sodium acetate (3.2 g, 39.3 mmol) was placed in a sealed tube and heated at 160° C. for 3 h. After cooling, the mixture was poured into water (100 mL) and extracted with ethyl acetate (300 mL). The organic layer was washed with 2N aqueous NaOH (100 mL) and brine (100 mL), then dried (Na$_2$SO$_4$), and concentrated. Purification by flash column chromatography on silica gel eluting with hexane/ethyl acetate (1:1) to afford 4.57 g (72%) of the title compound as a red oil: $^1$H-NMR (CDCl$_3$) δ 7.09–7.28 (6H, m), 6.91 (1H, dd, J=2.0, 7.1 Hz), 3.87 (2H, t, J=6.6 Hz), 2.86 (2H, t, J=6.6 Hz).

Step 2. 2-[4-(2-Amino-3-chloroanilino)phenyl]ethanol

The title compound was prepared according to the procedure described in step 2 of Example 28 from 2-[4-(3-chloro-2-nitroanilino)phenyl]ethanol (step 1).

$^1$H-NMR (CDCl$_3$) δ 7.06–7.10 (3H, m), 7.00 (1H, dd, J=1.0 Hz, 7.9 Hz), 6.62–6.73 (3H, m), 5.16 (1H, br.s), 4.14 (2H, br.s), 3.81 (2H, t, J=6.1 Hz), 2.77 (2H, t, J=6.1 Hz).

Step 3. 2-[4-(4-Chloro-2-ethyl-1H-benzimidazol-1-yl)phenyl]ethyl propionate

The title compound was prepared according to the procedure described in step 5 of Example 1 from 2-[4-(2-amino-3-chloroanilino)phenyl]ethanol (step 2) and propionyl chloride.

TLC Rf=0.5 (hexane: ethyl acetate=1:1).

Step 4. 2-[4-(4-Chloro-2-ethyl-1H-benzimidazol-1-yl)phenyl]ethanol

The title compound was prepared according to the procedure described in step 6 of Example 1 from 2-[4-(4-Chloro-2-ethyl-1H-benzimidazol-1-yl)phenyl]ethyl propionate (step 3).

¹H-NMR (CDCl₃) δ 7.45 (2H, d, J=8.6 Hz), 7.26–7.31 (3H, m), 7.09 (1H, d, J=7.9 Hz), 6.96 (1H, dd, J=0.9 Hz, 7.9 Hz), 3.99 (2H, t, J=6.6 Hz), 3.00 (2H, t, J=6.6 Hz), 2.84 (2H, q, J=7.5 Hz), 1.30 (3H, t, J=7.5 Hz).

Step 5. 4-Chloro-1-[4-(2-chloroethyl)phenyl]-2-ethyl-1H-benzimidazole

The title compound was prepared according to the procedure described in step 7 of Example 1 from 2-[4-(4-chloro-2-ethyl-1H-benzimidazol-1-yl)phenyl]ethanol (step 4).

¹H-NMR (CDCl₃) δ 7.45 (2H, d, J=8.6 Hz), 7.30 (2H, d, J=8.6 Hz), 7.27 (1H, s), 7.10 (1H, d, J=8.1 Hz), 6.98 (1H, d, J=8.1 Hz), 3.81 (2H, t, J=7.1 Hz), 3.19 (2H, t, J=7.1 Hz), 2.84 (2H, q, J=7.6 Hz), 1.31 (3H, t, J=7.6 Hz).

Step 6. 2-[4-(4-Chloro-2-ethyl-1H-benzimidazol-1-yl)phenyl]ethyl azide

The title compound was prepared according to the procedure described in step 8 of Example 1 from 4-chloro-1-[4-(2-chloroethyl)phenyl]-2-ethyl-1H-benzimidazole (step 5).

¹H-NMR (CDCl₃) δ 7.45 (2H, d, J=8.2 Hz), 7.29–7.33 (3H, m), 7.10 (1H, dd, J=8.1 Hz, 7.7 Hz), 6.96 (1H, d, J=7.7 Hz), 3.62 (2H, t, J=7.1 Hz), 3.02 (2H, t, J=7.1 Hz), 2.84 (2H, q, J=7.6 Hz), 1.30 (3H, t, J=7.6 Hz).

Step 7. 2-[4-(4-Chloro-2-ethyl-1H-benzimidazol-1-yl)phenyl]ethylamine

The title compound was prepared according to the procedure described in step 7 of Example 37 from 2-[4-(4-chloro-2-ethyl-1H-benzimidazol-1-yl)phenyl]ethyl azide (step 6).

¹H-NMR (CDCl₃) δ 7.42 (2H, d, J=8.1 Hz), 7.29–7.33 (3H, m), 7.09 (1H, dd, J=7.7 Hz, 7.9 Hz), 7.99 (1H, d, J=7.9 Hz), 3.07 (2H, t, J=6.8 Hz), 2.87 (2H, t, J=6.8 Hz), 2.85 (2H, q, J=7.6 Hz) 1.30 (3H, t, J=7.6 Hz).

Step 8. 4-Chloro-2-ethyl-1-(4-{2-[({[(4-methylphenyl)sulfonyl]amino}carbonyl)amino]ethyl}phenyl)-1H-benzimidazole The title compound was prepared according to the procedure described in step 10 of Example 1 from 2-[4-(4-chloro-2-ethyl-1H-benzimidazol-1-yl)phenyl]ethylamine (step 7).

MS (ESI) m/z 498 (M+H)⁺; ¹H-NMR (CDCl₃) δ 7.73 (2H, d, J=8.5 Hz), 7.28–7.38 (7H, m), 7.09 (1H, d, J=7.9 Hz), 6.97 (1H, d, J=7.9 Hz), 6.69 (1H, br.s), 3.58 (2H, t, J=6.9 Hz), 2.94 (2H, t, J=6.9 Hz), 2.83 (2H, q, J=7.5 Hz), 2.40 (3H, s), 1.31 (3H, t, J=7.5 Hz).

Example 56
4-CHLORO-2-ETHYL-3-(4-{2-[({[(4-METHYLPHENYL)SULFONYL]AMINO}CARBONYL)AMINO]ETHYL}PHENYL)-1H-BENZIMIDAZOLE, SODIUM SALT The title compound was prepared according to the procedure described in Example 2 from 4-chloro-2-ethyl-1-(4-{2-[({[(4-methylphenyl)sulfonyl]amino}carbonyl)amino]ethyl}phenyl)-1H-benzimidazole (Example 54).

¹H-NMR (DMSO-d₆) δ 7.62 (2H, d, J=8.0 Hz), 7.41 (4H, s), 7.29 (1H, d, J=6.6 Hz), 7.12–7.18 (3H, m), 7.02–7.04 (1H, m), 3.18 (2H, br.s), 2.70–2.79 (4H, m), 2.27 (3H, s), 1.23 (3H, t, J=7.4 Hz); IR (KBr) α_{max} 3385, 1602, 1519, 1433, 1174, 1130, 1085, 813 cm⁻¹.

Example 57
5-CHLORO-2-ETHYL-1-(4-{2-[({[(4-METHYLPHENYL)SULFONYL]AMINO}CARBONYL)AMINO]ETHYL}PHENYL)-1H-BENZIMIDAZOLE Step 1. 2-[4-(4-Chloro-2-nitroanilino)phenyl]ethanol The title compound was prepared according to the procedure described in step 3 of Example 1 from 2,5-dichloronitrobenzene and 4-aminophenylethyl alcohol.

¹H-NMR (CDCl₃) δ 9.42 (1H, s), 8.20 (1H, d, J=2.0 Hz), 7.35–7.10 (6H, m), 3.96–3.85 (2H, m), 2.91 (2H, t, J=7.0 Hz).

Step 2. 2-[4-(2-Amino-4-chloroanilino)phenyl]ethanol

The title compound was prepared according to the procedure described in step 3 of Example 6 from 2-[4-(4-chloro-2-nitroanilino)phenyl]ethanol (step 1).

¹H-NMR (CDCl₃) δ 7.30–7.05 (4H, m), 6.83–6.62 (3H, m), 5.15 (1H, br.s), 3.86–3.75 (2H, m,), 3.75 (2H, br.s), 2.77 (2H, t, J=7.0 Hz).

Step 3. 2-[4-(5-Chloro-2-ethyl-1H-benzimidazol-1-yl)phenyl]ethyl propionate

The title compound was prepared according to the procedure described in step 5 of Example 1 from 2-[4-(2-amino-4-chloroanilino)phenyl]ethanol (step 2) and propionyl chloride.

¹H-NMR (CDCl₃) δ 7.75 (1H, d, J=2.0 Hz), 7.43 (2H, d, J=8.0 Hz), 7.28 (2H, d, J=8.0 Hz), 7.15 (1H, dd, J=2.0, 8.6 Hz), 6.99 (1H, d, J=8.6 Hz), 4.38 (2H, t, J=7.0 Hz), 3.07 (2H, t, J=7.0 Hz), 2.78 (2H, q, J=7.5 Hz), 2.36 (2H, q, J=7.5 Hz), 1.24 (3H, t, J=7.5 Hz), 1.15 (3H, t, J=7.5 Hz).

Step 4. 2-[4-(5-Chloro-2-ethyl-1H-benzimidazol-1-yl)phenyl]ethanol

The title compound was prepared according to the procedure described in step 6 of Example 1 from 2-[4-(5-chloro-2-ethyl-1H-benzimidazol-1-yl)phenyl]ethyl propionate (step 3).

¹H-NMR (CDCl₃) δ 7.75 (1H, d, J=2.0 Hz), 7.46 (2H, d, J=8.4 Hz), 7.29 (2H, d, J=8.4 Hz), 7.15 (1H, dd, J=2.0, 8.6 Hz), 7.00 (1H, d, J=8.6 Hz), 3.99 (2H, t, J=6.5 Hz), 3.00 (2H, t, J=6.5 Hz), 2.78 (2H, q, J=7.5 Hz), 1.26 (3H, t, J=7.5 Hz).

Step 5. 2-[4-(5-Chloro-2-ethyl-1H-benzimidazol-1-yl)phenyl]ethyl azide

The title compound was prepared according to the procedure described in step 5 Example 26 from 2-[4-(5-chloro-2-ethyl-1H-benzimidazol-1-yl)phenyl]ethanol (step 4).

MS (EI) m/z 325 (M⁺); ¹H-NMR (CDCl₃) δ 7.75 (1H, d, J=2.0 Hz), 7.45 (2H, d, J=8.3 Hz), 7.29 (2H, d, J=8.3 Hz), 7.15 (1H, dd, J=2.0, 8.6 Hz), 6.99 (1H, d, J=8.6 Hz), 3.62 (2H, t, J=7.0 Hz), 3.02 (2H, t, J=7.0 Hz), 2.78 (2H, q, J=7.5 Hz), 1.26 (3H, t, J=7.5 Hz).

Step 6. 2-[4-(5-Chloro-2-ethyl-1H-benzimidazol-1-yl)phenyl]ethylamine

The title compound was prepared according to the procedure described in step 7 of Example 37 from 2-[4-(5-chloro-2-ethyl-1H-benzimidazol-1-yl)phenyl]ethyl azide (step 5).

¹H-NMR (CDCl₃) δ 7.75 (1H, d, J=2.0 Hz), 7.41 (2H, d, J=8.3 Hz), 7.27 (2H, d, J=8.3 Hz), 7.14 (1H, dd, J=2.0, 8.6 Hz), 6.99 (1H, d, J=8.6 Hz), 3.08 (2H, t, J=7.0 Hz), 2.86 (2H, t, J=7.0 Hz), 2.77 (2H, q, J=7.5 Hz), 1.34 (3H, t, J=7.5 Hz).

Step 7. 5-Chloro-2-ethyl-1-(4-{2-[({[(4-methylphenyl)sulfonyl]amino}carbonyl)amino]ethyl}phenyl)-1H-benzimidazole The title compound was prepared according to the procedure described in step 10 of Example 1 from 2-[4-(5-chloro-2-ethyl-1H-benzimidazol-1-yl)phenyl]ethylamine (step 6).

¹H-NMR (CDCl₃) δ 7.76 (1H, d, J=1.8 Hz), 7.72 (2H, d, J=8.4 Hz), 7.39 (2H, d, J=8.3 Hz), 7.30 (2H, d, J=8.4 Hz), 7.28 (2H, d, J=8.3 Hz), 7.17 (1H, dd, J=8.6, 1.8 Hz), 7.00 (1H, d, J=8.6 Hz), 6.73 (1H, br.s), 3.59–3.53 (2H, m), 2.94 (2H, t, J=7.0 Hz), 2.81 (2H, q, J=7.5 Hz), 1.34 (3H, t, J=7.5 Hz).

Example 58
2-[4-(5-CHLORO-2-ETHYL-1H-BENZIMIDAZOL-1-YL)PHENYL]ETHYL(4-METHYLPHENYL)SULFONYLCARBAMATE The title compound was prepared according to the procedure described in Example 3 from 2-[4-(5-chloro-2-ethyl-1H-benzimidazol-1-yl)phenyl]ethanol (step 4 of Example 57).

¹H-NMR (CDCl₃) δ 7.92 (2H, d, J=8.4 Hz), 7.74 (1H, d, J=2.0 Hz), 7.34 (2H, d, J=8.4 Hz), 7.33 (2H, d, J=8.4 Hz), 7.23 (2H, d, J=8.4 Hz), 7.16 (1H, dd, J=8.5, 2.0 Hz), 6.99 (1H, d, J=8.5 Hz), 4.74 (1H, br.s), 4.37 (2H, t, J=6.8 Hz), 3.01 (2H, t, J=6.8 Hz), 2.75 (2H, q, J=7.6 Hz), 1.33 (3H, t, J=7.6 Hz).

Example 59
6-CHLORO-2-ETHYL-1-(4-{2-[({[(4-METHYLPHENYL)SULFONYL]AMINO}CARBONYL)AMINO]ETHYL}PHENYL)-1H-BENZIMIDAZOLE Step 1. 2-[(5-Chloro-2-nitroanilino)phenyl]ethanol The title compound was prepared according to the procedure described in step 3 of Example 1 from 2,4-dichloronitrobenzene and 4-aminophenylethyl alcohol.

¹H-NMR (CDCl₃) δ 9.52 (1H, br.s), 8.16 (1H, d, J=9.2H), 7.33 (2H, d, J=8.2 Hz), 7.13 (1H, d, J=2.2 Hz), 6.71 (1H, dd, J=9.2, 2.2 Hz), 3.92 (q, 2H, J=6.4 Hz), 2.92 (t, 2H, J=6.4 Hz).

Step 2. 2-[(2-Amino-5-chloroanilino)phenyl]ethanol

The title compound was prepared according to the procedure described in step 2 of Example 28 from 2-[(5-chloro-2-nitroanilino)phenyl]ethanol (step 1).

¹H-NMR (CDCl₃) δ 7.12–7.09 (3H, m), 6.92 (1H, dd, J=8.4, 2.4 Hz), 6.78–6.70 (3H, m), 5.16 (1H, br.s), 3.83 (2H, t, J=6,6 Hz), 2.81 (2H, t, J=6.6 Hz).

Step 3. 2-[4-(6-Chloro-2-ethyl-1H-benzimidazol-1-yl)phenyl]ethyl propionate

The title compound was prepared according to the procedure described in step 5 of Example 1 from 2-[(2-amino-5-chloroanilino)phenyl]ethanol (step 2) and propionyl chloride.

¹H-NMR (CDCl₃) δ 7.67 (1H, d, J=8.6 Hz), 7.44 (2H, d, J=8.4 Hz), 7.28 (2H, d, J=8.4 Hz), 7.22 (1H, dd, J=8.4, 2.0 Hz), 7.07 (1H, d, J=2.0 Hz), 4.38 (2H, t, J=7.0 Hz), 3.07 (2H, t, J=7.0 Hz), 2.77 (2H, q, J=7.5 Hz), 2.36 (2H, q, J=7.5 Hz), 1.35 (3H, t, J=7.5 Hz), 1.15 (3H, t, J=7.5 Hz).

Step 4. 2-[4-(6-Chloro-2-ethyl-1H-benzimidazol-1-yl)phenyl]ethanol

The title compound was prepared according to the procedure described in step 6 of Example 1 from 2-[4-(6-chloro-2-ethyl-1H-benzimidazol-1-yl)phenyl]ethyl propionate (step 3).

¹H-NMR (CDCl₃) δ 7.67 (1H, d, J=8.6 Hz), 7.46 (2H, d, J=8.6 Hz), 7.30–7.26 (3H, m), 7.22 (1H, dd, J=8.6, 2.2 Hz), 7.08 (1H, d, J=2.0 Hz), 3.99 (2H, q, J=6.4 Hz), 3.01 (2H, t, J=6.4 Hz), 2.78 (2H, q, J=7.6 Hz), 1.72 (1H, t, J=5.6 Hz), 1.35 (3H, t, J=7.6 Hz).

Step 5. 2-[4-{6-Chloro-2-ethyl-1H-benzimidazol-1-yl)phenyl]ethyl azide

The title compound was prepared according to the procedure described in step 5 of Example 26 from 2-[4-(6-chloro-2-ethyl-1H-benzimidazol-1-yl)phenyl]ethanol (step 4).

MS (EI) m/z 325 (M⁺ᴴᶻ).

Step 6. 2-[4-(6-Chloro-2-ethyl-1H-benzimidazol-1-yl)phenyl]ethylamine

The title compound was prepared according to the procedure described in step 9 of Example 1 from 2-[4-(6-chloro-2-ethyl-1H-benzimidazol-1-yl)phenyl]ethyl azide (step 5).

¹H-NMR (CDCl₃) δ 7.67 (1H, d, J=8.6 Hz), 7.41 (2H, d, J=8.4 Hz), 7.31–7.19 (3H, m), 7.12 (1H, d, J=2.0 Hz), 4.66 (2H, br.s), 3.23–3.17 (2H, m), 3.08–3.04 (2H, m), 2.75 (2H, q, J=7.5 Hz), 1.33 (3H, t, J=7.5 Hz).

Step 7. 6-Chloro-2-ethyl-1-(4-{2-[({[(4-methylphenyl)sulfonyl]amino}carbonyl)amino]ethyl}phenyl)-1H-benzimidazole The title compound was prepared according to the procedure described in step 10 of Example 1 from 2-[4-(6-chloro-2-ethyl-1H-benzimidazol-1-yl)phenyl]ethylamine (step 6).

¹H-NMR (CDCl₃) δ 7.74 (2H, d, J=8.4 Hz), 7.67 (1H, d, J=8.4 Hz), 7.37 (2H, d, J=8.4 Hz), 7.30–7.20 (6H, m), 7.05 (1H, d, J=2.0 Hz), 6.73 (1H, m), 3.62–3.55 (2H, m), 2.93 (2H, t, J=7.2 Hz), 2.77 (2H, t, J=7.5 Hz), 1.32 (3H, t, J=7.5 Hz).

Example 60
6-CHLORO-2-ETHYL-1-(4-{2-[({[(4-METHYLPHENYL)SULFONYL]AMINO}CARBONYL)AMINO]ETHYL}PHENYL)-1H-BENZIMIDAZOLE, SODIUM SALT The title compound was prepared according to the procedure described in Example 2 from 6-chloro-2-ethyl-1-(4-{2-[({[(4-methylphenyl)sulfonyl]amino}carbonyl)amino]ethyl}phenyl)-1H-benzimidazole (Example 59).

¹H-NMR (DMSO-d₆) δ 7.64 (1H, d, J=8.6 Hz), 7.59 (2H, d, J=8.1 Hz), 7.38 (4H, m), 7.38 (4H, m), 7.22 (1H, dd, J=8.6, 2.0 Hz), 7.11 (2H, d, J=8.1 Hz), 7.05 (1H, d, J=2.0 Hz), 3.15 (2H, m) 2.74–2.66 (4H, m), 2.25 (3H, s), 1.21 (3H, t, J=7.4 Hz); IR (KBr) α_max 1601, 1516, 1398, 1178, 1130, 1084 cm⁻¹.

Example 61
4-(6-CHLORO-2-ETHYL-1H-BENZIMIDAZOL-1-YL)PHENETHYL-(4-METHYLPHENYL)SULFONYLCARBAMATE The title compound was prepared according to the procedure described in Example 3 from 2-[4-(6-chloro-2-ethyl-1H-benzimidazol-1-yl)phenyl]ethanol (step 4 of Example 59).

mp 183–187° C.; ¹H-NMR (DMSO-d₆) δ 7.75 (2H, d, J=8.1 Hz), 7.66 (1H, d, J=8.6 Hz), 7.43 (4H, s), 7.40 (2H, d, J=8.1 Hz), 7.24 (1H, dd, J=8.6, 2.0 Hz), 7.03 (1H, d, J=2.0 Hz), 4.27 (2H, t, J=6.6 Hz), 2.95 (2H, t, J=6.6 Hz), 2.70 (2H, q, J=7.5 Hz), 2.34 (3H, s), 1.22 (3H, t, J=7.5 Hz); IR(KBr) α_max 1744, 1516, 1352, 1225, 1165cm⁻¹.

Example 62
2-BUTYL-6-CHLORO-1-(4-{2-[({[(4-METHYLPHENYL)SULFONYL]AMINO}CARBONYL)AMINO]BUTYL}PHENYL)-1H-BENZIMIDAZOLE Step 1. 2-[4-(2-Butyl-6-chloro-1H-benzimidazol-1-yl)phenyl]ethyl Pentanoate The title compound was prepared according to the procedure described in step 5 of Example 1 from 2-[(2-amino-5-chloroanilino)phenyl]ethanol (step 2 of Example 59) and pentanoyl chloride.

¹H-NMR (CDCl₃) δ 7.66 (1H, d, J=8.4 Hz), 7.44 (2H, d, J=8.1 Hz), 7.28 (2H, d, J=8.1 Hz), 7.22 (1H, dd, J=8.4, 2.0 Hz), 7.06 (1H, d, J=2.0 Hz), 4.38 (2H, t, J=6.8 Hz), 3.07 (2H, t, J=6.8 Hz), 2.74 (2H, t, J=7.7 Hz), 2.33 (2H, t, J=7.5 Hz), 1.81–1.70 (2H, m), 1.66–1.56 (2H, m,), 1.40–1.28 (4H, m), 0.94–0.84 (6H, m).

Step 2. 2-[4-(2-Butyl-6-chloro-1H-benzimidazol-1-yl)phenyl]ethanol

The title compound was prepared according to the procedure described in step 6 of Example 1 from 2-[4-(2-butyl-6-chloro-1H-benzimidazol-1-yl)phenyl]ethyl pentanoate (step 1).

¹H-NMR (CDCl₃) δ 7.66 (1H, d, J=8.6 Hz), 7.46 (2H, d, J=8.1 Hz), 7.29–7.26 (2H, m), 7.22 (1H, dd, J=8.6, 2.0 Hz), 7.07 (1H, d, J=2.0 Hz), 4.00 (2H, q, J=6.4 Hz), 3.01 (2H, t, J=6.4 Hz), 2.75 (2H, t, J=7.5 Hz), 2.24–2.19 (1H, m), 1.81–1.71 (2H, m), 1.37–1.26 (2H, m), 0.87 (3H, t, J=7.3 Hz).

Step 3. 2-[4-(2-Butyl-6-chloro-1H-benzimidazol-1-yl)phenyl]ethyl azide

The title compound was prepared according to the procedure described in step 4 of Example from 2-[4-(2-butyl-6-chloro-1H-benzimidazol-1-yl)phenyl]ethanol (step 2).

¹H-NMR (CDCl₃) δ 7.66 (1H, d, J=8.6 Hz), 7.45 (2H, d, J=8.3 Hz), 7.29 (2H, d, J=8.3 Hz), 7.22 (1H, dd, J=8.6, 2.0 Hz), 7.07 (1H, d, J=2.0 Hz), 3.62 (2H, t, J=7.0 Hz), 3.02 (2H, d, J=7.0 Hz), 2.74 (2H, t, J=7.5 Hz), 1.80–1.70 (2H, m), 1.40–1.26 (2H, m), 0.86 (2H, t, J=7.3 Hz)

Step 3. 2-[4-(2-Butyl-6-chloro-1H-benzimidazol-1-yl)phenyl]ethylamine

The title compound was prepared according to the procedure described in step 9 of Example 1 from 2-[4-(2-butyl-6-chloro-1H-benzimidazol-1-yl)phenyl]ethyl azide (step 2).

¹H-NMR (CDCl₃) δ 7.66 (1H, d, J=8.6 Hz), 7.43 (2H, d, J=8.2 Hz), 7.27 (2H, d, J=8.2 Hz), 7.21 (1H, dd, J=8.6, 2.0 Hz), 7.08 (1H, d, J=2.0 Hz), 3.11 (2H, t, J=7.1 Hz), 2.91 (2H, t, J=7.1 Hz), 2.74 (2H, t, J=7.4 Hz), 1.81–1.70 (2H, m), 1.41–1.27 (2H, m), 0.86 (3H, t, J=7.4 Hz)

Step 4. 2-Butyl-6-chloro-1-(4-{2-[({[(4-methylphenyl)sulfonyl]amino}carbonyl)amino]ethyl}phenyl)-1H-benzimidazole The title compound was prepared according to the procedure described in step 10 of Example 1 from 2-[4-(2-butyl-6-chloro-1H-benzimidazol-1-yl)phenyl]ethylamine (step 3).

¹H-NMR (CDCl₃) δ 7.75 (2H, d, J=8.4 Hz), 7.66 (1H, d, J=8.2 Hz), 7.38 (2H, d, J=8.4 Hz), 7.30–7.20 (6H, m), 7.05 (1H, d, J=2.0 Hz), 6.77–6.72 (1H, m), 3.61–3.55 (2H, m), 2.96–2.92 (2H, m), 2.74 (2H, t, J=7.5 Hz), 2.39 (3H, s), 1.78–1.67 (2H, m), 1.35–1.26 (2H, m), 0.84 (3H, t, J=7.3 Hz).

Example 63

2-BUTYL-6-CHLORO-1-(4-{2-[({[(4-METHYLPHENYL)SULFONYL]AMINO}CARBONYL)AMINO]BUTYL}PHENYL)-1H-BENZIMIDAZOLE, SODIUM SALT

The title compound was prepared according to the procedure described in Example 2 from 2-butyl-6-chloro-1-(4-{2-[({[(4-methylphenyl)sulfonyl]amino}carbonyl)amino]ethyl}phenyl)-1H-benzimidazole (Example 62).

mp 137–145° C.; ¹H-NMR (DMSO-d₆) δ 7.65–7.63 (1H, m), 7.59 (2H, d, J=7.8 Hz), 7.38 (4H, s), 7.23–7.20 (1H, m), 7.12 (2H, d, J=7.8 Hz), 7.04 (1H, s), 3.15 (2H, m), 2.72–2.67 (4H, m), 2.26 (3H, s), 1.66–1.61 (2H, m), 1.29–1.22 (2H, m), 0.79 (3H, t, J=7.5 Hz); IR (KBr) α$_{max}$ 1603, 1520, 1458, 1396, 1130, 1086 cm⁻¹.

Example 64

7-CHLORO-2-ETHYL-3-(4-{2-[({[(4-METHYLPHENYL)SULFONYL]AMINO}CARBONYL)AMINO]ETHYL}PHENYL)-1H-BENZIMIDAZOLE

Step 1. 2-[4-(2-Chloro-6-nitroanilino)phenyl]ethanol

The title compound was prepared according to the procedure described in step 3 of Example 1 from 2,3-dichloronitrobenzene and 4-aminophenylethyl alcohol.

¹H-NMR (CDCl₃) δ 8.11 (1H, br.s), 8.00 (1H, dd, J=1.5 Hz, 8.5 Hz), 7.61 (1H, dd, J=1.5 Hz, 7.9 Hz), 7.12 (2H, d, J=8.4 Hz), 7.03 (1H, dd, J=7.9 Hz, 8.5 Hz), 6.80 (2H, d, J=8.4 Hz), 3.82 (2H, t, J=6.6 Hz), 2.81 (2H, d, J=6.6 Hz).

Step 2. 2-[4-(2-Amino-6-chloroanilino)phenyl]ethanol

The title compound was prepared according to the procedure described in step 2 of Example 28 from 2-[4-(2-cloro-6-nitroanilino)phenyl]ethanol (step 1).

¹H-NMR (CDCl₃) δ 7.04 (2H, d, J=7.8 Hz), 6.97 (1H, dd, J=7.9 Hz, 8.0 Hz), 6.82 (1H, dd, J=1.5 Hz, 7.9 Hz), 6.66 (1H, dd, J=1.5 Hz, 8.0 Hz), 6.59 (2H, d, J=7.8 Hz), 5.36 (1H, br.s), 3.94 (2H, br.s), 3.78 (2H, t, J=6.6 Hz), 2.75 (2H, d, J=6.6 Hz).

Step 3. 2-[4-(7-Chloro-2-ethyl-1H-benzimidazol-1-yl)phenyl]ethyl propionate

The title compound was prepared according to the procedure described in step 5 of Example 1 from 2-[4-(2-amino-6-chloroanilino)phenyl]ethanol (step 2) and propionyl chloride.

TLC Rf=0.6 (hexane: ethyl acetate=1:1).

Step 4. 2-[4-(7-Chloro-2-ethyl-1H-benzimidazol-1-yl)phenyl]ethanol

The title compound was prepared according to the procedure described in step 6 of Example 1 from 2-[4-(2-amino-6-chloroanilino)phenyl]ethyl propionate (step 3).

¹H-NMR (CDCl₃) δ 7.68 (1H, dd, J=1.9 Hz, 7.0 Hz), 7.39 (2H, d, J=8.2 Hz), 7.28 (2H, d, J=8.2 Hz), 7.11–7.20 (2H, m), 3.97 (2H, t, J=6.6 Hz), 3.01 (2H, t, J=6.6 Hz), 2.65 (2H, q, J=7.6 Hz), 1.32 (3H, t, J=7.6 Hz).

Step 5. 7-Chloro-1-[4-(2-chloroethyl)phenyl]-2-ethyl-1H-benzimidazole

The title compound was prepared according to the procedure described in step 7 of Example 1 from 2-[4-(7-chloro-2-ethyl-1H-benzimidazol-1-yl)phenyl]ethanol (step 4).

¹H-NMR (CDCl₃) δ 7.69 (1H, dd, J=2.2 Hz, 7.1 Hz), 7.37 (2H, d, J=8.2 Hz), 7.31 (2H, d, J=8.2 Hz), 7.11–7.17 (2H, m), 3.81 (2H, t, J=7.3 Hz), 3.19 (2H, t, J=7.3 Hz), 2.65 (2H, q, J=7.5 Hz), 1.33 (3H, t, J=7.5 Hz).

Step 6. 2-[4-(7-Chloro-2-ethyl-1H-benzimidazol-1-yl)phenyl]ethyl azide

The title compound was prepared according to the procedure described in step 8 of Example 1 from 7-chloro-1-[4-(2-chloroethyl)phenyl]-2-ethyl-1H-benzimidazole (step 5).

¹H-NMR (CDCl₃) δ 7.69 (1H, dd, J=1.8 Hz, 7.4 Hz), 7.38 (2H, d, J=8.2 Hz), 7.34 (2H, d, J=8.2 Hz), 7.11–7.28 (2H, m), 3.60 (2H, t, J=7.0 Hz), 3.02 (2H, t, J=7.0 Hz), 2.64 (2H, q, J=7.6 Hz), 1.32 (3H, t, J=7.6 Hz).

Step 7. 2-[4-(7-Chloro-2-ethyl-1H-benzimidazol-1-yl)Phenyl]ethylamine

The title compound was prepared according to the procedure described in step 7 of Example 37 from 2-[4-(7-chloro-2-ethyl-1H-benzimidazol-1-yl)phenyl]ethyl azide (step 6).

¹H-NMR (CDCl₃) δ 7.69 (1H, d, J=7.9 Hz), 7.35 (2H, d, J=8.3 Hz), 7.28 (2H, d, J=8.3 Hz), 7.11–7.19 (2H, m), 3.06 (2H, t, J=6.8 Hz), 2.88 (2H, t, J=6.8 Hz), 2.65 (2H, q, J=7.5 Hz), 1.33 (3H, t, J=7.5 Hz).

Step 8. 7-Chloro-2-ethyl-1-(4-{2-[({[(4-methylphenyl)sulfonyl]amino}carbonyl)amino]ethyl}phenyl)-1H-benzimidazole The title compound was prepared according to the procedure described in step 10 of Example 1 from 2-[4-(7-chloro-2-ethyl-1H-benzimidazol-1-yl)phenyl]ethylamine (step 7).

MS (ESI) m/z 498 (M+H)⁺; ¹H-NMR (CDCl₃) δ 7.74 (2H, d, J=8.4 Hz), 7.69 (1H, dd, J=1.9 Hz, 7.4 Hz), 7.29–7.32 (6H, m), 7.11–7.20 (2H, m), 6.72 (1H, br.s), 3.59 (2H, t, J=6.9 Hz), 2.93 (2H, t, J=6.9 Hz), 2.64 (2H, q, J=7.6 Hz), 2.42 (3H, s), 1.31 (3H, t, J=7.6 Hz).

Example 65

7-CHLORO-2-ETHYL-3-(4-{2-[({[(4-METHYLPHENYL)SULFONYL]AMINO}CARBONYL)AMINO]ETHYL}PHENYL)-1H-BENZIMIDAZOLE, SODIUM SALT

The title compound was prepared according to the procedure described in Example 2 from 7-chloro-2-ethyl-1-(4-{2-[({[(4-methylphenyl)sulfonyl]amino}carbonyl)amino]ethyl}phenyl)-1H-benzimidazole (Example 64).

¹H-NMR (DMSO-d₆) δ 7.62–7.64 (3H, m), 7.31–7.39 (4H, m), 7.14–7.20 (4H, m), 6.00 (1H, br.s), 3.17 (2H, br.s), 2.75 (2H, br.s), 2.55 (2H, q, J=7.8 Hz), 2.29 (3H, s), 1.21 (3H, t, J=7.8 Hz); IR (KBr) α$_{max}$ 3380, 2891, 1605, 1520, 1425, 1285, 1126, 1075, 798 cm⁻.

Example 66

5-FLUORO-2-ETHYL-3-(4-{2-[({[(4-METHYLPHENYL)SULFONYL]AMINO}CARBONYL)AMINO]ETHYL}PHENYL)-1H-BENZIMIDAZOLE

Step 1. 2-[4-(4-Fluoro-2-nitroanilino)phenyl]ethanol

The title compound was prepared according to the procedure described in step 3 of Example 1 from 2,5-difluoronitrobenzene and 4-aminophenylethyl alcohol.

$^1$H-NMR (CDCl$_3$) δ 9.32 (1H, s), 7.88–7.93 (1H, m), 7.11–7.30 (5H, m), 3.90 (2H, t, J=6.2 Hz), 2.90 (2H, t, J=6.2 Hz).

Step 2. 2-[4-(2-Amino-4-fluoroanilino)phenyl]ethanol

The title compound was prepared according to the procedure described in step 2 of Example 26 from 2-[4-(4-fluoro-2-nitroanilino)phenyl]ethanol (step 1).

$^1$H-NMR (CDCl$_3$) δ 6.98–7.06 (3H, m), 6.60 (2H, d, J=8.2 Hz), 6.49 (1H, dd, J=2.8 Hz, 12.8 Hz), 6.41 (1H, dd, J=2.8 Hz, 8.4 Hz), 4.99 (1H, br.s), 3.94 (2H, br.s), 3.79 (2H, t, J=6.4 Hz).

Step 3. 2-[4-(2-Ethyl-5-fluoro-1H-benzimidazol-1-yl)phenyl]ethyl propionate

The title compound was prepared according to the procedure described in step 5 of Example 1 from 2-[4-(2-amino-4-fluoroanilino)phenyl]ethanol (step 2) and propionyl chloride.

MS (EI) m/z 340 (M$^+$).

Step 4. 2-[4-(2-Ethyl-5-fluoro-1H-benzimidazol-1-yl)phenyl]ethanol

The title compound was prepared according to the procedure described in step 6 of Example 1 from 2-[4-(2-amino-4-fluoroanilino)phenyl]ethyl propionate (step 3).

$^1$H-NMR (CDCl$_3$) δ 7.40–7.47 (3H, m), 7.28 (2H, d, J=8.0 Hz), 6.88–7.02 (2H, m), 3.98 (2H, t, J=6.3 Hz), 3.01 (2H, t, J=6.3 Hz), 2.78 (2H, q, J=7.5 Hz), 1.34 (3H, t, J=7.5 Hz).

Step 5. 1-[4-(2-Chloroethyl)phenyl]-2-ethyl-5-fluoro-1H-benzimidazole

The title compound was prepared according to the procedure described in step 7 of Example 1 from 2-[4-(2-ethyl-5-fluoro-1H-benzimidazol-1-yl)phenyl]ethanol (step 4).

$^1$H-NMR (CDCl$_3$) δ 7.42–7.46 (3H, m), 7.31 (2H, d, J=8.1 Hz), 6.89–7.02 (2H, m), 3.81 (2H, t, J=7.1 Hz), 3.19 (2H, t, J=7.1 Hz), 2.78 (2H, q, J=7.6 Hz), 1.35 (3H, t, J=7.6 Hz).

Step 6. 2-[4-(2-Ethyl-5-fluoro-1H-benzimidazol-1-yl)phenyl]ethyl azide

The title compound was prepared according to the procedure described in step 8 of Example 1 from 1-[4-(2-chloroethyl)phenyl]-2-ethyl-5-fluoro-1H-benzimidazole (step 5).

$^1$H-NMR (CDCl$_3$) δ 7.43–7.45 (3H, m), 7.31 (2H, d, J=8.2 Hz), 6.89–7.02 (2H, m), 3.62 (2H, t, J=7.0 Hz), 3.01 (2H, t, J=7.0 Hz), 2.77 (2H, q, J=7.5 Hz), 1.34 (3H, t, J=7.5 Hz).

Step 7. 2-[4-(2-Ethyl-5-fluoro-1H-benzimidazol-1-yl)phenyl]ethylamine

The title compound was prepared according to the procedure described in step 9 of Example 1 from 2-[4-(2-ethyl-5-fluoro-1H-benzimidazol-1-yl)phenyl]ethyl azide (step 6).

$^1$H-NMR (CDCl$_3$) δ 7.40–7.46 (3H, m), 7.27–7.29 (2H, m), 6.87–6.99 (2H, m), 3.06 (2H, t, J=7.1 Hz), 2.87 (2H, t, J=7.1 Hz), 2.78 (2H, q, J=7.5 Hz), 1.35 (3H, t, J=7.5 Hz).

Step 8. 5-Fluoro-2-ethyl-3-(4-{2-[({[(4-methylphenyl)sulfonyl]amino}carbonyl)amino]ethyl}phenyl)-1H-benzimidazole The title compound was prepared according to the procedure described in step 10 of Example 1 from 2-[4-(2-ethyl-5-fluoro-1H-benzimidazol-1-yl)phenyl]ethylamine (step 7).

MS (ESI) m/z 481 (M+H)$^+$; $^1$H-NMR (CDCl$_3$) δ 7.73 (2H, d, J=8.2 Hz), 7.35–7.45 (3H, m), 7.24–7.29 (4H, m), 6.87–7.00 (2H, m), 6.73 (1H, br.s), 3.57 (2H, t, J=7.0 Hz), 2.77 (2H, q, J=7.6 Hz), 2.39 (3H, s), 1.31 (3H, t, J=7.6 Hz).

Example 67

5-FLUORO-2-ETHYL-3-(4-{2-[({[(4-METHYLPHENYL)SULFONYL]AMINO}CARBONYL)AMINO]ETHYL}PHENYL)-1H-BENZIMIDAZOLE, SODIUM SALT

The title compound was prepared according to the procedure described in Example 2 from 5-fluoro-2-ethyl-3-(4-{2-[({[(4-methylphenyl)sulfonyl]amino}carbonyl)amino]ethyl}phenyl)-1H-benzimidazole (Example 66).

mp 135–146° C.; MS (ESI) m/z 481 (M+H)$^+$; $^1$H-NMR (DMSO-d$_6$) δ 7.62 (2H, d, J=8.1 Hz), 7.39–7.48 (5H, m), 6.97–7.15 (4H, m), 5.92 (1H, br.s), 2.67–2.76 (4H, m), 2.51 (2H, d, br.s), 2.27 (3H, s), 1.23 (3H, t, J=7.6Hz).

Example 68

2-BUTYL-6-FLUORO-1-{2-[({[(4-METHYLPHENYL)SULFONYL]AMINO}CARBONYL)AMINO]ETHYL}-1H-BENZIMIDAZOLE

Step 1. 2-[4-(5-Fluoro-2-nitroanilino)phenyl]ethanol

The title compound was prepared according to the procedure described in step 3 of Example 1 from 2,4-difluoronitrobenzene and 4-aminophenylethyl alcohol.

$^1$H-NMR (CDCl$_3$) δ 9.61 (1H, br.s), 8.26 (1H, dd, J=6.1, 9.5 Hz), 7.32 (2H, d, J=8.2 Hz), 7.22 (2H, d, J=8.3 Hz), 6.78 (1H, dd, J=2.6, 11.3 Hz), 6.47 (1H, ddd, J=2.2, 7.2, 9.7 Hz), 3.91 (2H, dt, J=6.2, 6.2 Hz), 2.91 (2H, t, J=6.4 Hz), 1.52 (1H, t, J=5,7 Hz).

Step 2. 2-[4-(2-Amino-5-fluoroanilino)phenyl]ethanol

The title compound was prepared according to the procedure described in step 2 of Example 28 from 2-[4-(5-fluoro-2-nitroanilino)phenyl]ethanol (step 1).

$^1$H-NMR (CDCl$_3$) δ 7.12 (2H, d, J=8.4 Hz), 6.87 (1H, dd, J=2.7, 10.1 Hz), 6.83 (2H, d, J=8.4 Hz), 6.72 (1H, dd, J=5,7, 8.6 Hz), 6.63 (1H, ddd, J=2.7, 8.4, 8.4 Hz), 5.30 (1H, s), 3.83 (2H, t, J=6.4 Hz), 2.80 (2H, t, J=6.4 Hz).

Step 3. 2-[4-(2-butyl-6-fluoro-1H-benzimidazol-1-yl)phenyl]ethyl Pentanoate

The title compound was prepared according to the procedure described in step 5 of Example 1 from 2-[4-(2-amino-5-fluoroanilino)phenyl]ethanol (step 2) and pentanoyl chloride.

$^1$H-NMR (CDCl$_3$) δ 7.67 (1H, dd, J=4.8, 8.8 Hz), 7.44 (2H, d, J=8.3 Hz), 7.28 (2H, d, J=8.1 Hz), 7.04–6.95 (1H, m), 6.76 (1H, dd, J=2.6, 8.8 Hz), 4.38 (2H, t, J=6.8 Hz), 3.07 (2H, t, J=6.8 Hz), 2.74 (2H, t, J=7.5 Hz), 2.33 (2H, t, J=7.7 Hz), 1.81–1.55 (4H, m), 1.42–1.25 (4H, m), 6.91 (3H, t, J=7.3 Hz), 0.87 (3H, t, J=7.3 Hz).

Step 4. 2-[4-(2-butyl-6-fluoro-1H-benzimidazol-1-yl)phenyl]ethanol

The title compound was prepared according to the procedure described in step 6 of Example 1 from 2-[4-(2-butyl-6-fluoro-1H-benzimidazol-1-yl)phenyl]ethyl pentanoate (step 3).

$^1$H-NMR (CDCl$_3$) δ 7.67 (1H, dd, J=4.8, 8.8 Hz), 7.46 (2H, d, J=8.2 Hz), 7.28 (2H, d, J=8.3 Hz), 6.99 (1H, ddd, J=2.4, 9.0, 9.5 Hz), 4.10–3.85 (2H, m), 3.01 (2H, t, J=6.4 Hz), 2.74 (2H, t, J=7.7 Hz), 1.84–1.69 (2H, m), 1.41–1.27 (2H, m), 0.87 (3H, t, J=7.3 Hz).

Step 5. 2-[4-(2-Butyl-6-fluoro-1H-benzimidazol-1-yl)phenyl]ethyl azide

The title compound was prepared according to the procedure described in step 5 Example 26 from 2-[4-(2-butyl-6-fluoro-1H-benzimidazol-1-yl)phenyl]ethanol (step 4).

MS (EI) m/z 337 (M$^+$); $^1$H-NMR (CDCl$_3$) δ 7.68 (1H, dd, J=4.8, 8.8 Hz), 7.45 (2H, d, J=8.1 Hz), 7.30 (2H, d, J=8.1 Hz), 7.04–6.94 (1H, m), 6.77 (1H, dd, J=2.4, 8.6 Hz), 3.62 (2H, t, J=7.0 Hz), 3.02 (2H, t, J=6.8 Hz), 2.74 (2H, t, J=7.7 Hz), 1.86–1.69 (2H, m), 1.41–1.2 (2H, m), 0.86 (3H, t, J=7.3 Hz).

Step 6. 2-[4-(2-Butyl-6-fluoro-1H-benzimidazol-1-yl)phenyl]ethylamine

The title compound was prepared according to the procedure described in step 7 of Example 37 from 2-[4-(2-butyl-6-fluoro-1H-benzimidazol-1-yl)phenyl]ethyl azide (step 5).

$^1$H-NMR (CDCl$_3$) δ 7.67 (1H, dd, J=4.8, 8.8 Hz), 7.42 (2H, d, J=8.1 Hz), 7.27 (2H, d, J=8.2 Hz), 7.05–6.95 (1H, m), 6.78 (1H, dd, J=2.6, 8.6 Hz), 3.08 (2H, t, J=7.1 Hz), 2.88 (2H, t, J=6.8 Hz), 2.75 (2H, t, J=7.5 Hz), 1.82–1.69 (2H, m), 1.41–1.24 (2H, m), 0.87 (3H, t, J=7.3 Hz).

Step 7. 2-Butyl-6-fluoro-3-(4-{2-[({[(4-methylphenyl)sulfonyl]amino}carbonyl)amino]ethyl}phenyl)-1H-benzimidazole The title compound was prepared according to the procedure described in step 10 of Example 1 from 2-[4-(2-butyl-6-fluoro-1H-benzimidazol-1-yl)phenyl]ethylamine (step 6).

$^1$H-NMR (CDCl$_3$) δ 7.73 (2H, d, J=8.4 Hz), 7.68 (1H, dd, J=4.6, 8.8 Hz), 7.38 (2H, d, J=8.4 Hz), 7.32–7.24 (4H, m), 7.00 (1H, ddd, J=2.4, 8.8, 11.2 Hz), 6.75 (1H, dd, J=2.4, 8.6 Hz), 3.64–3.54 (2H, m), 2.94 (2H, t, J=7.0 Hz), 2.74 (2H, d, J=7.5 Hz), 1.80–1.65 (2H, m), 1.40–1.20 (2H, m), 0.84 (3H, t, J=7.3 Hz).

Example 69

2-BUTYL-6-FLUORO-1-{2-[({[(4-METHYLPHENYL)SULFONYL]AMINO}CARBONYL)AMINO]ETHYL}-1H-BENZIMIDAZOLE, SODIUM SALT

The title compound was prepared according to the procedure described in Example 2 from 2-butyl-6-fluoro-3-(4-{2-[({[(4-methylphenyl)sulfonyl]amino}carbonyl)amino]ethyl}phenyl)benzimidazole (Example 69).

$^1$H-NMR (DMSO-d$_6$) δ 7.70–7.57 (3H, m), 7.39 (4H, br), 7.14 (2H, d, J=8.0 Hz), 7.11–7.02 (1H, m), 8.85 (1H, dd, J=2.4, 9.2 Hz), 3.48–3.34 (2H, m), 3.17 (2H, br), 2.80–2.65 (4H, m), 2.28 (3H, s), 1.72–1.55 (2H, m), 1.35–1.20 (2H, m), 0.80 (3H, t, J=7.1Hz); IR (KBr) α$_{max}$ 3387, 2872, 1601, 1516, 1479, 1400, 1130, 1086 cm$^{-1}$.

Example 70

2-ETHYL-6-FLUORO-1-(4-{2-[({[(4-METHYLPHENYL)SULFONYL]AMINO}CARBONYL)AMINO]ETHYL}PHENYL)-1H-BENZIMIDAZOLE

Step 1. 2-[4-(6-Fluoro-2-ethyl-1H-benzimidazol-1-yl)phenyl]ethyl propionate

The title compound was prepared according to the procedure described in step 5 of Example 1 from 2-[4-(2-amino-5-fluoroanilino)phenyl]ethanol (step 2 of Example 68) and propionyl chloride.

MS (EI) m/z 340 (M$^+$); $^1$H-NMR (CDCl$_3$) δ 7.67 (1H, dd, J=4.8, 8.8 Hz), 7.43 (2H, d, J=8.4 Hz), 7.28 (2H, d, J=8.4 Hz), 6.99 (1H, ddd, J=2.5, 8.8, 9.5 Hz), 6.77 (1H, dd, J=2.5, 8.8 Hz), 4.38 (2H, t, J=6.6 Hz), 3.07 (2H, t, J=6.6 Hz), 2.79 (2H, q, J=7.4 Hz), 2.35 (2H, q, J=7.4 Hz), 1.35 (3H, t, J=7.4 Hz), 1.14 (3H, t, J=7.4 Hz).

Step 2. 2-[4-(6-fluoro-2-ethyl-1H-benzimidazol-1-yl)phenyl]ethanol

The title compound was prepared according to the procedure described in step 6 of Example 1 from 2-[4-(6-fluoro-2-ethyl-1H-benzimidazol-1-yl)phenyl]ethyl propionate (step 1).

$^1$H-NMR (CDCl$_3$) δ 7.67 (1H, dd, J=4.8, 8.8 Hz), 7.45 (2H, d, J=8.4 Hz), 7.29 (2H, d, J=8.4 Hz), 6.99 (1H, ddd, J=2.5, 8.8, 9.5 Hz), 6.78 (1H, dd, J=2.5, 8.8 Hz), 3.99 (2H, t, J=6.6 Hz), 3.00 (2H, t, J=6.6 Hz), 2.77 (2H, q, J=7.5 Hz), 1.35 (3H, t, J=7.5 Hz).

Step 3. 6-fluoro-1-[4-(2-chloroethyl)phenyl]-2-ethyl-1H-benzimidazole

The title compound was prepared according to the procedure described in step 7 Example 1 from 2-[4-(6-fluoro-2-ethyl-1H-benzimidazol-1-yl)phenyl]ethanol (step 2).

MS (EI) m/z 302 (M$^+$).

Step 4. 2-[4-(6-Fluoro-2-ethyl-1H-benzimidazol-1-yl)phenyl]ethyl azide

The title compound was prepared according to the procedure described in step 8 Example 1 from 6-fluoro-1-[4-(2-chloroethyl)phenyl]-2-ethyl-1H-benzimidazole (step 3).

MS (EI) m/z 309 (M$^+$); $^1$H-NMR (CDCl$_3$) δ 7.68 (1H, dd, J=4.8, 8.8 Hz), 7.44 (2H, d, J=8.3 Hz), 7.31 (2H, d, J=8.3 Hz), 6.99 (1H, ddd, J=2.5, 8.8, 9.6 Hz), 6.77 (1H, dd, J=2.5, 8.8 Hz), 3.62 (2H, t, J=6.9 Hz), 3.02 (2H, t, J=6.9 Hz), 2.77 (2H, q, J=7.4 Hz), 1.34 (3H, t, J=7.4 Hz)

Step 5. 2-[4-(6-Fluoro-2-ethyl-1H-benzimidazol-1-yl)phenyl]ethylamine

The title compound was prepared according to the procedure described in step 7 of Example 37 from 2-[4-(6-fluoro-2-ethyl-1H-benzimidazol-1-yl)phenyl]ethyl azide (step 4).

$^1$H-NMR (CDCl$_3$) δ 7.68 (1H, dd, J=4.8, 8.8 Hz), 7.43 (2H, d, J=8.2 Hz), 7.28 (2H, d, J=8.2 Hz), 6.98 (1H, ddd, J=2.4, 8.8, 8.8 Hz), 6.82 (1H, dd, J=2.4, 8.8 Hz), 3.37 (2H, br.s), 3.18 (2H, t, J=7.1 Hz), 3.01 (2H, t, J=7.1 Hz), 2.76 (2H, q, J=7.5 Hz), 1.33 (3H, t, J=7.5 Hz).

Step 6. 2-Ethyl-6-fluoro-1-(4-{2-[({[(4-methylphenyl)sulfonyl]amino}carbonyl)amino]ethyl}phenyl)-1H-benzimidazole The title compound was prepared according to the procedure described in step 10 of Example 1 from 2-[4-(6-fluoro-2-ethyl-1H-benzimidazol-1-yl)phenyl]ethylamine (step 5).

$^1$H-NMR (CDCl$_3$) δ 7.73 (2H, d, J=8.4 Hz), 7.68 (1H, dd, J=8.7, 4.9 Hz), 7.37 (2H, d, J=8.4 Hz), 7.32–7.23 (4H, m), 7.00 (1H, ddd, J=9.5, 8.7, 2.5 Hz), 6.79–6.69 (2H, m), 3.63–3.53 (2H, m), 2.94 (2H, t, J=7.5 Hz), 2.76 (2H, q, J=7.5 Hz), 2.40 (3H, s), 1.32 (3H, t, J=7.5 Hz).

Example 71

5-METHOXY-2-ETHYL-3-(4-{2-[({[(4-METHYLPHENYL)SULFONYL]AMINO}CARBONYL)AMINO]ETHYL}PHENYL)-1H-BENZIMIDAZOLE

Step 1. 2-[4-(4-Methoxy-2-nitroanilino)phenyl]ethanol

The title compound was prepared according to the procedure described in step 3 of Example 1 from 2-chloro-5-methoxynitrobenzene and 4-aminophenylethyl alcohol.

$^1$H-NMR (CDCl$_3$) δ 9.33 (1H, br.s), 7.63 (1H, d, J=3.0 Hz), 7.17–7.27 (5H, m), 7.04–7.08 (1H, m), 3.88 (2H, br.s), 3.82 (3H, s), 2.88 (2H, t, J=6.6 Hz).

Step 2. 2-[4-(2-Amino-4-methoxyanilino)phenyl]ethanol

The title compound was prepared according to the procedure described in step 2 of Example 26 from 2-[4-(4-methoxy-2-nitroanilino)phenyl]ethanol (step 1).

$^1$H-NMR (CDCl$_3$) δ 7.03 (2H, d, J=8.6 Hz), 6.98 (1H, d, J=8.4 Hz), 6.59 (2H, d, J=8.6 Hz), 6.28–6.36 (2H, m), 3.77–3.85 (5H, m), 2.76 (2H, t, J=6.6 Hz).

Step 3. 2-[4-(2-Ethyl-5-methoxy-1H-benzimidazol-1-yl)phenyl]ethyl propionate

The title compound was prepared according to the procedure described in step 5 of Example 1 from 2-[4-(2-amino-4-methoxyanilino)phenyl]ethanol (step 2).

$^1$H-NMR (CDCl$_3$) δ 7.40 (2H, d, J=8.0 Hz), 7.12–7.29 (3H, m), 6.97 (1H, d, J=8.8 Hz), 6.82 (1H, dd, J=2.4 Hz, 8.8 Hz), 4.37 (2H, t, J=6.7 Hz), 3.86 (3H, s), 3.05 (2H, t, J=6.7 Hz), 2.77 (2H, q, J=7.5 Hz), 2.36 (2H, q, J=7.5 Hz), 1.36 (3H, t, J=7.5 Hz), 1.14 (3H, t, J=7.5 Hz).

Step 4. 2-[4-(2-Ethyl-5-methoxy-1H-benzimidazol-1-yl)phenyl]ethanol

The title compound was prepared according to the procedure described in step 6 of Example 1 from 2-[4-(2-ethyl-5-methoxy-1H-benzimidazol-1-yl)phenyl]ethyl propionate (step 3).

$^1$H-NMR (CDCl$_3$) δ 7.43 (2H, d, J=8.2 Hz), 7.27–7.30 (3H, m), 6.98 (1H, d, J=8.8 Hz), 6.82 (1H, dd, J=2.3 Hz, 8.8 Hz), 3.98 (2H, t, J=6.5 Hz), 3.86 (3H, s), 2.99 (2H, t, J=6.5 Hz), 2.77 (2H, q, J=7.6 Hz), 1.33 (3H, t, J=7.6 Hz).

Step 5. 1-[4-(2-Chloroethyl)phenyl]-2-ethyl-5-methoxy-1H-benzimidazole

The title compound was prepared according to the procedure described in step 7 of Example 1 from 2-[4-(2-ethyl-5-methoxy-1H-benzimidazol-1-yl)phenyl]ethanol (step 4).

$^1$H-NMR (CDCl$_3$) δ 7.42 (2H, d, J=8.2 Hz), 7.26–7.33 (3H, m), 6.99 (1H, d, J=8.8 Hz), 6.82 (1H, dd, J=2.5 Hz, 8.8 Hz), 3.86 (3H, s), 3.81 (2H, t, J=7.2 Hz), 3.18 (2H, t, J=7.2 Hz), 2.78 (2H, q, J=7.6 Hz), 1.34 (3H, t, J=7.6 Hz).

Step 6. 1-[4-(2-Azidoethyl)phenyl]-2-ethyl-1H-benzimidazol-5-yl methyl ether

The title compound was prepared according to the procedure described in step 8 of Example 1 from 1-[4-(2-chloroethyl)phenyl]-2-ethyl-5-methoxy-1H-benzimidazole (step 5).

$^1$H-NMR (CDCl$_3$) δ 7.42 (2H, d, J=8.4 Hz), 7.27–7.32 (3H, m), 6.98 (1H, d, J=8.8 Hz), 6.82 (1H, dd, J=2.3 Hz, 8.8 Hz), 3.87 (3H, s), 3.61 (2H, t, J=6.9 Hz), 3.01 (2H, t, J=6.9 Hz), 2.76 (2H, q, J=7.7 Hz), 1.34 (3H, t, J=7.7 Hz).

Step 7. 2-[4-(2-Ethyl-5-methoxy-1H-benzimidazol-1-yl)phenyl]ethylamine

The title compound was prepared according to the procedure described in step 9 of Example 1 from 1-[4-(2-azidoethyl)phenyl]-2-ethyl-1H-benzimidazol-5-yl methyl ether (step 6).

$^1$H-NMR (CDCl$_3$) δ 7.39 (2H, d, J=8.2 Hz), 7.26–7.30 (3H, m), 6.99 (1H, d, J=8.7 Hz), 6.82 (1H, dd, J=2.3 Hz, 8.7 Hz), 3.86 (3H, s), 3.07 (2H, t, J=6.9 Hz), 2.84 (2H, t, J=2.9 Hz), 2.77 (2H, q, J=7.6 Hz), 1.34 (3H, t, J=7.6 Hz).

Step 8. 5-Methoxy-2-Ethyl-3-(4-{2-[({[(4-methylphenyl)sulfonyl]amino}carbonyl)amino]ethyl}phenyl)-1H-benzimidazole The title compound was prepared according to the procedure described in step 10 of Example 1 from 2-[4-(2-ethyl-5-methoxy-1H-benzimidazol-1-yl)phenyl]ethylamine (step 7).

$^1$H-NMR (CDCl$_3$) δ 7.74 (2H, d, J=8.2 Hz), 7.23–7.34 (7H, m), 6.97 (1H, d, J=8.7 Hz), 6.82 (1H, dd, J=1.8 Hz, 8.7 Hz), 6.67 (1H, br.s), 3.86 (3H, s), 3.57 (2H, t, J=6.4 Hz), 2.92 (2H, t, 6.4 Hz), 2.75 (2H, q, J=7.6 Hz), 2.40 (3H, s), 1.31 (3H, t, J=7.6 Hz).

Example 72

5-METHOXY-2-ETHYL-3-(4-{2-[({[(4-METHYLPHENYL)SULFONYL]AMINO}CARBONYL)AMINO]ETHYL}PHENYL)-1H-BENZIMIDAZOLE, SODIUM SALT

The title compound was prepared according to the procedure described in Example 2 from 5-methoxy-2-ethyl-3-(4-{2-[({[(4-methylphenyl)sulfonyl]amino}carbonyl)amino]ethyl}phenyl)-1H-benzimidazole (Example 72).

mp 163–175° C.; $^1$H-NMR (DMSO-d$_6$) δ 7.60 (2H, d, J=7.5 Hz), 7.34–7.41 (4H, m), 7.12–7.18 (3H, m), 6.97 (1H, d, J=8.7 Hz), 6.78 (1H, d, J=8.7 Hz), 3.78 (3H, s), 2.66–2.76 (4H, m), 2.50 (2H, br.s), 2.78 (3H, s), 1.22 (3H, t, J=7.6 Hz); IR (KBr) α$_{max}$ 3363, 2833, 1596, 1404, 1128, 1085, 1026, 950 cm$^{-1}$.

Example 73

2-[4-(2-ETHYL-5-METHOXY-1H-BENZIMIDAZOLE-1-YL)PHENYL]ETHYL(4-METHYLPHENYL)SULFONYLCARBAMATE

The title compound was prepared according to the procedure described in Example 3 from 2-[4-(2-ethyl-5-methoxy-1H-benzimidazol-1-yl)phenyl]ethanol (step 4 of Example 71)

mp 95–98° C.; MS (ESI) m/z 494 (M+H)$^+$; $^1$H-NMR (CDCl$_3$) δ 7.93 (2H, d, J=8.2 Hz), 7.23–7.30 (3H, m), 7.16 (2H, d, J=8.2 Hz), 7.06 (2H, d, J=8.3 Hz), 6.92 (1H, d, J=8.8 Hz), 6.81 (1H, dd, J=2.2 Hz, 8.6 Hz), 4.33 (2H, t, J=6.3 Hz), 3.84 (3H, s), 2.93 (2H, t, J=6,3 Hz), 2.68 (2H, q, J=7.5 Hz), 2.37 (3H, s), 1.22 (3H, t, J=7.5 Hz); IR (KBr) α$_{max}$ 1743, 1596, 1517, 1487, 1444, 1278, 1159, 1074, 813 cm$^{-1}$.

Example 74

2-ETHYL-6-MRTHOXY-1-(4-{2-[({[(4-METHYLPHENYL)SULFONYL]AMINO}CARBONYL)AMINO]ETHYL}PHENYL)-1H-BENZIMIDAZOLE

Step 1. 2-[(5-Methoxy-2-nitroanilino)phenyl]ethanol

The title compound was prepared according to the procedure described in step 3 of Example 1 from 2-chloro-4-methoxynitrobenene and 4-aminophenylethyl alcohol.

$^1$H-NMR (CDCl$_3$) δ 9.74 (1H, br.s), 8.18 (1H, d, J=9.5 Hz), 7.30 (2H, d, J=8.4 Hz), 7.24 (2H, d, J=8.4 Hz), 6.55 (1H, d, J=2.8 Hz), 6.34 (1H, dd, J=9,5, 2.8 Hz), 3.90 (2H, m), 3.74 (3H, s), 2.90 (3H, t, J=6.6 Hz).

Step 2. 2-[(2-Amino-5-methoxyanilino)phenyl]ethanol

The title compound was prepared according to the procedure described in step 2 of Example 28 from 2-[(5-methoxy-2-nitroanilino)phenyl]ethanol (step 1).

$^1$H-NMR (CDCl$_3$) δ 7.09 (2H, d, J=8.4 Hz), 6.80 (2H, d, J=8.4 Hz), 6.76–6.73 (2H, m), 6.54 (1H, dd, J=8.6, 2.8 Hz), 3.81 (2H, t, J=6.6 Hz), 3.71 (3H, s), 2.79 (2H, t, J=6.6 Hz).

Step 3. 2-[4-(2-Ethyl-6-methoxy-1H-benzimidazol-1-yl)phenyl]ethyl propionate

The title compound was prepared according to the procedure described in step 5 of Example 1 from 2-[(2-amino-5-methoxyanilino)phenyl]ethanol (step 2) and propionyl chloride.

MS (EI) m/z 352 (M$^+$).

Step 4. 2-[4-(2-Ethyl-6-methoxy-1H-benzimidazol-1-yl)phenyl]ethanol

The title compound was prepared according to the procedure described in step 6 of Example 1 from 2-[4-(2-ethyl-6-methoxy-1H-benzimidazol-1-yl)phenyl]ethyl propionate (step 3).

$^1$H-NMR (CDCl$_3$) δ 7.63 (1H, d, J=8.8 Hz), 7.45 (2H, d, J=8.3 Hz), 7.29 (2H, d, J=8.3 Hz), 6.89 (1H, dd, J=8.8, 2.6 Hz), 6.56 (1H, d, J=2.6 Hz), 4.00 (2H, t, J=6.6 Hz), 3.75 (3H, s), 3.01 (2H, t, J=6.6 Hz), 2.74 (2H, q, J=7.5 Hz), 1.32 (3H, t, J=7.5 Hz).

Step 5. 2-[4-(2-Ethyl-6-methoxy-1H-benzimidazol-1-yl)phenyl]ethyl azide

The title compound was prepared according to the procedure described in step 4 of Example 26 from 2-(4-(2-ethyl-6-methoxy-1H-benzimidazol-1-yl)phenyl)ethanol (step 4).

TLC Rf=0.50 (hexane/ethyl acetate=1:1).

Step 6. 2-[4-(2-Ethyl-6-methoxy-1H-benzimidazol-1-yl)phenyl]ethylamine

The title compound was prepared according to the procedure described in step 9 of Example 1 from 2-[4-(2-ethyl-6-methoxy-1H-benzimidazol-1-yl)phenyl]ethyl azide (step 5).

$^1$H-NMR (CDCl$_3$) δ 7.65 (1H, d, J=8.8 Hz), 7.41 (2H, d, J=8.3 Hz), 7.29 (2H, d, J=8.3 Hz), 6.89 (1H, dd, J=8.8, 2.4 Hz), 6.56 (1H, d, J=2.4 Hz), 3.76 (3H, s), 3.09 (2H, t, J=7.0 Hz), 2.89 (2H, t, J=7.0 Hz), 2.75 (2H, q, J=7.5 Hz), 1.32 (3H, t, J=7.5 Hz).

Step 7. 2-Ethyl-6-methoxy-1-(4-{2-[({[(4-methylphenyl)sulfonyl]amino}carbonyl)amino]ethyl}phenyl)-1H-benzimidazole The title compound was prepared according to the procedure described in step 10 of Example 1 from 2-[4-(2-ethyl-6-methoxy-1H-benzimidazol-1-yl)phenyl]ethylamine (step 6).

$^1$H-NMR (CDCl$_3$) δ 7.75 (2H, d, J=8.2 Hz), 7.62 (1H, d, J=8.7 Hz), 7.35–7.23 (6H, m), 6.89 (1H, dd, J=8.7, 2.5 Hz), 6.66 (1H, m), 6.55 (1H, d, J=2.5 Hz), 3.72 (3H, s), 3.59–3.57 (2H, m), 2.93 (2H, t, J=7.0 Hz), 2.73 (2H, q, J=7.6 Hz), 1.29 (3H, t, J=7.6 Hz).

Example 75

2-ETHYL-6-METHOXY-1-(4-{2-[({[(4-METHYLPHENYL)SULFONYL]AMINO}CARBONYL)AMINO]ETHYL}PHENYL)-1H-BENZIMIDAZOLE, SODIUM SALT

The title compound was prepared according to the procedure described in Example 2 from 2-ethyl-6-methoxy-1-(4-{2-[({[(4-methylphenyl)sulfonyl]amino}carbonyl)amino]ethyl}phenyl)-1H-benzimidazole (Example 74).

$^1$H-NMR (DMSO-d$_6$) δ 7.59 (2H, d, J=8.3 Hz), 7.50 (1H, d, J=8.8 Hz), 7.41–7.35 (4H, m), 7.12 (2H, d, J=8.3 Hz), 6.80 (1H, dd, J=8.8, 2.4 Hz), 6.53 (1H, d, J=2.4 Hz), 3.67 (3H, s), 3.15 (2H, m), 2.73–2.62 (4H, m), 1.19 (3H, t, J=7.7 Hz); IR (KBr) α$_{max}$ 1595, 1516, 1485, 1454, 1400, 1157, 1128, 1086 cm$^{-1}$.

Example 76

5-TRIFLUOROMETHYL-2-ETHYL-3-(4-{2-[({[(4-METHYLPHENYL)SULFONYL]AMINO}CARBONYL)AMINO]ETHYL}PHENYL)-1H-BENZIMIDAZOLE

Step 1. 2-[2-Nitro-4-(trifluoromethyl)anilino]phenyl}ethanol

The title compound was prepared according to the procedure described in step 3 of Example 1 from 2-chloro-5-trifluoromethylnitrobenzene and 4-aminophenylethyl alcohol.

$^1$H-NMR (CDCl$_3$) δ 9.68 (1H, br.s), 8.50 (1H, s), 7.51 (1H, dd, J=2.2 Hz, 9.2 Hz), 7.33 (2H, d, J=8.2 Hz), 7.19–7.26 (3H, m), 3.92 (2H, t, J=6.3 Hz), 2.92 (2H, t, J=6.3 Hz).

Step 2. 2-[2-Amino-4-(trifluoromethyl)anilino]phenyl}ethanol

The title compound was prepared according to the procedure described in step 2 of Example 26 from 2-[2-nitro-4-(trifluoromethyl)anilino]phenyl}ethanol (step 1).

$^1$H-NMR (CDCl$_3$) δ 7.10–7.16 (3H, m), 6.97 (2H, d, J=8.2 Hz), 6.82 (2H, d, J=8.2 Hz), 3.82 (2H, t, J=6.6 Hz), 2.79 (2H, t, J=6.6 Hz).

Step 3. 2-{4-[2-Ethyl-5-(trifluoromethyl)-1H-benzimidazol-1-yl]phenyl}ethyl propionate The title compound was prepared according to the procedure described in step 5 of Example 1 from 2-[2-amino-4-(trifluoromethyl)anilino]phenyl}ethanol (step 2) and propionyl chloride.

$^1$H-NMR (CDCl$_3$) δ 8.05 (1H, s), 7.42–7.47 (2H, m), 7.27–7.31 (2H, m), 7.13 (2H, d, =8.4 Hz), 4.39 (2H, t, J=7.0 Hz), 3.08 (2H, t, J=7.0 Hz), 2.80 (2H, q, J=7.6 Hz), 2.36 (2H, q, J=7.6 Hz), 1.36 (3H, t, J=7.6 Hz), 1.14 (3H, t, J=7.6 Hz).

Step 4. 2-{4-[2-Ethyl-5-(trifluoromethyl)-1H-benzimidazol-1-yl]phenyl}ethanol

The title compound was prepared according to the procedure described in step 6 of Example 1 from 2-{4-[2-ethyl-5-(trifluoromethyl)-1H-benzimidazol-1-yl]phenyl}ethyl propionate (step 3)

$^1$H-NMR (CDCl$_3$) δ 8.05 (1H, s), 7.49 (1H, d, J=8.4 Hz), 7.44 (2H, d, J=8.6 Hz), 7.30 (2H, d, J=8.6 Hz), 7.16 (1H, d, J=8.4 Hz), 4.01 (2H, t, J=6.4 Hz), 3.03 (2H, t, J=6.4 Hz), 2.80 (2H, q, J=7.6 Hz), 1.36 (3H, t, J=7.6 Hz).

Step 5. 2-{4-[2-Ethyl-5-(trifluoromethyl)-1H-benzimidazol-1yl]phenyl}ethyl azide The title compound was prepared according to the procedure described in step 5 of Example 26 from 2-{4-[2-ethyl-5-(trifluoromethyl)-1H-benzimidazol-1-yl]phenyl}ethanol (step 4).

$^1$H-NMR (CDCl$_3$) δ: 8.05 (1H, s), 7.22–7.48 (5H, m), 7.15 (1H, d, J=8.4 Hz), 3.62 (2H, t, J=6.8 Hz), 3.02 (2H, t, J=6.8 Hz), 2.80 (2H, q, J=7.5 Hz), 1.36 (3H, t, J=7.5 Hz).

Step 6. 2-{4-[2-Ethyl-5-(trifluoromethyl)-1H-benzimidazol-1yl]phenyl}ethylamine

The title compound was prepared according to the procedure described in step 9 of Example 1 from 2-{4-[2-ethyl-5-(trifluoromethyl)-1H-benzimidazol-1yl]phenyl}ethyl azide (step 5).

$^1$H-NMR (CDCl$_3$) δ 8.05 (1H, s), 7.44 (3H, d, J=8.8 Hz), 7.29 (2H, d, J=8.8 Hz), 7.16 (1H, d, J=8.6 Hz), 3.09 (2H, t, J=6.8 Hz), 2.89 (2H, t, J=6.8 Hz), 2.81 (2H, q, J=7.6 Hz), 1.36 (3H, t, J=7.6 Hz).

Step 7. 5-Trifluoromethyl-2-ethyl-3-(4-{2-[({[(4-methylphenyl)sulfonyl]amino}carbonyl)amino]ethyl}phenyl)-1H-benzimidazole The title compound was prepared according to the procedure described in step 10 of Example 1 from 2-{4-[2-ethyl-5-(trifluoromethyl)-1H-benzimidazol-1yl]phenyl}ethylamine (step 6).

MS (ESI) m/z 533 (M+H)$^+$; $^1$H-NMR (CDCl$_3$) δ 8.03 (1H, s), 7.80 (2H, d, J=8.2 Hz), 7.73 (2H, d, J=8.2 Hz), 7.38–7.43 (3H, m), 7.26–7.29 (2H, m), 7.13 (1H, d, J=8.4 Hz), 6.70 (1H, br.s), 3.57 (2H, t, 6.7 Hz), 2.94 (2H, t, J=6.7 Hz), 2.80 (2H, q, J=7.6 Hz), 2.43 (3H, s), 1.34 (3H, t, J=7.6 Hz).

Example 77

5-TRIFLUOROMETHYL-2-ETHYL-3-(4-{2-[({[(4-METHYLPHENYL)SULFONYL]AMINO}CARBONYL)AMINO]ETHYL}PHENYL)-1H-BENZIMIDAZOLE, SODIUM SALT

The title compound was prepared according to the procedure described in Example 2 from 5-trifluoromethyl-2-ethyl-3-(4-{2-[({[(4-methylphenyl)sulfonyl]amino}carbonyl)amino]ethyl}phenyl)-1H-benzimidazole (Example 76).

$^1$H-NMR (DMSO-d$_6$) δ 8.02 (1H, s), 7.61–7.66 (4H, m), 7.48–7.51 (1H, m), 7.24–7.28 (3H, m), 7.14 (2H, d, 7.9 Hz), 3.09 (2H, br.s), 2.60–2.83 (4H, m), 2.22 (3H, s), 1.13 (3H, t, J=7.5 Hz).

Example 78

5-ACETYL-2-ETHYL-3-(4-{2-[({[(4-METHYLPHENYL)SULFONYL]AMINO}CARBONYL)AMINO]ETHYL}PHENYL)-1H-BENZIMIDAZOLE

Step 1. 1-{4-[4-(2-Hydroxyethyl )anilino]-3-nitrophenyl}ethanol

A mixture of 2-chloro-5-acetylnitrobenzene (Oelschlaeger, H.; Schreiber, O. Liebigs Ann. Chem., 1961, 641, 81., 2 g, 10 mmol), 4-aminophenylethyl alcohol (1.64 g, 12 mmol) and NaHCO$_3$ (1 g, 12 mmol) in DMF (60 mL) was heated at 150° C. for 3 h. After cooling, the mixture was poured into water (100 mL) and extracted with ethyl acetate (300 mL). The organic layer was washed with 2N aqueous NaOH (100 mL) and brine (100 mL), then dried (Na$_2$SO$_4$), and concentrated. Purification by flash column chromatography on silica gel eluting with hexane/ethyl acetate (1:1) to afford 1.36 g (45%) of the title compound as an orange oil;

$^1$H-NMR (CDCl$_3$) δ 9.83 (1H, br.s), 8.20 (1H, d, J=2.1 Hz), 7.94 (1H, dd, J=2.1 Hz, 9.3 Hz), 7.34 (2H, d, J=8.2 Hz), 7.24 (2H, d, J=8.2 Hz), 7.16 (1H, d, J=9.3 Hz), 3.91 (2H, t, J=6.6 Hz), 2.92 (2H, t, J=6.6 Hz), 2.57 (3H, s).

Step 2. 1-{3-Amino-4-[4-(2-hydroxyethyl)anilino]phenyl}ethanol

The title compound was prepared according to the procedure described in step 4 of Example 1 from 1-{4-[4-(2-hydroxyethyl)anilino]-3-nitrophenyl}ethanol (step 1).

$^1$H-NMR (CDCl$_3$) δ: 7.41 (1H, d, J=2.0 Hz), 7.37 (1H, dd, J=2.0 Hz, 8.2 Hz), 7.11–7.17 (3H, m), 6.94 (2H, d, J=8.2 Hz), 5.72 (1H, br.s), 3.85 (2H, t, J=6.6 Hz), 3.65 (2H, br.s), 2.83 (2H, t, J=6.6 Hz), 2.52 (3H, s).

Step 3. 2-4-(5-Acetyl-2-ethyl-1H-benzimidazol-1-yl)phenyl)ethyl propionate

The title compound was prepared according to the procedure described in step 5 of Example 1 from 1-{3-amino-4-[4-(2-hydroxyethyl)anilino]phenyl}ethanol (step 2) and propionyl chloride.

TLC Rf=0.4 (hexane/ethyl acetate=1:1).

Step 4. 1-{2-Ethyl-1-[4-(2-hydroxyethyl)phenyl]-1H-benzimidazol-5-yl}ethyl propionate The title compound was prepared according to the procedure described in step 6 of Example 1 from 2-4-(5-acetyl-2-ethyl-1H-benzimidazol-1-yl)phenyl)ethyl propionate (step 3).

$^1$H-NMR (CDCl$_3$) δ 8.39 (1H, d, J=1.2 Hz), 7.89 (1H, dd, J=1.2 Hz, 8.6 Hz), 7.48 (2H, d, J=7.4 Hz), 7.30 (2H, d, J=7.4 Hz), 7.13 (1H, d, J=8.6 Hz), 4.00 (2H, t, J=6.4 Hz), 3.02 (2H, t, J=6.4 Hz), 2.80 (2H, q, J=7.6 Hz), 2.68 (3H, s), 1.38 (2H, t, J=7.6 Hz).

Step 5. 1-{1-[4-(2-Chloroethyl)phenyl]-2-ethyl-1H-benzimidazol-5-yl}ethanol

The title compound was prepared according to the procedure described in step 7 of Example 1 from 1-{2-ethyl-1-[4-(2-hydroxyethyl)phenyl]-1H-benzimidazol-5-yl}ethanol (step 4).

$^1$H-NMR (CDCl$_3$) δ 8.40 (1H, d, J=1.2 Hz), 7.90 (1H, dd, J=1.2 Hz, 8.4 Hz), 7.47 (2H, d, J=8.4 Hz), 7.32 (2H, d, J=8.4 Hz), 7.13 (1H, d, J=8.4 Hz), 3.83 (2H, t, J=7.3 Hz), 3.21 (2H, t, J=7.3 Hz), 2.82 (2H, q, J=7.6 Hz), 2.68 (3H, s), 1.38 (3H, t, J=7.6 Hz).

Step 6. 1-{1-[4-(2-Azidoethyl)phenyl]-2-ethyl-1H-benzimidazol-5-yl}ethanol

The title compound was prepared according to the procedure described in step 8 of Example 1 from 1-{1-[4-(2-chloroethyl)phenyl]-2-ethyl-1H-benzimidazol-5-yl}ethanol (step 5).

$^1$H-NMR (CDCl$_3$) δ 8.40 (1H, d, J=1.5 Hz), 7.90 (1H, dd, J=1.5 Hz, 8.6 Hz), 7.46 (2H, d, J=8.3 Hz), 7.12 (2H, d, J=8.3 Hz), 7.02 (1H, d, J=8.6 Hz), 3.63 (2H, t, J=6.9 Hz), 3.03 (2H, t, J=6.9 Hz), 2.80 (2H, q, J=7.4 Hz), 2.67 (3H, s), 1.37 (3H, t, J=7.4 Hz).

Step 7. 1-{1-[4-(2-Aminoethyl)phenyl]-2-ethyl-1H-benzimidazol-5-yl}ethanol

The title compound was prepared according to the procedure described in step 7 of Example 37 from 1-{1-[4-(2-azidoethyl)phenyl]-2-ethyl-1H-benzimidazol-5-yl}ethanol (step 6).

$^1$H-NMR (CDCl$_3$) δ 8.40 (1H, d, J=1.7 Hz), 7.90 (1H, dd, J=1.7 Hz, 8.6 Hz), 7.43 (2H, d, J=8.2 Hz), 7.30 (2H, d, J=8.2 Hz), 7.13 (1H, d, J=8.6 Hz), 3.08 (2H, t, J=6.7 Hz), 2.88 (2H, t, J=6.7 Hz), 2.80 (2H, q, J=7.6 Hz), 2.68 (3H, s), 1.38 (3H, t, J=7.6 Hz).

Step 8. 5-Acetyl-2-ethyl-1-(4-{2-[({[(4-methylphenyl)sulfonyl]amino}carbonyl) amino]ethyl}phenyl)-1H-benzimidazole The title compound was prepared according to the procedure described in step 10 of Example 1 from 1-{1-[4-(2-aminoethyl)phenyl]-2-ethyl-1H-benzimidazol-5-yl}ethanol (step 7).

MS (ESI) m/z 505 (M+H)$^+$; $^1$H-NMR CDCl$_3$) δ 8.40 (1H, d, J=1.1 Hz), 7.88 (1H, dd, J=1.1 Hz, 8.6 Hz), 7.73 (2H, d, J=8.4 Hz), 7.40 (2H, d, J=8.4 Hz), 7.27–7.31 (4H, m), 7.10 (1H, d, J=8.6 Hz), 6.74 (1H, br.s), 3.59 (2H, t, J=6.9 Hz), 2.95 (2H, t, J=6.9 Hz), 2.80 (2H, q, J=7.6 Hz), 2.67 (3H, s), 2.40 (3H, s), 1.36 (3H, t, J=7.6 Hz).

Example 79

5-ACETYL-2-ETHYL-3-(4-{2-[({[(4-METHYLPHENYL)SULFONYL]AMINO}CARBONYL)AMINO]ETHYL}PHENYL)-1H-BENZIMIDAZOLE, SODIUM SALT

The title compound was prepared according to the procedure described in Example 2 from 5-acetyl-2-ethyl-1-(4-{2-[({[(4-methylphenyl)sulfonyl]amino}carbonyl) amino]ethyl}phenyl)-1H-benzimidazole (Example 78).

mp 155–160° C.; $^1$H-NMR (DMSO-d$_6$) δ 8.32 (1H, d, J=1.6 Hz), 7.81 (1H, dd, J=1.6 Hz, 8.6 Hz), 7.62 (2H, d, J=8.1 Hz), 7.42 (4H, s), 7.12–7.17 (3H, m), 3.18 (2H, br.s), 2.71–2.79 (4H, m), 2.63 (3H, s), 2.27 (3H, s), 1.25 (3H, t, J=7.4 Hz); IR (KBr) α$_{max}$ 3373, 1676, 1604, 1519, 1294, 1130, 1085, 885, 813 cm$^{-1}$.

Example 80

2-ETHYL-5-METHYLSULFONYL-1-(4-{2-[({[(4-METHYLPHENYL)SULFONYL]AMINO}CARBONYL)AMINO]ETHYL}PHENYL)-1H-BENZIMIDAZOLE

Step 1. 2-{4-[4-(Methylsulfonyl)-2-nitroanilino]phenyl}ethanol

A mixture of 2-chloro-5-methylsulfonylnitrobenzene (Kavalek, J.; et al. Collect. Czech. Chem. Commun, 1971, 36,209., 2 g, 8.5 mmol), 4-aminophenylethyl alcohol (1.4 g, 10.2 mmol) and Na$_2$CO$_3$ (1.4 g, 12.7 mmol) in ethanol was stirred at 100° C. for 16 h. The insoluble matter was removed by filtration and washed with ethanol (100 mL). The filtrate was concentrated and the residue was purified by flash column chromatography on silica gel eluting with hexane/ethyl acetate (1:4) to afford 960 mg (34%) of the title compound as yellow solids: $^1$H-NMR (CDCl$_3$) δ 9.84 (1H, br.s), 8.82 (1H, d, J=2.1 Hz), 7.79 (1H, dd, J=2.1 Hz, 9.1 Hz), 7.36 (2H, d, J=8.4 Hz), 7.22–7.38 (3H, m), 3.94 (2H, br.s), 3.07 (3H, s), 2.93 (2H, t, J=6.6 Hz).

Step 2. 2-{4-[2-Amino-4-(methylsulfonyl)anilino]phenyl}ethanol

The title compound was prepared according to the procedure described in step 2 of Example 28 from 2-{4-[4-(methylsulfonyl)-2-nitroanilino]phenyl}ethanol (step 1).

$^1$H-NMR (CDCl$_3$) δ 7.31 (1H, s), 7.28 (1H, s), 7.16–7.21 (3H, m), 6.96 (2H, d, J=8.5 Hz), 5.56 (1H, br.s), 3.86 (2H, t, J=6.4 Hz), 3.76 (2H, br.s), 3.03 (3H, s), 2.84 (2H, t, J=6.4 Hz).

Step 3. 2-{4-[2-Ethyl-5-(methylsulfonyl)-1H-benzimidazol-1-yl]phenyl}ethyl propionate The title compound was prepared according to the procedure described in step 5 of Example 1 from 2-{4-[2-amino-4-(methylsulfonyl)anilino]phenyl}ethanol (step 2) and propionyl chloride.

TLC Rf=0.8 (dichloromethane/methanol=10:1).

Step 4. 2-{4-[2-Ethyl-5-(methylsulfonyl)-1H-benzimidazol-1-yl]phenyl}ethanol

The title compound was prepared according to the procedure described in step 6 of Example 1 from 2-{4-[2-ethyl-5-(methylsulfonyl)-1H-benzimidazol-1-yl]phenyl}ethyl propionate (step 3).

$^1$H-NMR (CDCl$_3$) δ 8.38 (1H, d, J=1.4 Hz), 7.77 (1H, dd, J=1.4 Hz, 8.6 Hz), 7.50 (2H, d, J=8.4 Hz), 7.24–7.32 (2H, m), 7.22 (1H, d, J=8.6 Hz), 4.01 (t, J=6.6 Hz), 3.08 (3H, s), 3.02 (2H, t, J=6.6 Hz), 2.82 (2H, q, J=7.6 Hz), 1.37 (3H, t, J=7.6 Hz).

Step 5. 1-[4-(2-Chloroethyl)phenyl]-2-ethyl-5-(methylsulfonyl)-1H-benzimidazole

The title compound was prepared according to the procedure described in step 7 of Example 1 from 2-{4-[2-ethyl-5-(methylsulfonyl)-1H-benzimidazol-1-yl]phenyl}ethanol (step 4).

$^1$H-NMR (CDCl$_3$) δ 8.38 (1H, d, J=1.6 Hz), 7.78 (1H, d, J=1.6 Hz, 8.6 Hz), 7.49 (2H, d, J=8.1 Hz), 7.32 (2H, d, J=8.1 Hz), 7.23 (1H, d, J=8.6 Hz), 3.84 (2H, t, J=6.9 Hz), 3.22 (2H, t, J=6.9 Hz), 3.08 (3H, s), 2.82 (2H, q, J=7.5 Hz), 1.38 (3H, t, J=7.5 Hz).

Step 6. 1-[4-(2-Azidoethyl)phenyl]-2-ethyl-1H-benzimidazol-5-yl methyl sulfone

The title compound was prepared according to the procedure described in step 8 of Example 1 from 1-[4-(2-chloroethyl)phenyl]-2-ethyl-5-(methylsulfonyl)-1H-benzimidazole (step 5).

$^1$H-NMR (CDCl$_3$) δ 8.38 (1H, d, J=1.5 Hz), 7.78 (1H, dd, J=1.5 Hz, 8.6 Hz), 7.49 (2H, d, J=8.4 Hz), 7.32 (2H, d, J=8.4 Hz), 7.21 (1H, d, J=8.6 Hz), 3.64 (2H, t, J=6.9 Hz), 3.08 (3H, s), 3.03 (2H, t, J=6.9 Hz), 2.83 (2H, q, J=7.6 Hz), 1.37 (3H, t, J=7.6 Hz).

Step 7. 2-{4-[2-Ethyl-5-(methylsulfonyl)-1H-benzimidazol-1-yl]phenyl}ethylamine

The title compound was prepared according to the procedure described in step 7 of Example 37 from 1-[4-(2-azidoethyl)phenyl]-2-ethyl-1H-benzimidazol-5-yl methyl sulfone (step 6).

$^1$H-NMR (CDCl$_3$) δ 8.38 (1H, d, J=1.7 Hz), 7.77 (1H, dd, J=1.7 Hz, 8.6 Hz), 7.46 (2H, d, J=8.4 Hz), 7.21–7.30 (3H, m), 3.03–3.08 (5H, m), 2.89 (2H, t, J=6.7 Hz), 2.82 (2H, q, J=7.6 Hz), 1.37 (3H, t, J=7.6 Hz).

Step 8. 2-Ethyl-5-(methylsulfonyl)-1-(4-{2-[({[(4-methylphenyl)sulfonyl]amino}carbonyl)amino]ethyl}phenyl)-1H-benzimidazole The title compound was prepared according to the procedure described in step 10 of Example 1 from 2-{4-[2-ethyl-5-(methylsulfonyl)-1H-benzimidazol-1-yl]phenyl}ethylamine (step 7).

$^1$H-NMR (CDCl$_3$) δ 8.37 (1H, d, J=1.6 Hz), 7.75 (1H, dd, J=1.6 Hz, 8.6 Hz), 7.74 (2H, d, J=8.4 Hz), 7.43 (2H, d, J=8.2 Hz), 7.27–7.32 (4H, m), 7.18 (1H, d, J=8.6 Hz), 6.70 (1H, br.s), 3.59 (2H, t, J=6.8 Hz), 3.08 (3H, s), 2.96 (2H, t. J=6.8 Hz), 2.82 (2H, q, J=7.6 Hz), 2.41 (3H, s), 1.35 (4H, t, J=7.6 Hz).

Example 81

2-ETHYL-5-METHYLSULFONYL-3-(4-{2-[({[(4-METHYLPHENYL)SULFONYL]AMINO}CARBONYL)AMINO]ETHYL}PHENYL)-1H-BENZIMIDAZOLE, SODIUM SALT

The title compound was prepared according to the procedure described in Example 2 from 2-ethyl-5-(methylsulfonyl)-1-(4-{2-[({[(4-methylphenyl)sulfonyl]amino}carbonyl)amino]ethyl}phenyl)-1H-benzimidazole (Example 80).

mp 171–178° C.; $^1$H-NMR (DMSO-d$_6$) δ 8.08 (1H, br.s), 7.51–7.62 (3H, m), 7.32 (4H, s), 7.16 (1H, d, J=8.6 Hz), 7.03 (2H, d, J=7.3 Hz), 3.09–3.25 (7H, m), 2.63–2.66 (2H, m), 2.16 (3H, s), 1.13 (3H, t, J=7.3 Hz); IR (KBr) α$_{max}$ 3386, 1604, 1519, 1396, 1299, 1128, 1085, 962, 887 cm$^{-1}$.

Example 82

5-CYANO-2-ETHYL-1-(4-{2-[({[(4-METHYLPHENYL)SULFONYL]AMINO}CARBONYL)AMINO]ETHYL}PHENYL)-1H-BENZIMIDAZOLE

Step 1. 2-[(4-Cyano-2-nitroanilino)phenyl]ethanol

The title compound was prepared according to the procedure described in step 3 of Example 1 from 4-chloro-3-nitrobenzonitrile and 4-aminophenylethyl alcohol.

$^1$H-NMR (CDCl$_3$) δ 9.80 (1H, br.s), 8.54 (1H, d, J=2.0 Hz), 7.50 (1H, dd, J=9.1, 2.0 Hz), 7.36 (2H, d, J=8.4 Hz), 7.23 (2H, d, J=8.4 Hz), 7.16 (1H, d, J=9.1Hz), 3.94–3.91 (2H, m), 2.93 (2H, t, J=6.6 Hz), 1.81 (1H, m).

Step 2. 2-[(2-Amino-4-cyanoanilino)phenyl]ethanol

The title compound was prepared according to the procedure described in step 2 of Example 28 from 2-[(4-cyano-2-nitroanilino)phenyl]ethanol (step 1).

$^1$H-NMR (CDCl$_3$) δ 7.18–7.10 (3H, m), 7.01–6.95 (4H, m), 6.09 (1H, m), 3.97 (2H, br.s), 3.83–3.82 (2H, m), 2.83 (2H, t, J=6.8 Hz), 2.31 (1H, m).

Step 3. 2-[4-(5-Cyano-2-ethyl-1H-benzimidazol-1-yl)phenyl]ethyl propionate

The title compound was prepared according to the procedure described in step 5 of Example 1 from 2-[(2-amino-4-cyanoanilino)phenyl]ethanol (step 2).

MS (EI) m/z 347 (M$^+$).

Step 4. 2-[4-(5-Cyano-2-ethyl-1H-benzimidazol-1-yl)phenyl]ethanol

The title compound was prepared according to the procedure described in step 6 of Example 1 from 2-[4-(5-cyano-2-ethyl-1H-benzimidazol-1yl)phenyl]ethyl propionate (step 3).

$^1$H-NMR (CDCl$_3$) δ 8.09 (1H, s), 7.50–7.43 (3H, m), 7.32–7.28 (2H, m), 7.15 (1H, d, J=8.2 Hz), 4.00 (2H, q, H=6.4 Hz), 3.01 (2H, t, J=6.4 Hz), 2.81 (2H, t, J=7.6Hz), 1.37 (3H, t, J=7.6Hz).

Step 5. 2-[4-(5-Cyano-2-ethyl-1H-benzimidazol-1yl)phenyl]ethyl azide

The title compound was prepared according to the procedure described in step 5 of Example 26 from 2-[4-(5-cyano-2-ethyl-1H-benzimidazol-1yl)phenyl]ethanol (step 4).

TLC RF=0.83 (dichloromethane/methanol=10:1).

Step 6. 2-[4-(5-Cyano-2-ethyl-1H-benzimidazol-1-yl)phenyl]ethylamine

The title compound was prepared according to the procedure described in step 9 of Example 1 from 2-[4-(5-cyano-2-ethyl-1H-benzimidazol-1yl))phenyl]ethyl azide (step 5).

$^1$H-NMR (CDCl$_3$) δ 8.09 (1H, s), 7.47–7.42 (3H, m), 7.29–7.26 (2H, m), 7.15 (1H, d, J=8.4 Hz), 3.09 (2H, t, J=6.8 Hz), 2.91 (2H, t, J=6.8 Hz), 2.81 (2H, q, J=7.6 Hz), 1.37 (3H, t, J=7.6 Hz).

Step 7. 5-Cyano-2-ethyl-1-(4-{2-[({[(4-methylphenyl)sulfonyl]amino}carbonyl)amino]ethyl}phenyl)-1H-benzimidazole The title compound was prepared according to the procedure described in step 10 of Example 1 from 2-[4-(5-cyano-2-ethyl-1H-benzimidazol-1-yl)phenyl]ethylamine (step 6).

$^1$H-NMR (CDCl$_3$) δ 8.05 (1H, d, J=0.9 Hz), 7.75 (2H, d, J=8.4 Hz), 7.43–7.40 (3H, m), 7.30–7.26 (4H, m), 7.12 (1H, d, J=8.4 Hz), 6.74 (1H, m), 3.60–3.58 (2H, m), 2.96 (2H, t, J=7.0 Hz), 2.81 (2H, q, J=7.5 Hz), 2.41 (3H, s), 1.34 (3H, t, J=7.5 Hz).

Example 83

5-CYANO-2-ETHYL-1-(4-{2-[{[(4-METHYLPHENYL)SULFONYL]AMINO}CARBONYL)AMINO]ETHYL}PHENYL)-1H-BENZIMIDAZOLE, SODIUM SALT

The title compound was prepared according to the procedure described in Example 2 from 5-cyano-2-ethyl-1-(4-{2-[({[(4-methylphenyl)sulfonyl]amino}carbonyl)amino]ethyl}phenyl)-1H-benzimidazole (Example 82).

$^1$H-NMR (DMSO-d$_6$) δ 8.19 (1H, d, J=1.5 Hz), 7.59 (2H, d, J=7.9 Hz), 7.54 (1H, dd, J=8.4, 1.5 Hz), 7.41 (4H, s), 7.23 (1H, d, J=8.4 Hz), 7.11 (2H, d, J=7.9 Hz), 3.14 (2H, m), 2.78–2.70 (4H, m), 2.26 (3H, s), 1.24 (3H, t, J=7.4 Hz).

Example 84

2-ETHYL-1-(4-{2-[({[(4-METHYLPHENYL)SULFONYL]AMINO}CARBONYL)AMINO]ETHYL}PHENYL)-1H-BENZIMIDAZOLE-5-CARBOXAMIDE

Step 1. 2-Ethyl-1-[4-(2-hydroxyethyl)phenyl]-1H-benzimidazole-5-carboxamide

To a mixture of 2-[4-(5-cyano-2-ethyl-1H-benzimidazol-1-yl)phenyl]ethanol (step 4 of Example 82, 200 mg, 0.68 mmol), DMSO (0.06 mL, 0.82 mmol) and methanol (10 mL) was added 30% aqueous solution of hydrogen peroxide (0.12 mL, 1.0 mmol) and 0.2 M aqueous NaOH (0.06 mL). The mixture was stirred at 50° C. for 4 h, then cooled. The mixture was poured into water (50 mL) and extracted with ethyl acetate (100 mL). The organic layer was washed with 2N aqueous NaOH (50 mL) and brine (50 mL), then dried ($Na_2SO_4$), and concentrated to afford the title compound as pale yellow solids: $^1$H-NMR ($CDCl_3$) δ 8.23 (1H, d, J=1.1 Hz), 7.96 (1H, br.s), 7.76 (1H, dd, J=1.1 Hz, 8.4 Hz), 7.42–7.51 (4H, m), 7.25 (1H, br.s), 7.09 (1H, d, J=8.4 Hz), 3.70 (2H, t, J=6.6 Hz), 2.85 (2H, t, J=6.9 Hz), 2.76 (2H, q, J=7.4 Hz), 1.24 (3H, t, J=7.4 Hz).

Step 2. 1-[4-(2-Chloroethyl)phenyl]-2-ethyl-1H-benzimidazole-5-carboxamide

The title compound was prepared according to the procedure described in step 7 of Example 1 from 2-ethyl-1-[4-(2-hydroxyethyl)phenyl]-1H-benzimidazole-5-carboxamide (step 1).

$^1$H-NMR ($CDCl_3$) δ 8.17 (1H, d, J=1.7 Hz), 7.79 (1H, dd, J=1.7 Hz, 8.5 Hz), 7.46 (2H, d, J=8.3 Hz), 7.33 (2H, d, J=8.3 Hz), 7.15 (1H, d, J=8.5 Hz), 3.83 (2H, t, J=7.0 Hz), 3.21 (2H, t, J=7.0 Hz), 2.82 (2H, q, J=7.6 Hz), 1.37 (3H, t, J=7.6 Hz).

Step 3. 1-[4-(2-Azidoethyl)phenyl]-2-ethyl-1H-benzimidazole-5-carboxamide

The title compound was prepared according to the procedure described in step 8 of Example 1 from 1-[4-(2-chloroethyl)phenyl]-2-ethyl-1H-benzimidazole-5-carboxamide (step 2).

$^1$H-NMR ($CDCl_3$) δ 8.17 (1H, d, J=1.5 Hz), 7.78 (1H, dd, J=1.5 Hz, 8.4 Hz), 7.46 (2H, d, J=8.2 Hz), 7.32 (2H, d, J=8.2 Hz), 7.13 (1H, d, J=8.4 Hz), 3.62 (2H, t, J=6.8 Hz), 3.03 (2H, t, J=6.8 Hz), 2.81 (2H, q, J=7.5 Hz), 1.36 (3H, t, J=7.5 Hz).

Step 4. 1-[4-(2-Aminoethyl)phenyl]-2-ethyl-1H-benzimidazole-5-carboxamide

The title compound was prepared according to the procedure described in step 9 of Example 1 from 1-[4-(2-azidoethyl)phenyl]-2-ethyl-1H-benzimidazole-5-carboxamide (step 3).

$^1$H-NMR ($CDCl_3$) δ 8.21 (1H, d, J=1.5 Hz), 7.79 (1H, dd, J=1.5 Hz, 8.4 Hz), 7.43 (2H, d, J=8.2 Hz), 7.28–7.31 (2H, m), 7.13 (1H, d, J=8.4 Hz), 3.05 (2H, t, J=6.7 Hz), 2.88 (2H, t, J=6.7 Hz), 2.81 (2H, q, J=7.6 Hz), 1.35 (3H, t, J=7.6 Hz).

Step 5. 2-Ethyl-1-(4-{2-[({[(4-methylphenyl)sulfonyl]amino}carbonyl) amino]ethyl}phenyl)-1H-benzimidazole-5-carboxamide The title compound was prepared according to the procedure described in step 10 of Example 1 from 1-[4-(2-aminoethyl)phenyl]-2-ethyl-1H-benzimidazole-5-carboxamide (step 4).

MS (ESI) m/z 506 (M+M)$^+$; $^1$H-NMR ($CD_3OD$) δ 8.13 (1H, s), 7.65–7.73 (3H, m), 7.32 (2H, d J=8.2 Hz), 7.16–7.21 (4H, m), 7.00 (1H, d, J=8.6 Hz), 3.31 (2H, t, J=6.9H), 2.75 (2H, t, J=6.9 Hz), 2.69 (2H, q, J=7.6 Hz), 2.21 (3H, s), 1.48 (3H, t, J=7.6 Hz).

Example 85
6-CYANO-2-ETHYL-1-(4-{2-[({[(4-METHYLPHENYL)SULFONYL]AMINO}CARBONYL)AMINO]ETHYL}PHENYL)-1H-BENZIMIDAZOLE Step 1. 3-[4-(2-Hydroxyethyl)anilino]-4-nitrobenzonitrile The title compound was prepared according to the procedure described in step 3 of Example 1 from 3-chloro-4-nitrobenzonitrile (Tsuji, K. Chem. Pharm. Bull. 1992, 40, 2399) and 4-aminophenylethyl alcohol.

MS (EI) m/z 383 (M$^+$).

Step 2. 3-[4-(2-Chloroethyl)anilino]-4-nitrobenzonitrile

The title compound was prepared according to the procedure described in step 7 Example 1 from 3-[4-(2-hydroxyethyl)anilino]-4-nitrobenzonitrile (step 1).

$^1$H-NMR ($CDCl_3$) δ 9.46 (1H, br.s), 8.29 (1H, d, J=8.8 Hz), 7.42 (1H, d, J=1.7 Hz), 7.35 (2H, d, J=8.3 Hz), 7.22 (2H, d, J=8.3 Hz), 6.97 (1H, dd, J=8.8, 1.7 Hz), 3.77 (2H, t, J=7.2), 3.3 (2H, t, J=7.2 Hz).

Step 3. 4-Amino-3-[4-(2-chloroethyl)anilino]benzonitrile

The title compound was prepared according to the procedure described in step 4 of Example 1 from 3-[4-(2-chloroethyl)anilino]-4-nitrobenzonitrile (step 2).

MS (EI) m/z 383 (M$^+$).

Step 4. 1-[4-(2-Chloroethyl)phenyl]-2-ethyl-1H-benzimidazole-6-carbonitrile

The title compound was prepared according to the procedure described in step 5 Example 1 from 4-amino-3-[4-(2-chloroethyl)anilino]benzonitrile (step 3) and propionyl chloride.

MS (EI) m/z 309 (M$^+$); $^1$H-NMR ($CDCl_3$) δ 7.82 (1H, d, J=8.6 Hz), 7.53 (1H, dd, J=8.6, 2.0 Hz), 7.48 (2H, d, J=8.3 Hz), 7.42 (1H, d, J=2.0 Hz), 7.31 (2H, d, J=8.3 Hz), 3.84 (2H, t, J=7.0 Hz), 3.21 (2H, t, J=7.0 Hz), 2.82 (2H, q, J=7.4 Hz), 1.39 (3H, t, J=7.4 Hz).

Step 5. 2-[4-(6-Cyano-2-ethyl-1H-benzimidazol-1-yl)phenyl]ethyl azide

The title compound was prepared according to the procedure described in step 8 Example 1 from 1-[4-(2-chloroethyl)phenyl]-2-ethyl-1H-benzimidazole-6-carbonitrile (step 4).

MS (EI) m/z 316 (M$^+$); $^1$H-NMR ($CDCl_3$) δ 7.83 (1H, d, J=8.4 Hz), 7.54 (1H, dd, J=8.4, 2.0 Hz), 7.50 (2H, d, J=8.3 Hz), 7.40 (1H, d, J=2.0 Hz), 7.30 (2H, d, J=8.3 Hz), 3.64 (2H, t, J=6.5 Hz), 3.04 (2H, t, J=6.5 Hz), 2.83 (2H, q, J=7.3 Hz), 1.37 (3H, t, J=7.3 Hz).

Step 6. 2-[4-(6-Cyano-2-ethyl-1H-benzimidazol-1yl))phenyl]ethylamine

The title compound was prepared according to the procedure described in step 9 of Example 1 from 2-[4-(6-cyano-2-ethyl-1H-benzimidazol-1-yl)phenyl]ethyl azide (step 5).

$^1$H-NMR (DMSO-$d_6$) δ 8.11 (2H, br.s), 7.87 (1H, d, J=8.4 Hz), 7.64 (1H, dd, J=8.4, 2.0 Hz), 7.60–7.53 (5H, m), 3.20–3.02 (4H, m), 2.79 (2H, q, J=7.4 Hz), 1.28 (3H, t, J=7.4 Hz).

Step 7. 6-Cyano-2-ethyl-1-(4-{2-[({[(4-methylphenyl)sulfonyl]amino}carbonyl)amino]ethyl}phenyl)-1H-benzimidazole The title compound was prepared according to the procedure described in step 10 of Example 1 from 2-[4-(6-cyano-2-ethyl-1H-benzimidazol-1-yl)phenyl]ethylamine (step 6).

$^1$H-NMR ($CDCl_3$) δ 7.83 (1H, d, J=8.4 Hz), 7.74 (2H, d, J=8.4 Hz), 7.53 (1H, dd, J=8.4, 1.5 Hz), 7.43 (2H, d, J=8.4 Hz), 7.39 (1H, d, J=1.5 Hz), 7.33 (2H, d, J=8.4 Hz), 7.29 (2H, d, J=8.4 Hz), 6.75 (1H, br.s), 3.65–3.54 (2H, m), 2.97 (2H, t, J=7.0 Hz), 2.82 (2H, q, J=7.5 Hz), 2.42 (3H, s), 1.37 (3H, t, J=7.5 Hz).

Example 86
2-ETHYL-1-(4-{2-[({[(4-METHYLPHENYL)SULFONYL]AMINO}CARBONYL)AMINO]ETHYL}PHENYL)-1H-BENZIMIDAZOLE-6-CARBOXAMIDE To a solution of 6-cyano-2-ethyl-1-(4-{2-[({[(4-methylphenyl)sulfonyl]amino}carbonyl)amino]ethyl}phenyl)-1H-benzimidazole (Example 85, 162 mg, 0.33 mmol) in 2-methyl-2-propanol (10 mL) was added powdered KOH (66 mg, 1.0 mmol). The resulting mixture was heated at reflux temperature for 3 h. After removal of solvent, the reaction mixture was partitioned between dichloromethane (50 mL) and phosphate buffer (50 mL). The organic phase was separated and the aqueous phase was extracted with dichloromethane (50 mL). The combined organic phases were washed with brine (50 mL), dried ($Na_2SO_4$), and concentrated. The residual solids were recrystallized from ethyl acetate to afford 105 mg (63%) of the title compound as white solids: H-NMR (CDCl$_3$) δ: 7.79 (2H, d, J=8.4 Hz), 7.75 (1H, d, J=8.8 Hz), 7.71–7.63 (2H, m), 7.35–7.25 (4H, m), 7.16 (2H, d, J=8.4 Hz), 6.75 (2H, br.s), 6.55 (1H, br.s), 3.54 (2H, t, J=6.4 Hz), 2.8 (2H, t, J=6.4 Hz), 2.79 (2H, q, J=7.5 Hz), 2.40 (3H, s), 1.34 (3H, t, J=7.5 Hz).

Example 87
5-[(tert-BUTYLAMINO)SULFONYL]-2-ETHYL-1-(4-{2-[({[(4-METHYLPHENYL)SULFONYL]AMINO}CARBONYL)AMINO]ETHYL}PHENYL)-1H-BENZIMIDAZOLE Step 1. N-(tert-Butyl)-4-chloro-3-nitrobenzenesulfonamide To a stirred solution of tert-butylamine (5.1 g, 70 mmol) in dichloromethane (200 mL) was added dropwise a solution of 4-chloro-3-nitrobenzenesulfonyl chloride (17.9 g, 70 mmol) in dichloromethane (100 mL) at room temperature over a period of 30 min, and then the reaction mixture was stirred for 2 h. The reaction mixture was poured into water (100 mL), the organic phase was separated, and the aqueous phase was extracted with ethyl acetate (100 mL). The combined organic extracts were washed with water (50 mL) and brine (20 mL), dried ($Na_2SO_4$), and concentrated to give 21.3 g (quant.) of the title compound as yellow solids: $^1$H-NMR (CDCl$_3$) δ 8.38 (1H, d, J=2.0 Hz), 8.02 (1H, dd, J=2.0, 8.6 Hz), 7.70 (1H, d, J=8.6 Hz), 4.95 (1H, br.s), 1.28 (9H, s).

Step 2. N-(tert-Butyl)-4-[4-(2-hydroxyethyl)anilino]-3-nitrobenzenesulfonamide

The title compound was prepared according to the procedure described in step 3 of Example 1 from N-(tert-butyl)-4-chloro-3-nitrobenzenesulfonamide (step 1) and 4-aminophenylethyl alcohol.

MS (EI) m/z 393 (M$^+$); $^1$H-NMR (CDCl$_3$) δ 9.76 (1H, br.s), 8.75 (1H, d, J=2.0 Hz), 7.74 (1H, dd, J=2.0, 8.5 Hz), 7.35 (2H, d, J=8.3 Hz), 7.24 (2H, d, J=8.3 Hz), 7.17 (1H, d, J=8.5 Hz), 4.42 (1H, br.s), 3.97–3.88 (2H, m), 2.94 (2H, t, J=7.0 Hz), 1.27 (9H, s).

Step 3. N-(tert-Butyl)-4-[4-(2-chloroethyl)anilino]-3-nitrobenzenesulfonamide

The title compound was prepared according to the procedure described in step 7 Example 1 from N-(tert-butyl)-4-[4-(2-hydroxyethyl )anilino]-3-nitrobenzenesulfonamide (step 2).

MS (EI) m/z 411 (M$^+$); $^1$H-NMR (CDCl$_3$) δ 9.77 (1H, br.s), 8.77 (1H, d, J=2.0 Hz), 7.77 (1, dd, J=2.0, 8.4 Hz), 7.34 (2H, d, J=8.3 Hz), 7.25 (2H, d, J=8.3 Hz), 7.18 (1H, d, J=8.4 Hz), 4.46 (1H, br.s), 3.76 (2H, t, J=6.8 Hz), 3.13 (2H, t, J=6.8 Hz), 1.28 (9H, s).

Step 4. 3-Amino-N-(tert-butyl)-4-[4-(2-chloroethyl)anilino]benzenesulfonamide

The title compound was prepared according to the procedure described in step 4 of Example 1 from N-(tert-butyl)-4-[4-(2-chloroethyl)anilino]-3-nitrobenzenesulfonamide (step 3).

$^1$H-NMR (CDCl$_3$) δ 7.31 (1H, d, J=2.0 Hz), 7.26 (1H, dd, J=2.0, 8.3 Hz), 7.15 (1H, d, J=8.3 Hz), 7.14 (2H, d, J=8.4 Hz), 6.89 (2H, d, J=8.4 Hz), 5.49 (1H, br.s), 4.64 (1H, br.s), 3.77 (2H, br.s), 3.69 (2H, t, J=7.4 Hz), 3.02 (2H, t, J=7.4 Hz), 1.24 (9H, s).

Step 5. N-(tert-Butyl)-1-[4-(2-chloroethyl)phenyl]-2-ethyl-1H-benzimidazole-5-sulfonamide The title compound was prepared according to the procedure described in step 5 Example 1 from 3-amino-N-(tert-butyl)-4-[4-(2-chloroethyl)anilino]benzenesulfonamide (step 4) and propionyl chloride.

MS (EI) m/z 419 (M$^+$); $^1$H-NMR (CDCl$_3$) δ 8.34 (1H, d, J=2.0 Hz), 7.74 (1H, dd, J=2.0, 8.3 Hz), 7.47 (2H, d, J=8.6 Hz), 7.33 (2H, d, J=8.6 Hz), 7.16 (1H, d, J=8.3 Hz), 4.62 (1H, br.s), 3.83 (2H, t, J=7.0 Hz), 3.21 (2H, t, J=7.0 Hz), 2.82 (2H, q, J=7.4 Hz), 1.39 (3H, t, J=7.4 Hz) 1.24 (9H, s).

Step 6. 1-[4-(2-Azidoethyl)phenyl]-N-(tert-butyl)-2-ethyl-1H-benzimidazole-5-sulfonamide The title compound was prepared according to the procedure described in step 8 Example 1 from N-(tert-butyl)-1-[4-(2-chloroethyl)phenyl]-2-ethyl-1H-benzimidazole-5-sulfonamide (step 5).

MS (EI) m/z 426 (M$^+$); $^1$H-NMR (CDCl$_3$) δ 8.33 (1H, d, J=2.0 Hz), 7.73 (1H, dd, J=2.0, 8.4 Hz), 7.48 (2H, d, J=8.4 Hz), 7.33 (2H, d, J=8.4 Hz), 7.14 (1H, d, J=8.4 Hz), 4.47 (1H, br.s), 3.62 (2H, t, J=7.0 Hz), 3.03 (2H, t, J=7.0 Hz), 2.82 (2H, q, J=7.2 Hz), 1.38 (3H, t, J=7.2 Hz) 1.24 (9H, s).

Step 7. 1-[4-(2-Aminoethyl)phenyl]-N-(tert-butyl)-2-ethyl-1H-benzimidazole-5-sulfonamide The title compound was prepared according to the procedure described in step 9 of Example 1 from 1-[4-(2-azidoethyl)phenyl]-N-(tert-butyl)-2-ethyl-1H-benzimidazole-5-sulfonamide (step 6).

$^1$H-NMR (CDCl$_3$) δ 8.34 (1H, d, J=1.9 Hz), 7.74 (1H, dd, J=1.9, 8.3 Hz), 7.44 (2H, d, J=8.4 Hz), 7.28 (2H, d, J=8.4 Hz), 7.15 (1H, d, J=8.3 Hz), 4.88 (1H, br.s), 3.09 (2H, t, J=7.0 Hz), 2.95 (2H, t, J=7.0 Hz), 2.83 (2H, q, J=7.4 Hz), 1.37 (3H, t, J=7.4 Hz), 1.23 (9H, s).

Step 8. 5-[(tert-Butylamino)sulfonyl]-2-ethyl-1-(4-{2-[({[(4-methylphenyl)sulfonyl]amino}carbonyl)amino]ethyl}phenyl)-1H-benzimidazole The title compound was prepared according to the procedure described in step 10 of Example 1 from 1-[4-(2-aminoethyl)phenyl]-N-(tert-butyl)-2-ethyl-1H-benzimidazole-5-sulfonamide (step 7).

MS (ESI) m/z 598 (M+M)$^+$; $^1$H-NMR (CDCl$_3$) δ 8.32 (1H, d, J=1.3 Hz), 7.77–7.69 (3H, m), 7.41 (2H, d, J=8.3 Hz), 7.33–7.25 (4H, m), 7.11 (1H, d, J=8.6 Hz), 6.65 (1H, br.s), 4.59 (1H, s), 3.63–3.53 (2H, m), 2.95 (2H, t, J=7.0 Hz), 2.80 (2H, q, J=7.6 Hz), 2.41 (3H, s), 1.36 (3H, t, J=7.6 Hz) 1.23 (9H, s).

Example 88
5-(AMINOSULFONYL)-2-ETHYL-1-(4-{2-[({[(4-METHYLPHENYL)SULFONYL]AMINO}CARBONYL)AMINO]ETHYL}PHENYL)-1H-BENZIMIDAZOL[

A solution of 5-[(tert-butylamino)sulfonyl]-2-ethyl-1-(4-{2-[({[(4-methylphenyl)sulfonyl]amino}carbonyl)amino]ethyl}phenyl)-1H-benzimidazole (Example 87, 330 mg, 0.55 mmol) in trifluoroacetic acid (10 mL) was heated at 80° C. for 2 h. The mixture was concentrated and the residue was purified by flash chromatography on silica gel eluting with dichloromethane/methanol (10:1) to afford 215 mg (73%) of the title compound: MS (ESI) m/z 542 (M+M)$^+$; $^1$H-NMR (CDCl$_3$) δ 8.32 (1H, d, J=1.3 Hz), 7.77–7.69 (3H, m), 7.41 (2H, d, J=8.3 Hz), 7.33–7.25 (4H, m), 7.11 (1H, d, J=8.6 Hz), 6.65 (1H, br.s), 4.59 (1H, s), 3.63–3.53 (2H, m), 2.95 (2H, t, J=7.0 Hz), 2.80 (2H, q, J=7.6 Hz), 2.41 (3H, s), 1.36 (3H, t, J=7.6 Hz) 1.23 (9H, s).

Example 89
2-ETHYL-1-{2-[({[(4-METHYLPHENYL)SULFONYL]AMINO}CARBONYL)AMINO]ETHYL}-5-[(METHYLSULFONYL)AMINO]-1H-BENZIMIDAZOLE Step 1. 2-[4-(2,4-Dinitroanilino)phenyl]ethanol The title compound was prepared according to the procedure described in step 3 of Example 1 from 2-chloro-1,5-dinitrobenzene and 4-aminophenylethyl alcohol.

$^1$H-NMR (CDCl$_3$) δ 9.95 (1H, s), 9.18 (1H, d, J=2.4 Hz), 8.16 (1H, dd, J=2.7, 9.7Hz), 7.39 (2H, d, J=8.4 Hz), 7.26 (2H, d, J=8.1 Hz), 7.16 (1H, d, J=9.5 Hz), 3.93 (2H, dt, J=5.7, 6.2 Hz), 2.94 (2H, t, J=6.8 Hz), 1.50 (1H, t, J=5.7 Hz).

Step 2. 2-[4-(2-Amino-4-nitroanilino)phenyl]ethanol

The title compound was prepared according to the procedure described in step 2 of Example 40 from 2-[4-(2,4-dinitroanilino)phenyl]ethanol (step 1).

$^1$H-NMR (CDCl$_3$) δ 7.73–7.67 (2H, m), 7.22 (2H, d, J=8.3 Hz), 7.11 (1H, d, J=9.3 Hz), 7.04 (2H, d, J=8.3 Hz), 5.80 (1H, s), 3.88 (2H, dt, J=5.7, 6.0 Hz), 3.69 (2H, br.s), 2.87 (2H, t, J=6.4 Hz), 1.48 (1H, br).

Step 3. 2-[4-(2-ethyl-5-nitro-1H-benzimidazol-1-yl)phenyl] ethyl propionate

The title compound was prepared according to the procedure described in step 5 of Example 1 from 2-[4-(2-amino-4-nitroanilino)phenyl]ethanol (step 2) and propionyl chloride.

$^1$H-NMR (CDCl$_3$) δ 8.68 (1H, d, J=2.2 Hz), 8.13 (1H, dd, J=2.2, 9.0 Hz), 7.48 (2H, d, J=8.3 Hz), 7.31 (2H, d, J=8.3 Hz), 7.13 (1H, d, J=8.97 Hz), 4.39 (2H, t, J=6.8 Hz), 3.09 (2H, t, J=7.0 Hz), 2.81 (2H, q, J=7.5 Hz), 2.36 (2H, q, J=7.5 Hz), 1.38 (3H, t, J=7.5 Hz), 1.15 (3H, q, J=7.5 Hz).

Step 4. 2-[4-(5-Amino-2-ethyl-1H-benzimidazol-1-yl)phenyl]ethyl propionate

To a stirred solution of 2-[4-(2-ethyl-5-nitro-1H-benzimidazol-1yl)]phenyl]ethyl propionate (step 3, 1.12 g, 3.0 mmol) in ethanol/water (v/v, 2:1, 15 mL) was added ammonium chloride (80 mg, 1.5 mmol) and iron powder (840 mg, 15 mmol) at room temperature. The mixture was heated at reflux temperature for 4 h and filtered through a pad of Celite. The filtrate was concentrated, and the residue was dissolved in dichloromethane (200 mL), then dried (MgSO$_4$). Removal of solvent gave 0.84 g (83%) of the title compound as a yellow oil: $^1$H-NMR (CDCl$_3$) δ 7.41 (2H, d, J=8.3 Hz), 7.29 (2H, d, J=8.6 Hz), 7.10 (1H, d, J=1.8 Hz), 6.89 (1H, d, J=8.4 Hz), 6.63 (1H, dd, J=2.2, 8.4 Hz), 4,37 (2H, t, J=7.0 Hz), 3.05 82H, t, J=7.1 Hz), 2.79 (2H, q, J=7.5 Hz), 2.35 (2H, q, J=7.5 Hz), 1.33 (3H, t, J=7.50 Hz), 1.14 (3H, t, J=7.7 Hz).

Step 5. 2-(4-{2-Ethyl-5-[(methylsulfonyl)amino]-1H-benzimidazol-1-yl}phenyl)ethyl propionate To a stirred solution of 2-[4-(5-amino-2-ethyl-1H-benzimidazol-1-yl)phenyl]ethyl propionate (step 4, 1.18 g, 3.50 mmol) in dichloromethane (20 mL) was added methanesulfonyl chloride (0.40 mL, 5.25 mmol) and pyridine (0.42 mL, 5.25 mmol) at room temperature. After stirring for 6 h, the mixture was poured into 10% aqueous citric acid (100 mL) and extracted with ethyl acetate (100 mL). The aqueous layer was made basic with saturated aqueous sodium bicarbonate (100 mL) and extracted with ethyl acetate (100 mL). The combined organic extracts were washed with brine (100 mL) and dried (MgSO$_4$), and concentrated to afford 1.28 g (88%) of the title compound as brown amorphous: $^1$H-NMR (CDCl$_3$) δ 8.47 (1H, s), 7.66 (1H, d, J=1.7 Hz), 7.50 (2H, d, J=8.4 Hz), 7.42 (1H, dd, J=2.0, 8.8 Hz), 7.41 (2H, d, J=8.4 Hz), 7.09 (1H, d, J=8.8 Hz), 4.39 (2H, t, J=7.0 Hz), 3.09 (2H, t, J=6.8 Hz), 3.00 (2H, q, J=7.7 Hz), 2.36 (2H, q, J=7.7 Hz), 1.42 (3H, t, J=7.7 Hz), 1.15 (3H, t, J=7.5 Hz).

Step 6. 2-Ethyl-1-[4-(2-hydroxyethyl)phenyl]-1H-benzimidazol-5-yl}methanesulfonamide The title compound was prepared according to the procedure described in step 6 of Example 1 from 2-(4-{2-ethyl-5-[(methylsulfonyl)amino]-1H-benzimidazol-1-yl}phenyl)ethyl propionate (step 5).

$^1$H-NMR (CDCl$_3$) δ 7.63 (1H, d, J=1.8 Hz), 7.46 (2H, d, J=8.2 Hz), 7.29 (2H, d, J=8.4 Hz), 7.18 (1H, dd, J=2.1, 8.6 Hz), 7.07 (1H, d, J=8.6 Hz), 6.68 (1H, br), 3.99 (2H, t, J=6.4 Hz), 3.01 (2H, t, J=6.8 Hz), 2.98 (3H, s), 2.79 (2H, q, J=7.4 Hz), 1.35 (3H, t, J=7.6 Hz).

Step 7. N-{1-[4-(2-chloroethyl)phenyl]-2-ethyl-1H-benzimidazol-5-yl}methanesulfonamide The title compound was prepared according to the procedure described in step 7 of Example 1 from 2-ethyl-1-[4-(2-hydroxyethyl)phenyl]-1H-benzimidazol-5-yl}methanesulfonamide (step 6).

$^1$H-NMR (CDCl$_3$) δ 7.74–6.85 (7H, m), 3.83 (2H, t, J=7.1 Hz), 3.21 (2H, t, J=7.1 Hz), 2.98 (3H, s), 2.85 (2H, q, J=7.5 Hz), 1.38 (3H, t, J=7.5 Hz). 7.5 Hz).

Step 8. N-{1-[4-(2-Azidoethyl)phenyl]-2-ethyl-1H-benzimidazol-5-yl}methanesulfonamide The title compound was prepared according to the procedure described in step 8 of Example 1 from N-{1-[4-(2-chloroethyl)phenyl]-2-ethyl-1H-benzimidazol-5-yl}methanesulfonamide (step 7).

$^1$H-NMR (CDCl$_3$) δ 7.64 (1H, br), 7.45 (2H, d, J=8.3 Hz), 7.31 (2H, d, J=8.1 Hz), 7.19 (1H, dd, J=1.8, 8.8 Hz), 7.07 (1H, d, J=8.4 Hz), 6.81 (1H, s), 3.62 (2H, t, J=6.8 Hz), 3.02 (2H, t, J=7.0 Hz), 2.98 (3H, s), 2.79 (2H, q, J=7.5 Hz), 1.35 (3H, t, J=7.5 Hz).

Step 9. N-{1-[4-(2-Aminoethyl)phenyl]-6-chloro-2-ethyl-1H-benzimidazol-5-yl}methanesulfonamide The title compound was prepared according to the procedure described in step 9 of Example 1 from N-{1-[4-(2-azidoethyl)phenyl]-2-ethyl-1H-benzimidazol-5-yl}methanesulfonamide (step 8).

MS (EI) m/z 358 (M$^+$).

Step 10. N-{1-[4-(2-aminoethyl)phenyl]-2-ethyl-1H-benzimidazol-5-yl}methanesulfonamide The title compound was prepared according to the procedure described in step 10 of Example 1 from N-{1-[4-(2-aminoethyl)phenyl]-6-chloro-2-ethyl-1H-benzimidazol-5-yl}methanesulfonamide (step 9).

MS (ESI) m/z 556 (M+M)$^+$; $^1$H-NMR (CDCl$_3$) δ 9.49 (1H, s), 7.76 (2H, d, J=7.1 Hz), 7.51 (1H, br), 7.42–7.34 (6H, m), 7.07 (1H, d, J=8.6 Hz), 7.01 (1H, d, J=8.6 Hz), 6.53 (1H, br), 3.40–3.33 (2H, m), 2.89 (3H, s), 2.81–2.66 (4H, m), 2.33 (3H, s), 1.21 (3H, t, J=7.5 Hz); IR (KBr) α$_{max}$ 1697, 1684, 1508, 1458, 1148 cm$^{-1}$.

Example 90

2-ETHYL-5-HYDROXY-1-(4-{2-[({[(4-METHYLPHENYL)SULFONYL]AMINO}CARBONYL)AMINO]ETHYL}PHENYL)-1H-BENZIMIDAZOLE

Step 1. 1-[4-(2-Bromoethyl)phenyl]-2-ethyl-1H-benzimidazol-5-ol

A mixture of 1-[4-(2-chloroethyl)phenyl]-2-ethyl-5-methoxy-1H-benzimidazole (step 5 of Example 71, 600 mg, 1.9 mmol) in 48% hydrobromic acid (60 mL) was stirred at 100° C. for 6 h. After cooling, the mixture was neutralized with 2N aqueous NaOH and extracted with ethyl acetate (100 mL). The organic layer was washed with brine (50 mL), dried (Na$_2$SO$_4$), and concentrated to afford 890 mg (quant.) of the title compound as pale yellow solids: $^1$H-NMR (CDCl$_3$) δ 7.64 (4H, s), 7.16 (2H, m), 6.97–7.01 (1H, m), 3.86 (2H, t, J=7.1 Hz), 3.30 (2H, t, J=7.1 Hz), 2.92 (2H, q, J=7.8 Hz), 1.29 (3H, t, J=7.8 Hz).

Step 2. 1-[4-(2-Bromoethyl)phenyl]-2-ethyl-1H-benzimidazol-5-yl tert-butyl(dimethyl)silyl ether A mixture of 1-[4-(2-bromoethyl)phenyl]-2-ethyl-1H-benzimidazol-5-ol (step 1, 200 mg, 0.58 mmol), tert-butyldimethylsilyl chloride (100 mg, 0.7 mmol) and imidazole (47 mg, 1.45 mmol) in DMF (5 mL) was stirred at room temperature for 3 h. The reaction mixture was poured into water (50 mL), and extracted with ethyl acetate (100 mL). The organic layer was washed with brine (50 mL), then dried (Na$_2$SO$_4$). After removal of solvent, the crude product was purified by flash column chromatography on silica gel eluting with hexane/ethyl acetate (1:1) to afford 119 mg (45%) of the title compound as white solids: $^1$H-NMR (CDCl$_3$) δ 7.20 (2H, d, J=8.4 Hz), 7.10 (2H, d, J=8.4 Hz), 7.01 (1H, d, J=2.3 Hz), 6.72 (1H, d, J=8.6 Hz), 6.52 (1H, dd, J=2.3 Hz, 8.6 Hz), 3.45 (2H, t, J=7.4 Hz), 3.07 (2H, t, J=7.4 Hz),2.56 (2H, q, J=7.5 Hz), 1.14 (3H, t, J=7.5 Hz), 0.79 (9H, s), 0.05 (6H, s).

Step 3. 1-[4-(2-Azidoethyl)phenyl]-2-ethyl-1H-benzimidazol-5-yl tert-butyl(dimethyl)silyl ether The title compound was prepared according to the procedure described in step 8 of Example 1 from 1-[4-(2-bromoethyl)phenyl]-2-ethyl-1H-benzimidazol-5-yl tert-butyl(dimethyl)silyl ether (step 2).

$^1$H-NMR (CDCl$_3$) δ 7.20 (2H, d, J=8.3 Hz), 7.02–7.12 (3H, m), 6.70 (1H, d, J=8.6 Hz), 6.50–6.54 (1H, m), 3.39 (2H, t, J=6.9 Hz), 2.79 (2H, t, J=6.9 Hz), 2.55 (2H, q, J=7.6 Hz), 1.13 (3H, t, J=7.6 Hz), 0.79 (9H, s), 0.00 (6H, s).

Step 4. 2-[4-(5-{[tert-Butyl(dimethyl)silyl]oxy}-2-ethyl-1H-benzimidazol-1-yl)phenyl]ethylamine The title compound was prepared according to the procedure described in step 7 of Example 37 from 1-[4-(2-azidoethyl)phenyl]-2-ethyl-1H-benzimidazol-5-yl tert-butyl (dimethyl)silyl ether (step 3).

$^1$H-NMR (CDCl$_3$) δ 7.18 (2H, d, J=8.2 Hz), 7.02–7.08 (3H, m), 6.72 (1H, d, J=8.6 Hz), 6.52 (1H, dd, J=2.2 Hz, 8.6 Hz), 2.86 (2H, t, J=6.6 Hz), 2.66 (2H, t, J=6.6 Hz), 2.55 (2H, q, J=7.5 Hz), 1.13 (3H, t, J=7.5 Hz), 0.79 (9H, s), 0.00 (6H, s).

Step 5. 5-{[tert-Butyl(dimethyl)silyl]oxy}-2-ethyl-1-(4-{2-[({[(4-methylphenyl)sulfonyl]amino}carbonyl)amino]ethyl}phenyl)-1H-benzimidazole The title compound was prepared according to the procedure described in step 10 of Example 1 from 2-[4-(5-{[tert-butyl(dimethyl)silyl]oxy}-2-ethyl-1H-benzimidazol-1-1-yl))phenyl]ethylamine (step 4).

$^1$H-NMR (CDCl$_3$) δ 7.53 (2H, d, J=8.3 Hz), 7.02–7.13 (7H, m), 6.70 (1H, d, J=8.6 Hz), 6.52 (1H, dd, J=2.2 Hz, 8.6 Hz), 6.46 (1H, br.s), 3.37 (2H, t, J=6.4 Hz), 2.71 (2H, t, J=6.4 Hz), 2.53 (2H, q, J=7.6 Hz), 2.18 (3H, s), 1.11 (3H, t, J=7.6 Hz), 0.79 (9H, s), 0.00 (6H, s).

Step 6. 2-Ethyl-5-hydroxy-1-(4-{2-[({[(4-methylphenyl)sulfonyl]amino}carbonyl)amino]ethyl}phenyl)-1H-benzimidazole A solution of 5-{[tert-butyl(dimethyl)silyl]oxy}-2-ethyl-1-(4-{2-[({[(4-methylphenyl)sulfonyl]amino}carbonyl)amino]ethyl}phenyl)-1H-benzimidazole (step 5, 78 mg, 0.13 mmol) in THF (5 mL) was added tetrabutylammonium fluoride (1.0 M solution in THF, 0.16 mL, 0.16 mmol) at 0° C. The mixture was stirred at 0° C. for 2.5 h, then concentrated. The residue was dissolved in water (30 mL) and extracted with dichloromethane (50 mL). The organic layer was dried (Na$_2$SO$_4$) and concentrated. The residue was purified by flash column chromatography on silica gel eluting with dichloromethane/methanol (gradient elution from 20:1 to 10:1) to afford 57 mg (92%) of the title compound as white amorphous: MS (ESI) m/z 479 (M+M)$^+$; $^1$H-NMR (DMSO-d$_6$) δ 7.76 (2H, d, J=7.6 Hz), 7.35–7.39 (6H, m), 6.9 (1H, s), 6.85 (1H, d, J=8.6 Hz), 6.65 (1H, d, J=8.6 Hz), 6.51 (1H, br.s), 3.17 (2H, br.s), 2.76 (2H, t, 6.6 Hz), 2.67 (2H, q, J=7.6 Hz), 2.34 (3H, s), 1.20 (3H, t, J=7.6 Hz).

Example 91

2-ETHYL-4,5-DIMETHYL-1-(4-{2-[({[(4-METHYLPHENYL)SULFONYL]AMINO}CARBONYL)AMINO]ETHYL}PHENYL)-1H-BENZIMIDAZOLE

Step 1. 2-[(3,4-Dimethyl-2-nitroanilino)phenyl]ethanol

The title compound was prepared according to the procedure described in step 1 of Example 45 from 3,4-dimethyl-2-nitroaniline and 4-bromophenylethyl ethanol.

$^1$H-NMR (CDCl$_3$) δ 7.16 (2H, d, J=8.4 Hz), 7.09 (1H, s), 7.03 (2H, d, J=8.4 Hz), 6.91 (1H, s), 3.89–3.81 (2H, m), 2.83 (2H, t, J=6.4 Hz), 2.27 (3H, s), 2.25 (3H, s).

Step 2. 2-[(2-Amino-3,4-dimethylanilino)phenyl]ethanol

The title compound was prepared according to the procedure described in step 2 of Example 28 from 2-[(3,4-dimethyl-2-nitroanilino)phenyl]ethanol (step 1).

$^1$H-NMR (CDCl$_3$) δ 7.02 (2H, d, J=8.6 Hz), 6.86 (1H, d, J=7.9 Hz), 6.62–6.58 (3H, m), 5.09 (1H, br.s), 3.77 (2H, t, J=6.6 Hz), 2.74 (2H, t, J=6.6 Hz), 2.27 (3H, s), 2.11 (3H, s).

Step 3. 2-[4-(2-Ethyl-4,5-dimethyl-1H-benzimidazol-1-yl)phenyl]ethyl propionate

The title compound was prepared according to the procedure described in step 5 of Example 1 from 2-[(2-amino-3,4-dimethylanilino)phenyl]ethanol (step 2) and propionyl chloride.

MS (EI) m/z 350 (M$^+$).

Step 4. 2-[4-(2-Ethyl-4,5-dimethyl-1H-benzimidazol-1yl))phenyl]ethanol

The title compound was prepared according to the procedure described in step 6 of Example 1 from 2-[4-(2-ethyl-4,5-dimethyl-1H-benzimidazol-1yl))phenyl]ethyl propionate (step 3).

$^1$H-NMR (CDCl$_3$) δ 7.42 (2H, d, J=8.4 Hz), 7.27 (2H, d, J=8.4 Hz), 6.99 (1H, d, J=8.3 Hz), 6.82 (1H, d, J=8.3 Hz), 3.98 (2H, t, J=6.6 Hz), 2.99 (2H, t, J=6.6 Hz), 2.82 (2H, q, J=7.5 Hz), 2.63 (3H, s), 2.39 (3H, s), 1.26 (3H, t, J=7.5 Hz).

Step 5. 2-[4-(2-Ethyl-4,5-dimethyl-1H-benzimidazol-1-yl)phenyl]ethyl azide

The title compound was prepared according to the procedure described in step 5 of Example 26 from 2-[4-(2-ethyl-4,5-dimethyl-1H-benzimidazol-1yl))phenyl]ethanol (step 4).

$^1$H-NMR (CDCl$_3$) δ 7.42 (2H, d, J=8.6 Hz), 7.30 (2H, d, J=8.6 Hz), 7.00 (1H, d, J=8.2 Hz), 6.82 (1H, d, J=8.2 Hz), 3.61 (2H, t, J=7.1 Hz), 3.01 (2H, t, J=7.1 Hz), 2.83 (2H, q, J=7.6 Hz), 2.63 (3H, s), 2.39 (3H, s), 1.26 (3H, t, J=7.6 Hz).

Step 6. 2-[4-(2-Ethyl-4,5-dimethyl-1H-benzimidazol-1yl))phenyl]ethylamine

The title compound was prepared according to the procedure described in step 9 of Example 1 from 2-[4-(2-ethyl-4,5-dimethyl-1H-benzimidazol-1-yl)phenyl]ethyl azide (step 5).

$^1$H-NMR (CDCl$_3$) δ 7.39 (2H, d, J=8.4 Hz), 7.28 (2H, d, J=8.4 Hz), 6.99 (1H, d, J=8.2 Hz), 6.83 (1H, d, J=8.2 Hz), 3.09 (2H, t, J=6.6 Hz), 2.92–2.79 (4H, m), 2.63 (3H, s), 2.39 (3H, s), 1.27 (3H, t, J=7.6 Hz).

Step 7. 2-Ethyl-4,5-dimethyl-1-(4-{2-[({[(4-methylphenyl)sulfonyl]amino}carbonyl)amino]ethyl}phenyl)-1H-benzimidazole The title compound was prepared according to the procedure described in step 10 of Example 1 from 2-[4-(2-ethyl-4,5-dimethyl-1H-benzimidazol-1-yl)phenyl]ethylamine (step 6).

$^1$H-NMR (CDCl$_3$) δ 7.76 (2H, d, J=8.2 Hz), 7.30–7.19 (6H, m), 7.00 (1H, d, J=8.2 Hz), 6.81 (1H, d, J=8.2 Hz), 6.65 (1H, m), 3.56–3.54 (2H, m), 2.89 (2H, t, J=6.9 Hz), 2.80 (2H, q, J=7.6 Hz), 2.59 (3H, s), 2.38 (6H, s), 1.22 (3H, t, J=7.6 Hz).

Example 92

2-ETHYL-4,5-DIMETHYL-1-(4-{2-[({[(4-METHYLPHENYL)SULFONYL]AMINO}CARBONYL)AMINO]ETHYL}PHENYL)-1H-BENZIMIDAZOLE, SODIUM SALT

The title compound was prepared according to the procedure described in Example 2 from 2-ethyl-4,5-dimethyl-1-(4-{2-[({[(4-methylphenyl)sulfonyl]amino}carbonyl)amino]ethyl}phenyl)-1H-benzimidazole (Example 91).

$^1$H-NMR (DMSO-d$_6$) δ 7.59 (2H, d, J=8.4 Hz), 7.39–7.30 (4H, m), 7.12 (2H, d, J=8.4 Hz), 6.94 (1H, d, J=8.3 Hz), 6.77 (1H, d, J=8.3 Hz), 3.13 (2H, m), 2.74–2.67 (4H, m), 2.48 (3H, s), 2.30 (3H, s), 2.27 (3H, s), 1.19 (3H, t, J=7.5 Hz); IR (KBr)$_{\nu max}$ 1599, 1516, 1425, 1227, 1128, 1086 cm$^{-1}$.

Example 93
4,6-DIMETHYL-2-ETHYL-3-(4-{2-[({[(4-METHYLPHENYL)SULFONYL]AMINO}CARBONYL)AMINO]ETHYL}PHENYL)-1H-BENZIMIDAZOLE Step 1. 2-[4-(3,5-Dimethyl-2-nitroanilino)phenyl]ethanol The title compound was prepared according to the procedure described in step 3 of Example 1 from 4,6-dimethyl-2-fluoronitrobenzene and 4-aminophenylethyl alcohol.

$^1$H-NMR (CDCl$_3$) δ 8.08 (1H, br.s), 7.22 (2H, d, J=8.4 Hz), 7.13 (2H, d, J=8.4 Hz), 6.91 (1H, s), 6.51 (1H, s), 3.89 (2H, t, J=6.4 Hz), 2.87 (2H, t, J=6.4 Hz), 2.47 (3H, s).

Step 2. 2-[4-(2-Amino-3,5-dimethylanilino)phenyl]ethanol

The title compound was prepared according to the procedure described in step 4 of Example 1 from 2-[4-(3,5-dimethyl-2-nitroanilino)phenyl]ethanol (step 1).

$^1$H-NMR (CDCl$_3$) δ 6.97–7.04 (2H, m), 6.78 (1H, s), 6.74 (1H, s), 6.59–6.67 (1H, s), 5.15 (1H, br.s), 3.76 (2H, t, J=6.6 Hz), 2.74 (2H, t, J=6.6 Hz), 2.18 (3H, s), 2.17 (3H, s).

Step 3. 2-[4-(2-Ethyl-4,6-dimethyl-1H-benzimidazol-1-yl)phenyl]ethyl propionate

The title compound was prepared according to the procedure described in step 5 of Example 1 from 2-[4-(2-amino-3,5-dimethylanilino)phenyl]ethanol (step 2) and propionyl chloride.

TLC RF=0.7 (hexane/ethyl acetate=1:1).

Step 4. 2-[4-(2-Ethyl-4,6-dimethyl-1H-benzimidazol-1-yl)phenyl]ethanol

The title compound was prepared according to the procedure described in step 6 of Example 1 from 2-[4-(2-amino-3,5-dimethylanilino)phenyl]ethyl propionate (step 3).

$^1$H-NMR (CDCl$_3$) δ 7.42 (2H, d, J=8.1 Hz), 7.27 (2H, d, J=8.1 Hz), 6.90 (1H, s), 6.71 (1H, s), 3.98 (2H, t, J=6.4 Hz), 2.99 (2H, t, J=6.4 Hz), 2.81 (2H, q, J=7.3 Hz), 2.65 (3H, s), 2.36 (3H, s), 1.24 (3H, t, J=7.3 Hz).

Step 5. 1-[4-(2-Chloroethyl)phenyl]-2-ethyl-4,6-dimethyl-1H-benzimidazole

The title compound was prepared according to the procedure described in step 7 of Example 1 from 2-[4-(2-ethyl-4,6-dimethyl-1H-benzimidazol-1yl))phenyl]ethanol (step 4).

$^1$H-NMR (CDCl$_3$) δ 7.42 (2H, d, J=8.0 Hz), 7.30 (2H, d, J=8.0 Hz), 6.90 (1H, s), 6.71 (1H, s), 3.81 (2H, t, J=7.2 Hz), 3.19 (2H, t, J=7.2 Hz), 2.81 (2H, q, J=7.7 Hz), 2.67 (3H, s), 2.37 (3H, s), 1.25 (3H, t, J=7.7 Hz).

Step 6. 2-[4-(2-Ethyl-4,6-dimethyl-1H-benzimidazol-1-yl)phenyl]ethyl azide

The title compound was prepared according to the procedure described in step 8 of Example 1 from 1-[4-(2-chloroethyl)phenyl]-2-ethyl-4,6-dimethyl-1H-benzimidazole (step 5).

$^1$H-NMR (CDCl$_3$) δ 7.42 (2H, d, J=8.3 Hz), 7.30 (2H, d, J=8.3 Hz), 6.90 (1H, s), 3.62 (2H, t, J=7.0 Hz), 3.01 (2H, d, J=7.0 Hz), 2.81 (2H, q, J=7.5 Hz), 2.66 (3H, s), 2.36 (3H, s), 1.25 (3H, t, J=7.5 Hz).

Step 7. 2-[4-(2-Ethyl-4,6-dimethyl-1H-benzimidazol-1yl))phenyl]ethylamine

The title compound was prepared according to the procedure described in step 9 of Example 1 from 2-[4-(2-ethyl-4,6-dimethyl-1H-benzimidazol-1yl))phenyl]ethyl azide (step 6).

$^1$H-NMR (CDCl$_3$) δ 7.40 (2H, d, J=8.2 Hz), 7.27 (2H, d, J=8.2 Hz), 6.89 (1H, s), 6.71 (1H, s), 3.07 (2H, t, J=6.9 Hz), 2.77–2.89 (4H, m), 2.67 (3H, s), 2.36 (3H, s), 1.25 (3H, t, J=7.6 Hz).

Step 8. 2-Ethyl-4,6-dimethyl-1-(4-{2-[({[(4-methylphenyl)sulfonyl]amino}carbonyl)amino]ethyl}phenyl)-1H-benzimidazole The title compound was prepared according to the procedure described in step 10 of Example 1 from 2-[4-(2-ethyl-4,6-dimethyl-1H-benzimidazol-1-yl)phenyl]ethylamine (step 7). mp 108–112° C.; MS (ESI) m/z 491 (M+M)$^+$; $^1$H-NMR (CDCl$_3$) δ 7.75 (2H, d, J=8.2 Hz), 7.18–7.29 (6H, m), 6.89 (1H, s), 6.67 (1H, s), 6.62 (1H, br.s), 3.51 (2H, br. 2.86 (2H, br.s), 2.76 (2H, q, J=7.4 Hz), 2.63 (3H, s), 2.37 (3H, s), 2.33 (3H, s), 1.20 (3H, t, J=7.4 Hz).

Example 94
5,6-DIMETHYL-1-(4-{2-[({[(4-METHYLPHENYL)SULFONYL]AMINO}CARBONYL)AMINO]ETHYL}PHENYL)-1H-BENZIMIDAZOLE Step 1. 2-[(4,5-Dimethyl-2-nitroanilino)phenyl]ethanol The title compound was prepared according to the procedure described in step 1 of Example 45 from 4,5-dimethyl-2-nitroaniline and 4-bromophenylethyl alcohol.

$^1$H-NMR (CDCl$_3$) δ 9.39 (1H, br.s), 7.96 (1H, s), 7.27 (2H, d, J=8.4 Hz), 7.21 (2H, d, J=8.4 Hz), 7.01 (1H, s), 3.91 (2H, q, H=6.4 Hz), 2.90 (2H, t, J=6.4 Hz), 2.20 (3H, s), 2.19 (3H, s).

Step 2. 2-[(2-Amino-4,5-dimethylanilino)phenyl]ethanol

The title compound was prepared according to the procedure described in step 2 of Example 28 from 2-[(4,5-dimethyl-2-nitroanilino)phenyl]ethanol (step 1).

$^1$H-NMR (CDCl$_3$) δ 7.04 (2H, d, J=8.4 Hz), 6.86 (1H, s), 6.64 (2H, d, J=8.4 Hz), 6.61 (1H, s), 3.79 (2H, t, J=6.6 Hz), 2.76 (2H, t, J=6.6 Hz), 2.19 (3H, s), 2.12 (3H, s).

Step 3. 2-[4-(2-Ethyl-5,6-dimethyl-1H-benzimidazol-1-yl)phenyl]ethyl propionate

The title compound was prepared according to the procedure described in step 5 of Example 1 from 2-[(2-amino-4,5-dimethylanilino)phenyl]ethanol (step 2) and propionyl chloride.

MS (EI) m/z 350 (M$^+$).

Step 4. 2-[4-(2-Ethyl-5,6-dimethyl-1H-benzimidazol-1yl))phenyl]ethanol

The title compound was prepared according to the procedure described in step 6 of Example 1 from 2-[4-(2-ethyl-5,6-dimethyl-1H-benzimidazol-1yl))phenyl]ethyl propionate (step 3).

$^1$H-NMR (CDCl$_3$) δ 7.52 (1H, s), 7.44 (2H, d, J=8.3 Hz), 7.28 (2H, d, J=8.3 Hz), 6.87 (1H, s), 4.00 (2H, t, J=6.6 Hz), 3.01 (2H, t, J=6.6 Hz), 2.76 (2H, q, J=7.5 Hz), 2.36 (3H, s), 2.29 (3H, s), 1.31 (3H, t, J=7.5 Hz).

Step 5. 2-[4-(2-Ethyl-5,6-dimethyl-1H-benzimidazol-1-yl)phenyl]ethyl azide

The title compound was prepared according to the procedure described in step 5 of Example 26 from 2-[4-(2-ethyl-5,6-dimethyl-1H-benzimidazol-1yl))phenyl]ethanol (step 4).

TLC RF=0.70 (hexane/ethyl acetate=1:1).

Step 6. 2-[4-(2-Ethyl-5,6-dimethyl-1H-benzimidazol-1yl))phenyl]ethylamine

The title compound was prepared according to the procedure described in step 9 of Example 1 from 2-[4-(2-ethyl-5,6-dimethyl-1H-benzimidazol-1-yl)phenyl]ethyl azide (step 5).

$^1$H-NMR (CDCl$_3$) δ 7.53 (1H, s), 7.40 (2H, d, J=8.1 Hz), 7.28 (2H, d, J=8.1 Hz), 6.87 (1H, s), 3.17 (2H, t, J=7.3 Hz), 3.00 (2H, t, J=7.3 Hz), 2.76 (2H, q, J=7.5 Hz), 2.36 (3H, s), 2.29 (3H, s), 1.31 (3H, t, J=7.5 Hz).

Step 7. 2-Ethyl-5,6-dimethyl-1-(4-{2-[({[(4-methylphenyl)sulfonyl]amino}carbonyl)amino]ethyl}phenyl)-1H-benzimidazole The title compound was prepared according to the procedure described in step 10 of Example 1 from 2-[4-(2-ethyl-5,6-dimethyl-1H-benzimidazol-1yl))phenyl]ethylamine (step 6).

$^1$H-NMR (CDCl$_3$) δ 7.79 (2H, d, J=8.1 Hz), 7.48 (1H, s), 7.29–7.15 (6H, m), 6.86 (1H, s), 6.60 (1H, br.s), 3.57–3.55 (2H, m), 2.91–2.89 (2H, m), 2.70 (2H, q, J=7.5 Hz), 2.39 (3H, s), 2.35 (3H, s), 2.27 (3H, s), 1.25 (3H, t, J=7.5 Hz).

Example 95
5,6-DIMETHYL-1-(4-{2-[({[(4-METHYLPHENYL) SULFONYL]AMINO}CARBONYL)AMINO] ETHYL}PHENYL)-1H-BENZIMIDAZOLE, SODIUM SALT The title compound was prepared according to the procedure described in Example 2 from 2-ethyl-5,6-dimethyl-1-(4-{2-[({[(4-methylphenyl)sulfonyl]amino}carbonyl) amino]ethyl}phenyl)-1H-benzimidazole (Example 94).

$^1$H-NMR (DMSO-d$_6$) δ 7.60 (2H, d, J=8.1 Hz), 7.39–7.32 (5H, m), 7.13 (2H, d, J=8.1), 6.86 (1H, s), 3.16 (2H, m), 2.73–2.64 (4H, m), 2.29 (3H, s), 2.27 (3H, s), 2.23 (3H, s), 1.20 (3H, t, J=7.4 Hz); IR (KBr)α$_{max}$ 1599, 1516, 1468, 1404, 1283, 1236, 1130, 1086 cm$^{-1}$.

Example 96
5,6-DICHLORO-2-ETHYL-1-(4-{2-[({[(4-METHYLPHENYL)SULFONYL]AMINO}CARBONYL) AMINO]ETHYL}PHENYL)-1H-BENZIMIDAZOLE Step 1. 2-[4-(4,5-Dichloro-2-nitroanilino)phenyl]ethanol The title compound was prepared according to the procedure described in step 3 of Example 1 from 2,4,5-trichloronitrobenzene and 4-aminophenylethyl alcohol.

MS (EI) m/z 327 (M$^+$).

Step 2. 2-[4-(2-Amino-4,5-dichloroanilino)phenyl]ethanol

The title compound was prepared according to the procedure described in step 2 of Example 28 from 2-[4-(4,5-dichloro-2-nitroanilino)phenyl]ethanol (step 1).

$^1$H-NMR (CDCl$_3$) δ 7.16 (1H, s), 7.11 (2H, d, J=8.0 Hz), 6.87 (1H, s), 6.74 (2H, d, J=8.0 Hz), 5.10 (1H, br.s), 3.90–3.60 (2H, m), 2.79 (2H, t, J=7.0 Hz).

Step 3. 2-[4-(5,6-Dichloro-2-ethyl-1H-benzimidazol-1-yl) phenyl]ethyl propionate The title compound was prepared according to the procedure described in step 5 of Example 1 from 2-[4-(2-amino-4,5-dichloroanilino)phenyl]ethanol (step 2) and propionyl chloride.

MS (EI) m/z 390 (M$^+$); $^1$H-NMR (CDCl$_3$) δ 7.84 (1H, s), 7.45 (2H, d, J=8.1 Hz), 7.27 (2H, d, J=8.1 Hz), 7.16 (1H, s), 4.37 (2H, t, J=6.8 Hz), 3.09 (2H, t, J=6.8 Hz), 2.77 (2H, q, J=7.5 Hz), 2.36 (2H, q, J=7.5 Hz), 1.35 (3H, t, J=7.5 Hz), 1.16 (3H, t, J=7.5 Hz).

Step 4. 2-[4-(5,6-Dichloro-2-ethyl-1H-benzimidazol-1-yl) phenyl]ethanol

The title compound was prepared according to the procedure described in step 6 of Example 1 from 2-[4-(5,6-dichloro-2-ethyl-1H-benzimidazol-1yl))phenyl]ethyl propionate (step 3).

$^1$H-NMR (CDCl$_3$) δ 7.84 (1H, s), 7.47 (2H, d, J=8.0 Hz), 7.28 (2H, d, J=8.0 Hz), 7.18 (1H, s), 4.10–3.94 (2H, m), 3.01 (2H, t, J=6.4 Hz), 2.77 (2H, q, J=7.5 Hz), 1.34 (3H, t, J=7.5 Hz).

Step 5. 2-[4-(5,6-Dichloro-2-ethyl-1H-benzimidazol-1-yl) phenyl]ethyl azide

The title compound was prepared according to the procedure described in step 5 Example 26 from 2-[4-(5,6-dichloro-2-ethyl-1H-benzimidazol-1yl)phenyl]ethanol (step 4).

MS (EI) m/z 359 (M$^+$); $^1$H-NMR (CDCl$_3$) δ 7.85 (1H, s), 7.46 (2H, d, J=8.1 Hz), 7.28 (2H, d, J=8.1 Hz), 7.17 (1H, s), 3.62 (2H, t, J=7.0 Hz), 3.02 (2H, t, J=7.0 Hz), 2.76 (2H, q, J=7.5 Hz), 1.34 (3H, t, J=7.5 Hz).

Step 6. 2-[4-(5,6-Dichloro-2-ethyl-1H-benzimidazol-1-yl) phenyl]ethylamine

The title compound was prepared according to the procedure described in step 7 of Example 37 from 2-[4-(5,6-dichloro-2-ethyl-1H-benzimidazol-1yl))phenyl]ethyl azide (step 5).

$^1$H-NMR (CDCl$_3$) δ 7.84 (1H, s), 7.43 (2H, d, J=8.4 Hz), 7.27 (2H, d, J=8.4 Hz), 7.22 (1H, s), 3.14 (2H, t, J=7.2 Hz), 2.97 (2H, t, J=7.2 Hz), 2.76 (2H, q, J=7.6 Hz), 2.10 (2H, br.s), 1.34 (3H, t, J=7.6 Hz).

Step 7. 5,6-Dichloro-2-ethyl-1-(4-{2-[({[(4-methylphenyl)sulfonyl]amino}carbonyl)amino] ethyl}phenyl)-1H-benzimidazole The title compound was prepared according to the procedure described in step 10 of Example 1 from 2-[4-(5,6-dichloro-2-ethyl-1H-benzimidazol-1yl))phenyl]ethylamine (step 6).

$^1$H-NMR (CDCl$_3$) δ 8.01 (1H, s), 7.70 (2H, d, J=8.3 Hz), 7.46 (2H, d, J=8.3 Hz), 7.36–7.29,(3H, m) 7.24 (2H, d, J=8.3 Hz), 6.81 (1H, br.s), 3.57–3.46 (2H, m), 3.06–2.88 (4H, m), 2.38 (3H, s), 1.43 (3H, t, J=6.9 Hz).

Example 97
2-[4-(5,6-DICHLORO-2-ETHYL-1H-BENZIMIDAZOL-1-YL)PHENYL]ETHYL(4-METHYLPHENYL) SULFONYLCARBAMATE The title compound was prepared according to the procedure described in Example 3 from 2-[4-(5,6-dichloro-2-ethyl-1H-benzimidazol-1-yl)phenyl]ethanol (step 4 of Example 96).

$^1$H-NMR (CDCl$_3$) δ 7.92 (2H, d, J=8.4 Hz), 7.85 (1H, s), 7.37 (2H, d, J=8.4 Hz), 7.35 (2H, d, J=8.4 Hz), 7.24 (2H, d, J=8.4 Hz), 7.16 (1H, s), 4.72 (1H, br.s), 4.38 (2H, t, J=6.8 Hz), 3.03 (2H, t, J=6.8 Hz), 2.75 (2H, q, J=7.5 Hz), 2.44 (3H, s), 1.34 (3H, t, J=7.5 Hz).

Example 98
5,6-DICHLORO-2-ETHYL-1-(4-{2-[HYDROXY({[(4-METHYLPHENYL)SULFONYL]AMINO}CARBONYL) AMINO]ETHYL}PHENYL)-1H-BENZIMIDAZOLE Step 1. 1-[4-(2-{(tert-Butoxycarbonyl)[(tert-butoxycarbonyl)oxy]amino}ethyl)phenyl]-5,6-dichloro-2-ethyl-1H-benzimidazole To a stirred mixture of 2-[4-(5,6-dichloro-2-ethyl-1H-benzimidazol-1-yl)phenyl]ethanol (Example 96, 100 mg, 0.3 mmol), N,O-Bis-tert-butoxycarbonylhydroxylamine (Baillie, L. C.; Batsanov, A.; Bearder, J. R.; Whiting, D. A. J. Chem. Soc. Perkin Trans. 1, 1998, 20, 3471., 140 mg, 0.6 mmol) and triphenylphosphine (158 mg, 0.6 mmol) in THF (10 mL) was added diethyl azodicarboxylate (DEAD) (0.1 mL, 0.6 mmol). The mixture was stirred under nitrogen atmosphere at room temperature for 2.5 h. The solvent was removed and the residue was purified by flash column chromatography on silica gel eluting with hexane/ethyl acetate (1:1) to afford 174 mg (quant.) of the title compound as yellow amorphous: $^1$H-NMR (CDCl$_3$) δ 7.84 (1H, s), 7.46 (2H, d, J=8.4 Hz), 7.25 (2H, d, J=8.4 Hz), 7.16 (1H, s), 3.92 (2H, t, J=6.7 Hz), 3.05 (2H, t, J=6.7 Hz), 2.76 (2H, q, J=7.6 Hz), 1.56 (9H, s), 1.46 (9H, s), 1.33 (3H, t, J=7.6 Hz).

Step 2. N-{2-[4-(5,6-Dichloro-2-ethyl-1H-benzimidazol-1-yl)phenyl]ethyl}hydroxylamine A mixture of 1-[4-(2-{(tert-butoxycarbonyl)[(tert-butoxycarbonyl)oxy]amino}ethyl)phenyl]-5,6-dichloro-2-ethyl-1H-benzimidazole (step 1, 174 mg, 0.3 mmol) and 2N hydrochloric acid (3 mL) in ethyl acetate (20 mL) was stirred at room temperature for 1 day. The reaction mixture was poured into water (100 mL), neutralized with saturated aqueous sodium bicarbonate, and extracted with ethyl acetate (100 mL). The organic layer was washed with brine (50 mL), dried (Na$_2$SO$_4$), and concentrated to afford 162 mg (quant.) of the title compound as a yellow oil: $^1$H-NMR (CDCl$_3$) δ 10.35 (2H, br.s), 7.89 (1H, s), 7.46–7.50 (2H, m), 7.29 (2H, d, J=6.8 Hz), 7.17 (1H, s), 3.37 (2H, t, J=6.9 Hz), 3.12 (2H, t, J=6.9 Hz), 2.80 (2H, J=6.9 Hz), 1.34 (3H, m).

Step 3. 5,6-Dichloro-2-ethyl-1-(4-{2-[hydroxy({[(4-methylphenyl)sulfonyl]amino}carbonyl)amino] ethyl}phenyl)-1H-benzimidazole The reaction was carried out according to the procedure described in step 10 of Example 1 from N-{2-[4-(5,6- dichloro-2-ethyl-1H-benzimidazol-1yl))phenyl]ethyl}hydroxylamine (step 2)

MS (ESI) m/z 547 (M+M)⁺; ¹H-NMR (CDCl₃) δ: 7.92 (2H, d, J=8.4 Hz), 7.79 (2H, d, J=7.2 Hz), 7.34–7.45 (2H, m), 7.13–7.18 (4H, m), 3.85 (1H, br.s), 3.05 (2H, br.s), 2.66–2.80 (4H, m), 2.38 (3H, s), 1.32 (3H, t, J=7.4 Hz); IR (KBr)α$_{max}$ 1654, 1517, 1452, 1164, 1095, 869 cm⁻¹.

Example 99
5,6-DICHLORO-2-ETHYL-1-(4-{cis-3-[({[(4-METHYLPHENYL)SULFONYL]AMINO}CARBONYL)AMINO]CYCLOBUTYL}PHENYL)-1H-BENZIMIDAZOLE Step 1. trans-3-Phenylcyclobutyl Benzoate To a stirred solution of cis-3-phenylcyclobutanol (Eckehard, V. D.; et al. *Chem. Ber.*, 1993, 126, 2759., 4.6 g, 30.2 mmol), triphenylphosphine (3.3 g, 59.1 mmol) and benzoic acid (7.6 mg, 62.3 mmol) was added diethyl azodicarboxylate (DEAD) (10.9 g, 62.3 mmol) at room temperature. The resulting mixture was stirred at room temperature for 40 min, then the mixture was concentrated. The residue was dissolved in diethyl ether (100 mL) and washed with saturated aqueous sodium bicarbonate (50 mL), water (50 mL), and brine (50 mL). The organic layer was dried (Na₂SO₄), and concentrated. Purification by flash column chromatography on silica gel eluting with hexane/ethyl acetate (10:1) to afford 6.52 g (86%) of the title compound as a pale yellow oil: ¹H-NMR (CDCl₃) δ 7.71–7.20 (10H, m), 5.49–5.41 (1H, m), 3.82–3.72 (1H, m), 2.78–2.64 (4H, m).

Step 2. trans-3-Phenylcyclobutanol

To a solution of trans-3-phenylcyclobutyl benzoate (step 1, 6.5 g, 26.0 mmol) in methanol (100 mL) was added 4N aqueous LiOH (20 mL, 80 mmol) and the resulting mixture was stirred at room temperature for 10 min. The mixture was concentrated. The residue was dissolved in water (100 mL) and extracted with ethyl acetate (100 mL). The organic layer was washed with brine (100 mL), dried (Na₂SO₄), and concentrated. Purification by flash column chromatography on silica gel eluting with hexane/ethyl acetate (5:1) to afford 3.65 g (93%) of the title compound as a colorless oil: ¹H-NMR (CDCl₃) δ 7.34–7.16 (5H, m), 4.60–4.51 (1H, m), 3.69–3.59 (1H, m), 2.55–2.37 (4H, m).

Step 3. trans-3-(4-Nitrophenyl)cyclobutanol

To a mixture of nitric acid (fuming, 2.3 mL) and acetic anhydride (25 mL) was added dropwise a mixture of trans-3-phenylcyclobutyl benzoate (step 2, 3.7 g, 24.6 mmol) and sulfuric acid in acetic anhydride (25 mL) at −23° C. The resulting mixture was stirred in an ice-bath for 1.5 h. The mixture was poured into ice water (200 mL) and extracted with dichloromethane (2×100 mL). The organic layer was washed with water and brine (100 mL), then dried (Na₂SO₄), and concentrated. The oily residue was dissolved in methanol (100 mL), and 4N aqueous LiOH (50 mL) was added. The resulting mixture was stirred at room temperature for 10 min, then concentrated. The residue was dissolved in water (100 mL) and extracted with ethyl acetate (100 mL). The organic layer was washed with brine, dried (Na₂SO₄), and concentrated. Purification by flash column chromatography on silica gel eluting with hexane/ethyl acetate (2:1) to afford 2.7 g (56%) of the title compound as a pale yellow oil: MS (EI) m/z 193 (M⁺); ¹H-NMR (CDCl₃) δ 8.18 (2H, d, J=8.6 Hz), 7.38 (2H, d, J=8.6 Hz), 4.62–4.52 (1H, m), 3.81–3.71 (1H, m), 2.54–2.45 (4H, m).

Step 4. trans-3-(4-Aminophenyl)cyclobutanol

To a stirred solution of trans-3-(4-nitrophenyl)cyclobutanol (step 3, 1.0 g, 4.9 mmol) in methanol (20 mL) was added 10% Pd—C (50 mg). The mixture was stirred at room temperature under hydrogen atmosphere for 2.5 h. The palladium catalyst was removed by filtration and washed with methanol (100 mL) and ethyl acetate (100 mL). The filtrate was concentrated under reduced pressure to afford 0.9 g (quant.) of the title compound as pale yellow solids: MS (EI) m/z 163 (M⁺); ¹H-NMR (CDCl₃) δ 7.03 (2H, d, J=8.3 Hz), 6.66 (2H, d, J=8.3 Hz), 4.56–4.47 (1H, m), 3.58–3.48 (3H, m), 2.48–2.31 (2H, m), 1.73 (1H, d, J=5.1 Hz).

Step 5. trans-3-[4-(4,5-Dichloro-2-nitroanilino)phenyl]cyclobutanol

The title compound was prepared according to the procedure described in step 3 of Example 1 from 2,4,5-trichloronitrobenzene and trans-3-(4-aminophenyl)cyclobutanol (step 4).

¹H-NMR (CDCl₃) δ 9.40 (1H, br.s), 8.27 (1H, s), 7.33 (2H, d, J=8.1 Hz), 7.22 (2H, d, J=8.1 Hz), 7.19 (1H, s), 4.63–4.55 (1H, m), 3.73–3.63 (1H, m), 2.57–2.43 (4H, m).

MS (EI) m/z: 352 (M⁺).

Step 6. trans-3-[4-(2-Amino-4,5-dichloroanilino)phenyl]cyclobutanol

The title compound was prepared according to the procedure described in step 3 of Example 6 from trans-3-[4-(4,5-dichloro-2-nitroanilino)phenyl]cyclobutanol (step 5).

¹H-NMR (CDCl₃) δ 7.16 (1H, s), 7.12 (2H, d, J=8.6 Hz), 6.86 (1H, s), 6.75 (2H, d, J=8.6 Hz), 5.08 (1H, br.s), 4.58–4.49 (1H, m), 3.77 (2H, br.s), 3.62–3.52 (1H, m), 2.50–2.34 (4H, m).

Step 7. trans-3-[4-(5,6-Dichloro-2-ethyl-1H-benzimidazol-1-yl)phenyl]cyclobutyl propionate The title compound was prepared according to the procedure described in step 5 of Example 1 from trans-3-[4-(2-amino-4,5-dichloroanilino)phenyl]cyclobutanol (step 6) and propionyl chloride.

TLC RF=0.56 (ethyl acetate/hexane=1:1).

Step 8. trans-3-[4-(5,6-Dichloro-2-ethyl-1H-benzimidazol-1-yl)phenyl]cyclobutanol The title compound was prepared according to the procedure described in step 6 of Example 1 from trans-3-[4-(2-amino-4,5-dichloroanilino)phenyl]cyclobutyl propionate (step 7).

MS (EI) m/z: 360 (M⁺); ¹H-NMR (CDCl₃) δ 7.85 (1H, br.s), 7.45 (2H, d, J=8.1 Hz), 7.27 (2H, d, J=8.1 Hz), 7.18 (1H, br.s), 4.65–4.55 (1H, m), 3.83–3.73 (1H, m), 2.77 (2H, q, J=7.5 Hz, (2.63–2.48 (4H, m), 1.34 (3H, t, J=7.5 Hz).

Step 9. cis-3-[4-(5,6-Dichloro-2-ethyl-1H-benzimidazol-1-yl)phenyl]cyclobutyl azide To a stirred solution of trans-3-[4-(5,6-dichloro-2-ethyl-1H-benzimidazol-1-yl)phenyl]cyclobutanol (step 8, 572 mg, 1.6 mmol), triphenylphosphine (623 mg, 2.4 mmol) and diphenylphosphoryl azide (DPPA) (655 mg, 2.4 mmol) in THF (8 mL) was added diethyl azodicarboxylate (415 mg, 2.4 mmol) at room temperature. The resulting mixture was stirred at room temperature for 3 h, then the mixture was diluted with ethyl acetate (100 mL) and washed with water (100 mL) and brine (100 mL). The organic layer was dried (Na₂SO₄), and concentrated. Purification by flash column chromatography on silica gel eluting with hexane/ethyl acetate (2:1) to afford 506 mg (83%) of the title compound as colorless solids:

MS (EI) m/z: 385 (M⁺); ¹H-NMR (CDCl₃) δ 7.84 (1H, br.s), 7.42 (2H, d, J=8.3 Hz), 7.28 (2H, d, J=8.3 Hz), 7.17 (1H, br.s), 3.98–3.88 (1H, m), 3.37–3.25 (1H, m), 2.89–2.75 (2H, m), 2.77 (2H, q, J=7.6 Hz), 2.34–2.23 (2H, m), 1.34 (3H, t, J=7.6 Hz).

Step 10. cis-3-[4-(5,6-Dichloro-2-ethyl-1H-benzimidazol-1-yl)phenyl]cyclobutylamine The title compound was prepared according to the procedure described in step 7 of Example 37 from cis-3-[4-(5,6-dichloro-2-ethyl-1H-benzimidazol-1yl))phenyl]cyclobutyl azide (step 9).

MS (EI) m/z: 359 (M⁺); ¹H-NMR (CDCl₃) δ 7.84 (1H, br.s), 7.41 (2H, d, J=8.4 Hz), 7.24 (2H, d, J=8.4 Hz), 7.17

(1H, br.s), 3.55–3.43 (1H, m), 3.24–3.12 (1H, m), 2.87–2.73 (4H, m), 1.91–1.80 (2H, m), 1.34 (3H, t, J=7.5 Hz).

Step 11. 5,6-Dichloro-2-ethyl-1-(4{-cis-3-[({[(4-methylphenyl)sulfonyl]amino}carbonyl)amino]cyclobutyl}phenyl)-1H-benzimidazole The title compound was prepared according to the procedure described in step 10 of Example 1 from cis-3-[4-(5,6-dichloro-2-ethyl-1H-benzimidazol-1-yl)phenyl]cyclobutylamine (step 10)

MS (ESI) m/z 557 (M+H)$^+$; $^1$H-NMR (CDCl$_3$) δ 7.85 (1H, br.s), 7.79 (2H, d, J=8.4 Hz), 7.42 (2H, d, J=8.1 Hz), 7.36 (2H, d, J=8.1 Hz), 7.28 (2H, d, J=8.4 Hz), 7.17 (1H, br.s), 4.35–4.26 (1H, m), 3.35–3.25 (1H, m), 2.93–2.83 (2H, m), 2.78 (2H, q, J=7.6 Hz), 2.46 (3H, s), 2.19–2.07 (2H, m), 1.34 (3H, t, J=7.6 Hz).

Example 100

5,6-DICHLORO-1-(4-{1,1-DIMETHYL-2-[({[(4-METHYLPHENYL)SULFONYL]AMINO}CARBONYL)AMINO]ETHYL}PHENYL)-2-ETHYL-1H-BENZIMIDAZOLE

Step 1. 2-[4-(4,5-Dichloro-2-nitroanilino)phenyl]-2-methylpropanenitrile

The title compound was prepared according to the procedure described in step 3 of Example 1 from 2,4,5-trichloronitroaniline and 2-(4-aminophenyl)-2-methylpropanenitrile (Axton, C. A.; et al. J.Chem.Soc.Perkin Trans.1, 1992, 17, 2203).

$^1$H-NMR (CDCl$_3$) δ 9.38 (1H, br), 8.31 (1H, s), 7.54 (2H, d, J=8.58 Hz), 7.30–7.22 (3H, m) 1.75 (6H, s).

Step 2. 2-[4-(2-Amino-4,5-dichloroanilino)phenyl]-2-methylpropanenitrile

The title compound was prepared according to the procedure described in step 2 of Example 28 from 2-[4-(4,5-dichloro-2-nitroanilino)phenyl]-2-methylpropanenitrile (step 1).

$^1$H-NMR (CDCl$_3$) δ 7.41 (1H, s), 7.30 (2H, d, J=8.4 Hz), 7.09 (1H, s), 6.90 (1H, s), 6.80 (2H, d, J=8.4 Hz), 5.22 (2H, s), 1.62 (6H, s).

Step 3. 2-[4-(5,6-Dichloro-2-ethyl-1H-benzimidazol-1-yl)phenyl]-2-methylpropanenitrile The title compound was prepared according to the procedure described in step 5 of Example 1 from 2-[4-(2-amino-4,5-dichloroanilino)phenyl]-2-methylpropanenitrile (step 2) and propionyl chloride.

$^1$H-NMR (CDCl$_3$) δ 7.91 (1H, s), 7.78 (2H, d, J=8.4 Hz), 7.45 (2H, d, J=8.4 Hz), 7.24 (1H, s), 2.83 (2H, q, J=7.5 Hz), 1.89 (6H, s), 1.42 (3H, t, J=7.3 Hz).

Step 4. 5,6-Dichloro-1-(4-{1,1-dimethyl-2-[{[(4-methylphenyl)sulfonyl]amino}carbonyl)amino]ethyl}phenyl)-2-ethyl-1H-benzimidazole A mixture of 2-[4-(5,6-dichloro-2-ethyl-1H-benzimidazol-1-yl)phenyl]-2-methylpropanenitrile (step 3, 102 mg, 0.28 mmol), PtO$_2$ (one portion), chloroform (0.5 mL) in ethanol (15 mL) was stirred under hydrogen atmosphere (4.5 Kg/cm$^2$) at room temperature. After 8 h, the mixture was filtered through a pad of Celite, and the filtrate was concentrated. The residue was suspended in dichloromethane (10 mL). To the suspension was added p-toluenesulfonyl isocyanate (0.3 mL, 1.96 mmol), and triethylamine (0.3 mL, 2.1 mmol) at room temperature. After 0.5 h, the mixture was concentrated. The residue was dissolved in dichloromethane (100 mL) and washed with 10% aqueous citric acid (50 mL), water (50 mL), and brine (50 mL). The organic layer was dried (MgSO$_4$) and concentrated. The residue was purified by preparative TLC (ethyl acetate/hexane=2:1) to give 62 mg (37%) of the title compound as white solids: $^1$H-NMR (CDCl$_3$) δ 7.83 (1H, s), 7.67 (2H, d, J=9.3 Hz), 7.55 (2H, d, J=9.3 Hz), 7.38–7.22 (4H, m), 7.18 (1H, s), 3.45 (1H, br), 2.76 (2H, q, J=8.4 Hz), 2.34 (3H, s), 1.37 (6H, s), 1.31 (3H, t, J=8.2 Hz).

Example 101

Step 1. Ethyl [4-(4,5-dichloro-2-nitroanilino)phenyl]acetate

The title compound was prepared according to the procedure described in step 3 of Example 1 from ethyl 2,4,5-trichloronitrobenzene and 4-aminophenylacetate.

$^1$H-NMR (CDCl$_3$) δ 9.41 (1H, s), 8.32 (1H, s), 7.37 (2H, d, J=8.4 Hz), 7.28 (1H, s), 7.22 (2H, d, J=8.3 Hz), 4.19 (2H, q, J=7.1 Hz), 3.66 (2H, s), 1.29 (3H, t, J=7.1 Hz).

Step 2. Ethyl [4-(2-Amino-4,5-dichloroanilino)phenyl]acetate

The title compound was prepared according to the procedure described in step 2 of Example 28 from ethyl [4-(4,5-dichloro-2-nitroanilino)phenyl]acetate (step 1).

$^1$H-NMR (CDCl$_3$) δ 7.16 (1H, s), 7.15 (2H, d, J=7.5 Hz), 6.86 (1H, s), 6.72 (2H, d, J=7.1 Hz), 5.12 (1H, br.s), 4.15 (2H, q, J=7.0 Hz), 3.79 (2H, br), 3.54 (2H, s), 1.26 (3H, t, J=7.1 Hz).

Step 3. Ethyl [4-(5,6-dichloro-2-ethyl-1H-benzimidazol-1-yl)phenyl]acetate

The title compound was prepared according to the procedure described in step 5 of Example 1 from ethyl [4-(2-amino-4,5-dichloroanilino)phenyl]acetate (step 2) and propionyl chloride.

$^1$H-NMR (CDCl$_3$) δ 7.84 (1H, s), 7.52 (2H, d, J=8.2 Hz), 7.30 (2H, d, J=8.4 Hz), 7.19 (1H, s), 4.22 (2H, q, J=7.1 Hz), 3.75 (2H, s), 2.77 (2H, q, J=7.5 Hz), 1.34 (3H, t, J=7.5 Hz), 1.32 (3H, t, J=7.1 Hz).

Step 4. [4-(5,6-Dichloro-2-ethyl-1H-benzimidazol-1-yl)phenyl]acetic Acid

To a stirred solution of ethyl [4-(5,6-dichloro-2-ethyl-1H-benzimidazol-1-yl)phenyl]acetate (step 3, 1.30 g, 3.4mmol) in methanol was added 2N aqueous NaOH (3.4 mL) at room temperature. After 1 h, the mixture was concentrated and the residue was diluted in water (200 mL) and the mixture was washed with diethyl ether (100 mL). The aqueous layer was acidified with 2N hydrochloric acid and extracted with ethyl acetate/THF (v/v, 1:1, 300 mL). The organic extract was washed with water (200 mL), brine (200 mL), and dried (MgSO$_4$). Removal of solvent gave 1.02 g (86%) of the title compound as a white powder: $^1$H-NMR (CDCl$_3$) δ 7.94 (1H, s), 7.56–7.45 (4H, m), 7.26 (1H, s), 3.72 (2H, s), 2.72 (2H, q, J=7.3 Hz), 1.22 (3H, t, J=7.5 Hz).

Step 5. 2-[4-(5,6-Dichloro-2-ethyl-1H-benzimidazol-1-yl)phenyl]acetamide

A mixture of [4-(5,6-dichloro-2-ethyl-1H-benzimidazol-1-yl)phenyl]acetic acid (step 4, 0.81 g, 2.3 mmol) and thionyl chloride (10 mL) was stirred for 0.5 h, and concentrated. To the residue was added ammonium hydroxide (28% NH$_3$ in water, 50 mL) and the mixture was extracted with ethyl acetate/THF (v/v, 1:1, 200 mL). The extract was washed with brine (2×100 mL), dried (MgSO$_4$), and concentrated. The residue was purified by flash column chromatography on silica gel eluting with dichloromethane/methanol (20:1) to give 349 mg (44%) of the title compound as yellow solids: $^1$H-NMR (CDCl$_3$) δ 7.93 (1H, s), 7.58 (1H, br), 7.51 (2H, d, J=8.4 Hz), 7.47 (2H, d, J=8.4 Hz), 7.27 (1H, s), 7.00 (1H, br), 3.51 (2H, s), 2.71 (2H, q, J=7.5 Hz), 1.21 (3H, t, J=7.5 Hz).

Step 6. 2-[4-(5,6-Dichloro-2-ethyl-1H-benzimidazol-1-yl)phenyl]-N-({[(4-methylphenyl)sulfonyl]amino}carbonyl)acetamide A mixture of 2-[4-(5,6-dichloro-2-ethyl-1H-benzimidazol-1-yl)phenyl]acetamide (step 5, 105 mg, 0.30 mmol), p-toluenesulfonyl isocyanate (0.07 mL, 0.45 mmol), toluene (10 mL) and THF (5 mL) was heated at reflux temperature. After 6 h, an additional 0.1 mL of p-toluenesulfonyl isocyanate was added and the mixture was heated for 3 h. The mixture was cooled and left at room temperature for 2 days. The mixture was concentrated and the residue was purified by preparative TLC (ethyl acetate)

to afford 150 mg (92%) of the title compound as colorless amorphous solids: $^1$H-NMR (CDCl$_3$) δ 9.78 (1H, s), 7.95 (2H, d, J=8.3 Hz), 7.84 (1H, s), 7.54 (2H, d, J=8.4 Hz), 7.34 (2H, d, J=8.0 Hz), 7.32 (2H, d, J=8.4 Hz), 7.18 (1H, s), 3.78 (2H, s), 2.77 (2H, q, J=7.5 Hz), 2.41 (3H, s), 1.35 (3H, t, J=7.5 Hz).

Example 102
5,6-DICHLORO-1-(4-{2-[({[(4-METHYLPHENYL)SULFONYL]AMINO}CARBONYL)AMINO]ETHYL}PHENYL)-1H-BENZIMIDAZOLE Step 1. 2-[4-(5,6-Dichloro-1H-benzimidazol-1-yl)phenyl]ethyl formate A mixture of 2-[(4,5-dichloro-2-anilino)phenyl]ethanol (450 mg, 1.42 mmol) and formic acid (7 mL) was stirred at reflux for 4 h. After cooling, the mixture was made basic with 2N aqueous NaOH and extracted with ethyl acetate (50 mL). The extracts was dried (MgSO$_4$) to afford 480 mg (quant.) of the title compound as a brown oil: $^1$H-NMR (CDCl$_3$) δ 8.10 (1H, s), 8.08 (1H, s), 7.95 (1H, s), 7.61 (1H, s), 7.49–7.41 (4H, m), 4.47 (2H, t, J=6.8 Hz), 3.10 (2H, t, J=6.8 Hz).

Step 2. 2-[4-(5.6-Dichloro-1H-benzimidazol-1-phenyl]ethanol

The title compound was prepared according to the procedure described in step 6 of Example 1 from 2-[4-(5,6-dichloro-1H-benzimidazol-1-yl)phenyl]ethyl formate (step 1).

$^1$H-NMR (CDCl$_3$) δ 8.08 (1H, s), 7.96 (1H, s), 7.61 (1H, s), 7.49–7.40 (4H, m), 3.97 (2H, q, J=6.4 Hz), 2.99 (2H, t, J=6.4 Hz).

Step 3. 2-[4-(5,6-Dichloro-1H-benzimidazol-1-yl)phenyl]ethyl azide

The title compound was prepared according to the procedure described in step 5 of Example 26 from 2-[4-(5,6-dichloro-1H-benzimidazol-1-yl)phenyl]ethanol (step 2).

MS (EI) m/z 332 (M$^+$).

Step 4. 2-[4-(5,6-Dichloro-1H-benzimidazol-1-yl)phenyl]ethylamine

The title compound was prepared according to the procedure described in step 9 of Example 1 from 2-[4-(5,6-dichloro-1H-benzimidazol-1-yl)phenyl]ethyl azide (step 3).

$^1$H-NMR (CDCl$_3$) δ 8.09 (1H, s), 7.96 (1H, s), 7.62 (1H, s), 7.45–7.38 (4H, m), 3.06 (2H, m), 2.87 (2H, t, J=6.6 Hz).

Step 5. 5,6-Dichloro-1-(4-{2-[({[(4-methylphenyl)sulfonyl]amino}carbonyl)amino]ethyl}phenyl)-1H-benzimidazole The title compound was prepared according to the procedure described in step 10 of Example 1 from 2-[4-(5,6-dichloro-1H-benzimidazol-1-yl)phenyl]ethylamine (step 3).

$^1$H-NMR (CDCl$_3$) δ 8.11 (1H, s), 7.96 (1H, s), 7.72 (2H, d, J=8.4 Hz), 7.58 (1H, s) 7.38 (4H, s), 7.28 (2H, d, J=8.4 Hz), 6.72 (1H, m), 3.56 (2H, q, J=6.9 Hz), 2.92 (2H, t, J=6.9 Hz), 2.38 (3H, s).

Example 103
5,6-DICHLORO-1-(4-{2-[({[(4-METHYLPHENYL)SULFONYL]AMINO}CARBONYL)AMINO]1ETHYL}PHENYL)-1H-BENZIMIDAZOLE, SODIUM SALT The title compound was prepared according to the procedure described in Example 2 from 5,6-dichloro-1-(4-{2-[({[(4-methylphenyl)sulfonyl]amino}carbonyl)amino]ethyl}phenyl)-1H-benzimidazole (Example 102).

$^1$H-NMR (DMSO-d$_6$) δ 8.55 (1H, s), 7.97 (1H, s), 7.71 (1H, s), 7.50–7.44 (4H, m), 7.29 (2H, d, J=8.4 Hz), 7.01 (2H, d, 3.02 (2H, m), 2.61 (2H, m), 2.16 (3H, s); IR (KBr) α$_{max}$ 1601, 1516, 1487, 1450, 1128, 1084 cm$^{-1}$.

Example 104
6-CHLORO-5-TRIFLUOROMETHYL-1-(4-{2-[({[(4-METHYLPHENYL)SULFONYL]AMINO}CARBONYL)AMINO]ETHYL}PHENYL)-1H-BENZIMIDAZOLE Step 1. 2-[(5-Chloro-4-trifluoromethyl-2-nitroanilino)phenyl]ethanol The title compound was prepared according to the procedure described in step 3 of Example 1 from 2,4-dichloro-5-trifluoromethylnitrobenzene and 4-aminophenylethyl alcohol.

$^1$H-NMR (CDCl$_3$) δ 9.69 (1H, br.s), 8.58 (1H, s), 7.37 (2H, d, J=8.4 Hz), 7.23 (2H, d, J=8.4 Hz), 7.19 (1H, s), 3.93 (2H, t, J=6.4 Hz), 2.94 (2H, t, J=6.4 Hz).

Step 2. 2-[(2-Amino-5-chloro-4-trifluoromethylanilino)phenyl]ethanol

The title compound was prepared according to the procedure described in step 2 of Example 28 from 2-[(5-chloro-4-trifluoromethyl-2-nitroanilino)phenyl]ethanol (step 1).

$^1$H-NMR (CDCl$_3$) δ 7.17–7.15 (3H, m), 7.05 (1H, s), 6.92–6.88 (2H, m), 5.48 (1H, br.s), 3.85 (2H, t, J=6.6 Hz), 2.83 (2H, t, J=6.6 Hz).

Step 3. 2-[4-(6-Chloro-2-ethyl-5-trifluoromethyl-1H-benzimidazol-1-yl)phenyl]ethyl propionate The title compound was prepared according to the procedure described in step 5 of Example 1 from 2-[(2-amino-5-chloro-4-trifluoromethylanilino)phenyl]ethanol (step 2) and propionyl chloride.

MS (EI) 424 (M$^+$).

Step 4. 2-[4-(6-Chloro-2-ethyl-5-trifluoromethyl-1H-benzimidazol-1-yl)phenyl]ethanol The title compound was prepared according to the procedure described in step 6 of Example 1 from 2-[4-(6-chloro-2-ethyl-5-trifluoromethyl-1H-benzimidazol-1-yl)phenyl]ethyl propionate (step 3).

$^1$H-NMR (CDCl$_3$) δ 8.11 (1H, s), 7.50 (2H, d, J=8.3 Hz), 7.29 (2H, d, J=8.3 Hz), 7.21 (1H, s), 4.03–3.98 (2H, m), 3.02 (2H, t, J=6.4 Hz), 2.79 (2H, q, J=7.5 Hz), 1.36 (3H, t, J=7.5 Hz).

Step 5. 2-[4-(6-Chloro-2-ethyl-5-trifluoromethyl-1H-benzimidazol-1-yl)phenyl]ethyl azide The title compound was prepared according to the procedure described in step 5 of Example 26 from 2-[4-(6-Chloro-2-ethyl-5-trifluoromethyl-1H-benzimidazol-1-yl)phenyl]ethanol (step 4).

$^1$H-NMR (CDCl$_3$) δ 8.11 (1H, s), 7.49 (2H, d, J=8.4 Hz), 7.30 (2H, d, J=8.4 Hz), 7.20 (1H, s), 3.63 (2H, t, J=6.9 Hz), 3.03 (2H, t, J=6.9 Hz), 2.79 (2H, q, J=7.4 Hz), 1.36 (3H, t, J=7.4 Hz).

Step 6. 2-[4-(6-Chloro-2-ethyl-5-trifluoromethyl-1H-benzimidazol-1-yl)phenyl]ethylamine The title compound was prepared according to the procedure described in step 9 of Example 1 from 2-[4-(6-chloro-2-ethyl-5-trifluoromethyl-1H-benzimidazol-1-yl)phenyl]ethyl azide (step 5).

$^1$H-NMR (CDCl$_3$) δ 8.11 (1H, s), 7.45 (2H, d, J=8.3 Hz), 7.29–7.26 (2H, m), 7.23 (1H, s), 3.11 (2H, t, J=7.0 Hz), 2.92 (2H, t, J=7.0 Hz), 2.79 (2H, q, J=7.5 Hz), 1.36 (3H, t, J=7.5 Hz).

Step 7 2-Ethyl-6-chloro-5-trifluoromethyl-1-(4-{2-[({[(4-methylphenyl)sulfonyl]amino}carbonyl)amino]ethyl}phenyl)-1H-benzimidazole The title compound was prepared according to the procedure described in step 10 of Example 1 from 2-[4-(6-chloro-2-ethyl-5-trifluoromethyl-1H-benzimidazol-1-yl)phenyl]ethylamine (step 6).

$^1$H-NMR (CDCl$_3$) δ 8.09 (1H, s), 7.74 (2H, d, J=8.4 Hz), 7.42 (2H, d, J=8.2 Hz), 7.30–7.26 (4H, m), 7.18 (1H, s), 6.76 (1H, m), 3.59 (2H, q, J=7.0 Hz), 2.96 (2H, t, J=7.0 Hz), 2.79 (2H, q, J=7.6 Hz), 1.34 (3H, t, J=7.6 Hz).

Example 105
6-CHLORO-5-TRIFLUOROMETHYL-1-(4-{2-[({[(4-METHYLPHENYL)SULFONYL]AMINO}CARBONYL)AMINO]ETHYL}PHENYL)-1H-BENZIMIDAZOLE, SODIUM SALT The title compound was prepared according to the procedure described in Example 2 from 2-ethyl-6-chloro-5-trifluoromethyl-1-(4-{2-[({[(4-methylphenyl)sulfonyl]amino}carbonyl)amino]ethyl}phenyl)-1H-benzimidazole (Example 104).

$^1$H-NMR (DMSO-d$_6$) δ☐8.15 (1H, s), 7.59 (2H, d, J=8.4 Hz), 7.46–7.39 (4H, m), 7.33 (1H, s), 7.12 (2H, d, J=8.4 Hz), 3.15 (2H, m), 2.78–2.71 (4H, m), 1.24 (3H, t, J=7.5 Hz); IR (KBr) α$_{max}$ 1601, 1518, 1431, 1398, 1348, 1306, 1128, 1084 cm$^{-1}$.

Example 106
4-(6-CHLORO-2-ETHYL-5-TRIFLUOROMETHYL-1H-BENZIMIDAZOL-1-YL)PHENETHYL-(4-METHYLPHENYL)SULFONYLCARBAMATE The title compound was prepared according to the procedure described in Example 3 from 2-[4-(6-chloro-2-ethyl-5-trifluoromethyl-1H-benzimidazol-1-yl)phenyl]ethanol (step 4 of Example 104).

mp 170–173° C.; $^1$H-NMR (CDCl$_3$) δ 8.12 (1H, s), 7.94–7.91 (2H, m), 7.41–7.24 (6H, m) 7.19 (1H, s), 4.39 (2H, t, J=6.8 Hz), 3.04 (2H, t, J=6.8 Hz), 2.78 (2H, q, J=7.6 Hz), 2.44 (3H, s), 1.35 (3H, t, J=7.6 Hz); IR (KBr) α$_{max}$ 1746, 1518, 1342, 1232, 1159, 1132, 1086 cm$^-$.

Example 107
4-(6-CHLORO-2-ETHYL-5-TRIFLUOROMETHYL-1H-BENZIMIDAZOL-1-YL)PHENETHYL-(4-METHYLPHENYL)SULFONYLCARBAMATE, SODIUM SALT The title compound was prepared according to the procedure described in Example 2 from 4-(6-chloro-2-ethyl-5-trifluoromethyl-1H-benzimidazol-1-yl)phenethyl-(4-methylphenyl)sulfonylcarbamate (Example 106).

$^1$H-NMR (DMSO-d$_6$) δ 8.15 (1H, s), 7.59 (2H, d, J=8.1 Hz), 7.47 (4H, s), 7.34 (1H, s), 7.15 (2H, d, J=8.1 Hz), 3.96 (2H, t, J=6.6 Hz), 2.86 (2H, t, J=6.6 Hz), 2.75 (2H, q, J=7.4 Hz), 2.28 (3H, s), 1.24 (3H, t, J=7.4 Hz).

Example 108
5-CHLORO-6-METHYL-1-(4-{2-[({[(4-METHYLPHENYL)SULFONYL]AMINO}CARBONYL)AMINO]ETHYL}PHENYL)-1H-BENZIMIDAZOLE Step 1. 2-[(4-Chloro-5-methyl-2-nitroanilino)phenyl]ethanol The title compound was prepared according to the procedure described in step 3 of Example 1 from 2,5-dichloro-4-methylnitrobenzene and 4-aminophenylethyl alcohol.

$^1$H-NMR (CDCl$_3$) δ 9.40 (1H, s), 8.20 (1H, s), 7.31 (2H, d, J=8.4 Hz), 7.21 (2H, d, J=8.4 Hz), 7.05 (1H, s), 3.93–3.91 (2H, m), 2.91 (2H, t, J=6.4 Hz), 2.29 (3H, s).

Step 2. 2-[(2-Amino-4-chloro-5-methylanilino)phenyl]ethanol

The title compound was prepared according to the procedure described in step 2 of Example 28 from 2-[(4-chloro-5-methyl-2-nitroanilino)phenyl]ethanol (step 1).

$^1$H-NMR (CDCl$_3$) δ 7.06 (2H, d, J=8.6 Hz), 6.93 (1H, s), 6.79 (1H, s), 6.67 (2H, d, J=8.6 Hz), 3.80 (2H, d, J=6.4 Hz), 2.77 (2H, t, J=6.4 Hz), 2.21 (3H, s).

Step 3. 2-[4-(5-Chloro-2-ethyl-6-methyl-1H-benzimidazol-1-yl)phenyl]ethyl propionate The title compound was prepared according to the procedure described in step 5 of Example 1 from 2-[(2-amino-4-chloro-5-methylanilino)phenyl]ethanol (step 2) and propionyl chloride.

MS (EI) m/z 370 (M$^+$)

Step 4. 2-[4-(5-Chloro-2-ethyl-6-methyl-1H-benzimidazol-1-yl)phenyl]ethanol

The title compound was prepared according to the procedure described in step 6 of Example 1 from 2-[4-(5-chloro-2-ethyl-6-methyl-1H-benzimidazol-1-yl)phenyl] ethyl propionate (step 3).

$^1$H-NMR (CDCl$_3$) δ 7.74 (1H, s), 7.47 (2H, d, J=8.3 Hz), 7.27 (2H, d, J=8.3 Hz), 6.93 (1H, s), 4.00 (2H, t, J=6.6 Hz), 3.02 (2H, t, J=6.6 Hz), 2.76 (2H, q, J=7.5 Hz), 2.39 (3H, t, J=7.5 Hz).

Step 5. 2-[4-(5-Chloro-2-ethyl-6-methyl-1H-benzimidazol-1-yl)phenyl]ethyl azide

The title compound was prepared according to the procedure described in step 5 of Example 26 from 2-[4-(5-chloro-2-ethyl-6-methyl-1H-benzimidazol-1-yl)phenyl] ethanol (step 4).

$^1$H-NMR (CDCl$_3$) δ 7.75 (1H, s), 7.45 (2H, d, J=8.4 Hz), 7.30 (2H, d, J=8.4 Hz), 7.27 (1H, s), 3.62 (2H, t, J=7.0 Hz), 3.02 (2H, t, J=7.0 Hz), 2.76 (2H, q, J=7.5 Hz), 2.40 (3H, t,) 1.33 (3H, t, J=7.5 Hz).

Step 6. 2-[4-(5-Chloro-2-ethyl-6-methyl-1H-benzimidazol-1-yl)phenyl]ethylamine

The title compound was prepared according to the procedure described in step 9 of Example 1 from 2-[4-(5-chloro-2-ethyl-6-methyl-1H-benzimidazol-1-yl)phenyl] ethyl azide (step 5).

$^1$H-NMR (CDCl$_3$) δ 7.75 (1H, s), 7.42 (2H, d, J=8.3 Hz), 7.27 (2H, d, J=8.3 Hz), 6.93 (1H, s), 3.10 (2H, t, J=7.0 Hz), 2.90 (2H, t, J=7.0 Hz), 2.76 (2H, q, J=7.5 Hz), 2.40 (3H, s), 1.33 (3H, t, J=7.5 Hz).

Step 7. 2-Ethyl-5-chloro-6-methyl-1-(4-{2-[([[(4-methylphenyl)sulfonyl]amino]carbonyl)amino]ethyl}phenyl)-1H-benzimidazole The title compound was prepared according to the procedure described in step 10 of Example 1 from 2-[4-(5-chloro-2-ethyl-6-methyl-1H-benzimidazol-1-yl)phenyl] ethylamine (step 6).

$^1$H-NMR (CDCl$_3$) δ 7.75–7.72 (3H, m), 7.38–7.23 (6H, m), 6.91 (1H, s), 6.73–6.69 (1H, m), 3.62–3.55 (2H, m), 2.94 (2H, t, J=6.8 Hz), 2.75 (2H, q, J=7.6 Hz), 2.40 (3H, s), 2.37 (3H, s), 1.30 (3H, t, J=7.6 Hz).

Example 109
5-CHLORO-6-METHYL-1-(4-{2-[({[(4-METHYLPHENYL)SULFONYL]AMINO}CARBONYL)AMINO]ETHYL}PHENYL)-1H-BENZIMIDAZOLE, SODIUM SALT The title compound was prepared according to the procedure described in Example 2 from 2-ethyl-5-chloro-6-methyl-1-(4-{2-[([[(4-methylphenyl)sulfonyl]amino]carbonyl)amino]ethyl}phenyl)-1H-benzimidazole (Example 108).

$^1$H-NMR (DMSO-d$_6$) δ 7.68 (1H, s), 7.60 (2H, d, J=8.1 Hz), 7.41–7.35 (4H, m), 7.13 (2H, d, J=8.1 Hz), 7.05 (1H, s), 3.17–3.15 (2H, m), 2.75–2.65 (4H, m), 2.34 (3H, s), 2.27 (3H, s), 1.20 (3H, t, J=7.5 Hz); IR (KBr) α$_{max}$ 1599, 1516, 1456, 1402, 1128, 1084, 1001 cm$^{-1}$.

Example 110
6-CHLORO-2-ETHYL-1-(4-{2-[({[(4-METHYLPHENYL)SULFONYL]AMINO}CARBONYL)AMINO]ETHYL}PHENYL)-5-[(METHYLSULFONYL)AMINO]-1H-BENZIMIDAZOLE Step 1. 2-[4-(5-Chloro-2,4-dinitroanilino)phenyl]ethanol The title compound was prepared according to the procedure described in step 3 of Example 1 from 2,4-dichloro-1,5-dinitrobenzene and 4-aminophenylethyl alcohol.

$^1$H-NMR (CDCl$_3$) δ 9.81 (1H, br.s), 9.07 (1H, s), 7.40 (2H, d, J=8.3 Hz), 7.25 (2H, d, J=8.3 Hz), 7.17 (1H, s), 3.95 (2H, t, J=6.6 Hz), 2.95 (2H, t, J=6.6 Hz).

Step 2. 2-[4-(2-Amino-5-chloro-4-nitroanilino)phenyl]ethanol

The title compound was prepared according to the procedure described in step 2 of Example 40 from 2-[4-(5-chloro-2,4-dinitroanilino)phenyl]ethanol (step 1).

$^1$H-NMR (CDCl$_3$) δ 7.54 (1H, s), 7.24 (2H, d, J=8.6 Hz), 7.11 (1H, s), 7.03 (2H, d, J=8.6 Hz), 5.76 (1H, br.s), 3.89 (2H, t, J=6.4 Hz), 3.65 (2H, br.s), 2.87 (2H, t, J=6.4 Hz), 1.28 (1H, s).

Step 3. 2-[4-(6-Chloro-2-ethyl-5-nitro-1H-benzimidazol-1-yl)phenyl]ethyl propionate The title compound was prepared according to the procedure described in step 5 of Example 1 from 2-[4-(2-amino-5-chloro-4-nitroanilino)phenyl]ethanol (step 2) and propionyl chloride. TLC Rf=0.8 (hexane/ethyl acetate=1:2).

Step 4. 2-[4-(6-Chloro-2-ethyl-5-nitro-1H-benzimidazol-1-yl)phenyl]ethanol

The title compound was prepared according to the procedure described in step 6 of Example 1 from 2-[4-(2-amino-5-chloro-4-nitroanilino)phenyl]ethyl propionate (step 3).

$^1$H-NMR (CDCl$_3$) δ 8.34 (1H, s), 7.50 (2H, d, J=8.0 Hz), 7.28 (2H, d, J=8.0 Hz), 7.19 (1H, s), 4.00 (2H, t, J=6.3 Hz), 3.02 (2H, t, J=6.3 Hz), 2.79 (2H, q, J=7.6 Hz), 1.62 (1H, s) 1.36 (3H, t, J=7.6 Hz).

Step 5. 6-Chloro-1-[4-(2-chloroethyl)phenyl]-2-ethyl-5-nitro-1H-benzimidazole

The title compound was prepared according to the procedure described in step 7 of Example 1 from 2-[4-(6-chloro-2-ethyl-5-nitro-1H-benzimidazol-1-yl)phenyl]ethanol (step 4).

$^1$H-NMR (CDCl$_3$) δ 8.34 (1H, s), 7.50 (2H, d, J=8.4 Hz), 7.31 (2H, d, J=8.4 Hz), 7.19 (1H, s), 3.84 (2H, t, J=7.0 Hz), 3.22 (2H, t, J=7.0 Hz), 2.80 (2H, q, J=7.6 Hz), 1.37 (3H, t, J=7.6 Hz).

Step 6. 6-Chloro-1-[4-(2-chloroethyl)phenyl]-2-ethyl-1H-benzimidazol-5-ylamine

The title compound was prepared according to the procedure described in step 4 of Example 89 from 6-chloro-1-[4-(2-chloroethyl)phenyl]-2-ethyl-5-nitro-1H-benzimidazole (step 5).

$^1$H-NMR (CDCl$_3$) δ 7.43 (2H, d, J=8.6 Hz), 7.29 (2H, d, J=8.6 Hz), 7.16 (1H, s), 7.02 (1H, s), 3.96 (2H, br.s), 3.81 (2H, t, J=7.1 Hz), 3.19 (2H, t, J=7.1 Hz), 2.74 (2H, q, J=7.5 Hz), 1.33 (3H, t, J=7.5 Hz).

Step 7. N-{6-Chloro-1-[4-(2-chloroethyl)phenyl]-2-ethyl-1H-benzimidazol-5-yl}methanesulfonamide The title compound was prepared according to the procedure described in step 5 of Example 40 from 6-chloro-1-[4-(2-chloroethyl)phenyl]-2-ethyl-1H-benzimidazol-5-ylamine (step 6).

$^1$H-NMR (CDCl$_3$) δ 7.70 (1H, s), 7.55 (2H, d, J=7.9 Hz), 7.50 (2H, d, J=7.9 Hz), 7.13 (1H, s), 3.95 (2H, t, J=7.0 Hz), 3.16 (2H, t, J=7.0 Hz), 2.97 (3H, s), 2.71 (2H, q, J=7.6 Hz), 1.21 (3H, t, J=7.6 Hz).

Step 8. N-{1-[4-(2-Azidoethyl)phenyl]-6-chloro-2-ethyl-1H-benzimidazol-5-yl}methanesulfonamide The title compound was prepared according to the procedure described in step 8 of Example 1 from N-{6-chloro-1-[4-(2-chloroethyl)phenyl]-2-ethyl-1H-benzimidazol-5-yl}methanesulfonamide (step 7).

$^1$H-NMR (CDCl$_3$) δ 7.47 (2H, d, J=8.4 Hz), 7.29 (2H, d, J=8.4 Hz), 7.16 (1H, s), 6.78 (1H, s), 3.63 (2H, t, J=6.9 Hz), 2.98–3.05 (5H, m), 2.77 (2H, q, J=7.4 Hz), 1.35 (3H, t, J=7.4 Hz).

Step 9. N-{1-[4-(2-Aminoethyl)phenyl]-6-chloro-2-ethyl-1H-benzimidazol-5-yl}methanesulfonamide The title compound was prepared according to the procedure described in step 7 of Example 37 from N-{1-[4-(2-azidoethyl)phenyl]-6-chloro-2-ethyl-1H-benzimidazol-5-yl}methanesulfonamide (step 8).

$^1$H-NMR (CDCl$_3$) δ 8.03 (1H, s), 7.43 (2H, d, J=8.4 Hz), 7.26 (2H, d, J=8.4 Hz), 7.17 (1H, s), 3.33 (2H, br.s), 3.08 (2H, t, J=7.0 Hz), 2.96 (3H, s), 2.88 (2H, t, J=7.0 Hz), 2.77 (2H, q, J=7.6 Hz), 1.35 (3H, t, J=7.6 Hz).

Step 10. 6-Chloro-2-ethyl-1-(4-{2-[({[(4-methylphenyl)sulfonyl]amino}carbonyl)amino]ethyl}phenyl)-5-[(methylsulfonyl)amino]-1H-benzimidazole The title compound was prepared according to the procedure described in step 10 of Example 1 from N-{1-[4-(2-aminoethyl)phenyl]-6-chloro-2-ethyl-1H-benzimidazol-5-yl}methanesulfonamide (step 9).

mp 101–123° C.; MS (ESI) m/z 590 (M+H)$^+$; $^1$H-NMR (CDCl$_3$) δ 8.04 (1H, s), 7.73 (2H, d, J=8.2 Hz), 7.42 (2H, d, J=8.2 Hz), 7.25–7.33 (4H, m), 7.16 (1H, s), 6.68 (1H, br.s), 3.58 (2H, t, J=7.2 Hz), 2.93–2.98 (5H, m), 2.77 (2H, q, J=7.5 Hz), 2.45 (3H, s), 1.35 (3H, t, J=7.5 Hz); IR (KBr) α$_{max}$ 1654, 1517, 1467, 1336, 1151, 1089, 972 cm$^{-1}$.

Example 111

6-CHLORO-2-ETHYL-1-(4-{2-[({[(4-METHYLPHENYL)SULFONYL]AMINO}CARBONYL)AMINO1ETHYL}PHENYL)-1H-BENZIMIDAZOLE-5-CARBOXAMIDE

Step 1. 2-Chloro-4-[4-(2-hydroxyethyl)anilino-]5-nitrobenzonitrile

The title compound was prepared according to the procedure described in step 3 of Example 1 from 2,4-dichloro-5-nitrobenzonitrile (Grivsky, E. M.; Hitchings, G. H. Ind. Chim. Belge., 1974, 39. 490.) and 4-aminophenylethyl alcohol.

$^1$H-NMR (CDCl$_3$) δ 9.81 (1H, br.s), 8.56 (1H, s), 7.39 (2H, d, J=8.3 Hz), 7.23 (2H, d, J=8.3 Hz), 7.15 (1H, s), 3.93 (2H, t, J=6.2 Hz), 2.94 (2H, t, J=6.2 Hz), 1.62 (1H, br.s).

Step 2. 5-amino-2-chloro-4-[4-(2-hydroxyethyl)anilino]benzonitrile

The title compound was prepared according to the procedure described in step 2 of Example 28 from 2-chloro-4-[4-(2-hydroxyethyl)anilino]-5-nitrobenzonitrile (step 1).

$^1$H-NMR (CDCl$_3$) δ 7.23 (4H, d, J=8.3 Hz), 6.99–7.33 (2H, m), 3.88 (2H, t, J=6.1 Hz), 3.56 (1H, br.s), 2.87 (2H, t, J=6.1 Hz).

Step 3. 2-[4-(6-Chloro-5-cyano-2-ethyl-1H-benzimidazol-1-yl)phenyl]ethyl propionate The title compound was prepared according to the procedure described in step 5 of Example 1 from 5-amino-2-chloro-4-[4-(2-hydroxyethyl)anilino]benzonitrile (step 2) and propionyl chloride.

TLC Rf=0.5 (hexane/ethyl acetate=1:2).

Step 4. 6-Chloro-2-ethyl-1-[4-(2-hydroxyethyl)phenyl]-1H-benzimidazole-5-carbonitrile The title compound was prepared according to the procedure described in step 6 of Example 1 from 2-[4-(6-chloro-5-cyano-2-ethyl-1H-benzimidazol-1-yl)phenyl]ethyl propionate (step 3).

$^1$H-NMR (CDCl$_3$) δ 8.04 (1H, s), 7.52 (2H, d, J=8.4 Hz), 7.29 (2H, d, J=8.4 Hz), 7.19 (1H, s), 4.02 (2H, t, J=6.5 Hz), 3.03 (2H, t, J=6.5 Hz), 2.80 (2H, q, J=7.6 Hz), 1.36 (3H, t, J=7.6 Hz).

Step 5. 6-Chloro-2-ethyl-1-[4-(2-hydroxyethyl)phenyl] 1–1H-benzimidazole-5-carboxamide To a mixture of 6-chloro-2-ethyl-1-[4-(2-hydroxyethyl) phenyl]-1H-benzimidazole-5-carbonitrile (step 4, 2.4 g, 7.4 mmol), DMSO (0.7 mL, 8.8 mmol) and methanol (100 mL) was added 30% aqueous hydrogen peroxide (1.3 mL, 11 mmol) and 0.2 M aqueous NaOH (0.7 mL, 0.14 mmol). The mixture was stirred at 50° C. for 2 h. The solvent was removed and the resulting precipitates were collected by filtration. The precipitates were washed with water and dried under reduced pressure to give 1.9 g (76%) of the title compound as pale pink solids: $^1$H-NMR (DMSO-d$_6$) δ 7.69 (1H, br.s), 7.61 (1H, s), 7.33–7.40 (4H, m), 6.95 (1H, s), 4.64 (1H, br.s), 3.59 (2H, t, J=6.4 Hz), 2.74 (2H, t, J=6.4 Hz), 2.62 (2H, q, J=7.4 Hz), 1.11 (3H, t, J=7.4 Hz).

Step 6. 6-Chloro-1-[4-(2-chloroethyl )phenyl]-2-ethyl-1H-benzimidazole-5-carboxamide The title compound was prepared according to the procedure described in step 7 of Example 1 from 6-chloro-2-ethyl-1-[4-(2-hydroxyethyl)phenyl]-1H-benzimidazole-5-carboxamide (step 5).

$^1$H-NMR (DMSO-d$_6$) δ 7.71 (1H, br.s), 7.62 (1H, s), 7.36–7.47 (5H, m), 6.95 (1H, s) 3.85 (2H, t, J=7.1 Hz), 3.06 (2H, t, J=7.1 Hz), 2.63 (2H, q, J=7.6 Hz), 1.11 (3H, t, J=7.6 Hz).

Step 7. 1-[4-(2-Azidoethyl)phenyl]-6-chloro-2-ethyl-1H-benzimidazole-5-carboxamide The title compound was prepared according to the procedure described in step 8 of Example 1 from 6-chloro-1-[4-(2-chloroethyl)phenyl]-2-ethyl-1H-benzimidazole-5-carboxamide (step 6).

$^1$H-NMR (DMSO-d$_6$) δ 7.80 (1H, br.s), 7.71 (1H, s), 7.46–7.57 (5H, m), 7.04 (1H, s), 3.65 (2H, t, J=6.9 Hz), 2.98 (2H, t, J=6.9 Hz), 2.72 (2H, q, J=7.5 Hz), 1.21 (3H, t, J=7.5 Hz).

Step 8. 1-[4-(2-Aminoethyl)phenyl]-6-chloro-2-ethyl-1H-benzimidazole-5-carboxamide The title compound was prepared according to the procedure described in step 7 of Example 37 from 1-[4-(2-azidoethyl)phenyl]-6-chloro-2-ethyl-1H-benzimidazole-5-carboxamide (step 7).

$^1$H-NMR (CDCl$_3$) δ 7.80 (1H, s), 7.71 (1H, s), 7.39–7.50 (5H, m), 7.08 (1H, s), 2.49–2.89 (6H, m), 1.21 (3H, t, J=7.4 Hz).

Step 9. 6-Chloro-2-ethyl-1-(4-{2-[({[(4-methylphenyl) sulfonyl]amino}carbonyl)amino]ethyl}phenyl)-1H-benzimidazole-5-carboxamide The title compound was prepared according to the procedure described in step 10 of Example 1 from 1-[4-(2-aminoethyl)phenyl]-6-chloro-2-ethyl-1H-benzimidazole-5-carboxamide (step 8).

mp 152–163° C.; MS (ESI) m/z 540 (M+H)$^+$; $^1$H-NMR (DMSO-d$_6$) δ 7.81 (1H, br.s), 7.72–7.75 (3H, m), 7.51 (1H, br.s), 7.33–7.44 (6H, m), 7.06 (1H, s), 3.26 (2H, br.s), 2.68–2.80 (4H, m), 2.34 (3H, s), 1.23 (3H, t, J=7.5 Hz); IR (KBr) α$_{max}$ 3395, 1664, 1519, 1396, 1161, 1089, 991 cm$^{-1}$.

Example 112

6-CHLORO-2-ETHYL-1-(4-{2-[({[(4-METHYLPHENYL)SULFONYL]AMINO}CARBONYL) AMINO]ETHYL}PHENYL)-1H-BENZIMIDAZOLE-5-CARBOXYLIC ACID

A mixture of 6-chloro-2-ethyl-1-(4-{2-[({[(4-methylphenyl)sulfonyl]amino}carbonyl)amino] ethyl}phenyl)-1H-benzimidazole-5-carboxamide (Example 111, 140 mg, 0.26 mmol) and KOH (63 mg, 0.8 mmol) in methanol (10 mL) was stirred at 100° C. for 1 day. The mixture was poured into water, acidified with 2N hydrochloric acid, and extracted with ethyl acetate (50 mL). The organic layer was washed with brine (30 mL), dried (Na$_2$SO$_4$), and concentrated. The residue was purified by flash column chromatography on silica gel eluting with dichloromethane/methanol (10:1) to afford 36 mg (25%) of the title compound as white solids: mp 145–150° C.; MS (ESI) m/z 541 (M+H)$^+$; $^1$H-NMR (DMSO-d$_6$) δ 8.10 (1H, s), 7.76 (2H, d, J=7.9 Hz), 7.36–7.47 (6H, m), 7.10 (1H, s) 3.28 (2H, m), 2.69–2.81 (4H, m), 2.34 (3H, s), 1.24 (3H, t, J=7.5 Hz); IR (KBr) α$_{max}$ : 3450, 1701, 1517, 1340, 1163, 1091, 900 cm$^{-1}$.

Example 113

N-[6-CHLORO-2-ETHYL-1-(4-{2-[({[(4-METHYLPHENYL)SULFONYL] AMINO}CARBONYL)AMINO] ETHYL}PHENYL)-1H-BENZIMIDAZOL-5-YL] ACETAMIDE

Step 1. N-{6-Chloro-1-[4-(2-chloroethyl)phenyl]-2-ethyl-1H-benzimidazol-5-yl}acetamide To a solution of 6-chloro-1-[4-(2-chloroethyl)phenyl]-2-ethyl-1H-benzimidazol-5-ylamine (step 6 of Example 110, 100 mg, 0.3 mmol) in pyridine (7 mL) was added dropwise acetyl chloride (0.03 mL, 0.33 mmol) under nitrogen atmosphere at 0° C., and the reaction mixture was stirred at room temperature for 1.5 h. The mixture was poured into water (20 mL) and extracted with ethyl acetate (50 mL). The organic layer was washed with 2N aqueous NaOH (30 mL), brine (30 mL), then dried (Na$_2$SO$_4$). After removal of solvent, the crude product was purified by flash column chromatography on silica gel eluting with hexane/ethyl acetate (1:3) to afford 110 mg (98%) of the title compound as white solids: $^1$H-NMR (CDCl$_3$) δ 8.66 (1H, s), 7.56 (1H, br.s), 7.45 (2H, d, J=8.2 Hz), 7.29 (2H, d, J=8.2 Hz), 7.12 (1H, s), 3.82 (2H, t, J=7.1 Hz), 3.19 (2H, t, J=7.1 Hz), 2.77 (2H, q, J=7.6 Hz), 2.26 (3H, s), 1.34 (3H, t, J=7.6 Hz).

Step 2. N-{1-[4-(2-Azidoethyl)phenyl]-6-chloro-2-ethyl-1H-benzimidazol-5-yl}acetamide The title compound was prepared according to the procedure described in step 8 of Example 1 from N-{6-chloro-1-[4-(2-chloroethyl)phenyl]-2-ethyl-1H-benzimidazol-5-yl}acetamide (step 1).

$^1$H-NMR (DMSO-d$_6$) δ 8.66 (1H, s), 7.55 (1H, br.s), 7.45 (2H, d, J=8.1 Hz), 7.30 (2H, d, J=8.1 Hz), 7.11 (1H, s), 3.62 (2H, t, J=7.1 Hz), 3.02 (2H, t, J=7.1 Hz), 2.76 (2H, q, J=7.6 Hz), 2.26 (3H, s), 1.34 (3H, t, J=7.6 Hz).

Step 3. N-{1-[4-(2-Aminoethyl)phenyl]-6-chloro-2-ethyl-1H-benzimidazol-5-yl}acetamide The title compound was prepared according to the procedure described in step 7 of Example 37 from N-{1-[4-(2-azidoethyl)phenyl]-6-chloro-2-ethyl-1H-benzimidazol-5-yl}acetamide (step 2).

$^1$H-NMR (CDCl$_3$) δ 8.66 (1H, s), 7.55 (1H, br.s), 7.42 (2H, d, J=6.6 Hz), 7.27–7.29 (2H, m), 7.12 (1H, s), 3.08 (2H, t, J=6.9 Hz), 2.88 (2H, t, J=6.9 Hz), 2.75 (2H, q, J=7.4 Hz), 2.26 (3H, s), 1.34 (3H, t, J=7.4 Hz).

Step 4. N-[6-Chloro-2-ethyl-1-(4-{2-[({[(4-methylphenyl) sulfonyl]amino}carbonyl)amino]ethyl}phenyl)-1H-benzimidazol-5-yl]acetamide The title compound was prepared according to the procedure described in step 10 of Example 1 from N-{1-[4-(2-aminoethyl)phenyl]-6-chloro-2-ethyl-1H-benzimidazol-5-yl}acetamide (step 3).

mp 125–133° C.; MS (ESI) m/z 554 (M+H)$^+$; $^1$H-NMR (CDCl$_3$) δ 8.64 (1H, s), 7.74 (2H, d, J=8.4 Hz), 7.55 (1H, br.s), 7.25–7.39 (1H, s), 7.08 (1H, s), 3.53–3.61 (2H, m), 2.94 (2H, t, J=7.1 Hz), 2.75 (2H, q, J=7.4 Hz), 2.41 (3H, s), 2.27 (3H, s), 1.32 (3H, t, J=7.4 Hz); IR (KBr) α$_{max}$ 3390, 1676, 1517, 1240, 1161, 1089, 1018, 972 cm$^{-1}$.

Example 114

6-ETHYL-5-(4-{2-[({[(4-METHYLPHENYL) SULFONYL]AMINO}CARBONYL)AMINO] ETHYL}PHENYL)-5H-[1,3]DIOXOLO[4,5-f] BENZIMIDAZOLE

Step 1. 2-{4-[(6-Nitro-1,3-benzodioxol-5-yl)amino] phenyl}ethanol

The title compound was prepared according to the procedure described in step 1 of Example 45 from 5-amino-6-nitro-1,3-benzodioxol and 4-bromophenylethyl alcohol.

$^1$H-NMR (CDCl$_3$) δ: 10.07 (1H, br.s), 7.62 (1H, s), 7.29 (2H, d, J=8.5 Hz), 7.20 (2H, d, J=8.5 Hz), 6.58 (1H, s), 5.98 (2H, s), 3.90 (2H, t, J=6.6 Hz), 2.90 (2H, t, J=6.6 Hz).

Step 2. 2-{4-[(6-Amino-1,3-benzodioxol-5-yl)amino] phenyl}ethanol

The title compound was prepared according to the procedure described in step 2 of Example 28 from 2-{4-[(6-nitro-1,3-benzodioxol-5-yl)amino]phenyl}ethanol (step 1).

$^1$H-NMR (CDCl$_3$) δ 7.26 (1H, s), 7.04 (2H, d, J=8.2 Hz), 6.60 (2H, d, J=8.2 Hz), 6.39 (1H, s), 5.87 (2H, s), 4.96 (1H, br.s), 3.80 (2H, t, J=6.4 Hz), 3.64 (2H, br.s), 2.76 (2H, t, J=6.4 Hz).

Step 3. 2-[4-(6-Ethyl-5H-[1,3]dioxol[4,5-f]benzimidazol-5-yl)phenyl]ethyl propionate The title compound was prepared according to the procedure described in step 5 of Example 1 from 2-{4-[(6-amino-1,3-benzodioxol-5-yl)amino]phenyl}ethanol (step 2) and propionyl alcohol.

TLC Rf=0.5 (hexane/ethyl acetate=1:2).

Step 4. 2-[4-(6-Ethyl-5H-[1,3]dioxolo[4,5-f]benzimidazol-5-yl)phenyl]ethanol

The title compound was prepared according to the procedure described in step 6 of Example 1 from 2-{4-[(6-amino-1,3-benzodioxol-5-yl)amino]phenyl}ethyl propionate (step 3).

$^1$H-NMR (CDCl$_3$) δ 7.43 (2H, d, J=8.4 Hz), 7.28 (2H, d, J=8.4 Hz), 7.19 (1H, s), 6.53 (1H, s), 5.94 (2H, s), 3.98 (2H, t, J=6.4 Hz), 2.99 (2H, t, J=6.4 Hz), 2.73 (2H, q, J=7.4 Hz), 1.31 (3H, t, J=7.4 Hz).

Step 5. 5-[4-(2-Chloroethyl)phenyl]-6-ethyl-5H-[1,3] dioxolo[4,5-f]benzimidazole The title compound was prepared according to the procedure described in step 7 of Example 1 from 2-[4-(6-ethyl-5H-[1,3]dioxolo[4,5-f]benzimidazol-5-yl)phenyl]ethanol (step 4).

$^1$H-NMR (CDCl$_3$) δ 7.42 (2H, d, J=8.1 Hz), 7.28 (2H, d, J=8.1 Hz), 7.19 (1H, s), 6.54 (1H, s), 5.94 (2H, s), 3.81 (2H, t, J=7.1 Hz), 3,19 (2H, t, J=7.1 Hz), 2.72 (2H, q, J=7.6 Hz), 1.31 (3H, t, J=7.6 Hz).

Step 6. 2-[4-(6-Ethyl-5H-[1,3]dioxolo[4,5-f]benzimidazol-5-yl)phenyl]ethyl azide The title compound was prepared according to the procedure described in step 8 of Example 1 from 5-[4-(2-chloroethyl)phenyl]-6-ethyl-5H-[1,3]dioxolo[4,5-f] benzimidazole (step 5).

$^1$H-NMR (CDCl$_3$) δ 7.42 (2H, d, J=8.3 Hz), 7.29 (2H, d, J=8.3 Hz), 7.19 (1H, s), 6.53 (1H, s), 5.93 (2H, s), 3.60 (2H, t, J=7.1 Hz), 3.00 (2H, t, J=7.1 Hz), 2.73 (2H, q, J=7.6 Hz), 1.31 (3H, t, J=7.6 Hz).

Step 7. 2-[4-(6-Ethyl-5H-[1,3]dioxolo[4,5-f]benzimidazol-5-yl)phenyl]ethylamine

The title compound was prepared according to the procedure described in step 9 of Example 1 from 2-[4-(6-ethyl-5H-[1,3]dioxolo[4,5-f]benzimidazol-5-yl)phenyl]ethyl azide (step 6).

$^1$H-NMR (CDCl$_3$) δ 7.40 (2H, d, J=8.2 Hz), 7.22–7.28 (2H, m), 7.19 (1H, s), 6.54 (1H, s), 5.93 (2H, s), 3.05 (2H, t, J=6.8 Hz), 2.86 (2H, t, J=6.8 Hz), 2.73 (2H, q, J=7.6 Hz), 1.31 (3H, t, J=7.6 Hz).

Step 8. 6-Ethyl-5-(4-{2-[({[(4-methylphenyl)sulfonyl] amino}carbonyl)amino]ethyl}phenyl)-5H-[1,3]dioxolo[4,5-f]benzimidazole The title compound was prepared according to the procedure described in step 10 of Example 1 from 2-[4-(6-ethyl-5H-[1,3]dioxolo[4,5-f]benzimidazol-5-yl)phenyl] ethylamine (step 7).

MS (ESI) m/z 507 (M+H)$^+$; $^1$H-NMR (DMSO-d$_6$) δ 7.75 (2H, d, J=8.1 Hz), 7.35–7.37 (6H, m), 7.16 (1H, s), 6.55 (1H, s), 5.97 (2H, s), 2.76 (2H, t, J=6.9 Hz), 2.65 (2H, q, J=7.6 Hz), 2.50 (2H, br.s), 2.34 (3H, s), 1.18 (3H, t, J=7.6 Hz).

Example 115

6-ETHYL-5-(4-{2-[({[(4-METHYLPHENYL) SULFONYL]AMINO}CARBONYL)AMINO] ETHYL}PHENYL)-5H-[1,3]DIOXOLO[4,5-f] BENZIMIDAZOLE, SODIUM SALT

The title compound was prepared according to the procedure described in Example 2 from 6-ethyl-5-(4-{2-[({[(4-methylphenyl)sulfonyl]amino}carbonyl)amino] ethyl}phenyl )-5H-[1,3]dioxolo[4,5-f]benzimidazole (Example 114).

mp 140–155° C.; IR (KBr) α$_{max}$ 3384, 2873, 1600, 1519, 1460, 1155, 1128, 1085, 1037, 945, 813 cm$^{-1}$.

Example 116

2-ETHYL-1-(4-{2-[({[(4-METHYLPHENYL) SULFONYL]AMINO}CARBONYL)AMINO] ETHYL}PHENYL)-6,7-DIHYDRO-1H-[1,4]DIOXINO[2, 3-f]BENZIMIDAZOLE

Step 1. 7-Nitro-2,3-dihydro-1,4-benzodioxin-6-amine

To a mixture of 6,7-dinitro-2,3-dihydrobenzo[1,4]dioxin (Takakis, I. M.; Hadjimihalakis, P. M. *J. Heterocyclic. Chem.*, 1991, 28, 625., 13 g, 57.8 mmol) and acetic acid (150 mL) was added iron powder (9.6 g, 172.5 mmol) at room temperature, then the mixture was refluxed for 30 min. After cooling, the mixture was filtered through a pad of Celite and the filtrate was concentrated. The residue was purified by flash column chromatography on silica gel eluting with hexane/ethyl acetate (gradient elution from 1:1 to 1:2) to afford 3.22 g (28%) of the title compound as orange solid: $^1$H-NMR (CDCl$_3$) δ 7.67 (1H, s), 6.23 (1H, s), 5,85 (2H, br.s), 4.19–4.33 (4H, m).

Step 2. 2-{4-[(7-Nitro-2,3-dihydro-1,4-benzodioxin-6-yl) amino]phenyl}ethanol

The title compound was prepared according to the procedure described in step 1 of Example 45 from 7-nitro-2,3-dihydro-1,4-benzodioxin-6-amine (step 1) and 4-bromophenylethyl alcohol.

$^1$H-NMR (CDCl$_3$) δ 7.77 (1H, s), 7.26 (2H, d, J=8.4 Hz), 7.19 (2H, d, J=8.4 Hz), 6.64 (1H, s), 4.20–4.31 (4H, m), 3.89 (2H, t, J=6.4 Hz), 2.88 (2H, t, J=6.4 Hz).

Step 3. 2-{4-[(7-Amino-2,3-dihydro-1,4-benzodioxin-6-yl) amino]phenyl}ethanol

The title compound was prepared according to the procedure described in step 2 of Example 28 from 2-{4-[(7-nitro-2,3-dihydro-1,4-benzodioxin-6-yl)amino] phenyl}ethanol (step 2).

$^1$H-NMR (CDCl$_3$) δ 7.02–7.05 (2H, m), 6.62–6.65 (3H, m), 6.33 (1H, s), 5.00 (1H, br.s), 4.15–4.24 (4H, m), 3.79 (2H, t, J=6.6 Hz), 3.53 (2H, br.s), 2.76 (2H, t, J=6.6 Hz)

Step 4. 2-[4-(2-Ethyl-6,7-dihydro-1H-[1,4]dioxino[2,3-f] benzimidazol-1-yl)phenyl]ethyl propionate The title compound was prepared according to the procedure described in step 5 of Example 1 from 2-{4-[(7-amino-2,3-dihydro-1,4-benzodioxin-6-yl)amino] phenyl}ethanol (step 3) and propionyl chloride.

TLC Rf=0.5 (hexane:ethyl acetate=1:2).

Step 5. 2-[4-(2-Ethyl-6,7-dihydro-1H-[1,4]dioxino[2,3-f]benzimidazol-1-yl)phenyl]ethanol The title compound was prepared according to the procedure described in step 6 of Example 1 from 2-{4-[(7-amino-2,3-dihydro-1,4-benzodioxin-6-yl)amino]phenyl}ethyl propionate (step 4).

$^1$H-NMR (CDCl$_3$) δ 7.42 (2H, d, J=8.1 Hz), 7.25–7.28 (3H, m), 6.58 (1H, s), 4.21–4.27 (4H, m) 3.97 (2H, t, J=6.6 Hz), 2.98 (2H, t, J=6.6 Hz), 2.74 (2H, q, J=7.3 Hz), 1.31 (3H, t, J=7.3 Hz).

Step 6. 1-[4-(2-Chloroethyl)phenyl]-2-ethyl-6,7-dihydro-1H-[1,4]dioxino[2,3-f]benzimidazole The title compound was prepared according to the procedure described in step 7 of Example 1 from 2-[4-(2-ethyl-6,7-dihydro-1H-[1,4]dioxino[2,3-f]benzimidazol-1-yl)phenyl]step 5).

$^1$H-NMR (CDCl$_3$) δ 7.40 (2H, d, J=8.1 Hz), 7.26–7.39 (3H, m), 6.58 (1H, s), 4.25 (4H, s), 3.80 (2H, t, J=7.3 Hz), 3.20 (2H, t, J=7.3 Hz), 2.74 (2H, q, J=7.6Hz), 1.31 (3H, t, J=7.6 Hz).

Step 7. 2-[4-(2-Ethyl-6,7-dihydro-1H-[1,4]dioxino[2,3-f]benzimidazol-1-yl)phenyl]ethyl azide The title compound was prepared according to the procedure described in step 8 of Example 1 from 1-[4-(2-chloroethyl)phenyl]-2-ethyl-6,7-dihydro-1H-[1,4]dioxino[2,3-f]benzimidazole (step 6).

$^1$H-NMR (CDCl$_3$) δ 7.40 (2H, d, J=8.3 Hz), 7.24–7.29 (3H, m), 6.57 (1H, s), 4.21–4.26 (4H, m), 3.59 (2H, t, J=7.0 Hz), 2.99 (2H, t, J=7.0 Hz), 2.73 (2H, q, J=7.5 Hz), 1.30 (3H, t, J=7.5 Hz).

Step 8. 2-[4-(2-Ethyl-6,7-dihydro-1H-[1,4]dioxino[2,3-f]benzimidazol-1-yl)phenyl]ethylamine The title compound was prepared according to the procedure described in step 9 of Example 1 from 2-[4-(2-ethyl-6,7-dihydro-1H-[1,4]dioxino[2,3-f]benzimidazol-1-yl)phenyl]ethyl azide (step 6).

$^1$H-NMR (CDCl$_3$) δ 77.40 (2H, d, J=8.3 Hz), 7.24–7.27 (3H, m), 6.62 (1H, s), 4.21 (4H, s), 3.24–3.26 (2H, m), 3.11 (2H, t, J=6.9 Hz), 2.72 (2H, q, J=7.4 Hz), 1.30 (3H, t, J=7.4 Hz).

Step 9. 2-Ethyl-1-(4-{2-[({[(4-methylphenyl)sulfonyl]amino}carbonyl)amino]ethyl}phenyl)-6,7-dihydro-1H-[1,4]dioxino[2,3f-]benzimidazole The title compound was prepared according to the procedure described in step 10 of Example 1 from 2-[4-(2-ethyl-6,7-dihydro-1H-[1,4]dioxino[2,3-f]benzimidazol-1-yl)phenyl]ethylamine (step 8).

MS (ESI) m/z 521 (M+H)$^+$; $^1$H-NMR (CDCl$_3$) δ 7.76 (2H, d, J=8.4 Hz), 7.18–7.31 (7H, m), 6.64 (1H, br.s), 6.56 (1H, br.s), 4.24 (4H, s), 3.56 (2H, t, J=6.9 Hz), 2.90 (2H, t, J=6.9 Hz), 2.70 (2H, q, J=7.6 Hz), 2.41 (3H, s), 1.27 (3H, t, J=7.6 Hz).

Example 117

2-ETHYL-1-(4-{2-[({[(4-METHYLPHENYL)SULFONYL]AMINO}CARBONYL)AMINO]ETHYL}PHENYL)-6,7-DIHYDRO-1H-[1,4]DIOXINO[2,3-f]BENZIMIDAZOLE, SODIUM SALT

The title compound was prepared according to the procedure described in Example 2 from 2-ethyl-1-(4-{2-[({[(4-methylphenyl)sulfonyl]amino}carbonyl)amino]ethyl}phenyl)-6,7-dihydro-1H-[1,4]dioxino[2,3-f]benzimidazole (Example 116).

mp 162–173° C.; $^1$H-NMR (DMSO-d$_6$) δ 7.83 (2H, d, J=8.0 Hz), 7.58 (2H, d, J=8.6 Hz), 7.54 (2H, d, J=8.0 Hz), 7.35 (2H, d, J=8.6 Hz), 7.29 (1H, s), 6.68 (1H, s), 4.42 (4H, s), 3.38 (2H, br.s), 2.94 (2H, t, J=6.9 Hz), 2.86 (2H, q, J=7.6 Hz), 2.49 (3H, s), 1.39 (3H, t, J=7.6 Hz); IR (KBr)α$_{max}$ 3360, 2875, 1596, 1516, 1468, 1335, 1167, 1130, 1064, 920 cm$^{-1}$.

Example 118–Example 161

The compounds disclosed hereinafter were prepared according to the following procedure: To a solution of requisite commercially available sulfonamide (0.05 mmol) in DMF (1 mL) was added a suspension of NaH (0.1 mmol) in DMF (0.5 mL) and the mixture was shaken for 5 min. To this mixture was added a solution of phenyl 2-[4-(2-ethyl-5,7-dimethyl-3H-imidazo[4,5-b]pyridin-3-yl)phenyl]ethylcarbamate (step 1 of Example 18, 7 mg, 0.05 mmol) in DMF (0.5 mL), and the mixture was shaken at room temperature for 30 min. After removal of DMF by nitrogen blow, the residue was dissolved in water (3 mL) and loaded onto a 0.5 g/3 mL BondElute SCX. The solid phase was washed with MeOH (5 mL), and then eluted with 10% HCl/MeOH (3 mL). The eluate was concentrated under reduced pressure to give the title compound.

Example 118

3-(4-{2-[({[(3,4-DICHLOROPHENYL)SULFONYL]AMINO}CARBONYL)AMINO]ETHYL}PHENYL)-2-ETHYL-5,7-DIMETHYL-3H-IMIDAZO[4,5-b]PYRIDINE, HYDROCHLORIDE

MS (ESI) m/z 546.6 (M+H)$^+$.

Example 119

2-ETHYL-3-{4-[2-({[({3-NITROPHENYL}SULFONYL)AMINO]CARBONYL}AMINO)ETHYL]PHENYL}-5,7-DIMETHYL-3H-IMIDAZO[4,5-b]PYRIDINE, HYDROCHLORIDE

MS (ESI) m/z 523.3 (M+H)$^+$.

Example 120

3-(4-{2-[({[(4-CHLOROPHENYL)SULFONYL]AMINO}CARBONYL)AMINO]ETHYL}PHENYL)-2-ETHYL-5,7-DIMETHYL-3H-IMIDAZO[4,5-b]PYRIDINE, HYDROCHLORIDE

MS (ESI) m/z 512.5 (M+H)$^+$.

Example 121

2-ETHYL-3-{4-[2-({[({4-NITROPHENYL}SULFONYL)AMINO]CARBONYL}AMINO)ETHYL]PHENYL}-5,7-DIMETHYL-3H-IMIDAZO[4,5-b]PYRIDINE, HYDROCHLORIDE

MS (ESI) m/z 523.3 (M+H)$^+$.

Example 122

N-[4-({[({2-[4-(2-ETHYL-5,7-DIMETHYL-3H-IMIDAZO[4,5-b]PYRIDIN-3-YL)PHENYL]ETHYL}AMINO)CARBONYL]AMINO}SULFONYL)PHENYL]-2,2-DIMETHYLPROPANAMIDE, HYDROCHLORIDE

MS (ESI) m/z 577.5 (M+H)$^+$.

Example 123

3-(4-{2-[({[(2-CHLOROPHENYL)SULFONYL]AMINO}CARBONYL)AMINO]ETHYL}PHENYL)-2-ETHYL-5,7-DIMETHYL-3H-IMIDAZO[4,5-b]PYRIDINE, HYDROCHLORIDE

MS (ESI) m/z 512.4 (M+H)$^+$.

Example 124

3-(4-{2-[({[(3-CHLOROPHENYL)SULFONYL]AMINO}CARBONYL)AMINO]ETHYL}PHENYL)-2-ETHYL-5,7-DIMETHYL-3H-IMIDAZO[4,5-b]PYRIDINE, HYDROCHLORIDE

MS (ESI) m/z 512.5 (M+H)$^+$.

Example 125

3-(4-{2-[({[(5-CHLORO-2-THIENYL)SULFONYL]AMINO}CARBONYL)AMINO]ETHYL}PHENYL)-2-

ETHYL-5,7-DIMETHYL-3H-IMIDAZO[4,5-b]
PYRIDINE, HYDROCHLORIDE
  MS (ESI) m/z 518.6 (M+H)+.

Example 126
3-(4-{2-[({[(5-BROMO-2-THIENYL)SULFONYL]
AMINO}CARBONYL)AMINO]ETHYL}PHENYL)-2-
ETHYL-5,7-DIMETHYL-3H-IMIDAZO[4,5-b]
PYRIDINE, HYDROCHLORIDE
  MS (ESI) m/z 564.2 (M+H)+.

Example 127
2-ETHYL-3-{4-[2-({[({2-METHYL-5-NITRO-
PHENYL}SULFONYL)AMINO]CARBONYL}AMINO)
ETHYL]PHENYL}-5,7-DIMETHYL-3H-IMIDAZO[4,5-
b]PYRIDINE, HYDROCHLORIDE
  MS (ESI) m/z 537.3 (M+H)+.

Example 128
3-(4-{2-[({[(3,4-DIMETHOXYPHENYL)SULFONYL]
AMINO}CARBONYL)AMINO]ETHYL}PHENYL)-2-
ETHYL-5,7-DIMETHYL-3H-IMIDAZO[4,5-b]
PYRIDINE, HYDROCHLORIDE
  MS (ESI) m/z 538.4 (M+H)+.

Example 129
3-(4-{2-[({[(4-BUTYLPHENYL)SULFONYL]
AMINO}CARBONYL)AMINO]ETHYL}PHENYL)-2-
ETHYL-5,7-DIMETHYL-3H-IMIDAZO[4,5-b]
PYRIDINE, HYDROCHLORIDE
  MS (ESI) m/z 534.5 (M+H)+.

Example 130
2-ETHYL-3-(4-{2-[({[(4-METHOXYPHENYL)
SULFONYL]AMINO}CARBONYL)AMINO]
ETHYL}PHENYL)-5,7-DIMETHYL-3H-IMIDAZO[4,5-
b]PYRIDINE, HYDROCHLORIDE
  MS (ESI) m/z 508.4 (M+H)+.

Example 131
2-ETHYL-5,7-DIMETHYL-3-[4-(2-{[({[5-
(PHENYLSULFANYL)-2-THIENYL]
SULFONYL}AMINO)CARBONYL]AMINO}ETHYL)
PHENYL]-3H-IMIDAZO[4,5-b]PYRIDINE,
HYDROCHLORIDE
  MS (ESI) m/z 592.4 (M+H)+.

Example 132
3-(4-{2-[({[(3,5-DICHLOROPHENYL)SULFONYL]
AMINO}CARBONYL)AMINO]ETHYL}PHENYL)-2-
ETHYL-5,7-DIMETHYL-3H-IMIDAZO[4,5-b]
PYRIDINE, HYDROCHLORIDE
  MS (ESI) m/z 546.6 (M+H)+.

Example 133
3-(4-{2-[({[(2-BROMOPHENYL)SULFONYL]
AMINO}CARBONYL)AMINO]ETHYL}PHENYL)-2-
ETHYL-5,7-DIMETHYL-3H-IMIDAZO[4,5-b]
PYRIDINE, HYDROCHLORIDE
  MS (ESI) m/z 558.0 (M+H)+.

Example 134
3-(4-{2-[({[(4,5-DICHLORO-2-THIENYL)SULFONYL]
AMINO}CARBONYL)AMINO]ETHYL}PHENYL)-2-
ETHYL-5,7-DIMETHYL-3H-IMIDAZO[4,5-b]
PYRIDINE, HYDROCHLORIDE
  MS (ESI) m/z 552.6 (M+H)+.

Example 135
3-[4-(2-{[({[2-(2,4-DICHLOROPHENOXY)PHENYL]
SULFONYL}AMINO)CARBONYL]AMINO}ETHYL)
PHENYL]-2-ETHYL-5,7-DIMETHYL-3H-IMIDAZO[4,5-
b]PYRIDINE, HYDROCHLORIDE
  MS (ESI) m/z 638.8 (M+H)+.

Example 136
3-(4-{2-[({[(5-CHLORO-1,3-DIMETHYL-1H-
PYRAZOL-4-YL)SULFONYL]AMINO}CARBONYL)
AMINO]ETHYL}PHENYL)-2-ETHYL-5,7-DIMETHYL-
3H-IMIDAZO[4,5-b]PYRIDINE, HYDROCHLORIDE
  MS (ESI) m/z 530.3 (M+H)+.

Example 137
3-(4-{2-[({[(2,4-DIMETHYL-1,3-THIAZOL-5-YL)
SULFONYL]AMINO}CARBONYL)AMINO]
ETHYL}PHENYL)-2-ETHYL-5,7-DIMETHYL-3H-
IMIDAZO[4,5-b]PYRIDINE, HYDROCHLORIDE
  MS (ESI) m/z 523.2 (M+H)+.

Example 138
3-(4-{2-[({[(4-CYANOPHENYL)SULFONYL]
AMINO}CARBONYL)AMINO]ETHYL}PHENYL)-2-
ETHYL-5,7-DIMETHYL-3H-IMIDAZO[4,5-b]
PYRIDINE, HYDROCHLORIDE
  MS (ESI) m/z 503.2 (M+H)+.

Example 139
3-(4-{2-[({[(3,4-DIFLUOROPHENYL)SULFONYL]
AMINO}CARBONYL)AMINO]ETHYL}PHENYL)-2-
ETHYL-5,7-DIMETHYL-3H-IMIDAZO[4,5-b]
PYRIDINE, HYDROCHLORIDE
  MS (ESI) m/z 514.3 (M+H)+.

Example 140
3-(4-{2-[({[(2,5-DICHLORO-3-THIENYL)SULFONYL]
AMINO}CARBONYL)AMINO]ETHYL}PHENYL)-2-
ETHYL-5,7-DIMETHYL-3H-IMIDAZO[4,5-b]
PYRIDINE, HYDROCHLORIDE
  MS (ESI) m/z 552.3 (M+H)+.

Example 141
N-[5-({[({2-[4-(2-ETHYL-5,7-DIMETHYL-3H-IMIDAZO
[4,5-b]PYRIDIN-3-YL)PHENYL]ETHYL}AMINO)
CARBONYL]AMINO}SULFONYL)-1,3,4-
THIADIAZOL-2-YL]ACETAMIDE, HYDROCHLORIDE
  MS (ESI) m/z 543.0 (M+H)+.

Example 142
3-{4-[2-({[({4-CHLORO-3-
NITROPHENYL}SULFONYL)AMINO]
CARBONYL}AMINO)ETHYL]PHENYL}-2-ETHYL-5,
7-DIMETHYL-3H-IMIDAZO[4,5-b]PYRIDINE,
HYDROCHLORIDE
  MS (ESI) m/z 557.2 (M+H)+.

Example 143
3-(4-{2-[({[(4-BUTOXYPHENYL)SULFONYL]
AMINO}CARBONYL)AMINO]ETHYL}PHENYL)-2-
ETHYL-5,7-DIMETHYL-3H-IMIDAZO[4,5-b]
PYRIDINE, HYDROCHLORIDE
  MS (ESI) m/z 550.4 (M+H)+.

Example 144
3-[4-(2-{[({[2,6-DICHLORO-4-(TRIFLUOROMETHYL)
PHENYL]SULFONYL}AMINO)CARBONYL]
AMINO}ETHYL)PHENYL]-2-ETHYL-5,7-DIMETHYL-
3H-IMIDAZO[4,5-b]PYRIDINE, HYDROCHLORIDE
  MS (ESI) m/z 614.4 (M+H)+.

Example 145
3-[4-(2-[{({[4-(1-ADAMANTYL)PHENYL]
SULFONYL}AMINO)CARBONYL]AMINO}ETHYL)

PHENYL]-2-ETHYL-5,7-DIMETHYL-3H-IMIDAZO[4,5-b]PYRIDINE, HYDROCHLORIDE
MS (ESI) m/z 612.4 (M+H)$^+$.

Example 146

3-(4-{2-[({[(4,5-DIBROMO-2-THIENYL)SULFONYL]AMINO}CARBONYL)AMINO]ETHYL}PHENYL)-2-ETHYL-5,7-DIMETHYL-3H-IMIDAZO[4,5-b]PYRIDINE, HYDROCHLORIDE
MS (ESI) m/z 642.0 (M+H)$^+$.

Example 147

2-ETHYL-5,7-DIMETHYL-3-[4-(2-{[({[5-(2-THIENYLSULFANYL)-2-THIENYL]SULFONYL}AMINO)CARBONYL]AMINO}ETHYL)PHENYL]-3H-IMIDAZO[4,5-b]PYRIDINE, HYDROCHLORIDE
MS (ESI) m/z 598.2 (M+H)$^+$.

Example 148

3-(4-{2-[({[(4-TERT-BUTYLPHENYL)SULFONYL]AMINO}CARBONYL)AMINO]ETHYL}PHENYL)-2-ETHYL-5,7-DIMETHYL-3H-IMIDAZO[4,5-b]PYRIDINE, HYDROCHLORIDE
MS (ESI) m/z 534.4 (M+H)$^+$.

Example 149

3-(4-{2-[({[(4-AMINO-3-CHLOROPHENYL)SULFONYL]AMINO}CARBONYL)AMINO]ETHYL}PHENYL)-2-ETHYL-5,7-DIMETHYL-3H-IMIDAZO[4,5-b]PYRIDINE, HYDROCHLORIDE
MS (ESI) m/z 527.3 (M+H)$^+$.

Example 150

2-ETHYL-5,7-DIMETHYL-3-(4-{2-[({[(2,4,5-TRICHLOROPHENYL)SULFONYL]AMINO}CARBONYL)AMINO]ETHYL}PHENYL)-3H-IMIDAZO[4,5-b]PYRIDINE, HYDROCHLORIDE
MS (ESI) m/z 580.4 (M+H)$^+$.

Example 151

3-(4-{2-[({[(2,5-DIMETHOXYPHENYL)SULFONYL]AMINO}CARBONYL)AMINO]ETHYL}PHENYL)-2-ETHYL-5,7-DIMETHYL-3H-IMIDAZO[4,5-b]PYRIDINE, HYDROCHLORIDE
MS (ESI) m/z 538.3 (M+H)$^+$.

Example 152

3-(4-{2-[({[(6-ETHOXY-1,3-BENZOTHIAZOL-2-YL)SULFONYL]AMINO}CARBONYL)AMINO]ETHYL}PHENYL)-2-ETHYL-5,7-DIMETHYL-3H-IMIDAZO[4,5-b]PYRIDINE, HYDROCHLORIDE
MS (ESI) m/z 579.1 (M+H)$^+$.

Example 153

3-(4-{2-[({[(2-AMINO-4-CHLOROPHENYL)SULFONYL]AMINO}CARBONYL)AMINO]ETHYL}PHENYL)-2-ETHYL-5,7-DIMETHYL-3H-IMIDAZO[4,5-b]PYRIDINE, HYDROCHLORIDE
MS (ESI) m/z 527.2 (M+H)$^+$.

Example 154

2-ETHYL-5,7-DIMETHYL-3-[4-(2-{[({[5-(2-THIENYLSULFONYL)-2-THIENYL]SULFONYL}AMINO)CARBONYL]AMINO}ETHYL)PHENYL]-3H-IMIDAZO[4,5-b]PYRIDINE, HYDROCHLORIDE
MS (ESI) m/z 630.2 (M+H)$^+$.

Example 155

3-[4-(2-{[({[2-CHLORO-5-(TRIFLUOROMETHYL)PHENYL]SULFONYL}AMINO)CARBONYL]AMINO}ETHYL)PHENYL]-2-ETHYL-5,7-DIMETHYL-3H-IMIDAZO[4,5-b]PYRIDINE, HYDROCHLORIDE
MS (ESI) m/z 580.2 (M+H)$^+$.

Example 156

3-{4-[2-({[(2,3-DIHYDRO-1,4-BENZODIOXIN-6-YLSULFONYL)AMINO]CARBONYL}AMINO)ETHYL]PHENYL}-2-ETHYL-5,7-DIMETHYL-3H-IMIDAZO[4,5-b]PYRIDINE, HYDROCHLORIDE
MS (ESI) m/z 536.2 (M+H)$^+$.

Example 157

2-ETHYL-5,7-DIMETHYL-3-[4-(2-{[({[2-(PHENYLSULFANYL)PHENYL]SULFONYL}AMINO)CARBONYL]AMINO}ETHYL)PHENYL]-3H-IMIDAZO[4,5-b]PYRIDINE, HYDROCHLORIDE
MS (ESI) m/z 586.3 (M+H)$^+$.

Example 158

3-(4-{2-[({[(4-CHLORO-2,5-DIMETHYLPHENYL)SULFONYL]AMINO}CARBONYL)AMINO]ETHYL}PHENYL)-2-ETHYL-5,7-DIMETHYL-3H-IMIDAZO[4,5-b]PYRIDINE, HYDROCHLORIDE
MS (ESI) m/z 540.3 (M+H)$^+$.

Example 159

3-(4-{2-[({[(3-BROMO-5-CHLORO-2-THIENYL)SULFONYL]AMINO}CARBONYL)AMINO]ETHYL}PHENYL)-2-ETHYL-5,7-DIMETHYL-3H-IMIDAZO[4,5-b]PYRIDINE, HYDROCHLORIDE
MS (ESI) m/z 598.1 (M+H)$^+$.

Example 160

2-ETHYL-5,7-DIMETHYL-3-(4-{2-[({[(4-VINYLPHENYL)SULFONYL]AMINO}CARBONYL)AMINO]ETHYL}PHENYL)-3H-IMIDAZO[4,5-b]PYRIDINE, HYDROCHLORIDE
MS (ESI) m/z 504.4 (M+H)$^+$.

Example 161

METHYL 2,4-DICHLORO-5-({[({2-[4-(2-ETHYL-5,7-DIMETHYL-3H-IMIDAZO[4,5-b]PYRIDIN-3-YL)PHENYL]ETHYL}AMINO)CARBONYL]AMINO}SULFONYL)BENZOATE, HYDROCHLORIDE
MS (ESI) m/z 604.5 (M+H)$^+$.

Example 162–Example 194

The compounds disclosed hereinafter were prepared according to the following procedure: To a mixture of requisite commercially available carbonic acid and dichloromethane was added 1-ethyl-3-(3-dimethylaminopropyl)carbodiimide, hydrochloride (WSC) (0.05 mmol, 0.5 mL), then to the reaction mixture was added a solution of 3-amino-4,6-dimethyl-2-(4-{2-[({[(4-methylphenyl)sulfonyl]amino}carbonyl)amino]ethyl}anilino)pyridine* (0.038 mmol) in dichloromethane (0.5 mL) at room temperature. The reaction mixture was stirred for 3 days at room temperature, then stirred for an additional 1 day at 40° C. After removal of the solvent, the residue was dissolved in MeOH (1 mL) and the solution was filtered through a membrane filter. The filtrate was purified by preparative LC/MS (Shiseido capcell pack UG80 C18 (4.6×50 mm) eluting with MeOH/0.1% HCOOH (v/v, 20/80 to 90/10)) to give the title compound.

*3-Amino-4,6-dimethyl-2-(4-{2-[({[(4-methylphenyl)sulfonyl]amino}carbonyl )amino]ethyl}anilino)pyridine was prepared as follows;

Step 1. 3-{4-[(4,6-Dimethyl-3-nitro-2-pyridinyl)amino]phenyl}propanoic acid

To a solution of 2-chloro-4,6-dimethyl-3-nitropyridine (17.9 g, 96 mmol) and methyl 3-(4-aminophenyl)propanoate (19 g, 96 mmol) in DMSO (100 mL) was added N,N-diisopropylethylamine (26 g, 200 mmol), and the reaction mixture was heated at 140° C. overnight. The reaction mixture was partitioned between water (400 mL) and ethyl acetate/toluene (v/v, 2:1, 300 mL). The organic phase was separated and the aqueous phase was extracted with ethyl acetate/toluene (v/v, 2:1, 200 mL). The combined organic extracts were washed with brine (200 mL), dried ($Na_2SO_4$), and concentrated. To a solution of residual oil in methanol (100 mL) was added 2 N aqueous NaOH (150 mL, 300 mmol) and the resulting mixture was stirred at room temperature for 2 h. The volatile component was removed under reduced pressure and the residue was washed with ethyl acetate (200 mL). The aqueous phase was acidified with 2N hydrochloric acid (200 mL, 400 mmol) and extracted with ethyl acetate (3×200 mL). The extracts were washed with brine (200 mL), dried ($Na_2SO_4$), and concentrated to give 23.2 g (77%) of the title compound as pale brown solids.

$^1$H-NMR (CDCl$_3$) δ: 9.57 (1H, s), 7.56 (2H, d, J=8.4 Hz), 7.19 (2H, d, J=8.4 Hz), 6.52 (1H, s), 2.95 (2H, t, J=7.5 Hz), 2.66 (2H, t, J=7.5 Hz), 2.55 (3H, s), 2.43 (3H, s).

Step 2. Phenyl 2-{4-[(4,6-dimethyl-3-nitro-2-pyridinyl)amino]phenyl}ethylcarbamate To a stirred solution of 3-{4-[(4,6-dimethyl-3-nitro-2-pyridinyl)amino]phenyl}propanoic acid (step 1, 10 g, 31.7 mmol) in dioxane (200 mL) was added diphenylphosphoryl azide (DPPA) (7.54 ml, 35 mmol) and triethylamine (4.87 mL, 35 mmol). The reaction mixture was heated at 120° C. for 2 h. To the reaction mixture was added phenol (6.6 g, 70 mmol) and the reaction mixture was refluxed. After 3 h, to the reaction mixture was added an additional amount of phenol (3.3 g, 35 mmol). The resulting mixture was heated under reflux temperature overnight. The volatile component was removed and the residue was partitioned between aqueous 10% aqueous citric acid (200 mL) and ethyl acetate (300 mL). The organic phase was separated and the aqueous phase was extracted with ethyl acetate (300 mL). The combined organic extracts were washed with water (300 mL) and brine (300 mL), then dried ($Na_2SO_4$), and concentrated. The crude product was purified by flash column chromatography on silica gel eluting with hexane/EtOAc (2:1) to afford 10.3 g (77%) of the title compound as orange solids.

$^1$H-NMR (CDCl$_3$) δ: 9.60 (1H, s), 7.61 (2H, d, J=8.6 Hz), 7.38–7.32 (2H, m), 7.24–7.16 (3H, m), 7.14–7.09 (2H, m), 6.54 (1H, s), 5.06 (1H, br.s), 3.58–3.50 (2H, m), 2.89 (2H, t, J=6.9 Hz), 2.56 (3H, s), 2.44 (3H, s).

Step 3. 4,6-Dimethyl-2-(4-{2-[({[(4-methylphenyl)sulfonyl]amino}carbonyl)amino]ethyl}anilino)-3-nitropyridine To a stirred solution of phenyl 2-{4-[(4,6-dimethyl-3-nitro-2-pyridinyl)amino]phenyl}ethylcarbamate (step 2, 10.0 g, 24.6 mmol) and p-toluenesulfonamide (6.3 g, 36.8 mmol) in DMF (100 mL) was added sodium hydride (2.0 g, 50 mmol). The reaction mixture was stirred at room temperature for 1 h. The reaction mixture was poured into water (300 mL) and extracted with ethyl acetate/toluene (v/v, 2:1, 2×300 mL). The organic extracts were washed with water (100 mL) and brine (200 mL), then dried ($Na_2SO_4$). Removal of the solvent gave crude product. Recrystallization from ethyl acetate gave 9.6 g (81%) of the title compound as brown solids. The mother liquor was concentrated and the residue was purified by flash column chromatography on silica gel eluting with hexane/ethyl acetate (1:1) to afford 1.9 g (16%) of the title compound as brown solids.

$^1$H-NMR (CDCl$_3$) δ: 9.75 (1H, s), 7.62 (2H, d, J=8.4 Hz), 7.59 (2H, d, J=8.4 Hz), 7.26 (2H, d, J=8.4 Hz), 7.15 (2H, d, J=8.4 Hz), 6.62–6.50 (2H, m), 3.55–3.42 (2H, m), 2.80 (2H, t, J=6.9 Hz), 2.56 (3H, s), 2.43 (3H, s), 2.39 (3H, s).

Step 4. 3-Amino-4,6-dimethyl-2-(4-{2-[({[(4-methylphenyl)sulfonyl]amino}carbonyl)amino]ethyl}anilino)pyridine To a solution of 4,6-dimethyl-2-(4-{2-[({[(4-methylphenyl)sulfonyl]amino}carbonyl)amino]ethyl}anilino)-3-nitropyridine (step 3, 11.4 g, 23.6 mmol) in methanol (250 mL) was added 10% Pd—C (2.0 g). The resulting mixture was stirred under the medium pressure of hydrogen (4.0 kgf/cm$^2$) for 4 h. The catalyst was removed by filtration, and the filtrate was concentrated. The residue was recrystallized from ethyl acetate to afford 9.0 g (85%) of the title compound as off white solids.

$^1$H-NMR (CDCl$_3$) δ: 7.69 (2H, d, J=8.0 Hz), 7.26 (2H, d, J=8.0 Hz), 7.00–6.95 (4H, m), 6.61 (1H, s), 6.24 (1H, br.s), 3.44–3.38 (2H, m), 2.70 (2H, t, J=6.7 Hz), 2.39 (3H, s), 2.33 (3H, s), 2.19 (3H, s).

Example 162

5,7-DIMETHYL-3-(4-{2-[({[(4-METHYLPHENYL)SULFONYL]AMINO}CARBONYL)AMINO]ETHYL}PHENYL)-2-[3-OXO-3-(2-THIENYL)PROPYL]-3H-IMIDAZO[4,5-b]PYRIDINE, FORMATE

MS (ESI) m/z 602.48 (M+H)$^+$.

Example 163

5,7-DIMETHYL-3-(4-{2-[({[(4-METHYLPHENYL)SULFONYL]AMINO}CARBONYL)AMINO]ETHYL}PHENYL)-2-(PHENOXYMETHYL)-3H-IMIDAZO[4,5-b]PYRIDINE, FORMATE

MS (ESI) m/z 570.5 (M+H)$^+$.

Example 164

5,7-DIMETHYL-3-(4-[2-[({[(4-METHYLPHENYL)SULFONYL]AMINO}CARBONYL)AMINO]ETHYL}PHENYL)-2-[2-(3-PYRIDINYL)ETHYL]-3H-IMIDAZO[4,5-b]PYRIDINE, FORMATE

MS (ESI) m/z 569.49 (M+H)$^+$.

Example 165

5,7-DIMETHYL-3-(4-{2-[({[(4-METHYLPHENYL)SULFONYL]AMINO}CARBONYL)AMINO]ETHYL}PHENYL)-2-(3-OXO-3-PHENYLPROPYL)-3H-IMIDAZO[4,5-b]PYRIDINE, FORMATE

MS (ESI) m/z 596.28 (M+H)$^+$.

Example 166

5,7-DIMETHYL-3-(4-{2-[({[(4-METHYLPHENYL)SULFONYL]AMINO}CARBONYL)AMINO]ETHYL}PHENYL)-2-(3-PHENYLPROPYL)-3H-IMIDAZO[4,5-b]PYRIDINE, FORMATE

MS (ESI) m/z 582.52 (M+H)$^+$.

Example 167

2-(ETHOXYMETHYL)-5,7-DIMETHYL-3-(4-{2-[({[(4-METHYLPHENYL)SULFONYL]AMINO}CARBONYL)AMINO]ETHYL}PHENYL)-3H-IMIDAZO[4,5-b]PYRIDINE, FORMATE

MS (ESI) m/z 522.46 (M+H)$^+$.

Example 168

5,7-DIMETHYL-3-(4-{2-[({[(4-METHYLPHENYL)SULFONYL]AMINO}CARBONYL)AMINO]ETHYL}PHENYL)-2-[(PHENYLSULFANYL)METHYL]-3H-IMIDAZO[4,5-b]PYRIDINE, FORMATE

MS (ESI) m/z 586.49 (M+H)$^+$.

Example 169
5,7-DIMETHYL-3-(4-{2-[({[(4-METHYLPHENYL)SULFONYL]AMINO}CARBONYL)AMINO]ETHYL}PHENYL)-2-PENTYL-3H-IMIDAZO[4,5-b]PYRIDINE, FORMATE
MS (ESI) m/z 534.51 (M+H)$^+$.

Example 170
5,7-DIMETHYL-3-(4-{2-[({[(4-METHYLPHENYL)SULFONYL]AMINO}CARBONYL)AMINO]ETHYL}PHENYL)-2-(2-PHENYLETHYL)-3H-IMIDAZO[4,5-b]PYRIDINE, FORMATE
MS (ESI) m/z 568.51 (M+H)$^+$.

Example 171
2-(3-BUTYNYL)-5,7-DIMETHYL-3-(4-{2-[({[(4-METHYLPHENYL)SULFONYL]AMINO}CARBONYL)AMINO]ETHYL}PHENYL)-3H-IMIDAZO[4,5-b]PYRIDINE, FORMATE
MS (ESI) m/z 516.45 (M+H)$^+$.

Example 172
5,7-DIMETHYL-3-(4-{2-[({[(4-METHYLPHENYL)SULFONYL]AMINO}CARBONYL)AMINO]ETHYL}PHENYL)-2-(3-THIENYLMETHYL)-3H-IMIDAZO[4,5-b]PYRIDINE, FORMATE
MS (ESI) m/z 560.44 (M+H)$^+$.

Example 173
5,7-DIMETHYL-3-(4-{2-[({[(4-METHYLPHENYL)SULFONYL]AMINO}CARBONYL)AMINO]ETHYL}PHENYL)-2-(4-PENTYNYL)-3H-IMIDAZO[4,5-b]PYRIDINE, FORMATE
MS (ESI) m/z 530.46 (M+H)$^+$.

Example 174
5,7-DIMETHYL-3-(4-{2-[({[(4-METHYLPHENYL)SULFONYL]AMINO}CARBONYL)AMINO]ETHYL}PHENYL)-2-(2-THIENYLMETHYL)-3H-IMIDAZO[4,5-b]PYRIDINE, FORMATE
MS (ESI) m/z 560.44 (M+H)$^+$.

Example 175
5,7-DIMETHYL-3-(4-{2-[({[(4-METHYLPHENYL)SULFONYL]AMINO}CARBONYL)AMINO]ETHYL}PHENYL)-2-(3-PYRIDINYLMETHYL)-3H-IMIDAZO[4,5-b]PYRIDINE, FORMATE
MS (ESI) m/z 555.48 (M+H)$^+$.

Example 176
5,7-DIMETHYL-3-(4-{2-[({[(4-METHYLPHENYL)SULFONYL]AMINO}CARBONYL)AMINO]ETHYL}PHENYL)-2-[(2E)-2-PENTENYL]-3H-IMIDAZO[4,5-b]PYRIDINE, FORMATE
MS (ESI) m/z 532.48 (M+H)$^+$.

Example 177
2-BENZYL-5,7-DIMETHYL-3-(4-{2-[({[(4-METHYLPHENYL)SULFONYL]AMINO}CARBONYL)AMINO]ETHYL}PHENYL)-3H-IMIDAZO[4,5-b]PYRIDINE, FORMATE
MS (ESI) m/z 554.48 (M+H)$^+$.

Example 178
2-(CYANOMETHYL)-5,7-DIMETHYL-3-(4-{2-[({[(4-METHYLPHENYL)SULFONYL]AMINO}CARBONYL)AMINO]ETHYL}PHENYL)-3H-IMIDAZO[4,5-b]PYRIDINE, FORMATE
MS (ESI) m/z 503.41 (M+H)$^+$.

Example 179
2-(METHOXYMETHYL)-5,7-DIMETHYL-3-(4-{2-[({[(4-METHYLPHENYL)SULFONYL]AMINO}CARBONYL)AMINO]ETHYL}PHENYL)-3H-IMIDAZO[4,5-b]PYRIDINE, FORMATE
MS (ESI) m/z 508.44 (M+H)$^+$.

Example 180
2-HEPTYL-5,7-DIMETHYL-3-(4-{2-[({[(4-METHYLPHENYL)SULFONYL]AMINO}CARBONYL)AMINO)]ETHYL}PHENYL)-3H-IMIDAZO[4,5-b]PYRIDINE, FORMATE
MS (ESI) m/z 562.33 (M+H)$^+$.

Example 181
5,7-DIMETHYL-3-(4-{2-[({[(4-METHYLPHENYL)SULFONYL]AMINO}CARBONYL)AMINO]ETHYL}PHENYL)-2-OCTYL-3H-IMIDAZO[4,5-b]PYRIDINE, FORMATE
MS (ESI) m/z 576.37 (M+H)$^+$.

Example 182
5,7-DIMETHYL-2-(4-METHYLPENTYL)-3-(4-{2-[({[(4-METHYLPHENYL)SULFONYL]AMINO}CARBONYL)AMINO]ETHYL}PHENYL)-3H-IMIDAZO[4,5-b]PYRIDINE, FORMATE
MS (ESI) m/z 548.53 (M+H)$^+$.

Example 183
2-[(BENZYLOXY)METHYL]-5,7-DIMETHYL-3-(4-{2-[({[(4-METHYLPHENYL)SULFONYL]AMINO}CARBONYL)AMINO]ETHYL}PHENYL)-3H-IMIDAZO[4,5-b]PYRIDINE, FORMATE
MS (ESI) m/z 584.52 (M+H)$^+$.

Example 184
5,7-DIMETHYL-3-(4-{2-[({[(4-METHYLPHENYL)SULFONYL]AMINO}CARBONYL)AMINO]ETHYL}PHENYL)-2-(2-PHENOXYETHYL)-3H-IMIDAZO[4,5-b]PYRIDINE, FORMATE
MS (ESI) m/z 584.33 (M+H)$^+$.

Example 185
5,7-DIMETHYL3-(4-{2-[({[(4-METHYLPHENYL)SULFONYL]AMINO}CARBONYL)AMINO]ETHYL}PHENYL)-2-[3-(2-THIENYL)PROPYL]-3H-IMIDAZO[4,5-b]PYRIDINE, FORMATE
MS (ESI) m/z 588.5 (M+H)$^+$.

Example 186
5,7-DIMETHYL-3-(4-{2-[({[(4-METHYLPHENYL)SULFONYL]AMINO}CARBONYL)AMINO]ETHYL}PHENYL)-2-(2-NAPHTHYLMETHYL)-3H-IMIDAZO[4,5-b]PYRIDINE, FORMATE
MS (ESI) m/z 604.37 (M+H)$^+$.

Example 187
5,7-DIMETHYL-3-(4-{2-[({[(4-METHYLPHENYL)SULFONYL]AMINO}CARBONYL)AMINO]ETHYL}PHENYL)-2-(4-PHENYLBUTYL)-3H-IMIDAZO[4,5-b]PYRIDINE, FORMATE
MS (ESI) m/z 596.42 (M+H)$^+$.

Example 188
5,7-DIMETHYL-3-(4-{2-[({[(4-METHYLPHENYL)SULFONYL]AMINO}CARBONYL)AMINO]ETHYL}PHENYL)-2-(5-PHENYLPENTYL)-3H-IMIDAZO[4,5-b]PYRIDINE, FORMATE
MS (ESI) m/z 610.45 (M+H)$^+$.

Example 189
2-(2-ETHOXYETHYL)-5,7-DIMETHYL-3-(4-{2-[({[(4-METHYLPHENYL)SULFONYL]AMINO}CARBONYL)AMINO]ETHYL}PHENYL)-3H-IMIDAZO[4,5-b]PYRIDINE, FORMATE MS (ESI) m/z 536.38 (M+H)+.

Example 190
2-(2,3-DIHYDRO-1H-INDEN-2-YLMETHYL)-5,7-DIMETHYL-3-(4-{2-[({[(4-METHYLPHENYL)SULFONYL]AMINO}CARBONYL)AMINO]ETHYL}PHENYL)-3H-IMIDAZO[4,5-b]PYRIDINE, FORMATE MS (ESI) m/z 594.45 (M+H)+.

Example 191
2-(CYCLOPROPYLMETHYL)-5,7-DIMETHYL-3-(4-{2-[({[(4-METHYLPHENYL)SULFONYL]AMINO}CARBONYL)AMINO]ETHYL}PHENYL)-3H-IMIDAZO[4,5-b]PYRIDINE, FORMATE MS (ESI) m/z 518.45 (M+H)+.

Example 192
5,7-DIMETHYL-3-(4-{2-[({[(4-METHYLPHENYL)SULFONYL]AMINO}CARBONYL)AMINO]ETHYL}PHENYL)-2-[2-(METHYLSULFANYL)ETHYL]-3H-IMIDAZO[4,5-b]PYRIDINE, FORMATE MS (ESI) m/z 538.44 (M+H)+.

Example 193
2-HEXYL-5,7-DIMETHYL-3-(4-{2-[({[(4-METHYLPHENYL)SULFONYL]AMINO}CARBONYL)AMINO]ETHYL}PHENYL)-3H-IMIDAZO[4,5-b]PYRIDINE, FORMATE MS (ESI) m/z 548.44 (M+H)+.

Example 194
5,7-DIMETHYL-3-(4-{2-[({[(4-METHYLPHENYL)SULFONYL]AMINO}CARBONYL)AMINO]ETHYL}PHENYL)-2-(4-PENTENYL)-3H-IMIDAZO[4,5-b]PYRIDINE, FORMATE MS (ESI) m/z 532.42 (M+H)+.

Example 195
6-CHLORO-5-CYANO-2-ETHYL-1-(4-{2-[({[(4-METHYLPHENYLSULFONYL]AMINO}CARBONYL)AMINO]ETHYL}PHENYL)-1H-BENZIMIDAZOLE Step 1. 6-Chloro-1-[4-(2-chloroethyl)phenyl]-2-ethyl-1H-benzimidazole-5-carbonitrile The reaction was carried out according to the procedure described in step 7 of Example 1 from 6-chloro-2-ethyl-1-[4-(2-hydroxyethyl)phenyl]-1H-benzimidazole-5-carbonitrile (Example 1 from 6-chloro-2-ethyl-1-[4-(2-chloroethyl)phenyl]-2-ethyl-1H-benzimidazole-5-carbonitrile (Example 111, step 4).

$^1$H-NMR (CDCl$_3$) δ 8.07 (1H, s), 7.50 (2H, d, J=8.4 Hz), 7.30 (2H, d, J=8.4 Hz), 7.19 (1H, s), 3.83 (2H, t, J=7.1 Hz), 3.22 (2H, t, J=7.1 Hz), 2.79 (2H, q, J=7.5 Hz), 1.37 (3H, t, J=7.5 Hz).

Step 2. 1-[4-(2-Azidoethyl)phenyl]-6-chloro-2-ethyl-1H-benzimidazole-5-carbonitrile The reaction was carried out according to the procedure described in step 8 of Example 1 from 6-chloro-1-[4-(2-chloroethyl)phenyl]-2-ethyl-1H-benzimidazole-5-carbonitrile (step 1).

$^1$H-NMR (CDCl$_3$) δ 8.07 (1H, s), 7.49 (2H, d, J=8.4 Hz), 7.29 (2H, d, J=8.4 Hz), 7.18 (1H, s), 3.64 (2H, t, J=7.0 Hz), 3.04 (2H, t, J=7.0 Hz), 2.79 (2H, q, J=7.6 Hz), 1.36 (3H, t, J=7.6 Hz).

Step 3. 1-[4-(2-Aminoethyl)phenyl]-6-chloro-2-ethyl-1H-benzimidazole-5-carbonitrile The reaction was carried out according to the procedure described in step 7 of Example 37 from 1-[4-(2-azidoethyl)phenyl]-6-chloro-2-ethyl-1H-benzimidazole-5-carbonitrile (step 2).

$^1$H-NMR (CDCl$_3$) δ 8.06 (1H, s), 7.46 (2H, d, J=8.1 Hz), 7.26 (2H, d, J=8.1 Hz), 7.19 (1H, s), 3.09 (2H, t, J=7.1 Hz), 2.89 (2H, t, J=7.1 Hz), 2.79 (2H, q, J=7.6 Hz), 1.36 (3H, t, J=7.6 Hz).

Step 4. 6-Chloro-5-cyano-2-ethyl-1-(4-{2-[({[(4-methylphenyl)sulfonyl]amino}carbonyl)amino]ethyl}phenyl)-1H-benzimidazole The reaction was carried out according to the procedure described in step 10 of Example 1 from 1-[4-(2-aminoethyl)phenyl]-6-chloro-2-ethyl-1H-benzimidazole-5-carbonitrile (step 3).

mp 219–224° C.; IR (KBr) v: 3388, 2229, 1708, 1618, 1514, 1466, 1344, 1161, 1089cm$^{-1}$.

MS (ESI) m/z 522 (M+H)+, 520 (M−H)−; $^1$H-NMR (DMSO-d$_6$) δ 8.38 (1H, s), 7.77 (2H, d, J=8.2 Hz), 7.31–7.49 (6H, m), 7.32 (1H, s), 6.53 (1H, br.s), 3.26–3.28 (2H, m), 2.69–2.81 (4H, m), 2.35 (3H, s), 1.25 (3H, t, J=7.6 Hz).

The Synthetic Procedure of Example 196–Example 197

The compounds disclosed hereinafter were prepared according to the following procedure: To a mixture of requisite commercially available carbonic acid and dichloromethane (DCM) was added 1-ethyl-3-(3-dimethylaminopropyl)carbodiimide, hydrochloride (WSC) (0.05 mmol, 0.5 mL) followed by a solution of 3-amino-4,6-dimethyl-2-(4-{2-[({[(4-methylphenyl)sulfonyl]amino}carbonyl)amino]ethyl}anilino)pyridine (0.038 mmol) in DCM (0.5 mL) at room temperature. The reaction mixture was stirred for 3 days at room temperature, then stirred for an additional day at 40° C. After removal of the solvent, the residue was dissolved in MeOH (1 mL) and the solution was filtered through a membrane filter. The filtrate was purified by preparative LC/MS (Shiseido capcell pack UG80 C18 (20×50 mm) eluting with MeOH/0.1% HCOOH (v/v, 20/80 to 90/10) to give the title compound.

Example 196
N-{[(2-{4-[5,7-DIMETHYL-2-(4-METHYLPENTYL)-3H-IMIDAZO[4,5-b]PYRIDIN-3-YL]PHENYL}ETHYL)AMINO]CARBONYL}-4-METHYLBENZENESULFONAMIDE, FORMATE MS (ESI) m/z 548.53 (M+H)+.

Example 197
N-{[(2-{4-[5,7-DIMETHYL-2-(3-OXO-3-PHENYLPROPYL)-3H-IMIDAZO[4,5-b]PYRIDIN-3-YL]PHENYL}ETHYL)AMINO]CARBONYL)-4-METHYLBENZENESULFONAMIDE, FORMATE MS (ESI) m/z 596.28 (M+H)+.

The Synthetic Procedure of Example 198-Example 216

The compounds disclosed hereinafter were prepared according to the following procedure: The carboxylic acid (0.06 mmol) was dissolved with N,N-diisopropylethylamine (DIEA) (0.106 mmol) and dichloromethane (DCM) (0.3 mL). To this mixture was added 1-hydroxybenzotriazole hydrate (HOBT) (0.06 mmol) in N,N-dimethylformamide (DMF) (0.02 mL). To the reaction were added 3-amino-4,6-dimethyl-2-(4-{2-[({[(4-methylphenyl)sulfonyl]amino}carbonyl)amino]ethyl}anilino)pyridine (0.044 mmol) in DCM (0.3 mL) and DMF (0.08 mL), then O-benzotriazol-1-yl-N,N,N',N'-tetramethyluronium hexafluorophosphate (HBTU) (0.13 mmol) in DMF (0.25 mL). The reaction solution was stirred for 6 hr at room temperature, then heated at 40° C. over night. After removal of the solvent, the residue was dissolved in MeOH (0.8 mL). The solution was loaded onto a Varian BondElute® SCX cartridge (500 mg/3 mL) which was preconditioned with 2 mL of MeOH. The solid-phase matrix was washed with 5 mL of MeOH and then eluted with 2N ammonia/MeOH (3 mL). After the removal of solvent, the product was used for the next step reaction.

The intermediate product of 1$^{st}$ step was dissolved with EtOH (2 mL), then to the reaction solution was added excess 2N aq.NaOH (1 mL). The reaction mixture was stirred at 40° C. to 70° C. over night. After the reaction finished, the solvent was removed. To the residue was added 2N aq.HCl (1 mL, adjusted with pH 7.0). The aqueous layer was extracted with DCM (1 mL×3). The organic layer was concentrated to afford the residue. The crude product was purified by preparative LC/MS (Shiseido capcellpack UG 80 C18 (20×50 mm) eluting with MeOH/0.1% HCOOH (v/v, 20/80 to 90/10) to give the title compound as a formate.

Example 198
N-{5-{5,7-DIMETHYL-3-(4-{2-[({[(4-METHYLPHENYL)SULFONYL]AMINO}CARBONYL)AMINO]ETHYL}PHENYL)-3H-IMIDAZO[4,5-b]PYRIDIN-2-YL]PENTYL}ACETAMIDE, FORMATE
MS (ESI) m/z 591.33 (M+H)$^+$.

Example 199
N-{[(2-(4-[5,7-DIMETHYL-2-(5-OXO-5-PHENYLPENTYL)-3H-IMIDAZO[4,5-b]PYRIDIN-3-YL]PHENYL}ETHYL)AMINO]CARBONYL}-4-METHYLBENZENESULFONAMIDE, FORMATE
MS (ESI) m/z 624.37 (M+H)$^+$.

Example 200
N-{[(2-{4-[2-(2-CYCLOPENTEN-1-YLMETHYL)-5,7-DIMETHYL-3H-IMIDAZO[4,5-b]PYRIDIN-3-YL]PHENYL}ETHYL)AMINO]CARBONYL}-4-METHYLBENZENESULFONAMIDE, FORMATE
MS (ESI) m/z 544.40 (M+H)$^+$.

Example 201
N-{[(2-{4-[2-(1-CYCLOPENTEN-1-YLMETHYL)-5,7-DIMETHYL-3H-IMIDAZO[4,5-b]PYRIDIN-3-YL]PHENYL}ETHYL)AMINO]CARBONYL}-4-METHYLBENZENESULFONAMIDE, FORMATE
MS (ESI) m/z 544.40 (M+H)$^+$.

Example 202
(2Z)-3-[5,7-DIMETHYL-3-(4-{2-[({[(4-METHYLPHENYL)SULFONYL]AMINO}CARBONYL)AMINO]ETHYL}PHENYL)-3H-IMIDAZO[4,5-b]PYRIDIN-2-YL]-N-PROPYL-2-PROPENAMIDE, FORMATE
MS (ESI) m/z 575.44 (M+H)$^+$.

Example 203
N-{[(2-{4-[5,7-DIMETHYL-2-(1-METHYL-3-OXO-3-PHENYLPROPYL)-3H-IMIDAZO[4,5-b]PYRIDIN-3-YL]PHENYL}ETHYL)AMINO]CARBONYL}-4-METHYLBENZENESULFONAMIDE, FORMATE
MS (ESI) m/z 610.49 (M+H)$^+$.

Example 204
N-{[(2-{4-[5,7-DIMETHYL-2-(3,3,3-TRIFLUORO-2-METHYLPROPYL)-3H-IMIDAZO[4,5-b]PYRIDIN-3-YL]PHENYL}ETHYL)AMINO]CARBONYL}-4-METHYLBENZENESULFONAMIDE, FORMATE
MS (ESI) m/z 574.43 (M+H)$^+$.

Example 205
N-({[2-(4-{2-[2-(DIETHYLAMINO)ETHYL]-5,7-DIMETHYL-3H-IMIDAZO[4,5-b]PYRIDIN-3-YL}PHENYL)ETHYL]AMINO}CARBONYL)-4-METHYLBENZENESULFONAMIDE, FORMATE
MS (ESI) m/z 563.49 (M+H)$^+$.

Example 206
N-({[2-(4-{2-[2-(4-FLUOROPHENYL)ETHYL]-5,7-DIMETHYL-3H-IMIDAZO[4,5-b]PYRIDIN-3-YL}PHENYL)ETHYL]AMINO}CARBONYL)-4-METHYLBENZENESULFONAMIDE, FORMATE
MS (ESI) m/z 586.46 (M+H)$^+$.

Example 207
3-[5,7-DIMETHYL-3-(4-{2-[({[(4-METHYLPHENYL)SULFONYL]AMINO}CARBONYL)AMINO]ETHYL}PHENYL)-3H-IMIDAZO[4,5-b]PYRIDIN-2-YL]-N,N-DIETHYLPROPANAMIDE, FORMATE
MS (ESI) m/z 591.50 (M+H)$^+$.

Example 208
N-[({2-[4-(5,7-DIMETHYL-2-TETRAHYDRO-3-FURANYL-3H-IMIDAZO[4,5-b]PYRIDIN-3-YL)PHENYL]ETHYL}AMINO)CARBONYL]-4-METHYLBENZENESULFONAMIDE, FORMATE
MS (ESI) m/z 534.41 (M+H)$^+$.

Example 209
N-{[(2-{4-[5,7-DIMETHYL-2-(1-METHYLBUTYL)-3H-IMIDAZO[4,5-b]PYRIDIN-3-YL]PHENYL}ETHYL)AMINO]CARBONYL}-4-METHYLBENZENESULFONAMIDE, FORMATE
MS (ESI) m/z 534.45 (M+H)$^+$.

Example 210
N-{[(2-{4-[2-(CYCLOPENTYLMETHYL)-5,7-DIMETHYL-3H-IMIDAZO[4,5-b]PYRIDIN-3-YL]PHENYL}ETHYL)AMINO]CARBONYL}-4-METHYLBENZENESULFONAMIDE, FORMATE
MS (ESI) m/z 546.46 (M+H)$^+$.

Example 211
N-{[(2-{4-[5,7-DIMETHYL-2-(2-METHYLCYCLOPROPYL)-3H-IMIDAZO[4,5-b]PYRIDIN-3-YL]PHENYL}ETHYL)AMINO]CARBONYL}-4-METHYLBENZENESULFONAMIDE, FORMATE
MS (ESI) m/z 518.41 (M+H)$^+$.

Example 212
N-[({2-[4-(5,7-DIMETHYL-2-{3-[4-(METHYLOXY)PHENYL]-3-OXOPROPYL}-3H-IMIDAZO[4,5-b]PYRIDIN-3-YL)PHENYL]ETHYL}AMINO)CARBONYL]-4-METHYLBENZENESULFONAMIDE, FORMATE
MS (ESI) m/z 626.45 (M+H)$^+$.

Example 213
N-({[2-(4-{2-[3-(3,4-DIMETHYLPHENYL)PROPYL]-5,7-DIMETHYL-3H-IMIDAZO[4,5-b]PYRIDIN-3-YL}PHENYL)ETHYL]AMINO}CARBONYL)-4-METHYLBENZENESULFONAMIDE, FORMATE
MS (ESI) m/z 610.28 (M+H)$^+$.

Example 214
N-({[2-(4-{2-[(Z)-2-(4-FLUOROPHENYL)ETHENYL]-5,7-DIMETHYL-3H-IMIDAZO[4,5-b]PYRIDIN-3-

YL}PHENYL)ETHYL]AMINO}CARBONYL)-4-METHYLBENZENE SULFONAMIDE, FORMATE

MS (ESI) m/z 584.41 (M+H)+.

Example 215

N-[({2-[4-(5,7-DIMETHYL-2-{(Z)-2-[2-(METHYLOXY) PHENYL]ETHENYL}-3H-IMIDAZO[4,5-b]PYRIDIN-3-YL)PHENYL]ETHYL}AMINO)CARBONYL]-4-METHYLBENZENESULFONAMIDE, FORMATE

MS (ESI) m/z 596.29 (M+H)+.

Example 216

N-{[(2-{4-[2-(5-HEXYNYL)-5,7-DIMETHYL-3H-IMIDAZO[4,5-b]PYRIDIN-3-YL]PHENYL}ETHYL)AMINO]CARBONYL}-4-METHYLBENZENESULFONAMIDE, FORMATE

MS (ESI) m/z 544.33 (M+H)+.

The Synthetic Procedure of Example 217-Example 220

The compounds disclosed hereinafter were prepared according to the following procedure: To a solution of 3-amino-4,6-dimethyl-2-(4-{2-[({[(4-methylphenyl)sulfonyl]amino}carbonyl)amino]ethyl}anilino)pyridine (0.044 mmol) in dichloromethane (DCM) (0.2 mL) and DMF (0.05 mL) was added pyridine (0.103 mmol) in DCM (0.2 mL), and excess of acid chloride (0.066 mmol–0.088 mmol) at room temperature. The reaction mixture was stirred at ambient temperature until the starting compound was disappeared (4–6 hr). After the reaction was stopped, to the reaction mixture was added MeOH (0.2 mL), then stirred for 1 hr. The solvent was removed by vacuum centrifuge. The residue, which was dissolved with MeOH (0.8 mL), was loaded onto a Varian BondElute® SCX cartridge (500 mg/3 mL) which was preconditioned with 2 mL of MeOH. The solid-phase matrix was washed with 5 mL of MeOH and then eluted with 2N ammonia/MeOH (3 mL). The eluate was concentrated in vacuo to provide the intermediate product.

The intermediate product of 1$^{st}$ step was dissolved with EtOH (2 mL), then to the reaction solution was added excess 2N aq.NaOH (1 mL). The reaction mixture was stirred at 70° C. over night. After the removal of solvent, to the residue was added 2N aq.HCl to neutralize. The aqueous layer was extracted with DCM (1 mL×5 times). The organic layer was dried with sodium sulfate, then concentrated. The crude product was purified by preparative LC/MS (Shiseido capcellpack UG 80 C18 (20×50 mm) eluting with MeOH/0.1% HCOOH (v/v, 20/80 to 90/10) to give the title compound as a formate.

Example 217

4-METHYL-N-[({2-[4-(2,5,7-TRIMETHYL-3H-IMIDAZO[4,5-b]PYRIDIN-3-YL)PHENYL]ETHYL}AMINO)CARBONYL]BENZENESULFONAMIDE, FORMATE

MS (ESI) m/z 478.31 (M+H)+.

Example 218

N-{[(2-{4-[2-(2,2-DIMETHYLPROPYL)-5,7-DIMETHYL-3H-IMIDAZO[4,5-b]PYRIDIN-3-YL]PHENYL}ETHYL)AMINO]CARBONYL}-4-METHYLBENZENESULFONAMIDE, FORMATE

MS (ESI) m/z 534.40 (M+H)+.

Example 219

N-[({2-[4-(2-CYCLOBUTYL-5,7-DIMETHYL-3H-IMIDAZO[4,5-b]PYRIDIN-3-YL)PHENYL]ETHYL}AMINO)CARBONYL]-4-METHYLBENZENESULFONAMIDE, FORMATE

MS (ESI) m/z 518.38 (M+H)+.

Example 220

N-[({2-[4-(2-CYCLOPENTYL-5,7-DIMETHYL-3H-IMIDAZO[4,5-b]PYRIDIN-3-YL)PHENYL]ETHYL}AMINO)CARBONYL]-4-METHYLBENZENESULFONAMIDE, FORMATE

MS (ESI) m/z 532.44 (M+H)+.

Example 221

4-(6-CHLORO-2-ETHYL-5-TRIFLUOROMETHYL-1H-BENZIMIDAZOL-1-YL)PHENETHYL(4-METHYLPHENYL)SULFONYLCARBAMATE P-TOLUENESULFONATE

A mixture of 4-(6-chloro-2-ethyl-5-trifluoromethyl-1H-benzimidazol-1-yl)phenethyl(4-methylphenyl)sulfonylcarbamate (Example 106, 150 mg, 0.265 mmol), p-toluenesulfonic acid (50.5 mg, 0.265 mmol) in acetone (3% H$_2$O, 0.3 ml) was stirred at room temperature for 16 h. The precipitated crystalline solids were filtered, washed with acetone (0.05 ml×5), and dried in vacuo at 40° C. for 2 h to afford 158 mg (81%) of the title compound as white solids.

m.p.: 234.8° C.

$^1$H-NMR (CDCl$_3$) δ: 8.66 (1H, br.s), 8.35 (1H, s), 7.85 (2H, d, J=8.1 Hz), 7.81 (2H, d, J=8.4 Hz), 7.53 (2H, d, J=8.4 Hz), 7.39–7.35 (3H, m), 7.29 (2H, d, J=7.9 Hz), 7.19 (2H, d, J=7.9 Hz), 4.35 (2H, t, J=6.2 Hz), 3.13 (2H, q, J=7.6 Hz), 3.04 (2H, t, J=6.3 Hz), 2.42 (3H, s), 2.36 (3H, s), 1.43 (3H, t, J=7.4 Hz).

Example 222

4-(6-CHLORO-2-ETHYL-5-TRIFLUOROMETHYL-1H-BENZIMIDAZOL-1-YL)PHENETHYL(4-METHYLPHENYL)SULFONYLCARBAMATE BENZENESULFONATE

The title compound was prepared according to the procedure described in Example 221 from 4-(6-chloro-2-ethyl-5-trifluoromethyl-1H-benzimidazol-1-yl) phenethyl(4-methylphenyl)sulfonylcarbamate (Example 106).

m.p.: 194.9° C.

$^1$H-NMR (CDCl$_3$) δ: 8.83 (1H, br.s), 8.39 (1H, s), 7.99–7.95 (2H, m), 7.81 (2H, d, J=8.4 Hz), 7.54 (2H, d, J=8.4 Hz), 7.41–7.36 (6H, m), 7.29 (2H, d, J=8.4 Hz), 4.34 (2H, t, J=6.1 Hz), 3.14 (2H, q, J=7.6 Hz), 3.03 (2H, t, J=6.1 Hz), 2.41 (3H, s), 1.42 (3H, t, J=7.4 Hz).

Example 223

4-(6-CHLORO-2-ETHYL-5-TRIFLUOROMETHYL-1H-BENZIMIDAZOL-1-YL)PHENETHYL(4-METHYLPHENYL)SULFONYLCARBAMATE METHANESULFONATE

The title compound was prepared according to the procedure described in Example 221 from 4-(6-chloro-2-ethyl-5-trifluoromethyl-1H-benzimidazol-1-yl)phenethyl(4-methylphenyl)sulfonylcarbamate (Example 106).

m.p.: 172.2° C.

$^1$H-NMR (CDCl$_3$) δ: 9.03 (1H, br.s), 8.52 (1H, s), 7.81 (2H, d, J=8.2 Hz), 7.56 (2H, d, J=8.2 Hz), 7.40 (2H, d, J=8.1 Hz), 7.39 (1H, s), 7.29 (2H, d, J=8.1 Hz), 4.35 (2H, t, J=6.3 Hz), 3.16 (2H, q, J=7.6 Hz), 3.06 (2H, t, J=6.3 Hz), 2.94 (3H, s), 2.41 (3H, s), 1.45 (3H, t, J=7.6 Hz).

Example 224
5-ACETYL-2-ETHYL-3-(4-}2-[({[(4-METHYLPHENYL) SULFONYL]AMINO}CARBONYL)AMINO] ETHYL}PHENYL)BENZIMIDAZOLE P-TOLUENESULFONATE A mixture of 5-acetyl-2-ethyl-3-(4-{2-[({[(4-methylphenyl)sulfonyl]amino}carbonyl)amino]ethyl}phenyl)benzimidazole (Example 78, 43 mg, 0.085 mmol), p-toluenesulfonic acid (16.2 mg, 0.085 mmol) in ethanol (0.1 ml) was stirred at room temperature for 16 h. The precipitated crystalline solids were filtered, washed with ethanol (0.05 ml×5), and dried in vacuo at 40° C. for 2 h to afford 54 mg (91%) of the title compound as white solids.
m.p.: 166.7° C.
$^1$H-NMR (CDCl$_3$) δ: 9.85 (1H, br.s), 8.50 (1H, s), 8.02 (1H, d, J=8.9 Hz), 7.86 (2H, d, J=8.1 Hz), 7.68 (2H, dd, J=1.8, 8.2 Hz), 7.47 (2H, d, J=8.4 Hz), 7.36–7.31 (3H, m), 7.22 (2H, d, J=8.4 Hz), 7.17 (2H, d, J=8.4 Hz), 7.00 (1H, br.s), 3.47–3.39 (2H, m) 3.14 (2H, q, J=7.3 Hz), 2.88 (2H, t, J=6.3 Hz), 2.58 (3H, s), 2.35 (3H, s), 2.34 (3H, s), 1.45 (3H, t, J=7.6 Hz).

Example 225
5-ACETYL-2-ETHYL-3-(4-{2-[({[(4-METHYLPHENYL) SULFONYL]AMINO}CARBONYL)AMINO] ETHYL}PHENYL)BENZIMIDAZOLE BENZENE-SULFONATE The title compound was prepared according to the procedure described in Example 224 from 5-acetyl-2-ethyl-3-(4-{2-[({[(4-methylphenyl)sulfonyl]amino}carbonyl)amino]ethyl}phenyl)benzimidazole (Example 78).
m.p.: 117.7° C.
$^1$H-NMR (CDCl$_3$) δ: 9.62 (1H, br.s), 8.52 (1H, s), 8.05–7.96 (3H, m), 7.67 (2H, d, J=8.2 Hz), 7.49–7.43 (5H, m), 7.37–7.32 (3H, m), 7.19 (2H, d, J=8.2 Hz), 6.92–6.88 (1H, m), 3.48–3.42 (2H, m) 3.17 (2H, q, J=7.6 Hz), 2.89 (2H, t, J=6.1 Hz), 2.61 (3H, s), 2.35 (3H, s), 1.49 (3H, t, J=7.6 Hz).

Example 226
4-CHLORO-2-ETHYL-6-METHYL-1-(4-{2-[({[(4-METHYLPHENYL)SULFONYL]AMINO}CARBONYL) AMINO]ETHYL}PHENYL)-1H-IMIDAZO[4,5-c]PYRIDINE Step 1. tert-butyl 2-{4-[(2-chloro-6-methyl-3-nitro-4-pyridinyl)amino]phenyl}ethylcarbamate A mixture of 2,4-dichloro-6-methyl-3-nitro-pyridine (Chorvat, Robert J. et al., J.Med.Chem., 1999, 42, 833., 7.5 g, 36.2 mmol), [2-(4-amino-phenyl)-ethyl]-carbamic acid tert-butyl ester (Stark, Peter A. et al., J.Med.Chem., 1992, 35, 4264., 1.14 g, 4.83 mmol) in N,N-diisopropylethylamine (50 ml) was heated at reflux temperature for 16 h. After cooling, the mixture was concentrated. The residue was diluted with dichloromethane (200 ml) and washed with saturated aqueous NaHCO$_3$ solution (50 ml×2). The organic layer was dried (MgSO$_4$), and concentrated. Purification by flash column chromatography eluting with hexane/ethyl acetate (1:1) to afford 310 mg (16%) of the title compound as orange solids.
$^1$H-NMR (CDCl$_3$) δ: 8.19 (1H, s), 7.28 (2H, d, J=8.4 Hz), 7.16 (2H, d, J=8.3 Hz), 6.69 (1H, s), 4.62 (1H, br s), 3.43–3.37 (2H, m), 2.84 (2H, t, J=7.0 Hz), 2.37 (3H, s), 1.44 (9H, s).

Step 2. tert-butyl 2-{4-[(3-amino-2-chloro-6-methyl-4-pyridinyl)amino]phenyl}ethylcarbamate The title compound was prepared according to the procedure described in step 1 of Example 6 from tert-butyl 2-{4-[(2-chloro-6-methyl-3-nitro-4-pyridinyl)amino] phenyl}ethylcarbamate (step 1).
$^1$H-NMR (CDCl$_3$) δ: 7.18 (2H, d, J=8.3 Hz), 7.03 (2H, d, J=8.2 Hz), 6.76 (1H, s), 6.02 (1H, br. s), 4.61 (1H, br. s), 3.40–3.37 (4H, m), 2.78 (2H, t, J=7.0 Hz), 2.33 (3H, s), 1.44 (9H, s).

Step 3. tert-butyl 2-[4-(4-chloro-2-ethyl-6-methyl-1H-imidazo[4,5-c]pyridin-1-yl)phenyl]ethylcarbamate A mixture of tert-butyl 2-{4-[(3-amino-2-chloro-6-methyl-4-pyridinyl)amino]phenyl}ethylcarbamate (step 2, 238 mg, 0.63 mmol), propionyl chloride (70 mg, 0.76 mmol) in toluene (4.6 ml) and dichloromethane (0.6 ml) was heated at reflux temperature for 1 h. After cooling, the mixture was diluted with ethyl acetate (100 ml) and washed with 1N aqueous NaOH solution (30 ml×2) and brine (30 ml). The organic layer was dried (MgSO$_4$), and concentrated. The residue and p-toluenesulfonic acid monohydrate (5 mg, 0.026 mmol) in toluene (5.0 ml) was heated at reflux temperature for 16 h. After cooling, the mixture was diluted with dichloromethane (100 ml) and washed with saturated aqueous NaHCO$_3$ solution (30 ml) and brine (30 ml). The organic layer was dried (MgSO$_4$), and concentrated. Purification by PTLC eluting with hexane/ethyl acetate (1:1) to afford 90 mg (34%) of the title compound as a brown oil.
$^1$H-NMR (CDCl$_3$) δ: 7.44 (2H, d, J=8.2 Hz), 7.27 (2H, d, J=8.2 Hz), 6.81 (1H, s), 4.75 (1H, br s), 3.52–3.44 (2H, m), 2.94 (2H, t, J=7.1 Hz), 2.82 (2H, q, J=7.6 Hz), 2.55 (3H, s), 1.46 (9H, s), 1.32 (3H, t, J=7.6 Hz).

Step 4. 2-[4-(4-chloro-2-ethyl-6-methyl-1H-imidazo[4,5-c]pyridin-1-yl)phenyl]ethanamine To a stirred solution of tert-butyl 2-[4-(4-chloro-2-ethyl-6-methyl-1H-imidazo[4,5-c]pyridin-1-yl)phenyl]ethylcarbamate (step 3, 90 mg, 0.22 mmol) in dichloromethane (8.5 ml) was added trifluoroacetic acid (1.0 ml, 13.0 mmol) at 0° C., and the mixture was stirred at 0° C. for 30 min, then at room temperature for 5 h. The mixture was concentrated, and diluted with dichloromethane (50 ml), washed with saturated aqueous NaHCO$_3$ solution (10 ml) and brine (10 ml). The organic layer was dried (MgSO$_4$), and concentrated. Purification by PTLC eluting with ethyl acetate to afford 50 mg (73%) of the title compound as a brown oil.
$^1$H-NMR (CDCl$_3$) δ: 7.45 (2H, d, J=8.2 Hz), 7.27 (2H, d, J=8.2 Hz), 6.81 (1H, s), 3.09 (2H, t, J=6.9 Hz), 2.89 (2H, t, J=6.8 Hz), 2.83 (2H, q, J=7.4 Hz), 2.55 (3H, s), 1.31 (3H, t, J=7.4 Hz).

Step 5. 4-chloro-2-ethyl-6-methyl-1-(4-}2-[({[(4-methylphenyl)sulfonyl]amino}carbonyl)amino]ethyl}phenyl)-1H-imidazo[4,5-c]pyridine The title compound was prepared according to the procedure described in step 10 of Example 1 from 2-[4-(4-chloro-2-ethyl-6-methyl-1H-imidazo[4,5-c]pyridin-1-yl) phenyl]ethanamine (step 4).
m.p.: 163° C.
MS (ESI) m/z: 512 [(MH)$^+$], 510 [(M−H)$^−$].
$^1$H-NMR (CDCl$_3$) δ: 7.73 (2H, d, J=8.2 Hz), 7.38–7.21 (6H, m), 6.78 (1H, s), 3.53–3.51 (2H, m), 2.91–2.89 (2H, m), 2.79 (2H, q, J=7.2 Hz), 2.52 (3H, s), 2.37 (3H, s), 1.29 (3H, t, J=7.2 Hz).

Example 227
2-[4-(2-ETHYL-4,6-DIMETHYL-1H-IMIDAZO[4,5-c] PYRIDIN-1-YL)PHENYL]ETHYL(4-METHYLPHENYL)SULFONYLCARBAMATE The title compound was prepared according to the procedure described in Example 3 from 2-[4-(2-ethyl-4,6-dimethyl-1H-imidazo[4,5-c]pyridin-1-yl)phenyl]ethanol (step 4 of Example 42).
m.p.: 158° C.
MS (ESI) m/z: 493 [(MH)$^+$], 491 [(M−H)$^−$].
$^1$H-NMR (DMSO-d$_6$) δ: 7.72 (2H, d, J=8.2 Hz), 7.47 (2H, d, J=8.6 Hz), 7.43 (2H, d, J=8.6 Hz), 7.34 (2H, d, J=8.0 Hz), 6.96 (1H, s), 4.18 (2H, t, J=6.6 Hz), 2.94 (2H, t, J=6.4 Hz), 2.76 (3H, s), 2.74 (2H, q, J=7.3 Hz), 2.50 (3H, s), 2.35 (3H, s), 1.23 (3H, t, J=7.3 Hz).

Example 228
2-[4-(8-ETHYL-2,6-DIMETHYL-9H-PURIN-9-YL) PHENYL]ETHYL(4-METHYLPHENYL) SULFONYLCARBAMATE Step 1. 2-{4-[(6-chloro-2-methyl-5-nitro-4-pyrimidinyl) amino]phenyl}ethanol To a stirred solution of 4,6-dichloro-2-methyl-5-nitro-pyrimidine (Albert et al., *J.Chem.Soc.*, 1954, 3832, 7.5 g, 36.1 mmol) in THF (150 ml) was added 4-aminophenylethyl alcohol (2.47 g, 18.0 mmol), triethylamine (3.65 g, 36.1 mmol), and the mixture was stirred at room temperature for 1 h. The reaction was quenched with water (10 ml), and the mixture was extracted with ethyl acetate (100 ml×3). The organic layer was washed with brine (50 ml), dried (MgSO$_4$), and concentrated. Purification by flash column chromatography eluting with hexane/ethyl acetate (gradient elution from 1:1 to 1:2) to afford 4.0 g (72%) of the title compound as a yellow solid.

$^1$H-NMR (CDCl$_3$) δ: 9.34 (1H, s), 7.50 (2H, d, J=8.4 Hz), 7.28 (2H, d, J=8.8 Hz), 3.89 (2H, t, J=6.6 Hz), 2.90 (2H, t, J=6.4 Hz), 2.57 (3H, s).

Step 2. diethyl 2-(6-{[4-(2-Hydroxyethyl)phenyl]amino}-2-methyl-5-nitro-4-pyrimidinyl)propanedioate To a stirred solution of 2-{4-[(6-chloro-2-methyl-5-nitro-4-pyrimidinyl)amino]phenyl}ethanol (step 1, 2.0 g, 6.48 mmol) in acetone (61 ml) was added diethyl malonate (1.53 g, 9.54 mmol) at 0° C., then aqueous NaOH solution (11N, 2 ml, 22 mmol) was added dropwise over 20 min. After addition, the mixture was stirred at room temperature for 1 h. The reaction was quenched with water (120 ml), and the pH value was adjusted to 8.0 by addition of acetic acid. The whole was extracted with ethyl acetate (100 ml×3). The organic layer was washed with brine (50 ml), dried (MgSO$_4$), and concentrated. Removal of excess diethyl malonate by azetropical distillation with toluene afforded 3.26 g (72%) of the title compound as a brown oil.

MS (EI) m/z: 432 (M$^+$).

$^1$H-NMR (CDCl$_3$) δ: 10.15 (1H, s), 7.55 (2H, d, J=8.4 Hz), 7.27 (2H, d, J=8.4 Hz), 5.36 (1H, s), 4.31 (4H, q, J=7.1 Hz), 3.90 (2H, t, J=6.6 Hz), 2.90 (2H, t, J=6.4 Hz), 2.56 (3H, s), 1.32 (6H, t, J=7.1 Hz).

Step 3. 2-{4-[(2,6-dimethyl-5-nitro-4-pyrimidinyl)amino] phenyl}ethanol

A mixture of diethyl 2-(6-{[4-(2-hydroxyethyl)phenyl] amino}-2-methyl-5-nitro-4-pyrimidinyl)propanedioate (step 2, 2.0 g, 6.48 mmol) in 2N aqueous HCl (15 ml) was heated at reflux temperature for 5 h. After cooling, the reaction was quenched with saturated NaHCO$_3$ aqueous solution (100 ml), and the whole was extracted with ethyl acetate (100 ml×3). The organic layer was washed with brine (50 ml), dried (MgSO$_4$), and concentrated. Purification by flash column chromatography eluting with hexane/ethyl acetate (gradient elution from 1:1 to 0:100) to afford 1.33 g (71%) of the title compound as a yellow solid.

MS (EI) m/z: 288 (M$^+$).

$^1$H-NMR (CDCl$_3$) δ: 9.81 (1H, s), 7.56 (2H, d, J=8.4 Hz), 7.27 (2H, d, J=8.4 Hz), 3.92–3.86 (2H, m), 2.89 (2H, t, J=6.4 Hz), 2.76 (3H, s), 2.56 (3H, s).

Step 4. 2-{4-[(5-amino-2,6-dimethyl-4-pyrimidinyl)amino] phenyl}ethanol

The title compound was prepared according to the procedure described in step 1 of Example 6 from 2-{4-[(2,6-dimethyl-5-nitro-4-pyrimidinyl)amino]phenyl}ethanol (step 3).

MS (EI) m/z: 258 (M$^+$).

$^1$H-NMR (DMSO-d$_6$) δ: 8.14 (1H, s), 7.63 (2H, d, J=8.6 Hz), 7.12 (2H, d, J=8.4 Hz), 4.67 (2H, br.s), 3.58 (2H, t, J=7.3 Hz), 2.67 (2H, t, J=7.2 Hz), 2.28 (3H, s), 2.20 (3H, s).

Step 5. 2-[4-(8-ethyl-2,6-dimethyl-9H-purin-9-yl)phenyl] ethyl propanoate

The title compound was prepared according to the procedure described in step 5 of Example 1 from 2-{4-[(5-amino-2,6-dimethyl-4-pyrimidinyl)amino]phenyl}ethanol (step 4).

$^1$H-NMR (CDCl$_3$) δ: 7.44 (2H, d, J=8.2 Hz), 7.31 (2H, d, J=8.2 Hz), 4.37 (2H, t, J=6.9 Hz), 3.06 (2H, t, J=6.8 Hz), 2.84 (3H, s), 2.82 (2H, q, J=7.4 Hz), 2.70 (3H, s), 2.35 (2H, q, J=7.6 Hz), 1.31 (3H, t, J=7.6 Hz), 1.15 (3H, t, J=7.6 Hz).

Step 6. 2-[4-(8-ethyl-2,6-dimethyl-9H-purin-9-yl)phenyl] ethanol

The title compound was prepared according to the procedure described in step 6 of Example 1 from 2-[4-(8-ethyl-2,6-dimethyl-9H-purin-9-yl)phenyl]ethyl propanoate (step 5).

$^1$H-NMR (CDCl$_3$) δ: 7.46 (2H, d, J=8.4 Hz), 7.31 (2H, d, J=8.3 Hz), 3.99–3.92 (2H, m), 2.99 (2H, t, J=6.4 Hz), 2.85 (3H, s), 2.83 (2H, q, J=7.5 Hz), 2.70 (3H, s), 1.32 (3H, t, J=7.3 Hz).

Step 7. 2-[4-(8-ethyl-2,6-dimethyl-9H-purin-9-yl)phenyl] ethyl (4-methylphenyl)sulfonylcarbamate The title compound was prepared according to the procedure described in Example 3 from 2-[4-(8-ethyl-2,6-dimethyl-9H-purin-9-yl)phenyl]ethanol (step 6).

m.p.: 162° C.

MS (ESI) m/z: 494 [(MH)$^+$], 492 [(M−H)$^−$].

$^1$H-NMR (CDCl$_3$) δ: 7.94 (2H, d, J=8.4 Hz), 7.34 (2H, d, J=8.1 Hz), 7.24 (2H, d, J=8.6 Hz), 7.18 (2H, d J=8.4 Hz), 4.36 (2H, t, J=6.4 Hz), 2.97 (2H, t, J=6.2 Hz), 2.86 (3H, s), 2.79 (2H, q, J=7.6 Hz), 2.64 (3H, s), 2.44 (3H, s), 1.28 (3H, t, J=7.6 Hz).

Example 229
2-[4-(4,6-DIMETHYL-2-PHENYL-1H-IMIDAZO[4,5-c] PYRIDIN-1-YL)PHENYL]ETHYL (4-METHYLPHENYL)SULFONYLCARBAMATE Step 1. 2-[4-(4,6-dimethyl-2-phenyl-1H-imidazo[4,5-c] pyridin-1-yl)phenyl]ethyl benzoate A mixture of 2-{4-[(3-Amino-2,6-dimethyl-4-pyridinyl) amino]phenyl}ethanol (step 2 of Example 42, 500 mg, 1.94 mmol), benzoic acid (4.45 g 36.4 mmol), benzoic anhydride (4.8 g, 21.2 mmol) was heated at 120° C. for 4 h. After cooling, the mixture was diluted with dichloromethane (100 ml). The solution was washed with saturated NaHCO$_3$ aqueous solution (50 ml), brine (50 ml), dried (MgSO$_4$), and concentrated. Purification by flash column chromatography eluting with ethyl acetate to afford 813 mg (94%) of the title compound as a white solid.

MS (EI) m/z: 447(M$^+$).

$^1$H-NMR (CDCl$_3$) δ: 8.02–7.21 (14H, m), 6.87 (1H, s), 4.61 (2H, t, J=7.0 Hz), 3.18 (2H, t, J=6.8 Hz), 2.96 (3H, s), 2.61 (3H, s).

Step 2. 2-[4-(4,6-dimethyl-2-phenyl-1H-imidazo[4,5-c] pyridin-1-yl)phenyl]ethanol The title compound was prepared according to the procedure described in step 6 of Example 1 from 2-[4-(4,6-dimethyl-2-phenyl-1H-imidazo[4,5-c]pyridin-1-yl)phenyl] ethyl benzoate (step 1).

$^1$H-NMR (CDCl$_3$) δ: 7.57–7.18 (9H, m), 6.87 (1H, s), 3.95 (2H, t, J=6.6 Hz), 2.96 (2H, t, J=6.6 Hz), 2.94 (3H, s), 2.59 (3H, s).

Step 3. 2-[4-(4,6-dimethyl-2-phenyl-1H-imidazo[4,5-c] pyridin-1-yl)phenyl]ethyl (4-methylphenyl) sulfonylcarbamate The title compound was prepared according to the procedure described in Example 3 from 2-[4-(4,6-dimethyl-2-phenyl-1H-imidazo[4,5-c]pyridin-1-yl)phenyl]ethanol (step 2).

m.p.: 194° C.

MS (ESI) m/z: 541 [(MH)$^+$], 539 [(M−H)$^−$].

$^1$H-NMR (CDCl$_3$) δ: 7.89 (2H, d, J=8.2 Hz), 7.46–6.95 (11H, m), 6.77 (1H, s), 4.35 (2H, t, J=6.0 Hz), 3.03 (3H, s), 2.96 (2H, t, J=6.0 Hz), 2.56 (3H, s), 2.42 (3H, s).

Example 230
2-[4-(2-BUTYL-4,6-DIMETHYL-1H-IMIDAZO[4,5-c]PYRIDIN-1-YL)PHENYL]ETHYL (4-METHYLPHENYL)SULFONYLCARBAMATE Step 1. 2-[4-(2-butyl-4,6-dimethyl-1H-imidazo[4,5-c]pyridin-1-yl)phenyl]ethyl pentanoate The title compound was prepared according to the procedure described in step 1 of Example 229 from 2-{4-[(3-Amino-2,6-dimethyl-4-pyridinyl)amino]phenyl}ethanol (step 2 of Example 42).

$^1$H-NMR (CDCl$_3$) δ: 7.44 (2H, d, J=8.1 Hz), 7.26 (2H, d, J=8.2 Hz), 6.71 (1H, s), 4.38 (2H, t, J=6.9 Hz), 3.07 (2H, t, J=6.9 Hz), 2.88 (3H, s), 2.78 (2H, t, J=7.6 Hz), 2.56 (3H, s), 2.33 (2H, t, J=7.4 Hz), 1.74–1.55 (4H, m), 1.41–1.24 (4H, m), 0.91 (3H, t, J=7.2 Hz), 0.84 (3H, t, J=7.2 Hz).

Step 2. 2-[4-(2-butyl-4,6-dimethyl-1H-imidazo[4,5-c]pyridin-1-yl)phenyl]ethanol

The title compound was prepared according to the procedure described in step 6 of Example 1 from 2-[4-(2-butyl-4,6-dimethyl-1H-imidazo[4,5-c]pyridin-1-yl)phenyl]ethyl pentanoate (step 1).

$^1$H-NMR (CDCl$_3$) δ: 7.46 (2H, d, J=8.2 Hz), 7.25 (2H, d, J=8.2 Hz), 6.72 (1H, s), 4.00 (2H, t, J=6.6 Hz), 3.02 (2H, t, J=6.4 Hz), 2.88 (3H, s), 2.78 (2H, t, J=7.6 Hz), 2.54 (3H, s), 1.76–1.64 (2H, m), 1.39–1.25 (2H, m), 0.85 (3H, t, J=7.4 Hz).

Step 3. 2-[4-(2-butyl-4,6-dimethyl-1H-imidazo[4,5-c]pyridin-1-yl)phenyl]ethyl (4-methylphenyl)sulfonylcarbamate The title compound was prepared according to the procedure described in Example 3 from 2-[4-(2-butyl-4,6-dimethyl-1H-imidazo[4,5-c]pyridin-1-yl)phenyl]ethanol (step 2).

m.p.: 162° C.

MS (ESI) m/z: 521 [(MH)$^+$], 519 [(M−H)$^−$].

$^1$H-NMR (CD$_3$OD) δ: 7.97 (2H, d, J=8.3 Hz), 7.31 (2H, d, J=7.9 Hz), 7.18 (2H, d, J=8.4 Hz), 6.84 (2H, d, J=8.4 Hz), 6.60 (1H, s), 4.34 (2H, t, J=5.5 Hz), 3.03 (3H, s), 2.96 (2H, t, J=5.5 Hz), 2.71 (2H, t, J=7.5 Hz), 2.52 (3H, s), 2.43 (3H, s), 1.72–1.62 (2H, m), 1.36–1.24 (2H, m), 0.84 (3H, t, J=7.3 Hz).

Example 231
2-[4-(2-BUTYL-4,6-DIMETHYL-1H-IMIDAZO[4,5-c]PYRIDIN-1-YL)PHENYL]ETHYL (4-METHYLPHENYL)SULFONYLCARBAMATE P-TOLUENESULFONATE To a solution of 2-[4-(2-butyl-4,6-dimethyl-1H-imidazo[4,5-c]pyridin-1-yl)phenyl]ethyl (4-methylphenyl)sulfonylcarbamate (Example 230) in methanol was added TsOH (1.0 eq.). The resulting mixture was stirred at room temperature for 5 min and concentrated. The residual solids were collected and dried under reduced pressure at 50° C. to afford the title compound as white solids:

$^1$H-NMR (CDCl$_3$) δ: 7.89–7.86 (4H, m), 7.49 (2H, d, J=8.3 Hz), 7.30 (2H, d, J=8.1 Hz), 7.24 (2H, d, J=8.3 Hz), 7.18 (2H, d, J=7.9 Hz), 7.03 (1H, s), 4.34 (2H, t, J=6.2 Hz), 3.12 (3H, s), 3.02 (2H, t, J=6.2 Hz), 2.80 (3H, s), 2.77 (2H, t, J=8.1 Hz), 2.42 (3H, s), 2.34 (3H, s), 1.78–1.68 (2H, m), 1.39–1.27 (2H, m), 0.86 (3H, t, J=7.3 Hz).

Example 232
2-[4-(4,6-DIMETHYL-2-(1-METHYLETHYL)-1H-IMIDAZO[4,5-c]PYRIDIN-1-YL)PHENYL]ETHYL (4-METHYLPHENYL)SULFONYLCARBAMATE Step 1. 2-{4-[4,6-dimethyl-2-(1-methylethyl)-1H-imidazo[4,5-c]pyridin-1-yl]phenyl}ethyl 2-methylpropanoate The title compound was prepared according to the procedure described in step 1 of Example 229 from 2-{4-[(3-Amino-2,6-dimethyl-4-pyridinyl)amino]phenyl}ethanol (step 2 of Example 42).

$^1$H-NMR (CDCl$_3$) δ: 7.44 (2H, d, J=8.4 Hz), 7.26 (2H, d, J=8.4 Hz), 6.66 (1H, s), 4.38 (2H, t, J=7.0 Hz), 3.08 (2H, t, J=6.8 Hz), 3.12–3.02 (1H, m), 2.89 (3H, s), 2.55 (3H, s), 2.61–2.48 (1H, m), 1.33 (6H, d, J=7.0 Hz), 1.15 (6H, d, J=7.0 Hz).

Step 2. 2-{4-[4,6-dimethyl-2-(1-methylethyl)-1H-imidazo[4,5-c]pyridin-1-yl]phenyl}ethanol The title compound was prepared according to the procedure described in step 6 of Example 1 from 2-{4-[4,6-dimethyl-2-(1-methylethyl)-1H-imidazo[4,5-c]pyridin-1-yl]phenyl}ethyl 2-methylpropanoate (step 1).

$^1$H-NMR (CDCl$_3$) δ: 7.46 (2H, d, J=8.2 Hz), 7.25 (2H, d, J=8.3 Hz), 6.68 (1H, s), 4.00 (2H, t, J=6.6 Hz), 3.13–3.04 (1H, m), 3.02 (2H, t, J=6.6 Hz), 2.88 (3H, s), 2.53 (3H, s), 1.33 (6H, d, J=7.0 Hz).

Step 3. 2-{4-[4,6-dimethyl-2-(1-methylethyl)-1H-imidazo[4,5-c]pyridin-1-yl]phenyl}ethyl (4-methylphenyl)sulfonylcarbamate The title compound was prepared according to the procedure described in Example 3 from 2-{4-[4,6-dimethyl-2-(1-methylethyl)-1H-imidazo[4,5-c]pyridin-1-yl]phenyl}ethanol (step 2).

m.p.: 213° C.

MS (ESI) m/z: 507 [(MH)$^+$], 505 [(M−H)$^−$].

$^1$H-NMR (CD$_3$OD) δ: 7.80 (2H, d, J=8.4 Hz), 7.51 (2H, d, J=8.6 Hz), 7.34 (2H, d, J=8.6 Hz), 7.29 (2H, d, J=8.1 Hz), 7.01 (1H, s), 4.26 (2H, t, J=6.6 Hz), 3.15–3.09 (1H, m), 3.00 (2H, t, J=6.4 Hz), 2.90 (3H, s), 2.58 (3H, s), 2.36 (3H, s), 1.33 (6H, d, J=6.8 Hz).

Example 233
2-{4-[2-(1,1-DIMETHYLETHYL)-4,6-DIMETHYL-1H-IMIDAZO[4,5-c]PYRIDIN-1-YL]PHENYL}ETHYL (4-METHYLPHENYL)SULFONYLCARBAMATE Step 1. 2-{4-[2-(1,1-dimethylethyl)-4,6-dimethyl-1H-imidazo[4,5-c]pyridin-1-yl]phenyl}ethyl 2,2-dimethylpropanoate The title compound was prepared according to the procedure described in step 1 of Example 229 from 2-{4-[(3-Amino-2,6-dimethyl-4-pyridinyl)amino]phenyl}ethanol (step 2 of Example 42).

$^1$H-NMR (CDCl$_3$) δ: 7.41 (2H, d, J=8.4 Hz), 7.26 (2H, d, J=8.4 Hz), 6.35 (1H, s), 4.38 (2H, t, J=6.6 Hz), 3.08 (2H, t, J=6.6 Hz), 2.87 (3H, s), 2.50 (3H, s), 1.34 (9H, s), 1.17 (9H, s).

Step 2. 2-{4-[2-(1,1-dimethylethyl)-4,6-dimethyl-1H-imidazo[4,5-c]pyridin-1-yl]phenyl}ethanol The title compound was prepared according to the procedure described in step 6 of Example 1 from 2-{4-[2-(1,1-dimethylethyl)-4,6-dimethyl-1H-imidazo[4,5-c]pyridin-1-yl]phenyl}ethyl 2,2-dimethylpropanoate (step 1).

$^1$H-NMR (CDCl$_3$) δ: 7.42 (2H, d, J=8.1 Hz), 7.27 (2H, d, J=8.6 Hz), 6.38 (1H, s), 4.00 (2H, t, J=6.4 Hz), 3.01 (2H, t, J=6.6 Hz), 2.87 (3H, s), 2.50 (3H, s), 1.34 (9H, s).

Step 3. 2-{4-[2-(1,1-dimethylethyl)-4,6-dimethyl-1H-imidazo[4,5-c]pyridin-1-yl]phenyl}ethyl (4-methylphenyl)sulfonylcarbamate The title compound was prepared according to the procedure described in Example 3 from 2-{4-[2-(1,1-dimethylethyl)-4,6-dimethyl-1H-imidazo[4,5-c]pyridin-1-yl]phenyl}ethanol (step 2).

m.p.: 226° C.

MS (ESI) m/z: 521 [(MH)$^+$], 519 [(M−H)$^−$].

$^1$H-NMR (DMSO-d$_6$) δ: 7.71 (2H, d, J=8.3 Hz), 7.46 (2H, d, J=8.6 Hz), 7.41 (2H, d, J=8.6 Hz), 7.35 (2H, d, J=8.1 Hz), 6.55 (1H, s), 4.20 (2H, t, J=7.0 Hz), 2.95 (2H, t, J=7.0 Hz), 2.74 (3H, s), 2.44 (3H, s), 2.36 (3H, s), 1.27 (9H, s).

Example 234
2-[4-(2-CYCLOHEXYL-4,6-DIMETHYL-1H-IMIDAZO[4,5-c]PYRIDIN-1-YL)PHENYL]ETHYL(4-METHYLPHENYL)SULFONYLCARBAMATE Step 1. 2-[4-(2-cyclohexyl-4,6-dimethyl-1H-imidazo[4,5-c]pyridin-1-yl)phenyl]ethyl cyclohexanecarboxylate The title compound was prepared according to the procedure described in step 1 of Example 229 from 2-{4-[(3-Amino-2,6-dimethyl-4-pyridinyl)amino]phenyl}ethanol (step 2 of Example 42).

$^1$H-NMR (CDCl$_3$) δ: 7.44 (2H, d, J=8.4 Hz), 7.24 (2H, d, J=8.4 Hz), 6.65 (1H, s), 4.39 (2H, t, J=6.8 Hz), 3.08 (2H, t, J=6.8 Hz), 2.88 (3H, s), 2.54 (3H, s), 2.71–1.21 (22H, m).

Step 2. 2-[4-(2-cyclohexyl-4,6-dimethyl-1H-imidazo[4,5-c]pyridin-1-yl)phenyl]ethanol The title compound was prepared according to the procedure described in step 6 of Example 1 from 2-[4-(2-cyclohexyl-4,6-dimethyl-1H-imidazo[4,5-c]pyridin-1-yl)phenyl]ethyl cyclohexanecarboxylate (step 1).

$^1$H-NMR (CDCl$_3$) δ: 7.46 (2H, d, J=8.2 Hz), 7.25 (2H, d, J=8.2 Hz), 6.68 (1H, s), 4.01 (2H, t, J=6.4 Hz), 3.02 (2H, t, J=6.4 Hz), 2.88 (3H, s), 2.72–2.70 (1H, m), 2.54 (3H, s), 2.30–1.15 (10H, m).

Step 3. 2-[4-(2-cyclohexyl-4,6-dimethyl-1H-imidazo[4,5-c]pyridin-1-yl)phenyl]ethyl (4-methylphenyl)sulfonylcarbamate The title compound was prepared according to the procedure described in Example 3 from 2-[4-(2-cyclohexyl-4,6-dimethyl-1H-imidazo[4,5-c]pyridin-1-yl)phenyl]ethanol (step 2).

m.p.: 168° C.

MS (ESI) m/z: 547 [(MH)$^+$], 545 [(M–H)$^-$].

$^1$H-NMR (CD$_3$OD) δ: 7.97 (2H, d, J=8.4 Hz), 7.29 (2H, d, J=8.1 Hz), 7.19 (2H, d, J=8.3 Hz), 6.77 (2H, d, J=8.2 Hz), 6.53 (1H, s), 4.33 (2H, t, J=5.3 Hz), 3.09 (3H, s), 2.97 (2H, t, J=5.5 Hz), 2.65–2.55 (1H, m), 2.50 (3H, s), 2.42 (3H, s), 1.77–1.18 (10H, m).

Example 235
2-{4-[4,6-DIMETHYL-2-(3-PHENYLPROPYL)-1H-IMIDAZO[4,5-c]PYRIDIN-1-YL]PHENYL}ETHYL (4-METHYLPHENYL)SULFONYLCARBAMATE Step 1. 2-{4-[4,6-dimethyl-2-(3-phenylpropyl)-1H-imidazo[4,5-c]pyridin-1-yl]phenyl}ethyl 4-phenylbutanoate The title compound was prepared according to the procedure described in step 1 of Example 229 from 2-{4-[(3-Amino-2,6-dimethyl-4-pyridinyl)amino]phenyl}ethanol (step 2 of Example 42).

$^1$H-NMR (CDCl$_3$) δ: 7.39 (2H, d, J=8.2 Hz), 7.30–7.15 (10H, m), 7.06 (2H, d, J=6.4 Hz), 6.70 (1H, s), 4.37 (2H, t, J=7.1 Hz), 3.06 (2H, t, J=6.9 Hz), 2.88 (3H, s), 2.80 (2H, t, J=7.6 Hz), 2.68–2.60 (4H, m), 2.54 (3H, s), 2.36 (2H, t, J=7.4 Hz), 2.09–1.91 (4H, m).

Step 2. 2-{4-[4,6-dimethyl-2-(3-phenylpropyl)-1H-imidazo[4,5-c]pyridin-1-yl]phenyl}ethanol The title compound was prepared according to the procedure described in step 6 of Example 1 from 2-{4-[4,6-dimethyl-2-(3-phenylpropyl)-1H-imidazo[4,5-c]pyridin-1-yl]phenyl}ethyl 4-phenylbutanoate (step 1).

$^1$H-NMR (CDCl$_3$) δ: 7.41 (2H, d, J=8.2 Hz), 7.25–7.15 (5H, m), 7.07 (2H, d, J=6.8 Hz), 6.72 (1H, s), 3.99 (2H, t, J=6.6 Hz), 3.00 (2H, t, J=6.3 Hz), 2.88 (3H, s), 2.81 (2H, t, J=7.6 Hz), 2.64 (2H, d, J=7.6 Hz), 2.55 (3H, s), 2.11–2.00 (2H, m).

Step 3. 2-{4-[4,6-dimethyl-2-(3-phenylpropyl)-1H-imidazo[4,5-c]pyridin-1-yl]phenyl}ethyl (4-methylphenyl)sulfonylcarbamate The title compound was prepared according to the procedure described in Example 3 from 2-{4-[4,6-dimethyl-2-(3-phenylpropyl)-1H-imidazo[4,5-c]pyridin-1-yl]phenyl}ethanol (step 2).

m.p.: 175° C.

MS (ESI) m/z: 583 [(MH)$^+$], 581 [(M–H)$^-$].

$^1$H-NMR (CDCl$_3$) δ: 7.95 (2H, d, J=8.3 Hz), 7.30–7.14 (7H, m), 7.03 (2H, d, J=8.1 Hz), 6.81 (2H, d, J=8.0 Hz), 6.64 (1H, s), 4.33 (2H, t, J=5.7 Hz), 3.00 (3H, s), 2.95 (2H, t, J=5.7 Hz), 2.72 (2H, t, J=7.5 Hz), 2.62 (2H, t, J=7.4 Hz), 2.51 (3H, s), 2.41 (3H, s), 2.07–1.97 (2H, m).

Example 236
4-METHYL-N-{[(2-{4-[5-(METHYLOXY)-2-(1H-PYRAZOL-3-YL)-1H-BENZIMIDAZOL-1-YL]PHENYL}ETHYL)AMINO]CARBONYL}BENZENESULFONAMIDE P-TOLUENESULFONATE Step 1. 2-{4-[5-(methyloxy)-2-(1H-pyrazol-3-yl)-1H-benzimidazol-1-yl]phenyl}ethanol A mixture of 2-(4-{[2-amino-4-(methyloxy)phenyl]amino}phenyl)ethanol (step 2 of Example 71, 1.95 g, 7.56 mmol), pyrazol-3-carbaldehyde (726 mg, 7.56 mmol) in ethanol (45 ml) was heated at reflux temperature for 2 h. After cooling, the mixture was concentrated. A mixture of the residue, lead tetraacetate (4.61 g, 8.32 mmol) in benzene (50 ml) was stirred at room temperature for 16 h. The mixture was quenched with saturated NaHCO$_3$ aqueous solution (150 ml). The whole was extracted with ethyl acetate (150 ml×4). The organic layer was washed with water (100 ml×5), brine (50 ml), dried (MgSO$_4$), and concentrated. Purification by flash column chromatography eluting with dichloromethane/methanol (gradient elution from 20:1 to 10:1) to afford 408 mg (16%) of the title compound as an amber solid.

MS (EI) m/z: 334 (M$^+$).

$^1$H-NMR (DMSO-d$_6$) δ: 7.6 (1H, br.s), 7.43 (2H, d, J=7.7 Hz), 7.29–7.23 (3H,m), 7.04 (1H, d, J=8.8 Hz), 6.90 (1H, d, J=8.8 Hz), 6.34 (1H, br.s), 3.85–3.81 (5H, m), 2.92 (2H, t, J=6.6 Hz).

Step 2. 1-[4-(2-chloroethyl)phenyl]-5-(methyloxy)-2-(1H-pyrazol-3-yl)-1H-benzimidazole The title compound was prepared according to the procedure described in step 7 Example 1 from 2-{4-[5-(methyloxy)-2-(1H-pyrazol-3-yl)-1H-benzimidazol-1-yl]phenyl}ethanol (step 1).

MS (EI) m/z: 352 (M$^+$).

$^1$H-NMR (CDCl$_3$) δ: 8.96 (0.5H, s), 8.11 (0.5H, d, J=2.9 Hz), 7.50 (0.5H, d, J=2.0 Hz), 7.46–7.34 (5H, m), 7.05 (1H, dd, J=16.5, 8.8 Hz), 6.93 (1H, ddd, J=1.4, 9.0, 2.4 Hz), 6.71 (0.5H, dd, J=2.9, 1.1 Hz), 5.81 (1H, s), 3.85 (3H, s), 3.82 (2H, t, J=7.0 Hz), 3.22 (2H, t, J=7.0 Hz).

Step 3. 1-[4-(2-azidoethyl)phenyl]-5-(methyloxy)-2-(1H-pyrazol-3-yl)-1H-benzimidazole The title compound was prepared according to the procedure described in step 8 Example 1 from 1-[4-(2-chloroethyl)phenyl]-5-(methyloxy)-2-(1H-pyrazol-3-yl)-1H-benzimidazole (step 2).

MS (EI) m/z: 359 (M$^+$).

$^1$H-NMR (CDCl$_3$) δ: 14.05 (1H, br.s), 7.53–7.50 (2H, m), 7.45 (2H, d, J=8.4 Hz), 7.37 (2H, d, J=8.4 Hz), 7.01 (1H, d, J=8.7 Hz), 6.89 (1H, dd, J=8.7, 2.4 Hz), 5.81 (1H, s), 3.85 (3H, s), 3.61 (2H, t, J=6.9 Hz), 3.03 (2H, t, J=6.9 Hz).

Step 4. 2-{4-[5-(methyloxy)-2-(1H-pyrazol-3-yl)-1H-benzimidazol-1-yl]phenyl}ethylamine The title compound was prepared according to the procedure described in step 9 Example 1 from 1-[4-(2-azidoethyl)phenyl]-5-(methyloxy)-2-(1H-pyrazol-3-yl)-1H-benzimidazole (step 3).

MS (EI) m/z: 333 (M$^+$).

$^1$H-NMR (CDCl$_3$) δ: 7.47 (1H, d, J=2.0 Hz), 7.43–7.29 (5H, m), 7.00 (1H,d, J=8.8 Hz), 6.88 (1H, dd, J=9.0, 2.4 Hz), 5.81 (1H, s), 3.80 (3H, s), 3.09 (2H, t, J=7.1 Hz), 2.90 (2H, t, J=6.8 Hz).

Step 5. 4-methyl-N-{[(2-{4-[5-(methyloxy)-2-(1H-pyrazol-3-yl)-1H-benzimidazol-1-yl]phenyl}ethyl)amino]carbonyl}benzenesulfonamide The title compound was prepared according to the procedure described in step 10 of Example 1 from 2-{4-[5-(methyloxy)-2-(1H-pyrazol-3-yl)-1H-benzimidazol-1-yl]phenyl}ethylamine (step 4).

MS (ESI) m/z: 531 [(MH)$^+$], 529 [(M−H)$^−$].

$^1$H-NMR (CDCl$_3$) δ: 7.77 (2H, d, J=8.3 Hz), 7.44 (1H, s), 7.24 (2H, d, J=7.5 Hz), 7.14–7.07 (5H, m), 6.98 (1H, d, J=9.0 Hz), 6.88 (1H, d, J=9.0 Hz), 6.10 (1H, s), 3.83 (3H, s), 3.57–3.55 (2H, m), 2.88–2.84 (2H, m), 2.35 (3H, s).

Step 6. 4-methyl-N-{[(2-{4-[5-(methyloxy)-2-(1H-pyrazol-3-yl)-1H-benzimidazol-1-yl]phenyl}ethyl)amino]carbonyl}benzenesulfonamide p-toluenesulfonamide mono-p-toluenesulfonate The title compound was prepared according to the procedure described in Example 231 from 4-methyl-N-{[(2-{4-[5-(methyloxy)-2-(1H-pyrazol-3-yl)-1H-benzimidazol-1-yl]phenyl}ethyl)amino]carbonyl}benzenesulfonamide (step 5).

$^1$H-NMR (CDCl$_3$) δ: 12.65 (1H, s), 9.99 (1H, s), 7.87 (2H, d, J=8.1 Hz), 7.78 (2H, d, J=8.3 Hz), 7.50 (2H, d, J=9.0 Hz), 7.39 (2H, d, J=8.4 Hz), 7.20 (2H, d, J=7.9 Hz), 7.18 (2H, d, J=8.1 Hz), 7.08–6.93 (5H, m), 6.44 (1H, s), 3.76 (3H, s), 3.42–3.40 (2H, m), 2.92–2.88 (2H, m), 2.86 (6H, s).

Example 237
2-{4-[5-METHYLOXY-2-(1H-PYRAZOL-3-YL)-1H-BENZIMIDAZOL-1-YL]PHENYL}ETHYL (4-METHYLPHENYL)SULFONYLCARBAMATE P-TOLUENESULFONATE Step 1. 2-{4-[5-(methyloxy)-2-(1H-pyrazol-3-yl)-1H-benzimidazol-1-yl]phenyl}ethyl (4-methylphenyl)sulfonylcarbamate The title compound was prepared according to the procedure described in Example 3 from 2-{4-[5-(methyloxy)-2-(1H-pyrazol-3-yl)-1H-benzimidazol-1-yl]phenyl}ethanol (step 1 of Example 236).

MS (ESI) m/z: 532 [(MH)$^+$], 530 [(M−H)$^−$].

$^1$H-NMR (DMSO-d$_6$) δ: 7.75 (2H, d, J=8.1 Hz), 7.58 (2H, d, J=8.1 Hz), 7.38 (2H, d, J=7.8 Hz), 7.33–7.21 (3H, m), 7.22 (2H, d, J=8.1 Hz), 6.96 (1H, d, J=8.1 Hz), 6.88 (1H, d, J=8.1 Hz), 4.26–4.24 (2H, m), 3.82 (3H, s), 2.95–2.93 (2H, m), 2.34 (3H, s).

Step 2. 2-{4-[5-(methyloxy)-2-(1H-pyrazol-3-yl)-1H-benzimidazol-1-yl]phenyl}ethyl (4-methylphenyl)sulfonylcarbamate mono-p-toluenesulfonate The title compound was prepared according to the procedure described in Example 231 from 2-{4-[5-(methyloxy)-2-(1H-pyrazol-3-yl)-1H-benzimidazol-1-yl]phenyl}ethyl (4-methylphenyl)sulfonylcarbamate (step 1).

$^1$H-NMR (CDCl$_3$) δ: 7.88 (2H, d, J=8.2 Hz), 7.80–7.65 (6H, m), 7.44 (2H, d, J=8.1 Hz), 7.38–7.26 (3H, m), 7.17 (2H, d, J=8.1 Hz), 7.10 (2H, d, J=7.6 Hz), 4.37–4.33 (2H, m), 3.03–2.99 (2H, m), 2.39 (3H, s), 2.35 (3H, s), 2.31 (3H, s).

Example 238
2-{4-[6-CHLORO-2-(1,5-DIMETHYL-1H-PYRAZOL-3-YL)-5-(TRIFLUOROMETHYL)-1H-BENZIMIDAZOL-1-YL]PHENYL}ETHYL (4-METHYLPHENYL)SULFONYLCARBAMATE Step 1. 2-(4-{[5-chloro-2-nitro-4-(trifluoromethyl)phenyl]amino}phenyl)ethyl (4-methylphenyl)sulfonylcarbamate To a stirred solution of 2-(4-{[5-chloro-2-nitro-4-(trifluoromethyl)phenyl]amino}phenyl)ethanol (step 2 of Example 104, 1.0 g, 2.77 mmol) in dichloromethane (45 ml) was added p-toluenesulfonyl isocyanate (574 mg, 2.91 mmol), and the mixture was stirred at room temperature for 2 h. The mixture was quenched with water (100 ml). The organic layer was separated. The aqueous layer was extracted with dichloromethane (100 ml×3). The combined organic layer was washed with brine (50 ml), dried (MgSO$_4$), and concentrated. Purification by flash column chromatography eluting with hexane/ethyl acetate (gradient elution from 2:1 to 1:1) to afford 1.51 g (98%) of the title compound as an orange solid.

$^1$H-NMR (CDCl$_3$) δ: 9.68 (1H, s), 8.58 (1H, s), 7.91 (2H, d, J=8.4 Hz), 7.34 (2H, d, J=7.9 Hz), 7.27 (2H, d, J=7.9 Hz), 7.20 (2H, d, J=8.4 Hz), 7.17 (1H, s), 4.33 (2H, t, J=7.0 Hz), 2.96 (2H, t, J=6.8 Hz), 2.45 (3H, s).

Step 2. 2-(4-{[2-amino-5-chloro-4-(trifluoromethyl)phenyl]amino}phenyl)ethyl (4-methylphenyl)sulfonylcarbamate To a stirred solution of 2-(4-{[5-chloro-2-nitro-4-(trifluoromethyl)phenyl]amino}phenyl)ethyl (4-methylphenyl)sulfonylcarbamate (step 1, 1.51 g, 2.71 mmol) in methanol (250 ml) was added 5% platinum-sulfided on carbon (600 mg). The mixture was stirred at room temperature for 5 h under hydrogen atmosphere (4 atm). The palladium catalyst was removed by filtration and washed with dichloromethane (100 ml). The filtrate was concentrated under reduced pressure to afford 1.46 g (99%) of the title compound as a brown oil.

$^1$H-NMR (CDCl$_3$) δ: 7.90 (2H, d, J=8.4 Hz), 7.33 (2H, d, J=8.2 Hz), 7.16 (1H, s), 7.07 (2H, d, J=8.2 Hz), 7.06 (1H, s), 6.86 (2H, d, J=8.2 Hz), 5.40 (2H, s), 4.26 (2H, t, J=6.9 Hz), 2.85 (2H, t, J=7.2 Hz), 2.44 (3H, s).

Step 3. 2-(4-{[5-chloro-2-{[(1,5-dimethyl-1H-pyrazol-3-yl)carbonyl]amino}-4-(trifluoromethyl)phenyl]amino}phenyl)ethyl (4-methylphenyl)sulfonylcarbamate To a stirred solution of 2-(4-{[2-amino-5-chloro-4-(trifluoromethyl)phenyl]amino}phenyl)ethyl (4-methylphenyl)sulfonylcarbamate (step 2, 200 mg, 0.379 mmol) in dichloromethane (1.7 ml) was added a solution of 1,5-dimethyl-1H-pyrazole-3-carboxylic acid (63.8 mg, 0.455 mmol) and N,N-diisoprppylethylamine (118 mg, 0.909 mmol) in dichloromethane (1.7 ml), then to the mixture was added a solution of HOBt (61.5 mg, 0.455 mmol) and HBTU (431 mg, 1.14 mmol) in DMF (2.5 ml), and the mixture was stirred at room temperature for 20 h. The mixture was quenched with water (100 ml). The whole was extracted with ethyl acetate (100 ml×3). The combined organic layer was washed with water (100 ml×3), brine (50 ml), dried (MgSO$_4$), and concentrated. Purification by PTLC eluting with hexane/ethyl acetate (1:1) to afford 145 mg (59%) of the title compound as a red solid.

$^1$H-NMR (CDCl$_3$) δ: 8.70 (1H, s), 7.87 (2H, d, J=8.1 Hz), 7.79 (1H, s), 7.28 (2H, d, J=8.1 Hz), 7.04 (2H, d, J=8.3 Hz), 6.95 (2H, d, J=8.3 Hz), 6.72 (1H, s), 6.60 (1H, s), 4.22 (2H, t, J=6.8 Hz), 3.78 (3H, s), 2.84–2.80 (2H, m), 2.40 (3H, s), 2.30 (3H, s).

Step 4. 2-{4-[6-chloro-2-(1,5-dimethyl-1H-pyrazol-3-yl)-5-(trifluoromethyl)-1H-benzimidazol-1-yl]phenyl}ethyl (4-methylphenyl)sulfonylcarbamate A mixture of 2-(4-{[5-chloro-2-{[(1,5-dimethyl-1H-pyrazol-3-yl)carbonyl]amino}-4-(trifluoromethyl)phenyl]amino}phenyl)ethyl (4-methylphenyl)sulfonylcarbamate (step 3, 145 mg, 0.223 mmol) in 2N NaOH (1 ml) and ethanol (2 ml) was stirred at 50° C. for 85 h. After cooling, the pH value was adjusted to 4.0 by addition of 2N HCl. The mixture was diluted with water (80 ml), and extracted with dichloromethane (80 ml×3). The combined organic layer was washed with brine (50 ml), dried (MgSO$_4$), and concentrated. Purification by PTLC eluting with hexane/ethyl acetate (1:3) to afford 30 mg (21%) of the title compound as a red solid.

MS (ESI) m/z: 632 [(MH)$^+$], 630 [(M−H)$^−$].

$^1$H-NMR (CDCl$_3$) δ: 8.15 (1H, s), 7.90 (2H, d, J=8.4 Hz), 7.34–7.24 (6H, m), 7.19 (1H, s), 5.81 (1H, s), 4.40 (2H, t, J=6.8 Hz), 3.76 (3H, s), 3.04 (2H, t, J=6.4 Hz), 2.41 (3H, s), 2.20 (3H, s).

Example 239

N-[({2-[4-(2-BUTYL-4,6-DIMETHYL-1H-IMIDAZO[4,5-c]PYRIDIN-1-YL)PHENYL]ETHYL}AMINO)CARBONYL]-4-METHYLBENZENESULFONAMIDE

Step 1. 2-butyl-1-[4-(2-chloroethyl)phenyl]-4,6-dimethyl-1H-imidazo[4,5-c]pyridine The title compound was prepared according to the procedure described in step 7 of Example 1 from 2-[4-(2-butyl-4,6-dimethyl-1H-imidazo[4,5-c]pyridin-1-yl)phenyl]ethanol (step 2 of Example 230).

MS (EI) m/z: 341 (M⁺).

$^1$H-NMR (CDCl$_3$) δ: 7.45 (2H, d, J=8.2 Hz), 7.28 (2H, d, J=8.2 Hz), 6.73 (1H, s), 3.82 (2H, t, J=7.1 Hz), 3.22 (2H, t, J=7.1 Hz), 2.89 (3H, s), 2.79 (2H, t, J=8.2 Hz), 2.58 (3H, s), 1.76–1.64 (2H, m), 1.39–1.25 (2H, m), 0.84 (3H, t, J=7.2 Hz).

Step 2. 1-[4-(2-azidoethyl)phenyl]-2-butyl-4,6-dimethyl-1H-imidazo[4,5-c]pypridine The title compound was prepared according to the procedure described in step 8 of Example 1 from 2-butyl-1-[4-(2-chloroethyl)phenyl]-4,6-dimethyl-1H-imidazo[4,5-c]pyridine (step 1).

MS (EI) m/z: 348 (M⁺).

$^1$H-NMR (CDCl$_3$) δ: 7.46 (2H, d, J=8.2 Hz), 7.29 (2H, d, J=8.6 Hz), 6.72 (1H, s), 3.62 (2H, t, J=6.8 Hz), 3.03 (2H, t, J=6.8 Hz), 2.88 (3H, s), 2.78 (2H, t, J=7.6 Hz), 2.55 (3H, s), 1.74–1.63 (2H, m), 1.38–1.24 (2H, m), 0.84 (3H, t, J=7.3 Hz).

Step 3. 2-[4-(2-butyl-4,6-dimethyl-1H-imidazo[4,5-c]pyridin-1-yl)phenyl]ethylamine The title compound was prepared according to the procedure described in step 9 of Example 1 from 1-[4-(2-azidoethyl)phenyl]-2-butyl-4,6-dimethyl-1H-imidazo[4,5-c]pyridine (step 2).

MS (EI) m/z: 322 (M⁺).

$^1$H-NMR (CDCl$_3$) δ: 7.43 (2H, d, J=8.3 Hz), 7.26 (2H, d, J=8.1 Hz), 6.72 (1H, s), 3.10–3.04 (2H, m), 2.90–2.86 (5H, m), 2.78 (2H, t, J=7.7 Hz), 2.55 (3H, s), 1.74–1.64 (2H, m), 1.35–1.25 (2H, m), 0.84 (3H, t, J=7.3 Hz).

Step 4. N-[({2-[4-(2-butyl-4,6-dimethyl-1H-imidazo[4,5-c]pyridin-1-yl)phenyl]ethyl}amino)carbonyl]-4-methylbenzenesulfonamide The title compound was prepared according to the procedure described in step 10 of Example 1 from 2-[4-(2-butyl-4,6-dimethyl-1H-imidazo[4,5-c]pyridin-1-yl)phenyl]ethylamine (step 3).

MS (ESI) m/z: 520 [(MH)⁺], 518 [(M–H)⁻].

$^1$H-NMR (CDCl$_3$) δ: 7.77 (2H, d, J=8.1 Hz), 7.37 (2H, d, J=7.9 Hz), 7.27 (2H, d, J=7.8 Hz), 7.19 (2H, d, J=7.5 Hz), 6.76 (1H, s), 3.57–3.51 (2H, m), 2.92 (2H, t, J=6.6 Hz), 2.88 (3H, s), 2.76 (2H, t, J=7.5 Hz), 2.52 (3H, s), 2.38 (3H, s), 1.73–1.62 (2H, m), 1.36–1.23 (2H, m), 0.82 (3H, t, J=7.3 Hz).

Step 5. N-[({2-[4-(2-butyl-4,6-dimethyl-1H-imidazo[4,5-c]pyridin-1-yl)phenyl]ethyl}amino)carbonyl]-4-methylbenzenesulfonamide mono-p-toluenesulfonate The title compound was prepared according to the procedure described in Example 231 from N-[({2-[4-(2-butyl-4,6-dimethyl-1H-imidazo[4,5-c]pyridin-1-yl)phenyl]ethyl}amino)carbonyl]-4-methylbenzenesulfonamide (step 4).

$^1$H-NMR (CDCl$_3$) δ: 9.85 (1H, br.s), 7.78 (4H, d, J=8.1 Hz), 7.45 (2H, d, J=7.9 Hz), 7.27–7.13 (6H, m), 7.01 (1H, s), 3.45–343 (2H, m), 3.03 (3H, s), 2.89–2.87 (2H, m), 2.79–2.73 (5H, m), 2.36 (3H, s), 2.34 (3H, s), 1.74–1.65 (2H, m), 1.35–1.23 (2H, m), 0.84 (3H, t, J=7.2 Hz).

Example 240

2-[4-(2-ETHYL-5,7-DIMETHYL-3H-IMIDAZO[4,5-B]PYRIDIN-3-YL)PHENYL]-1-METHYLETHYL (4-METHYLPHENYL)SULFONYLCARBAMATE MONO-HYDROCHLORIDE

To a solution of 2-[4-(2-ethyl-5,7-dimethyl-3H-imidazo[4,5-b]pyridin-3-yl)phenyl]-1-methylethyl (4-methylphenyl)sulfonylcarbamate (Example 7, 694 mg, 1.37 mmol) in methanol (4 ml) was added 10% HCl in methanol (2 ml) at room temperature. This mixture was concentrated, and treated with diethylether to afford 624 mg (90%) of the title compound as a slight yellow solid.

$^1$H-NMR (DMSO-d$_6$) δ: 11.92 (1H, br.s), 7.76 (2H, d, J=7.9 Hz), 7.49–7.39 (6H, m), 7.26 (1H, br.s), 4.98–4.88 (1H, m), 2.94–2.83 (4H, m), 2.63 (3H, s), 2.46 (3H, s), 2.34 (3H, s), 1.23 (3H, t, J=7.5 Hz), 1.12 (3H, d, J=6.1 Hz).

MS (ESI) m/z: 507 [(MH)⁺], 505 [(M–H)⁻].

Example 241

N-{[(2-{4-[5,7-DIMETHYL-2-(3-PHENYLPROPYL)-3H-IMIDAZO[4,5-B]PYRIDIN-3-YL]PHENYL}ETHYL)AMINO]CARBONYL}-4-METHYLBENZENESULFONAMIDE

A mixture of N-{[(2-{4-[(3-amino-4,6-dimethyl-2-pyridinyl)amino]phenyl}ethyl)amino]carbonyl}-4-methylbenzenesulfonamide (step 4 of Example 162, 86 mg, 0.19 mmol), 4-phenylbutyric acid (37 mg, 0.23 mmol) and 1-ethyl-3-(3-dimethylaminopropyl)carbodiimide hydrochloride (40 mg, 0.21 mmol) was stirred at room temperature for 5 days. The mixture was concentrated to give an orange syrup. This material was dissolved in toluene (8 ml), added p-toluenesulfonic acid mono-hydrate (3 mg, 0.02 mol), then stirred under reflux temperature for 5 h. The mixture was diluted with dichloromethane and washed with diluted hydrochloric acid. The organic layer was concentrated. Purification by TLC developing with hexane/ethyl acetate (1:3) gave 32 mg (29%) of the title compound as a colorless solid.

$^1$H-NMR (CDCl$_3$) δ: 7.85 (2H, d, J=8.4 Hz), 7.31–7.01 (11H, m), 6.91 (1H, s), 3.52–3.45 (2H, m), 2.83 (2H, t, J=6.4 Hz), 2.71–2.65 (2H, m), 2.64 (3H, s), 2.58–2.53 (2H, m), 2.41 (3H, s), 2.39 (3H, s), 2.00–1.90 (2H, m).

MS (ESI) m/z: 582 [(MH)⁺], 580 [(M–H)⁻].

Example 242

N-{[(2-{4-[5,7-DIMETHYL-2-(3-OXO-3-PHENYLPROPYL)-3H-IMIDAZO[4,5-B]PYRIDIN-3-YL]PHENYL}ETHYL)AMINO]CARBONYL}-4-METHYLBENZENESULFONAMIDE

The title compound was prepared according to the procedure described in Example 241 from N-{[(2-{4-[(3-amino-4,6-dimethyl-2-pyridinyl)amino]phenyl}ethyl)amino]carbonyl}-4-methylbenzenesulfonamide (step 4 of Example 162) and 3-benzoylpropionic acid.

$^1$H-NMR (CDCl$_3$) δ: 8.04–7.14 (11H, m), 6.90 (1H, s), 6.20–6.15 (1H, m), 3.50–3.38 (4H, m), 3.03–2.81 (4H, m), 2.56 (3H, s), 2.44 (3H, s), 2.41 (3H, s).

MS (ESI) m/z: 596 [(MH)⁺], 594 [(M–H)⁻].

Example 243

2-{4-[6-CHLORO-2-ETHYL-5-(TRIFLUOROMETHYL)-1H-BENZIMIDAZOL-1-YL]PHENYL}ETHYL 3-PYRIDINYLSULFONYLCARBAMATE

Step 1. 2-{4-[6-chloro-2-ethyl-5-(trifluoromethyl)-1H-benzimidazol-1-yl]phenyl}ethyl phenyl carbonate To a stirred solution of 2-[4-(6-Chloro-2-ethyl-5-trifluoromethyl-1H-benzimidazol-1-yl)phenyl]ethanol (step 4 of Example 104, 3.90 g, 10.6 mmol) in dichloromethane (20 mL) and pyridine (2 ml) was added dropwise phenyl chloroformate (1.6 mL, 12.7 mmol), and the mixture was stirred at room temperature for 16 h. The reaction mixture was diluted with dichloromethane (50 mL), washed with water (50 ml). The organic layer was dried over $Na_2SO_4$, and concentrated under reduced pressure. Purification by flash column chromatography eluting with hexane/ethyl acetate (3:1) afforded 4.2 g (82%) of the title compound as a colorless syrup.

$^1$H NMR (CDCl$_3$) δ 8.12 (1H, s), 7.53–7.15 (10H, m), 4.56 (2H, t, J=6.8 Hz), 3.20 (2H, t, J=6.8 Hz), 2.79 (2H, q, J=7.6 Hz), 1.36 (3H, t, J=7.6 Hz).

MS (EI) m/z: 488 (M$^+$).

Step 2. 2-{4-[6-chloro-2-ethyl-5-(trifluoromethyl)-1H-benzimidazol-1-yl]phenyl}ethyl 3-pyridinylsulfonylcarbamate To a stirred solution of 3-pyridinesulfonamide (Rafik, Karaman; et al., *J. Am. Chem. Soc.*, 1992, 114, 4889, 120 mg, 0.76 mmol) in DMF (3 mL) was added NaH (60% oil dispersion, 27 mg, 0.68 mmol) at room temperature. After 10min., phenyl 2-[4-(2-ethyl-5,7-dimethyl-3H-imidazo[4,5-b]pyridin-3-yl)phenyl]ethylcarbamate (step 1, 313 mg, 0.64 mmol) was added, and the mixture was stirred for 9 h at 80° C. The mixture was diluted with ethyl acetate (50 mL), and washed with water and brine. The organic layer was dried (Na2SO4) and concentrated. Purification by TLC developing with dichloromethane/methanol (6:1) and TLC developing with dichloromethane/methanol (10:1) gave 67 mg (19%) of the title compound as colorless solid.

$^1$H-NMR (CDCl$_3$) δ□□9.18 (1H, s), 8.73–8.72 (1H, m), 8.32–8.29 (1H, m), 8.09 (1H, s), 7.40–7.15 (6H, m), 4.33–4.29 (2H, m), 2.99–2.94 (2H, m), 2.78–2.71 (2H, m), 1.35–1.32 (3H, m).

MS (ESI) m/z: 553 (MH$^+$), 551 ([M–H]$^-$)

Example 244

2-{4-[6-CHLORO-2-ETHYL-5-(TRIFLUOROMETHYL)-1H-BENZIMIDAZOL-1-YL]PHENYL}ETHYL 2-PYRIDINYLSULFONYLCARBAMATE

The title compound was prepared according to the procedure described in step 2 of Example 243 from 2-pyridinesulfonamide (Naito, T.; et al., *Chem. Pharm. Bull.*, 1955, 3, 38) and 2-[4-(2-ethyl-5,7-dimethyl-3H-imidazo[4,5-b]pyridin-3-yl)phenyl]ethylcarbamate (step 1 of Example 243).

m.p.: 127.0–130.0° C.

$^1$H-NMR (CDCl$_3$) δ□8.76–8.73 (1H, m), 8.24–8.21 (2H, m), 8.16 (1H, s), 8.03–7.97 (1H, m), 7.62–7.56 (1H, m), 7.37 (2H, d, J=8.2 Hz), 7.23 (2H, d, J=8.2 Hz), 7.17 (1H, s), 4.37 (2H, t, J=6.8 Hz), 3.01 (2H, t, J=6.8 Hz), 2.77 (2H, q, J=7.6 Hz), 1.35 (3H, t, J=7.6 Hz).

MS (ESI) m/z: 553 (MH$^+$), 551 ([M–H]$^-$).

Example 245

2-{4-[6-CHLORO-2-ETHYL-5-(TRIFLUOROMETHYL)-1H-BENZIMIDAZOL-1-YL]PHENYL}ETHYL 4-PYRIDINYLSULFONYLCARBAMATE

The title compound was prepared according to the procedure described in step 2 of Example 243 from 4-pyridinesulfonamide (Comrie, A. M.; et al., *J. Chem. Soc.*, 1958, 3514) and 2-[4-(2-ethyl-5,7-dimethyl-3H-imidazo[4,5-b]pyridin-3-yl)phenyl]ethylcarbamate (step 1 of Example 243).

$^1$H-NMR (CDCl$_3$) δ□8.82 (2H, d, J=5.2 Hz), 8.10 (1H, s), 7.87 (2H, d, J=4.9 Hz), 7.44 (2H, d, J=7.9 Hz), 7.27 (2H, d, J=7.9 Hz), 7.20 (1H, s), 4.34 (2H, t, J=7.3 Hz), 3.04 (2H, t, J=7.3 Hz), 2.78 (2H, q, J=7.6 Hz), 1.36 (3H, t, J=7.6 Hz).

MS (ESI) m/z: 553 (MH$^+$), 551 ([M–H]$^-$).

Example 246

2-[4-(5-ACETYL-2-ETHYL-1H-BENZIMIDAZOL-1-YL) PHENYL]-1-METHYL ETHYL (4-METHYLPHENYL) SULFONYLCARBAMATE

Step 1. 1-(4-{[4-(2-hydroxypropyl)phenyl]amino}-3-nitrophenyl)ethanone

The title compound was prepared according to the procedure described in step 1 of Example 162 from 1-(4-chloro-3-nitrophenyl)ethanone and 1-(4-aminophenyl)-2-propanol (step 1 of Example 6).

$^1$H-NMR (CDCl$_3$) δ: 9.85 (1H, br.s), 8.83–8.82 (1H, m), 7.99–7.95 (1H, m), 7.33 (2H, d, J=8.4 Hz), 7.24 (2H, d, J=8.4 Hz), 7.18 (1H, d, J=9.0 Hz), 4.13–4.04 (1H, m), 2.87–2.72 (2H, m), 2.58 (3H, s), 1.29 (3H, d, J=6.2 Hz).

Step 2. 1-(3-amino-4-{[4-(2-hydroxypropyl)phenyl] amino}phenyl)ethanone

The title compound was prepared according to the procedure described in step 4 of Example 1 from 1-(4-{[4-(2-hydroxypropyl)phenyl]amino}-3-nitrophenyl)ethanone (step 1).

MS (EI) m/z: 284 (M$^+$).

Step 3. 2-[4-(5-acetyl-2-ethyl-1H-benzimidazol-1-yl) phenyl]-1-methylethyl propanoate The title compound was prepared according to the procedure described in step 5 of Example 1 from 1-(3-amino-4-{[4-(2-hydroxypropyl)phenyl]amino}phenyl)ethanone (step 2).

$^1$H-NMR (CDCl$_3$) δ: 8.41–8.40 (1H, m), 8.83–8.82 (1H, m), 7.92–7.89 (1H, m), 7.43 (2H, d, J=8.4 Hz), 7.29 (2H, d, J=8.4 Hz), 7.12–7.09 (1H, m), 5.25–5.18 (1H, m), 3.07–2.88 (2H, m), 2.80 (2H, q, J=7.3 Hz), 2.68 (3H, s), 2.34–2.26 (2H, m), 1.37 (3H, q, J=7.5 Hz), 1.32 (3H, d, J=6.2 Hz), 1.10 (3H, t, J=7.5 Hz).

Step 4. 1-{2-ethyl-1-[4-(2-hydroxypropyl)phenyl]-1H-benzimidazol-5-yl}ethanone

The title compound was prepared according to the procedure described in step 6 of Example 1 from 2-[4-(5-acetyl-2-ethyl-1H-benzimidazol-1-yl)phenyl]-1-methylethyl propanoate (step 3).

$^1$H-NMR (CDCl$_3$) δ: 8.39 (1H, s), 7.89–7.86 (1H, m), 7.47 (2H, d, J=8.3 Hz), 7.29 (2H, d, J=8.3 Hz), 7.13–7.10 (1H, m), 4.23–4.13 (1H, m), 2.94–2.86 (2H, m), 2.80 (2H, q, J=7.5 Hz), 2.66 (3H, s), 1.39–1.33 (6H, m).

Step 5. 2-[4-(5-acetyl-2-ethyl-1H-benzimidazol-1-yl) phenyl]-1-methylethyl (4-methylphenyl)sulfonylcarbamate The title compound was prepared according to the procedure described in Example 3 from 1-{2-ethyl-1-[4-(2-hydroxypropyl)phenyl]-1H-benzimidazol-5-yl}ethanone (step 4).

$^1$H-NMR (CDCl$_3$) δ: 8.40 (1H, d, J=1.1 Hz), 7.91–7.86 (3H, m), 7.32–7.24 (4H, m), 7.17 (2H, d, J=7.9 Hz), 7.07 (1H, d, J=8.4 Hz), 5.09–5.03 (1H, m), 2.99–2.75 (2H, m), 2.77 (2H, q, J=7.5 Hz), 2.67 (3H, s), 2.37 (3H, s), 1.33 (3H, t, J=7.5 Hz), 1.21 (3H, d, J=6.1 Hz).

MS (ESI) m/z: 520 (MH$^+$), 518 ([M–H]$^-$).

Example 247

2-{4-[6-CHLORO-2-ETHYL-5-(TRIFLUOROMETHYL)-1H-BENZIMIDAZOL-1-YL]PHENYL}-1-METHYLETHYL(4-METHYLPHENYL) SULFONYLCARBAMATE

Step 1. 1-(4-{[5-chloro-2-nitro-4-(trifluoromethyl)phenyl] amino}phenyl)-2-propanol The title compound was prepared according to the procedure described in step 1 of Example 162 from 2,4-dichloro-5-nitrobenzotrifluoride and 1-(4-aminophenyl)-2-propanol (step 1 of Example 6).

$^1$H-NMR (CDCl$_3$) δ: 9.69 (1H, br.s), 8.58 (1H, s), 7.36 (2H, d, J=8.4 Hz), 7.24 (2H, d, J=8.4 Hz), 7.20 (1H, s), 4.13–4.06 (1H, m), 2.88–2.73 (2H, m), 1.48 (1H, d, J=4.2 Hz), 1.30 (3H, d, J=6.2 Hz).

Step 2. 1-(4-{[2-amino-5-chloro-4-(trifluoromethyl)phenyl]amino}phenyl)-2-propanol The title compound was prepared according to the procedure described in step 2 of Example 28 from 1-(4-{[5-chloro-2-nitro-4-(trifluoromethyl)phenyl]amino}phenyl)-2-propanol (step 1).

$^1$H-NMR (CDCl$_3$) δ: 7.17 (1H, s), 7.15 (2H, d, J=8.4 Hz), 7.06 (1H, s), 6.90 (2H, d, J=8.4 Hz), 4.05–3.98 (1H, m), 2.79–2.61 (2H, m), 1.26 (3H, d, J=6.3 Hz).

Step 3. 2-{4-]6-chloro-2-ethyl-5-(trifluoromethyl)-1H-benzimidazol-1-yl]phenyl}-1-methylethyl propanoate The title compound was prepared according to the procedure described in step 5 of Example 1 from 1-(4-{[2-amino-5-chloro-4-(trifluoromethyl)phenyl]amino}phenyl)-2-propanol (step 2).

MS (EI) m/z: 438 (M$^+$).

Step 4. 1-{4-[6-chloro-2-ethyl-5-(trifluoromethyl)-1H-benzimidazol-1-yl]phenyl}-2-propanol The title compound was prepared according to the procedure described in step 6 of Example 1 from 2-{4-[6-chloro-2-ethyl-5-(trifluoromethyl)-1H-benzimidazol-1-yl]phenyl}-1-methylethyl propanoate (step 3).

$^1$H-NMR (CDCl$_3$) δ: 8.12 (1H, s), 7.47 (2H, d, J=8.4 Hz), 7.28 (2H, d, J=8.4 Hz), 7.21 (1H, s), 4.20–4.10 (1H, m), 2.95–2.83 (2H, m), 2.79 (2H, q, J=7.5 Hz), 1.56 (1H, d, J=4.2 Hz), 1.36 (3H, t, J=7.5 Hz), 1.34 (3H, d, J=6.2 Hz).

Step 5. 2-{4-[6-chloro-2-ethyl-5-(trifluoromethyl)-1H-benzimidazol-1-yl]phenyl}-1methylethyl(4-methylphenyl)sulfonylcarbamate The title compound was prepared according to the procedure described in Example 3 from 1-{4-[6-chloro-2-ethyl-5-(trifluoromethyl)-1H-benzimidazol-1-yl]phenyl}-2-propanol (step 4).

$^1$H-NMR (CDCl$_3$) δ: 8.09 (1H, s), 7.87 (2H, d, J=8.4 Hz), 7.41 (2H, d, J=8.4 Hz), 7.31 (2H, d, J=8.4 Hz), 7.24 (2H, d, J=8.4 Hz), 7.21 (1H, s), 5.06–5.00 (1H, m), 3.04–2.74 (4H, m), 2.40 (3H, s), 1.36 (3H, t, J=7.5 Hz), 1.23 (3H, d, J=6.2 Hz).

MS (ESI) m/z: 580 (MH$^+$), 578 ([M–H]$^-$).

Example 248

(1S)-2-[4-(5-ACETYL-2-ETHYL-1H-BENZIMIDAZOL-1-YL)PHENYL]-1-METHYLETHYL (4-METHYLPHENYL)SULFONYLCARBAMATE

Step 1. (2S)-1-(4-nitrophenyl)-2-propanol and (1R)-1-methyl-2-(4-nitrophenyl)ethyl propanoate To a mixture of 1-(4-nitrophenyl)-2-propanol (Schadt, F. L. et al., *J. Am. Chem. Soc.*, 1978, 100, 228., 2.5 g, 13.8 mmol) and propanoic anhydride (1.8 g, 13.8 mmol) in benzene (34 ml) was added Lipase PS/Celite (0.5 g, Bianichi, D. et al. *J. Org. Chem.* 1988, 53, 5531). The resulting mixture was stirred at room temperature for 72 h. The reaction mixture was filtered through a pad of Celite. The filtrate was washed with saturated aqueous sodium hydrogencarbonate and brine. The organic layer was dried (MgSO4), and concentrated. Purification by flash column chromatography eluting with hexane/diethyl ether (4:1 to 1:1) afforded 1.91 g (58%) of (1R)-1-methyl-2-(4-nitrophenyl)ethyl propanoate as a slight yellow oil and 1.14 g (46%) of (2S)-1-(4-nitrophenyl)-2-propanol as a colorless solid (93% e.e.). Recrystallization of 1.14 g of (2S)-1-(4-nitrophenyl)-2-propanol from hexane/diethyl ether afforded 617 mg of a colorless needle (99% e.e.). (1R)-1-methyl-2-(4-nitrophenyl)ethyl propanoate $^1$H-NMR (CDCl$_3$) δ: 8.16 (2H, d, J=8.8 Hz), 7.37 (2H, d, J=8.8 Hz), 5.22–5.11 (1H, m), 3.04–2.87 (2H, m), 2.30–2.19 (2H, m), 1.26 (3H, d, J=6.1 Hz), 1.07 (3H, t, J=7.5 Hz).

(2S)-1-(4-nitrophenyl)-2-propanol $^1$H-NMR (CDCl$_3$) δ: 8.18 (2H, d, J=8.8 Hz), 7.39 (2H, d, J=8.8 Hz), 4.14–4.04 (1H, m), 2.92–2.79 (2H, m), 1.49 (1H, d, J=4.0 Hz), 1.28 (3H, d, J=6.1 Hz).

□□□$^{23}_D$+31.0° (c 1.00, diethyl ether)

Step 2. (2S)-1-(4-aminophenyl)-2-propanol

The title compound was prepared according to the procedure described in step 4 of Example 1 from (2S)-1-(4-nitrophenyl)-2-propanol (step 1).

$^1$H-NMR (CDCl$_3$) δ: 7.00 (2H, d, J=8.4 Hz), 6.65 (2H, d, J=8.4 Hz), 3.99–3.89 (1H, m), 3.60 (2H, br.s) 2.73–2.52 (2H, m), 1.22 (3H, d, J=6.2 Hz).

Step 3. 1-[4-({4-[(2S)-2-hydroxypropyl]phenyl}amino)-3-nitrophenyl]ethanone

The title compound was prepared according to the procedure described in step 1 of Example 162 from 1-(4-chloro-3-nitrophenyl)ethanone and (2S)-1-(4-aminophenyl)-2-propanol (step 2).

$^1$H-NMR (CDCl$_3$) δ: 9.85 (1H, br.s), 8.83–8.82 (1H, m), 7.99–7.95 (1H, m), 7.33 (2H, d, J=8.4 Hz), 7.24 (2H, d, J=8.4 Hz), 7.18 (1H, d, J=9.0 Hz), 4.13–4.04 (1H, m), 2.87–2.72 (2H, m), 2.58 (3H, s), 1.29 (3H, d, J=6.2 Hz).

Step 4. 1-[3-amino-4-({4-[(2S)-2-hydroxypropyl]phenyl}amino)phenyl]ethanone

The title compound was prepared according to the procedure described in step 4 of Example 1 from 1-[4-({4-[(2S)-2-hydroxypropyl]phenyl}amino)-3-nitrophenyl]ethanone (step 3).

MS (EI) m/z: 284 (M$^+$).

Step 5. (1S)-2-[4-(5-acetyl-2-ethyl-1H-benzimidazol-1-yl)phenyl]-1-methylethyl propanate The title compound was prepared according to the procedure described in step 5 of Example 1 from 1-[3-amino-4-({4-[(2S)-2-hydroxypropyl]phenyl}amino)phenyl]ethanone (step 4).

$^1$H-NMR (CDCl$_3$) δ: 8.41–8.40 (1H, m), 8.83–8.82 (1H, m), 7.92–7.89 (1H, m), 7.43 (2H, d, J=8.4 Hz), 7.29 (2H, d, J=8.4 Hz), 7.12–7.09 (1H, m), 5.25–5.18 (1H, m), 3.07–2.88 (2H, m), 2.80 (2H, q, J=7.3 Hz), 2.68 (3H, s), 2.34–2.26 (2H, m), 1.37 (3H, q, J=7.5 Hz), 1.32 (3H, d, J=6.2 Hz), 1.10 (3H, t, J=7.5 Hz).

Step 6. 1-(2-ethyl-1-{4-[(2S)-2-hydroxypropyl]phenyl}-1H-benzimidazol-5-yl)ethanone The title compound was prepared according to the procedure described in step 6 of Example 1 from (1S)-2-[4-(5-acetyl-2-ethyl-1H-benzimidazol-1-yl)phenyl]-1-methylethyl propanoate (step 5).

$^1$H-NMR (CDCl$_3$) δ: 8.39 (1H, d, J=1.1 Hz), 7.87 (1H, dd, J=8.6, 1.1 Hz), 7.48 (2H, d, J=8.4 Hz), 7.30 (2H, d, J=8.4 Hz), 7.12 (1H, d, J=8.6 Hz), 4.22–4.12 (1H, m), 2.94–2.89 (2H, m), 2.80 (2H, q, J=7.5 Hz), 2.69 (3H, s), 2.42 (1H, br.s), 1.37 (3H, t, J=7.5 Hz), 1.33 (3H, d, J=6.2 Hz).

Step 7. (1S)-2-[4-(5-acetyl-2-ethyl-1H-benzimidazol-1-yl)phenyl]-1-methylethyl (4-methylphenyl)sulfonylcarbamate The title compound was prepared according to the procedure described in Example 3 from 1-(2-ethyl-1-{4-[(2S)-2-hydroxypropyl]phenyl}-1H-benzimidazol-5-yl)ethanone (step 6).

$^1$H-NMR (CDCl$_3$) δ: 8.40 (1H, d, J=1.1 Hz), 7.91–7.86 (3H, m), 7.32–7.24 (4H, m), 7.17 (2H, d, J=7.9 Hz), 7.07 (1H, d, J=8.4 Hz), 5.09–5.03 (1H, m), 2.99–2.75 (2H, m), 2.77 (2H, q, J=7.5 Hz), 2.67 (3H, s), 2.37 (3H, s), 1.33 (3H, t, J=7.5 Hz), 1.21 (3H, d, J=6.1 Hz).

MS (ESI) m/z: 520 (MH$^+$), 518 ([M–H]$^-$).

□□□$^{24}_D$–3.09° (c 0.120, methanol)

Example 249

(1R)-2-[4-(5-ACETYL-2-ETHYL-1H-BENZIMIDAZOL-1-YL)PHENYL]-1-METHYLETHYL (4-METHYLPHENYL)SULFONYLCARBAMATE

Step 1. (2R)-1-(4-nitrophenyl)-2-pronpanol

To a solution of (1R)-1-methyl-2-(4-nitrophenyl)ethyl propanoate (step 1 of Example 248, 1.91 g, 8.05 mmol) in ethanol (20 ml) was added 2N aqueous NaOH (5 ml) at room temperature. The resulting mixture was stirred at room temperature for 2 h. The reaction mixture was poured into water, extracted with diethyl ether (2×50 ml). The organic layer was washed with brine, dried (MgSO4), and concentrated. Purification by flash column chromatography eluting with hexane/diethyl ether (1:1) afforded 1.16 g (80%) of title compound as a colorless solid (79% e.e.). Recrystallization from hexane/diethyl ether afforded 717 mg of a colorless needle (99% e.e.).

$^1$H-NMR (CDCl$_3$) δ: 8.18 (2H, d, J=8.8 Hz), 7.39 (2H, d, J=8.8 Hz), 4.14–4.04 (1H, m), 2.92–2.79 (2H, m), 1.49 (1H, d, J=4.0 Hz), 1.28 (3H, d, J=6.1 Hz).

□□□$^{23}_D$−32.6° (c 1.00, diethyl ether).

Step 2. (2R)-1-(4-aminophenyl)-2-propanol

The title compound was prepared according to the procedure described in step 4 of Example 1 from (2R)-1-(4-nitrophenyl)-2-propanol (step 1).

$^1$H-NMR (CDCl$_3$) δ: 7.00 (2H, d, J=8.4 Hz), 6.65 (2H, d, J=8.4 Hz), 3.99–3.89 (1H, m), 3.60 (2H, br.s) 2.73–2.52 (2H, m), 1.22 (3H, d, J=6.2 Hz).

Step 3. 1-[4-({4-[(2R)-2-hydroxypropyl]phenyl}amino)-3-nitrophenyl]ethanone

The title compound was prepared according to the procedure described in step 1 of Example 162 from 1-(4-chloro-3-nitrophenyl)ethanone and (2R)-1-(4-aminophenyl)-2-propanol (step 2).

$^1$H-NMR (CDCl$_3$) δ: 9.85 (1H, br.s), 8.83–8.82 (1H, m), 7.99–7.95 (1H, m), 7.33 (2H, d, J=8.4 Hz), 7.24 (2H, d, J=8.4 Hz), 7.18 (1H, d, J=9.0 Hz), 4.13–4.04 (1H, m), 2.87–2.72 (2H, m), 2.58 (3H, s), 1.29 (3H, d, J=6.2 Hz).

Step 4. 1-[3-amino-4-({4-[(2R)-2-hydroxypropyl]phenyl}amino)phenyl]ethanone

The title compound was prepared according to the procedure described in step 4 of Example 1 from 1-[4-({4-[(2R)-2-hydroxypropyl]phenyl}amino)-3-nitrophenyl]ethanone (step 3).

MS (EI) m/z: 284 (M$^+$).

Step 5. (1R)-2-[4-(5-acetyl-2-ethyl-1H-benzimidazol-1-yl)phenyl]-1-methylethyl propanate The title compound was prepared according to the procedure described in step 5 of Example 1 from 1-[3-amino-4-({4-[(2R)-2-hydroxypropyl]phenyl}amino)phenyl]ethanone (step 4).

$^1$H-NMR (CDCl$_3$) δ: 8.41–8.40 (1H, m), 8.83–8.82 (1H, m), 7.92–7.89 (1H, m), 7.43 (2H, d, J=8.4 Hz), 7.29 (2H, d, J=8.4 Hz), 7.12–7.09 (1H, m), 5.25–5.18 (1H, m), 3.07–2.88 (2H, m), 2.80 (2H, q, J=7.3 Hz), 2.68 (3H, s), 2.34–2.26 (2H, m), 1.37 (3H, q, J=7.5 Hz), 1.32 (3H, d, J=6.2 Hz), 1.10 (3H, t, J=7.5 Hz).

Step 6. 1-(2-ethyl-1-{4-[(2R)-2-hydroxypropyl]phenyl}-1H-benzimidazol-5-yl)ethanone The title compound was prepared according to the procedure described in step 6 of Example 1 from (1R)-2-[4-(5-acetyl-2-ethyl-1H-benzimidazol-1-yl)phenyl]-1-methylethyl propanoate (step 5).

$^1$H-NMR (CDCl$_3$) δ: 8.39 (1H, d, J=1.1 Hz), 7.87 (1H, dd, J=8.6, 1.1 Hz), 7.48 (2H, d, J=8.4 Hz), 7.30 (2H, d, J=8.4 Hz), 7.12 (1H, d, J=8.6 Hz), 4.22–4.12 (1H, m), 2.94–2.89 (2H, m), 2.80 (2H, q, J=7.5 Hz), 2.69 (3H, s), 2.42 (1H, br.s), 1.37 (3H, t, J=7.5 Hz), 1.33 (3H, d, J=6.2 Hz).

Step 7. (1R)-2-[4-(5-acetyl-2-ethyl-1H-benzimidazol-1-yl)phenyl]-1-methylethyl (4-methylphenyl)sulfonylcarbamate The title compound was prepared according to the procedure described in Example 3 from 1-(2-ethyl-1-{4-[(2R)-2-hydroxypropyl]phenyl}-1H-benzimidazol-5-yl)ethanone (step 6).

$^1$H-NMR (CDCl$_3$) δ: 8.40 (1H, d, J=1.1 Hz), 7.91–7.86 (3H, m), 7.32–7.24 (4H, m), 7.17 (2H, d, J=7.9 Hz), 7.07 (1H, d, J=8.4 Hz), 5.09–5.03 (1H, m), 2.99–2.75 (2H, m), 2.77 (2H, q, J=7.5 Hz), 2.67 (3H, s), 2.37 (3H, s), 1.33 (3H, t, J=7.5 Hz), 1.21 (3H, d, J=6.1 Hz).

MS (ESI) m/z: 520 (MH$^+$), 518 ([M−H]$^−$).

[α]$^{24}_D$+6.05° (c 0.118, methanol).

Example 250

(1S)-2-{4-[6-CHLORO-2-ETHYL-5-(TRIFLUOROMETHYL)-1H-BENZIMIDAZOL-1-YL]PHENYL}-1-METHYLETHYL (4-METHYLPHENYL)SULFONYLCARBAMATE

Step 1. (2S)-1-(4-{[5-chloro-2-nitro-4-(trifluoromethyl)phenyl]amino}phenyl)-2-propanol The title compound was prepared according to the procedure described in step 1 of Example 162 from 2,4-dichloro-5-nitrobenzotrifluoride and (2S)-1-(4-aminophenyl)-2-propanol (step 2 of Example 248).

$^1$H-NMR (CDCl$_3$) δ: 9.69 (1H, br.s), 8.58 (1H, s), 7.36 (2H, d, J=8.4 Hz), 7.24 (2H, d, J=8.4 Hz), 7.20 (1H, s), 4.13–4.06 (1H, m), 2.88–2.73 (2H, m), 1.48 (1H, d, J=4.2 Hz), 1.30 (3H, d, J=6.2 Hz).

Step 2. (2S)-1-(4-{[2-amino-5-chloro-4-(trifluoromethyl)phenyl]amino}phenyl)-2-propanol The title compound was prepared according to the procedure described in step 2 of Example 28 from (2S)-1-(4-{[5-chloro-2-nitro-4-(trifluoromethyl)phenyl]amino}phenyl)-2-propanol (step 1).

$^1$H-NMR (CDCl$_3$) δ: 7.17 (1H, s), 7.15 (2H, d, J=8.4 Hz), 7.06 (1H, s), 6.90 (2H, d, J=8.4 Hz), 4.05–3.98 (1H, m), 2.79–2.61 (2H, m), 1.26 (3H, d, J=6.3 Hz).

Step 3. (1S)-2-{4-[6-chloro-2-ethyl-5-(trifluoromethyl)-1H-benzimidazol-1-yl]phenyl}-2-methylethyl propanoate The title compound was prepared according to the procedure described in step 5 of Example 1 from (2S)-1-(4-{[2-amino-5-chloro-4-(trifluoromethyl)phenyl]amino}phenyl)-2-propanol (step 2).

MS (EI) m/z: 438 (M$^+$).

Step 4. (2S)-1-{4-[6-chloro-2-ethyl-5-(trifluoromethyl)-1H-benzimidazol-1-yl]phenyl}-2-propanol The title compound was prepared according to the procedure described in step 6 of Example 1 from (1S)-2-{4-[6-chloro-2-ethyl-5-(trifluoromethyl)-1H-benzimidazol-1-yl]phenyl}-1-methylethyl propanoate (step 3).

$^1$H-NMR (CDCl$_3$) δ: 8.12 (1H, s), 7.47 (2H, d, J=8.4 Hz), 7.28 (2H, d, J=8.4 Hz), 7.21 (1H, s), 4.20–4.10 (1H, m), 2.95–2.83 (2H, m), 2.79 (2H, q, J=7.5 Hz), 1.56 (1H, d, J=4.2 Hz), 1.36 (3H, t, J=7.5 Hz), 1.34 (3H, d, J=6.2 Hz).

Step 5. (1S)-2-{4-[6-chloro-2-ethyl-5-(trifluoromethyl)-1H-benzimidazol-1-yl]phenyl}-1-methylethyl (4-methylphenyl)sulfonylcarbamate The title compound was prepared according to the procedure described in Example 3 from (2S)-1-{4-[6-chloro-2-ethyl-5-(trifluoromethyl)-1H-benzimidazol-1-yl]phenyl}-2-propanol (step 4).

m.p.: 200.3° C.

$^1$H-NMR (CDCl$_3$) δ: 8.09 (1H, s), 7.87 (2H, d, J=8.4 Hz), 7.41 (2H, d, J=8.4 Hz), 7.31 (2H, d, J=8.4 Hz), 7.24 (2H, d, J=8.4 Hz), 7.21 (1H, s), 5.06–5.00 (1H, m), 3.04–2.74 (4H, m), 2.40 (3H, s), 1.36 (3H, t, J=7.5 Hz), 1.23 (3H, d, J=6.2 Hz).

MS (ESI) m/z: 580 (MH$^+$), 578 ([M−H]$^−$).

[α]$^{24}_D$+1.31° (c 0.398, methanol) ee: 98%.

Example 251

(1S)-2-{4-[6-CHLORO-2-ETHYL-5-(TRIFLUOROMETHYL)-1H-BENZIMIDAZOL-1-YL]PHENYL}-1-METHYLETHYL (4-METHYLPHENYL)SULFONYLCARBAMATE MONO-P-TOLUENESULFONATE

The title compound was prepared according to the procedure described in Example 231 from (1S)-2-{4-[6-chloro-2-ethyl-5-(trifluoromethyl)-1H-benzimidazol-1-yl]phenyl}-1-methylethyl (4-methylphenyl)sulfonylcarbamate (step 5 of Example 250).

¹H-NMR (DMSO-d6) δ: 11.91 (1H, br.s), 8.23 (1H, s), 7.75 (2H, d, J=8.3 Hz), 7.50–7.37 (9H, m), 7.11 (2H, d, J=8.1 Hz), 4.97–4.91 (1H, m), 2.92–2.76 (4H, m), 2.30 (3H, s), 2.27 (3H, s), 1.24 (3H, t, J=7.3 Hz), 1.14 (3H, d, J=6.2 Hz).

MS (ESI) m/z: 580 (MH⁺), 578 ([M−H]⁻).

Example 252

(1R)-2-{4-[6-CHLORO-2-ETHYL-5-(TRIFLUOROMETHYL)-1H-BENZIMIDAZOL-1-YL]PHENYL}-1-METHYLETHYL (4-METHYLPHENYL)SULFONYLCARBAMATE

Step 1. (2R)-1-(4-{[5-chloro-2-nitro-4-(trifluoromethyl)phenyl]amino}phenyl)-2-propanol The title compound was prepared according to the procedure described in step 1 of Example 162 from 2,4-dichloro-5-nitrobenzotrifluoride and (2R)-1-(4-aminophenyl)-2-propanol (step 2 of Example 249).

¹H-NMR (CDCl₃) δ: 9.69 (1H, br.s), 8.58 (1H, s), 7.36 (2H, d, J=8.4 Hz), 7.24 (2H, d, J=8.4 Hz), 7.20 (1H, s), 4.13–4.06 (1H, m), 2.88–2.73 (2H, m), 1.48 (1H, d, J=4.2 Hz), 1.30 (3H, d, J=6.2 Hz).

Step 2. (2R)-1-(4-{[2-amino-5-chloro-4-(trifluoromethyl)phenyl]amino}phenyl)-2-propanol The title compound was prepared according to the procedure described in step 2 of Example 28 from (2R)-1-(4-{[5-chloro-2-nitro-4-(trifluoromethyl)phenyl]amino}phenyl)-2-propanol (step 1).

¹H-NMR (CDCl₃) δ: 7.17 (1H, s), 7.15 (2H, d, J=8.4 Hz), 7.06 (1H, s), 6.90 (2H, d, J=8.4 Hz), 4.05–3.98 (1H, m), 2.79–2.61 (2H, m), 1.26 (3H, d, J=6.3 Hz).

Step 3. (1R)-2-{4-[6-chloro-2-ethyl-5-(trifluoromethyl)-1H-benzimidazol-1-yl]phenyl}1-methylethyl propanoate The title compound was prepared according to the procedure described in step 5 of Example 1 from (2R)-1-(4-{[2-amino-5-chloro-4-(trifluoromethyl)phenyl]amino}phenyl)-2-propanol (step 2).

MS (EI) m/z: 438 (M⁺).

Step 4. (2R)-1-{4-[6-chloro-2-ethyl-5-(trifluoromethyl)-1H-benzimidazol-1-yl]phenyl}-2-propanol The title compound was prepared according to the procedure described in step 6 of Example 1 from (1R)-2-{4-[6-chloro-2-ethyl-5-(trifluoromethyl)-1H-benzimidazol-1-yl]phenyl}-1-methylethyl propanoate (step 3).

¹H-NMR (CDCl₃) δ: 8.12 (1H, s), 7.47 (2H, d, J=8.4 Hz), 7.28 (2H, d, J=8.4 Hz), 7.21 (1H, s), 4.20–4.10 (1H, m), 2.95–2.83 (2H, m), 2.79 (2H, q, J=7.5 Hz), 1.56 (1H, d, J=4.2 Hz), 1.36 (3H, t, J=7.5 Hz), 1.34 (3H, d, J=6.2 Hz).

Step 5. (1R)-2-{4-[6-chloro-2-ethyl-5-(trifluoromethyl)-1H-benzimidazol-1-yl]phenyl}-1-methylethyl (4-methylphenyl)sulfonylcarbamate The title compound was prepared according to the procedure described in Example 3 from (2R)-1-{4-[6-chloro-2-ethyl-5-(trifluoromethyl)-1H-benzimidazol-1-yl]phenyl}-2-propanol (step 4).

m.p.: 199.9° C.

¹H-NMR (CDCl₃) δ: 10.70 (1H, br.s), 8.10 (1H, s), 7.89 (2H, d, J=8.3 Hz), 7.40 (2H, d, J=8.3 Hz), 7.30 (2H, d, J=8.3 Hz), 7.22 (2H, d, J=8.3 Hz), 7.20 (1H, s), 5.32–5.00 (1H, m), 3.04–2.82 (2H, m), 2.78 (2H, q, J=7.5 Hz), 2.40 (3H, s), 1.36 (3H, t, J=7.5 Hz), 1.23 (3H, d, J=6.2 Hz).

MS (ESI) m/z: 580 (MH⁺), 578 ([M−H]⁻).

$[\alpha]^{24}_D$ −2.19° (c 0.402, methanol) ee: 97%.

Example 253

N-{[(2-{4-[6-CHLORO-2-ETHYL-5-(TRIFLUOROMETHYL)-1H-BENZIMIDAZOL-1-YL]PHENYL}-1-METHYLETHYL)AMINO]CARBONYL}-4-METHYLBENZENESULFONAMIDE

Step 1. 1-[4-(2-azidopropyl)phenyl]-6-chloro-2-ethyl-5-(trifluoromethyl)-1H-benzimidazole To a stirred solution of 1-{4-[6-chloro-2-ethyl-5-(trifluoromethyl)-1H-benzimidazol-1-yl]phenyl}-2-propanol (step 8 of Example 247, 1.96 g, 5.12 mmol), triphenylphosphine (1.75 g, 6.66 mmol) and diphenylphosphoryl azide (1.83 mg, 6.66 mmol) in tetrahydrofuran (15 ml) was added diethyl azodicarboxylate (1.16 mg, 6.66 mmol) at room temperature. The resulting mixture was stirred at temperature for 3 h, then under reflux temperature. The mixture was diluted with ethyl acetate and washed with water and brine. The organic layer was dried (Na2SO4), and concentrated. Purification by flash column chromatography eluting with hexane/ethyl acetate (2:1) and TLC developing with hexane/ethyl acetate (1:1) afforded 769 mg (37%) of the title compound as a slight yellow syrup.

¹H-NMR (CDCl₃) δ: 8.12 (1H, s), 7.47 (2H, d, J=8.3 Hz), 7.30 (2H, d, J=8.3 Hz), 7.21 (1H, s), 3.85–3.77 (1H, m), 2.92–2.89 (2H, m), 2.80 (2H, q, J=7.5 Hz), 1.37 (3H, d, J=6.6Hz), 1.36 (3H, t, J=7.5 Hz).

MS (ESI) m/z: 408 (MH⁺).

Step 2. 2-{4-[6-chloro-2-ethyl-5-(trifluoromethyl)-1H-benzimidazol-1-yl]phenyl}-1-methylethylamine The title compound was prepared according to the procedure described in step 7 of Example 37 from 1-[4-(2-azidopropyl)phenyl]-6-chloro-2-ethyl-5-(trifluoromethyl)-1H-benzimidazole (step 1).

¹H-NMR (CDCl₃) δ: 8.12 (1H, s), 7.44 (2H, d, J=8.3 Hz), 7.28 (2H, d, J=8.3 Hz), 7.21 (1H, s), 3.49–3.26 (1H, m), 2.86–2.95 (2H, m), 2.79 (2H, q, J=7.5 Hz), 1.36 (3H, t, J=7.5 Hz), 120 (3H, d, J=6.2 Hz).

Step 3. N-{[(2-{4-[6-chloro-2-ethyl-5-(trifluoromethyl)-1H-benzimidazol-1-yl]phenyl}-1-methylethyl)amino]carbonyl}-4-methylbenzenesulfonamide The title compound was prepared according to the procedure described in step 10 of Example 1 from 2-{4-[6-chloro-2-ethyl-5-(trifluoromethyl)-1H-benzimidazol-1-yl]phenyl}-1-methylethylamine (step 2).

¹H-NMR (CDCl₃) δ: 8.12 (1H, s), 7.73 (2H, d, J=8.4 Hz), 7.41 (2H, d, J=8.3 Hz), 7.29–7.23 (4H, m), 7.17 (1H, s), 4.20–4.11 (1H, m), 2.99–2.82 (2H, m), 2.78 (2H, q, J=7.3 Hz), 2.38 (3H, s), 1.35 (3H, t, J=7.3 Hz), 1.24 (3H, d, J=6.6 Hz).

MS (ESI) m/z: 579 (MH⁺), 577 ([M−H]⁻).

Example 254

N-{[((1S)-2-{4-[6-CHLORO-2-ETHYL-5-(TRIFLUOROMETHYL)-1H-BENZIMIDAZOL-1-YL]PHENYL}-1-METHYLETHYL)AMINO]CARBONYL}-4-METHYLBENZENESULFONAMIDE

Step 1. 1-[4-[(2s)-2-azidopropyl)phenyl]-6-chloro-2-ethyl-5-(trifluoromethyl)-1H-benzimidazole The title compound was prepared according to the procedure described in step 1 of Example 253 from (2R)-1-{4-[6-chloro-2-ethyl-5-(trifluoromethyl)-1H-benzimidazol-1-yl]phenyl}-2-propanol (step 4 of Example 252).

¹H-NMR (CDCl₃) δ: 8.12 (1H, s), 7.46 (2H, d, J=7.9 Hz), 7.29 (2H, d, J=7.9 Hz), 7.21 (1H, s), 3.84–3.77 (1H, m), 2.92–2.89 (2H, m), 2.79 (2H, q, J=7.6 Hz), 1.39–1.33 (6H, m).

Step 2. (1S)-2-{4-[6-chloro-2-ethyl-5-(trifluoromethyl)-1H-benzimidazol-1-yl]phenyl}-1-methylethylamine The title compound was prepared according to the procedure described in step 7 of Example 37 from 1-[4-[(2s)-2-azidopropyl)phenyl]-6-chloro-2-ethyl-5-(trifluoromethyl)-1H-benzimidazole (step 1).

¹H-NMR (CDCl₃) δ: 8.12 (1H, s), 7.44 (2H, d, J=8.3 Hz), 7.28 (2H, d, J=8.3 Hz), 7.21 (1H, s), 3.49–3.26 (1H, m), 2.86–2.65 (2H, m), 2.79 (2H, q, J=7.5 Hz), 1.36 (3H, t, J=7.5 Hz), 1.20 (3H, d, J=6.2 Hz).

Step 3. N-{[((1S)-2-{4-[6-chloro-2-ethyl-5-(trifluoromethyl)-1H-benzimidazol-1-yl]phenyl}-1-methylethyl)amino]carbonyl}-4-methylbenzenesulfonamide The title compound was prepared according to the procedure described in step 10 of Example 1 from (1S)-2-{4-[6-chloro-2-ethyl-5-(trifluoromethyl)-1H-benzimidazol-1-yl]phenyl}-1-methylethylamine (step 2).

m.p.: 141.0–143.0° C.

¹H-NMR (CDCl₃) δ: 8.12 (1H, s), 7.73 (2H, d, J=8.3 Hz), 7.41 (2H, d, J=8.3 Hz), 7.30 (2H, d, J=8.3 Hz), 7.25 (2H, d, J=8.3 Hz), 7.17 (1H, s), 6.58 (1H, d, J=7.7 Hz), 4.22–4.14 (1H, m), 2.82–2.30 (2H, m), 2.78 (2H, q, J=7.6 Hz), 2.39 (3H, s), 1.35 (3H, t, J=7.5 Hz), 1.24 (3H, d, J=6.6 Hz).

MS (ESI) m/z: 579 (MH⁺), 691 ([M+CF₃COOH−H]⁻).

$[\alpha]^{24}{}_D$ −5.08° (c 0.394, methanol) ee: 99%.

Example 255

N-{[((1R)-2-{4-[6-CHLORO-2-ETHYL-5-(TRIFLUOROMETHYL)-1H-BENZIMIDAZOL-1-YL]PHENYL}-1-METHYLETHYL)AMINO]CARBONYL}-4-METHYLBENZENESULFONAMIDE

Step 1. 1-[4-[(2R)-2-azidopropyl)phenyl]-6-chloro-2-ethyl-5-(trifluoromethyl)-1H-benzimidazole The title compound was prepared according to the procedure described in step 1 of Example 253 from (2S)-1-{4-[6-chloro-2-ethyl-5-(trifluoromethyl)-1H-benzimidazol-1-yl]phenyl}-2-propanol (step 4 of Example 250).

¹H-NMR (CDCl₃) δ: 8.12 (1H, s), 7.46 (2H, d, J=7.9 Hz), 7.29 (2H, d, J=7.9 Hz), 7.21 (1H, s), 3.84–3.77 (1H, m), 2.92–2.89 (2H, m), 2.79 (2H, q, J=7.6 Hz), 1.39–1.33 (6H, m).

Step 2. (1R)-2-{4-[6-chloro-2-ethyl-5-(trifluoromethyl)-1H-benzimidazol-1-yl]phenyl}-1-methylethylamine The title compound was prepared according to the procedure described in step 7 of Example 37 from 1-[4-[(2R)-2-azidopropyl)phenyl]-6-chloro-2-ethyl-5-(trifluoromethyl)-1H-benzimidazole (step 1).

¹H-NMR (CDCl₃) δ: 8.12 (1H, s), 7.44 (2H, d, J=8.3 Hz), 7.28 (2H, d, J=8.3 Hz), 7.21 (1H, s), 3.49–3.26 (1H, m), 2.86–2.65 (2H, m), 2.79 (2H, q, J=7.5 Hz), 1.36 (3H, t, J=7.5 Hz), 1.20 (3H, d, J=6.2 Hz).

Step 3. N-{[((1R)-2-{4-[6-chloro-2-ethyl-5-(trifluoromethyl)-1H-benzimidazol-1-yl]phenyl}-1-methylethyl)amino]carbonyl}-4-methylbenzenesulfonamide The title compound was prepared according to the procedure described in step 10 of Example 1 from (1R)-2-{4-[6-chloro-2-ethyl-5-(trifluoromethyl)-1H-benzimidazol-1-yl]phenyl}-1-methylethylamine (step 2).

m.p.: 138.0–141.0° C.

¹H-NMR (CDCl₃) δ: 8.12 (1H, s), 7.73 (2H, d, J=8.3 Hz), 7.41 (2H, d, J=8.3 Hz), 7.30 (2H, d, J=8.3 Hz), 7.25 (2H, d, J=8.3 Hz), 7.17 (1H, s), 6.58 (1H, d, J=7.7 Hz), 4.22–4.14 (1H, m), 2.82–2.30 (2H, m), 2.78 (2H, q, J=7.6 Hz), 2.39 (3H, s), 1.35 (3H, t, J=7.5 Hz), 1.24 (3H, d, J=6.6 Hz).

MS (ESI) m/z: 579 (MH⁺), 691 ([M+CF₃COOH−H]⁻).

$[\alpha]^{24}{}_D$ +3.43° (c 0.408, methanol) ee: 99%.

Example 256

2-{4-[6-CHLORO-2-(1H-PYRAZOL-3-YL)-5-(TRIFLUOROMETHYL)-1H-BENZIMIDAZOL-1-YL]PHENYL}ETHYL(4-METHYLPHENYL)SULFONYLCARBAMATE

Step 1. 2-{4-[6-chloro-2-(1H-pyrazol-3-yl)-5-(trifluoromethyl)-1H-benzimidazol-1-yl]phenyl}ethanol A mixture of 2-(4-{[2-amino-5-chloro-4-(trifluoromethyl)phenyl]amino}phenyl) ethanol (step 2 of Example 104, 2.28 g, 5.85 mmol) and 1H-pyrazole-3-carbaldehyde (562 mg, 2.85 mmol) in ethanol (35 ml) was stirred under reflux temperature for 1 h. The mixture was concentrated and dissolved in benzene (40 ml). To this solution was added lead tetraacetate (2.85 g, 6.44 mmol) at rt. After stirring at room temperature for 18 h, to the mixture were added saturated aqueous sodium hydrogencarbonate (50 ml) and ethyl acetate. The organic layer was separated and washed with brine, dried (Na2SO4) and concentrated. Purification by flash column chromatography eluting with dichloromethane/methanol (20:1 to 10:1), then dichloromethane/2-propanol (5:1) afforded 979 mg (41%) of the title compound as a slight brown solid.

¹H-NMR (CDCl₃/CD3OD=4/1) δ: 8.12 (1H, br.s), 7.74 (1H, s), 7.59 (1H, br.s), 7.47 (2H, d, J=7.9 Hz), 7.34–7.30 (3H, m), 6.36 (1H, br.s), 3.87 (2H, br.t, J=6.8 Hz), 2.95 (2H, t, J=6.8 Hz).

MS (ESI) m/z: 407 (MH⁺), 405 ([M−H]⁻).

Step 2. 2-{4-[6-chloro-2-(1H-pyrazol-3-yl)-5-(trifluoromethyl)-1H-benzimidazol-1-yl]phenyl}ethyl (4-methylphenyl)sulfonylcarbamate The title compound was prepared according to the procedure described in Example 3 from 2-{4-[6-chloro-2-(1H-pyrazol-3-yl)-5-(trifluoromethyl)-1H-benzimidazol-1-yl]phenyl}ethanol (step 1).

¹H-NMR (CDCl₃) δ: 8.18 (1H, s), 7.91 (2H, d, J=8.3 Hz), 7.54–7.53 (1H, m), 7.34–7.23 (8H, m), 6.31 (1H, br.s), 4.40 (2H, t, J=6.4 Hz), 3.01 (2H, t, J=6.4 Hz), 2.42 (3H, s).

MS (ESI) m/z: 604 (MH⁺), 602 ([M−H]⁻).

Example 257

2-{4-[6-CHLORO-2-(1H-PYRAZOL-3-YL)-5-(TRIFLUOROMETHYL)-1H-BENZIMIDAZOL-1-YL]PHENYL}ETHYL(4-METHYLPHENYL)SULFONYLCARBAMATE MONO-P-TOLUENESULFONATE

The title compound was prepared according to the procedure described in Example 231 from 2-{4-[6-chloro-2-(1H-pyrazol-3-yl)-5-(trifluoromethyl)-1H-benzimidazol-1-yl]phenyl}ethyl (4-methylphenyl)sulfonylcarbamate (step 2 of Example 256).

¹H-NMR (DMSO-d6) δ: 8.24 (1H, s), 7.77–7.74 (2H, m), 7.48–7.38 (10H, m), 7.26 (1H, s), 7.11 (2H, d, J=7.9 Hz), 6.44 (1H, br.s), 4.30–4.20 (2H, m), 2.98–2.93 (2H, m), 2.33 (3H, s), 2.27 (3H, s).

MS (ESI) m/z: 604 (MH⁺), 602 ([M−H]⁻).

Example 258

(1S)-2-[4-(2-ETHYL-5,7-DIMETHYL-3H-IMIDAZO[4,5-B]PYRIDIN-3-YL)PHENYL]-1-METHYLETHYL(4-METHYLPHENYL)SULFONYLCARBAMATE MONO-HYDROCHLORIDE

Step 1. (2S)- -{4-[(4,6-dimethyl-3-nitro-2-pyridinyl)amino]phenyl}-2-propanol

The title compound was prepared according to the procedure described in step 1 of Example 162 from 2-chloro-4,6-dimethyl-3-nitropyridine (step 2 of Example 1) and (2S)-1-(4-aminophenyl)-2-propanol (step 2 of Example 248).

¹H-NMR (CDCl₃) δ: 9.58 (1H, br.s), 7.59 (2H, d, J=8.6 Hz), 7.19 (2H, d, J=8.6 Hz), 6.53 (1H, s), 4.05–3.98 (1H, m), 2.82–2.63 (2H, m), 2.55 (3H, s), 2.43 (3H, s), 1.26 (3H, d, J=6.3 Hz).

Step 2. (2S)-1-{4-[(3-amino-4,6-dimethyl-2-pyridinyl)amino]phenyl}-2-propanol

The title compound was prepared according to the procedure described in step 2 of Example 28 from (2S)-1-{4-[(4,6-dimethyl-3-nitro-2-pyridinyl)amino]phenyl}-2-propanol (step 1).

¹H-NMR (CDCl₃) δ: 7.13–7.07 (4H, m), 6.60 (1H, s), 6.21 (1H, br.s), 4.02–3.91 (1H, m), 3.26 (2H, br.s), 2.77–2.57 (2H, m), 2.37 (3H, s), 2.20 (3H, s), 1.24 (3H, d, J=6.1 Hz).

Step 3. (1S)-2-[4-(2-Ethyl-5,7-dimethyl-3H-imidazo[4,5-b]pyridin-3-yl)phenyl]1-methylethyl propanoate The title compound was prepared according to the procedure described in step 5 of Example 1 from (2S)-1-{4-[(3-amino-4,6-dimethyl-2-pyridinyl)amino]phenyl}-2-propanol (step 2).

MS (EI) m/z: 365 (M⁺).

Step 4. (2S)-1-[4-(2-Ethyl-5,7-dimethyl-3H-imidazo[4,5-b]pyridin-3-yl)phenyl]-2-propanol The title compound was prepared according to the procedure described in step 6 of Example 1 from (1S)-2-[4-(2-Ethyl-5,7-dimethyl-3H-imidazo[4,5-b]pyridin-3-yl)phenyl]-1-methylethyl propanoate (step 3).

¹H-NMR (CDCl₃) δ: 7.42 (2H, d, J=8.4 Hz), 7.35 (2H, d, J=8.4 Hz), 6.91 (1H, s), 4.18–4.05 (1H, m), 2.92–2.75 (4H, m), 2.66 (3H, s), 2.52 (3H, s), 1.34–1.25 (6H, m).

Step 5. (1S)-2-[4-(2-ethyl-5,7-dimethyl-3H-imidazo[4,5-b]pyridin-3-yl)phenyl]-1-methylethyl (4-methylphenyl)sulfonylcarbamate The title compound was prepared according to the procedure described in Example 3 from (2S)-1-[4-(2-Ethyl-5,7-dimethyl-3H-imidazo[4,5-b]pyridin-3-yl)phenyl]-2-propanol (step 4).

¹H-NMR (CDCl₃) δ: 7.92 (2H, d, J=8.2 Hz), 7.33 (2H, d, J=8.2 Hz), 7.30–7.26 (4H, m), 5.14–5.02 (1H, m), 2.99–2.77 (4H, m), 2.66 (3H, s), 2.51 (3H, s), 2.42 (3H, s), 1.29–1.23 (6H, m).

MS (ESI) m/z: 507 (MH⁺), 505 ([M−H]⁻).

Step 6. 2-[4-(2-ethyl-5,7-dimethyl-3H-imidazo[4,5-b]pyridin-3-yl)phenyl-[1-methylethyl (4-methylphenyl)sulfonylcarbamate mono-hydrochloride The title compound was prepared according to the procedure described in Example 240 from (1S)-2-[4-(2-ethyl-5,7-dimethyl-3H-imidazo[4,5-b]pyridin-3-yl)phenyl]-1-methylethyl (4-methylphenyl)sulfonylcarbamate (step 5).

¹H-NMR (DMSO-d₆) δ: 11.92 (1H, br.s), 7.76 (2H, d, J=7.9 Hz), 7.49–7.39 (6H, m), 7.26 (1H, br.s), 4.98–4.88 (1H, m), 2.94–2.83 (4H, m), 2.63 (3H, s), 2.46 (3H, s), 2.34 (3H, s), 1.23 (3H, t, J=7.5 Hz), 1.12 (3H, d, J=6.1 Hz).

MS (ESI) m/z: 507 [(MH)⁺], 505 [(M−H)⁻].

□□□²⁴_D−12.49° (c 1.014, methanol)

Example 259
2-[4-(6-ACETYL-2-ETHYL-3H-IMIDAZO[4,5-B]PYRIDIN-3-YL)PHENYL]-1-METHYLETHYL (4-METHYLPHENYL)SULFONYLCARBAMATE Step 1. 1-[6-({4-[2-hydroxypropyl]phenyl}amino)-5-nitro-3-pyridinyl]ethanone The title compound was prepared according to the procedure described in step 1 of Example 162 from 1-(6-chloro-5-nitro-3-pyridinyl)ethanone (Paul, B. et al. *J. Med. Chem.*, 1990, 33, 2231–2239.) and 1-(4-aminophenyl)-2-propanol (step 1 of Example 6).

¹H-NMR (CDCl₃) δ: 10.37 (1H, br.s), 9.06–9.03 (2H, m), 7.60 (2H, d, J=8.3 Hz), 7.29 (2H, d, J=8.3 Hz), 4.10–4.00 (1H, m), 2.86–2.69 (2H, m), 2.60 (3H, s), 1.53 (1H, d, J=4.0 Hz), 1.28 (3H, d, J=6.2 Hz).

MS (EI) m/z: 315 (M⁺).

Step 2. 1-[5-amino-6-({4-[(2-hydroxypropyl]phenyl}amino)-3-pyridinyl]ethanone

To a solution of 1-[6-({4-[2-hydroxypropyl]phenyl}amino)-5-nitro-3-pyridinyl]ethanone (step 1, 1.54 g, 4.88 mmol) in tetrahydrofuran (10 ml) and ethanol (30 ml) was added 10% palladium on carbon (150 mg). The resulting mixture was stirred for 19 h under hydrogen atmosphere. The mixture was filtered through a pad of Celite and the filtrate was concentrated to afford 1.74 g (100%) of the title compound as green syrup.

¹H-NMR (CDCl₃) δ: 8.46 (1H, d, J=1.8 Hz), 7.56 (1H, d, J=1.8 Hz), 7.50 (2H, d, J=8.3 Hz), 7.20 (2H, d, J=8.3 Hz), 6.85 (1H, br.s), 3.76–3.67 (1H, m), 3.38 (2H, br.s), 2.81–2.62 (2H, m), 2.53 (3H, s), 1.26 (3H, d, J=6.1 Hz).

Step 3. 2-[4-(6-acetyl-2-ethyl-3H-imidazo[4,5-b]pyridin-3-yl)phenyl]-1-methylethyl propanoate The title compound was prepared according to the procedure described in step 5 of Example 1 from 1-[5-amino-6-({4-[(2-hydroxypropyl]phenyl}amino)-3-pyridinyl]ethanone (step 2).

MS (EI) m/z: 379 (M⁺).

Step 4. 1-(2-ethyl-3-{4-[2-hydroxypropyl]phenyl}-3H-imidazo[4,5-b]pyridin-6-yl)ethanone The title compound was prepared according to the procedure described in step 6 of Example 1 from 2-[4-(6-acetyl-2-ethyl-3H-imidazo[4,5-b]pyridin-3-yl)phenyl]-1-methylethyl propanoate (step 3).

¹H-NMR (CDCl₃) δ: 8.93 (1H, d, J=1.8 Hz), 8.59 (1H, d, J=1.8 Hz), 7.48 (2H, d, J=8.3 Hz), 7.36 (2H, d, J=8.3 Hz), 4.18–4.08 (1H, m), 2.94–2.80 (2H, m), 2.68 (3H, s), 1.39 (3H, t, J=7.5 Hz), 1.33 (3H, d, J=6.2 Hz).

Step 5. 2-[4-(6-acetyl-2-ethyl-3H-imidazo[4,5-b]pyridin-3-yl)phenyl]-1-methylethyl (4-methylphenyl)sulfonylcarbamate The title compound was prepared according to the procedure described in Example 3 from 1-(2-ethyl-3-{4-[2-hydroxypropyl]phenyl}-3H-imidazo[4,5-b]pyridin-6-yl)ethanone (step 4).

¹H-NMR (CDCl₃) δ: 8.93 (1H, d, J=1.8 Hz), 8.60 (1H, d, J=1.8 Hz), 7.92 (2H, d, J=8.4 Hz), 7.38–7.29 (6H, m), 5.12–5.03 (1H, m), 3.03–2.82 (4H, m), 2.69 (3H, s), 2.43 (3H, s), 1.28–1.24 (6H, m).

MS (ESI) m/z: 521 [(MH)⁺], 519 [(M−H)⁻].

Example 260
(1S)-2-[4-(6-ACETYL-2-ETHYL-3H-IMIDAZO[4,5-B]PYRIDIN-3-YL)PHENYL]-1-METHYLETHYL (4-METHYLPHENYL)SULFONYLCARBAMATE Step 1. 1-[6-({4-[(2S)-2-hydroxypropyl]phenyl}amino)-5-nitro-3-pyridinyl]ethanone The title compound was prepared according to the procedure described in step 1 of Example 162 from 1-(6-chloro-5-nitro-3-pyridinyl)ethanone (Paul, B. et al. *J. Med. Chem.*, 1990, 33, 2231–2239.) and (2S)-1-(4-aminophenyl)-2-propanol (step 2 of Example 248).

¹H-NMR (CDCl₃) δ: 10.37 (1H, br.s), 9.06–9.03 (2H, m), 7.60 (2H, d, J=8.3 Hz), 7.29 (2H, d, J=8.3 Hz), 4.10–4.00 (1H, m), 2.86–2.69 (2H, m), 2.60 (3H, s), 1.53 (1H, d, J=4.0 Hz), 1.28 (3H, d, J=6.2 Hz).

Step 2. 1-[5-amino-6-({4-[(2S)-2-hydroxypropyl]phenyl}amino)-3-pyridinyl]ethanone The title compound was prepared according to the procedure described in step 2 of Example 259 from 1-[6-({4-[(2S)-2-hydroxypropyl]phenyl}amino)-5-nitro-3-pyridinyl]ethanone (step 1).

¹H-NMR (CDCl₃) δ: 8.46 (1H, d, J=1.8 Hz), 7.56 (1H, d, J=1.8 Hz), 7.50 (2H, d, J=8.3 Hz), 7.20 (2H, d, J=8.3 Hz), 6.85 (1H, br.s), 3.76–3.67 (1H, m), 3.38 (2H, br.s), 2.81–2.62 (2H, m), 2.53 (3H, s), 1.26 (3H, d, J=6.1 Hz).

Step 3. (1S)-2-[4-(6-acetyl-2-ethyl-3H-imidazo[4,5-b]pyridin-3-yl)phenyl]-1-methylethyl propanoate The title compound was prepared according to the procedure described in step 5 of Example 1 from 1-[5-amino-6-({4-[(2S)-2-hydroxypropyl]phenyl}amino)-3-pyridinyl]ethanone (step 2).

MS (EI) m/z: 379 (M⁺).

Step 4. 1-(2-ethyl-3-{4-[(2S)-2-hydroxyproryl]phenyl}-3H-imidazo[4,5-b]pyridin-6-yl)ethanone The title compound was prepared according to the procedure described in step 6 of Example 1 from (1S)-2-[4-(6-acetyl-2-ethyl-3H-imidazo[4,5-b]pyridin-3-yl)phenyl]-1-methylethyl propanoate (step 3).

¹H-NMR (CDCl₃) δ: 8.93 (1H, d, J=1.8 Hz), 8.59 (1H, d, J=1.8 Hz), 7.48 (2H, d, J=8.3 Hz), 7.36 (2H, d, J=8.3 Hz), 4.18–4.08 (1H, m), 2.94–2.80 (2H, m), 2.68 (3H, s) 1.39 (3H, t, J=7.5 Hz), 1.33 (3H, d, J=6.2 Hz).

Step 5. (1S)-2-[4-(6-acetyl-2-ethyl-3H-imidazo[4,5-b]pyridin-3-yl)phenyl]-1-methylethyl (4-methylphenyl)sulfonylcarbamate The title compound was prepared according to the procedure described in Example 3 from 1-(2-ethyl-3-{4-[(2S)-2-hydroxypropyl]phenyl}-3H-imidazo[4,5-b]pyridin-6-yl)ethanone (step 4).

¹H-NMR (CDCl₃) δ: 8.93 (1H, d, J=1.8 Hz), 8.60 (1H, d, J=1.8 Hz), 7.92 (2H, d, J=8.4 Hz), 7.38–7.29 (6H, m), 5.12–5.03 (1H, m), 3.03–2.82 (4H, m), 2.69 (3H, s), 2.43 (3H, s), 1.24–1.24 (6H, m).

MS (ESI) m/z: 521 [(MH)⁺], 519 [(M−H)⁻].

Example 261

(1S)-2-[4-(6-ACETYL-2-ETHYL-3H-IMIDAZO[4,5-B]PYRIDIN-3-YL)PHENYL]-1-METHYLETHYL (4-METHYLPHENYL)SULFONYLCARBAMATE MONO-P-TOLUENESULFONATE

The title compound was prepared according to the procedure described in Example 231 from (1S)-2-[4-(6-acetyl-2-ethyl-3H-imidazo[4,5-b]pyridin-3-yl )phenyl]-1-methylethyl (4-methylphenyl)sulfonylcarbamate (step 5 of Example 260).

¹H-NMR (DMSO-d6) δ: 11.93 (1H, br.s), 8.90 (1H, d, J=1.8 Hz), 8.63 (1H, d, J=1.8 Hz), 7.76 (2H, d, J=8.4 Hz), 7.38–7.29 (8H, m), 7.11 (2H, d, J=8.4 Hz), 4.96–4.87 (1H, m), 2.90–2.79 (4H, m), 2.32 (3H, s), 2.27 (3H, s), 1.26 (3H, t, J=7.5 Hz), 1.12 (3H, d, J=6.2 Hz).

MS (ESI) m/z: 521 [(MH)⁺], 519 [(M−H)⁻].

□□□²⁴_D -8.17° (c 1.020, methanol)

Example 262

2-{4-[6-CHLORO-2-(2-PYRIDINYL)-5-(TRIFLUOROMETHYL)-1H-BENZIMIDAZOL-1-YL]PHENYL}ETHYL(4-METHYLPHENYL)SULFONYLCARBAMATE MONO-P-TOLUENESULFONATE

Step 1. 2-{4-[6-chloro-2-(2-pyridinyl)-5-(trifluoromethyl)-1h-benzimidazol-1-yl]phenyl}ethanol A mixture of 2-(4-{[2-amino-5-chloro-4-(trifluoromethyl)phenyl]amino}phenyl)ethanol (1.83 g, 5.54 mmol), 2-pyridinecarboxaldehyde (0.53 ml, 5.54 mmol), and EtOH (40 ml) was refluxed for 1 hour. After cooling to room temperature, the solvent was removed. The residue was dissolved with benzene (50 ml) and treated with Pb(OAc)₄ (3.38 g, 6.10 mmol) at room temperature for 1 hour. The mixture was diluted with EtOAc and the solution was washed with sat. NaHCO₃ aq. and brine. The organic fraction was dried over MgSO₄, then filtered. After evaporation in vacuo, the residue was purified by silica-gel column chromatography eluting with hexane/EtOAc=5/2 to afford 1.20 g (52%) of the title compound.

¹H-NMR (CDCl₃) δ: 8.42–8.39 (1H, m), 8.23 (1H, s), 8.10–8.07 (1H, m), 7.79–7.75 (1H, m), 7.40–7.23 (6H, m), 3.97 (2H, t, J=6.6 Hz), 2.99 (2H, t, J=6.6 Hz)

MS (ESI) m/z: 418 [(M+H)⁺], 476 ([M+CF₃CO₂]⁻)

Step 2. 2-{4-[6-chloro-2-(2-pyridinyl)-5-(trifluoromethyl)-1h-benzimidazol-1-yl]phenyl}ethyl(4-methylphenyl)sulfonylcarbamate The title compound was prepared according to the procedure described in example 3 from 2-{4-[6-chloro-2-(2-pyridinyl)-5-(trifluoromethyl)-1H-benzimidazol-1-yl]phenyl}ethanol.

¹H-NMR (CDCl₃) δ: 8.39–8.37 (1H, m), 8.23 (1H, s), 8.10–8.06 (1H, m), 7.92–7.87 (2H, m), 7.81–7.76 (1H, m), 7.33–7.18 (8H, m), 4.35 (2H, t, J=6.8 Hz), 2.98 (2H, t, J=6.8 Hz), 2.41 (3H, s)

MS (ESI) m/z: 615 ([M+H]⁺), 613 ([M−H]⁻)

Example 263

2-{4-[6-CHLORO-2-(2-PYRIDINYL)-5-(TRIFLUOROMETHYL)-1H-BENZIMIDAZOL-1-YL]PHENYL}ETHYL(4-METHYLPHENYL)SULFONYLCARBAMATE MONO-P-TOLUENESULFONATE

The title compound was prepared according to the procedure described in Example 231 from 2-{4-[6-chloro-2-(2-pyridinyl)-5-(trifluoromethyl )-1H-benzimidazol-1-yl]phenyl}ethyl(4-methylphenyl)sulfonylcarbamate.

MS (ESI) m/z: 615 ([M+H]⁺)

Example 264

N-{[(2-{4-[6-CHLORO-2-(2-PYRIDINYL)-5-(TRIFLUOROMETHYL)-1H-BENZIMIDAZOL-1-YL]PHENYL}ETHYL)AMINO]CARBONYL}-4-METHYLBENZENESULFONAMIDE MONO-P-TOLUENESULFONATE

Step 1. 6-chloro-1-[4-(2-chloroethyl)phenyl]-2-(2-pyridinyl)-5-(trifluoromethyl)-1H-benzimidazole The title compound was prepared according to the procedure described in step 7 of Example 1 from 2-{4-[6-chloro-2-(2-pyridinyl)-5-(trifluoromethyl)-1H-benzimidazol-1-yl]phenyl}ethanol (step 1 of Example 262).

¹H-NMR (CDCl₃) δ: 8.41–8.39 (1H, m), 8.24 (1H, s), 8.11 (1H, d, J=8.8 Hz), 7.82–7.76 (1H, m), 7.38 (2H, d, J=8.4 Hz), 7.35 (1H, s), 7.30–7.25 (3H, m), 3.31 (2H, t, J=7.2 Hz), 3.19 (2H, t, J=7.2 Hz).

Step 2. 1-[4-(2-azidoethyl)phenyl-6-chloro-2-(2-pyridinyl)-5-(trifluoromethyl)-1H-benzimidazole The title compound was prepared according to the procedure described in step 8 of Example 1 from 6-chloro-1-[4-(2-chloroethyl)phenyl]-2-(2-pyridinyl)-5-(trifluoromethyl)-1H-benzimidazole (step 1).

¹H-NMR (CDCl₃) δ: 8.40–8.39 (1H, m), 8.24 (1H, s), 8.10 (1H, d, J=7.9 Hz), 7.81–7.75 (1H, m), 7.39 (2H, d, J=8.4 Hz), 7.34 (1H, s), 7.29–7.25 (3H, m), 3.61 (2H, t, J=6.8 Hz), 3.01 (2H, t, J=6.8 Hz).

Step 3. 2-{4-[6-chloro-2-(2-pyridinyl)-5-(trifluoromethyl)-1H-benzimidazol-1-yl]phenyl}ethylamine The title compound was prepared according to the procedure described in step 7 of Example 37 from 1-[4-(2-azidoethyl)phenyl]-6-chloro-2-(2-pyridinyl)-5-(trifluoromethyl)-1H-benzimidazole (step 2).

¹H-NMR (CDCl₃) δ: 8.37–8.36 (1H, m), 8.19 (1H, s), 8.03–8.00 (1H, m), 7.78–7.71 (1H, m), 7.32–7.18 (6H, m), 3.02 (2H, t, J=6.8 Hz), 2.82 (2H, t, J=6.8 Hz), 2.17 (2H, br.s).

Step 4. N-{[(2-{4-[6-chloro-2-(2-pyridinyl)-5-(trifluoromethyl)-1H-benzimidazol-1-yl]phenyl}ethyl)amino]carbonyl}-4-methylbenzenesulfonamide The title compound was prepared according to the procedure described in step 10 of Example 1 from 2-{4-[6-chloro-2-(2-pyridinyl)-5-(trifluoromethyl)-1H-benzimidazol-1-yl]phenyl}ethylamine (step 3).

¹H-NMR (CDCl₃) δ: 8.42–8.39 (1H, m), 8.24 (1H, s), 8.10 (1H, d, J=8.1 Hz), 7.81–7.75 (1H, m), 7.69 (2H, d, J=8.3 Hz), 7.33–7.24 (8H, m), 6.72–6.69 (1H, m), 3.63–3.56 (2H, m), 2.93 (2H, t, J=6.8 Hz), 2.38 (3H, s).

MS (ESI) m/z: 614 [(MH)⁺], 612 [(M−H)⁻].

Step 5. N-{[(2-{4-[6-chloro-2-(2-pyridinyl)-5-(trifluoromethyl)-1H-benzimidazol-1-yl]phenyl}ethyl)amino]carbonyl}-4-methylbenzenesulfonamide mono-p-toluenesulfonate The title compound was prepared according to the procedure described in Example 231 from N-{[(2-{4-[6-chloro-2-(2-pyridinyl)-5-(trifluoromethyl)-1H-benzimidazol-1-yl]phenyl}ethyl)amino]carbonyl}-4-methylbenzenesulfonamide (step 4).

$^1$H-NMR (DMSO-d6) δ: 10.63 (1H, br.s), 8.41–8.39 (1H, m), 8.35 (1H, s), 8.08–7.95 (2H, m), 7.75 (2H, d, J=8.3 Hz), 7.49 (2H, d, J=8.3 Hz), 7.44–7.27 (8H, m), 7.10 (2H, d, J=7.7 Hz), 6.61–6.57 (1H, m), 3.30–3.23 (2H, m), 2.74 (2H, t, J=7.0 Hz), 2.31 (3H, s) 2.27 (3H, s).

MS (ESI) m/z: 614 [(MH)$^+$], 612 [(M−H)$^-$].

Example 265

N-{[(2-{4-[6-CHLORO-2-(1H-PYRAZOL-3-YL)-5-(TRIFLUOROMETHYL)-1H-BENZIMIDAZOL-1-YL]PHENYL}ETHYL)AMINO1CARBONYL}-4-METHYLBENZENESULFONAMIDE MONO-P-TOLUENESULFONATE

Step 1. 6-chloro-1-[4-(2-chloroethyl)phenyl]-2-(1H-pyrazol-3-yl)-5-(trifluoromethyl)-1H-benzimidazole The title compound was prepared according to the procedure described in step 7 of Example 1 from 2-{4-[6-chloro-2-(1H-pyrazol-3-yl)-5-(trifluoromethyl)-1H-benzimidazol-1-yl]phenyl}ethanol (step 1, Example 255).

$^1$H-NMR (DMSO-d6) δ: 13.29 (1H, s), 8.25 (1H, s), 7.83–7.81 (1H, m), 7.52–7.43 (4H, m), 7.23 (1H, s), 6.67–6.65 (1H, m), 3.95 (2H, t, J=7.0 Hz), 3.16 (2H, t, J=7.0 Hz).

Step 2. 1-[4-(2-azidoethyl)phenyl-6-chloro-2-(1H-pyrazol-3-yl)-5-(trifluoromethyl)-1H-benzimidazole The title compound was prepared according to the procedure described in step 8 of Example 1 from 6-chloro-1-[4-(2-chloroethyl)phenyl]-2-(1H-pyrazol-3-yl)-5-(trifluoromethyl)-1H-benzimidazole (step 1).

$^1$H-NMR (DMSO-d6) δ: 13.27 (1H, s), 8.25 (1H, s), 7.82 (1H, s), 7.52–7.43 (4H, m), 7.21 (1H, s), 6.65 (1H, s), 3.67 (2H, t, J=7.0 Hz), 2.99 (2H, t, J=7.0 Hz).

Step 3. 2-{4-[6-chloro-2-(1H-pyrazol-3-yl)-5-(trifluoromethyl)-1H-benzimidazol-1-yl]phenyl}ethylamine The title compound was prepared according to the procedure described in step 7 of Example 37 from 1-[4-(2-azidoethyl)phenyl-6-chloro-2-(1H-pyrazol-3-yl)-5-(trifluoromethyl)-1H-benzimidazole (step 2).

MS (EI) m/z: 405 (M$^+$).

Step 4. N-{[(2-{4-]6-chloro-2-(1H-pyrazol-3-yl)-5-(trifluoromethyl)-1H-benzimidazol-1-yl]phenyl}ethyl)amino]carbonyl}-4-methylbenzenesulfonamide The title compound was prepared according to the procedure described in step 10 of Example 1 from 2-{4-[6-chloro-2-(1H-pyrazol-3-yl)-5-(trifluoromethyl)-1H-benzimidazol-1-yl]phenyl}ethylamine (step 3).

$^1$H-NMR (CDCl$_3$) δ: 8.17 (1H, s), 7.69 (2H, d, J=8.4 Hz), 7.57 (1H, d, J=2.2 Hz), 7.30–7.18 (8H, m), 6.82–6.77 (1H, m), 6.60 (1H, d, J=2.2 Hz), 3.64–3.58 (2H, m), 2.91 (2H, t, J=6.4 Hz), 2.39 (3H, s).

5. N-{[(2-{4-[6-chloro-2-(1H-pyrazol-3-yl)-5-(trifluoromethyl)-1H-benzimidazol-1-yl]phenyl}ethyl)amino]carbonyl}-4-methylbenzenesulfonamide mono-p-toluenesulfonate The title compound was prepared according to the procedure described in Example 231 from N-{[(2-{4-[6-chloro-2-(1H-pyrazol-3-yl)-5-(trifluoromethyl)-1H-benzimidazol-1-yl]phenyl}ethyl)amino]carbonyl}-4-methylbenzenesulfonamide (step 4).

$^1$H-NMR (DMSO-d6) δ: 10.64 (1H, br.s), 8.24 (1H, s), 8.35 (1H, s), 7.78–7.75 (3H, m), 7.49–7.80 (8H, m), 7.11 (2H, d, J=7.9 Hz), 6.60–6.57 (1H, m), 6.38–6.37 (1H, m), 3.33–3.26 (2H, m), 2.78 (2H, t, J=7.2 Hz), 2.32 (3H, s), 2.28 (3H, s).

MS (ESI) m/z: 603 [(MH)$^+$], 601 [(M−H)$^-$].

Example 266

3-(3-CHLORO-4-{2-[({[(4-METHYLPHENYL)SULFONYL]AMINO}CARBONYL)AMINO]ETHYL}PHENYL)-2-ETHYL-5,7-DIMETHYL-3H-IMIDAZO[4,5-B]PYRIDINE

Step 1. diethyl 2-(2-chloro-4-nitrophenyl)malonate

Diethylmalonate (5.2 ml, 34.2 mmol) was added to the suspension of NaH (1.4 g, 34.2 mmol) in 80 ml of 1,4-dioxane followed by the successive addition of CuBr (4.9 g, 34.2 mmol) and 3-chloro-4-fluoronitrobenzene (5.0 g, 28.5 mmol). The mixture was stirred at room temperature for 0.5 h and under reflux temperature for 12 h. The mixture was poured into water, and the precipitate was filtered off through a pad of celite. The filtrate was extracted with ethyl acetate (2×50 ml). The organic layer was washed with brine, dried (MgSO$_4$), and concentrated to give a green oil. This mixture was purified by SiO2 column chromatography developing with hexane/ethyl acetate (10/1) gave 7.6 g (85%) of the title compound as yellow oil.

$^1$H-NMR (CDCl$_3$) δ: 8.30 (1H, d, J=2.4 Hz), 8.16 (1H, dd, J=2.2, 8.6 Hz), 7.74 (1H, d, J=8.6 Hz), 5.27 (1H, s), 4.28 (2H, q, J=7.2 Hz), 4.27 (2H, q, J=7.2 Hz), 1.29 (6H, t, J=7.2 Hz).

Step 2. 2-(2-chloro-4-nitrophenyl)acetic acid

To a solution of diethyl 2-(2-chloro-4-nitrophenyl)malonate (step 1, 7.6 g, 24.2 mmol) in methanol (18 ml) was added 6M-NaOH (12 ml) and stirred for 1 h at 50° C. The reaction was quenched by the addition of saturated citric acid aqueous solution (16 ml) and water. The organic layer was extracted with ethyl acetate (2×50 ml), washed with brine, dried (MgSO$_4$) and concentrated to give 4.52 g (87%) of title compound as light yellow solid.

$^1$H-NMR (CDCl$_3$) δ: 12.6 (1H, br.s), 8.30 (1H, d, J=2.6 Hz), 8.18 (1H, dd, J=2.4, 8.4 Hz), 7.73 (1H, d, J=8.6 Hz), 3.90 (2H, s).

Step 3. methyl 2-(2-chloro-4-nitrophenyl)acetate

To a solution of 2-(2-chloro-4-nitrophenyl)acetic acid (step 2, 4.5 g, 21 mmol) in dimethyl acetale/methanol (4/1) was added trimethylsillylchloride (0.3 ml) and stirred for 7 h at room temperature. The solvent was removed and the residue was purified by SiO$_2$ column chromatography with developing hexane/ethyl acetate (10/1) to give 3.6 g (74%) of title compound as yellow oil.

$^1$H-NMR (CDCl$_3$) δ: 8.28 (1H, d, J=2.3 Hz), 8.11 (1H, dd, J=2.3, 8.6 Hz), 7.50 (1H, d, J=8.6 Hz), 3.88 (2H, s), 3.74 (3H, s).

Step 4. methyl 2-(4-amino-2-chlorophenyl)acetate

To a solution of methyl 2-(2-chloro-4-nitrophenyl)acetate (step 3, 3.6 g, 15.6 mmol) in ethanol/water (4/1) were added Fe (4.4 g, 78.0 mmol) and NH$_4$Cl (409 mg, 7.8 mmol). The mixture was stirred for 1 h under reflux temperature. The solvent was removed and the residue was diluted with CH$_2$Cl$_2$. The mixture was washed with brine, dried (MgSO$_4$) and concentrated to give 2.59 g (83%) of title compound as orange oil.

The title compound was prepared according to the procedure described in step 2 of Example 28 from methyl methyl 2-(2-chloro-4-nitrophenyl)acetate (step 3)

$^1$H-NMR (CDCl$_3$) δ: 7.04 (1H, d, J=8.2 Hz), 6.72 (1H, d, J=2.3 Hz), 6.54 (1H, dd, J=2.5, 8.2 Hz), 3.70 (3H, s), 3.66 (2H, s).

Step 5. methyl {2-chloro-4-[(4,6-dimethyl-3-nitro-2-pyridinyl)amino]phenyl}acetate To a mixture of methyl 2-(4-amino-2-chlorophenyl)acetate (step 4, 2.6 g, 13.0 mmol) and 4,6-Dimethyl-3-nitro-2-pyridine (step 2 of Example 1, 2.4 g, 13.0 mmol) in DMSO was added diisopropylethylamine. The resulting mixture was stirred for 9 h at 50° C. To the mixture was poured into water and extracted with ethyl acetate (3×30 ml). The organic layer was washed with brine, dried (MgSO$_4$) and concentrated to give a brown oil. This was purified by SiO$_2$ column chromatography with developing hexane/ethyl acetate (10/1) to give 1.4 g (29%) of title compound as yellow solid.

$^1$H-NMR (CDCl$_3$) δ: 9.55 (1H, br.s), 7.90 (1H, d, J=2.2 Hz), 7.43 (1H, dd, J=2.2, 8.3 Hz), 7.24 (1H, d, J=8.3 Hz), 6.59 (1H, s), 3.76 (2H, s), 3.72 (3H, s), 2.56 (3H, s), 2.46 (3H, s).

MS (EI) m/z: 349 (M$^+$).

Step 6. methyl 2-chloro-{4-[(3-amino-4,6-dimethyl-2-pyridinyl)amino]phenyl}acetate The title compound was prepared according to the procedure described in step 2 of Example 28 from methyl {2-chloro-4-[(4,6-dimethyl-3-nitro-2-pyridinyl)amino]phenyl}acetate (step 5)

$^1$H-NMR (CDCl$_3$) δ: 7.26 (1H, d, J=2.2 Hz), 7.20 (1H, d, J=8.3 Hz), 7.00 (1H, dd, J=2.2, 8.3 Hz), 6.64 (1H, s), 6.37 (1H, br.s), 3.70 (3H, s), 3.27 (1H, br.s), 2.68 (3H, s), 2.20 (3H, s).

Step 7. methyl 2-[2-chloro-4-(2-ethyl-5,7-dimethyl-3H-imidazo[4,5-b]pyridin-3-yl) phenylethyl acetate The title compound was prepared according to the procedure described in step 5 of Example 1 from methyl 2-chloro-{4-[(3-amino-4,6-dimethyl-2-pyridinyl)amino]phenyl}acetate (step 6)

$^1$H-NMR (CDCl$_3$) δ: 7.50 (1H, d, 8.3 Hz), 7.47 (1H, d, J=2.2 Hz), 7.31 (1H, dd, J=2.2, 8.3 Hz), 6.92 (1H, s), 3.87 (2H, s), 3.77 (3H, s), 2.85 (2H, q, J=7.5 Hz), 2.65 (3H, s) 2.53 (3H, s), 1.31 (3H, t, J=7.5 Hz).

MS (EI) m/z: 357 (M$^+$).

Step 8. 2-[2-chloro-4-(2-ethyl-5,7-dimethyl-3H-imidazo[4,5-b]pyridin-3-yl) phenylethanol To a solution of methyl 2-[2-chloro-4-(2-ethyl-5,7-dimethyl-3H-imidazo[4,5-b]pyridin-3-yl)phenylethyl acetate (step 7, 1.13 g, 3.15 mmol) was added carefully LAH and stirred for 1 h at room temperature. The reaction was quenched with water and the mixture was diluted with ethyl acetate (50 ml). To this mixture was added saturated potassium sodium tartarate aqueous solution (50 ml) and stirred for 2.5 h. The organic layer was separated and aqueous layer was extracted with ethyl acetate (2×20 ml). The combined organic layer was washed with brine, dried (Mg2SO4) and concentrated to give 1.0 g of title compound as white solid.

$^1$H-NMR (CDCl$_3$) δ: 7.41–7.53 (2H, m), 7.25–7.29 (1H, m), 6.92 (1H, s), 3.96 (2H, m), 3.11 (3H, t, J=7.4 Hz), 2.82 (2H, m), 2.65 (3H, s), 2.53 (3H, s), 1.30 (3H, t, J=7.4 Hz).

MS (EI) m/z: 329 (M$^+$).

Step 9. 3-[3-chloro-4-(2-chloroethyl)phenyl-2-ethyl-5,7-dimethyl-3H-imidazo[4,5-b]pyridine The title compound was prepared according to the procedure described in step 7 of Example 1 from methyl 2-[2-chloro-4-(2-ethyl-5,7-dimethyl-3H-imidazo[4,5-b]pyridin-3-yl)phenylethanol (step 8)

$^1$H-NMR (CDCl$_3$) δ: 7.45–7.52 (2H, m), 7.23–7.31 (1H, m), 6.92 (1H, s), 3.82 (2H, t, J=7.3 Hz), 3.29 (2H, t, J=7.3 Hz), 2.83 (2H, q, J=7.6 Hz), 2.65 (3H, s), 2.53 (3H, s), 1.30 (3H, t, J=7.6 Hz).

Step 10. 3-[4-(2-azidoethyl)-3-chlorophenyl-2-ethyl-5,7-dimethyl-3H-imidazo[4,5-b]pyridine The title compound was prepared according to the procedure described in step 8 of Example 1 from 3-[3-chloro-4-(2-chloroethyl)phenyl-2-ethyl-5,7-dimethyl-3H-imidazo[4,5-b]pyridine (step 9)

$^1$H-NMR (CDCl$_3$) δ: 7.45–7.48 (2H, m), 7.29 (1H, dd, J=2.1, 7.9 Hz), 6.92 (1H, s), 3.62 (1H, t, J=7.1 Hz), 3.12 (1H, t, J=7.3 Hz), 2.83 (2H, q, J=7.4 Hz), 2.65 (3H, s), 2.53 (3H, s), 1.30 (3H, t, J=7.4 Hz).

Step 11. 2-[2-chloro-4-(-2-ethyl-5,7-dimethyl-3H-imidazo[4,5-b]pyridin-3-yl)phenyl]ethanamine To a solution of methyl 3-[4-(2-azidoethyl)-3-chlorophenyl-2-ethyl-5,7-dimethyl-3H-imidazo[4,5-b]pyridine (step 10, 430 mg, 1.2 mmol) in ethanol/water (4/1) were added Fe (335 mg, 6.0 mmol) and NH$_4$Cl (409 mg, 7.8 mmol). The mixture was stirred for 1 h under reflux temperature. The solvent was removed and the residue was diluted with CH$_2$Cl$_2$. The mixture was washed with brine, dried (MgSO$_4$) and concentrated to give 390 mg of title compound as orange oil.

$^1$H-NMR (CDCl$_3$) δ: 7.44 (2H, d, J=7.4 Hz), 7.25 (1H, m), 6.92 (1H, s), 2.92–3.15 (6H, m),2.83 (2H, q, J=7.4 Hz), 2.65 (3H, s), 2.53 (3H, s), 1.30 (3H, t, J=7.4 Hz).

Step 12. 2-[2-chloro-4-(-2-ethyl-5,7-dimethyl-3H-imidazo[4,5-b]pyridin-3-yl)phenyl]ethanamine The title compound was prepared according to the procedure described in step 10 of Example 1 from 2-[2-chloro-4-(-2-ethyl-5,7-dimethyl-3H-imidazo[4,5-b]pyridin-3-yl) phenyl]ethanamine (Step 11)

$^1$H-NMR (CDCl$_3$) δ: 7.83 (2H, d, J=8.4 Hz), 7.28–7.36 (4H, m), 7.14 (1H, d, J=7.7 Hz),6.92 (1H, s), 6.28 (1H, br.s), 3.58 (2H, dt, J=6.3 Hz), 3.02 (2H, t, J=6.4 Hz), 2.74 (2H, q, J=7.6 Hz), 2.66 (3H, s), 2.45 (3H, s), 2.41 (3H, s),1.25 (3H, t, J=7.6 Hz).

MS (ESI) m/z: 526 (M$^+$).

Example 267

3-(2-CHLORO-4-{2-[({[(4-METHYLPHENYL)SULFONYL]AMINO}CARBONYL)AMINO]ETHYL}PHENYL)-2-ETHYL-5,7-DIMETHYL-3H-IMIDAZO[4,5-B]PYRIDINE

Step 1. 2-{3-chloro-4-[(4,6-dimethyl-3-nitro-2-pyridinyl)amino]phenyl}ethanol

The title compound was prepared according to the procedure described in step 3 of Example 1 from 4,6-Dimethyl-3-nitro-2-pyridine (0.66 g, 3.8 mmol, step 2 of Example 1) and 4-amino-2-chloro-phenylethanol (0.72 g, 3.8 mmol, *Eur. J. Med. Chem.*, 1996, 31, 133.).

$^1$H-NMR (CDCl$_3$) δ: 9.85 (1H, s), 8.37 (1H, d, J=8.4 Hz), 7.31 (1H, d, J=2.0 Hz), 7.14 (1H, dd, J=2.0, 8.3 Hz), 6.60 (1H, s), 3.87 (2H, dt, J=6.2, 6.4 Hz), 2.84 (2H, t, J=6.4 Hz), 2.56 (3H, s), 2.46 (3H, s), 1.40 (1H, t, J=6.2 Hz).

MS (EI) m/z: 321 (M$^+$).

Step 2. methyl 3-chloro-{4-[(3-amino-4,6-dimethyl-2-pyridinyl)amino]phenyl}ethanol The title compound was prepared according to the procedure described in step 2 of Example 28 from 2-{3-chloro-4-[(4,6-dimethyl-3-nitro-2-pyridinyl)amino]phenyl}ethanol (step 1).

$^1$H-NMR (CDCl$_3$) δ: 7.26 (1H, d, J=2.2 Hz), 7.20 (1H, d, J=8.3 Hz), 7.00 (1H, dd, J=2.2, 8.3 Hz), 6.64 (1H, s), 6.37 (1H, br.s), 3.70 (3H, s), 3.27 (1H, br.s), 2.68 (3H, s), 2.20 (3H, s).

Step 3. 2-[2-chloro-4-(2-ethyl-5,7-dimethyl-3H-imidazo[4,5-b]pyridin-3-yl)phenylethyl propionate The title compound was prepared according to the procedure described in step 5 of Example 1 from 3-chloro-{4-[(3-amino-4,6-dimethyl-2-pyridinyl)amino]phenyl}ethyl propionate (step 2).

$^1$H-NMR (CDCl$_3$) δ: 7.50 (1H, d, 8.3 Hz), 7.47 (1H, d, J=2.2 Hz), 7.31 (1H, dd, J=2.2, 8.3 Hz), 6.92 (1H, s), 3.87 (2H, s), 3.77 (3H, s), 2.85 (2H, q, J=7.5 Hz), 2.65 (3H, s), 2.53 (3H, s), 1.31 (3H, t, J=7.5 Hz).

MS (EI) m/z: 357 (M$^+$).

Step 4. 2-[3-chloro-4-(2-ethyl-5,7-dimethyl-3H-imidazo[4,5-b]pyridin-3-yl) phenylethanol The title compound was prepared according to the procedure described in step 6 of Example 1 from methyl 2-[2-chloro-4-(2-ethyl-5,7-dimethyl-3H-imidazo[4,5-b]pyridin-3yl) phenylethyl propionate (step 3).

$^1$H-NMR (CDCl$_3$) δ: 7.51 (1H, s), 7.34 (2H, s), 6.91 (1H, s), 3.96 (2H, dd, J=6.2, 12.0 Hz), 2.96 (2H, t, J=7.4 Hz), 2.70 (2H, m), 2.66 (3H, s), 2.51 (3H, s), 1.67 (1H, br.t, J=6.2 Hz), 1.28 (3H, t, J=7.4 Hz).

MS (ESI) m/z: 329 (M⁺).
Step 5. 3-[2-chloro-4-(2-chloroethyl)phenyl-2-ethyl-5,7-dimethyl-3H-imidazo[4,5-b]pyridine The title compound was prepared according to the procedure described in step 7 of Example 1 from 2-[3-chloro-4-(2-ethyl-5,7-dimethyl-3H-imidazo[4,5-b]pyridin-3-yl)phenylethanol (step 4).

¹H-NMR (CDCl₃) δ: 7.49 (1H, d, J=1.3 Hz), 7.34–7.49 (2H, m), 6.91 (1H, s), 3.80 (2H, t, J=7.2 Hz), 3.17 (2H, t, J=7.0 Hz), 2.60–2.85 (2H, m), 2.66 (3H, s), 2.51 (3H, s), 1.28 (3H, t, J=7.5 Hz).

MS (EI) m/z: 347 [(M−H)⁻].

Step 6. 3-[4-(2-azidoethyl)-3-chlorophenyl-2-ethyl-5,7-dimethyl-3H-imidazo[4,5-b]pyridine The title compound was prepared according to the procedure described in step 8 of Example 1 from 3-[2-chloro-4-(2-chloroethyl)phenyl-2-ethyl-5,7-dimethyl-3H-imidazo[4,5-b]pyridine (step 5).

¹H-NMR (CDCl₃) δ: 7.49 (1H, m, J=1.8 Hz), 7.31–7.38 (2H, m), 6.91 (1H, s), 3.62 (2H, t, J=7.0 Hz), 2.98 (2H, t, J=7.3 Hz), 2.60–2.80 (2H, m), 2.66 (3H, s), 2.51 (3H, s), 1.27 (3H, t, J=7.5 Hz).

MS (EI) m/z: 354 (M⁺).

Step 7. 2-[3-chloro-4-(-2-ethyl-5,7-dimethyl-3H-imidazo[4,5-b]pyridin-3-yl)phenyl]ethanamine To a stirred solution of 3-[4-(2-azidoethyl)-3-chlorophenyl-2-ethyl-5,7-dimethyl-3H-imidazo[4,5-b]pyridine (step 6, 149 mg, 0.4 mmol) in THF (4 ml) was added triphenylphosphine (116 mg, 0.4 mmol) at room temperature. After completion of the addition, the stirring was continued for an additional 2.5 h at the same temperature and 3.5 h under reflux temperature. To the resulting mixture was added H₂O (1.0 ml) at room temperature, and the solvent was removed. The mixture was dissolved in CH₂Cl₂ (100 ml), washed with brine. The Organic layer was dried (MgSO₄), and concentrated to give a yellow oil.

MS (EI) m/z: 328 (M⁺).

Step 8. 2-[3-chloro-4-(2-ethyl-5,7-dimethyl-3H-imidazo[4,5-b]pyridin-3-yl)phenyl]ethanamine The title compound was prepared according to the procedure described in step 10 of Example 1 from 2-[3-chloro-4-(-2-ethyl-5,7-dimethyl-3H-imidazo[4,5-b]pyridin-3-yl)phenyl]ethanamine (step 7).

¹H-NMR (CDCl₃) δ: 7.88 (1H, s), 7.85 (1H, s), 7.19–7.34 (5H, m), 6.92 (1H, s), 6.94 (1H, s), 6.13 (1H, br.s), 3.54 (2H, m), 2.78 (2H, t, J=6.4 Hz), 2.67 (3H, s), 2.63 (3H, m), 2.42 (3H, s), 2.40 (3H, s), 1.25 (3H, t, J=7.5 Hz).

MS (EI) m/z: 526 (M⁺).

Example 268

2-ETHYL-3-(3-METHOXY-4-{2-[({[(4-METHYLPHENYL)SULFONYL]AMINO}CARBONYL)AMINO]ETHYL}PHENYL)-5,7-DIMETHYL-3H-IMIDAZO[4,5-B]PYRIDINE

Step 1. diethyl 2-(2-methoxy-4-nitrophenyl)malonate

The title compound was prepared according to the procedure described in step 1 of Example 266 from 4-bromo-3-methoxynitrobenzene.

¹H-NMR (CDCl₃) δ: 7.78 (1H, dd, J=2.2, 8.4 Hz), 7.75 (1H, d, J=2.2 Hz), 7.54 (1H, d, J=8.4 Hz), 5.15 (1H, s), 4.25 (2H, q, J=7.2 Hz), 4.25 (2H, q, J=7.2 Hz), 3.94 (3H, s), 1.28 (6H, t, J=7.2 Hz).

Step 2. 2-(2-methoxy-4-nitrophenyl)acetic acid

The title compound was prepared according to the procedure described in step 2 of Example 266 from diethyl 2-(2-methoxy-4-nitrophenyl)malonate (step 1).

¹H-NMR (CDCl₃) δ: 12.4 (1H, br.s), 7.82 (1H, dd, J=2.2, 8.4 Hz), 7.75 (1H, dd, J=2.2 Hz), 7.50 (1H, d, J=8.4 Hz), 3.90 (3H, s), 3.66 (2H, s).

Step 3. methyl 2-(2-methoxy-4-nitrophenyl)acetate

To a solution of 2-(2-methoxy-4-nitrophenyl)acetic acid (step 2, 1.2 g, 5.5 mmol) in methanol/dichloromethane (11 ml, 1/1) was added trimethylsillyldiazomethane (2 M, 5.6 ml, 11.8 mmol) and stirred for 10 min at room temperature. The mixture was quenched with saturated citric acid aqueous solution and the extracted with ethyl acetate (3×20 ml). The organic layer was washed with brine, dried (MgSO₄) and concentrated to give 1.2 g of title compound as orange solid.

¹H-NMR (CDCl₃) δ: 7.83 (1H, dd, J=2.2, 8.3 Hz), 7.73 (1H, dd, J=2.2 Hz), 7.34 (1H, d, J=8.1 Hz), 3.93 (3H, s), 3.71 (2H, s), 3.71 (3H, s).

Step 4. methyl 2-(4-amino-2-methoxyphenyl)acetate

To a solution of methyl 2-(2-methoxy-4-nitrophenyl)acetate (step 3, 1.2 g, 5.5 mmol) in methanol (10 ml) was added 10% Pd/C (130 mg, 0.12 mmol) and stirred under hydrogen atmosphere for 3 h at room temperature. The catalyst was filtered off through a pad of celite and well washed with ethanol and ethyl acetate. The filtrate was concentrated to give 1.1 g of title compound as pink oil.

¹H-NMR (CDCl₃) δ: 6.94 (1H, d, J=7.7 Hz), 6.26 (1H, d, J=2.0 Hz), 6.23 (1H, s), 3.70 (3H, s), 3.76 (3H, s), 3.52 (2H, s).

Step 5. methyl {4-[(4,6-dimethyl-3-nitro-2-pyridinyl)amino]-2-methoxyphenyl}acetate The title compound was prepared according to the procedure described in step 3 of Example 1 from methyl 2-(4-amino-2-methoxyphenyl) acetate (step 4).

¹H-NMR (CDCl₃) δ: 9.60 (1H, s), 7.47 (1H, d, J=1.7 Hz), 7.06–7.15 (2H, m), 6.55 (1H, s), 3.84 (3H, s), 3.69 (3H, s), 3.62 (2H, s), 2.56 (3H, s), 2.44 (3H, s).

MS (EI) m/z: 345 (M⁺).

Step 6. methyl {4-[(3-amino-4,6-dimethyl-2-pyridinyl)amino]-2-methoxyphenyl}acetate The title compound was prepared according to the procedure described in step 2 of Example 28 from methyl {4-[(4,6-dimethyl-3-nitro-2-pyridinyl)amino]-2-methoxyphenyl}acetate (step 5).

¹H-NMR (CDCl₃) δ: 7.03 (1H, d, J=5.1 Hz), 7.02 (1H, s), 6.60 (1H, s), 6.57 (1H, dd, J=2.2, 8.3 Hz), 3.79 (3H, s), 3.68 (3H, s), 3.56 (2H, s), 3.25–3.35(br.s, 2H), 2.38 (3H, s), 2.20 (3H, s).

MS (EI) m/z: 315 (M⁺).

Step 7. methyl 2-[4-(2-ethyl-5,7-dimethyl-3H-imidazo[4,5-b]pyridin-3-yl)-2-methoxyphenylethyl acetate The title compound was prepared according to the procedure described in step 5 of Example 1 from methyl {4-[(3-amino-4,6-dimethyl-2-pyridinyl)amino]-2-methoxyphenyl}acetate (step 6).

¹H-NMR (CDCl₃) δ: 7.36 (1H, d, J=7.9 Hz), 6.89–6.99 (3H, m), 3.84 (2H, s), 3.74 (3H, s), 3.71 (2H, s), 2.85 (2H, q, J=7.5 Hz), 2.66 (3H, s), 2.53 (3H, s), 1.30 (3H, t, J=7.5 Hz).

MS (EI) m/z: 353 (M⁺).

Step 8. 2-[4-(2-ethyl-5,7-dimethyl-3H-imidazo[4,5-b]pyridin-3-yl)-2-methoxyphenylethanol The title compound was prepared according to the procedure described in step 8 of Example 266 from methyl 2-[4-(2-ethyl-5,7-dimethyl-3H-imidazo[4,5-b]pyridin-3-yl)-2-methoxyphenylethyl acetate (step 7).

¹H-NMR (CDCl₃) δ: 7.33 (1H, d, J=7.7 Hz), 6.87–6.95 (3H, m), 3.90 (2H, dt, J=6.0, 6.2 Hz), 3.84 (3H, s), 2.98(2H, t, J=6.4 Hz), 2.84(2H, q, J=7.5 Hz), 2.66 (3H, s), 2.53 (3H, s), 1.76 (1H, br.t), 1.30 (3H, t, J=7.5 Hz).

MS (EI) m/z: 324 [(M−H)⁻].

Step 9. 3-[4-(2-chloroethyl)-3-methoxyphenyl-2-ethyl-5,7-dimethyl-3H-imidazo[4,5-b]pyridine The title compound was prepared according to the procedure described in step 7 of Example 1 from 2-[4-(2-ethyl-5,7-dimethyl-3H-imidazo[4,5-b]pyridin-3-yl)-2-methoxyphenylethanol (step 8).

¹H-NMR (CDCl₃) δ: 7.33 (1H, d, J=7.7 Hz), 6.87–6.94 (3H, m), 3.84 (3H, s), 3.77 (3H, t, J=7.6 Hz), 3.16 (2H, t, J=7.3 Hz), 2.84 (2H, q, J=7.6 Hz), 2.66 (3H, s), 2.53 (3H, s), 1.30 (3H, t, J=7.6 Hz).

Step 10. 3-[4-(2-azidoethyl)-3-methoxyphenyl-2-ethyl-5,7-dimethyl-3H-imidazo[4,5-b]pyridine The title compound was prepared according to the procedure described in step 8 of Example 1 from 3-[4-(2-chloroethyl )-3-methoxyphenyl-2-ethyl-5,7-dimethyl-3H-imidazo[4,5-b]pyridine (step 9).

¹H-NMR (CDCl₃) δ: 7.45–7.48 (2H, m), 7.29 (1H, dd, J=2.1, 7.9 Hz), 6.92 (1H, s), 3.62 (1H, t, J=7.1 Hz), 3.12 (1H, t, J=7.3 Hz), 2.83 (2H, q, J=7.4 Hz), 2.65 (3H, s), 2.53 (3H, s), 1.30 (3H, t, J=7.4 Hz).

Step 11. 2-[4-(2-ethyl-5,7-dimethyl-3H-imidazo[4,5-b]pyridin-3-yl-2-methoxy)phenyl]ethanamine The title compound was prepared according to the procedure described in step 9 of Example 1 from 3-[4-(2-azidoethyl)-3-methoxyphenyl-2-ethyl-5,7-dimethyl-3H-imidazo[4,5-b]pyridine (step 10).

¹H-NMR (CDCl₃) δ: 7.30 (1H, d, J=7.7 Hz), 6.92 (1H, dd, J=2.0, 7.9 Hz), 6.91 (1H, br.s), 6.86 (1H, d, J=2.0 Hz), 3.83 (3H, s), 2.65 (3H, s), 2.99 (2H, br.t, J=4.5 Hz), 2.85 (2H, q, J=8.3 Hz), 2.84 (2H, q, J=7.7 Hz), 2.66 (3H, s), 2.53 (3H, s), 1.29 (3H, t, J=7.7 Hz).

Step 12. 2-ethyl-(3-methoxy-4-{2-[({[(4-methylphenyl)sulfonyl]amino}carbonyl)amino]ethyl}phenyl)-5,7-dimethyl-3H-imidazo[4,5-b]pyridine The title compound was prepared according to the procedure described in step 10 of Example 1 from 2-[4-(-2-ethyl-5,7-dimethyl-3H-imidazo[4,5-b]pyridin-3-yl-2-methoxy)phenyl]ethanamine (step 11).

¹H-NMR (CDCl₃) δ: 7.86 (2H, d, J=8.3 Hz), 7.30 (4H, m), 7.14 (1H, d, J=8.1Hz), 7.01 (1H, d, J=7.9 Hz), 6.92 (1H, s), 6.79 (1H, d, J=2.0 Hz), 6.63 (1H, dd, J=1.8, 7.7 Hz), 6.04 (1H, br.t, J=5.1 Hz), 3.74 (3H, s), 3.51 (2H, dt, J=6.0 Hz), 2.85 (2H, t, J=6.2 Hz), 2.70 (2H, q, J=7.5 Hz), 2.66 (3H, s), 2.44 (3H, s), 2.41 (3H, s), 1.23 (3H, t, J=7.5 Hz).

MS (ESI) m/z: 522 [(M+H)⁺], 520 [(M−H)⁻].

Example 269

2-ETHYL-3-(3-METHYL-4-{2-[({[(4-METHYLPHENYL)SULFONYL]AMINO}CARBONYL)AMINO[ETHYL}PHENYL)-5,7-DIMETHYL-3H-IMIDAZO[4,5-B]PYRIDINE

Step 1. diethyl 2-(2-methyl-4-nitrophenyl)malonate

The title compound was prepared according to the procedure described in step 1 of Example 268 from 4-bromo-3-methylnitrobenzene.

¹H-NMR (CDCl₃) δ: 8.10 (1H, s), 8.05–8.10 (1H, m), 7.62 (1H, d, J=9.2 Hz), 4.93 (1H, s), 4.26 (2H, q, J=7.3 Hz), 4.25 (2H, q, J=7.3Hz), 2.46 (3H, s), 1.28 (6H, t, J=7.3 Hz).

Step 2. 2-(2-methyl-4-nitrophenyl)acetic acid

The title compound was prepared according to the procedure described in step 2 of Example 266 from diethyl 2-(2-methyl-4-nitrophenyl) malonate (step 1)

¹H-NMR (CDCl₃) δ: :8.08 (1H, br.s), 8.02 (1H, dd, J=8.6 Hz), 7.49 (1H, d, J=8.4 Hz), 3.77 (2H, s), 2.35 (3H, s).

Step 3. methyl 2-(2-methyl-4-nitrophenyl)acetate

The title compound was prepared according to the procedure described in step 3 of Example 266 from 2-(2-methyl-4-nitrophenyl)acetic acid (step 2).

¹H-NMR (CDCl₃) δ: 8.07 (1H, d, J=2.1 Hz), 8.02 (1H, dd, J=2.3, 5.9 Hz), 7.36 (1H, d, J=8.4 Hz), 3.74 (2H, s), 3.71 (3H, s), 2.42 (3H, s).

Step 4. methyl 2-(4-amino-2-methylphenyl)acetate

The title compound was prepared according to the procedure described in step 4 of Example 268 from methyl 2-(2-methyl-4-nitrophenyl)acetate (step 3)

¹H-NMR (CDCl₃) δ: 6.97 (1H, d, J=7.9 Hz), 6.48–6.52 (2H,m), 3.67 (3H, s), 3.57 (2H, s), 3.53 (3H, s), 2.22 (3H, s).

Step 5. methyl {4-[(4,6-dimethyl-3-nitro-2-pyridinyl)amino]-2-methyl phenyl}acetate The title compound was prepared according to the procedure described in step 3 of Example 1 from methyl 2-(4-amino-2-methylphenyl) acetate (step 4).

¹H-NMR (CDCl₃) δ: 7.54 (1H, br.d, J=8.3 Hz), 7.38 (1H, br.s), 7.17 (1H, d, J=8.39 Hz), 6.52 (1H, s), 3.69 (3H, s), 3.63 (2H, s), 2.55 (3H, s), 2.43 (3H, s), 2.32 (3H, s).

MS (EI) m/z: 345 (M⁺).

Step 6. methyl {4-[(3-amino-4,6-dimethyl-2-pyridinyl)amino]-2-methylphenyl}acetate The title compound was prepared according to the procedure described in step 2 of Example 28 from methyl {4-[(4,6-dimethyl-3-nitro-2-pyridinyl)amino]-2-methylphenyl}acetate (step 5).

¹H-NMR (CDCl₃) δ: 7.07 (1H, d, J=9.0 Hz), 6.91–6.93 (2H, m), 6.62 (1H, s), 6.36 (1H, br.s), 3.79 (3H, s), 3.67 (3H, s), 3.57 (2H, s), 3.30 (br.s, 2H), 2.37 (3H, s), 2.26 (3H, s), 2.2 (3H, s).

Step 7. methyl 2-[4-(2-ethyl-5,7-dimethyl-3H-imidazo[4,5-b]pyridin-3-yl)-2-methylphenylethyl acetate The title compound was prepared according to the procedure described in step 5 of Example 1 from methyl {4-[(3-amino-4,6-dimethyl-2-pyridinyl)amino]-2-methylphenyl}acetate (step 6).

¹H-NMR (CDCl₃) δ: 7.39 (1H, d, J=7.6 Hz), 7.17–7.25 (2H, m), 6.90 (1H, s), 3.74 (3H, s), 3.72 (2H, s), 2.82 (2H, q, J=7.4 Hz), 2.65 (3H, s), 2.52 (3H, s), 2.40 (3H, s), 1.28 (3H, t, J=7.6 Hz).

MS (EI) m/z: 337 (M⁺).

Step 8. 2-[4-(2-ethyl-5,7-dimethyl-3H-imidazo[4,5-b]pyridin-3-yl)-2-methylphenylethanol The title compound was prepared according to the procedure described in step 8 of Example 266 from methyl 2-[4-(2-ethyl-5,7-dimethyl-3H-imidazo[4,5-b]pyridin-3-yl)-2-methylphenylethyl acetate (step 7).

¹H-NMR (CDCl₃) δ: 7.35 (1H, d, J=7.9 Hz), 7.17 (1H, s), 7.16 (1H, d, J=7.9 Hz), 6.90 (1H, s), 3.84 (2H, dt, J=6.8 Hz), 2.96 (2H, t, J=7.0 Hz), 2.81 (2H, q, J=7.5 Hz), 2.66 (3H, s), 2.52 (3H, s), 2.40 (s, 3H), 1.91 (1H, br.t), 1.28 (3H, t, J=7.5 Hz).

MS (EI) m/z: 324 [(M−H)⁻].

Step 9. 3-[4-(2-chloroethyl)-3-methyl]phenyl-2-ethyl-5,7-dimethyl-3H-imidazo[4,5-b]pyridine The title compound was prepared according to the procedure described in step 7 of Example 1 from 2-[4-(2-ethyl-5,7-dimethyl-3H-imidazo[4,5-b]pyridin-3-yl)-2-methylphenylethanol (step 8).

¹H-NMR (CDCl₃) δ: 7.35 (1H, d, J=8.4 Hz), 7.17–7.19 (2H, m), 6.90 (1H, s), 3.75 (2H, t, J=7.6 Hz), 3.17 (2H, t, J=7.6 Hz), 2.81 (2H, q, J=7.5 Hz), 2.65 (3H, s), 2.41 (3H, s), 2.36 (3H, s), 1.28 (3H, t, J=7.5 Hz).

Step 10. 3-[4-(2-azidoethyl)-3-methylphenyl-2-ethyl-5,7-dimethyl-3H-imidazo[4,5-b]pyridine The title compound was prepared according to the procedure described in step 8 of Example 1 from 3-[4-(2-chloroethyl)-3-methylphenyl-2-ethyl-5,7-dimethyl-3H-imidazo[4,5-b]pyridine (step 9).

¹H-NMR (CDCl₃) δ: 7.34 (1H, d, J=8.7 Hz), 7.19–7.26 (2H, m), 6.90 (1H, s), 3.62 (1H, t, J=7.1 Hz), 3.56 (2H, t, J=7.6 Hz) , 2.99 (2H, t, J=7.6 Hz), 2.81 (2H, q, J=7.6 Hz), 2.65 (3H, s), 2.52 (3H, s) , 2.41 (3H, s), 1.27 (3H, t, J=7.6 Hz).

Step 11. 2-[4-(-2-ethyl-5,7-dimethyl-3H-imidazo[4,5-b]pyridin-3-yl-2-methyl)phenyl]ethanamine The title compound was prepared according to the procedure described in step 9 of Example 1 from 3-[4-(2-azidoethyl)-3-methylphenyl-2-ethyl-5,7-dimethyl-3H-imidazo[4,5-b]pyridine (step 10).

¹H-NMR (CDCl₃) δ: 7.32 (1H, d, J=7.7 Hz), 7.14–7.16 (2H, m), 6.91 (1H, br.s), 6.90 (1H, s), 3.02 (2H, br.t, J=7.3

Hz), 2.77–2.87 (4H, m), 2.65 (3H, s), 2.53 (3H, s), 2.40 (3H, s) 1.28 (3H, t, J=7.5 Hz).

Step 12. 2-ethyl-(3-methyl-4-{2-[({[(4-methylphenyl)sulfonyl]amino}carbonyl)amino]ethyl}phenyl)-5,7-dimethyl-3H-imidazole[4,5-b]pyridine The title compound was prepared according to the procedure described in step 10 of Example 1 from 2-[4-(-2-ethyl-5,7-dimethyl-3H-imidazo[4,5-b]pyridin-3-yl-2-methyl)phenyl]ethanamine (step 11).

$^1$H-NMR (CDCl$_3$) δ: 7.86 (1H, d, J=8.0 Hz), 7.31 (1H, d, J=8.0 Hz), 7.03 (1H, d, J=7.9 Hz), 6.91 (1H, s), 6.85 (1H, d, J=8.4 Hz), 6.07–6.11 (1H, m), 3.51 (2H, q, J=6.4 Hz), 2.85 (2H, t, J=6.4 Hz), 261–2.69 (2H, m), 2.69 (3H, s), 2.44 (3H, s), 2.28 (3H, s), 1.23 (3H, t, J=7.5 Hz).

MS (ESI) m/z: 506 [(M+H)$^+$], 504 [(M−H)$^−$].

Example 270
6-CHLORO-2-ETHYL-1-(6-{2-[({[(4-METHYLPHENYL)SULFONYL]AMINO}CARBONYL)AMINO]ETHYL}-3-PYRIDINYL)-5-(TRIFLUOROMETHYL)-1H-BENZIMIDAZOLE Step 1. (4-amino-2-pyridinyl)acetonitrile The title compound was prepared according to the procedure described in step 2 of Example 28 from (4-nitro-2-pyridinyl)acetonitrile (8.6 g, 52.9 mmol, Katz; R. B.; Voyle, M., *Synthesis.*, 1989, 4, 314.).

$^1$H-NMR (CDCl$_3$) δ: 8.04 (1H, d, J=2.8 Hz), 7.17 (1H, d, J=8.2 Hz), 6.99 (1H, dd, J=2.8, 8.4 Hz), 3.81 (2H, s), 3.76 (2H, br.s).

Step 2. {5-[5-chloro-2-nitro-4-(trifluoromethyl)anilino]-2-pyridinyl}acetonitrile The title compound was prepared according to the procedure described in step 3 of Example 1 from (5-aminopyridine-2-yl)acetonitrile (step 1). $^1$H-NMR (CDCl$_3$) 67: 9.66 (1H, s), 8.60 (2H,m), 7.71 (1H, dd, J=2.6, 8.4 Hz), 7.60 (1H, d, J=8.3 Hz), 7.13 (1H, s), 4.03 (2H, s)

MS (EI) m/z: 356 (M$^+$).

Step 3. {5-[2-amino-5-chloro-4-(trifluoromethyl)anilino]-2-pyridinyl}acetonitrile The title compound was prepared according to the procedure described in step 2 of Example 28 from {5-[5-chloro-2-nitro4-(trifluoromehyl)anilino]-2-pyridinyl}acetonitrile (step 2).

$^1$H-NMR (CDCl$_3$) δ: 8.25 (1H, d, J=2.1 Hz), 7.12–7.34 (3H, m), 5.47 (1H, br.s), 3.89 (2H, s), 3.78 (2H, br.s).

Step 4. {5-[6-chloro-2-ethyl-5-(trifluoromehyl)-1H-benzimidazol-1-yl]-2-pyridinyl}acetonitrile The title compound was prepared according to the procedure described in step 5 of Example 1 from {5-[2-amino-5-chloro-4-(trifluoromehyl)anilino]-2-pyridinyl}acetonitrile (step 3). $^1$H-NMR (CDCl$_3$) δ: 8.66 (1H, s), □□□□□(1H, s), 7.73–7.83 (2H, m), 7.12 (1H, s), 4.12 (2H, s), 2.79 (2H, q, J=7.6 Hz), 1.40 (3H, t, J=7.6 Hz).

Step 5. 2-{5-[6-chloro-2-ethyl-5-(trifluoromehyl)-1H-benzimidazol-1-yl]-2-pyridinyl}ethanamine To a solution of {5-[6-chloro-2-ethyl-5-(trifluoromehyl)-1H-benzimidazol-1-yl]-2-pyridinyl}acetonitrile (step 4, 1.0 g, 2.8 mmol), in ammonia-ethanol (30 ml) was added Raney-Ni and stirred for 8 h under hydrogen atmosphere (3.0 kgf/cm$^2$). The catalyst was filtered off and the solvent was removed. The residue was diluted with ethyl acetate, washed with brine, dried (MgSO$_4$) and concentrated to give 813 mg of title compound as black solid.

MS (EI) m/z: 368 (M$_+$).

Step 6. 6-chloro-2-ethyl-1-(6-{2-[({[(4methylphenyl)sulfonyl]amino}carbonyl)amino]ethyl}-3-pyridinyl)-5-(trifluoromehyl)-1H-benzimidazol The title compound was prepared according to the procedure described in step 10 of Example 1 from 2-{5-[6-chloro-2-ethyl-5-(trifluoromethyl)-1H-benzimidazol-1-yl]-2-pyridinyl}ethanamine (step 5).

$^1$H-NMR (CDCl$_3$) δ: 8.63 (1H, d, J=2.2 Hz), 8.14 (1H, s), 7.77 (2H, d, J=8.3 Hz), 7.66 (1H, dd, J=2.6, 8.3 Hz), 7.45 (1H, d, J=8.3 Hz), 7.30 (2H, d, J=8.4 Hz), 7.21(1H, s), 3.73–3.80 (2H, m), 3.17 (2H, t, J=6.2 Hz), 2.79 (2H, q, J=7.5 Hz), 2.42 (3H, s), 1.38 (3H, t, J=7.5 Hz).

MS (ESI) m/z: 566 [(M+H)$^+$], 564 [(M−H)$^−$].

Example 271
6-CHLORO-2-ETHYL-1-(6-{2-[({[(4-METHYLPHENYL)SULFONYL]AMINO}CARBONYL)AMINO]ETHYL}-3-PYRIDINYL)-5-(TRIFLUOROMETHYL)-1H-BENZIMIDAZOLE SODIUMSALT The title compound was prepared according to the procedure described in Example 2 from 6-chloro-2-ethyl-1-(6-{2-[({[(4methylphenyl)sulfonyl]amino}carbonyl)amino]ethyl}-3-pyridinyl)-5-(trifluoromehyl)-1H-benzimidazol (Example 270). $^1$H-NMR (DMSO-d$_6$) δ: 8.71 (1H, br.s), 8.20 (1H, br.s) 7.95 (1H, m), 7.43–7.64 (4H, m), 7.12 (2H, br.s), 6.09 (1H, br.s), 3.39 (2H, br.s), 2.92 (2H, br.s), 2.73 (2H, br.s), 2.28 (3H, br.s), 1.27 (3H, br.s).

MS (ESI) m/z: 566 [(M+H)$^{30}$ ], 564 [(M−H)$^−$].

Example 272
2-{5-[6-CHLORO-2-ETHYL-5-(TRIFLUOROMETHYL)-1H-BENZIMIDAZOL-1-YL]-2-PYRIDINYL}ETHYL(4-METHYLPHENYL)SULFONYLCARBAMATE Step 1. ethyl(5-amino-2-pyridinyl)acetate To a solution of (5-amino-2-pyridinyl)acetic acid (1.46 g, 9.6 mmol, Daisley; R. W.; Hanbali, J. R., *Synthetic Communications.*, 1981, 11(9), 743.) in ethanol was added conc. H$_2$SO$_4$ and stirred for 16.5 h under hydrogen atmosphere at room temperature. The mixture was neutralized with saturated NaHCO$_3$ aqueous solution and the solvent was removed. The mixture was diluted with water and extracted with ethyl acetate (5×20 ml). The organic layer was washed with brine, dried (MgSO$_4$) and concentrated to give 1.2 g of title compound as brown oil.

$^1$H-NMR (CDCl$_3$) δ: 8.04 (1H, d, J=2.8 Hz), 7.07 (1H, d, J=8.2 Hz), 6.96 (1H, dd, J=2.6, 8.2 Hz), 4.71 (2H, q, J=7.1 Hz), 3.72 (2H, s), 3.66 (2H, br.s), 1.25 (3H, t, J=7.1 Hz).

Step 2. Ethyl {5-[5-chloro-2-nitro4-(trifluoromehyl)anilino]-2-pyridinyl}acetate The title compound was prepared according to the procedure described in step 3 of Example 1 from ethyl (5-amino-2-pyridinyl)acetate (step 1).

$^1$H-NMR (CDCl$_3$) δ: 9.66 (1H, s), 8.60 (2H,m), 7.71 (1H, dd, J=2.6, 8.4 Hz), 7.60 (1H, d, J=8.3 Hz), 7.13 (1H, s), 4.03 (2H, s)

MS (EI) m/z: 356 (M$^+$).

Step 3. ethyl {5-[2-amino-5-chloro-4-(trifluoromehyl)anilino]-2-pyridinyl}acetate The title compound was prepared according to the procedure described in step 2 of Example 28 from ethyl {5-[5-chloro-2-nitro4-(trifluoromehyl)anilino]-2-pyridinyl}acetate (step 2).

$^1$H-NMR (CDCl$_3$) δ: 7.25 (1H, d, J=1.5 Hz), 7.21 (1H, m), 7.16 (1H, s), 7.09 (1H, s), 7.47 (1H, d, J=8.2 Hz), 5.47 (1H, s), 4.20 (2H, q, J=7.2 Hz), 3.80 (2H, s), 3.77 (2H, br.s), 1.28 (3H, t, J=7.2 Hz).

Step 4. ethyl {5-[6-chloro-2-ethyl-5-(trifluoromehyl)-1H-benzimidazol-1-yl]-2-pyridinyl}acetate The title compound was prepared according to the procedure described in step 5 of Example 1 from ethyl {5-[2-amino-5-chloro-4-(trifluoromehyl)anilino]-2-pyridinyl}acetate (step 3).

$^1$H-NMR (CDCl$_3$) δ: 8.61 (1H, d, J=2.0 Hz), □□□□□ (1H. s), 7.71 (1H, dd, J=2.0, 8.2 Hz), 7.62 (1H, d, J=8.2 Hz), 7.21 (1H, s), 4.27 (1H, q, J=7.3 Hz), 4.01 (2H, s), 2.79 (2H, q, J=7.6 Hz), 1.38 (3H, t, J=7.4 Hz), 1.33 (3H, t, J=7.1 Hz).

Step 5. 2-{5-[6-chloro-2-ethyl-5-(trifluoromehyl)-1H-benzimidazol-1-yl]-2-pyridinyl}ethanol The title compound was prepared according to the procedure described in step 8 of Example 266 from ethyl {5-[6-chloro-2-ethyl-5-(trifluoromehyl)-1H-benzimidazol-1-yl]-2-pyridinyl}acetate (step 4).

$^{1}$H-NMR (CDCl$_{3}$) δ: 8.57 (1H, d, J=2.50 Hz), ☐☐☐☐ (1H, s), 7.67 (1H, dd, J=2.6, 8.2 Hz), 7.49 (1H, d, J=8.2 Hz), 7.20 (1H, s), 4.15 (1H, q, J=5.6 Hz), 3.20 (2H, t, J=5.4 Hz), 2.79 (2H, q, J=7.4 Hz), 1.39 (3H, t, J=7.6 Hz).

Step 6. 2-{5-[6-chloro-2-ethyl-5-(trifluoromehyl) -1H-benzimidazol-1-yl-]-2-pyridinyl}ethyl](4methylphenyl)sulfonylcarbamate The title compound was prepared according to the procedure described in Example 3 from 2-{5-[6-chloro-2-ethyl-5-(trifluoromehyl )-1H-benzimidazol-1-yl]-2-pyridinyl}ethanol (step 5).

$^{1}$H-NMR (CDCl$_{3}$) δ: 8.59 (1H, d, J=2.3 Hz), 8.13 (1H, s), 7.88 (2H, d, J=8.4 Hz), 7.56 (1H, dd, J=2.5, 8.2 Hz), 7.44 (1H, d, J=8.1 Hz), 7.32 (2H, d, J=8.1 Hz), 7.20(1H, s), 4.57 (2H, t, J=6.4 Hz), 3.25 (2H, t, J=6.6 Hz), 2.79 (2H, q, J=7.4 Hz), 2.42 (3H, s), 1.38 (3H, t, J=7.4 Hz).

MS (ESI) m/z: 567 [(M+H)$^{+}$].

Example 273
2-{5-[6-CHLORO-2-ETHYL-5-(TRIFLUOROMETHYL)-1H-BENZIMIDAZOL-1-YL]-2-PYRIDINYL}ETHYL(4-METHYLPHENYL)SULFONYLCARBAMATE HYDROCHLORIDE The title compound was prepared according to the procedure described in Example 240 from 2-{5-[6-chloro-2-ethyl-5-(trifluoromehyl) -1H-benzimidazol-1-yl]-2-pyridinyl}ethyl](4methylphenyl)sulfonylcarbamate (Example 273).

$^{1}$H-NMR (DMSO-d$_{6}$) δ: 11.9 (1H, br.s), 8.72 (1H, br.s), 8.18 (1H, s), 8.03–8.07 (1H, m), 7.74 (1H, d, J=7.6 Hz), 7.58 (1H, d, J=8.2 Hz), 7.43 (2H, d, J=5.1 Hz), 7.39(1H, s), 4.45 (2H, t, J=6.2 Hz), 3.17 (2H, t, J=6.2 Hz), 2.76 (2H, q, J=7.6 Hz), 2.35 (3H, s), 1.27 (3H, t, J=7.3 Hz).

MS (ESI) m/z: 567 [(M+H)$^{+}$], 565 [(M−H)$^{−}$].

Example 274
2-ETHYL-3-(4-{2-[({[4-PYRIDINYLSULFONYL]AMINO}CARBONYL)AMINO]ETHYL}PHENYL)-5,7-DIMETHYL-3H-IMIDAZO[4,5-b]PYRIDINE The title compound was prepared according to the procedure described in step 2 of Example 18 from phenyl 2-[4-(2-ethyl-5,7-dimethy]-3H-imidazo[4,5-b]pyridin-3-yl)phenyl]ethylcarbamate (step 1 of Example 18) and pyridinyl-4-sulfonamide (Chern, Ji-Wang; Leu, Yu-Ling; et al., J. Med. Chem., 1997, 40, 2276.; Graham, Samuel L.; Shepard, Kenneth L.; et al.,J. Med. Chem., 1989, 32, 2548).

m.p.: 227.9–228.7° C.

$^{1}$H-NMR (CDCl$_{3}$) δ: 8.63 (2H, d, J=5.9 Hz), 7.65 (2H, d, J=5.9 Hz), 7.36 (4H, s), 6.96 (1H, s), 3.20 (2H, br.s), 2.75(br.s, 2H), 2.70 (2H, q, J=7.6 Hz), 2.53 (2H, s), 2.40 (3H, s), 1.20 (3H, t, J=7.6 Hz).

MS (ESI) m/z: 479 [(M+H)$^{+}$], 477 [(M−H)$^{−}$].

Example 275
2-ETHYL-3-(4-{2-[({[2-PYRIDINYLSULFONYL]AMINO}CARBONYL)AMINO]ETHYL}PHENYL)-5,7-DIMETHYL-3H-IMIDAZO[4,5-b]PYRIDINE The title compound was prepared according to the procedure described in step 2 of Example 18 from phenyl 2-[4-(2-ethyl-5,7-dimethyl-3H-imidazo[4,5-b]pyridin-3-yl)phenyl]ethylcarbamate (step 1 of Example 18) and pyridinyl-2-sulfonamide (Chern, Ji-Wang; Leu, Yu-Ling; et al., J. Med. Chem., 1997, 40, 2276.; Graham, Samuel L.; Shepard, Kenneth L.; et al.,J. Med. Chem., 1989, 32, 2548).

$^{1}$H-NMR (CDCl$_{3}$) δ: 8.51 (1H, br.s), 8.08 (1H, br.s), 7.94 (1H, br.s), 7.29 (2H, s), 7.19 (1H, br.s), 6.91 (1H, s), 2.81 (2H, br.s), 2.73 (2H, q, J=7.6 Hz), 2.66 (3H, s), 2.78 (3H, s), 2.49 (m, 2H), 1.26 (3H, t, J=7.3 Hz).

MS (ESI) m/z: 479 [(M+H)$^{+}$], 477 [(M−H)$^{−}$].

Example 276
2-ETHYL-3-(4-{2-[({[3-PYRIDINYLSULFONYL]AMINO}CARBONYL)AMINO]ETHYL}PHENYL)-5,7-DIMETHYL-3H-IMIDAZO[4,5-b]PYRIDINE The title compound was prepared according to the procedure described in step 2 of Example 18 from phenyl 2-[4-(2-ethyl-5,7-dimethyl-3H-imidazo[4,5-b]pyridin-3-yl)phenyl]ethylcarbamate (step 1 of Example 18) and pyridinyl-3-sulfonamide (Chern, Ji-Wang; Leu, Yu-Ling; et al., J. Med. Chem., 1997, 40, 2276.; Graham, Samuel L.; Shepard, Kenneth L.; et al.,J. Med. Chem., 1989, 32, 2548).

$^{1}$H-NMR (CDCl$_{3}$) δ: 9.15 (1H, d, J=1.9 Hz), 8.83 (1H, dd, J=1.9, 5.1 Hz), 8.34 (1H, dd, J=6.5 Hz), 7.50 (1H, dd, J=4.9, 8.1 Hz), 7.12–7.23 (4H, m), 6.93 (1H, s), 5.92 (1H, br.s), 3.51 (2H, q J=5.9 Hz), 2.86 (2H, m), 2.69 (3H, m), 2.66 (3H, s), 2.43(3H, s), 1.27 (3H, t, J=7.6 Hz).

MS (ESI) m/z: 479 [(M+H)$^{+}$]

Example 277
2-{4-[6-CHLORO-2-ETHYL-5-(TRIFLUOROMETHYL)-1H-BENZIMIDAZOL-1-YL1-2-PHENYL}ETHYL-(2-CHLOROPHENYL)SULFONYLCARBAMATE The title compound was prepared according to the procedure described in step 2 of Example 243 from 2-{4-[6-chloro-2-ethyl-5-(trifluoromethyl)-1H-benzimidazol-1-yl]phenyl}ethyl phenyl carbonate and 2-chlorophenylsulfonamide.

$^{1}$H-NMR (CDCl$_{3}$) δ: 8.18 (1H, s), 8.07 (1H, d, J=7.8Hz), 7.69 (1H, d, J=3.8 Hz), 7.59 (1H, dd, J=4.3, 8.1 Hz), 7.51 (2H, d, J=8.4 Hz), 7.44 (2H, d, J=8.4Hz), 7.31 (1H, s), 4.29 (2H, t, J=6.2 Hz), 2.94 (2H, t, J=6.5 Hz), 2.76 (2H, q, J=7.6 Hz), 1.26 (3H, t, J=7.3 Hz)

m.p. 202.4–202.8° C.

MS (ESI) m/z: 586 [(M+H)$^{+}$], 584 [(M−H)$^{−}$]

Example 278
2-[4-(2-ETHYL-5,7-DIMETHYL-3H-IMIDAZO[4,5-b]PYRIDIN-3-YL)PHENYL]-1,1-DIMETHYLETHYL(4-METHYLPHENYL)SULFONYLCARBAMATE Step 1. 2-methyl-1-(4-nitrophenyl)-2-propanol To a solution of 1,1-dimethyl-2-(4-nitrophenyl)ethyl acetate (52 mmol) in MeOH (50 ml) was added 4N-LiOH (40 ml) and the mixture was stirred at 50° C. for 2 h. After the solvent was removed, this mixture was diluted with water and extracted with EtOAc (4×50ml). The organic layer was washed with brine, dried (MgSO$_{4}$) and concentrated. This crude was purified by SiO$_{2}$ column chromatography developing with hexane/ethyl acetate (5/1) to give the title compound as yellow oil (3.3 g, 33%).

$^{1}$H-NMR (CDCl$_{3}$) δ: 8.17 (2H, d, J=8.9 Hz), 7.40 (2H, d, J=8.6 Hz), 2.88 (2H, s), 1.63 (1H, br.s) 1.25 (6H, s)

Step 2. 1-(4-aminophenyl)-2-methyl-2-propanol

The title compound was prepared according to the procedure described in step 2 of Example 28 from 2-methyl-1-(4-nitrophenyl)-2-propanol (step 1).

$^{1}$H-NMR (CDCl$_{3}$) δ: 7.00 (2H, d, J=8.4 Hz), 6.65 (2H, d, J=8.4 Hz), 3.61 (2H, br.s), 2.65 (2H, s), 1.39 (1H, br.s), 1.20 (6H, s)

Step 3. 1-{4-[(4-,6-dimethyl-3-nitro-2-pyridinyl)aminophenyl}-2-methyl-2-propanol The title compound was prepared according to the procedure described in step 5 of Example 266 from 1-(4-aminophenyl)-2-methyl-2-propanol (step 2)

$^{1}$H-NMR (CDCl$_{3}$) δ: 9.60 (1H, s), 7.59 (2H, d, J=8.7 Hz), 7.19 (2H, d, J=8.4 Hz), 6.52 (1H, s), 2.75 (2H, s), 2.54 (3H, s), 2.43 (3H, s), 1.24 (6H, s)

Step 4. 1-{4-[(3-amino-4,6-dimethyl-2-pyridinyl)amino]phenyl}-2-methyl-2-propanol The title compound was prepared according to the procedure described in step 2 of Example 28 from 1-{4-[(4,6-dimethyl-3-nitro-2-pyridinyl)amino]phenyl}-2-methyl-2-propanol (step 3)

$^1$H-NMR (CDCl$_3$) δ: 7.10 (4H, s), 6.61 (1H, s), 6.33 (2H, s), 3.28 (1H, br.s), 2.70 (2H, s), 2.73 (3H, s), 2.20 (3H, s), 1.22 (6H, s)

Step 5. 2-[4-(2-ethyl-5,7-dimethyl-3H-imidazo[4,5-b]pyridin-3-yl)phenyl]-2-methyl-2-propanol The title compound was prepared according to the procedure described in step 5 of Example 1 from 1-{4-[(3-amino-4,6-dimethyl-2-pyridinyl)amino]phenyl}-2-methyl-2-propanol (step 4).

$^1$H-NMR (CDCl$_3$) δ: 7.42 (2H, d, J=8.1 Hz), 7.33 (2H, d, J=8.47 Hz), 6.91 (1H, s), 2.87 (2H, s), 2.84 (2H, q, J=7.6 Hz), 2.66 (3H, s), 2.52 (3H, s), 1.31 (6H, s), 1.28 (2H, d, J=7.6 Hz)

Step 6. 2-[4-(2-ethyl-5,7-dimethyl-3H-imidazo[4,5-b]pyridin-3-yl)phenyl]-1,1-dimethylethyl(4-methylphenyl)sulfonylcarbamate The title compound was prepared according to the procedure described in Example 3 from 2-[4-(2-ethyl-5,7-dimethyl-3H-imidazo[4,5-b]pyridin-3-yl)phenyl]-2-methyl-2-propanol (step 5).

$^1$H-NMR (CDCl$_3$) δ: 7.94 (2H, t, J=8.6 Hz), 7.33 (2H, d, J=8.6 Hz), 7.16 (4H, m), 6.93 (1H, s), 3.10 (2H, s), 2.81 (2H, q, J=7.6 Hz), 2.67 (3H, s), 2.54 (3H, s), 2.40 (3H, s), 2.42 (3H, s), 1.48 (6H, s), 1.28 (3H, t, J=7.6 Hz)

m.p. 173.5–174.0° C.

MS (ESI) m/z: 521 [(M+H)$^+$], 519 [(M−H)$^−$]

Example 279

6-CHLORO-2-ETHYL-1-(6-{2-[({[(4-METHYLPHENYL)SULFONYL]AMINO}CARBONYL)AMINO]ETHYL}-3-PYRIDINYL)-5-(TRIFLUOROMETHYL)-1H-BENZIMIDAZOLE

Step 1. (6-{[5-chloro-2-nitro-4-(trifluoromehyl)phenyl]amino}-3-pyridinyl)methanol The title compound was prepared according to the procedure described in step 5 of Example 266 from 1-(6-amino-3-pyridinyl)methanol.

$^1$H-NMR (CDCl$_3$) δ: 10.51 (1H, br.s), 9.26 (1H, s), 8.60 (1H, s), 8.42 (1H, s), 7.79 (1H, d, J=8.1 Hz), 7.01 (1H, d, J=8.1 Hz), 4.75 (2H, s).

Step 2. (6-{[2-amino-5-chloro-4-(trifluoromehyl)phenyl]amino}-3-pyridinyl)methanol The title compound was prepared according to the procedure described in step 2 of Example 28 from {5-[5-chloro-2-nitro-4-(trifluoromehyl)anilino]-3-pyridinyl}methanol (step 1).

MS (EI) m/z: 317 (M$^+$).

Step 3. {6-[6-chloro-2-ethyl-5-(trifluoromehyl)-1H-benzimidazol-1-yl]-3-pyridinyl}methanol proionate The title compound was prepared according to the procedure described in step 5 of Example 1 from {6-{[2-amino-5-chloro-4-(trifluoromehyl)phenyl]amino}-3-pyridinyl}methanol. (Step 2).

MS (EI) m/z: 411 (M$^+$).

Step 4 {6-[6-chloro-2-ethyl-5-(trifluoromehyl)-1H-benzimidazol-1-yl]-3-pyridinyl}methanol;

The title compound was prepared according to the procedure described in step 6 of Example 1 from {5-[5-chloro-2-nitro4-(trifluoromehyl)anilino]-3-pyridinyl}methyl propionate (step 3).

$^1$H-NMR (CDCl$_3$) δ: 8.67 (1H, s), 8.19 (1H, s), 8.09 (1H, d, J=8.6 Hz), 7.79 (1H, d, J=8.4 Hz), 7.65 (1H, s), 5.54 (1H, t, J=5.6 Hz), 4.69 (2H, d, J=5.6 Hz), 2.95 (2H, q, J=7.3 Hz), 1.27 (3H, t, J=7.2 Hz).

Step 5 6-chloro-1-[5-(chloromethyl )-2-pyridinyl]-2-ethyl-5-(trifluoromehyl)-1H-benzimidazole The title compound was prepared according to the procedure described in step 7 of Example 1 from {5-[5-chloro-2-nitro4-(trifluoromehyl)anilino]-3-pyridinyl}methanol (step 4).

$^1$H-NMR (CDCl$_3$) δ: 8.72 (1H, d, J=2.2 Hz), 8.12 (1H, s), 8.07 (1H, dd, J=2.2, 8.1 Hz), 7.45–7.48 (2H, m), 4.72 (2H, s), 3.01 (2H, q, J=7.6 Hz), 1.39 (3H, t, J=7.6 Hz).

Step 6 {6-[6-chloro-2-ethyl-5-(trifluoromethyl)-1H-benzimidazol-yl]-3-pyridinyl}acetonitrile To a solution of 6-chloro-1-[5-(chloromethyl)-2-pyridinyl]-2-ethyl-5-(trifluoromethyl)-1H-benzimidazole (from step 5, 550 mg, 1.5 mmol) in DMF (5 ml) and water (1 ml) was added KCN (470 g, 7.2 mmol) at room temperature, and then the reaction mixture was stirred for 2h. The mixture was diluted with water and extracted with ethyl acetate/toluene (4/1) solution (3×30 ml). The organic layer was washed with water, dried (MgSO$_4$) and concentrated. This was purified by SiO$_2$ column chromatography developing with hexane/ethyl acetate (1/) gave 198 mg (37%) of title compound as orange oil.

$^1$H-NMR (CDCl$_3$) δ: 8.70 (1H, d, J=2.6 Hz), 8.13 (1H, s), 8.06 (1H, dd, J=2.6, 8.0 Hz), 7.52 (1H, d, J=8.20 Hz), 7.47 (1H, s), 3.94 (2H, s), 3.01 (2H, q, J=7.5 Hz), 1.40 (3H, t, J=7.5 Hz)

Step 7 2-{6-[6-chloro-2-ethyl-5-(trifluoromethyl)-1H-benzimidazol-yl]-3-pyridinyl}ethanamine The title compound was prepared according to the procedure described in step 5 of Example 270 from {6-[6-chloro-2-ethyl-5-(trifluoromethyl)-1H-benzimidazol-yl]-3-pyridinyl}acetonitrile (step 6).

MS (EI) m/z: 368 (M$^+$).

Step 8 6-chloro-2-ethyl-1-(6-{2-[({[(4methylphenyl)sulfonyl]amino}carbonyl)amino]ethyl}2-pyridinyl)-5-(trifluoromehyl)-1H-benzimidazol The title compound was prepared according to the procedure described in step 10 of Example 1 from 2-{5-[6-chloro-2-ethyl-5-(trifluoromethyl)-1H-benzimidazol-1-yl]-3-pyridinyl}ethanamine (step 7).

$^1$H-NMR (CDCl$_3$) δ: 8.50 (1H, s), 8.12 (1H, s), 7.817 (1H, d, J=6.0 Hz), 7.72 (2H, dt, J=8.4 Hz), 7.42 (1H, s), 7.24–7.37 (3H, m), 7.21 (1H, s), 6.77 1, br.s), 3.60 (2H, dt, J=6.2 Hz), 2.94–3.01 (4H, m), 2.37 (3H, s), 1.37 (3H, t, J=7.5 Hz).

MS (ESI) m/z: 566 [(M+H)$^+$], 564 [(M−H)$^−$].

Example 280

2-{4-[5-CHLORO-2-ETHYL-5-(TRIFLUOROMETHYL)-1H-BENZIMIDAZOL-1-YL]PHENYL}-1,1-DIMETHYLETHYL(4-METHYLPHENYL)SULFONYLCARBAMATE

Step 1. 1-(4-{[5-chloro-2-nitro-4-(trifluoromehyl)phenyl]amino}phenyl)-2-methyl-2-propanol The title compound was prepared according to the procedure described in step 5 of Example 266 from 1-(4-aminophenyl)-2-methyl-2-propanol $^1$H-NMR (CDCl$_3$) δ: 9.70 (1H, br.s), 8.58 (1H, s), 7.36 (2H, d, J=8.4Hz), 7.21–7.25 (3H, m) 2.83 (2H, s), 1.28 (6H, s)

MS (EI) m/z: 388 (M$^+$)

Step 2. 1-(4-{[2-amino-5-chloro-4-(trifluoromethyl)phenyl]amino}phenyl)-2-methyl-2-propanol The title compound was prepared according to the procedure described in step 2 of Example 28 from 1-(4-{[5-chloro-2-nitro-4-(trifluoromehyl)phenyl]amino}phenyl)-2-methyl-2-propanol (step 1)

$^1$H-NMR (CDCl$_3$) δ: 7.10 (4H, s), 6.61 (1H, s), 6.33 (2H, s), 3.28 (1H, br.s), 2.70 (2H, s), 2.37 (3H, s), 2.20 (3H, s), 1.22 (6H, s)

MS (EI) 388 (M$^+$)

Step 3. 1-{4-[6-chloro-2-ethyl-5-(trifluoromethyl)-1H-benzimidazol-1-yl]Phenyl}-2-propanol The title compound was prepared according to the procedure described in step 5 of Example 1 from 1-(4-{[2-amino-5-chloro-4-(trifluoromethyl)phenyl]amino}phenyl)-2-methyl-2-propanol (step 2).

$^1$H-NMR (CDCl$_3$) δ: 8.12 (1H, s), 7.48 (2H, d, J=8.4 Hz), 7.28 (2H, d, J=8.4 Hz), 7.22 (1H, s), 2.90 (2H, s), 2.80 (2H, q, J=7.3 Hz), 1.36 (3H, t, J=7.3 Hz) 1.32 (6H, s)

MS (EI) m/z: 396 (M$^+$)

Step 4. 2-{4-[5-chloro-2-ethyl-5-(trifluoromethyl)-1H-benzimidazol-1-yl]phenyl}-1,1-dimethylethyl(4-methylphenyl)sulfonylcarbamate The title compound was prepared according to the procedure described in Example 3 from 2-[4-(2-ethyl-5,7-dimethyl-3H-imidazo[4,5-b]pyridin-3-yl)phenyl]-2-methyl-2-propanol (step 3).

$^1$H-NMR (CDCl$_3$) δ: 8.12 (1H, s), 7.94 (2H, d, J=8.7 Hz), 7.36 (2H, d, J=8.1 Hz), 7.15–7.27 (5H, m), 3.16 (2H, s), 2.78 (2H, q, J=7.6 Hz), 2.43 (3H, s), 1.47 (6H, s), 1.37 (3H, t, J=7.6 Hz)

m.p. 174.6–175.3° C.

MS (ESI) m/z: 594 [(M+H)$^+$], 592 [(M−H)$^−$]

Example 281

2-{4-[6-CHLORO-2-ETHYL-5-(TRIFLUOROMETHYL)-1H-BENZIMIDAZOL-1-YL]PHENYL}ETHYL(2,4-DIMETHYL-1,3-THIAZOL-5-YL)SULFONYLCARBAMATE

The title compound was prepared according to the procedure described in step 2 of Example 243 from 2-{4-[6-chloro-2-ethyl-5-(trifluoromethyl)-1H-benzimidazol-1-yl]phenyl}ethyl phenyl carbonate and 2,4-dimethyl-1,3-thiazol-5-yLsulfonamide.

$^1$H-NMR (CDCl$_3$) δ: 8.12 (1H, s), 7.41 (2H, d, J=7.9 Hz), 7.27 (2H, d, J=7.9 Hz), 7.20 (1H, s), 4.45 (2H, t, J=6.9 Hz), 3.08 (2H, t, J=6.6 Hz), 2.79 (2H, q, J=7.7 Hz), 2.71 (3H, s), 2.68 (3H, s), 1.36 (3H, t, J=7.7 Hz)

m.p. 168.3–169.0° C.

MS (ESI) m/z: 587 [(M+H)$^+$], 585 [(M−H)$^−$]

Example 282

2-{4-[6-CHLORO-2-ETHYL-5-(TRIFLUOROMETHYL)-1H-BENZIMIDAZOL-1-YL]PHENYL}ETHYL(5-CHLORO-1,3-DIMETHYL-1H-PYRAZOL-4-YL)SULFONYLCARBAMATE

The title compound was prepared according to the procedure described in step 2 of Example 243 from 2-{4-[6-chloro-2-ethyl-5-(trifluoromethyl)-1H-benzimidazol-1-yl]phenyl}ethyl phenyl carbonate and 5-chloro-1,3-dimethyl-1H-pyrazol-4-yl sulfonamide.

$^1$H-NMR (CDCl$_3$) δ: 8.12 (1H, s), 7.41 (2H, d, J=7.9 Hz), 7.27 (2H, d, J=7.9 Hz), 7.20 (1H, s), 4.45 (2H, t, J=6.9 Hz), 3.08 (2H, t, J=6.6 Hz), 2.79 (2H, q, J=7.7 Hz), 2.71 (3H, s), 2.68 (3H, s), 1.36 (3H, t, J=7.7 Hz)

m.p. 192.0–192.7° C.

MS (ESI) m/z: 604 [(M+H)$^+$], 602 [(M−H)$^−$]

Example 283

2-{4-[5-CHLORO-2-ETHYL-5-(TRIFLUOROMETHYL)-1H-BENZIMIDAZOL-1-YL]PHENYL}PROPYL(4-METHYLPHENYL)SULFONYLCARBAMATE

Step 1. 2-(4-aminophenyl)1-propanol

To a stirred solution of 2-(4-amino-phenyl)-propionic acid ethyl ester (5.0 g, 25.9 mmol, Takahashi, I. et al., *Heterocycles* 1996, 43, 2343–2346.) in tetrahydrofurane (200 ml) was slowly added lithiumaluminium hydride (1.96 g, 51.8 mmol), and the mixture was stirred at room temperature for 14 h. The reaction mixture was quenched with 25% ammonia solution (50 ml) under ice-bath cooling. The resulting precipitate was filtered off, and the filtrate concentrated under reduced pressure to afford 3.88 g (99%) of the title compound as slight brown syrup.

$^1$H-NMR (CDCl$_3$) δ: 7.03 (2H, d, J=8.5 Hz), 6.66 (2H, d, J=8.5 Hz), 3.70–3.57 (4H, m), 2.90–2.78 (1H, m), 1.34–1.30 (1H, m), 1.22 (3H, d, J=7.1 Hz).

MS (EI) m/z: 151 (M$^+$).

Step 2. 2-(4-{[5-chloro-2-nitro-4-(trifluoromethyl)phenyl]amino}phenyl)-1-propanol The title compound was prepared according to the procedure described in step 5 of Example 266 from 2-(4-aminophenyl)1-propanol (step 1)

$^1$H-NMR (CDCl$_3$) δ: 9.69 (1H, br.s), 8.58 (1H, s), 7.38 (2H, d, J=8.3 Hz), 7.21–7.26 (3H, m), 3.77 (2H, m), 3.03 (1H, m), 1.41 (1H, t, J=5.7 Hz), 1.33 (3H, d, J=7.1 Hz)

Step 3. 2-(4-{[2-amino-5-chloro-4-(trifluoromethyl)phenyl]amino}phenyl)-1-propanol The title compound was prepared according to the procedure described in step 2 of Example 28 from 2-(4-{[5-chloro-2-nitro-4-(trifluoromethyl)phenyl]amino}phenyl)-1-propanol (step 2)

$^1$H-NMR (CDCl$_3$) δ: 7.21–7.26 (3H, m), 7.07 (1H, s), 6.93 (2H, d, J=8.4 Hz), 5.41 (1H, br.s), 3.68–3.69 (2H, br.s), 2.93 (1H, m), 1.38 (1H, br.s), 1.28 (3H, d, J=7.1 Hz)

Step 4. 2-{4-[6-chloro-2-ethyl-5-(trifluoromethyl)-1H-benzimidazol-1-yl]phenyl}-1-propanol The title compound was prepared according to the procedure described in step 5 of Example 1 from 2-(4-{[2-amino-5-chloro-4-(trifluoromethyl)phenyl]amino}phenyl)1-propanol (step 3).

$^1$H-NMR (CDCl$_3$) δ: 8.12 (1H, s), 7.49 (2H, d, J=2.3 Hz), 7.30 (2H, d, J=8.4 Hz), 7.22 (1H, s), 3.83 (2H, m), 3.11 (1H, m), 2.80 (2H, q, J=7.6 Hz) 1.57 (1H, m), 1.33–1.40 (6H, m).

Step 5. 2-{4-[5-chloro-2-ethyl-5-(trifluoromethyl)-1H-benzimidazol-1-yl]phenyl-1,1-dimethylethyl(4-methylphenyl)sulfonylcarbamate The title compound was prepared according to the procedure described in Example 3 from 2-[4-(2-ethyl-5,7-dimethyl-3H-imidazo[4,5-b]pyridin-3-yl)phenyl]-1-propanol (step 4).

$^1$H-NMR (CDCl$_3$) δ: 8.11 (1H, s), 7.904 (2H, d, J=8.4 Hz), 7.40 (2H, d, J=8.4 Hz), 7.34 (2H, d, J=8.4 Hz), 7.27 (1H, s), 7.24 (1H, s), 7.20 (1H, s), 4.19–4.30 (2H, m), 3.20 91H, m), 2.78 (2H, q, J=7.5 Hz), 2.43 (3H, s), 1.53 (3H, t, J=7.56 Hz), 1.34 (3H, t, J=6.9 Hz)

m.p. 179.9–180.5° C.

MS (ESI) m/z: 581 [(M+H)$^+$], 579 [(M−H)$^−$]

Example 284

2-[4-(5-ACETYL-2-ETHYL-1H-BENZIMIDAZOL-1-YL)PHENYL]-1,1-DIMETHYLETHYL(4-METHYLPHENYL)SULFONYLCARBAMATE

Step 1. 1-(4-{[4-hydroxy-2-methylpropyl)phenyl]amino}-3-nitrophenyl)ethanone

The title compound was prepared according to the procedure described in step 5 of Example 266 from 1-(4-aminophenyl)-2-methyl-2-propanol $^1$H-NMR (CDCl$_3$) δ: 9.85 (1H, br.s), 8.83 (1H, s), 7.97 (1H, d, J=9.0 Hz), 7.10–7.40 (4H, m), 2.82 (2H, s), 2.58 (3H, s), 1.28 (6H, s)

Step 2. 1-(3-amino-4-{[4-(2-hydroxy-2-methylpropyl)phenyl]amino}phenyl)ethanone

The title compound was prepared according to the procedure described in step 2 of Example 28 from 1-(4-{[4-hydroxy-2-methylpropyl)phenyl]amino}-3-nitrophenyl)ethanone (step 1)

$^1$H-NMR (CDCl$_3$) δ: 7.38–7.46 (2H, m), 7.16 (2H, dd, J=8.4 Hz), 6.96 (2H, d, J=8.4 Hz), 5.62 (1H, br.s), 3.60 (1H, br.s), 2.73 (2H, s), 2.54 (3H, s), 1.39 (1H, br.s), 1.24 (6H, s)

Step 3. 1-{2-ethyl-1-4-(2-hydroxy-2-methylpropyl)phenyl]-1H-benzimidazol-5-yl}ethanone The title compound was prepared according to the procedure described in step 5 of Example 1 from 1-(3-amino-4-{[4-(2-hydroxy-2-methylpropyl)phenyl]amino}phenyl)ethanone (step 2).

¹H-NMR (CDCl₃) δ: 8.40 (1H, s), 7.90 (1H, d, J=8.6 Hz), 7.46 (2H, d, J=8.1 Hz), 7.30 (2H, d, J=8.1 Hz), 7.14 (1H, d, J=8.6 Hz), 2.96 (2H, s), 2.82 (2H, q, J=7.6 Hz), 2.68 (3H, s), 1.63 (1H, br.s), 1.38 (3H, t, J=7.6 Hz), 1.32 (6H, s)

Step 4. 2-[4-(5-acetyl-2-ethyl-1H-benzimidazol-1-yl)phenyl]-1,1-dimethylethyl(4-methylphenyl)sulfonylcarbamate The title compound was prepared according to the procedure described in Example 3 from 1-{2-ethyl-1-[4-(2-hydroxy-2-methylpropyl)phenyl]-1H-benzimidazol-5-yl}ethanone (step 3).

¹H-NMR (CDCl₃) δ: 8.41 (1H, s), 7.88–7.95 (3H, m), 7.09–7.35 (7H, m), 3.14 (2H, s), 2.80 (2H, q, J=7.6 Hz), 2.68 (3H, s), 2.40 (3H, s), 1.45 (6H, s), 1.38 (3H, t, J=7.6 Hz)

m.p. 103.4–104.2° C.

MS (ESI) m/z: 534 [(M+H)⁺], 532 [(M−H)⁻]

Example 285
2-{4-[6-CHLORO-2-ETHYL-5-(TRIFLUOROMETHYL)-1H-BENZIMIDAZOL-1-YL]PHENYL}ETHYL(5-METHYL-2-PYRIDINYL)SULFONYLCARBAMATEMONO-HYDROCHLORIDE The title compound was prepared according to the procedure described in step 2 of Example 243 from 2-{4-[6-chloro-2-ethyl-5-(trifluoromethyl)-1H-benzimidazol-1-yl]phenyl}ethyl phenyl carbonate.

¹H-NMR (CDCl₃) δ: 8.57 (1H, s), 8.15 (1H, s), 8.12 (1H, d, J=8.0 Hz), 7.77 (1H, d, J=7.9 Hz), 7.37 (1H, d, J=7.9 Hz), 7.17–7.25 (4H, m,), 4.36 (2H, t, J=6.6 Hz), 3.00 (2H, t, J=6.6 Hz), 2.77 (2H, q, J=7.5 Hz), 2.46 (3H, s), 1.36 (3H, t, J=7.3 Hz)

m.p. 205.8° C.

MS (ESI) m/z: 567 [(M+H)⁺], 565 [(M−H)⁻]

Example 286
2-{4-[6-CHLORO-2-ETHYL-5-(TRIFLUOROMETHYL)-1H-BENZIMIDAZOL-1-YL]PHENYL}ETHYL(5-METHYL-2-PYRIDINYL)SULFONYLCARBAMATEMONO-HYDROCHLORIDE MONO-HYDROCHLORIDE The title compound was prepared according to the procedure described Example 240 from 2-{4-[6-chloro-2-ethyl-5-(trifluoromethyl)-1H-benzimidazol-1-yl]phenyl}ethyl(5-methyl-2-pyridinyL)sulfonylcarbamate (Example 285).

¹H-NMR (CDCl₃) δ: 8.53 (1H, s), 8.49 (1H, s), 8.08 (1H, d, J=7.6 Hz), 7.78 (1H, d, J=6.8 Hz), 7.53 (2H, br.s), 7.41 (3H, br.s), 4.38 (2H, t, J=5.9 Hz), 3.21 (2H, br.s), 3.07 (2H, t, J=5.9 Hz), 2.47 (3H, s), 1.51 (3H, br.s)

m.p. 200.2° C.

MS (ESI) m/z: 567 [(M+H)⁺], 565 [(M−H)⁻]

Example 287
2-{5-[6-CHLORO-2-ETHYL-5-(TRIFLUOROMETHYL)-1H-BENZIMIDAZOL-1-YL]-3-PYRIDINYL}ETHYL(4-METHYLPHENYL)SULFONYLCARBAMATE Step 1. benzyl ethyl 2-(6-nitro-3-pyridinyl)malonate To a mixture of 5-bromo-2-nitropyridine (8.66 g, 42.7 mmol) and benzyl ethyl malonate (9.50 g, 42.7 mmol) in tetrahydrofuran (160 ml) and dimethylformamide (40 ml) was added K₂CO₃ (5.90 g, 42.7 mmol) and stirred under reflux temperature for 20 h. The mixture was diluted with water (1 l) and extracted with ethyl acetate (3×200 ml). The organic layer was washed with brine, dried (MgSO₄) and concentrated to give 5.26 g of title compound as orange oil.

¹H-NMR (CDCl₃) δ: 8.61 (1H, d, J=2.2 Hz), 8.26 (1H, d, J=8.4 Hz), 8.19 (1H, dd, J=2.2, 8.6 Hz), 7.29–7.38 (5H, m), 5.22 (2H, d, J=3.6 Hz), 4.84 (1H, s), 4.22 (2H, m), 1,23 (3H, t, J=7.1 Hz).

Step 2. ethyl(6-nitro-3-pyridinyl)acetate

To a solution of benzyl ethyl 2-(6-nitro-3-pyridinyl)malonate (5.26 g, 15.3 mmol,) in ethanol was added palladium on carbon (530 mg) and stirred for 6 h under hydrogen atmosphere at room temperature. The catalyst was filtered off through a pad of celite and the filtrate was concentrated to give a title compound as yellow brown oil.

¹H-NMR (CDCl₃) δ: 7.95 (1H, d, J=1.8 Hz), 7.40 (1H, dd, J=2.4, 8.4 Hz), 6.48 (1H, d, J=8.1 Hz), 4.42 (2H, br.s), 4.14 (2H, q, J=7.1 Hz), 3.46 (2H, s), 1.26 (3H, t, J=7.1 Hz).

Step 3. 2-(6-amino-3-pyridinyl)ethanol

To a solution of ethyl (6-nitro-3-pyridinyl)acetate (468 mg, 2.60 mmol) in tetrahydrofuran was added LiAlH₄ and stirred for 2 h at room temperature. The reaction was quenched with saturated 25% NH₃ aqueous solution and the precipitate was removed. The filtrate was concentrated to give a title compound as yellow oil.

¹H-NMR (CDCl₃) δ: 7.73 (1H, d, J=2.8 Hz), 7.23 (1H, dd, J=8.6 Hz), 6.37 (1H, d, J=2.6, 8.1 Hz), 5.63 (2H, br.s), 3.49 (2H, t, J=7.3 Hz), 2.51 (2H, t, J=7.3 Hz).

MS (EI) m/z: 138 (M⁺).

Step 4. (6-{[5-chloro-2-nitro-4-(trifluoromehyl)phenyl]amino}-3-pyridinyl)ethanol The title compound was prepared according to the procedure described in step 3 of Example 1 from 2-(6-amino-3-pyridinyl)ethanol (step 3).

¹H-NMR (CDCl₃) δ: 8.49 (1H, s), 8.32 (1H, d, J=2.2 Hz), 7.64 (1H, dd, J=2.4, 8.4 Hz), 7.36 (1Hs), 6.97 (1H, d, J=8.4 Hz), 3.91 (2H, t, J=6.5 Hz), 2.89 (2H, t, J=6.5 Hz)

MS (EI) m/z: 361 (M⁺).

Step 5. (6-{[2-amino-5-chloro-4-(trifluoromehyl)phenyl]amino}-3-pyridinyl)ethanol The title compound was prepared according to the procedure described in step 2 of Example 28 from (6-{[5-chloro-2-nitro-4-(trifluoromehyl)phenyl]amino}-3-pyridinyl)ethanol (step 4).

MS (EI) m/z: 331 (M⁺).

Step 6. 2-{6-[6-chloro-2-ethyl-5-(trifluoromehyl)-1H-benzimidazol-1-yl]-3-pyridinyl}ethylpropionate To (6-{[2-amino-5-chloro-4-(trifluoromehyl)phenyl]amino}-3-pyridinyl)ethanol (787 mg, 2.37 mmol, from step 5) was added propionic acid and propionic anhydride and stirred at 120° C. for 15 h. The mixture was quenched with NaOH and extracted with dichloromethane (3×30 ml). The organic layer was washed with brine, dried (MgSO₄) and concentrated to give 5.26 g of title compound as orange oil.

¹H-NMR (CDCl₃) δ: 8.58 (1H, d, J=1.9 Hz), 8.12 (1H, s), 7.83 (1H, dd, J=2.2, 8.1 Hz), 7.45 (1H, s), 7.39 (1H, d, J=8.1 Hz), 4.40 (2H, t, J=6.8 Hz), 4.12 (2H, q, J=7.3 Hz), 3.10 (2H, t, J=6.5 Hz), 2.99 (2H, q, J=7.6 Hz), 2.29–2.44 (2H, m), 1.38 (3H, t, J=7.4 Hz), 1.15 (3H, t, J=7.6 Hz).

Step 5. 2-{6-[6-chloro-2-ethyl-5-(trifluoromehyl)-1H-benzimidazol-1-yl]-3-pyridinyl}ethanol The title compound was prepared according to the procedure described in step 8 of Example 266 from 2-{6-[6-chloro-2-ethyl-5-(trifluoromehyl)-1H-benzimidazol-1-yl]-2-pyridinyl}ethylpropionate (step 4).

¹H-NMR (CDCl₃) δ: 8.60 (1H, d, J=2.3 Hz), ☐☐☐☐☐ (1H, s), 7.91 (1H, dd, J=2.5, 8.0 Hz), 7.45 (1H, s), 7.38 (1H, d, J=8.1 Hz), 4.01 (1H, t, J=6.2 Hz), 3.72–3.77 (2H, m), (2H, m), 2.94–3.04 (2H, m), 1.38 (3H, t, J=7.4 Hz).

Step 6. 2-{6-[6-chloro-2-ethyl-5-(trifluoromehyl)-1H-benzimidazol-1-yl]-3-pyridinyl}ethyl-(4-methylphenyl)sulfonylcarbamate The title compound was prepared according to the procedure described in Example 3 from 2-{6-[6-chloro-2-ethyl-5-(trifluoromehyl)-1H-benzimidazol-1-yl]-2-pyridinyl}ethanol (step 5).

¹H-NMR (CDCl₃) δ: 8.33 (1H, d, J=1.9 Hz), 8.08 (1H, s), 7.91 (2H, d, J=8.4 Hz), 7.70 (1H, dd, J=2.4, 8.1 Hz), 7.29–7.42 (4H, m), 7.20(1H, s), 4.39 (2H, t, J=6.2 Hz), 3.00 (2H, t, J=6.2 Hz), 2.93 (2H, t, J=7.6 Hz), 2.43 (3H, s), 1.32 (3H, t, J=7.4 Hz).

MS (ESI) m/z: 567 [(M+H)$^+$], 565 [(M−H)$^−$].

Example 288
2-{5-[6-CHLORO-2-ETHYL-5-(TRIFLUOROMETHYL)-1H-BENZIMIDAZOL-1-YL]-3-PYRIDINYL}ETHYL(4-METHYLPHENYL)SULFONYLCARBAMATEMONO-HYDROCHLORIDE Step 1

The title compound was prepared according to the procedure described in Example 240 from 2-{5-[6-chloro-2-ethyl-5-(trifluoromehyl)-1H-benzimidazol-1-yl]-3-pyridinyl}ethyl-4-methylphenyl)sulfonylcarbamate (Example 287).

$^1$H-NMR (CDCl$_3$) δ: 8.40 (1H, br.s), 8.49 (1H, br.s), 8.12 (1H, br.s), 7.82 (2H, br.s), 7.65 (1H, br.s), 7.25–7.28 (2H, m), 4.40 (2H, br.s), 3.35 (1H, s), 3.12 (2H, br.s), 2.41 (3H, s), 2.43 (3H, s), 1.53 (3H, br.s).

MS (ESI) m/z: 567 [(M+H)$^+$], 565 [(M−H)$^−$].

Example 289
2-{4-[6-CHLORO-2-ETHYL-5-(TRIFLUOROMETHYL)-1H-BENZIMIDAZOL-1-YL]PHENYL}ETHYL-5-ISOQUINOLINYLSULFONYLCARBAMATE The title compound was prepared according to the procedure described in step 2 of Example 243 from 2-{4-[6-chloro-2-ethyl-5-(trifluoromethyl)-1H-benzimidazol-1-yl] phenyl}ethyl phenyl carbonate and 5-isoquinolinylsulfonamide.

$^1$H-NMR (CDCl$_3$) δ: 9.39 (1H, s), 8.70 (2H, t, J=6.3 Hz), 8.43 (1H, d, J=6.2 Hz), 8.29 (1H, d, J=8.1 Hz), 8.12 (1H, s,), 7.78 (1H, t, J=7.6 Hz), 7.16–7.33 (5H, m), 4.32 (2H, t, J=6.9 Hz), 2.97 (2H, t, J=6.8 Hz), 2.77 (2H, q, J=7.4 Hz), 1.346 (3H, t, J=7.4 Hz)

MS (ESI) m/z: 603 [(M+H)$^+$], 601 [(M−H)$^−$]

Example 290
2-{4-[6-CHLORO-2-ETHYL-5-(TRIFLUOROMETHYL)-1H-BENZIMIDAZOL-1-YL]PHENYL}ETHYL-5-QUINOLINYLSULFONYLCARBAMATE The title compound was prepared according to the procedure described in step 2 of Example 243 from 4-(6-chloro-2-ethyl-5-trifluoromethyl-1-benzimidazol-1-yl)phenethyl-(4-methylphenyl)sulfonylcarbamate and 5-quinolinylsufonamide $^1$H-NMR (CDCl$_3$) δ: 8.43 (1H, d, J=8.6 Hz), 8.20–8.25 (2H, m), 8.13 (1H, s), 8.12 (1H, s), 7.81–7.91 (2H, m), 7.68–7.72 (1H, m), 7.30–7.34 (2H, m), 7.12–7.16 (3H, m), 4.37 (2H, t, J=6.6 Hz), 2.98 (2H, t, J=6.3 Hz), 2.74 (2H, q, J=7.4 Hz), 1.35 (3H, t, J=7.4 Hz).

MS (ESI) m/z: 567 [(M+H)$^+$], 565 [(M−H)$^−$]

Example 291
2-{4-[6-CHLORO-2-ETHYL-5-(TRIFLUOROMETHYL)-1H-BENZIMIDAZOL-1-YL]PHENYL-}ETHYL-[5-(DIMETHYLAMINO)-1-NAPHTHNYL] SULFONYLCARBAMATE The title compound was prepared according to the procedure described in step 2 of Example 243 from 2-{4-[6-chloro-2-ethyl-5-(trifluoromethyl)-1H-benzimidazol-1-yl] phenyl}ethyl phenyl carbonate and 5-(dimethylamino)-1-naphthnylsulfonamide.

$^1$H-NMR (CDCl$_3$) δ: 8.61 (1H, d, J=8.4 Hz), 8.46 (1H, dd, J=1.2, 7.5 Hz), 8.12 (1H, s), 87.58 (2H, t, J=8.3 Hz), 7.12–7.24 (6H, m), 4.30 (2H, t, J=6.8 Hz), 2.93 (2H, t, J=6.8 Hz), 2.75 (2H, q, J=7.5 Hz), 1.35 (3H, t, J=7.5 Hz)

m.p. 203.4° C.

MS (ESI) m/z: 645 [(M+H)$^+$], 643 [(M−H)$^−$]

Example 292
2-{4-[6-CHLORO-2-ETHYL-5-(TRIFLUOROMETHYL)-1H-BENZIMIDAZOL-1-YL]PHENYL}ETHYL-(1-METHYL-1H-IMIDAZOL-4-YL) SULFONYLCARBAMATE The title compound was prepared according to the procedure described in step 2 of Example 243 from 2-{4-[6-chloro-2-ethyl-5-(trifluoromethyl)-1H-benzimidazol-1-yl] phenyl}ethyl phenyl carbonate and 1-methyl-1H-imidazol-4-ylsulfonamide.

$^1$H-NMR (CDCl$_3$) δ: 8.13 (1H, s), 7.72 (1H, d, J=1.5 Hz), 7.55 (1H, d, J=1.3 Hz), 7.41 (2H, d, J=8.2 Hz), 7.26 (2H, d, J=8.2 Hz), 7.20 (1H, s), 4.38 (2H, t, J=6.6 Hz), 3.78 (3H, s), 3.04 (2H, d, J=6.8 Hz), 2.79 (2H, q, J=7.6 Hz), 1.36 (3H, t, J=7.6 Hz)

m.p. 204.3° C.

MS (ESI) m/z: 556 [(M+H)$^+$], 554 [(M−H)$^−$]

Example 293
2-{4-[6-CHLORO-2-ETHYL-5-(TRIFLUOROMETHYL)-1H-BENZIMIDAZOL-1-YL]PHENYL}ETHYL-(1-METHYL-1H-IMIDAZOL-4-YL) SULFONYLCARBAMATEMONO HYDROCHLORIDE The title compound was prepared according to the procedure described in Example 240 from 2-{4-[6-chloro-2-ethyl-5-(trifluoromethyl)-1H-benzimidazol-1-yl] phenyl}ethyl-(1-methyl-1H-imidazol-4-yl) sulfonylcarbamate (Example 292).

MS (ESI) m/z: 556 [(M+H)$^+$], 554 [(M−H)$^−$]

Example 294
2-{4-[6-CHLORO-2-ETHYL-5-(TRIFLUOROMETHYL)-1H-BENZIMIDAZOL-1-YL]PHENYL}ETHYL-(1,2-DIMETHYL-1H-IMIDAZOL-4-YL) SULFONYLCARBAMATE The title compound was prepared according to the procedure described in step 2 of Example 243 from 2-{4-[6-chloro-2-ethyl-5-(trifluoromethyl)-1H-benzimidazol-1-yl] phenyl}ethyl phenyl carbonate and 1,2-dimethyl-1H-imidazol-4-ylsulfonamide.

$^1$H-NMR (CDCl$_3$) δ: 8.12 (1H, s), 7.63 (1H, s), 7.41 (2H, d, J=8.2 Hz), 7.25 (2H, d, J=8.2 Hz), 7.19 (1H, s), 4.37 (2H, t, J=6.8 Hz), 3.64 (3H, s), 3.04 (2H, d, J=6.6 Hz), 2.79 (2H, q, J=7.6 Hz), 2.42 (3H, s), 1.36 (3H, t, J=7.6 Hz)

m.p. 221.2° C.

MS (ESI) m/z: 570 [(M+H)$^+$], 568 [(M−H)$^−$]

Example 295
2-{4-[6-CHLORO-2-ETHYL-5-(TRIFLUOROMETHYL)-1H-BENZIMIDAZOL-1-YL]PHENYL}ETHYL-(1,2-DIMETHYL-1H-IMIDAZOL-4-YL) SULFONYLCARBAMATE DI-HYDROCHLORIDE The title compound was prepared according to the procedure described in Example 240 from 2-{4-[6-chloro-2-ethyl-5-(trifluoromethyl)-1H-benzimidazol-1-yl] phenyl}ethyl-(1,2-dimethyl-1H-imidazol-4-yl) sulfonylcarbamate (Example 294).

MS (ESI) m/z: 570 [(M+H)$^+$], 568 [(M−H)$^−$]

Example 296
2-{4-[5,7-DIMETHYL-2-(1H-PYRAZOL-3-YL)-3H-IMIDAZO[4,5-b]PYRIDINE-3-YL-]PHENYL}ETHYL(4-METHYLPHENYL)SUFONYLCARBAMATE Step 1. 2-{4-[5,7-dimethyl-2-(1H-pyrazol-3-yl)-3H-imidazo [4,5-b]pyridin-3-yl]phenyl}ethanol The title compound was prepared according to the procedure described in step 1 of Example 236 from 4-[(3-amino-4,6-dimethyl-2-pyridinyl)amino]phenylethanol.

$^1$H-NMR (DMSO-d$_6$) δ: 13.15 (1H, br.s), 7.77 (3H, s), 7.35 (2H, d, J=7.7 Hz), 7.25 (2H, d, J=7.7 Hz), 7.02 (1H, s), 6.53 (1H, s), 4.75 (2H, t, J=4.8 Hz), 3.71 (2H, q, J=6.8 Hz), 2.81 (1H, t, J=6.6 Hz), 258 (3H, s), 2.42 (3H, s)

Step 2. 2-{4-[5,7-dimethyl-2-(1H-pyrazol-3-yl) 3H-imidazo[4,5-b]pyridine-3-yl-]phenyl}ethyl(4-methylphenyl)sufonylcarbamate The title compound was prepared according to the procedure described in Example 3 from 2-{4-[5,7-dimethyl-2-(1H-pyrazol-3-yl)-3H-imidazo[4,5-b]pyridin-3-yl]phenyl}ethanol (step 1).

$^1$H-NMR (DMSO-d$_6$) δ: 13.14 (1H, br.s), 7.69–7.78 (3H, m), 7.21–7.43 (6H, m), 7.02 (2H, s), 6.52 (1H, s), 4.18 (2H, t, J=6.4 Hz), 2.89 (2H, t, J=6.4 Hz), 2.58 (2H, s), 2.41(3H, s), 2.32 (3H, s)

MS (ESI) m/z: 531 (MH$^+$), 529 ([M–H]$^-$)

Example 297
2-{4-[5,7-DIMETHYL-2-(1H-PYRAZOL-3-YL)3H-IMIDAZO[4,5-b]PYRIDINE-3-YL-]PHENYL}ETHYL(4-METHYLPHENYL)SUFONYLCARBAMATE SODIUM SALT Step 1. 2-{4-[5,7-dimethyl-2-(1H-pyrazol-3-yl)-3H-imidazo[4,5-b]pyridin-3-yl]phenyl}ethanol The title compound was prepared according to the procedure described in Example 2 from 2-{4-[5,7-dimethyl-2-(1H-pyrazol-3-yl) 3H-imidazo[4,5-b]pyridine-3-yl-]phenyl}ethyl(4-methylphenyl)sufonylcarbamate (Example 296).

$^1$H-NMR (CDCl$_3$) δ: 9.85 (1H, s), 8.37 (1H, d, J=8.4 Hz), 7.31 (1H, d, J=2.0 Hz), 7.14 (1H, dd, J=2.0, 8.3 Hz), 6.60 (1H, s), 3.87 (2H, dt, J=6.2, 6.4 Hz), 2.84 (2H, t, J=6.4 Hz), 2.56 (3H, s), 2.46 (3H, s), 1.40 (1H, t, J=6.2 Hz).

MS (ESI) m/z: 531 (MH$^+$), 529 ([M–H]$^-$)

Example 298
N-{[(2-{4-[5,7-DIMETHYL-2-(1H-PYRAZOL-3-YL)-3H-IMIDAZO[4,5-b]PYRIDINE-3-YL]PHENYL}ETHYL)AMINO]CARBONYL}-4-METHYLBENZENESULFONAMIDE Step 1. 3-[4-(2-chloroethyl)phenyl]-5,7-dimethyl-2-(1H-pyrazol-3-yl)-3H-imidazo[4,5-b]pyridine The title compound was prepared according to the procedure described in step 2 of Example 28 from 2-{4-[5,7-dimethyl-2-(1H-pyrazol-3-yl)-3H-imidazo[4,5-b]pyridin-3-yl]phenyl}ethanol (Example 297, step 1).

$^1$H-NMR (CDCl$_3$) δ: 13.15 (1H, s), 7.77 (2H, br.s), 7.43 (2H, br.s), 7.20 (2H, br.s), 7.04 (1H, s), 6.54 (1H, br.s), 3.96 (2H, t, J=6.8 Hz), 3.15 (2H, tm J=6.8 Hz), 2.60 (3H, s), 2.30 (3H, s).

Step 2. 3-[4-(2-azidoethyl)phenyl]-5,7-dimethyl-2-(1H-pyrazol-3-yl)-3H-imidazo[4,5-b]pyridin The title compound was prepared according to the procedure described in step 5 of Example 1 from 3-[4-(2-chloroethyl)phenyl]-5,7-dimethyl-2-(1H-pyrazol-3-yl)-3H-imidazo[4,5-b]pyridine (step 1).

$^1$H-NMR (DMSO-d$_6$) δ: 13.15 (1H, br.s), 9.85 (1H, br.s), 7.76 (1H, br.s), 7.41 (2H, d, J=8.1 Hz), 7.31 (2H, d, J=8.1 Hz), 7.04 (1H, s), 6.53 (1H, s), 3.69 (2H, t, J=6.6 Hz), 2.95 (2H, t, J=6.8 Hz), 2.58 (3H, s), 2.42 (3H, s),

MS (EI) m/z: 358 (M$^+$).

Step 3. 2-{4-[5,7-dimethyl-2-(1H-pyrazol-3-yl)-3H-imidazo[4,5-b]pyridin-3-yl]phenyl}ethanamine The title compound was prepared according to the procedure described in step 6 of Example 1 from 3-[4-(2-azidoethyl)phenyl]-5,7-dimethyl-2-(1H-pyrazol-3-yl)-3H-imidazo[4,5-b]pyridine (step 2).

$^1$H-NMR (DMSO-d$_6$) δ: 9.83 (1H, br.s), 7.68 (2H, br.s), 7.23–7.43 (5H, m), 7.04 (1H, s,), 5.75 (1H, s), 2.68–2.90 (4H, m), 2.59 (3H, s), 2.42 (3H, s),

MS (EI) m/z: 332 (M$^+$).

Step 4. N-{](2-{4-[5,7-dimethyl-2-(1H-pyrazol-3-yl)-3H-imidazo[4,5-b]pyridine-3-yl]phenyl}ethyl)amino]carbonyl}-4-methylbenzenesulfonamide The title compound was prepared according to the procedure described in step 7 of Example 1 from 2-{4-[5,7-dimethyl-2-(1H-pyrazol-3-yl)-3H-imidazo[4,5-b]pyridin-3-yl]phenyl}ethanamine (step 3)

$^1$H-NMR (CD3OD) δ: 7.80 (2H, d, J=8.2 Hz), 7.58 (1H, br.s), 7.20–7.35 (6H, m), 7.08 (1H, s), 6.20 (1H, br.s), 3.42 (2H, t, J=6.8 Hz), 2.84 (2H, t, J=6.9 Hz), 2.68 (2H, s), 2.50 (3H, s), 2.34 (3H, s)

MS (ESI) m/z: 530 (MH$^+$), 528 ([M–H]$^-$)

Example 299
2-[4-(5-CYANO-2-ETHYL-6-METHYL-1H-BENZIMIDAZOL-1-YL)PHENYL]ETHYL(4-METHYLPHENYL)SULFONYLCARBAMATE Step 1. 4-Chloro-2-methyl-5-nitrobenzonitrile To a solution of 4-chloro-2-methyl-5-nitrobenzonitrile (10 g, 66 mmol) in conc. H$_2$SO$_4$ was added KNO$_3$ (7.0 g, 69.3 mmol) at 0° C. in small portions, and then the reaction mixture was stirred overnight at ambient temperature. It was then poured into ice and extracted with AcOEt. The combined extracts was washed by sat. NaHCO$_3$ aq., dried over MgSO$_4$ and concentrated. The resulting precipitates were collected by filtration, washed with ether, and dried under reduced pressure to give 5.5 g (42%) of the title compound.

$^1$H-NMR (CDCl$_3$) δ: 8.19 (1H, s), 7.57 (1H, s), 2.64 (3H, s).

Step 2. 4-{[4-(2-hydroxylethyl)phenyl]amino}-2-methyl-5-nitrobenzonitrile

The title compound was prepared according to the procedure described in step 3 of Example 1 from 3-bromo-6-chloro-2,4-dimethyl-5-nitropyridine (step 2).

$^1$H-NMR (CDCl$_3$) δ: 9.76 (1H, br.s), 8.51 (1H, s), 7.36 (1H, d, J=8.4 Hz), 7.22 (1H, d, J=8.3 Hz), 6.96 (1H, s), 3.94 (2H, dd, J=11.7, 6.2 Hz), 2.94 (2H, t, J=6.4 Hz), 2.42 (3H, s)

Step 3. 5-amino-4-{[4-(2-hydroxylethyl)phenyl]amino}-2-methylbenzonitrile

The title compound was prepared according to the procedure described in step 4 of Example 1 from 2-{4-[(5-bromo-4,6-dimethyl-3-nitro-2-pyridinyl)amino]phenyl}ethanol (step 3).

$^1$H-NMR (CDCl$_3$) δ: 7.19 (1h, d, J=8.4 Hz), 6.94–7.00 (4H, m), 5.59 (1H, br.s), 3.84–3.90 (2H, m), 3.50 (2H, br.s), 2.85 (2H, t, J=6.4 Hz), 2.37 (3H, s).

Step 5. 2-[4-(5-cyano-2-ethyl-6-methyl-1H-benzimidazo-1-yl)phenyl]ethyl propanoate The title compound was prepared according to the procedure described in step 5 of Example 1 from 2-{4-[(3-amino-5-bromo-4,6-dimethyl-2-pyridinyl)amino]phenyl}ethanol (step 4).

MS (EI) m/z: 361 (M+)

Step 6. 2-ethyl-1-[4-(2-hydroxylethyl)phenyl]-6-methyl-1H-benzimidazole-5-carbonitrile The title compound was prepared according to the procedure described in step 6 of Example 1 from 2-[4-(6-bromo-2-isopropyl-5,7-dimethyl-3H-imidazo[4,5-b]pyridin-3-yl)phenyl]ethyl 2-methylpropanoate (step 5).

$^1$H-NMR (CDCl$_3$) δ: 8.00 (1H, s), 7.50 (2H, d, J=8.4 Hz), 7.29 (2H, d, J=8.4 Hz), 6.98 (1H, s), 4.01 (2H, t, J=6.4 Hz), 3.03 (2H, t, J=6.6 Hz), 2.79 (2H, q, J=7.5 Hz), 2.56 (3H, s), 1.35 (3H, t, J=7.5 Hz)

Step 7. 2-[4-(5-cyano-2-ethyl-6-methyl-1H-benzimidazol-1-yl)phenyl]ethyl(4-methylphenyl)sulfonylcarbamate The title compound was prepared according to the procedure described in Example 3 from 2-ethyl-1-[4-(2-hydroxylethyl)phenyl]-6-methyl-1H-benzimidazole-5-carbonitrile (step 6).

¹H-NMR (CDCl₃) δ: 8.03 (1H, s), 7.92 (2H, d, J=8.4 Hz), 7.39 (2H, d, J=8.4 Hz), 7.35 (2H, d, J=8.1 Hz), 7.26 (2H, d, J=8.1 Hz), 6.96(1H, s), 4.39 (2H, t, J=6.8 Hz), 3.04 (2H, t, J=6.6 Hz), 2.77 (2H, q, J=7.7 Hz), 2.57 (3H, s), 2.44 (3H, s), 1.35 (3H, t, J=7.5 Hz)

Example 300
N-[({2-[4-(5-CYANO-2-ETHYL-6-METHYL-1H-BENZIMIDAZOL-1-YL)PHENYL]ETHYL}AMINO)CARBONYL](4-METHYLBENZENESULFOAMIDE Step 1. 1-[4-(2-chloroethyl)phenyl-]-2-ethyl-6-methyl-1H-benzimidazole-5-carbonitrile The title compound was prepared according to the procedure described in step 7 of Example 1 from 2-[4-(6-bromo-2-isopropyl-5,7-dimethyl-3H-imidazo[4,5-b]pyridin-3-yl)phenyl]ethanol (step 6).

¹H-NMR (CDCl₃) δ: 8.02 (1H, s), 7.48 (2H, d, J=8.4 Hz), 7.30 (2H, d, J=8.4 Hz), 6.96–6.98 (1H, m), 3.83 (2H, t, J=7.1 Hz), 3.21 (2H, t, J=7.0 Hz), 2.78 (2H, q, J=7.5 Hz), 2.58 (3H, s), 1.35 (3H, t, J=7.5 Hz).

Step 2. 1-[4-(2-azidoethyl)phenyl]-2-ethyl-6-methyl-1H-benzimidazole-5-carbonitrile The title compound was prepared according to the procedure described in step 8 of Example 1 from 6-bromo-3-[4-(2-chloroethyl)phenyl]-2-isopropyl-5,7-dimethyl-3H-imidazo[4,5-b]pyridine (step 7).

MS (EI) m/z: 412 (M+)

¹H-NMR (CDCl₃) δ: 8.02 (1H, s), 7.48 (2H, d, J=8.0 Hz), 7.30 (2H, d, J=8.2 Hz), 6.95 (1H, s), 3.63 (2H, t, J=6.8 Hz), 3.03 (2H, t, J=7.0 Hz), 2.78 (2H, q, J=7.5 Hz), 2.57 (3H, s), 1.35 (3H, t, J=7.3 Hz).

Step 3. 1-[4-(2-aminoethyl)phenyl]-2-ethyl-6-methyl-1H-benzimidazole-5-carbonitrile The title compound was prepared according to the procedure described in step 9 of Example 1 from 2-[4-(6-bromo-2-isopropyl-5,7-dimethyl-3H-imidazo[4,5-b]pyridin-3-yl)phenyl]ethyl azide (step 8).

¹H-NMR (CDCl₃) δ: 7.49 (2H, d, J=8.3 Hz), 7.28 (2H, d, J=8.3 Hz), 6.93 (1H, s), 6.60 (2H, br.s), 3.32–3.00 (5H, m), 2.65 (3H, s), 2.48 (3H, s), 1.31 (6H, d, J=6.8 Hz).

Step 4. N-[({2-[4-(5-cyano-2-ethyl-6-methyl-1H-benzimidazol-1-yl)phenyl]ethyl}amino)carbonyl](4-methylbenzenesulfoamide The title compound was prepared according to the procedure described in step 10 of Example 1 from [4-(2-isopropyl-5,7-dimethyl-3H-imidazo[4,5-b]pyridin-3-yl)phenyl]ethylamine (step 9).

¹H-NMR (CDCl₃) δ: 8.00 (1H, s), 7.72 (2H, d, J=8.4 Hz), 7.42 (2H, d, J=8.4 Hz), 7.28–7.32 (4H, m), 6.95 (1H, m), 3.56–3.63 (2H, m), 2.96 (2H, t, J=7.1 Hz), 2.78 (2H, q, J=7.7 Hz), 2.54 (3H, s), 2.41 (3H, s), 1.34 (3H, t, J=7.5 Hz)

Example 301
2-AMINO-5,7-DIMETHYL-3-(4-{2-[({[(4-METHYLPHENYL)SULFONYL]AMINO}CARBONYL)AMINO]ETHYL}PHENYL)-3H-IMIDAZO[4,5-b]PYRIDINE DI-HYDROCHLORIDE Step 1. 2-AMINO-5,7-DIMETHYL-3-(4-{2-[({[(4-METHYLPHENYL)SULFONYL]AMINO}CARBONYL)AMINO]ETHYL}PHENYL)-3H-IMIDAZO[4,5-b]PYRIDINE To a stirred solution of N-{[(2-{4-[(3-amino-4,6-dimethyl-2-pyridinyl)amino]phenyl}ethyl)amino]carbonyl}-4-methylbenzenesulfonamide (300 mg, 0.66 mmol) in THF (6 ml) was added a solution of BrCN (175 mg, 1.65 mmol) in water (2 ml). The resultant mixture was stirred at room temperature for 16 hours. The mixture was diluted with CH₂Cl₂ and washed with brine. The organic layer was dried over MgSO₄ and filtered. After concentration in vacuo, the residue was purified by preparative TLC (CH₂Cl₂/MeOH=10/1) to afford 224 mg (71%) of the title compound.

¹H-NMR (DMSO-d₆) δ: 10.82 (1H, s), 8.54 (2H, s), 7.79 (2H, d, J=8.3 Hz), 7.51–7.40 (6H, m), 7.06 (1H, s), 6.91 (1H, t, J=5.5 Hz), 3.29–3.24 (2H, m), 2.80–2.76 (2H, m), 2.48 (3H, s) 2.38 (3H, s), 2.36 (3H, s)

MS (ESI) m/z: 479 ([M+H]⁺), 477 ([M−H]⁻)

Step 2. 2-AMINO-5,7-DIMETHYL-3-(4-{2-[({[(4-METHYLPHENYL)SULFONYL]AMINO}CARBONYL)AMINO]ETHYL}PHENYL)-3H-IMIDAZO[4,5-b]PYRIDINE DI-HYDROCHLORIDE The title compound was prepared according to the procedure described in Example 240 from 2-amino-5,7-dimethyl-3-(4-{2-[({[(4-methylphenyl)sulfonyl]amino}carbonyl)amino]ethyl}phenyl)-3H-imidazo[4,5-b]pyridine.

MS (ESI) m/z: 479 ([M+H]⁺), 477 ([M−H]⁻)

Example 302
5,7-DIMETHYL-3-(4-{2-[({[(4-METHYLPHENYL)SULFONYL]AMINO}CARBONYL)AMINO]ETHYL}PHENYL)-2-(METHYLSULFANYL)-3H-IMIDAZO[4,5-b]PYRIDINE A mixture of N-{[(2-{4-[(3-amino-4,6-dimethyl-2-pyridinyl)amino]phenyl}ethyl)amino]carbonyl}-4-methylbenzenesulfonamide (110 mg, 0.24 mmol), di-2-pyridylthiocarbonate (68 mg, 0.29 mmol), and THF (5 ml) was stirred at room temperature for 3 days. The mixture was diluted with CH₂Cl₂ and washed with 0.1M HCl and brine. The organic fraction was dried over MgSO₄, and filtered. The solvent was removed to give N-[({2-[4-[(5,7-dimethyl-2-sulfanyl-3H-imidazo[4,5-b]pyridin-3-yl)phenyl]ethyl}amino)carbonyl}-4-methylbenzenesulfonamide [MS (ESI) m/z: 496 ([M+H]⁺), 494 ([M−H]⁻)]. This was dissolved with THF (2 ml), then 1M NaOMe in MeOH (0.49 ml) and MeI (45 □l, 0.73 mmol) was added to the mixture at room temperature. After 1 hour, the mixture was evaporated in vacuo and the residue was purified by preparative TLC (CH₂Cl₂/MeOH=10/1) to afford 31 mg (25%) of the title compounds.

¹H-NMR (CDCl₃) δ: 7.86 (2H, d, J=8.4 Hz), 7.31 (2H, d, J=8.1 Hz), 7.22–7.16 (4H, m), 6.88 (1H, s), 6.02 (1H, t, J=5.6 Hz), 3.51–3.45 (2H, m), 2.83 (2h, t, J=6.2 Hz), 2.67 (3H, s), 2.62 (3H, s) 2.42 (3H, s), 2.417 (3H, s)

MS (ESI) m/z: 510 ([M+H]⁺), 508 ([M−H]⁻)

Example 303
5,7-DIMETHYL-2-(METHYLAMINO)-3-(4-{2-[({[(4-METHYLPHENYL)SULFONYL]AMINO}CARBONYL)AMINO]ETHYL}PHENYL)-3H-IMIDAZO[4,5-b]PYRIDINE A mixture of N-{[(2-{4-[(3-amino-4,6-dimethyl-2-pyridinyl)amino]phenyl}ethyl)amino]carbonyl}-4-methylbenzenesulfonamide (300 mg, 0.66 mmol), methylisothiocyanate (56 □l, 0.86 mmol), and THF (6 ml) was stirred at room temperature for 3 days. The solvent was removed to give N-{[(2-{4-[(4,6-dimethyl-{[(methylamino)carbonothioyl]amino}-2-pyridinyl)amino]phenyl}ethyl)amino]carbonyl}-4-methylbenzenesulfonamide [MS (ESI) m/z: 527 ([M+H]⁺), 525 ([M−H]⁻)]. This was dissolved with MeCN (4 ml) and treated with MeI (54□□l) at 0° C. for 20 hours. After concentration under reduced pressure, the residue was purified by preparative TLC (EtOAc/EtOH=20/1) to afford 170 mg (52%) of the title compounds.

¹H-NMR (CD₃OD) δ: 7.72 (2H, d, J=8.3 Hz), 7.24 (4H, d, J=7.9 Hz), 7.15 (2H, d, J=8.4 Hz), 6.70 (1H, s), 3.28 (2H, t, J=7.0 Hz), 2.90 (3H, s), 2.72 (2H, t, J=7.0 Hz), 2.41 (3H, s), 2.26 (3H, s), 2.24 (3H, s)

MS (ESI) m/z: 493 ([M+H]⁺), 491 ([M−H]⁻)

Example 304
5,7-DIMETHYL-2-(METHYLAMINO)-3-(4-{2-[({[(4-METHYLPHENYL)SULFONYL]AMINO}CARBONYL)AMINO]ETHYL}PHENYL)-3H-IMIDAZO[4,5-b]PYRIDINE MONO-HYDROCHLORIDE

The title compound was prepared according to the procedure described in Example 240 from 5,7-dimethyl-2-(methylamino)-3-(4-{2-[({[(4-methylphenyl)sulfonyl]amino}carbonyl)amino]ethyl}phenyl)-3H-imidazo[4,5-b]pyridine hydrochloride.

MS (ESI) m/z: 493 ([M+H]$^+$), 491 ([M−H]$^−$)

Example 305
N-[5,7-DIMETHYL-3-(4-{2-[({[(4-METHYLPHENYL)SULFONYL]AMINO}CARBONYL)AMINO]ETHYL}PHENYL)-3H-IMIDAZO[4,5-b]PYRIDIN-2-YL]ACETAMIDE

2-amino-5,7-dimethyl-3-(4-{2-[({[(4-methylphenyl)sulfonyl]amino}carbonyl)amino]ethyl}phenyl)-3H-imidazo[4,5-b]pyridine (73 mg) was treated with pyridine (1 ml) and Ac$_2$O (0.2 ml) at room temperature for 3 hours. After evaporation in vacuo, the residue was purified by preparative TLC (hexane/acetone=1/1) to afford 4 mg (5%) of the title compounds.

$^1$H-NMR (CDCl$_3$) δ: 7.79 (2H, d, J=8.4 Hz), 7.34–7.22 (7H, m), 7.04 (1H, s), 6.30 (1H, br.s), 3.51–3.48 (2H, m), 2.87–2.83 (2H, m), 2.66 (3H, s), 2.53 (3H, s), 2.42 (3H, s),

MS (ESI) m/z: 521 ([M+H]$^+$), 519 ([M−H]$^−$)

Example 306
5,7-DIMETHYL-2-(DIMETHYLAMINO)-3-(4-{2-[({[(4-METHYLPHENYL)SULFONYL]AMINO}CARBONYL)AMINO]ETHYL}PHENYL)-3H-IMIDAZO[4,5-b]PYRIDINE

To a stirred solution of 2-amino-5,7-dimethyl-3-(4-{2-[({[(4-methylphenyl)sulfonyl]amino}carbonyl)amino]ethyl}phenyl)-3H-imidazo[4,5-b]pyridine (70 mg) in THF (1 ml) was added NaH (21 mg, 0.88 mmol) at room temperature. After 10 min, MeI (27 □l) was added to the mixture and stirred at room temperature for 2 days. The mixture was poured into ice-water and extracted with CH$_2$Cl$_2$, and the organic fraction was dried over MgSO$_4$, then filtered. After removal of solvent by evaporation, the residue was purified by preparative TLC (CH$_2$Cl$_2$/MeOH=10/1) to afford 27 mg (36%) of the title compounds.

$^1$H-NMR (CDCl$_3$) δ: 7.86 (2H, d, J=8.4 Hz), 7.32–7.24 (4H, m), 7.16 (2H, d, J=8.4 Hz), 6.77 (1H, s), 6.04 (1H, t, J=5.7 Hz), 3.50–3.44 (2H, m), 2.78 (2H, t, J=6.3 Hz), 2.71 (6H, s), 2.55 (3H, s), 2.41 (3H, s), 2.34 (3H, s)

MS (ESI) m/z: 507 ([M+H]$^+$), 505 ([M−H]$^−$)

Example 307
2-[4-(2-AMINO-5,7-DIMETHYL-3H-IMIDAZO[4,5-b]PYRIDIN-3-YL)PHENYL]ETHYL(4-METHYLPHENYL)SULFONYLCARBAMATE

Step 1. 2-{4-[(4,6-dimethyl-3-nitro-2-pyridinyl)amino]phenyl}ethyl (4-methylphenyl)sulfonylcarbamate The title compound was prepared according to the procedure described in Example 3 from 2-{4-[(4,6-dimethyl-3-nitro-2-pyridinyl)amino]phenyl}ethanol.

$^1$H-NMR (CDCl$_3$) δ: 9.55 (1H, s), 7.89 (2H, d, J=8.3 Hz), 7.54 (2H, d, J=8.6 Hz), 7.32 (2H, d, J=8.6 Hz), 7.11 (2H, d, J=8.4 Hz), 6.54 (1H, s), 4.28 (2H, t, J=7.0 Hz), 2.88 (2H, t, J=7.0 Hz), 2.55 (3H, s), 2.43 (6H, s)

MS (ESI) m/z: 485 ([M+H]$^+$), 483 ([M−H]$^−$)

Step 2. 2-{4-[(3-amino-4,6-dimethyl-2-pyridinyl)amino]phenyl}ethyl (4-methylphenyl)sulfonylcarbamate The title compound was prepared according to the procedure described in step 4 of Example 1 from 2-{4-[(4,6-dimethyl-3-nitro-2-pyridinyl)amino]phenyl}ethyl (4-methylphenyl)sulfonylcarbamate.

$^1$H-NMR (CDCl$_3$) δ: 7.82 (2H, d, J=8.3 Hz), 7.25 (2H, d, J=8.3 Hz), 6.93 (2H, d, J=8.4 Hz), 6.84 (2H, d, J=8.4 Hz), 6.66 (1H, s), 4.22 (2H, t, J=6.6 Hz), 2.77 (2H, t, J=6.6 Hz), 2.39 (3H, s), 2.37 (3H, s), 2.22 (3H, s)

MS (ESI) m/z: 455 ([M+H]$^+$), 453 ([M−H]$^−$)

Step 3. 2-[4-(2-AMINO-5,7-DIMETHYL-3H-IMIDAZO[4,5-b]PYRIDIN-3-YL)PHENYL]ETHYL(4-METHYLPHENYL)SULFONYLCARBAMATE The title compound was prepared according to the procedure described in Example 127 from 2-{4-[(3-amino-4,6-dimethyl-2-pyridinyl)amino]phenyl}ethyl (4-methylphenyl)sulfonylcarbamate.

$^1$H-NMR (DMSO-d$_6$) δ: 7.76 (2H, d, J=8.3 Hz), 7.42–7.35 (6H, m), 6.78 (1H, s), 6.61 (1H, br.s), 4.22 (2H, t, J=6.6 Hz), 2.92 (2H, d, J=6.6 Hz), 2.373 (3H, s), 2.365 (3H, s), 2.32 (3H, s)

MS (ESI) m/z: 480 ([M+H]$^+$), 478 ([M−H]$^−$)

Example 308
2-{4-[5,7-DIMETHYL-2-(METHYLAMINO)-3H-IMIDAZO[4,5-b]PYRIDIN-3-YL]PHENYL}ETHYL(4-METHYLPHENYL)SULFONYLCARBAMATE

The title compound was prepared according to the procedure described in Example 129 from 2-{4-[(3-amino-4,6-dimethyl-2-pyridinyl)amino]phenyl}ethyl (4-methylphenyl)sulfonylcarbamate.

$^1$H-NMR (DMDO-d$_6$) δ: 7.78 (2H, d, J=8.1 Hz), 7.43–7.33 (7H, m), 6.77 (1H, s), 6.43 (1H, br.s), 4.25 (2H, t, J=6.6 Hz), 2.93 (2H, t, J=6.6 Hz), 2.88 (3H, s), 2.41 (3H, s), 2.37 (3H, s), 2.31 (3H, s)

MS (ESI) m/z: 494 ([M+H]$^+$), 492 ([M−H]$^−$)

Example 309
2-{4-[5,7-DIMETHYL-2-(METHYLSULFANYL)-3H-IMIDAZO[4,5-b]PYRIDIN-3-YL]PHENYL}ETHYL(4-METHYLPHENYL)SULFONYLCARBAMATE

The title compound was prepared according to the procedure described in Example 128 from 2-{4-[(3-amino-4,6-dimethyl-2-pyridinyl)amino]phenyl}ethyl (4-methylphenyl)sulfonylcarbamate.

$^1$H-NMR (CDCl$_3$) δ: 7.92 (2H, d, J=8.4 Hz), 7.36–7.22 (6H, m), 6.88 (1H, s), 4.32 (2H, t, J=6.6 Hz), 2.93 (2H, t, J=6.6 Hz), 2.72 (3H, s), 2.62 (3H, s), 2.48 (3H, s), 2.41 (3H, s)

MS (ESI) m/z: 511 ([M+H]$^+$), 509 ([M−H]$^−$)

Example 310
2-{4-[5,7-DIMETHYL-2-(METHYLSULFONYL)-3H-IMIDAZO[4,5-b]PYRIDIN-3-YL]PHENYL}ETHYL(4-METHYLPHENYL)SULFONYLCARBAMATE

To a stirred solution of 2-{4-[5,7-dimethyl-2-(methylsulfanyl)-3H-imidazo[4,5-b]pyridin-3-yl]phenyl}ethyl (4-methylphenyl)sulfonylcarbamate (100 mg, 0.20 mmol) in AcOH (1 ml) was added a solution of KMnO$_4$ (62 mg, 0.39 mmol) in water (2 ml) at room temperature. After 1 hour, the mixture was poured into ice-sat. NaHCO$_3$ aq. and extracted with CH$_2$Cl$_2$. The organic layer was dried over MgSO$_4$, and the filtered. After concentration in vacuo, the residue was purified by preparative TLC (CH$_2$Cl$_2$/MeOH=1011) to afford 70 mg (66%) of the title compounds.

$^1$H-NMR (CDCl$_3$) δ: 7.91 (2H, d, J=8.4 Hz), 7.47 (2H, d, J=8.2 Hz), 7.34–7.26 (4H, m), 7.08 (1H, s), 4.35 (2H, t,

J=6.7 Hz), 3.45 (3H, s), 2.96 (2H, t, J=6.7 Hz), 2.68 (3H, s), 2.55 (3H, s), 2.42 (3H, s)

MS (ESI) m/z: 543 ([M+H]$^+$), 541 ([M−H]$^−$)

Example 311

5-ACETYL-2-(METHYLAMINO)-1-(4-{2-[({[(4-METHYLPHENYL)SULFONYL]AMINO}CARBONYL) AMINO]ETHYL}PHENYL)-1H-BENZIMIDAZOLE

The title compound was prepared according to the procedure described in Example 129 from N-{[(2-{4-[(4-acetyl-2-aminophenyl)amino]phenyl}ethyl)amino] carbonyl}-4-methylbenzenesulfonamide.

$^1$H-NMR (CDCl$_3$) δ: 8.06 (1H, s), 7.75–7.66 (3H, m), 7.38–7.26 (6H, m), 6.89 (1H, d, J=8.3 Hz), 6.60 (1H, br.s), 3.55 (2H, dd, J=12.5 and 6.6 Hz), 3.08 (3H, s), 2.91 (2H, t, J=6.6 Hz), 2.61 (3H, s), 2.38 (3H, s)

MS (ESI) m/z: 506 ([M+H]$^+$), 504 ([M−H]$^−$)

Example 312

2-{4-[6-CHLORO-2-(3-PYRIDINYL)-5-(TRIFLUOROMETHYL)-1H-BENZIMIDAZOL-1-YL] PHENYL}ETHYL(4-METHYLPHENYL) SULFONYLCARBAMATE

Step 1. 2-{4-[6-CHLORO-2-(3-PYRIDINYL)-5-(TRIFLUOROMETHYL)-1H-BENZIMIDAZOL-1-YL] PHENYL}ETHANOL The title compound was prepared according to the procedure described in Example 138 from 2-(4-{[2-amino-5-chloro-4-(trifluoromethyl)phenyl]amino}phenyl)ethanol.

$^1$H-NMR (CDCl$_3$) δ: 8.70 (1H, dd, J=2.2 and 0.7 Hz), 8.62 (1H, dd, J=4.5 and 1.7 Hz), 8.23 (1H, s), 8.01–7.97 (1H, m), 7.45 (2H, dd, J=6.5 and 2.2 Hz), 7.37–7.24 (7H, m), 3.97 (2H, t, J=6.6 Hz), 2.99 (2H, t, J=6.6 Hz)

MS (ESI) m/z: 418 ([M+H]$^+$), 476 ([M+CF$_3$CO$_2$]$^−$)

Step 2. 2-{4-[6-CHLORO-2-(3-PYRIDINYL)-5-(TRIFLUOROMETHYL)-1H-BENZIMIDAZOL-1-YL] PHENYL}ETHYL(4-METHYLPHENYL) SULFONYLCARBAMATE The title compound was prepared according to the procedure described in Example 3 from 2-{4-[6-chloro-2-(3-pyridinyl)-5-(trifluoromethyl)-1H-benzimidazol-1-yl] phenyl}ethanol.

$^1$H-NMR (CDCl$_3$) δ: 8.73 (1H, dd, J=4.9 and 1.8 Hz), 8.40–8.36 (1H, m), 8.23 (1H, s), 7.91 (1H, dd, J=2.2 and 0.7 Hz), 7.84–7.80 (2H, m), 7.49–7.43 (2H, m), 7.31–7.17 (6H m), 4.44 (2H, t, J=6.2 Hz), 3.02 (2H, t, J=6.2 Hz), 2.41 (3H, s)

MS (ESI) m/z: 615 ([M+H]$^+$), 613 ([M−H]$^−$)

Example 313

2-{4-[6-CHLORO-2-(4-PYRIDINYL)-5-(TRIFLUOROMETHYL)-1H-BENZIMIDAZOL-1-YL] PHENYL}ETHYL(4-METHYLPHENYL) SULFONYLCARBAMATE

Step 1. 2-{4-[6-CHLORO-2-(4-PYRIDINYL)-5-(TRIFLUOROMETHYL)-1H-BENZIMIDAZOL-1-YL] PHENYL}ETHANOL The title compound was prepared according to the procedure described in Example 138 from 2-(4-{[2-amino-5-chloro-4-(trifluoromethyl)phenyl]amino}phenyl)ethanol.

$^1$H-NMR (CDCl$_3$) δ: 8.60 (2H, dd, J=4.6 and 1.7 Hz), 8.25 (1H, s), 7.49–7.44 (4H, m), 7.37 (1H, s), 7.27–7.23 (2H, m), 4.00 (2H, t, J=6.4 Hz), 3.02 (2H, t, J=6.4 Hz)

MS (ESI) m/z: 418 ([M+H]$^+$), 476 ([M+CF$_3$CO$_2$]$^−$)

Step 2. 2-{4[6-CHLORO-2-(4-PYRIDINYL)-5-(TRIFLUOROMETHYL)-1H-BENZIMIDAZOL-1-YL] PHENYL}ETHYL(4-METHYLPHENYL) SULFONYLCARBAMATE The title compound was prepared according to the procedure described in Example 3 from 2-{4-[6-chloro-2-(4-pyridinyl)-5-(trifluoromethyl)-1H-benzimidazol-1-yl] phenyl}ethanol.

$^1$H-NMR (CDCl$_3$) δ: 8.60 (2H, dd, J=4.8 and 1.5 Hz), 8.27 (1H, s), 7.89 (2H, d, J=8.3 Hz), 7.44–7.18 (9H, m), 4.39 (2H, t, J=6.4 Hz), 3.03 (2H, t, J=6.4 Hz), 2.40 (3H, s)

MS (ESI) m/z: 615 ([M+H]$^+$), 613 ([M−H]$^−$)

Example 314

2-{4-[6-CHLORO-2-(2-METHYLPHENYL)-5-(TRIFLUOROMETHYL)-1H-BENZIMIDAZOL-1-YL] PHENYL}ETHYL(4-METHYLPHENYL) SULFONYLCARBAMATE

Step 1. 2-{4-[6-CHLORO-2-(2-METHYLPHENYL)-5-(TRIFLUOROMETHYL)-1H-BENZIMIDAZOL-1-YL] PHENYL}ETHANOL The title compound was prepared according to the procedure described in Example 138 from 2-(4-{[2-amino-5-chloro-4-(trifluoromethyl)phenyl]amino}phenyl)ethanol.

$^1$H-NMR (CDCl$_3$) δ: 8.22 (1H, s), 7.47 (1H, s), 7.33–7.10 (8H, m), 3.89 (2H, t, J=6.4 Hz), 2.89 (2H, t, J=6.4 Hz), 2.20 (3H, s)

MS (ESI) m/z: 431 ([M+H]$^+$)

Step 2. 2-{4-[6-CHLORO-2-(2-METHYLPHENYL)-5-(TRIFLUOROMETHYL)-1H-BENZIMIDAZOL-1-YL] PHENYL}ETHYL(4-METHYLPHENYL) SULFONYLCARBAMATE The title compound was prepared according to the procedure described in Example 3 from 2-{4-[6-chloro-2-(2-methylphenyl)-5-(trifluoromethyl)-1H-benzimidazol-1-yl] phenyl}ethanol.

$^1$H-NMR (CDCl$_3$) δ: 8.24 (1H, s), 7.78 (2H, d, J=8.2 Hz), 7.46 (1H, s), 7.35–7.09 (8H, m), 7.00 (2H, d, J=8.4 Hz), 4.27 (2H, t, J=6.8 Hz), 2.88 (2H, t, J=6.8 Hz), 2.41 (3H, s)

MS (ESI) m/z: 628 ([M+H]$^+$), 489 ([M+CH$_3$CO$_2$]$^−$)

Example 315

2-{4-[6-CHLORO-2-(1,3-THIAZOL-2-YL)-5-(TRIFLUOROMETHYL)-1H-BENZIMIDAZOL-1-YL] PHENYL}ETHYL(4-METHYLPHENYL) SULFONYLCARBAMATE

Step 1. 2-{4-[6-CHLORO-2-(1,3-THIAZOL-2-YL)-5-(TRIFLUOROMETHYL)-1H-BENZIMIDAZOL-1-YL] PHENYL}ETHANOL The title compound was prepared according to the procedure described in Example 138 from 2-(4-{[2-amino-5-chloro-4-(trifluoromethyl)phenyl]amino}phenyl)ethanol.

$^1$H-NMR (CDCl$_3$) δ: 8.23 (1H, s), 7.75 (1H, d, J=3.1 Hz), 7.47–7.45 (3H, m), 7.36–7.27 (3H, m), 3.99 (2H, t, J=6.4 Hz), 3.03 (2H, t, J=6.4 Hz)

MS (ESI) m/z: 424 ([M+H]$^+$), 482 ([M+CH$_3$CO$_2$]$^−$)

Step 2. 2-{4-[6-CHLORO-2-(1,3-THIAZOL-2-YL)-5-(TRIFLUOROMETHYL)-1H-BENZIMIDAZOL-1-YL] PHENYL}ETHYL(4-METHYLPHENYL) SULFONYLCARBAMATE The title compound was prepared according to the procedure described in Example 3 from 2-{4-[6-chloro-2-(1,3-thiazol-2-yl)-5-(trifluoromethyl)-1H-benzimidazol-1-yl] phenyl}ethanol.

$^1$H-NMR (CDCl$_3$) δ: 8.23 (1H, s), 7.91 (2H, d, J=8.4 Hz), 7.74 (1H, d, J=3.1 Hz), 7.46 (1H, d, J=3.1 Hz), 7.38–7.26 (7H, m), 4.40 (2H, t, J=6.8 Hz), 3.04 (2H, t, J=6.8 Hz), 2.42 (3H, s)

MS (ESI) m/z: 621 ([M+H]$^+$), 619 ([M−H]$^−$)

Example 316
2-{4-[6-CHLORO-2-(αH-IMIDAZOL-4-YL)-5-(TRIFLUOROMETHYL)-1H-BENZIMIDAZOL-1-YL]PHENYL}ETHYL(4-METHYLPHENYL)SULFONYLCARBAMATE Step 1. 2-{4-[6-CHLORO-2-(αH-IMIDAZOL-4-YL)-5-(TRIFLUOROMETHYL)-1H-BENZIMIDAZOL-1-YL]PHENYL}ETHANOL The title compound was prepared according to the procedure described in Example 138 from 2-(4-{[2-amino-5-chloro-4-(trifluoromethyl)phenyl]amino}phenyl)ethanol.

$^1$H-NMR (CDCl$_3$/CD$_3$OD=4/1) δ: 8.09 (1H, s), 7.65 (1H, s), 7.50 (2H, d, J=8.7 Hz), 7.33 (2H, d, J=8.2 Hz), 7.25 (1H, s), 6.91 (1H, s), 3.93 (2H, t, J=6.4 Hz), 3.00 (2H, t, J=6.4 Hz)

MS (ESI) m/z: 407 ([M+H]$^+$), 405 ([M–H]$^-$)

Step 2. 2-{4-[6-CHLORO-2-(αH-IMIDAZOL-4-YL)-5-(TRIFLUOROMETHYL)-1H-BENZIMIDAZOL-1-YL]PHENYL}ETHYL(4-METHYLPHENYL)SULFONYLCARBAMATE The title compound was prepared according to the procedure described in Example 3 from 2-{4-[6-chloro-2-(□H-imidazol-4-yl)-5-(trifluoromethyl)-1H-benzimidazol-1-yl]phenyl}ethanol.

MS (ESI) m/z: 604 ([M+H]$^+$), 602 ([M–H]$^-$)

Example 317
2-[4-(5,6-DIMETHYL-1H-BENZIMIDAZOL-1-YL)PHENYL]ETHYL(4-METHYLPHENYL)SULFONYLCARBAMATE Step. α4-(2-HYDROXYETHYL)PHENYLBORONIC ACID To a stirred solution of 4-bromophenethylalcohol (5.00 g, 24.9 mmol) in THF (80 ml) was added a solution of 1.5M n-BuLi in hexane (39.8 ml, 59.7 mmol) at −78° C. over 30 min. After 1 hour, a solution of B(O'Pr)$_3$ (8.61 ml, 37.3 mmol) in THF (20 ml) was added slowly to the mixture at −78° C. The resultant mixture was warmed to room temperature, and treated with 2M HCl (100 ml) for 1 hour. This was extracted with CH$_2$Cl$_2$ and dried over MgSO$_4$, then filtered. After evaporation in vacuo, the residue was purified by silica-gel column chromatography eluting with CH$_2$Cl$_2$/MeOH=20/1 to afford 2.61 g (63%) of the title compound.

$^1$H-NMR (CD$_3$OD) δ: 7.64–7.48 (2H, m), 7.19–7.13 (2H, m), 3.70 (2H, t, J=7.2 Hz), 2.77 (2H, t, J=7.2 Hz)

MS (ESI) m/z: 165 ([M–H]$^-$)

Step 2. 4-{2-[({[(4-METHYLPHENYL)SULFONYL]AMINO}CARBONYL)OXY]ETHYL}PHENYLBORONIC ACID 4-(2-hydroxyethyl)phenylboronic acid (1.00 g, 6.02 mmol) was treated with pTsNCO (1.01 ml, 6.63 mmol) and pyridine (90 ml) at room temperature for 2 hours. The mixture was poured into ice-2M HCl and extracted with EtOAc. The organic layer was dried over MgSO$_4$, and filtered. After removal of solvent, the residue was purified by silica-gel column chromatography eluting with CH$_2$Cl$_2$/MeOH=20/1 to afford 2.20 g (quant.) of the title compound.

$^1$H-NMR (DMSO-d$_3$) δ: 11.95 (1H, br.s), 7.97 (1H, s), 7.75–7.67 (2H, m), 7.40 (2H, d, J=8.6 Hz), 7.13 (2H, d, J=7.7 Hz), 4.18 (2H, t, J=6.6 Hz), 2.81 (2H, t, J=6.6 Hz), 2.40 (3H, s)

MS (ESI) m/z: 381 ([M+NH$_4$]$^+$), 362 ([M–H]$^-$)

Step 3. 2-[4-(5,6-DIMETHYL-1H-BENZIMIDAZOL-1-YL)PHENYL]ETHYL(4-METHYLPHENYL)SULFONYLCARBAMATE A mixture of 4-{2-[({[(4-methylphenyl)sulfonyl]amino}carbonyl)oxy]ethyl}phenylboronic acid (100 mg, 0.28 mmol), 5,6-dimethylbenzimidazole (40 mg, 0.28 mmol), Cu(OAc)$_2$ (60 mg, 0.33 mmol), triethylamine (115 □l, 0.83 mmol), MS4A (100 mg), and CH$_2$Cl$_2$ (4 ml) was stirred at room temperature for 1 week. After filtration through a bed of celite, the filtrate was diluted with CH$_2$Cl$_2$, and washed with water. The organic fraction was dried over MgSO$_4$ and filtered. After concentration under reduced pressure, the residue was purified by preparative TLC (CH$_2$Cl$_2$/MeOH=10/1) to afford 28 mg (22%) of the title compound.

$^1$H-NMR (CDCl$_3$) δ: 7.82 (2H, d, J=8.4 Hz), 7.72 (1H, s), 7.57 (1H, s), 7.33 (2H, d, J=8.1 Hz), 7.12 (2H, d, J=8.4 Hz), 7.07 (1H, s), 7.01 (2H, d, J=8.4 Hz), 4.39 (2H, t, J=6.1 Hz), 2.94 (2H, t, J=6.1 Hz), 2.42 (3H, s), 2.39 (3H, s), 2.26 (3H, s)

MS (ESI) m/z: 464 ([M+H]$^+$), 462 ([M–H]$^-$)

Example 318
6-CHLORO-5-CYANO-2-ETHYL-1-(4-{2-[({[(4-METHYLPHENYLSULFONYL]AMINO}CARBONYL)AMINO]ETHYL}PHENYL)-1H-BEVZIMIDAZOLE Step 1. 6-Chloro-1-[4-(2-chloroethyl)phenyl]-2-ethyl-1H-benzimidazole-5-carbonitrile The title compound was prepared according to the procedure described in step 7 of Example 1 from 6-chloro-2-ethyl-1-[4-(2-hydroxyethyl)phenyl]-1H-benzimidazole-5-carbonitrile (Example 111, step 4).

$^1$H-NMR (CDCl$_3$) δ 8.07 (1H, s), 7.50 (2H, d, J=8.4 Hz), 7.30 (2H, d, J=8.4 Hz), 7.19 (1H, s), 3.83 (2H, t, J=7.1 Hz), 3.22 (2H, t, J=7.1 Hz), 2.79 (2H, q, J=7.5 Hz), 1.37 (3H, t, J–7.5 Hz).

Step 2. 1-[4-(2-Azidoethyl)phenyl]-6-chloro-2-ethyl-1H-benzimidazole-5-carbonitrile The title compound was prepared according to the procedure described in step 8 of Example 1 from 6-chloro-1-[4-(2-chloroethyl)phenyl]-2-ethyl-1H-benzimidazole-5-carbonitrile (step 1).

$^1$H-NMR (CDCl$_3$) δ 8.07 (1H, s), 7.49 (2H, d, J=8.4 Hz), 7.29 (2H, d, J=8.4 Hz), 7.18 (1H, s), 3.64 (2H, t, J=7.0 Hz), 3.04 (2H, t, J=7.0 Hz), 2.79 (2H, q, J=7.6 Hz), 1.36 (3H, t, J=7.6 Hz).

Step 3. 1-[4-(2-Aminoethyl)phenyl]-6-chloro-2-ethyl-1H-benzimidazole-5-carbonitrile The title compound was prepared according to the procedure described in step 7 of Example 37 from 1-[4-(2-azidoethyl)phenyl]-6-chloro-2-ethyl-1H-benzimidazole-5-carbonitrile (step 2).

$^1$H-NMR (CDCl$_3$) δ 8.06 (1H, s), 7.46 (2H, d, J=8.1 Hz), 7.26 (2H, d, J=8.1 Hz), 7.19 (1H, s), 3.09 (2H, t, J=7.1 Hz), 2.89 (2H, t, J=7.1 Hz), 2.79 (2H, q, J=7.6 Hz), 1.36 (3H, t, J=7.6 Hz).

Step 4. 6-Chloro-5-cyano-2-ethyl-1-(4-{2-[({[(4-methylphenyl)sulfonyl]amino}carbonyl)amino]ethyl}phenyl)-1H-benzimidazole The title compound was prepared according to the procedure described in step 10 of Example 1 from 1-[4-(2-aminoethyl)phenyl]-6-chloro-2-ethyl-1H-benzimidazole-5-carbonitrile (step 3).

mp 219–224° C.; IR (KBr) v: 3388, 2229, 1708, 1618, 1514, 1466, 1344, 1161, 1089 cm$^{-1}$.

MS (ESI) m/z 522 (M+H)$^+$, 520 (M–H)$^-$; $^1$H-NMR (DMSO-d$_6$) δ: 8.38 (1H, s), 7.77 (2H, d, J=8.2 Hz), 7.31–7.49 (6H, m), 7.32 (1H, s), 6.53 (1H, br.s), 3.26–3.28 (2H, m), 2.69–2.81 (4H, m), 2.35 (3H, s), 1.25 (3H, t, J=7.6 Hz).

Example 319
6-CHLORO-5-(DIMETHYLAMINO)-2-ETHYL-1-(4-{2-[({[(4-METHYLPHENYL)SULFONYL]AMINO}CARBONYL)AMINO]ETHYL}PHENYL)-1H-BENZIMIDAZOLE Step 1. N-{6-chloro-1-]4-(2-chloroethyl)phenyl-2-ethyl-1H-benzimidazol-5-yl}-N,N-dimethylamine A mixture of 6-chloro-1-[4-(2-chloroethyl)phenyl]-2-ethyl-1H-benzimidazol-5-ylamine (Example 110, step 6, 100 mg, 0.3 mmol) and NaBH$_4$ (153 mg, 4 mmol) in THF (5 ml) was added to the mixture of 38% folmaldehyde (0.5 ml, 5.6 mmol) and 3M aqueous H$_2$SO$_4$ (0.4 ml, 0.12 mmol) at 0° C. The mixture was stirred at room temperature for 5 h. The reaction mixture was poured into water, and extracted with ethyl acetate (100 ml). The organic layer was washed with brine (50 ml), then dried (Na$_2$SO$_4$). After removal of solvent, the crude product was purified by flash column chromatography eluting with hexane/ethyl acetate (1:2) to afford 48 mg (46%) of the title compound as white solids.

MS (EI) m/z: 361 (M$^+$).

$^1$H-NMR (CDCl$_3$) δ: 7.54 (1H, s), 7.44 (2H, d, J=8.3 Hz), 7.29 (2H, d, J=8.3 Hz), 7.13 (1H, s), 3.82 (2H, t, J=7.0 Hz), 3.19 (2H, t, J=7.0 Hz), 2.82 (6H, s), 2.75 (2H, q, J=7.6 Hz), 1.35 (3H, t, J=7.6 Hz).

Step 2. N-{1-[4-(2-azidoethyl)phenyl]-6-chloro-2-ethyl-1H-benzimidazol-5-yl}-N,N-dimethylamine The title compound was prepared according to the procedure described in step 8 of Example 1 from N-{6-chloro-1-[4-(2-chloroethyl)phenyl]-2-ethyl-1H-benzimidazol-5-yl}-N,N-dimethylamine (step 1).

$^1$H-NMR (CDCl$_3$) δ: 7.54 (1H, s), 7.43 (2H, d, J=8.2 Hz), 7.29 (2H, d, J=8.2 Hz), 7.12 (1H, s), 3.62 (2H, t, J=7.0 Hz), 3.01 (2H, t, J=7.0 Hz), 2.82 (6H, s), 2.75 (2H, q, J=7.6 Hz), 1.34 (2H, t, J=7.6 Hz).

Step 3. N-{-[4-(2-aminoethyl)phenyl]-6-chloro-2-ethyl-1H-benzimidazol-5-yl}-N,N-dimethylamine The title compound was prepared according to the procedure described in step 7 of Example 37 from N-{1-[4-(2-azidoethyl)phenyl]-6-chloro-2-ethyl-1H-benzimidazol-5-yl}-N,N-dimethylamine (step 2).

$^1$H-NMR (CDCl$_3$) δ: 7.54 (1H, s), 7.41 (2H, d, J=8.1 Hz), 7.27 (2H, d, J=8.1 Hz), 7.13 (1H, s), 3.08 (2H, t, J=6.9 Hz), 2.87 (2H, t, J=6.9 Hz), 2.82 (6H, s), 2.75 (2H, q, J=7.6 Hz), 1.35 (3H, t, J=7.6 Hz).

Step 4. 6-chloro-5-(dimethylamino)-2-ethyl-1-(4-{2-[({[(4-methylphenyl)sulfonyl]amino}carbonyl)amino]ethyl}phenyl)-1H-benzimidazole The title compound was prepared according to the procedure described in step 10 of Example 1 from N-{1-[4-(2-aminoethyl)phenyl]-6-chloro-2-ethyl-1H-benzimidazol-5-yl}-N,N-dimethylamine (step 3).

m.p.: 108–114° C.

MS (ESI) m/z: 540 (MH$^+$), 538 ([M–H]$^-$).

$^1$H-NMR (CDCl$_3$) δ: 7.73 (2H, d,=8.0 Hz), 7.54 (1H, s), 7.25–7.39 (6H, m), 7.11 (1H, s), 6.73 (1H, br.s), 3.58 (2H, q, J=6.9 Hz), 2.94 (2H, t, J=6.9 Hz), 2.71–2.82 (8H, m), 2.40 (3H, s), 1.33 (3H, t, J=7.6 Hz).

Example 320
6-CHLORO-2-ETHYL-5-(METHYLAMINO)-1-(4-{2-[({[(4-METHYLPHENYL)SULFONYL]AMINO}CARBONYL)AMINO]ETHYL}PHENYL)-1H-BENZIMIDAZOLE Step 1. 6-chloro-1-[4-(2-chloroethyl)phenyl]-2-ethyl-1H-benzimidazol-5-ylformamide A solution of acetic anhydride (0.14 ml) in THF (5 ml) was added formic acid (0.06 ml, 1.65 mmol) at 0° C. under nitrogen and the mixture was stirred at 60° C. for 2 h. Then the mixture was recooled to 0° C. and was added 6-Chloro-1-[4-(2-chloroethyl)phenyl]-2-ethyl-1H-benzimidazol-5-ylamine (Example 110, step 6, 100 mg, 0.3 mmol) in THF (2 ml). The mixture was stirred at room temperature for 2 h. The volatile component was removed under reduced pressure, and the residue was dissolved with ethyl acetate (100 ml). The organic layer was washed with 2N aqueous NaOH (50 ml), brine (50 ml), then dried (Na2SO4). After removal of solvent, the crude product was purified by flash column chromatography eluting with hexane/ethyl acetate (1:10) to afford 68 mg (67%) of the title compound as pale yellow solids.

MS (EI) m/z: 361 (M$^+$).

$^1$H-NMR (CDCl$_3$) δ: 8.53–8.76 (1H, br.s), 7.66 (1H, s), 7.44–7.48 (2H, m), 7.26–7.31 (2H, m), 7.18 (1H, s), 3.83 (2H, t, J=6.9 Hz), 3.20 (2H, t, J=6.9 Hz), 2.78 (2H, q, J=7.4 Hz), 1.32–1.39 (3H, m).

Step 2. N-{6-chloro-1-[4-(2-chloroethyl)phenyl]-2-ethyl-1H-benzimidazol-5-yl}-N-methylamine A solution of (6-chloro-1-[4-(2-chloroethyl)phenyl]-2-ethyl-1H-benzimidazol-5-ylformamide, step 1, 112 mg, 0.3 mmol) in THF (15 ml) was added Me$_2$S BH$_3$ (0.07 ml, 0.77 mmol) under nitrogen at room temperature. The mixture was refluxed for 1 h. Then the mixture was cooled to room temperature and was added methanol (3 ml) and 2N aqueous HCl (12 ml). The mixture was stirred at 70° C. for 30 min. The volatile component was removed under reduced pressure, and the residue was dissolved with ethyl acetate (100 ml). The organic layer was washed with saturated aqueous NaHCO$_3$ (50 ml), brine (50 ml), then dried (Na2SO4). After removal of solvent, the crude product was purified by flash column chromatography eluting with hexane/ethyl acetate (1:4) to afford 93 mg (87%) of the title compound as white solids.

MS (EI) m/z: 347 (M$^+$)

$^1$H-NMR (CDCl$_3$) δ: 7.42 (2H, d, J=8.2 Hz), 7.29 (2H, d, J=8.2 Hz), 7.04 (1H, s), 7.03 (1H, s), 3.81 (2H, t, J=6.9 Hz), 3.18 (2H, t, J=6.9 Hz), 2.95 (3H, s), 2.75 (2H, q, J=7.6 Hz), 1.34 (3H, t, J=7.6 Hz).

Step 3. N-{1-[4-(2-azidoethyl)phenyl]-6-chloro-2-ethyl-1H-benzimidazol-5-yl}-N-methylamine The title compound was prepared according to the procedure described in step 8 of Example 1 from N-{6-chloro-1-[4-(2-chloroethyl)phenyl]-2-ethyl-1H-benzimidazol-5-yl}-N-methylamine (step 2).

$^1$H-NMR (CDCl$_3$) δ: 7.42 (2H, d, J=8.3 Hz), 7.29 (2H, d, J=8.3 Hz), 7.04–7.03 (2H, m), 4.19 (1H, br.s), 3.61 (2H, t, J=7.0 Hz), 3.00 (2H, t, J=7.0 Hz), 2.95 (3H, s), 2.75 (2H, q, J=7.6 Hz), 1.33 (3H, t, J=7.6 Hz).

Step 4. N-{1-[4-(2-aminoethyl)phenyl]-6-chloro-2-ethyl-1H-benzimidazol-5-yl}-N-methylamine The title compound was prepared according to the procedure described in step 7 of Example 37 from N-{1-[4-(2-azidoethyl)phenyl]-6-chloro-2-ethyl-1H-benzimidazol-5-yl}-N-methylamine (step 3).

$^1$H-NMR (CDCl$_3$) δ: 7.39 (2H, d, J=8.4 Hz), 7.25 (2H, d, J=8.4 Hz), 7.06 (1H, s), 7.03 (1H, s), 3.64 (2H, br.s), 3.15 (2H, t, J=7.2 Hz), 2.94–2.99 (5H, m), 2.73 (2H, q, J=7.5 Hz), 1.32 (3H, t, J=7.5 Hz).

Step 5. 6-chloro-2-ethyl-5-(methylamino)-1-(4-{2-[({[(4-methylphenyl)sulfonyl]amino}carbonyl)amino]ethyl}phenyl)-1H-benzimidazole The title compound was prepared according to the procedure described in step 10 of Example 1 from N-{1-[4-(2-aminoethyl)phenyl]-6-chloro-2-ethyl-1H-benzimidazol-5-yl}-N-methylamine (step 4).

m.p.: 95–100° C.

MS (ESI) m/z: 526 (MH$^+$), 524 ([M–H]$^-$).

$^1$H-NMR (CDCl$_3$) δ: 7.73 (2H, d, J=8.4 Hz), 7.23–7.36 (7H, m), 7.03 (1H, s), 3.57 (2H, t, J=6.6 Hz), 2.89–2.94 (5H, m), 2.73 (2H, q, J=7.4 Hz), 1.32 (3H, t, J=7.4 Hz).

Example 321
4-CYANO-2-ETHYL-1-(4-{2-[({[(4-METHYLPHENYL)SULFONYL]AMINO}CARBONYL)AMINO]ETHYL}PHENYL)-1H-BENZIMIDAZOLE Step 1. 3-chloro-2-nitrobenzamide A mixture of 3-chloro-2-nitro-benzoic acid (1 g, 4.9 mmol) and thionyl chloride (9 ml) was stirred at 80° C. for 1 h. The thionyl chloride was removed under reduced pressure, and the residue was dissolved with dichloromethane (15 ml). The mixture was cooled to 0° C. and was added 30% aqueous NH3 (2 ml) dropwise. The mixture was stirred at 0° C. for 25 min. The reaction mixture was poured into water and extracted with ethyl acetate (300 ml). The organic layer was washed with saturated aqueous $Na_2CO_3$ (100 ml), and brine (100 ml). This organic phase was dried ($Na_2SO_4$) and concentrated under reduced pressure to give 1.2 g (quant.) of the title compound as pale orange solids.

$^1$H-NMR (CDCl$_3$) δ: 7.68–7.92 (3H, m).

Step 2. 3-chloro-2-nitrobenzonitrile

A solution of 3-chloro-2-nitrobenzamide (step 1, 1.2 g, 4.9 mmol) in DMF (8 ml) was added thionyl chloride (2 ml, 24.8 mmol) in DMF (3 ml) dropwise at room temperature. The mixture was stirred at 120° C. for 2.5 h. The mixture was poured into ice-water and extracted with ethyl acetate (200 ml). The organic layer was washed with saturated aqueous NaHCO$_3$ (100 ml), brine (100 ml), then dried (MgSO4), and concentrated. The residue was purified by flash chromatography eluting with hexane/ethyl acetate (3:1/ 1:2) to give 1 g (quant.) of the title compound as pale yellow solids.

$^1$H-NMR (CDCl$_3$) δ: 7.61–7.68 (1H, m), 7.74–7.78 (2H, m).

Step 3. 2-[4-(3-Cyano-2-nitroanilino)phenyl]ethanol

The title compound was prepared according to the procedure described in step 3 of Example 1 from 3-chloro-2-nitrobenzonitrile (step 2) and 4-aminophenylethyl alcohol.

MS (EI) m/z: 283 (M$^+$).

$^1$H-NMR (CDCl$_3$) δ: 9.37 (1H, br.s), 7.15–7.41 (7H, m), 3.91 (2H, t, J=6.4 Hz), 2.91 (2H, t, J=6.4 Hz).

Step 4. 2-amino-3-[4-(2-hydroxyethyl)anilino]benzonitrile

The title compound was prepared according to the procedure described in step 2 of Example 40 from 2-[4-(3-Cyano-2-nitroanilino)phenyl]ethanol (step 3).

MS (EI) m/z: 253 (M$^+$).

$^1$H-NMR (CDCl$_3$) δ: 7.22–7.28 (2H, m), 7.10 (2H, d, J=8.4 Hz), 6.69–6.75 (3H, m), 5.13 (1H, br.s), 4.54 (2H, br.s), 3.84 (2H, t, J=6.4 Hz), 2.80 (2H, t, J=6.4 Hz).

Step 5. 2-[4-(4-cyano-2-ethyl-1H-benzimidazol-1-yl) phenyl]ethyl propionate

The title compound was prepared according to the procedure described in step 5 of Example 1 from 2-amino-3-[4-(2-hydroxyethyl)anilino]benzonitrile (step 4).

TLC, Rf=0.6, hexane:ethyl acetate (1:1).

Step 6. 2-ethyl-1-[4-(2-hydroxyethyl)phenyl]-1H-benzimidazole-4-carbonitrile

The title compound was prepared according to the procedure described in step 6 of Example 1 from 2-[4-(4-cyano-2-ethyl-1H-benzimidazol-1-yl)phenyl]ethyl propionate (step 5).

MS (EI) m/z: 291 (M$^+$).

$^1$H-NMR (CDCl$_3$) δ: 7.58 (1H, d, J=6.3 Hz), 7.49 (2H, d, J=8.3 Hz), 7.19–7.32 (4H, m), 4.01 (2H, t, J=6.4 Hz), 3.02 (2H, t, J=6.4 Hz), 2.86 (2H, q, J=7.6 Hz), 1.34 (3H, t, J=7.6 Hz).

Step 7. 1-[4-(2-chloroethyl)phenyl]-2-ethyl-1H-benzimidazole-4-carbonitrile

The title compound was prepared according to the procedure described in step 7 of Example 1 from 2-ethyl-1-[4-(2-hydroxyethyl)phenyl]-1H-benzimidazole-4-carbonitrile (step 6).

$^1$H-NMR (DMSO-d$_6$) δ: 7.72 (1H, dd, J=1.2 Hz, 7.4 Hz), 7.51–7.60 (4H, m), 7.30–7.42 (2H, m), 3.97 (2H, t, J=7.0 Hz), 3.18 (2H, t, J=7.0 Hz), 2.79 (2H, q, J=7.6 Hz), 1.26 (3H, t, J=7.6 Hz).

Step 8. 1-[4-(2-azidoethyl)phenyl]-2-ethyl-1H-benzimidazole-4-carbonitrile

The title compound was prepared according to the procedure described in step 8 of Example 1 from 1-[4-(2-chloroethyl)phenyl]-2-ethyl-1H-benzimidazole-4-carbonitrile (step 7).

$^1$H-NMR (CDCl$_3$) δ: 7.59 (1H, dd, J=1.2 Hz, 7.3 Hz), 7.48 (2H, d, J=8.0 Hz), 7.19–7.32 (4H, m), 3.63 (2H, t, J=6.6 Hz), 3.03 (2H, t, J=6.6 Hz), 2.84 (2H, q, J=7.6 Hz), 1.31 (3H, t, J=7.6 Hz).

Step 9. 1-[4-(2-aminoethyl)phenyl]-2-ethyl-1H-benzimidazole-4-carbonitrile

The title compound was prepared according to the procedure described in step 7 of Example 37 from 1-[4-(2-azidoethyl)phenyl]-2-ethyl-1H-benzimidazole-4-carbonitrile (step 8).

$^1$H-NMR (CDCl$_3$) δ: 7.58 (1H, dd, J=1.3 Hz, 7.4 Hz), 7.44 (2H, d, J=8.2 Hz), 7.19–7.32 (4H, m), 3.08 (2H, t, J=6.7 Hz), 2.81–2.93 (4H, m), 1.33 (3H, t, J=7.5 Hz).

Step 10. 4-cyano-2-ethyl-1-(4-{2-[({[(4-methylphenyl) sulfonyl]amino}carbonyl)amino]ethyl}phenyl)-1H-benzimidazole The title compound was prepared according to the procedure described in step 10 of Example 1 from 1-[4-(2-aminoethyl)phenyl]-2-ethyl-1H-benzimidazole-4-carbonitrile (step 9).

m.p.: 95–103° C.

IR (KBr) v: 2225, 1676, 1516, 1433, 1340, 1161, 1091, 794, 663 cm$^{-1}$.

MS (ESI) m/z : 488 (MH$^+$), 486 ([M–H]$^-$).

$^1$H-NMR (CDCl$_3$) δ: 7.72 (2H, d, J=8.1 Hz), 7.59 (1H, d, J=7.0 Hz), 7.42 (2H, d, J=8.1 Hz), 7.18–7.32 (6H, m), 6.72 (1H, br.s), 3.57 (2H, t, J=7.1 Hz), 2.96 (2H, t, J=7.1 Hz), 2.85 (2H, q, J=7.6 Hz), 2.41 (3H, s), 1.33 (3H, t, J=7.6 Hz).

Example 322

2-ETHYL-1-(4-{2-[({[(4-METHYLPHENYL) SULFONYL]AMINO}CARBONYL)AMINO] ETHYL}PHENYL)-1H-BENZIMIDAZOLE-4-CARBOXAMIDE

Step 1. 2-ethyl-1-(4-{2-[({[(4-methylphenyl)sulfonyl] amino}carbonyl)amino]ethyl}phenyl)-1H-benzimidazole-4-carboxamide To a stirred suspension of 2-{4-[(3-amino-4,6-dimethyl-2-pyridinyl)amino]phenyl}ethanol (step 4, 820 mg, 3.3 mmol) in toluene (30 ml) was added dropwise propionyl chloride (630 mg, 6.8 mmol) at 0° C., and the reaction mixture was refluxed for 1.5 h. After cooling, the mixture was poured into water (50 ml) and extracted with ethyl acetate (100 ml). The organic layer was washed with 2N aqueous NaOH (50 ml) and brine (50 ml), then dried (Na2SO4). The solvent was removed under reduced pressure and the residue was dissolved with THF(20 ml) and methanol (20 ml). The mixture was added 4N aqueous LiOH (10 ml) and stirred at room temperature for 14 h. The mixture was evaporated. The residue was dissolved with ethyl acetate (100 ml) and washed with water (50 ml). The organic layer was washed with brine (50 ml), and dried (Na2SO4). After removal of solvent, the crude product was purified by flash column chromatography eluting with hexane/ethyl acetate (1:2/1:5/0:1) to afford 260 mg (26%) of the title compound as white solids.

MS (EI) m/z: 309 (M$^+$)

$^1$H-NMR (CDCl$_3$) δ: 9.81 (1H, br.s), 8.13 (1H, dd, J=2.0 Hz, 7.0 Hz), 7.47 (2H, d, J=8.0 Hz), 7.25–7.31 (4H, m), 5.99 (1H, br.s), 4.00 (2H, t, J=6.4 Hz), 3.01 (2H, t, J=6.4 Hz), 2.82 (2H, q, J=7.6 Hz), 1.37 (3H, t, J=7.6 Hz).

Step 2. 1-[4-(2-chloroethyl)phenyl]-2-ethyl-1H-benzimidazole-4-carboxamide

The title compound was prepared according to the procedure described in step 7 of Example 1 from 2-[4-(6-chloro-2-ethyl-5-nitro-1H-benzimidazol-1-yl)phenyl] ethanol (step 1).

$^1$H-NMR (DMSO-d$_6$) δ: 9.29 (1H, br.s), 7.81–7.91 (1H, m), 7.79 (1H, br.s), 7.49–7.60 (4H, m), 7.24–7.33 (2H, m), 3.97 (2H, t, J=6.8 Hz), 3.18 (2H, t, J=6.8 Hz), 2.80 (2H, q, J=7.5 Hz), 1.27 (3H, t, J=7.5 Hz).

Step 3. 1-[4-(2-azidoethyl)phenyl]-2-ethyl-1H-benzimidazole-4-carboxamide

The title compound was prepared according to the procedure described in step 8 of Example 1 from 6-chloro-1-[4-(2-chloroethyl)phenyl]-2-ethyl-1H-benzimidazole-5-carboxamide (step 2).

$^1$H-NMR (DMSO-d$_6$) δ: 9.29 (1H, br.s), 7.89 (1H, d, J=7.3 Hz), 7.79 (1H, br.s), 7.51–7.59 (4H, m), 7.22–7.33 (2H, m), 3.68 (2H, t, J=6.6 Hz), 3.01 (2H, t, J=6.6 Hz), 2.77 (2H, q, J=7.5 Hz), 1.27 (3H, t, J=7.5 Hz).

Step 4. 1-[4-(2-aminoethyl)phenyl]-2-ethyl-1H-benzimidazole-4-carboxamide

The title compound was prepared according to the procedure described in step 7 of Example 37 from 1-[4-(2-azidoethyl)phenyl]-6-chloro-2-ethyl-1H-benzimidazole-5-carboxamide (step 3).

$^1$H-NMR (DMSO-d$_6$) δ: 9.30 (1H, br.s), 7.89 (1H, d, J=6.5 Hz), 7.81 (1H, br.s), 7.48–7.49 (4H, m), 7.26–7.30 (2H, m), 2.77–2.89 (6H, m), 1.28 (3H, t, J=6.4 Hz).

Step 5. 2-ethyl-1-(4-{2-[({[(4-methylphenyl)sulfonyl]amino}carbonyl)amino]ethyl}phenyl)-1H-benzimidazole-4-carboxamide The title compound was prepared according to the procedure described in step 10 of Example 1 from 1-[4-(2-aminoethyl)phenyl]-6-chloro-2-ethyl-1H-benzimidazole-5-carboxamide (step 4).

m.p.: 208–214° C.

IR (KBr) v: 3336, 1664, 1589, 1508, 1406, 1342, 1168, 976 cm$^{-1}$.

MS (ESI) m/z: 506 (MH$^+$), 504 ([M-H]$^-$).

$^1$H-NMR (DMSO-d$_6$) δ: 9.29 (1H, br.s), 7.89 (1H, dd, J=1.3 Hz, 7.2 Hz), 7.75–7.79 (3H, m), 7.22–7.49 (8H, m), 6.54 (1H, br.s), 2.75–2.83 (4H, m), 2.35 (3H, s), 1.27 (3H, t, J=7.4 Hz).

Example 323

6-CHLORO-2-ETHYL-1-(4-{2-[({[(4-METHYL)sulfonyl]AMINO}CARBONYL)AMINO]ETHYL}PHENYL)-5-(METHYSULFONYL)-1H-BENZIMIDAZOLE Step 1. 1,5-dichloro-2-(methylsulfinyl)-4-nitrobenzene A mixture of (2,4-dichloro-phenyl)-methyl sulfone (Ono Mitsunori, Nakamura Yoshisada, Sato Shingo, Itoh Isamu, *Chem. Lett*, 1988, 395–398.; 3.33 g, 16 mmol) and sulfuric acid (conc, 14 ml) was added a mixture of sulfuric acid (4 ml) and nitric acid (fuming, 2 ml) dropwise under ice-water bath. The mixture was stirred at 55° C. for 1 h. The mixture was poured onto ice-water and neutralized with 6N aqueous NaOH and then extracted with dichloromethane. The organic layer was washed with brine and dried (Na2SO4). The solvent was removed under reduced pressure and the residue was purified by flash chromatography eluting with hexane/ethyl acetate (2:1/1:1) to give 3 g (74%) of the title compound as white solids.

$^1$H-NMR (CDCl$_3$) δ: 8.45 (1H, s), 7.65 (1H, s), 2.89 (3H, s).

Step 2. 1,5-dichloro-2-(methylsulfonyl)-4-nitrobenzene

A solution of 1,5-dichloro-2-(methylsulfinyl)-4-nitrobenzene (1.0 g, 3.9 mmol) in dichloromethane (50 ml) was added 3-chloroperoxybenzoic acid (1.7 g, 9.8 mmol). The mixture was stirred under nitrogen at room temperature for 3 h. The mixture was added saturated aqueous NaHCO$_3$ (20 ml) and extracted with dichloromethane (50 ml). The organic layer was washed with brine (50 ml), dried (Na$_2$SO$_4$) and concentrated. The residue was purified by flash chromatography eluting with hexane/ethyl acetate (2:1) to give 1 g (100%) of the title compound as white solids.

MS (EI) m/z: 269 (M$^+$).

$^1$H-NMR (CDCl$_3$) δ: 8.68 (1H, s), 7.81 (1H, s), 3.30 (3H, s).

Step 3. 2-{4-[5-chloro-4-(methylsulfonyl)-2-Nitroanilino]phenyl}ethanol

The title compound was prepared according to the procedure described in step 3 of Example 1 from 1,5-dichloro-2-(methylsulfonyl)-4-nitrobenzene and 4-aminophenylethyl alcohol(step 2).

MS (EI) m/z: 370 (M$^+$)

$^1$H-NMR (CDCl$_3$) δ: 9.81 (1H, br.s), 8.99 (1H, s), 7.39 (2H, d, J=8.4 Hz), 7.24 (2H, d, J=8.4 Hz), 7.18 (1H, s), 3.94 (2H, t, J=6.2 Hz), 3.25 (3H, s), 2.95 (2H, t, J=6.2 Hz).

Step 4. 2-{4-[2-amino-5-chloro-4-(methylsulfonyl)anilino]phenyl}ethanol

The title compound was prepared according to the procedure described in step 2 of Example 40 from 2-{4-[5-chloro-4-(methylsulfonyl)-2-nitroanilino]phenyl}ethanol (step 3).

MS (EI) m/z: 340(M$^+$).

$^1$H-NMR (CDCl$_3$) δ: 7.50 (1H, s), 7.22 (2H, d, J=8.4 Hz), 7.15 (1H, s), 7.00 (2H, d, J=8.4 Hz), 5.71 (1H, br.s), 3.88 (2H, t, J=6.4 Hz), 3.67 (2H, br.s), 3.22 (3H, s), 2.86 (2H, t, J=6.4 Hz).

Step 5. 2-{4-[6-chloro-2-ethyl-5-(methylsulfonyl)-1H-benzimidazol-1-yl]phenyl}ethyl propionate The title compound was prepared according to the procedure described in step 5 of Example 1 from 2-{4-[2-amino-5-chloro-4-(methylsulfonyl)anilino]phenyl}ethanol (step 4).

TLC, Rf=0.7, hexane:ethyl acetate (1:2).

Step 6. 2-{4-[6-chloro-2-ethyl-5-(methylsulfonyl)-1H-benzimidazol-1-yl]phenyl}ethanol The title compound was prepared according to the procedure described in step 6 of Example 1 from 2-{4-[6-chloro-2-ethyl-5-(methylsulfonyl)-1H-benzimidazol-1-yl]phenyl}ethyl propionate (step 5).

MS (EI) m/z: 378 (M$^+$).

$^1$H-NMR (CDCl$_3$) δ: 8.60 (1H, s), 7.52 (2H, d, J=8.3 Hz), 7.28 (2H, d, J=8.3 Hz), 7.10 (1H, s), 3.97–4.04 (2H, m), 3.29 (3H, s), 3.03 (2H, t, J=6.5 Hz), 2.80 (2H, q, J=7.6 Hz), 1.36 (3H, t, J=7.6 Hz).

Step 7. 6-chloro-1-[4-(2-chloroethyl)phenyl]-2-ethyl-1H-benzimidazol-5-yl methyl sulfone The title compound was prepared according to the procedure described in step 7 of Example 1 from 2-{4-[6-chloro-2-ethyl-5-(methylsulfonyl)-1H-benzimidazol-1-yl]phenyl}ethanol (step 6).

$^1$H-NMR (CDCl$_3$) δ: 8.62 (1H, s), 7.50 (2H, d, J=8.4 Hz), 7.31 (2H, d, J=8.4 Hz), 7.24 (1H, s), 3.83 (2H, t, J=7.1 Hz), 3.29 (3H, s), 3.22 (2H, t, J=7.1 Hz), 2.80 (2H, q, J=7.6 Hz), 1.37 (3H, t, J=7.6 Hz).

Step 8. 1-[4-(2-azidoethyl)phenyl]-6-chloro-2-ethyl-1H-benzimidazol-5-yl methyl sulfone The title compound was prepared according to the procedure described in step 8 of Example 1 from 6-chloro-1-[4-(2-chloroethyl)phenyl]-2-ethyl-1H-benzimidazol-5-yl methyl sulfone (step 7).

$^1$H-NMR (CDCl$_3$) δ: 8.62 (1H, s), 7.50 (2H, d, J=8.4 Hz), 7.25 (2H, d, J=8.4 Hz), 7.23 (1H, s), 3.64 (2H, t, J=6.9 Hz), 3.29 (3H, s), 3.04 (2H, t, J=6.9 Hz), 2.80 (2H, q, J=7.6 Hz), 1.36 (3H, t, J=7.6 Hz).

Step 9. 2-{4-[6-chloro-2-ethyl-5-(methylsulfonyl)-1H-benzimidazol-1-yl]phenyl}ethanamine The title compound was prepared according to the procedure described in step 7 of Example 37 from 1-[4-(2-azidoethyl)phenyl]-6-chloro-2-ethyl-1H-benzimidazol-5-yl methyl sulfone (step 8).

$^1$H-NMR (CDCl$_3$) δ: 8.61 (1H, s), 7.47 (2H, d, J=8.4 Hz), 7.28 (2H, d, J=8.4 Hz), 7.24 (1H, s), 3.29 (3H, s), 3.10 (2H, t, J=7.1 Hz), 2.90 (2H, t, J=7.1 Hz), 2.80 (2H, q, J=7.5 Hz), 1.37 (3H, t, J=7.5 Hz).

Step 10. 6-chloro-2-ethyl-1-(4-{2-[({[(4-methylphenyl)sulfonyl]amino}carbonyl)amino]ethyl}phenyl)-5-(methylsulfonyl)-1H-benzimidazole The title compound was prepared according to the procedure described in step 10 of Example 1 from 2-{4-[6-chloro-2-ethyl-5-(methylsulfonyl)-1H-benzimidazol-1-yl]phenyl}ethanamine (step 9).

m.p.: 105–118° C.

IR (KBr) v: 2879, 1676, 1518, 1458, 1309, 1142, 1089, 993 $cm^{-1}$.

MS (ESI) m/z: 575 ($MH^+$), 573 ($[M-H]^-$).

$^1$H-NMR ($CDCl_3$) δ: 8.59 (1H, s), 7.75 (2H, d, J=8.4 Hz), 7.43 (2H, d, J=8.4 Hz), 7.29–7.33 (4H, m), 7.21 (1H, s), 6.69 (1H, br.s), 3.55–3.62 (2H, m), 3.29 (3H, s), 2.96 (2H, t, J=6.9 Hz), 2.80 (3H, q, J=7.5 Hz), 2.41 (3H, s), 1.34 (3H, t, J=7.5 Hz).

Example 324
6-CHLORO-2-ETHYL-1-(4-{2-[({[(4-METHYLPHENYL)SULFONYL]AMINO}CARBONYL)AMINO]ETHYL}PHENYL)-5-(METHYLSULFONYL)-1H-BENZIMIDAZOLE SODIUM SALT The title compound was prepared according to the procedure described in Example 2 from 6-chloro-2-ethyl-1-(4-{2-[({[(4-methylphenyl)sulfonyl]amino}carbonyl)amino]ethyl}phenyl)-5-(methylsulfonyl)-1H-benzimidazole (Example 323)

m.p.: 175–183° C.

IR (KBr) v: 3375, 1604, 1516, 1458, 1139, 1083, 993 $cm^{-1}$.

Example 325
2-{4-[6-CHLORO-2-ETHYL-5-(METHYLSULFONYL)-1H-BENZIMIDAZOL-1-YL]PHENYLI}ETHYL (4-METHYLPHENYL)SULFONYLCARBAMATE Step 1. 2-{4-[6-chloro-2-ethyl-5-(methylsulfonyl)-1H-benzimidazol-1-yl]phenyl}ethyl (4-methylphenyl)sulfonylcarbamate The title compound was prepared according to the procedure described in Example 3 from 2-{4-[6-chloro-2-ethyl-5-(methylsulfonyl)-1H-benzimidazol-1-yl]phenyl}ethanol (Example 323, step 6).

m.p.: 105–110° C.

IR (KBr) v: 1751, 1517, 1458, 1309, 1163, 1141, 1089 $cm^{-1}$.

MS (ESI) m/z: 576 ($MH^+$), 574 ($[M-H]^-$).

$^1$H-NMR ($CDCl_3$) δ: 8.60 (1H, s), 7.91–7.94 (2H, m), 7.21–7.43 (7H, m), 4.40 (2H, br.s), 3.31 (3H, s), 3.05 (2H, br.s), 2.78–2.81 (2H, m), 2.44 (3H, s), 1.33 (3H, t, J=7.6 Hz).

Example 326
5-(AMINOSULFONYL)-6-CHLORO-2-ETHYL-1-(4-{2-[({[(4-METHYLPHENYL)SULFONYL]AMINO}CARBONYL)AMINO]ETHYL}PHENYL)-1H-BENZIMIDAZOLE Step 1. 2,4-dichloro-5-nitrobenzenesulfonyl chloride 2,4-Dichloronitrobenzene (10 g, 52 mmol) was added $ClSO_3H$ (8 ml, 120 mmol) dropwise under ice-water bath. The mixture was stirred at 130° C. for 26 h. The mixture was cooled to rt and poured onto ice-water. The resulting precipitates were collected by filtration and dried under reduced pressure to give 9 g (60%) of the title compound as brown solids.

MS (EI) m/z: 290 ($M^+$)

$^1$H-NMR ($CDCl_3$) δ: 8.70 (1H, s), 7.90 (1H, s).

Step 2. N-(tert-butyl)-2,4-dichloro-5-nitrobenzenesulfonamide

The title compound was prepared according to the procedure described in step 1 of Example 87 from 2,4-dichloro-5-nitrobenzenesulfonyl chloride and tert-butylamine (step 1).

$^1$H-NMR ($CDCl_3$) δ: 8.65 (1H, s), 7.74 (1H, s), 5.01 (1H, br.s), 1.27 (9H, s).

Step 3. N-(tert-butyl)-2-chloro-4-[4-(2-hydroxyethyl)anilino]-5-nitrobenzenesulfonamide The title compound was prepared according to the procedure described in step 1 of Example 162 from N-(tert-butyl)-2,4-dichloro-5-nitrobenzenesulfonamide and 4-aminophenylethyl alcohol(step 2).

$^1$H-NMR ($CDCl_3$) δ: 9.72 (1H, br.s), 8.95 (1H, s), 7.37 (2H, d, J=8.3 Hz), 7.24 (2H, d,J=8.3 Hz), 7.17 (1H, s), 4.79 (1H, br.s), 3.90–3.96 (2H, m), 2.94 (2H, t, J=6.4 Hz), 1.26 (9H, s).

Step 4. 5-amino-N-(tert-butyl)-2-chloro-4-[4-(2-hydroxyethyl)anilino]benzenesulfonamide The title compound was prepared according to the procedure described in step 2 of Example 40 from N-(tert-butyl)-2-chloro-4-[4-(2-hydroxyethyl)anilino]-5-nitrobenzenesulfonamide (step 3).

MS (EI) m/z: 397($M^+$).

$^1$H-NMR ($CDCl_3$) δ: 7.51 (1H, s), 7.20 (2H, d, J=8.4 Hz), 7.14 (1H, s), 6.95 (2H, d, J=8.4 Hz), 5.22 (1H, br.s), 4.89 (1H, br.s), 3.87 (2H, t, J=6.4 Hz), 2.85 (2H, t, J=6.4 Hz), 1.23 (9H, s).

Step 5. 2-[4-(6-Chloro-2-ethyl-5-nitro-1H-benzimidazol-1-yl)phenyl]ethyl propionate The title compound was prepared according to the procedure described in step 5 of Example 1 from 5-amino-N-(tert-butyl)-2-chloro-4-[4-(2-hydroxyethyl)anilino]benzenesulfonamide (step 4).

TLC, Rf=0.8, hexane:ethyl acetate (1:2).

Step 6. N-(tert-butyl)-6-chloro-2-ethyl-1-[4-(2-hydroxyethyl)phenyl]-1H-benzimidazole-5-sulfonamide The title compound was prepared according to the procedure described in step 6 of Example 1 from 2-[4-(6-Chloro-2-ethyl-5-nitro-1H-benzimidazol-1-yl)phenyl]ethyl propionate (step 5).

$^1$H-NMR ($CDCl_3$) δ: 8.57 (1H, s), 7.49 (2H, d, J=8.4 Hz), 7.29 (2H, d, J=8.4 Hz), 7.20 (1H, s), 4.98 (1H, br.s), 4.00 (2H, br.s), 3.02 (2H, t, J=6.4 Hz), 2.79 (2H, q, J=7.5 Hz), 1.37 (3H, t, J=7.5 Hz), 1.21 (9H, s).

Step 7. N-(tert-butyl)-6-chloro-1-[4-(2-chloroethyl)phenyl]-2-ethyl-1H-benzimidazole-5-sulfonamide The title compound was prepared according to the procedure described in step 7 of Example 1 from N-(tert-butyl)-6-chloro-2-ethyl-1-[4-(2-hydroxyethyl)phenyl]-1H-benzimidazole-5-sulfonamide (step 6).

$^1$H-NMR ($CDCl_3$) δ: 8.58 (1H, s), 7.49 (2H, d, J=8.4 Hz), 7.32 (2H, d, J=8.4 Hz), 7.19 (1H, s), 4.96 (1H, br.s), 3.83 (2H, t, J=7.0 Hz), 3.21 (2H, t, J=7.0 Hz), 2.80 (2H, q, J=7.6 Hz), 1.37 (3H, t, J=7.6 Hz), 1.22 (9H, s).

Step 8. 1-[4-(2-azidoethyl)phenyl]-N-(tert-butyl)-6-chloro-2-ethyl-1H-benzimidazole -5-sulfonamide The title compound was prepared according to the procedure described in step 8 of Example 1 from N-(tert-butyl)-6-chloro-1-[4-(2-chloroethyl)phenyl]-2-ethyl-1H-benzimidazole-5-sulfonamide (step 7).

$^1$H-NMR ($CDCl_3$) δ: 8.57 (1H, s), 7.48 (2H, d, J=8.2 Hz), 7.32 (2H, d, J=8.2 Hz), 7.19 (1H, s), 4.96 (1H, br.s), 3.63 (2H, t, J=6.9 Hz), 3.03 (2H, t, J=6.9 Hz), 2.79 (2H, q, J=7.4 Hz), 1.37 (3H, t, J=7.4 Hz), 1.21 (9H, s).

Step 9. 1-[4-(2-aminoethyl)phenyl]-N-(tert-butyl)-6-chloro-2-ethyl-1H-benzimidazole-5-sulfonamide The title compound was prepared according to the procedure described in step 7 of Example 37 from 1-[4-(2-azidoethyl)phenyl]-N-(tert-butyl)-6-chloro-2-ethyl-1H-benzimidazole-5-sulfonamide (step 8).

$^1$H-NMR ($CDCl_3$) δ: 8.57 (1H, s), 7.44 (2H, d, J=8.5 Hz), 7.29 (2H, d, J=8.5 Hz), 7.20 (1H, s), 5.03 (1H, br.s), 3.09 (2H, t, J=6.9 Hz), 2.89 (2H, t, J=6.9 Hz), 2.79 (2H, q, J=7.6 Hz), 1.37 (3H, t, J=7.6 Hz), 1.22 (9H, s).

Step 10. 5-[(tert-butylamino)sulfonyl]-6-chloro-2-ethyl-1-(4-{2-[({[(4-methylphenyl)sulfonyl]amino}carbonyl)amino]ethyl}phenyl)-1H-benzimidazole The title compound was prepared according to the procedure described in step 10 of Example 1 from 1-[4-(2-aminoethyl)phenyl]-N-(tert-butyl)-6-chloro-2-ethyl-1H-benzimidazole-5-sulfonamide (step 9).

$^1$H-NMR (CDCl$_3$) δ: 8.54 (1H, s), 7.78 (2H, d, J=8.3 Hz), 7.41 (2H, d, J=8.3 Hz), 7.31 (2H, d, J=8.2 Hz), 7.23 (2H, d, J=8.2 Hz), 7.16 (1H, s), 6.61 (1H, br.s), 5.21 (1H, br.s), 3.54–3.60 (2H, m), 2.95 (2H, t, J=6.9 Hz), 2.78 (2H, q, J=7.5 Hz), 2.41 (3H, s), 1.35 (3H, t, J=7.5 Hz), 1.21 (9H, s).

Step 11. 5-(aminosulfonyl)-6-chloro-2-ethyl-1-(4-{2-[({[(4-methylphenyl)sulfonyl]amino}carbonyl)amino]ethyl}phenyl)-1H-benzimidazole The title compound was prepared according to the procedure described in step 1 of Example 88 from 5-[(tert-butylamino)sulfonyl]-6-chloro-2-ethyl-1-(4-{2-[({[(4-methylphenyl)sulfonyl]amino}carbonyl)amino]ethyl}phenyl)-1H-benzimidazole (step 9).

m.p.: 163–170° C.

IR (KBr) v: 1676, 1517, 1400, 1340, 1159, 1089, 995 cm$^{-1}$.

MS (ESI) m/z: 576 (MH$^+$), 574 ([M-H]$^-$).

$^1$H-NMR (DMSO-d$_6$) δ: 8.25 (1H, s), 7.77 (2H, d, J=8.3 Hz), 7.55 (2H, br.s), 7.37–7.48 (6H, m), 7.20 (1H, s), 6.54 (1H, br.s), 3.27 (2H, br.s), 2.71–2.81 (4H, m), 2.34 (3H, s), 1.23 (3H, t, J=7.6 Hz).

Example 327

2-{4-[5-(AMINOSULFONYL)-6-CHLORO-2-ETHYL-1H-BENZIMIDAZOL-1-YL]PHENYL}ETHYL (4-METHYLPHENYL)SULFONYLCARBAMATE

Step 1. 2-(4-{5-[(tert-butylamino)sulfonyl]-6-chloro-2-ethyl-1H-benzimidazol-1-yl}phenyl, ethyl (4-methylphenyl)sulfonylcarbamate The title compound was prepared according to the procedure described in Example 3 from N-(tert-butyl)-6-chloro-2-ethyl-1-[4-(2-hydroxyethyl )phenyl]-1H-benzimidazole-5-sulfonamide (Example 326, step 6).

$^1$H-NMR (CDCl$_3$) δ: 8.58 (1H, s), 7.93 (2H, d, J=8.2 Hz), 7.33–7.39 (4H, m), 7.20 (2H, d, J=~8.2 Hz), 7.16 (1H, s), 5.07 (1H, br.s), 4.38 (2H, t, J=6.2 Hz), 3.03 (2H, t, J=6.2 Hz), 2.78 (2H, q, J=7.5 Hz), 2.44 (3H, s), 1.35 (3H, t, J=7.5 Hz), 1.21 (9H, s).

Step 2. 2-{4-[5-(aminosulfonyl)-6-chloro-2-ethyl-1H-benzimidazol-1-yl]phenyl}ethyl (4-methylphenyl)sulfonylcarbamate The title compound was prepared according to the procedure described in step 1 of Example 88 from 2-(4-{5-[(tert-butylamino)sulfonyl]-6-chloro-2-ethyl-1H-benzimidazol-1-yl}phenyl)ethyl(4-methylphenyl)sulfonylcarbamate (step 1).

m.p.: 110–115° C.

IR (KBr) v: 1676, 1517, 1400, 1340, 1159, 1089, 995 cm$^{-1}$.

MS (ESI) m/z: 576 (MH$^+$), 574 ([M-H]$^-$).

$^1$H-NMR (DMSO-d$_6$) δ: 8.25 (1H, s), 7.76 (2H, d, J=8.4 Hz), 7.55 (2H, br.s), 7.47 (4H, s), 7.41 (2H, d, J=8.4 Hz), 7.20 (1H, s), 4.29 (2H, t, L=6.6 Hz), 2.96 (2H, t, J=6.6 Hz), 2.75 (2H, q, J=7.5 Hz), 2.35 (3H, s), 1.24 (3H, t, J=7.5 Hz).

Example 328

2-[4-(6-CHLORO-5-CYANO-2-ETHYL-1H-BENZIMIDAZOL-1-YL)PHENYL]ETHYL(4-METHYLPHENYL)SULFONYLCARBAMATE

Step 1. 2-[4-(6-chloro-5-cyano-2-ethyl-1H-benzimidazol-1-yl)phenyl]ethyl (4-methylphenyl)sulfonylcarbamate The title compound was prepared according to the procedure described in Example 3 from 6-chloro-2-ethyl-1-[4-(2-hydroxyethyl)phenyl]-1H-benzimidazole-5-carbonitrile (Example 111, step 4).

m.p.: 85–98° C.

IR (KBr) v: 1747, 1618, 1517, 1465, 1348, 1290, 1163, 1089 cm$^{-1}$

MS (ESI) m/z: 523 (MH$^+$), 521 ([M-H]$^-$)

$^1$H-NMR (CDCl$_3$) δ: 8.07 (1H, s), 7.92 (2H, d, J=8.4 Hz), 7.40 (2H, d, J=8.4 Hz), 7.35 (2H, d, J=8.1 Hz), 7.25 (2H, d, J=8.1 Hz), 7.17 (1H, s), 4.39 (2H, t, J=6.8 Hz), 3.04 (2H, t, J=6.8 Hz), 2.78 (2H, q, J=7.6 Hz), 2.44 (3H, s), 1.35 (3H, t, J=7.6 Hz).

Example 329

N-[({2-[4-(5-CYANO-2-ETHYL-4,6-DIMETHYL-1H-BENZIMIDAZOL-1-YL)PHENYL]ETHYL}AMINO)CARBONYL]-4-METHYKLBENZENESULFONAMIDE

Step 1. 4-cyano-3,5-dimethyl-2-nitrophenyl trifluoromethanesulfonate

To a solution of 4-hydroxy-2,6-dimethyl-3-nitrobenzonitrile (v.Auwers; Saurwein; Fortsch. Ch. Phys.; 18; Heft 2, S. 23; 2.6 g, 13.4 mmol) in dichloromethane (150 ml) was added triflic anhydride (3.4 ml, 20 mmol) and pyridine (1.5 ml, 20 mmol) at 0° C. The mixture was stirred at room temperature for 1.5 h. The reaction mixture was poured into water, and extracted with ethyl acetate (100 ml). The organic layer was washed with brine (50 ml), then dried (Na$_2$SO$_4$). After removal of solvent, the crude product was purified by flash column chromatography eluting with hexane/ethyl acetate (2:1) to afford 3 g (69%) of the title compound as pale yellow solids.

MS (EI) m/z: 324 (M+)

$^1$H-NMR (CDCl$_3$) δ: 7.34 (1H, s), 2.68 (3H, s), 2.61 (3H, s).

Step 2. 2-{4-[(4-cyano-3,5-dimethyl-2-nitrophenyl)amino]phenyl}ethyl acetate

The title compound was prepared according to the procedure described in step 3 of Example 1 from 4-cyano-3,5-dimethyl-2-nitrophenyl trifluoromethanesulfonate (step 1).

$^1$H-NMR (CDCl$_3$) δ: 8.08 (1H, br.s), 7.27 (2H, d, J=8.4 Hz), 7.15 (2H, d, J=8.4 Hz), 4.30 (2H, t, J=7.0 Hz), 2.96 (2H, t, J=7.0 Hz), 2.65 (3H, s), 2.41 (3H, s), 2.05 (3H, s).

Step 3. 2-{4-[(4-cyano-3,5-dimethyl-2-nitrophenyl)amino]phenyl}ethyl acetate

The title compound was prepared according to the procedure described in step 3 of Example 6 from 2-{4-[(4-cyano-3,5-dimethyl-2-nitrophenyl)amino]phenyl}ethyl acetate (step 2).

$^1$H-NMR (CDCl$_3$) δ: 7.14 (2H, d, J=8.4 Hz), 6.85–6.89 (3H, m), 5.50 (1H, br.s), 4.26 (2H, t, J=7.1 Hz), 3.54 (2H, br.s), 2.89 (2H, t, J=7.1 Hz), 2.41 (3H, s), 2.37 (3H, s), 2.05 (3H, s).

Step 4. 2-[4-(5-cyano-2-ethyl-4,6-dimethyl-1H-benzimidazol-1-yl)phenyl]ethyl acetate The title compound was prepared according to the procedure described in step 5 of Example 1 from 2-{4-[(4-cyano-3,5-dimethyl-2-nitrophenyl)amino]phenyl}ethyl acetate (step 3).

$^1$H-NMR (CDCl$_3$) δ: 7.45–7.47 (2H, m), 7.26–7.29 (2H, m), 6.79 (1H, br.s), 4.37 (2H, t, J=7.0 Hz), 3.08 (2H, t, J=7.0 Hz), 2.83–2.89 (5H, m), 2.56 (3H, s), 2.09 (3H, s), 1.28 (3H, br.s).

Step 5. 2-ethyl-1-[4-(2-hydroxyethyl)phenyl]-4,6-dimethyl-1H-benzimidazole-5-carbonitrile The title compound was prepared according to the procedure described in step 6 of Example 1 from 2-[4-(5-cyano-2-ethyl-4,6-dimethyl-1H-benzimidazol -1-yl)phenyl]ethyl acetate (step 4).

MS (EI) m/z: 319 (M+)

¹H-NMR (CDCl₃) δ: 7.40–7.51 (4H, m), 6.93 (1H, s), 3.68–3.75 (2H, m), 2.85 (2H, t, J=6.7 Hz), 2.68–2.76 (5H, m), 2.50 (3H, s), 1.22 (3H, t, J=7.4 Hz).

Step 6. 1-[4-(2-chloroethyl)phenyl]-2-ethyl-4,6-dimethyl-1H-benzimidazole-5-carbonitrile The title compound was prepared according to the procedure described in step 7 Example 1 from 2-ethyl-1-[4-(2-hydroxyethyl)phenyl]-4,6-dimethyl-1H-benzimidazole-5-carbonitrile (step 5).

¹H-NMR (CDCl₃) δ: 7.45 (2H, d, J=8.3 Hz), 7.28 (2H, d, J=8.3 Hz), 6.79 (1H, s), 3.83 (2H, t, J=7.1 Hz), 3.21 (2H, t, J=7.1 Hz), 2.88 (3H, s), 2.81 (2H, q, J=7.6 Hz), 2.55 (3H, s), 1.29 (3H, t, J=7.6 Hz).

Step 7. 1-[4-(2-azidoethyl)phenyl]-2-ethyl-4,6-dimethyl-1H-benzimidazole-5-carbonitrile The title compound was prepared according to the procedure described in step 8 Example 1 from 1-[4-(2-chloroethyl)phenyl]-2-ethyl-4,6-dimethyl-1H-benzimidazole-5-carbonitrile (step 6).

MS (EI) m/z: 412 (M+)

¹H-NMR (CDCl₃) δ: 7.47 (2H, d, J=8.1 Hz), 7.28 (2H, d, J=8.1 Hz), 6.78 (1H, s), 3.63 (2H, t, J=6.8 Hz), 3.03 (2H, t, J=6.8 Hz), 2.87 (3H, s), 2.80 (2H, q, J=7.6 Hz), 2.55 (3H, s), 1.29 (3H, t, J=7.6 Hz).

Step 8. 1-[4-(2-aminoethyl)phenyl]-2-ethyl-4,6-dimethyl-1H-benzimidazole-5-carbonitrile The title compound was prepared according to the procedure described in step 7 of Example 37 from 1-[4-(2-azidoethyl)phenyl]-2-ethyl-4,6-dimethyl-1H-benzimidazole-5-carbonitrile (step 7).

¹H-NMR (CDCl₃) δ: 7.43 (2H, d, J=8.6 Hz), 7.25 (2H, d, J=8.6 Hz), 6.79 (1H, s), 3.08 (2H, t, J=7.0 Hz), 2.63–2.91 (7H, m), 2.55 (3H, s), 1.29 (3H, t, J=7.6 Hz).

Step 9. N-[({2-[4-(5-cyano-2-ethyl-4,6-dimethyl-1H-benzimidazol-1-yl)phenyl]ethyl}amino)carbonyl]-4-methylbenzenesulfonamide The title compound was prepared according to the procedure described in step 10 of Example 1from 1-[4-(2-aminoethyl)phenyl]-2-ethyl-4,6-dimethyl-1H-benzimidazole-5-carbonitrile (step 8).

m.p.: 140–145° C.

IR (KBr) v: 3340, 2214, 1664, 1517, 1338, 1166, 1091 cm⁻¹

MS (ESI) m/z: 516 (MH⁺), 514 ([M−H]⁻)

¹H-NMR (CDCl₃) δ: 7.71 (2H, d, J=8.4 Hz), 7.41 (2H, d, J=8.4 Hz), 7.25–7.31 (4H,m), 6.77 (1H, s), 6.73 (1H, br.s), 3.55–3.62 (2H, m), 2.95 (2H, t, J=7.0 Hz), 2.87 (3H, s), 2.80 (2H, q, J=7.6 Hz), 2.52 (3H, s), 2.41 (3H, s), 1.28 (3H, t, J=7.6 Hz).

Example 330

2-{4-[5-(AMINOCARBONYL)-6-CHLORO-2-ETHYL-1H-BENZIMIDAZOL-1-YL]PHENYL}ETHYL(4-METHYLPHENYL)SULFONYLCARBAMATE

Step 1. 2-{4-[5-(aminocarbonyl)-6-chloro-2-ethyl-1H-benzimidazol-1-yl]phenyl}ethyl(4-methylphenyl)sulfonylcarbamate The title compound was prepared according to the procedure described in Example 3 from 6-chloro-2-ethyl-1-[4-(2-hydroxyethyl)phenyl]-1H-benzimidazole-5-carboxamide (Example 111, step 5)

m.p.: 170–175° C.

IR (KBr) v: 3463, 3342, 1747, 1685, 1593, 1161, 1080, 881 cm⁻¹

MS (ESI) m/z: 541 (MH⁺), 539 ([M−H]⁻)

¹H-NMR (CDCl₃) δ: 8.13 (1H, s), 7.96 (2H, d, J=8.4 Hz), 7.40 (2H, d, J=8.4 Hz), 7.36 (2H, d, J=8.1 Hz), 7.01 (2H, d, J=8.1 Hz), 6.94 (1H, s), 6.55 (1H, br.s), 4.38 (2H, t, J=6.1 Hz), 3.01 (2H, t, J=6.1 Hz), 2.70 (2H, q, J=7.5 Hz), 2.45 (3H, s), 1.29 (3H, t, J=7.5 Hz).

Example 331

2-[4-(5-CYANO-2-ETHYL-4,6-DIMETHYL-1H-BENZIMIDAZOL-1-YL)PHENYL]ETHYL(4-METHYLPHENYL)SULFONYLCARBAMATE

Step 1. 2-[4-(5-cyano-2-ethyl-4,6-dimethyl-1H-benzimidazol-1-yl)phenyl]ethyl (4-methylphenyl)sulfonylcarbamate The title compound was prepared according to the procedure described in Example 3 from 2-ethyl-1-[4-(2-hydroxyethyl)phenyl]-4,6-dimethyl-1H-benzimidazole-5-carbonitrile (Example 329, step 5)

m.p.: 208–213° C.

IR (KBr) v: 1747, 1517, 1230, 1161, 1089 cm⁻¹

MS (ESI) m/z: 517 (MH⁺), 515 ([M−H]⁻)

¹H-NMR (DMSO-d₆) δ: 7.76 (2H, d, J=8.4 Hz), 7.40–7.48 (6H, m), 6.91 (1H, s), 4.27 (2H, t, J=6.7 Hz), 2.96 (2H, t, J=6.7 Hz), 2.67–2.73 (5H, m), 2.48 (3H, s), 2.36 (3H, s), 1.21 (3H, t, J=7.6 Hz).

Example 332

2-[4-(5-ACETYL-2-ETHYL-1H-BENZIMIDAZOL-1-YL)PHENYL]ETHYL (4-METHYLPHENYL)SULFONYLCARBAMATE

Step 1. 2-[4-(5-acetyl-2-ethyl-1H-benzimidazol-1-yl)phenyl]ethyl(4-methylphenyl)sulfonylcarbamate The title compound was prepared according to the procedure described in Example 3 from 1-{2-ethyl-1-[4-(2-hydroxyethyl)phenyl]-1H-benzimidazol-5-yl}ethanone (Example 78, step 4)

m.p.: 188–190° C.

IR (KBr)v: 1743, 1683, 1606, 1515, 1348, 1163, 1076 cm⁻¹

MS (ESI) m/z: 506 (MH⁺), 504 ([M−H]⁻)

¹H-NMR (DMSO-d₆) δ: 8.33 (1H, d, J=1.4 Hz), 7.82 (1H, dd, J=1.4 Hz, 8.4 Hz), 7.76 (2H, d, J=8.4 Hz), 7.45 (4H, s), 7.40 (2H, d, J=8.4 Hz), 7.14 (1H, d, J=8.4 Hz), 4.28 (2H, t, J=6.5 Hz), 2,97 (2H, t, J=6.5 Hz), 2.75 (2H, q, J=7.4 Hz), 2.64 (3H, s), 2.35 (3H, s), 1.25 (3H, t, J=7.4 Hz).

Example 333

6-CHLORO-2-ETHYL-N-METHYL-1-(4-{2-[({[(4-METHYLPHENYL)SULFONYL]AMINO}CARBONYL)AMINO]ETHYL}PHENYL)-1H-BENZIMIDAZOLE-5-CARBOXAMIDE

Step 1. 2,4-dichloro-N-methyl-5-nitrobenzamide

To a solution of 2,4-dichloro-5-nitrobenzoic acid (8 g, 33.9 mmol) in toluene (200 ml) was added thionyl chloride (12.4 ml, 169 mmol) at room temperature. The mixture was stirred at 80° C. for 5 h. The solvent was removed and the residue was dissolved with tetrahydrofurane (60 ml). The mixture was added 40% methylamine (1.4 ml, 33.9 mmol) at 0° C. and the mixture was stirred at room temperature for 2.5 h. The volatile component was removed under reduced pressure, and the residue was extracted with ethyl acetate (100 ml). The organic layer was washed with water (100 ml), brine (100 ml), then dried (Na₂SO₄). After removal of solvent, the crude product was purified by flash column chromatography eluting with hexane/ethyl acetate (2:1/1:1/1:2) to afford 5.3 g (63%) of the title compound as pale yellow solids.

¹H-NMR (CDCl₃) δ: 8.27 (1H, s), 7.65 (1H, s), 3.15 (3H, s).

Step 2. 2-chloro-4-{[4-(2-hydroxyethyl)phenyl]amino}-N-methyl-5-nitrobenzamide

The title compound was prepared according to the procedure described in step 3 of Example 1from 2,4-dichloro-N-methyl-5-nitrobenzamide (step 1).

¹H-NMR (CDCl₃) δ: 9.62 (1H, s), 8.22 (1H, s), 7.24–7.35 (4H, m), 6.95 (1H, s), 3.60–3.67 (2H, m), 2.73–2.79 (5H, m).

Step 3. 5-amino-2-chloro-4-{[4-(2-hydroxyethyl)phenyl]amino}-N-methybenzamide

The title compound was prepared according to the procedure described in step 2 of Example 28 from 2-chloro-4-{[4-(2-hydroxyethyl)phenyl]amino}-N-methyl-5-nitrobenzamide (step 2).

¹H-NMR (CDCl₃) δ: 7.28 (1H, s), 7.15 (2H, d, J=8.4 Hz), 7.08 (1H, s), 6.89 (2H, d, J=8.4 Hz), 6.53 (1H, br.s), 5.41 (1H, br.s), 3.84–3.86 (2H, m), 3.66 (2H, br.s), 3.00 (3H, d, J=5.0 Hz), 2.83 (2H, t, J=6.6 Hz).

Step 4. 6-chloro-2-ethyl-1-[4-(2-hydroxyethyl)phenyl]-N-methyl-1H-benzimidazole-5-carboxamide The title compound was prepared according to the procedure described in step 5 of Example 1 from 5-amino-2-chloro-4-{[4-(2-hydroxyethyl)phenyl]amino}-N-methylbenzamide (step 3).

MS (EI) m/z: 357 (M⁺)

¹H-NMR (CDCl₃) δ: 7.98 (1H, s), 7.47 (2H, d, J=8.1 Hz), 7.27 (2H, d, J=8.1 Hz), 7.09 (1H, s), 6.23 (1H, br.s), 3.96–4.02 (2H, m), 3.05 (3H, d, J=4.9 Hz), 3.00 (2H, t, J=6.4 Hz), 2.77 (2H, q, J=7.6 Hz), 1.34 (3H, t, J=7.6 Hz).

Step 5. 6-chloro-1-[4-(2-chloroethyl)phenyl]-2-ethyl-N-methyl-1H-benzimidazole-5-carboxamide The title compound was prepared according to the procedure described in step 7 Example 1 from 6-chloro-2-ethyl-1-[4-(2-hydroxyethyl)phenyl]-N-methyl-1H-benzimidazole-5-carboxamide (step 4).

¹H-NMR (CDCl₃) δ: 7.98 (1H, s), 7.47 (2H, d, J=8.3 Hz), 7.31 (2H, d, J=8.3 Hz), 7.10 (1H, s), 6.35 (1H, br.s), 3.83 (2H, t, J=6.9 Hz), 3.21 (2H, t, J=6.9 Hz), 3.05 (3H, d, J=4.9 Hz), 2.82 (2H, q, J=7.6 Hz), 1.36 (3H, t, J=7.6 Hz).

Step 6. 1-[4-(2-azidoethyl)phenyl]-6-chloro-2-ethyl-N-methyl-1H-benzimidazole-5-carboxamide The title compound was prepared according to the procedure described in step 8 Example 1 from 6-chloro-1-[4-(2-chloroethyl)phenyl]-2-ethyl-N-methyl-1H-benzimidazole-5-carboxamide (step 5).

MS (EI) m/z: 382 (M+)

¹H-NMR (CDCl₃) δ: 7.94 (1H, s), 7.46 (2H, d, J=8.0 Hz), 7.27 (2H, d, J=8.0 Hz), 7.06 (1H, s), 3.63 (2H, t, J=7.0 Hz), 2.98–3.06 (5H, m), 2.77 (2H, q, J=7.5 Hz), 1.34 (3H, t, J=7.6 Hz).

Step 7. 1-[4-(2-aminoethyl)phenyl]-6-chloro-2-ethyl-N-methyl-1H-benzimidazole-5-carboxamide The title compound was prepared according to the procedure described in step 7 of Example 37 from 1-[4-(2-azidoethyl)phenyl]-6-chloro-2-ethyl-N-methyl-1H-benzimidazole-5-carboxamide (step 6).

¹H-NMR (CDCl₃) δ: 7.91 (1H, s), 7.42 (2H, d, J=8.4 Hz), 7.24 (2H, d, J=8.4 Hz), 7.06 (1H, s), 6.55 (1H, br.s), 3.03–3.10 (5H, m), 2.72–2.83 (2H, m), 1.33 (3H, t, J=7.6 Hz).

Step 8. 6-chloro-2-ethyl-N-methyl-1-(4-{2-[({[(4-methylphenyl)sulfonyl]amino}carbonyl)amino]ethyl}phenyl)-1H-benzimidazole-5-carboxamide The title compound was prepared according to the procedure described in step 10 of Example 1 from 1-[4-(2-aminoethyl)phenyl]-6-chloro-2-ethyl-N-methyl-1H-benzimidazole-5-carboxamide (step 7).

m.p.: 122–135° C.

IR (KBr) ν: 2877, 1637, 1519, 1400, 1340, 1161, 1091 cm⁻¹

MS (ESI) m/z: 554 (MH⁺), 552 ([M–H]⁻)

¹H-NMR (CDCl₃) δ: 7.79–7.84 (3H, m), 7.28–7.33 (4H, m), 7.12 (2H, d, J=8.2 Hz), 6.96 (1H, s), 6.80 (1H, br.s), 6.70 (1H, br.s), 3.48–3.54 (2H, m), 3.08 (3H, d, J=4.8 Hz), 2.89 (2H, t, J=6.9 Hz), 2.72 (2H, q, J=7.5 Hz), 2.41 (3H, s), 1.30 (3H, t, J=7.5 Hz).

Example 334

2-(4-{6-CHLORO-2-ETHYL-5-[(METHYLAMINO)CARBONYL]-1H-BENZIMIDAZOL-1-YL}PHENYL)ETHYL (4-METHYLPHENYL)SULFONYLCARBAMATE

Step 1. 2-(4-{6-chloro-2-ethyl-5-[(methylamino)carbonyl]-1H-benzimidazol-1-yl}phenyl)ethyl(4-methylphenyl)sulfonylcarbamate The title compound was prepared according to the procedure described in Example 3 from 6-chloro-2-ethyl-1-[4-(2-hydroxyethyl)phenyl]-N-methyl-1H-benzimidazole-5-carboxamide (Example 333, step 4).

m.p.: 201–204° C.

MS (ESI) m/z: 555 (MH⁺), 553 ([M–H]⁻)

¹H-NMR (DMSO-d₆) δ: 8.27–8.29 (1H, m), 7.76 (2H, d, J=8.1 Hz), 7.69 (1H, s), 7.40–7.48 (6H, m), 7.06 (1H, s), 4.28 (2H, t, J=6.3 Hz), 2.96 (2H, t, J=6.3 Hz), 2.69–2.78 (5H, m), 2.36 (3H, s), 1.23 (3H, t, J=7.5 Hz).

Example 335

2-{4-[6-CHLORO-5-[(DIMETHYLAMINO)CARBONYL]-2-(1-METHYLETHYL)-1H-BENZIMIDAZOL-1-YL]PHENYL}ETHYL (4-METHYLPHENYL)SULFONYLCARBAMATE

Step 1. 2,4-dichloro-N,N-dimethyl-5-nitrobenzamide

To a solution of 2,4-dichloro-5-nitrobenzoic acid (4 g, 17 mmol) in toluene (50 ml) was added thionyl chloride (6 ml, 84 mmol) at room temperature. The mixture was stirred at 80° C. for 2 days. The solvent was removed and the residue was dissolved with tetrahydrofurane (30 ml). The mixture was added 50% dimethylamine (760 mg) at 0° C. and the mixture was stirred at room temperature over night. The volatile component was removed under reduced pressure, and the residue was extracted with ethyl acetate (100 ml). The organic layer was washed with water (50 ml), brine (50 ml), then dried (Na₂SO₄). After removal of solvent, the crude product was purified by flash column chromatography eluting with hexane/ethyl acetate (1:1) to afford 3.6 g (82%) of the title compound as pale yellow solids.

¹H-NMR (CDCl₃) δ: 7.90 (1H, s), 7.65 (1H, s), 3.15 (3H, s), 2.91 (3H, s).

Step 2. 2-chloro-4-{[4-(2-hydroxyethyl)phenyl]amino}-N,N-dimethyl-5-nitrobenzamide The title compound was prepared according to the procedure described in step 3 of Example 1 from 2,4-dichloro-N,N-dimethyl-5-nitrobenzamide (step 1).

MS (EI) m/z: 363 (M+)

¹H-NMR (CDCl₃) δ: 9.52 (1H, br.s), 8.20 (1H, s), 7.34 (2H, d, J=8.2 Hz), 7.22 (2H, d, J=8.2 Hz), 7.16 (1H, s), 3.92 (2H, m), 3.13 (3H, s), 2.89–2.94 (5H, m).

Step 3. 5-amino-2-chloro-4-{[4-(2-hydroxyethyl)phenyl]amino}-N,N-dimethylbenzamide The title compound was prepared according to the procedure described in step 2 of Example 28 from 2-chloro-4-{[4-(2-hydroxyethyl)phenyl]amino}-N,N-dimethyl-5-nitrobenzamide (step 2).

¹H-NMR (CDCl₃) δ: 7.05–7.11 (3H, m), 6.79 (2H, d, J=8.5 Hz), 6.63 (1H, s), 5.59 (1H, s), 3.79–3.83 (4H, m), 3.11 (3H, s), 2.92 (3H, s), 2.79 (2H, t, J=6.4 Hz).

Step 4. 2-{4-[6-chloro-5-[(dimethylamino)carbonyl]-2-(1-methylethyl)-1H-benzimidazol-1-yl]phenyl}ethyl propanoate The title compound was prepared according to the procedure described in step 5 of Example 1 from 5-amino-2-chloro-4-{[4-(2-hydroxyethyl)phenyl]amino}-N,N-dimethylbenzamide (step 3).

Step 5. 6-chloro-1-[4-(2-hydroxyethyl)phenyl]-N,N-dimethyl-2-(1-methylethyl)-1H-benzimidazole-5-carboxamide The title compound was prepared according to the procedure described in step 6 of Example 1 from 2-{4-[6-chloro-5-[(dimethylamino)carbonyl]-2-(1-methylethyl)-1H-benzimidazol-1-yl]phenyl}ethyl propanoate (step 4).

MS (EI) m/z: 371 (M+)
$^1$H-NMR (CDCl$_3$) δ: 7.66 (1H, s), 7.46 (2H, d, J=8.5 Hz), 7.27 (2H, d, J=8.5 Hz), 7.12 (1H, s), 3.95–4.00 (2H, m), 3.17 (3H, s), 3.00 (2H, d, J=6.6 Hz), 2.87 (3H, s), 2.78 (2H, q, J=7.5 Hz), 1.34 (3H, t, J=7.5 Hz).

Step 6. 2-{4-[6-chloro-5-[(dimethylamino)carbonyl]-2-(1-methylethyl)-1H-benzimidazol-1-yl]phenyl}ethyl (4-methylphenyl)sulfonylcarbamate The title compound was prepared according to the procedure described in Example 3 from 6-chloro-1-[4-(2-hydroxyethyl)phenyl]-N,N-dimethyl-2-(1-methylethyl)-1H-benzimidazole-5-carboxamide (step 5).

m.p.: 173–176° C.
IR (KBr) v: 1741, 1637, 1519, 1398, 1344, 1159, 1078, 904 cm$^{-1}$
MS (ESI) m/z: 569 (MH$^+$), 567 ([M−H]$^−$)
$^1$H-NMR (CDCl$_3$) δ: 7.93 (2H, d, J=8.4 Hz), 7.70 (1H, s), 7.27–7.34 (4H, m), 7.09–7.12 (3H, m), 4.35 (2H, t, J=6.6 Hz), 3.19 (3H, s), 2.98 (2H, t, J=6.6 Hz), 2.88 (3H, s), 2.74 (2H, q, J=7.5 Hz), 2.42 (3H, s), 1.29 (3H, t, J=7.5 Hz).

Example 336

2-(4-{6-CHLORO-2-ETHYL-5-[(METHYLOXY) METHYL]-1H-BENZIMIDAZOL-1-YL}PHENYL) ETHYL (4-METHYLPHENYL) SUKLFONYLCARBAMATE

Step 1. 1,5-dichloro-2-[(methyloxy)methyl]-4-nitrobenzene

To a solution of 1,5-dichloro-2-(chloromethyl)-4-nitrobenzene (Hagmann, William K.; Dorn, Conrad P.; Frankshun, Robert A.; O'Grady, Laura A.; Bailey, Philip J.; et al.; JMCMAR; J.Med.Chem.; EN; 29; 8; 1986; 1436–1441, 10.6 g, 44 mmol) in methanol (30 ml) was added sodium methoxide (44 ml, 66 mmol) at room temperature. The mixture was stirred at 80° C. for 21 h. The volatile component was removed under reduced pressure, and the residue was extracted with ethyl acetate (100 ml). The organic layer was washed with water (50 ml), brine (50 ml), then dried (Na$_2$SO$_4$). After removal of solvent, the crude product was purified by flash column chromatography eluting with hexane/ethyl acetate (6:1/4:1) to afford 2.8 g (27%) of the title compound as pale yellow oil.

$^1$H-NMR (CDCl$_3$) δ: 8.01 (1H,s), 7.09 (1H, s), 4.49 (2H, s), 3.96 (3H, s).

Step 2. 2-[4-({5-chloro-4-[(methyloxy)methyl]-2-nitrophenyl}amino)phenyl]ethanol The title compound was prepared according to the procedure described in step 3 of Example 1 from 1,5-dichloro-2-[(methyloxy)methyl]-4-nitrobenzene (step 1).

$^1$H-NMR (CDCl$_3$) δ: 9.45 (1H, br.s), 8.28 (1H, s), 7.17–7.33 (5H, m), 4.44 (2H, s), 3.91 (1H, br.s), 3.45 (3H, s), 2.91 (2H, t, J=6.6 Hz).

Step 3. 2-[4-({2-amino-5-chloro-4-[(methyloxy)methyl]phenyl}amino)phenyl]ethanol The title compound was prepared according to the procedure described in step 2 of Example 28 from 2-[4-({5-chloro-4-[(methyloxy)methyl]-2-nitrophenyl}amino)phenyl]ethanol (step 2).

$^1$H-NMR (CDCl$_3$) δ: 7.07–7.01 (3H, m), 6.88 (1H, s), 6.74 (2H, d, J=8.4 Hz), 5.16 (1H, br.s), 4.47 (2H, s), 3.82 (2H, t, J=6.6 Hz), 3.71 (2H, br.s), 3.46 (3H, s), 2.79 (2H, t, J=6.6 Hz).

Step 4. 2-(4-{6-chloro-2-ethyl-5-[(methyloxy)methyl]-1H-benzimidazol-1-yl}phenyl)ethanol The title compound was prepared according to the procedure described in step 5 of Example 1 from 2-[4-({2-amino-5-chloro-4-[(methyloxy)methyl]phenyl}amino)phenyl]ethanol (step 3).

MS (EI) m/z: 344 (M+)
$^1$H-NMR (CDCl$_3$) δ: 7.82 (1H, s), 7.46 (2H, d, J=8.2 Hz), 7.28 (2H, d, J=8.2 Hz), 7.12 (1H, s), 4.65 (1H, s), 3.99 (2H, br.s), 3.45 (3H, s), 3.00 (3H, t, J=7.6 Hz), 2.78 (2H, q, J=7.6 Hz), 1.34 (3H, t, J=7.6 Hz).

Step 5. 2-(4-{6-chloro-2-ethyl-5-[(methyloxy)methyl]-1H-benzimidazol-1-yl}phenyl)ethyl(4-methylphenyl)sulfonylcarbamate The title compound was prepared according to the procedure described in Example 3 from 2-(4-{6-chloro-2-ethyl-5-[(methyloxy)methyl]-1H-benzimidazol-1-yl}phenyl)ethanol (step 4).

m.p.: 174.5° C.
IR (KBr) v: 3377, 2813, 1718, 1519, 1398, 1342, 1159, 1093, 1062 cm$^{-1}$
MS (ESI) m/z: 542 (MH$^+$), 540 ([M−H]$^−$)
$^1$H-NMR (CDCl$_3$) δ: 7.94 (2H, d, J=8.2 Hz), 7.83 (1H, s), 7.08–7.33 (7H, m), 4.64 (s, 2H), 4.37 (2H, t, J=6.4 Hz), 3.46 (3H, s), 2.97 (2H, t, J=6.4 Hz), 2.73 (2H, q, J=7.5 Hz), 2.42 (3H, s), 1.26 (3H, t, J=7.5 Hz).

Example 337

2-{4-[6-CHLORO-2-ETHYL-5-(HYDROXYMETHYL)-1H-BENZIMIDAZOL-1-YL]PHENYL}ETHYL(4-METHYLPHENYL)SULFONYLCARBAMATE

Step 1. 2-{4-[6-chloro-5-(chloromethyl)-2-ethyl-1H-benzimidazol-1-yl]phenyl}ethanol The title compound was prepared according to the procedure described in step 5 of Example 1 from 2-[4-({2-amino-5-chloro-4-[(methyloxy)methyl]phenyl}amino)phenyl]ethanol (Example 336, step 3).

MS (EI) m/z: 348 (M+)
$^1$H-NMR (CDCl$_3$) δ: 7.83 (1H, s), 7.46 (2H, d, J=8.2 Hz), 7.27 (2H, d, J=8.2 Hz), 7.15 (1H, s), 4.84 (2H, s), 3.96–4.02 (2H, m), 3.00 (2H, t, J=6.4 Hz), 2.77 (2H, q, J=7.5 Hz), 1.34 (2H, t, J=7.5 Hz).

Step 2. 6-chloro-5-(chloromethyl)-1-[4-(2-{[(1.1-dimethylethyl)(dimethyl)silyl]oxy}ethyl)phenyl]2-ethyl-1H-benzimidazole The title compound was prepared according to the procedure described in step 2 of Example 90 from 2-{4-[6-chloro-5-(chloromethyl)-2-ethyl-1H-benzimidazol-1-yl]phenyl}ethanol (step 1).

MS (EI) mlz: 405 (M+)
$^1$H-NMR (CDCl$_3$) δ: 7.83 (1H, s), 7.43 (2H, d, J=8.4 Hz), 7.23 (2H, d, J=8.4 Hz), 7.11 (1H, s), 4.85 (2H, s), 3.91 (2H, t, J=6.4 Hz), 2.94 (2H, t, J=6.4 Hz), 2.76 (2H, q, J=7.5 Hz), 1.33 (3H, t, J=7.5 Hz), 0.87 (9H, s), 0.00 (6H, s).

Step 3. {6-chloro-1-[4-(2-{[(1,1-dim ethylethyl)(dimethyl)silyl]oxy}ethyl)phenyl]-2-ethyl-1H-benzimidazol-5-yl}methyl propanoate To a solution of 6-chloro-5-(chloromethyl)-1-[4-(2-{[(1,1-dimethylethyl)(dimethyl)silyl]oxy}ethyl)phenyl]-2-ethyl-1H-benzimidazole (step 2, 403 mg, 0.86 mmol) in N,N-dimethylformamide (10 ml) was added propionic acid (0.06 ml, 0.86 mmol) and NaHCO$_3$ (144 mg, 1.72 mmol) at room temperature. The mixture was stirred at 60° C. for 7 h. The mixture was added water (50 ml) and extracted with ethyl acetate (100 ml). The organic layer was washed with brine (50 ml), then dried (Na$_2$SO$_4$). After removal of solvent, the crude product was purified by flash column chromatography eluting with hexane/ethyl acetate (8:1/2:1) to afford 235 mg (53%) of the title compound as pale yellow oil.

$^1$H-NMR (CDCl$_3$) δ: 7.81 (1H, s), 7.43 (2H, d, J=8.5 Hz), 7.24 (2H, d, J=8.5 Hz), 7.11 (1H, s), 5.33 (2H, s), 3.91 (2H, t, J=6.6 Hz), 2.93 (2H, t, J=6.6 Hz), 2.77 (2H, q, J=7.5 Hz), 2.42 (2H, q, J=7.5 Hz), 1.33 (3H, t, J=7.5 Hz), 1.18 (3H, t, J=7.5 Hz), 0.87 (9H, s), 0.00 (6H, s).

Step 4. {6-chloro-2-ethyl-1-[4-(2-hydroxyethyl)phenyl]-1H-benzimidazol-5-yl}methyl propanoate The title compound was prepared according to the procedure described in step 6 of Example 90 from {6-chloro-1-[4-(2-{[(1,1-dimethylethyl)(dimethyl)silyl]oxy}ethyl)phenyl]-2-ethyl-1H-benzimidazol-5-yl}methyl propanoate (step 3).

MS (EI) m/z: 386 (M+)
$^1$H-NMR (CDCl$_3$) δ: 7.70 (1H, s), 7.37 (2H, d, J=8.3 Hz), 7.17 (2H, d, J=8.3 Hz), 7.04 (1H, s), 5.21 (2H, s), 3.88 (2H, d, J=6.6 Hz), 2.91(2H, t, J=6.6 Hz), 2.67 (2H, q, J=7.5 Hz), 2.32 (2H, q, J=7.5 Hz), 1.24 (3H, t, J=7.5 Hz), 1.08 (3H, t, J=7.5 Hz).

Step 5. [6-chloro-2-ethyl-1-(4-{2-[({[(4-methylphenyl)sulfonyl]amino}carbonyl)oxy]ethyl}phenyl)-1H-benzimidazol-5-yl]methyl propanoate The title compound was prepared according to the procedure described in Example 3 from {6-chloro-2-ethyl-1-[4-(2-hydroxyethyl)phenyl]-1H-benzimidazol-5-yl}methyl propanoate (step 4).

$^1$H-NMR (CDCl$_3$) δ: 7.92 (2H, d, J=8.3 Hz), 7.81 (1H, s), 7.32–7.36 (4H, m), 7.21–7.25 (2H, m), 7.10 (1H, s), 5.32 (2H, s), 4.38 (2H, t, J=6.7 Hz), 3.02 (2H, t, J=6.7 Hz), 2.76 (2H, q, J=7.6 Hz), 2.37–2.49 (5H, m), 1.33 (3H, t, J=7.6 Hz), 1.18 (3H, t, J=7.6 Hz).

Step 6. 2-{4-[6-chloro-2-ethyl-5-(hydroxymethyl)-1H-benzimidazol-1-yl]phenyl}ethyl (4-methylphenyl)sulfonylcarbamate The title compound was prepared according to the procedure described in step 6 of Example 1from [6-chloro-2-ethyl-1-(4-{2-[({[(4-methylphenyl)sulfonyl]amino}carbonyl)oxy]ethyl}phenyl)-1H-benzimidazol-5-yl]methyl propanoate (step 5).

m.p.: 172.7° C.
IR (KBr) v: 1745, 1519, 1240, 1160, 1089, 1058 cm$^{-1}$
MS (ESI) m/z: 528 (MH$^+$), 526 ([M–H]$^-$)
$^1$H-NMR (DMSO-d$_6$) δ: □.74–7.77 (3H, m), 7.39–7.46 (6H, m), 7.03 (1H, s), 4.63 (2H, s), 4.27 (2H, t, J=6.6 Hz), 2.95 (2H, t, J=6.6 Hz), 2.72 (2H, q, J=7.5 Hz), 2.34 (3H, s), 1.23 (3H, t, J=7.5 Hz).

Example 338

N-({[2-(4-{6-CHLORO-2-ETHYL-5-[(METHYLOXY)METHYL]-1H-BENZIMIDAZOL-1-YL}PHENYL)ETHYL]AMINO}CARBONYL)-4-METHYLBENZENSULFONAMIDE

Step 1. 1-[4-(2-azidoethyl)phenyl]-6-chloro-2-ethyl-5-[(methyloxy)methyl]-1H-benzimidazole The title compound was prepared according to the procedure described in step 5 of Example 26 from 2-(4-{6-chloro-2-ethyl-5-[(methyloxy)methyl]-1H-benzimidazol-1-yl}phenyl)ethanol (Example 336, step 4).

MS (EI) m/z: 369 (M$^+$)
$^1$H-NMR (CDCl$_3$) δ: 7.82 (1H, s), 7.45 (2H, d, J=8.4 Hz), 7.30 (2H, d, J=8.4 Hz), 7.11 (1H, s), 4.65 (2H, s), 3.62 (2H, t, J=7.0 Hz), 3.45 (3H, s), 3.02 (2H, t, J=J=7.0 Hz), 2.77 (2H, q, J=7.7 Hz), 1.34 (3H, t, J=7.7 Hz).

Step 2. 2-(4-{6-chloro-2-ethyl-5-[(methyloxy)methyl]-1H-benzimidazol-1-yl}phenyl)ethanamine The title compound was prepared according to the procedure described in step 9 of Example 1 from 1-[4-(2-azidoethyl)phenyl]-6-chloro-2-ethyl-5-[(methyloxy)methyl]-1H-benzimidazole (step 1).

$^1$H-NMR (CDCl$_3$) δ: 7.82 (1H, s), 7.42 (2H, d, J=8.4 Hz), 7.24–7.29 (2H, m), 7.12 (1H,s), 4.65 (1H, s), 3.45 (3H, ds), 3.08 (2H, t, J=6.7 Hz), 2.88 (2H, t, J=6.7 Hz), 2.77 (2H, q, J=7.6 Hz), 1.34 (3H, t, J=7.6 Hz).

Step 3. N-({[2-(4-{6-chloro-2-ethyl-5-[(methyloxy)methyl]-1H-benzimidazol-1-yl}phenyl)ethyl]amino}carbonyl)-4-methylbenzenesulfonamide The title compound was prepared according to the procedure described in step 10 of Example 1from 2-(4-{6-chloro-2-ethyl-5-[(methyloxy)methyl]-1H-benzimidazol-1-yl}phenyl)ethanamine (step 2).

m.p.: 134.6° C.
IR (KBr) v: 3377, 2813, 1718, 1519, 1398, 1342, 1159, 1093, 1062 cm$^{-1}$
MS (ESI) m/z: 541 (MH$^+$), 539 ([M–H]$^-$)
$^1$H-NMR (CDCl$_3$) δ: 7.82 (1H, s), 7.72 (2H, d, J=8.4 Hz), 7.24–7.39 (4H, m), 7.09 (1H, s), 6.72 (1H, br.s), 4.65 (2H, s), 3.57 (2H, m), 3.45 (3H, s), 2.93 (2H, d, J=6.8 Hz), 2.77 (2H, q, J=7.5 Hz), 2.40 (3H, s), 1.32 (3H, t, J=7.5 Hz).

Example 339

2-{4-[6-CHLORO-2-[3-(4PYRIDINYL)PROPYL]-5-(TRIFLUOROMETHYL)-1H-BENZIMIDAZOL-1-YL]PHENYL}ETHYL(4-METHYLPHENYL)SULFONYLCARBAMATE

Step 1. 2-(4-{[5-chloro-2-nitro-4-(trifluoromethyl)phenyl]amino}phenyl)ethyl acetate To a mixture of 2-(4-{[5-chloro-2-nitro-4-(trifluoromethyl)phenyl]amino}phenyl)ethanol (Example 104, step 1, 8.1 g, 22.4 mmol) and pyridine (1.8 ml, 22.45 mmol) in dichloromethane (200 ml) was added acetyl chloride (1.6 ml, 22.4 mmol) at 0° C. The mixture was stirred at 0° C. for 45 min. The mixture was added water (50 ml) and extracted with dichloromethane (300 ml). The organic layer was washed with brine (100 ml), then dried (Na$_2$SO$_4$). After removal of solvent, the crude product was purified by flash column chromatography eluting with hexane/ethyl acetate (2:1) to afford 8.6 g (95%) of the title compound as yellow solids.

$^1$H-NMR (CDCl$_3$) δ: .9.68 (1H, br.s), 8.57 (1H, s), 7.35 (2H, d, J=8.4 Hz), 7.22 (2H, d, J=8.4 Hz), 7.17 (1H, s), 4.33 (2H, t, J=7.0 Hz), 3.00 (2H, t, J=7.0 Hz), 2.06 (3H, s).

Step 2. 2-(4-{[2-amino-5-chloro-4-(trifluoromethyl)phenyl]amino}phenyl)ethyl acetate The title compound was prepared according to the procedure described in step 2 of Example 28 from 2-(4-{[5-chloro-2-nitro-4-(trifluoromethyl)phenyl]amino}phenyl)ethyl acetate (step 1).

$^1$H-NMR (CDCl$_3$) δ: 7.13–7.16 (3H, m), 7.06 (1H, s), 6.89 (2H, d, J=8.4 Hz), 5.43 (1H, br.s), 4.26 (2H, t, J=7.2 Hz), 3.69 (2H, br.s), 2.89 (2H, d, J=7.2 Hz), 2.04 (3H, s).

Step 3. 2-(4-{[5-chloro-2-{[4-(4-pyridinyl)butanoyl]amino}-4-(trifluoromethyl)phenyl]amino}phenyl)ethyl acetate A mixture of 2-(4-{[2-amino-5-chloro-4-(trifluoromethyl)phenyl]amino}phenyl)ethyl acetate (step 2, 250 mg, 0.67 mmol), 4-(4-pyridinyl)butanoic acid (200 mg, 1 mmol), and WSC (191 mg, 1 mmol) in dichloromethane (7 ml) was stirred at room temperature for 1.5 h. The mixture was added water (5 ml) and extracted with dichloromethane (30 ml). The organic layer was washed with brine (5 ml), then dried (Na$_2$SO$_4$). The solvent was removed under reduced pressure to afford the title compound as pale brown amorphous.

MS (EI) m/z: 519 (M+)
Step 4. 2-{4-[6-chloro-2-[3-(4-pyridinyl)propyl]-5-(trifluoromethyl)-1H-benzimidazol-1-yl]phenyl}ethanol A mixture of 2-(4-{[5-chloro-2-{[4-(4-pyridinyl)butanoyl]amino}-4-(trifluoromethyl)phenyl]amino}phenyl)ethyl acetate (step 3, 220 mg, 0.42 mmol) and 2N NaOH (15 ml) in ethanol (20 ml) was stirred at 40° C. for 7 h. The solvent was removed and the residue was added water (50 ml). The mixture was extracted with ethyl acetate(100 ml). The organic layer was washed with brine (50 ml), then dried (Na₂SO₄). After removal of solvent, the crude product was purified by flash column chromatography eluting with dichloromethane:methanol (20:1) to afford 105 mg (54%) of the title compound as pale brown oil.

¹H-NMR (CDCl₃) δ: 8.40–8.42 (2H, m), 8.10 (1H, s), 7.43 (2H, d, J=8.3 Hz), 7.16–7.19 (3H, m), 7.02 (2H, d, J=6.0 Hz), 4.00 (2H, t, J=6.2 Hz), 3.00 (2H, t, J=6.2 Hz), 2.75 (2H, t, J=7.3 Hz), 2.68 (2H, t, J=7.3 Hz), 2.11–2.19 (2H, m).

Step 5. 2-{4-[6-chloro-2-[3-(4-pyridinyl)propyl]-5-(trifluoromethyl)-1H-benzimidazol-1-yl]phenyl}ethyl (4-methylphenyl)sulfonylcarbamate The title compound was prepared according to the procedure described in Example 3 from 2-{4-[6-chloro-2-[3-(4-pyridinyl)propyl]-5-(trifluoromethyl)-1H-benzimidazol-1-yl]phenyl}ethanol (step 4).

m.p.: 80–87° C.
IR (KBr) ν: 1743, 1610, 1517, 1431, 1346, 1161 cm⁻¹
MS (ESI) m/z: 657 (MH⁺), 655 ([M–H]⁻)
¹H-NMR (CDCl₃) δ: 8.32 (2H, d, J=6.0 Hz), 8.09 (1H, s), 7.99 (2H, d, J=8.2 Hz), 7.34 (2H, d, J=8.2 Hz), 7.22 (2H, d, J=8.2 Hz), 7.15 (1H, s), 6.94–7.02 (4H, m), 4.48 (2H, t, J=5.4 Hz), 3.01 (2H, t, J=5.4 Hz), 2.74 (2H, t, J=6.0 Hz), 2.54 (2H, t, J=7.9 Hz), 2.44 (3H, s), 2.16–2.21 (2H, m).

Example 340

2-{4-[6-CHLORO-2-[3-(3-PYRIDINYL)PROPYL]-5-(TRIFLUOROMETHYL)-1H-BENZIMIDAZOL-1-YL]PHENYL}ETHYL(4-METHYLPHENYL)SULFONYLCARBAMATE

Step 1. 2-(4-{[5-chloro-2-{[4-(3-pyridinyl)butanoyl]amino}-4-(trifluoromethyl)phenyl]amino}phenyl)ethyl acetate The title compound was prepared according to the procedure described in step 3 of Example 339 from 2-(4-{[2-amino-5-chloro-4-(trifluoromethyl)phenyl]amino}phenyl) ethyl acetate (Example 339, step 2).

¹H-NMR (CDCl₃) δ: 8.43 (2H, br.s), 7.50–7.71(2H, m), 7.15–7.28 (6H, m), 6.96 (2H, d, J=8.3 Hz), 6.43 (1H, br.s), 4.26 (2H, t, J=7.0 Hz), 2.90 (2H, t, J=7.0 Hz), 2.70 (2H, t, J=7.3 Hz), 2.41 (2H, t, J=7.3 Hz), 2.03–2.08 (5H, m).

Step 2. 2-{4-[6-chloro-2-[3-(3-pyridinyl)propyl]-5-(trifluoromethyl)-1H-benzimidazol-1-yl]phenyl}ethanol The title compound was prepared according to the procedure described in step 4 of Example 339 from 2-(4-{[5-chloro-2-{[4-(3-pyridinyl)butanoyl]amino}-4-(trifluoromethyl)phenyl]amino}phenyl)ethyl acetate (step 1).

MS (EI) m/z: 459 (M⁺)
¹H-NMR (CDCl₃) δ: 8.33 (1H, d, J=4.4 Hz), 8.09 (1H, s), 7.62 (1H, s), 7.43–7.50 (3H, m), 7.16–7.22 (4H, m), 4.02 (2H, t, J=5.6 Hz), 2.99 (2H, t, J=5.6 Hz), 2.74 (2H, t, J=7.5 Hz), 2.64 (2H, t, J=6.6 Hz), 2.04–2.13 (2H, m).

Step 3. 2-{4-[6-chloro-2-[3-(3-pyridinyl)propyl]-5-(trifluoromethyl )-1H-benzimidazol-1-yl]phenyl}ethyl (4-methylphenyl)sulfonylcarbamate The title compound was prepared according to the procedure described in Example 3 from 2-{4-[6-chloro-2-[3-(3-pyridinyl)propyl]-5-(trifluoromethyl)-1H-benzimidazol-1-yl]phenyl}ethanol (step 2).

m.p.: 90–95° C.
IR (KBr) ν: 1743, 1517, 1431, 1346, 1301, 1161, 1130, 1085 cm⁻¹
MS (ESI) m/z: 657 (MH⁺), 655 ([M–H]⁻)
¹H-NMR (CDCl₃) δ: 8.59 (1H, dd, J=1.7 Hz, 5.1 Hz), 8.08 (1H, s), 7.95 (2H, d, J=8.3 Hz), 7.86 (1H, d, J=1.7 Hz), 7.54–7.58 (1H, m), 7.27–7.34 (5H, m), 7.20 (1H, s), 7.12 (2H, d, J=8.4 Hz), 4.46 (2H, t, J=5.1 Hz), 3.00 (2H, t, J=5.1 Hz), 2.77–2.82 (2H, m), 2.62 (2H, t, J=7.0 Hz), 2.43 (3H, s), 1.85–1.91(2H, m).

Example 341

2-{4-[6-CHLORO-2-[3-OXO-3-(3-PYRIDINYL)PROPYL]-5-(TRIFLUOROMETHYL)-1H-BENZIMIDAZOL-1-YL]PHENYL}ETHYL (4-METHYLPHENYL)SULFONYLCARBAMATE

Step 1. 2-(4-{[5-chloro-2-{[4-oxo-4-(3-pyridinyl)butanoyl]amino}-4-(trifluoromethyl)phenyl]amino}phenyl)ethyl acetate The title compound was prepared according to the procedure described in step 3 of Example 339 from 2-(4-{[2-amino-5-chloro-4-(trifluoromethyl)phenyl]amino}phenyl) ethyl acetate (Example 339, step 2).

¹H-NMR (CDCl₃) δ: 9.19 (1H, d☐ J=2.2 Hz), 8.80 (1H, dd☐ J=1.8 Hz☐ 3.9 Hz), 8.20 (1H, d☐ J=7.9 Hz), 7.64 (2H, br.s), 7.44 (1H, dd, J=5.8 Hz, 7.9 Hz), 7.28 (1H, s), 7.19 (2H, d, J=8.3 Hz), 7.05 (2H, d, J=8.3 Hz), 6.70 (1H, br.s), 4.27 (2H, t, J=7.1 Hz), 3.49 (2H, t, J=5.5 Hz), 2.92 (2H, t, J=7.1 Hz), 2.78 (2H, t, J=5.8 Hz), 2.05 (3H, s).

Step 2. 3-[6-chloro-1-[4-(2-hydroxyethyl)phenyl]-5-(trifluoromethyl)-1H-benzimidazol-2-yl]-1-(3-pyridinyl)-1-propanone The title compound was prepared according to the procedure described in step 4 of Example 339 from 2-(4-{[5-chloro-2-{[4-oxo-4-(3-pyridinyl)butanoyl]amino}-4-(trifluoromethyl)phenyl]amino}phenyl)ethyl acetate (step 1).

¹H-NMR (CDCl₃) δ: 9.05–9.06 (1H, m), 8.77–8.79 (1H, m), 8.24–8.28 (1H, m), 8.06 (1H, s), 7.54 (2H, d, J=8.5 Hz), 7.40–7.46 (3H, m), 3.97–4.04 (2H, m), 3.66 (2H, t, J=7.0 Hz), 3.19 (2H, t, J=7.0 Hz), 3.02 (2H, t, J=6.4 Hz).

Step 3. 2-{4-[6-chloro-2-[3-oxo-3-(3-pyridinyl)propyl]-5-(trifluoromethyl)-1H-benzimidazol-1-yl]phenyl}ethyl (4-methylphenyl)sulfonylcarbamate The title compound was prepared according to the procedure described in Example 3 from 3-[6-chloro-1-[4-(2-hydroxyethyl)phenyl]-5-(trifluoromethyl)-1H-benzimidazol-2yl]-1-(3-pyridinyl)-1-propanone (step 2).

m.p.: 89–95° C.
IR (KBr) ν: 2972, 1747, 1693, 1517, 1346, 1230, 1161, 1085 cm⁻¹
MS (ESI) m/z: 671 (MH⁺), 669 ([M–H]⁻)
¹H-NMR (CDCl₃) δ: 8.91(1H, s), 8.83–8.85 (1H, m), 8.23–8.27 (1H, m), 8.05 (1H, s), 7.92 (2H, d, J=8.2 Hz), 7.33–7.48 (7H, m), 7.21(1H, s), 4.43 (2H, t, J=6.3 Hz), 3.47 (2H, t, J=7.1 Hz), 3.25 (2H, t, J=7.1 Hz), 3.04 (2H, t, J=6.3 Hz), 2.43 (3H, s).

Example 342

2-{4-[6-CHLORO-2-[3-OXO-3-(2-PYRIDINYL)PROPYL]-5-(TRIFLUOROMETHYL)-1H-BENZIMIDAZOL-1-YL]PHENYL}ETHYL (4-METHYLPHENYL)SULFONYLCARBAMATE

Step 1. 2-(4-{[5-chloro-2-{[4-oxo-4-(2-pyridinyl)butanoyl]amino}-4-(trifluoromethyl)phenyl]amino}phenyl)ethyl acetate The title compound was prepared according to the procedure described in step 3 of Example 339 from 2-(4-{[2-amino-5-chloro-4-(trifluoromethyl)phenyl]amino}phenyl) ethyl acetate (Example 339, step 2).

MS (EI) m/z: 533 (M⁺)

Step 2. 3-[6-chloro-1-[4-(2-hydroxyethyl)phenyl]-5-(trifluoromethyl)-1H-benzimidazol-2-yl]-1-(2-pyridinyl)-1-propanone The title compound was prepared according to the procedure described in step 4 of Example 339 from 2-(4-{[5-chloro-2-{[4-oxo-4-(2-pyridinyl)butanoyl]amino}-4-(trifluoromethyl)phenyl]amino}phenyl)ethyl acetate (step 1).

¹H-NMR (CDCl₃) δ: 8.67–8.69 (1H, m), 7.84 (1H, s), 7.96–7.99 (1H, m), 7.81–7.84 (1H, m), 7.39–7.51(5H, m), 7.23 (1H, s), 3.96–4.02 (2H, m), 3.91(2H, t, J=6.9 Hz) 3.15 (2H, t, J=6.9 Hz), 3.01 (2H, t, J=6.4 Hz).

Step 3. 2-{4-[6-chloro-2-[3-oxo-3-(2-pyridinyl)propyl]-5-(trifluoromethyl)-1H-benzimidazol-1-yl]phenyl}ethyl (4-methylphenyl)sulfonylcarbamate The title compound was prepared according to the procedure described in of Example 3 from 3-[6-chloro-1-[4-(2-hydroxyethyl)phenyl]-5-(trifluoromethyl)-1H-benzimidazol-2-yl]-1-(2-pyridinyl)-1-propanone (step 2).

m.p.: 233.6° C.
IR (KBr) v: 1743, 1703, 1515, 1481, 1336, 1203, 1120, 1087, 995 cm⁻¹
MS (ESI) m/z: 671(MH⁺), 669 ([M–H]⁻)
¹H-NMR (DMSO-d₆) δ: 8.74–8.76 (1H, m), 8.13 (1H, S), 7.90–8.03 (2H, m), 7.77 (2H, d, J=8.1 Hz), 7.66–7.70 (1H, m), 7.49–7.58 (4H, m), 7.42 (2H, d, J=8.1 Hz), 7.34 (1H, s), 4.30 (2H, t, J=6.4 Hz), 3.83 (2H, t, J=6.4 Hz), 3.09 (2H, t, J=6.4 Hz), 2.98 (2H, t, J=6.4 Hz), 2.50 (3H, s).

Example 343

2-{4-[6-CHLORO-2-[3-(2PYRIDINYL)PROPYL]-5-(TRIFLUOROMETHYL)-1H-BENZIMIDAZOL-1-YL]PHENYL}ETHYL (4-METHYLPHENYL) SULFONYLCARBAMATE

Step 1. 2-(4-{[5-chloro-2-{[4-(2-pyridinyl)butanoyl]amino}-4-(trifluoromethyl)phenyl]amino}phenyl)ethyl acetate The title compound was prepared according to the procedure described in step 3 of Example 339 from 2-(4-{[2-amino-5-chloro-4-(trifluoromethyl)phenyl]amino}phenyl)ethyl acetate (Example 339, step 2). ¹H-NMR (CDCl₃) δ: 9.26 (1H, br.s), 8.39–8.41 (1H, m), 7.86 (1H, s), 7.69–7.72 (1H, m), 7.49 (1H, s), 7.25–7.28 (1H, m), 7.15–7.21 (3H, m), 7.00 (2H, d, J=8.4 Hz), 4.27 (2H, t, J=7.1 Hz), 2.98 (2H, t, J=6.3 Hz), 2.91(2H, t, J=7.1Hz), 2.33 (2H, t, J=5.9 Hz), 2.05 (3H, s).

Step 2. 2-{4-[6-chloro-2-[3-(2-pyridinyl)propyl]-5-(trifluoromethyl)-1H-benzimidazol-1-yl]phenyl}ethanol The title compound was prepared according to the procedure described in step 4 of Example 339 from 2-(4-{[5-chloro-2-{[4-(2-pyridinyl)butanoyl]amino}-4-(trifluoromethyl)phenyl]amino}phenyl)ethyl acetate (step 1).

¹H-NMR (CDCl₃) δ: 8.43–8.45 (1H, m), 8.09 (1H, s), 7.53–7.59 (1H, m), 7.45 (2H, d, J=8.2 Hz), 7.22–7.25 (3H, m), 7.05–7.13 (2H, m), 3.98 (2H, t, J=6.3 Hz), 3.00 (2H, t, J=6.3 Hz), 2.84 (4H, t, J=7.5 Hz), 2.18–2.22 (2H, m), 1.81–1.90 (2H, m).

Step 3. 2-{4-[6-chloro-2-[3-(2-pyridinyl)propyl]-5-(trifluoromethyl)-1H-benzimidazol-1-yl]phenyl}ethyl (4-methylphenyl)sulfonylcarbamate The title compound was prepared according to the procedure described in Example 3 from 2-{4-[6-chloro-2-[3-(2-pyridinyl)propyl]-5-(trifluoromethyl)-1H-benzimidazol-1-yl]phenyl}ethanol (step 2).

m.p.: 193° C.
IR (KBr)v: 1747, 1626, 1517, 1433, 1350, 1159, 1120, 1085 cm⁻¹
MS (ESI) m/z: 657 (MH⁺), 655 ([M–H]⁻)
¹H-NMR (CDCl₃) δ: 8.47–8.49 (1H, m), 8.08 (1H, s), 7.90 (2H, d, J=8.4 Hz), 7.60–7.66 (1H, m), 7.36 (2H, d, J=8.4 Hz), 7.11–7.22 (7H, m), 4.44 (2H, t, J=6.0 Hz), 3.01 (2H, t, J=6.0 Hz), 2.82–2.88 (4H, m), 2.45 (3H, s), 1.84–1.94 (2H, m).

Example 344

2-{4-[6-CHLORO-2-[3-(2PYRIDINYL)PROPYL]-5-(TRIFLUOROMETHYL)-1H-BENZIMIDAZOL-1-YL]PHENYL}ETHYL (4-METHYLPHENYL) SULFONYLCARBAMATE P-TOLUENESULFONATE

The title compound was prepared according to the procedure described in Example 231from 2-{4-[6-chloro-2-[3-(2-pyridinyl)propyl]-5-(trifluoromethyl)-1H-benzimidazol-1-yl]phenyl}ethyl (4-methylphenyl)sulfonylcarbamate (Example 343)

m.p.: 108–110° C.
IR (KBr) v: 3062, 1745, 1456, 1232, 1163, 1010 cm⁻¹

Example 345

N-{[(2-{4-[2-ETHYL-5-(1-HYDROXETHYL)-1H-BENZIMIDAZOL-1-YL]PHENYL}ETHYL) AMINO]CARBONYL}-4-METHYLBENZENESULFONAMIDE

Step 1. N-{[(2-{4-[2-ethyl-5-(1-hydroxyethyl)-1H-benzimidazol-1-yl]phenyl}ethyl)amino]carbonyl}-4-methylbenzenesulfonamide A mixture N-[({2-[4-(5-acetyl-2-ethyl-1H-benzimidazol-1-yl)phenyl]ethyl}amino)carbonyl]-4-methylbenzenesulfonamide (Example 78, 238 mg, 0.47 mmol) and 2N NaOH (0.1ml) in ethanol (10 ml) was added a mixture of NaBH₄ (178 mg, 0.47 mmol) and 2N NaOH (0.1 ml) in ethanol (4 ml) at room temperature. The mixture was stirred at room temperature for 4 h. The mixture was added water (10 ml) and neutralized with NH₄Cl. The mixture was extracted with ethyl acetate(50 ml). The organic layer was washed with brine (10 ml), then dried (Na₂SO₄). After removal of solvent, the crude product was purified by flash column chromatography eluting with hexane/ethyl acetate (1:4/1:6)/CH₂Cl₂:methanol(10:1) to afford 198 mg (83%) of the title compound as white solids.

m.p.: 190° C.
IR (KBr) v:3384, 2979, 1716, 1514, 1404, 1159, 1087 cm⁻¹
MS (ESI) m/z: 507 (MH⁺), 505 ([M–H]⁻)
¹H-NMR (CDCl₃) δ: 7.73–7.76 (3H, m), 7.21–7.34 (7H, m), 7.20 (1H, d, J=8.5 Hz), 6.66 (1H, br.s), 5.02 (1H, q, J=6.4 Hz), 3.52–3.59 (2H, m), 2.91 (2H, t, J=7.0 Hz), 2.75 (2H, q, J=7.5 Hz), 2.39 (3H, s), 1.54 (3H, d, J=6.4 Hz), 1.30 (3H, t, J=7.5 Hz).

Example 346

N-{[(2-{4-[2-ETHYL-5-(1-HYDROXYETHYL)-1H-BENZIMIDAZOL-1-YL]PHENYL}ETHYL) AMINO]CARBONYL}-4-METHYLBENZENESULFONAMIDE P-TOLUENESULFONATE

The title compound was prepared according to the procedure described in Example 231 from N-{[(2-{4-[2-ethyl-5-(1-hydroxyethyl )-1H-benzimidazol-1-yl]phenyl}ethyl)amino]carbonyl}-4-methylbenzenesulfonamide (Example 345)

m.p.: 110–115° C.
IR (KBr) v: 3062, 1708,1519, 1340, 1163 cm⁻¹

Example 347

N-({[2-(4-{2-ETHYL-5-[1-(METHYLOXY)ETHYL]-1H-BENZIMIDAZOL-1-YL]PHENYL)ETHYL] AMINO}CARBONYL)-4-METHYLBENZENESULFONAMIDE

Step 1. N-({[2-(4-{2-ethyl-5-[1-(methyloxy)ethyl]-1H-benzimidazol-1-yl}phenyl)ethyl]amino}carbonyl)-4-methylbenzenesulfonamide A solution of N-{[(2-{4-[2-ethyl-5-(1-hydroxyethyl)-1H-benzimidazol-1-yl]phenyl}ethyl)amino]carbonyl}-4-methylbenzenesulfonamide (Example 345, 151 mg, 0.3 mmol) in CH₂Cl₂ (15 ml) was added thionyl chloride (0.1 ml, 1.5 mmol) at room temperature. The mixture was stirred at room temperature for 2 h. The solvent was removed and the residue was dissolved with methanol (15 ml). The mixture was added triethylamine (0.08 ml, 0.6 mmol) and stirred at room temperature for 5 h. The solvent was removed and the residue was extracted with $CH_2Cl_2$ (50 ml). The organic layer was washed with water(10 ml), brine (10 ml), then dried ($Na_2SO_4$). After removal of solvent, the crude product was purified by flash column chromatography eluting with hexane/ethyl acetate (1:6)/$CH_2Cl_2$:methanol (10:1) to afford 139 mg (89%) of the title compound as white solids.

MS (ESI) m/z: 521 (MH$^+$), 519 ([M–H]$^-$)

$^1$H-NMR (CDCl$_3$) δ: 7.65–7.75 (3H, m), 7.27–7.37 (6H, m), 7.16–7.20 (1H, m), 7.07 (1H, d, J=8.3 Hz), 6.69 (1H, br.s), 4.42 (1H, q, J=6.5 Hz), 3.54–3.62 (2H, m), 3.22 (3H, s), 2.93 (2H, t, J=7.0 Hz), 2.93 (2H, t, J=7.0 Hz), 2.78 (2H, q, J=7.6 Hz), 2.39 (3H, s), 1.49 (3H, d, J=6.5 Hz), 1.32 (3H, t, J=7.6 Hz).

Example 348

N-({[2-(4-{2-ETHYL-5-[1-(METHYLOXY)ETHYL]-1H-BENZIMIDAZOL-1-YL}PHENYL)ETHYL]AMINO}CARBONYL)-4-METHYLBENZENESULFONAMIDE P-TOLUENESULFONATE

The title compound was prepared according to the procedure described in Example 231 from N-({[2-(4-{2-ethyl-5-[1-(methyloxy)ethyl]-1H-benzimidazol-1-yl}phenyl)ethyl]amino}carbonyl)-4-methylbenzenesulfonamide (Example 347)

m.p.: 110–115° C.

IR (KBr) v: 3064, 1710, 1519, 1452, 1340, 1163, 1033 cm$^{-1}$

Example 349

N-{[(2-{4-[2-ETHYL-5-(1-HYDROXY-1-METHYLETHYL)-1H-BENZIMIDAZOL-1-YL]PHENYL}ETHYL)AMINO]CARBONYL}-4-METHYLBENZENESULFONAMIDE P-TOLUENESULFONATE

Step 1. N-{[(2-{4-[2-ethyl-5-(1-hydroxy-1-methylethyl)-1H-benzimidazol-1-yl]phenyl}ethyl)amino]carbonyl}-4-methylbenzenesulfonamide A solution of N-[({2-[4-(5-acetyl-2-ethyl-1H-benzimidazol-1-yl)phenyl]ethyl}amino)carbonyl]-4-methylbenzenesulfonamide (Example 78, 100 mg, 0.19 mmol) in tetrahydrfurane (15 ml) was added MeMgI (1.2 ml, 0.99 mmol) dropwise under nitrogen at 0° C. The mixture was stirred at 0° C. for 1 h and then was stirred at rt for 30 min. The mixture was added water (10 ml) and extracted with $CH_2Cl_2$(50 ml). The organic layer was washed with brine (10 ml), then dried ($Na_2SO_4$). After removal of solvent, the crude product was purified by flash column chromatography eluting with $CH_2Cl_2$:methanol (30:1/20:1/10:1) to afford 100 mg (97%) of the title compound as white solids.

MS (ESI) m/z: 521 (MH$^+$), 519 ([M–H]$^-$)

$^1$H-NMR (CDCl$_3$) δ: 7.87 (1H, s), 7.76 (2H, d, J=7.9 Hz), 7.17–7.38 (7H, m), 7.00 (1H, d, J=8.5 Hz), 6.69 (1H, br.s), 3.52 (2H, br.s), 2.88 (2H, br.s), 2.73 (2H, br.s), 2.36 (3H, s), 1.62 (6H, s), 1.27 (3H, m).

Step 2. N-{[(2-{4-[2-ethyl-5-(1-hydroxy-1-methylethyl)-1H-benzimidazol-1-yl]phenyl}ethyl)amino]carbonyl}-4-methylbenzenesulfonamide p-toluenesulfonate The title compound was prepared according to the procedure described in Example 231 from N-{[(2-{4-[2-ethyl-5-(1-hydroxy-1-methylethyl)-1H-benzimidazol-1-yl]phenyl}ethyl)amino]carbonyl}-4-methylbenzenesulfonamide (Step 1).

m.p.: 146–150° C.

IR (KBr) v: 2871, 1685, 1519, 1448, 1340, 1124 cm$^{-1}$

Example 350

2-ETHYL-4,6-DIMETHYL-1-(4-{2-[({[(4-METHYLPHENYL)SULFONYL]AMINO}CARBONYL)AMINO]ETHYL}PHENYL)-1H-BENZIMIDAZOLE-5-CARBOXAMIDE

Step 1. 1-[4-(2-chloroethyl)phenyl]-2-ethyl-4,6-dimethyl-1H-benzimidazole-5-carboxamide A solution of 1-[4-(2-chloroethyl)phenyl]-2-ethyl-4,6-dimethyl-1H-benzimidazole-5-carbonitrile (Example 329, step 6, 997 mg, 2.95 mmol) in c.H$_2$SO$_4$ (50 ml) was stirred at 80° C. for 15 h. The mixture was poured onto ice and was neutralized with NaOH. The mixture was extracted with ethyl acetate (600 ml). The organic layer was washed with brine (300 ml), then dried ($Na_2SO_4$). The solvent was removed to afford 871 mg (83%) of the title compound as white solids.

MS (EI) m/z: 355 (M+)

$^1$H-NMR (CDCl$_3$) δ: 7.43 (2H, d, J=8.4 Hz), 7.28 (2H, d, J=8.4 Hz), 6.73 (1H, s), 6.56 (1H, br.s), 5.88 (1H, br.s), 3.82 (2H, t, J=7.0 Hz), 3.19 (2H, t, J=7.0 Hz), 2.82 (2H, q, J=7.6 Hz), 2.72 (3H, s), 2.41 (3H, s), 1.26 (3H, t, J=7.6 Hz).

Step 2. 1-[4-(2-azidoethyl)phenyl]-2-ethyl-4,6-dimethyl-1H-benzimidazole-5-carboxamide The title compound was prepared according to the procedure described in step 8 Example 1 from 1-[4-(2-chloroethyl)phenyl]-2-ethyl-4,6-dimethyl-1H-benzimidazole-5-carboxamide (step 1).

$^1$H-NMR (CDCl$_3$) δ: 7.44 (2H, d, J=8.4 Hz), 7.27–7.30 (2H, m), 6.73 (1H, s), 5.97 (1H, br.s), 5.72 (1H, br.s), 3.62 (2H, t, J=7.1 Hz), 3.02 (2H, t, J=7.1 Hz), 2.80 (2H, q, J=7.5 Hz), 2.73 (3H, s), 2.42 (3H, s), 1.26 (3H, t, J=7.5 Hz).

Step 3. 1-[4-(2-aminoethyl)phenyl]-2-ethyl-4,6-dimethyl-1H-benzimidazole-5-carboxamide The title compound was prepared according to the procedure described in step 9 of Example 1 from 1-[4-(2-azidoethyl)phenyl]-2-ethyl-4,6-dimethyl-1H-benzimidazole-5-carboxamide (step 2).

$^1$H-NMR (CDCl$_3$) δ: 7.41 (2H, d, J=8.2 Hz), 7.26 (2H, d, J=8.2 Hz), 6.74 (1H, s), 6.00 (1H, br.s), 5.76 (1H, br.s), 3.07 (2H, t, J=7.1 Hz), 2.87 (2H, t, J=7.1 Hz), 2.81 (2H, q, J=7.5 Hz), 2.74 (3H, s), 2.43 (3H, s), 1.26 (3H, t, J=7.5 Hz).

Step 4. 2-ethyl-4,6-dimethyl-1-(4-{2-[({[(4-methylphenyl)sulfonyl]amino}carbonyl)amino]ethyl}phenyl)-1H-benzimidazole-5-carboxamide The title compound was prepared according to the procedure described in step 10 of Example 1 from 1-[4-(2-aminoethyl)phenyl]-2-ethyl-4,6-dimethyl-1H-benzimidazole-5-carboxamide (step 3).

MS (ESI) m/z: 534 (MH$^+$), 532 ([M–H]$^-$)

$^1$H-NMR (CD$_3$OD) δ: 7.88 (1H, s), 7.80 (2H, d, J=8.3 Hz), 7.25–7.42 (6H, m), 6.74 (1H, br.s), 3.42 (2H, t, J=6.8 Hz), 2.86 (2H, t, J=6.8 Hz), 2.79 (2H, q, J=7.6 Hz), 2.65 (3H, s), 2.37 (3H, s), 2.34 (3H, s), 1.21 (3H, t, J=7.6 Hz).

Step 5. 2-ethyl-4,6-dimethyl-1-(4-{2-[({[(4-methylphenyl)sulfonyl]amino}carbonyl)amino]ethyl}phenyl)-1H-benzimidazole-5-carboxamide p-toluenesulfonate The title compound was prepared according to the procedure described in Example 231 from 2-ethyl-4,6-dimethyl-1-(4-{2-[({[(4-methylphenyl)sulfonyl]amino}carbonyl)amino]ethyl}phenyl)-1H-benzimidazole-5-carboxamide (step 4).

Example 351
N-{[(2-{4-[2-ETHYL-5-(TRIFLUOROACETYL)-1H-BENZIMIDAZOL-1-YL]PHENYL}ETHYL)AMINO] CARBONYL}-4-METHYLBENZENESULFONAMIDE P-TOLUENESULFONATE Step 1. 2,2,2-trifluoro-1-(4-{[4-(2-hydroxyethyl)phenyl]amino}-3-nitrophenyl)ethanone The title compound was prepared according to the procedure described in step 1 of Example 45 from 1-(4-amino-3-nitrophenyl)-2,2,2-trifluoroethanone.

$^1$H-NMR (CDCl$_3$) δ: 9.47 (1H, br.s), 8.10 (1H, d, J=2.6 Hz), 7.16–7.33 (6H, m), 3.87–3.94 (2H, m), 2.91 (2H, t, J=6.4 Hz), 1.43 (1H, t, J=5.6 Hz).

Step 2. 1-(3-amino-4-{[4-(2-hydroxyethyl)phenyl]amino}phenyl)-2,2,2-trifluoroethanone The title compound was prepared according to the procedure described in step 4 of Example 1 from 2,2,2-trifluoro-1-(4-{[4-(2-hydroxyethyl)phenyl]amino}-3-nitrophenyl)ethanone (step 1).

$^1$H-NMR (CDCl$_3$) δ: 7.05–7.09 (3H, m), 6.57–6.70 (4H, m), 3.82 (2H, t, J=6.6 Hz), 2.78 (2H, t, J=6.6 Hz).

Step 3. 2-{4-[2-ethyl-5-(trifluoroacetyl)-1H-benzimidazol-1-yl]phenyl}ethyl propanoate The title compound was prepared according to the procedure described in step 5 of Example 1 from 1-(3-amino-4-{[4-(2-hydroxyethyl)phenyl]amino}phenyl)-2,2,2-trifluoroethanone (step 2).

$^1$H-NMR (CDCl$_3$) δ: 7.65 (1H, s), 7.45 (2H, d, J=8.3 Hz), 7.29 (2H, d, J=8.3 Hz), 7.06 (2H, s), 4.38 (2H, t, J=6.9 Hz), 3.07 (2H, t, J=6.9 Hz), 2.79 (2H, q, J=7.4 Hz), 2.35 (2H, q, J=7.5 Hz), 1.35 (3H, t, J=7.4 Hz), 1.14 (3H, t, J=7.5 Hz).

Step 4. 1-{2-ethyl-1-[4-(2-hydroxyethyl)phenyl]1H-benzimidazol-5-yl}-2,2,2-trifluoroethanone The title compound was prepared according to the procedure described in step 6 of Example 1 from 2-{4-[2-ethyl-5-(trifluoroacetyl)-1H-benzimidazol-1-yl]phenyl}ethyl propanoate (step 3).

$^1$H-NMR (CDCl$_3$) δ: 7.65 (1H, s), 7.47 (2H, d, J=8.4 Hz), 7.29 (2H, d, J=8.4 Hz), 7.06 (2H, s), 3.96–4.03 (2H, m), 3.01 (2H, t, J=6.6 Hz), 2.79 (2H, q, J=7.6 Hz), 1.35 (3H, t, J=7.6 Hz).

Step 5. 1-{1-[4-(2-chloroethyl)phenyl]-2-ethyl-1H-benzimidazol-5-yl}-2,2,2-trifluoroethanone The title compound was prepared according to the procedure described in step 7 Example 1 from 1-{2-ethyl-1-[4-(2-hydroxyethyl)phenyl]-1H-benzimidazol-5-yl}-2,2,2-trifluoroethanone (step 4).

$^1$H-NMR (CDCl$_3$) δ: 7.66 (1H, s), 7.45 (2H, d, J=8.4 Hz), 7.31 (2H, d, J=8.4 Hz), 7.07 (2H, s), 3.82 (2H, t, J=7.0 Hz), 3.20 (2H, t, J=7.0 Hz), 2.79 (2H, q, J=7.6 Hz), 1.36 (3H, t, J=7.6 Hz).

Step 6. 1-{1-[4-(2-azidoethyl)phenyl]-2-ethyl-1H-benzimidazol-5-yl}-2,2,2-trifluoroethanone The title compound was prepared according to the procedure described in step 8 Example 1 from 1-{1-[4-(2-chloroethyl)phenyl]-2-ethyl-1H-benzimidazol-5-yl}-2,2,2-trifluoroethanone (step 5).

$^1$H-NMR (CDCl$_3$) δ: 7.65 (1H, s), 7.46 (2H, d, J=8.4 Hz), 7.31 (2H, d, J=8.4 Hz), 7.06 (2H, s), 3.62 (2H, t, J=7.0 Hz), 3.02 (2H, t, J=7.0 Hz), 2.79 (2H, q, J=7.5 Hz), 1.35 (3H, t, J=7.5 Hz).

Step 7. 1-{1-[4-(2-aminoethyl)phenyl]-2-ethyl-1H-benzimidazol-5-yl}-2,2,2-trifluoroethanone The title compound was prepared according to the procedure described in step 9 of Example 1 from 1-{1-[4-(2-azidoethyl)phenyl]-2-ethyl-1H-benzimidazol-5-yl}-2,2,2-trifluoroethanone (step 6).

$^1$H-NMR (CDCl$_3$) δ: 7.65 (1H, s), 7.43 (2H, d, J=8.5 Hz), 7.28 (2H, d, J=8.5 Hz), 7.07 (2H, s), 3.09 (2H, t, J=6.7 Hz), 2.89 (2H, t, J=6.7 Hz), 2.79 (2H, q, J=7.4 Hz), 1.35 (3H, t, J=7.4 Hz).

Step 8. N-{[(2-{4-[2-ethyl-5-(trifluoroacetyl)-1H-benzimidazol-1-yl]phenyl}ethyl)amino]carbonyl}-4-methylbenzenesulfonamide The title compound was prepared according to the procedure described in step 10 of Example 1 from 1-{1-[4-(2-aminoethyl)phenyl]-2-ethyl-1H-benzimidazol-5-yl}-2,2,2-trifluoroethanone (step 7).

MS (ESI) m/z: 547 (MH$^+$), 545 ([M–H]$^-$)

$^1$H-NMR (CDCl$_3$) δ: 7.72 (2H, d, J=8.4 Hz), 7.64 (1H, s), 7.39 (2H, d, J=8.4 Hz), 7.27–7.29 (4H, m), 7.02–7.04 (2H, m), 6.75 (1H, br.s), 3.55–3.62 (2H, m), 2.94 (2H, t, J=6.9 Hz), 2.79 (2H, q, J=7.5 Hz), 2.39 (3H, s), 1.33 (3H, t, J=7.5 Hz).

Step 9. N-{[(2-{4-[2-ethyl-5-(trifluoroacetyl)-1H-benzimidazol-1-yl]phenyl}ethyl)amino]carbonyl}-4-methylbenzenesulfonamide p-toluenesulfonate The title compound was prepared according to the procedure described in Example 231 from N-{[(2-{4-[2-ethyl-5-(trifluoroacetyl)-1H-benzimidazol-1-yl]phenyl}ethyl)amino]carbonyl}-4-methylbenzenesulfonamide (step 8)

m.p.: 194.1° C.

IR (KBr) v: 3589, 1701, 1627, 1521, 1458, 1330, 1091 cm$^{-1}$

Example 352
2-{4-[2-ETHYL-5-(TRIFLUOROACETYL)-1H-BENZIMIDAZOL-1-YL]PHENYL}ETHYL(4-METHYLPHENYL)SULFONYLCARBAMATE P-TOLUENESULFONATE Step 1. 2-{4-[2-ethyl-5-(trifluoroacetyl)-1H-benzimidazol-1-yl]phenyl}ethyl (4-methylphenyl)sulfonylcarbamate The title compound was prepared according to the procedure described in Example 3 from 1-{2-ethyl-1-[4-(2-hydroxyethyl )phenyl]-1H-benzimidazol-5-yl}-2,2,2-trifluoroethane (Example 351, step 4).

MS (ESI) m/z: 548 (MH$^+$), 546 ([M–H]$^-$)

$^1$H-NMR (CDCl$_3$) δ: 7.93 (2H, d, J=8.4 Hz), 7.64(1H, s), 7.28–7.35 (4H, m), 7.20 (2H, d, J=8.4 Hz), 7.05–7.07 (2H, m), 4.37 (2H, t, J=6.6 Hz), 3.00 (2H, t, J=6.6 Hz), 2.76 (2H, q, J=7.6 Hz), 2.43 (3H, s), 1.31 (3H, t, J=7.6 Hz).

Step 2. 2-{4-[2-ethyl-5-(trifluoroacetyl)-1H-benzimidazol-1-yl]phenyl}ethyl(4-methylphenyl)sulfonylcarbamate p-toluenesulfonate The title compound was prepared according to the procedure described in Example 231 from 2-{4-[2-ethyl-5-(trifluoroacetyl)-1H-benzimidazol-1-yl]phenyl}ethyl(4-methylphenyl)sulfonylcarbamate (Step 1)

m.p.: 92–97° C.

IR (KBr)v: 1745, 1519, 1458, 1350, 1222,1163, 1122 cm$^{-1}$

Example 353
2-{4-[5-ACETYL-2-(1H-PYRAZOL-3-YL)-1H-BENZIMIDAZOL-1-YL]PHENYL}ETHLY(4-METHYLPHENYL)SULFONYLCARBAMATE P-TOLUENESULFONATE Step 1. 1-[1-[4-(2-hydroxyethyl)phenyl]-2-(1H-pyrazol-3-yl)-1H-benzimidazol-5-yl]ethanone The title compound was prepared according to the procedure described in step 1 of Example 236 from 1-(3-amino-4-{[4-(2-hydroxyethyl)phenyl]amino}phenyl)ethanone (Example 78, step 2).

MS (EI) m/z: 345 (M+)

$^1$H-NMR (CDCl$_3$) δ: 8.53 (1H, s), 7.94 (1H, d, J=8.4 Hz), 7.48–7.53 (3H, m), 7.37 (2H, d, J=8.2 Hz), 7.27 (1H, s), 7.18 (1H, d, J=8.4 Hz), 6.03 (1H, br.s), 4.02 (2H, t, J=6.6 Hz), 3.05 (2H, t, J=6.6 Hz), 2.69 (3H, s).

Step 2. 2-{4-[5-acetyl-2-(1H-pyrazol-3-yl)-1H-benzimidazol-1-yl]phenyl}ethyl(4-methylphenyl)sulfonylcarbamate The title compound was prepared according to the procedure described in Example 3 from 1-[1-[4-(2-hydroxyethyl)phenyl]-2-(1H-pyrazol-3-yl)-1H-benzimidazol-5-yl]ethanone (step 1).

MS (ESI) m/z: 544 (MH⁺), 542 ([M−H]⁻)

¹H-NMR (DMSO-d₆) δ: 8.41 (1H, s), 7.77–7.89 (4H, m), 7.38–7.42 (7H, m), 7.12 (1H, d, J=8.5 Hz), 6.65 (1H, br.s), 4.29 (2H, t, J=6.6 Hz), 2.96 (2H, t, J=6.6 Hz), 2.66 (3H, s).

Step 3. 2-{4-[5-acetyl-2-(1H-pyrazol-3-yl)-1H-benzimidazol-1-yl]phenyl}ethyl(4-methylphenyl) sulfonylcarbamate p-toluenesulfonate The title compound was prepared according to the procedure described in Example 231 from 2-{4-[5-acetyl-2-(1H-pyrazol-3-yl)-1H-benzimidazol-1-yl]phenyl}ethyl(4-methylphenyl)sulfonylcarbamate (step 2)

m.p.: 204° C.

IR (KBr) v: 3249, 1755, 1676, 1595, 1517, 1440, 1332, 1207, 1161, 1008 cm⁻¹

Example 354

N-{[(2-{4-[6-CHLORO-2-[1-(METHYLOXY)ETHYL]-5-(TRIFLUOROMETHYL)-1H-BENZIMIDAZOL-1-YL]PHENYL}ETHYL)AMINO]CARBONYL}-4-METHYLBENZENESULFONAMIDE P-TOLUENESULFONATE

Step 1. 2-(4-{[5-chloro-2-[(2-hydroxypropanoyl)amino]-4-(trifluoromethyl)phenyl]amino}phenyl)ethyl acetate The title compound was prepared according to the procedure described in step 3 of Example 339 from 2-(4-{[2-amino-5-chloro-4-(trifluoromethyl)phenyl]amino}phenyl)ethyl acetate (Example 339, step 2).

MS (EI) m/z: 444 (M⁺)

Step 2. 2-{4-[6-chloro-2-(1-hydroxyethyl)-5-(trifluoromethyl)-1H-benzimidazol-1-yl]phenyl}ethyl acetate The title compound was prepared according to the procedure described in step 4 of Example 339 from 2-(4-{[5-chloro-2-[(2-hydroxypropanoyl)amino]-4-(trifluoromethyl)phenyl]amino}phenyl)ethyl acetate (step 1)

¹H-NMR (CDCl₃) δ: 8.14 (1H, s), 7.48 (2H, d, J=8.4 Hz), 7.34 (2H, d, J=8.4 Hz), 7.24 (1H, s), 4.88–4.98 (1H, m), 4.38 (2H, t, J=7.0 Hz), 3.66 (1H, d, J=8.1Hz), 3.08 (2H, t, J=7.0 Hz), 2.09 (3H, s), 1.57 (3H, d, J=6.6 Hz).

Step 3. 1-[6-chloro-1-[4-(2-hydroxyethyl)phenyl]-5-(trifluoromethyl)-1H-benzimidazol-2-yl]ethanol The title compound was prepared according to the procedure described in step 6 of Example 1 from 2-{4-[6-chloro-2-(1-hydroxyethyl)-5-(trifluoromethyl)-1H-benzimidazol-1-yl]phenyl}ethyl acetate (step 2)

MS (ESI) m/z: 384 (M⁺)

¹H-NMR (CDCl₃) δ: 8.14 (1H, s), 7.49 (2H, d, J=8.6 Hz), 7.34 (2H, d, J=8.6 Hz), 7.25 (1H, s), 4.89–4.96 (1H, m), 3.98 (2H, t, J=6.2 Hz), 3.36 (1H, d, J=5.5 Hz), 3.01 (2H, t, J=6.2 Hz), 1.54 (3H, m).

Step 4. 1-[6-chloro-1-[4-(2-{[(1,1-dimethylethyl)(diphenyl)silyl]oxy}ethyl)phenyl]-5-(trifluoromethyl)-1H-benzimidazol-2-yl]ethanol A mixture of 1-[6-chloro-1-[4-(2-hydroxyethyl)phenyl]-5-(trifluoromethyl)-1H-benzimidazol-2-yl]ethanol (step 3, 461 mg, 1.19 mmol), tert-Butyldiphenylsilyl chloride (0.35 ml, 1.3 mmol), triethylamine (0.2 ml, 1.4 mmol) and N,N-dimetylaminopyridine (6 mg, 0.05 mmol) in dichloromethane (11 ml) was stirred under nitrogen at room temperature for 4 h. was added water (50 ml) and extracted with dichloromethane (100 ml). The organic layer was washed with water (50 ml), brine (50 ml), then dried (Na₂SO₄). After removal of solvent, the crude product was purified by flash column chromatography eluting with hexane/ethyl acetate (3:1/1:1) to afford 590 mg (80%) of the title compound as white amorphous.

¹H-NMR (CDCl₃) δ: 8.14 (1H, s), 7.59–7.63 (4H, m), 7.34–7.46 (8H, m), 7.22–7.30 (3H, m), 4.87–4.96 (1H, m), 3.94 (2H, t, J=6.4 Hz), 3.29 (1H, d, J=8.1Hz), 2.97 (2H, t, J=6.4 Hz), 1.52 (3H, d, J=6.6 Hz), 1.03 (9H, s).

Step 5. 6-chloro-1-[4-(2-{[(1,1-dimethylethyl)(diphenyl)silyl]oxy}ethyl)phenyl]-2-[1-(methyloxy)ethyl]-5-(trifluoromethyl)-1H-benzimidazole A solution of 1-[6-chloro-1-[4-(2-{[(1,1-dimethylethyl)(diphenyl)silyl]oxy}ethyl)phenyl]-5-(trifluoromethyl)-1H-benzimidazol-2-yl]ethanol (step 4, 590 mg, 0.95 mmol) in DMF (10 ml) was added NaH (45 mg, 1.13 mmol). Then the mixture was added MeI (0.08 ml, 1.23 mmol) at room temperature. The mixture was stirred at room temperature for 1 h. The mixture was added water (30 ml) and extracted with ethyl acetate (100 ml). The organic layer was washed with water (50 ml), brine (50 ml), then dried (Na₂SO₄). After removal of solvent, the crude product was purified by flash column chromatography eluting with hexane/ethyl acetate (3:1) to afford 550 mg (91%) of the title compound as colorless oil.

¹H-NMR (CDCl₃) δ: 8.17 (1H, s), 7.20–7.70 (15H, m), 4.54 (1H, q, J=6.6 Hz), 3.95 (2H, t, J=6.6 Hz), 3.22 (3H, s), 2.97 (2H, t, J=6.6 Hz), 1.55 (3H, d, J=6.6 Hz), 1.03 (9H, s).

Step 6. 2-{4-[6-chloro-2-[1-(methyloxy)ethyl]-5-(trifluoromethyl)-1H-benzimidazol-1-yl]phenyl}ethanol The title compound was prepared according to the procedure described in step 6 of Example 90 from 6-chloro-1-[4-(2-{[(1,1-dimethylethyl)(diphenyl)silyl]oxy}ethyl)phenyl]-2--[1-(methyloxy)ethyl]-5-(trifluoromethyl)-1H-benzimidazole (step 5).

MS (ESI) m/z:398

¹H-NMR (CDCl₃) δ: 8.18 (1H, s), 7.49 (2H, d, J=8.4 Hz), 7.33 (2H, d, J=8.4 Hz), 7.24 (1H, s), 4.58 (1H, q, J=6.6 Hz), 4.00 (2H, br.s), 3.24 (3H, s), 3.02 (2H, t, J=6.5 Hz), 1.55–1.60 (3H, m).

Step 7. 6-chloro-1-[4-(2-chloroethyl)phenyl]-2-[1-(methyloxy)ethyl]-5-(trifluoromethyl)-1H-benzimidazole The title compound was prepared according to the procedure described in step 7 of Example 1 from 2-{4-[6-chloro-2-[1-(methyloxy)ethyl]-5-(trifluoromethyl)-1H-benzimidazol-1yl]phenyl}ethanol (step 6).

MS (ESI) m/z: 416 (M⁺)

¹H-NMR (CDCl₃) δ: 8.18 (1H, s), 7.48 (2H, d, J=8.5 Hz), 7.35 (2H, d, J=8.5 Hz), 7.23 (1H, s), 5.57 (1H, q, J=6.6 Hz), 3.83 (2H, t, J=7.1 Hz), 3.19–3.24 (5H, m), 1.57 (3H, d, J=6.6 Hz).

Step 8. 1-[4-(2-azidoethyl)phenyl]-6-chloro-2-[1-(methyloxy)ethyl]-5-(trifluoromethyl)-1H-benzimidazole The title compound was prepared according to the procedure described in step 8 of Example 1 from 6-chloro-1-[4-(2-chloroethyl)phenyl]-2-[1-(methyloxy)ethyl]-5-(trifluoromethyl)-1H-benzimidazole (step 7).

MS (ESI) m/z: 423 (M⁺)

¹H-NMR (CDCl₃) δ: 8.18 (1H, s), 7.48 (2H, d, J=8.2 Hz), 7.35 (2H, d, J=8.2 Hz), 7.22 (1H, s), 4.57 (1H, q, =6.6 Hz), 3.63 (2H, t, J=6.9 Hz), 3.23 (3H, s), 3.04 (2H, t, J=6.9 Hz), 1.56 (3H, d, J=6.6 Hz).

Step 9. 2-{4-[6-chloro-2-[1-(methyloxy)ethyl]-5-(trifluoromethyl)-1H-benzimidazol-1-yl]phenyl}ethanamine The title compound was prepared according to the procedure described in step 7 of Example 37 from 1-[4-(2-azidoethyl)phenyl]-6-chloro-2-[1-(methyloxy)ethyl]-5-(trifluoromethyl)-1H-benzimidazole (step 8).

¹H-NMR (CDCl₃) δ: 8.18 (1H, s), 7.45 (2H, d, J=8.4 Hz), 7.32 (2H, d, J=8.4 Hz), 7.24 (1H, s), 4.57 (1H, q, J=6.6 Hz), 3.23 (3H, s), 3.10 (2H, br.s), 2.90 (2H, t, J=6.6 Hz), 1.57 (3H, d, J=6.6 Hz).

Step 10. N-{[(2-{4-[6-chloro-2-[1-(methyloxy)ethyl]-5-(trifluoromethyl )-1H-benzimidazol-1-yl]phenyl}ethyl)amino]carbonyl}-4-methylbenzenesulfonamide The title compound was prepared according to the procedure described in step 10 of Example 1 from 2-{4-[6-chloro-2-[1-(methyloxy)ethyl]-5-(trifluoromethyl)-1H-benzimidazol-1-yl]phenyl}ethanamine (step 9).

MS (ESI) m/z: 595 (MH$^+$), 593 ([M−H]$^-$)

$^1$H-NMR (CDCl$_3$) δ: 8.18 (1H, s), 7.73 (2H, d, J=8.4 Hz), 7.42 (2H, d, J=8.6 Hz), 7.27–7.34 (4H, m), 7.21 (1H, s), 6.76 (1H, br.s), 4.57 (1H, q, J=6.6 Hz), 3.56–3.63 (2H, m), 3.23 (3H, s), 2.96 (2H, t, J=7.1Hz), 2.41 (3H, s), 1.56 (3H, d, J=6.6 Hz).

Step 11. N-{[(2-{4-[6-chloro-2-[1-(methyloxy)ethyl]-5-(trifluoromethyl)-1H-benzimidazol-1-yl]phenyl}ethyl)amino]carbonyl}-4-methylbenzenesulfonamide p-toluenesulfonate The title compound was prepared according to the procedure described in Example 231 from N-{[(2-{4-[6-chloro-2-[1-(methyloxy)ethyl]-5-(trifluoromethyl)-1H-benzimidazol-1-yl]phenyl}ethyl)amino]carbonyl}-4-methylbenzenesulfonamide (step 10)

IR (KBr) v: 2873, 1712, 1517, 1454, 1342, 1122, 1033, 1010 cm$^{-1}$

Example 355

2-{4-[2-ETHYL-5-(1-HYDROXYETHYL)-1H-BENZIMIDAZOL-1-YL]PHENYL}ETHLY(4-METHYLPHENYL)SULFONYLCARBAMATE P-TOLUENESULFONATE

Step 1. 2-{4-[2-ethyl-5-(1-hydroxyethyl)-1H-benzimidazol-1-yl]phenyl}ethyl(4-methylphenyl)sulfonylcarbamate The title compound was prepared according to the procedure described in Example 345 from 2-[4-(5-acetyl-2-ethyl-1H-benzimidazol-1-yl)phenyl]ethyl(4-ethylphenyl)sulfonylcarbamate (Example 332)

MS (ESI) m/z: 508 (MH$^+$), 506 ([M−H]$^-$)

$^1$H-NMR (CDCl$_3$) δ: 7.94 (2H, d, J=8.3 Hz), 7.77 (1H, s), 7.03–7.35 (8H, m), 5.04 (1H, q, J=6.4 Hz), 4.36 (2H, t, J=6.6 Hz), 2.97 (2H, t, J=6.6 Hz), 2.74 (2H, q, J=7.5 Hz), 2.43 (3H, s), 1.56 (3H, d, J=6.4 Hz), 1.28 (3H, t, J=7.5 Hz).

Step 2. 2-{4-[2-ethyl-5-(1-hydroxyethyl)-1H-benzimidazol-1-yl]phenyl}ethyl(4-methylphenyl)sulfonylcarbamate P-toluenesulfonate The title compound was prepared according to the procedure described in Example 231 from 2-{4-[2-ethyl-5-(1-hydroxyethyl)-1H-benzimidazol-1-yl]phenyl}ethyl(4-methylphenyl)sulfonylcarbamate (step 1)

m.p.: 96–110° C.

IR (KBr) v: 1743, 1519, 1456, 1163, 1033, 1010 cm$^{-1}$

Example 356

2-{4-[2-ETHYL4-METHYL-5-(METHYLOXY)-1H-BENZIMIDAZOL-1-YL]PHENYL}ETHLY(4-METHYLPHENYL)SULFONYLCARBAMATE P-TOLUENESULFONATE

Step 1. 2-(4-{[3-methyl4-(methyloxy)-2-nitrophenyl]amino}phenyl)ethanol

The title compound was prepared according to the procedure described in step 3 of Example 1 from 1-chloro-3-methyl4-(methyloxy)-2-nitrobenzene MS (EI) m/z: 302 (M$^+$)

$^1$H-NMR (CDCl$_3$) δ: 7.11–7.20 (3H, m), 6.89–6.96 (3H, m), 6.53 (1H, br.s), 3.83 (5H, br.s), 2.81 (2H, t, J=6.4 Hz), 2.25 (3H, s).

Step 2. 2-(4-{[2-amino-3-methyl-4-(methyloxy)phenyl]amino}phenyl)ethanol

The title compound was prepared according to the procedure described in step 4 of Example 1 from 2-(4-{[3-methyl-4-(methyloxy)-2-nitrophenyl]amino}phenyl)ethanol (step ☐)

MS (EI) m/z: 272 (M$^+$)

$^1$H-NMR (CDCl$_3$) δ: 7.03 (2H, d, J=8.6 Hz), 6.92 (1H, d, J=8.6 Hz), 6.57 (2H, d, J=8.6 Hz), 6.32 (2H, d, J=8.6 Hz), 5.01 (1H, br.s), 3.77–3.90 (7H, m), 2.76 (2H, t, J=6.4 Hz), 2.09 (3H, s).

Step 3. 2-{4-[2-ethyl-4-methyl-5-(methyloxy)-1H-benzimidazol-1-yl]phenyl}ethyl propanoate The title compound was prepared according to the procedure described in step 5 of Example 1 from 2-(4-{[2-amino-3-methyl-4-(methyloxy)phenyl]amino}phenyl)ethanol (step 2).

MS (EI) m/z: 366 (M$^+$)

Step 4. 2-{4-[2-ethyl-4-methyl-5-(methyloxy)-1H-benzimidazol-1-yl]Phenyl}ethanol The title compound was prepared according to the procedure described in step 6 of Example 1 from 2-{4-[2-ethyl-4-methyl-5-(methyloxy)-1H-benzimidazol-1-yl]phenyl}ethyl propanoate (step 3).

$^1$H-NMR (CDCl$_3$) δ:7.42 (2H, d, =8.1Hz), 7.27 (2H, d, J=8.1Hz), 6.84 (2H, s), 3.97 (2H, t, J=6.4 Hz), 3.86 (3H, s), 2.99 (2H, t, J=6.4 Hz), 2.81 (2H, q, J=7.7 Hz), 2.58 (3H, s), 1.26 (3H, t, J=7.7 Hz).

Step 5. 2-{4-[2-ethyl-4-methyl-5-(methyloxy)-1H-benzimidazol-1-yl]phenyl}ethyl(4-methylphenyl)sulfonylcarbamate The title compound was prepared according to the procedure described in Example 3 from 2-{4-[2-ethyl-4-methyl-5-(methyloxy)-1H-benzimidazol-1-yl]phenyl}ethanol (step 4).

MS (ESI) m/z: 508 (MH$^+$), 506 ([M−H]$^-$)

$^1$H-NMR (CDCl$_3$) δ: 7.98 (2H, d, J=8.3 Hz), 7.33 (2H, d, J=8.9 Hz), 6.88–6.91 (6H, m), 4.28 (2H, t, J=6.0 Hz), 3.89 (3H, s), 2.84 (2H, t, J=6.0 Hz), 2.74 (2H, q, J=7.5 Hz), 2.56 (3H, s), 2.43 (3H, s), 1.05 (3H, t, J=7.5 Hz).

Step 6. 2-{4-[2-ethyl-4-methyl-5-(methyloxy)-1H-benzimidazol-1-yl]phenyl}ethyl(4-methylphenyl)sulfonylcarbamate p-toluenesulfonate The title compound was prepared according to the procedure described in Example 231 from 2-{4-[2-ethyl-4-methyl-5-(methyloxy)-1H-benzimidazol-1-yl]phenyl}ethyl(4-methylphenyl)sulfonylcarbamate (step 5)

m.p.: 94–103° C.

IR (KBr) v: 1747, 1458, 1232, 1163, 1120 cm$^{-1}$

Example 357

2-[4-(2-ETHYL-5-PHENYL-1H-BENZIMIDAZOL-1-YL)PHENYL]ETHYL(4-METHYLPHENYL)SULFONYLCARBAMATE

Step 1. 2-{4-[(4-bromo-2-nitrophenyl)amino]phenyl}ethanol

The title compound was prepared according to the procedure described in step 1 of Example 162 from 2,5-dibromonitrobenzene.

$^1$H-NMR (CDCl$_3$) δ: 9.43 (1H, br.s), 8.34 (1H, d, J=2.4 Hz), 7.43–7.39 (1H, m), 7.30 (2H, d, J=8.3 Hz), 7.20 (2H, d, J=8.3 Hz), 7.08 (1H, d, J=9.2 Hz), 3.94–3.88 (2H, m), 2.90 (2H, d, J=6.4 Hz), 1.43 (1H, t, J=5.7 Hz).

Step 2. 2-{4-[(2-amino-4-bromophenyl)amino]phenyl}ethanol

The title compound was prepared according to the procedure described in step 2 of Example 28 from 2-{4-[(4-bromo-2-nitrophenyl)amino]phenyl}ethanol (step 1).

$^1$H-NMR (CDCl$_3$) δ: 7.08 (2H, d, J=8.4 Hz), 6.97–6.93 (2H, m), 6.84 (1H, dd, J=8.3, 2.2 Hz), 6.69 (2H, d, J=8.6 Hz), 5.04 (1H, br.s), 3.80 (2H, br.s), 3.82 (2H, t, J=6.4 Hz), 2.79 (2H, t, J=6.4 Hz).

Step 3. 2-[4-(5-bromo-2-ethyl-1H-benzimidazol -1-yl)phenyl]ethyl propionate

The title compound was prepared according to the procedure described in step 5 of Example 1 from 2-{4-[(2-amino-4-bromophenyl)amino]phenyl}ethanol (step 2).

MS (EI) m/z 401 (M⁺)

Step 4. 2-[4-(5-bromo-2-ethyl-1H-benzimidazol-1-yl)phenyl]ethanol

The title compound was prepared according to the procedure described in step 6 of Example 1 from 2-[4-(5-bromo-2-ethyl-1H-benzimidazol-1-yl)phenyl]ethyl propionate (step 3).

$^1$H-NMR (CDCl$_3$) δ: 7.90 (1H, s), 7.45 (2H, d, J=8.1Hz), 7.26–7.30 (3H, m), 6.96 (1H, d, J=8.4 Hz), 3.98 (2H, m), 3.00 (2H, t, J=6.4 Hz), 2.78 (2H, q, J=7.6 Hz), 1.34 (3H, t, J=7.6 Hz).

Step 5. 2-[4-(2-ethyl-5-phenyl-1H-benzimidazol-1-yl)phenyl]ethanol

To a solution of 2-[4-(5-bromo-2-ethyl-1H-benzimidazol-1-yl)phenyl]ethanol (step 4,116 mg, 0.57 mmol) in 1,2-dimethoxyethane (DME, 6 ml) was added PhB(OH)$_2$ (141 mg, 1.16 mmol), K$_2$CO$_3$ (240 mg, 1.75 mmol) and Pd(PPh$_3$)$_4$ (67 mg, 0.06 mmol). This mixture was stirred at 95° C. for 11 h. The reaction mixture was diluted with water and extracted with CH$_2$Cl$_2$ (4×10 ml). The organic layer was dried (MgSO$_4$) and concentrated to give brown oil. This mixture was purified by SiO$_2$ preparative TLC (hexane/ethyl acetate=1/5) to afford 52 mg (27%) of the title compound.

MS (EI) m/z 342 (M⁺)

$^1$H-NMR (CDCl$_3$) δ: 8.00 (1H, d, J=1.6 Hz), 7.65 (2H, dd, J=1.6, 8.4 Hz), 7.42–7.48 (5H, m), 7.32–7.35 (3H, m), 7.15 (2H,.d, J=8.4 Hz), 4.00 (2H, brt), 3.01 (2H, t, J=6.5 Hz), 2.82 (2H, q, J=7.6 Hz), 1.37 (3H, t, J=7.6 Hz).

Step 6. 2-[4-(2-ethyl-5-phenyl-1H-benzimidazol-1-yl)phenyl]ethyl(4-methylphenyl)sulfonylcarbamate The title compound was prepared according to the procedure described in Example 3 from 2-[4-(2-ethyl-5-phenyl-1H-benzimidazol-1-yl)phenyl]ethanol (step 5).

MS (ESI) m/z 540 [M+H]⁺, 538 [M–H]⁻.

$^1$H-NMR (CDCl$_3$) δ: 8.00 (1H, s), 7.94 (2H, d, J=8.2 Hz), 7.65 (2H, d, J=8.6 Hz), 7.43–7.48 (3H, m), 7.29–7.36 (7H, m), 7.15 (2H, d, J=8.4 Hz), 4.39 (2H, t, J=6.8 Hz), 3.01 (2H, t, J=6.4 Hz), 2.70 (2H, q, J=7.4 Hz), 2.43 (s, 3H), 1.35 (3H, t, J=7.6 Hz).

Example 358

2-{4-[2-ETHYL-5-(5-PYRIMIDINYL)-1H-BENZIMIDAZOL-1-YL]PHENYL}ETHLY(4-METHYLPHENYL)SULFONYLCARBAMATE

Step 1. 2-{4-[2-ethyl-5-(4.4.5.5-tetramethyl-1.3,2-dioxaborolan-2-yl)-1H-benzimidazol-1-yl]pheny}ethanol To a solution of 2-[4-(5-bromo-2-ethyl-1H-benzimidazol-1-yl)phenyl]ethanol (Example 357 step 4, 2.5 g, 7.24 mmol) and bis(pinacolato)diboron (1.84 g, 7.24 mmol) in DMSO was added KOAc (2.13 g, 21.7 mmol), 1,1'-Bis(diphenylphosphino)ferrocene (241 mg, 0.43 mmol) and Pd(dppf)Cl$_2$CH$_2$Cl$_2$ (362 mg, 0.44 mmol). This mixture was stirred at 80° C. for 7 h. The reaction mixture was diluted with water and extracted with ethyl acetate (3×80 ml). The organic layer was washed with brine, dried (MgSO$_4$) and concentrated to give black oil. This mixture was purified by neutral SiO$_2$ chromatography eluting with hexane/ethyl acetate (1:4) to afford 1.38 g (35%) of the title compound as pink solids.

MS (EI) m/z 391 [M–H]⁺

$^1$H-NMR (CDCl$_3$) δ: 8.25 (1H, s), 7.64 (2H, dd, J=0.8, 8.1Hz), 7.45 (2H, d, J=8.4 Hz), 7.30 (2H, d, J=8.4 Hz), 7.08 (1H, d, J=8.1Hz), 3.99 (2H, t, J=6.5 Hz), 3.00 (2H, t, J=6.5 Hz), 2.81 (2H, q, J=7.6 Hz), 1.36 (12H, s), 1.32 (3H, t, J=7.8 Hz).

Step 2. 2-{4-[2-ethyl-5-(5-pyrimidinyl)-1H-benzimidazol-1-yl]phenyl}ethanol

To a solution of 2-{4-[2-ethyl-5-(4,4,5,5-tetramethyl-1,3,2-dioxaborolan-2-yl)-1H-benzimidazol-1-yl]phenyl}ethanol (step 1, 100 mg, 0.26 mmol) and 5-bromopyrimidine (45 mg, 0.28 mmol) in 1,2-dimethoxyethane (3.5 ml) was added sat. NaHCO$_3$ aq. (1.2 ml) and Pd(PPh$_3$)$_4$ (60 mg, 0.05 mmol). This mixture was stirred at 70° C. for 17 h. The reaction mixture was diluted with water and extracted with CH$_2$Cl$_2$ (3×10 ml). The organic layer was dried (MgSO$_4$) and concentrated to give light brown oil. This mixture was purified by SiO$_2$ preparative TLC (CH$_2$Cl$_2$/methanol=10/1) to afford 45 mg (50%) of the title compound.

MS (EI) m/z 344 (M⁺)

$^1$H-NMR (CDCl$_3$) δ: 9.19 (1H, s), 9.00(2H, s), 7.99 (1H, s), 7.49 (2H, d, J=8.2 Hz), 7.31–7.42 (3H, m), 7.23 (1H, d, J=8.4 Hz), 4.00 (2H, q, J=6.1 Hz), 3.02 (2H, t, J=6.4 Hz), 2.83 (2H, q, J=7.6 Hz), 1.39 (3H, t, J=7.6 Hz).

Step 3. 2-{4-[2-ethyl-5-(5-pyrimidinyl)-1H-benzimidazol-1-yl]phenyl}ethyl(4-methylphenyl)sulfonylcarbamate The title compound was prepared according to the procedure described in Example 3 from 2-{4-[2-ethyl-5-(5-pyrimidinyl)-1H-benzimidazol-1-yl]phenyl}ethanol (step 2)

MS (ESI) m/z 542 [M+H]⁺, 540 [M–H]³¹.

$^1$H-NMR (CDCl$_3$) δ: 9.20 (1H, s), 8.97 (2H, s), 7.30–7.42 (4H, m), 7.24 (2H, d, J=8.2 Hz), 7.14 (2H, d, J=8.2 Hz), 4.41 (2H, t, J=6.4 Hz), 3.03 (2H, t, J=6.1 Hz), 2.89 (2H, q, J=7.4 Hz), 2.43 (3H, s), 1.34 (3H, t, J=7.4 Hz).

Example 359

2{4-[2-ETHYL-5-(4-PYRIDINYL)-1H-BENZIMIDAZOL-1-YL]PHENYL}ETHLY(4-METHYLPHENYL)SULFONYLCARBAMATE

Step 1. 2-{4-[2-ethyl-5-(4-pyridinyl)-1H-benzimidazol-1-yl]phenyl}ethanol

The title compound was prepared according to the procedure described in step 1 of Example 358 from 4-bromopyrimidine hydrochloride (step 2).

MS (EI) m/z 343 (M)⁺.

$^1$H-NMR (CDCl$_3$) δ: 8.66 (2H, d, J=6.1Hz), 8.07 (1H, d, J=1.2 Hz), 7.57 (2H, d, J=6.1 Hz), 7.45–7.52 (3H, m), 7.34 (2H, d, J=8.4 Hz), 7.20 (1H, d, J=8.4 Hz), 4.00 (2H, br.s), 3.03 (2H, t, J=6.6 Hz), 2.83 (2H, q, J=7.4 Hz), 1.39 (3H, t, J=7.4 Hz).

Step 2. 2-{4-[2-ethyl-5-(4-Pyridinyl)-1H-benzimidazol-1-yl]phenyl}ethyl(4-methylphenyl)sulfonylcarbamate The title compound was prepared according to the procedure described in Example 3 from 2-{4-[2-ethyl-5-(4-pyridinyl)-1H-benzimidazol-1-yl]phenyl}ethanol (step 1).

MS (ESI) m/z 541 [M+H]⁺, 539 [M–H]⁻.

$^1$H-NMR (CDCl$_3$) δ: 8.52 (2H, d, J=5.8 Hz), 8.00 (1H, s), 7.94 (2H, d, J=8.1Hz), 7.48 (2H, d, J=5.8 Hz), 7.23–7.40 (5H, m), 7.20 (2H, d, J=8.1Hz), 7.00 (2H, d, J=8.2 Hz), 4.41 (2H, t, J=5.8 Hz), 3.02 (2H, t, J=5.8 Hz), 2.76 (2H, q, J=7.4 Hz), 2.39 (3H, s), 1.32 (3H, t, J=7.4 Hz).

Example 360

2-{4-[2-ETHYL-5-(3-PYRIDINYL)-1H-BENZIMIDAZOL-1-YL]PHENYL}ETHLY(4-METHYLPHENYL)SULFONYLCARBAMATE

Step 1. 2-{4-[2-ethyl-5-(3-pyridinyl)-1H-benzimidazol-1-yl]phenyl}ethanol

The title compound was prepared according to the procedure described in step 1 of Example 358 from 3-bromopyridine.

MS (EI) m/z 343 (M)⁺.

$^1$H-NMR (CDCl$_3$) δ: 8.91 (1H, d, J=1.8 Hz), 8.55–8.61 (1H, m), 8.00 (1H, s), 7.90–7.97 (1H, m), 7.48 (2H, d, J=8.2 Hz), 7.42 (1H, d, J=8.7 Hz), 7.35 (2H, d, J=8.2 Hz), 7.21 (1H, d, J=8.4 Hz), 4.00 (2H, m), 3.02 (2H, t, J=6.5 Hz), 2.83 (2H, q, J=7.6 Hz), 1.92 (1H, s), 1.39 (3H, t, J=7.6 Hz).

Step 2. 2-{4-[2-ethyl-5-(3-pyridinyl)-1H-benzimidazol-1-yl]phenyl}ethyl(4-methylphenyl)sulfonylcarbamate The title compound was prepared according to the procedure described in Example 3 from 2-{4-[2-ethyl-5-(3-pyridinyl)-1H-benzimidazol -1-yl]phenyl}ethanol (step 1).

MS (ESI) m/z 541 [M+H]⁺, 539 [M−H]⁻.

¹H-NMR (CDCl₃) δ: 8.76 (1H, s), 8.63 (1H, m), 7.87–8.01 (4H, m), 7.22–7.50 (6H, m), 7.23–7.40 (5H, m), 7.16 (2H, d, J=8.2 Hz), 7.00 (1H, d, J=8.2 Hz), 4.42 (2H, br.s), 3.01 (2H, br.s), 2.74 (2H, q, J=7.4 Hz), 2.43 (3H, s), 1.31 (3H, t, J=7.4 Hz).

Example 361

2-{4-[2-ETHYL-5-(2-PYRIDINYL)-1H-BENZIMIDAZOL-1-YL]PHENYL}ETHLY(4-METHYLPHENYL)SULFONYLCARBAMATE

Step 1. 2-{4-[2-ethyl-5-(2-pyridinyl)-1H-benzimidazol-1-yl]phenyl}ethanol

The title compound was prepared according to the procedure described in step 1 of Example 358 from 2-bromopyridine.

MS (EI) m/z 343 (M)⁺. ¹H-NMR (CDCl₃) δ: 8.70 (1H, dd, J=1.5, 5.3 Hz), 8.32 (1H, d, J=1.5 Hz), 8.00 (1H, dd, J=1.5, 8.4 Hz), 7.76–7.80 (2H, m), 7.48 (2H, d, J=8.2 Hz), 7.35 (2H, d, J=8.2 Hz), 7.16–7.23 (2H, m), 3.93–4.05 (2H, m), 3.01 (2H, t, J=6.6 Hz), 2.83 (2H, q, J=7.6 Hz), 1.91 (1H, s), 1.38 (3H, t, J=7.6 Hz).

Step 2. 2-{4-[2-ethyl-5-(2-pyridinyl)-1H-benzimidazol-1-yl]phenyl}ethyl(4-methylphenyl)sulfonylcarbamate The title compound was prepared according to the procedure described in Example 3 from 2-{4-[2-ethyl-5-(2-pyridinyl)-1H-benzimidazol-1-yl]phenyl}ethanol (step 1).

MS (ESI) m/z 541 [M+H]⁺, 539 [M−H]⁻.

¹H-NMR (CDCl₃) δ: 8.68 (1H, d, J=4.6 Hz), 8.31 (1H, s), 7.88–7.98 (3H, m), 7.73–7.82 (2H, m), 7.17–7.26 (5H, m), 7.07–7.17 (3H, m), 4.29 (2H, t, J=6.3 Hz), 2.90 (2H, t, J=6.4 Hz), 2.73 (2H, q, J=7.6 Hz), 2.36 (3H, s), 1.28 (3H, t, J=7.6 Hz).

Example 362

2-{4-[2-ETHYL-5-(4-PYRIDINYL)-1H-BENZIMIDAZOL-1-YL]PHENYL}ETHLY(4-METHYLPHENYL)SULFONYLCARBAMATE

Step 1. 2-{4-[2-ethyl-5-(1-methyl-1H-pyrazol-4-yl)-1H-benzimidazol-1-yl]phenyl}ethanol The title compound was prepared according to the procedure described in step 1 of Example 358 from 4-bromo-1-methyl-1H-pyrazole (Huettel et al., *Liebigs Ann. Chem.*, 1955, 593, 179).

MS (EI) m/z 343 (M⁺)

¹H-NMR (CDCl₃) δ: 7.86 (1H, s), 7.78 (1H, s), 7.46 (2H, d, J=8.4 Hz), 7.28–7.35 (3H, m), 7.09 (2H, d, J=8.2 Hz), 3.99 (2H, m), 3.01 (2H, t, J=6.4 Hz), 2.81 (2H, q, J=7.6 Hz), 1.36 (3H, t, J=7.6 Hz).

Step 2. 2-{4-[2-ethyl-5-(1-methyl-1H-pyrazol -4-yl)-1H-benzimidazol-1-yl]phenyl}ethyl(4-methylphenyl)sulfonylcarbamate The title compound was prepared according to the procedure described in Example 3 from 2-{4-[2-ethyl-5-(1-methyl-1H-pyrazol-4-yl)-1H-benzimidazol-1-]phenyl}ethanol (step 1).

MS(ESI) m/z 544 [M+H]⁺, 542 [M−H]⁻.

¹H-NMR (CDCl₃) δ: 7.95 (1H, s), 7.92 (1H, s); 7.86 (4H, m), 7.77 (1H, s), 7.62 (1H, s), 7.24–7.40 (7H, m), 7.06 (21H, d, J=7.7 Hz), 4.39 (2H, t, J=6.0 Hz), 3.97 (3H, s), 3.02 (2H, q, J=6.3 Hz), 2.78 (2H, q, J=7.4 Hz), 2.44 (3H. s), 1.35 (3H, t, J=7.4 Hz).

Example 363

2-{4-[6-CHLORO-2-[3-OXO-3-(1-PYRROLIDINYL)PROPYL]-5-(TRIFLUOROMETHYL)-1H-BENZIMIDAZOL-1-YL]PHENYL}ETHLY(4-METHYLPHENYL)SULFONYLCARBAMATE

The title compound was prepared according to the procedure described in Example 339 from 2-(4-{[2-amino-5-chloro-4-(trifluoromethyl)phenyl]amino}phenyl)ethyl acetate (Example 339, step 2) and 4-oxo-4-(1-pyrrolidinyl) butanoic acid (McCasland; Proskow, *J. Org. Chem.*, 1957, 22,122.).

m.p.: 98–105° C.

IR (KBr) v: 2875, 1747, 1624, 1517, 1400, 1346, 1130, 1085 cm⁻¹

MS (ESI) m/z: 663 (MH⁺), 661 ([M−H]⁻)

¹H-NMR (CDCl₃) δ: 8.08 (1H, s), 7.92 (2H, d, J=8.2 Hz), 7.22–7.36 (7H, m), 4.38 (2H, t, J=6.6 Hz), 3.49 (2H, t, J=6.8 Hz), 3.43 (2H, t, J=6.8 Hz), 2.97–3.07 (4H, m), 2.88 (2H, m), 2.44 (3H, s), 1.94–1.98 (2H, m), 1.82–1.86 (2H, m).

Example 364

2-{4-[6-CHLORO-2-[3-OXO-3-(1-PIPERIDINYL)PROPYL]-5-(TRIFLUOROMETHYL)-1H-BENZIMIDAZOL-1-YL]PHENYL}ETHLY(4-METHYLPHENYL)SULFONYLCARBAMATE

The title compound was prepared according to the procedure described in Example 339 from 2-(4-{[2-amino-5-chloro-4-(trifluoromethyl)phenyl]amino}phenyl)ethyl acetate (Example 339, step 2) and 4-oxo-4-(1-piperidinyl) butanoic acid (Becker, Frederick F.; Banik, Bimal K., *Bioorg. Med. Chem. Lett.*, 1998, 20, 2877).

m.p.: 210° C.

IR (KBr) v: 1753, 1649, 1515, 1433, 1406, 1366, 1161, 1118, 1091 cm⁻¹

MS (ESI) m/z: 677 (MH⁺), 675 ([M−H]⁻)

¹H-NMR (CDCl₃) δ: 8.14 (1H, s), 7.78 (2H, d, J=8.4 Hz), 7.47–7.56 (4H, m), 7.42 (2H, d, J=8.4 Hz), 7.31 (1H, s), 4.29 (2H, t, J=6.6 Hz), 3.37–3.40 (4H, m), 2.92–2.99 (6H, m), 2.36 (3H, s), 1.50–1.56 (4H, m), 1.35–1.36 (2H, m).

Example 365

2-{4-[6-CHLORO-2-[3-(2-OXO -1-PYRROLIDINYL)PROPYL]-5-(TRIFLUOROMETHYL)-1H-BENZIMIDAZOL-1-YL]PHENYL}ETHLY(4-METHYLPHENYL)SULFONYLCARBAMATE

The title compound was prepared according to the procedure described in Example 339 from 2-(4-{[2-amino-5-chloro-4-(trifluoromethyl)phenyl]amino}phenyl)ethyl acetate (Example 339, step 2) and 4-(2-oxo-1-pyrrolidinyl) butanoic acid (Miyano, Seiji; Fujii, Shinichiro; Yamashita, Osamu; Toraishi, Naoko; Sumoto, Kunihiro, *J. Heterocycl. Chem.*, 1982, 19, 1465).

m.p.: 85–90° C.

IR (KBr) v: 1745, 1624, 1517, 1433, 1348, 1299, 1161, 1130, 1085 cm⁻¹

MS (ESI) m/z: 663 (MH⁺), 661 ([M−H]⁻)

¹H-NMR (CDCl₃) δ: 8.09 (1H, s), 7.91 (2H, d, J=8.5 Hz), 7.19–7.33 (7H, m), 4.42 (2H, t, J=6.0 Hz), 3.38 (2H, t, J=7.0 Hz), 3.27 (2H, t, J=7.0 Hz), 3.00 (2H, t, J=6.0 Hz), 2.70–2.75 (2H, m), 2.42 (3H, s), 2.37–2.40 (2H, m), 1.93–2.04 (4H, m).

Example 366

2-{4-[6-CHLORO-2-[3-(2-OXO-1-PIPERIDINYL)PROPYL]-5-(TRIFLUOROMETHYL)-1H-BENZIMIDAZOL-1-YL]PHENYL}ETHLY(4-METHYLPHENYL)SULFONYLCARBAMATE

The title compound was prepared according to the procedure described in Example 339 from 2-(4-{[2-amino-5-chloro-4-(trifluoromethyl)phenyl]amino}phenyl)ethyl acetate (Example 339, step 2) and 4-(2-oxo-1-piperidinyl) butanoic acid (Miyano, Seiji; Fujii, Shinichiro; Yamashita, Osamu; Toraishi, Naoko; Sumoto, Kunihiro, *J. Heterocycl. Chem.*, 1982, 19, 1465).

m.p.: 98–105° C.

IR (KBr) v: 1745, 1618, 1433, 1348, 1301, 1230, 1161, 1130, 1085 cm$^{-1}$

MS (ESI) m/z: 677 (MH$^+$), 675 ([M-H]$^-$)

$^1$H-NMR (CDCl$_3$) δ: 8.08 (1H, s), 7.89 (2H, d, J=8.0 Hz), 7.16–7.29 (7H, m), 4.40 (2H, t, J=5.9 Hz), 3.35 (2H, t, J=7.2 Hz), 3.25–3.27 (2H, m), 2.98 (2H, t, J=5.9 Hz), 2.73 (2H, t, J=7.2 Hz), 2.35–2.40 (5H, m), 1.92–1.99 (2H, m), 1.73–1.76 (4H, m).

Example 367

N-{[(2-{4-[6-CHLORO-2-(1-HYDROXYETHYL)-5-(TRIFLUOROMETHYL)-1H-BENZIMIDAZOL-1-YL]PHENYL}ETHYL)AMINO]CARBONYL}-4-METHYLBENZENESULFONAMIDE

Step 1. 1-[6-chloro-1-[4-(2-chloroethyl)phenyl]-5-(trifluoromethyl)-1H-benzimidazol-2-yl]ethanol The title compound was prepared according to the procedure described in Example 339, step 3 & Example 1, step 5 from 4-chloro-N$^2$-[4-(2-chloroethyl)phenyl]-5-(trifluoromethyl)-1,2-benzenediamine and lactic acid.

$^1$H-NMR (CDCl$_3$) δ: 8.14 (1H, s), 7.49 (2H, d, J=8.2 Hz), 7.37 (2H, d, J=8.2 Hz), 4.90–4.96(1H, m), 3.83 (2H, t, J=6.8 Hz), 3.75 (1H, d, H=8.1Hz), 3.22 (2H, t, J=6.8 Hz), 1.57 (3H, d, J=6.9 Hz).

Step 2. N-{[(2-{4-[6-chloro-2-(1-hydroxyethyl)-5-(trifluoromethyl)-1H-benzimidazol-1-yl]phenyl}ethyl)amino]carbonyl}-4-methylbenzenesulfonamide The title compound was prepared according to the procedure described in Example 1 from 1-[6-chloro-1-[4-(2-chloroethyl)phenyl]-5-(trifluoromethyl)-1H-benzimidazol-2-yl]ethanol (step 1).

m.p.: 220 C.

IR (KBr) v: 3348, 1706, 1533, 1519, 1434, 1344, 1328, 1126 cm$^{-1}$

MS (ESI) m/z: 581 (MH$^+$), 579 ([M-H]$^-$)

$^1$H-NMR (CDCl$_3$) δ: 8.23 (1H, s), 7.78 (2H, d, J=8.1Hz), 7.32–7.50 (7H, m), 6.58 (1H, br.s), 5.66 (1H, br.s), 4.78 (1H, br.s), 3.30–3.32 (2H, m), 2.79–2.82 (2H, m), 2.34 (3H, s), 1.51 (3H, d, J=6.8 Hz).

Example 368

N-{[(2-{4-[2-ACETYL-6-CHLORO-5-(TRIFLUOROMETHYL)-1H-BENZIMIDAZOL-1-YL]PHENYL}ETHYL)AMINO]CARBONYL}-4-METHYLBENZENESULFONAMIDE

Step 1. 1-[6-chloro-1-[4-(2-chloroethyl)phenyl-5-(trifluoromethyl)-1H-benzimidazol-2yl]ethanone A solution of 1-[6-chloro-1-[4-(2-chloroethyl)phenyl]-5-(trifluoromethyl)-1H-benzimidazol-2-yl]ethanol (Example 367, step 1, 400 mg, 1 mmol) in CH$_2$Cl$_2$ was added MnO2 (2.7 g, 32 mmol) . The mixture was stirred at room temperature for 24 h. This was directly purified by flash column chromatography eluting with hexane/ethyl acetate (4:1) to afford 350 mg (88%) of the title compound as white solids.

H-NMR (CDCl$_3$) δ: 8.31 (1H, s), 7.44 (2H, d, J=8.1 Hz), 7.23–7.28 (3H, m), 3.82 (2H, t, J=7.3 Hz), 3.21 (2H, t, J=7.3 Hz), 2.80 (3H, s).

Step 2. N-{[(2-{4-[2-acetyl-6-chloro-5-(trifluoromethyl)-1H-benzimidazol -1-yl]phenyl}ethyl)amino]carbonyl}-4-methylbenzenesulfonamide The title compound was prepared according to the procedure described in Example 1 from 1-[6-chloro-1-[4-(2-chloroethyl)phenyl]-5-(trifluoromethyl)-1H-benzimidazol-2-yl]ethanone (step 1)

m.p.: 225° C.

IR (KBr) v: 3350, 1697, 1519, 1326, 1294, 1134, 1083 cm$^{-1}$

MS (ESI) m/z: 579 (MH$^+$), 577 ([M-H]$^-$)

$^1$H-NMR (CDCl$_3$) δ: 8.31 (1H, s), 7.74 (2H, d, J=8.4 Hz), 7.21–7.39 (7H, m), 6.70 (1H, br.s), 3.55–3.62 (2H, m), 2.94 (2H, t, J=7.2 Hz), 2.81 (3H, s), 2.40 (3H, s).

Example 369

N-{[(2-{4-[6-CHLORO-2-(1-HYDROXY-1-METHYLETHYL)-5-(TRIFLUOROMETHYL)-1H-BENZIMIDAZOL-1-YL]PHENYL}ETHYL)AMINO]CARBONYL}-4-METHYLBENZENESULFONAMIDE

Step 1. 2-[6-chloro-1-[4-(2-chloroethyl)phenyl]-5-(trifluoromethyl)-1H-benzimidaz-2-yl]-2-propanol The title compound was prepared according to the procedure described in Example 339, step 3 & Example 1, step 5 from 2-hydroxyisobutyric acid and 4-chloro-N$^2$-[4-(2-chloroethyl)phenyl]-5-(trifluoromethyl)-1,2-benzenediamine.

H-NMR (CDCl$_3$) δ: 8.13 (1H, s), 7.46 (2H, d, J=8.2 Hz), 7.34 (2H, d, J=8.2 Hz), 7.34 (2H, d, J=8.2 Hz) 7.00 (1H, s). 3.84 (2H, t, J=7.0 Hz), 3.38 (1H, s), 3.22 (2H, f, J=7.00 Hz), 1.53 (6H, s).

Step 2. N-{[(2-{4-[6-chloro-2-(1-hydroxy-1-methylethyl)-5-(trifluoromethyl)-1H-benzimidazol -1-yl]phenyl}ethyl)amino]carbonyl}-4-methylbenzenesulfonamide The title compound was prepared according to the procedure described in Example 1 from 2-[6-chloro-1-[4-(2-chloroethyl)phenyl]-5-(trifluoromethyl)-1H-benzimidazol-2-yl]-2-propanol (step 1).

H-NMR (CDCl$_3$) δ: 8.13 (1H, s), 7.73 (2H, d, J=8.2 Hz), 7.30–7.39 (6H, m), 6.99 (1H, s), 6.68 (1H, br.s), 3.55–3.66 (2H, m), 2.95 (2H, t, J=6.6 Hz), 2.42 (3H, s), 1.13 (6H, d, J=6.2 Hz).

Example 370

N-{[(2-{4-[6-CHLORO-2-(1-HYDROXY-1-METHYLETHYL)-5-(TRIFLUOROMETHYL)-1H-BENZIMIDAZOL-1-YL]PHENYL}ETHYL)AMINO]CARBONYL}-4-METHYLBENZENESULFONAMIDE MONO P-TOLUENESULFONATE

The title compound was prepared according to the procedure described in Example 231 from N-{[(2-{4-[6-chloro-2-(1-hydroxy-1-methylethyl)-5-(trifluoromethyl)-1H-benzimidazol-1-yl]phenyl}ethyl)amino]carbonyl}-4-methylbenzenesulfonamide (Example 369).

m.p.: 146–150° C.

IR (KBr) v: 1685, 1515, 1448, 1340, 1124, 1089, 1010 cm$^{-1}$

Example 371

N-{1-[6-CHLORO-1-(4-{2-[({[(4-METHYLPHENYL)SULFONYL]AMINO CARBONYL)AMINO]ETHYL}PHENYL)-5-(TRIFLUOROMETHYL)-1H-BENZIMIDAZOL-2-YL]ETHYL}ACETAMIDE

Step 1. 1,1-dimethylethyl1-[6-chloro-1-[4-(2-hydroxyethyl)phenyl]-5-(trifluoromethyl)-1H-benzimidazol-2-yl]ethylcarbamate The title compound was prepared according to the procedure described in Example 339, step 3 & Example 1, step 5 from N-(tert-butoxycarbonyl)-alanine and 2-(4-{[2-amino-5-chloro-4-(trifluoromethyl)phenyl]amino}phenyl)ethyl acetate (Example 339, step 2).

MS (EI) m/z: 483 (M$^+$)

$^1$H-NMR (CDCl$_3$) δ: 8.12 (1H, s), 7.50 (2H, d, J=8.6 Hz), 7.35–7.37 (2H, m), 7.24 (1H, s), 5.46 (1H, br.s), 4.92–4.98 (1H, m), 3.95–4.02 (2H, m), 3.00 (2H, t, J=6.5 Hz), 1.43 (3H, s), 1.40 (9H, s).

Step 2. 1,1-dimethylethyl 1-[6-chloro-1-(4-{2-[({[(4-methylphenyl)sulfonyl]amino}carbonyl)amino]

ethyl}phenyl)-5-(trifluoromethyl)-1H-benzimidazol-2-yl] ethylcarbamate

The title compound was prepared according to the procedure described in Example 1 from 1,1-dimethylethyl 1-[6-chloro-1-[4-(2-hydroxyethyl)phenyl]-5-(trifluoromethyl)-1H-benzimidazol-2-yl]ethylcarbamate (step 1)

$^1$H-NMR (CDCl$_3$) δ: 8.13 (1H, s), 7.79 (2H, d, J=8.2 Hz), 7.15–7.35 (7H, m), 6.50 (1H, br.s), 5.55 (1H, d, J=8.6 Hz), 4.88–4.93 (1H, m), 3.46–3.52 (2H, m), 2.87–2.96 (2H m), 2.41 (3H, s), 1.40 (12H, s).

Step 3. N-{[(2-{4-[2-(1-aminoethyl)-6-chloro-5-(trifluoromethyl)-1H-benzimidazol -1-yl]phenyl}ethyl) amino]carbonyl}-4-methylbenzenesulfonamide A solution of 1,1-dimethylethyl1-[6-chloro-1-(4-{2-[({[(4-methylphenyl)sulfonyl]amino}carbonyl)amino] ethyl}phenyl)-5-(trifluoromethyl)-1H-benzimidazol-2-yl] ethylcarbamate (step 2, 190 mg, 0.28 mmol) in CH$_2$Cl$_2$ (2 ml) was added trifluoroacetic acid (1 ml) and stirred at room temperature for 2 h. The mixture was added water (10 ml) and extracted with CH$_2$Cl$_2$ (20 ml). The organic layer was washed with brine (10 ml), then dried (Na$_2$SO$_4$). After removal of solvent, the crude product was purified by flash column chromatography eluting with CH$_2$Cl$_2$/MeOH (10:1/5:1) to afford 160 mg (99%) of the title compound as white solids.

MS (ESI) m/z: 580 (MH$^+$), 578 ([M–H]$^-$)

Step 4. N-{1-[6-chloro-1-(4-{2-[({[(4-methylphenyl) sulfonyl]amino}carbonyl)amino]ethyl}phenyl)-5-(trifluoromethyl)-1H-benzimidazol-2-yl[ethyl}acetamide A mixture of N-{[(2-{4-[2-(1-aminoethyl)-6-chloro-5-(trifluoromethyl) -1-benzimidazol-1-yl]phenyl}ethyl) amino]carbonyl}-4-methylbenzenesulfonamide (step 3, 100 mg, 0.17 mmol) in CH$_2$Cl$_2$ (12 ml) was added acetyl chloride (0.01 ml, 0.18 mmol) and stirred at room temperature for 5 h. The mixture was added water (10 ml) and extracted with CH$_2$Cl$_2$ (20 ml). The organic layer was washed with brine (10 ml), then dried (Na2SO4). After removal of solvent, the crude product was purified by flash column chromatography eluting with CH$_2$Cl$_2$/MeOH (10:1) to afford 59 mg (53%) of the title compound as white solids.

MS (ESI) m/z: 622 (MH$^+$), 620 ([M–H]$^-$)

$^1$H-NMR (CDCl$_3$) δ: 8.14 (1H, s), 7.80 (2H, d, J=8.2 Hz), 7.25–7.40 (7H, m), 7.00 (1H, br.s), 6.03 (1H, br.s), 5.15–5.20 (1H, m), 3.43–3.68 (2H, m), 2.88–2.98 (2H, m), 2.39 (3H, s), 1.96 (3H, s), 1.51 (3H, d, J=6.9 Hz).

Example 372
N-{1-[6-CHLORO-1-(4-{2-[({[(4-METHYLPHENYL) SULFONYL]AMINO}CARBONYL)AMINO] ETHYL}PHENYL)-5-(TRIFLUOROMETHYL)-1H-BENZIMIDAZOL-2-YL]ETHYL}ACETAMIDE MONO P-TOLUENESULFONATE The title compound was prepared according to the procedure described in Example 231 from N-{1-[6-chloro-1-(4-{2-[({[(4-methylphenyl)sulfonyl]amino}carbonyl) amino]ethyl}phenyl)-5-(trifluoromethyl)-1H-benzimidazol-2-yl]ethyl}acetamide (Example 371).

m.p.: 135–142° C.

IR (KBr) v: 3267, 1676, 1517, 1456, 1236,1163, 1122, 1010 cm$^{-1}$

Example 373
2-{4-[2-ETHYL-5-(PHENYLCARBONYL])-1H-BENZIMIDAZOL-1-YL]PHENYL}ETHLY(4-METHYLPHENYL)SULFONYLCARBAMATE Step 1. (3-amino-4-{[4-(2-hydroxyethyl)phenyl] amino}phenyl)(phenyl)methanone The title compound was prepared according to the procedure described in Example 78 from (4-chloro-3-nitrophenyl)(phenyl)methanone.

$^1$H-NMR (CDCl$_3$) δ: 7.77 (2H, d, J=6.9 Hz), 7.42–7.55 (3H, m), 7.36 (1H, s), 7.14–7.25 (4H, m), 6.97 (2H, d, J=8.5 Hz), 5.64 (1H, s), 3.83–3.89 (2H, m), 3.64 (2H, br.s), 2.84 (2H, t, J=6.6 Hz), 1.47 (1H, br.s).

Step 2. {2-ethyl-1-[4-(2-hydroxyethyl)phenyl]-1H-benzimidazol-5-yl}(phenyl)methanone The title compound was prepared according to the procedure described in Example 1 from (3-amino-4-{[4-(2-hydroxyethyl)phenyl]amino}phenyl)(phenyl)methanone (step 1).

$^1$H-NMR (CDCl$_3$) δ: 8.21 (1H, s), 7.80–7.84 (3H, m), 7.44–7.57 (5H, m), 7.27–7.34 (2H, m), 7.18 (1H, d, J=8.4 Hz), 3.98–4.03 (2H, m), 3.02 (2H, t, =6.3 Hz), 2.81 (2H, q, J=7.6 Hz), 1.89 (1H, t, J=5.4 Hz), 1.37 (3H, t, J=7.6 Hz).

Step 3. 2-{4-[2-ethyl-5-(phenylcarbonyl)-1H-benzimidazol-1-yl]phenyl}ethyl(4-methylphenyl)sulfonylcarbamate The title compound was prepared according to the procedure described in Example 3 from {2-ethyl-1-[4-(2-hydroxyethyl)phenyl]-1H-benzimidazol-5-yl}(phenyl) methanone (step 2).

MS (ESI) m/z: 568 (MH$^+$), 566 ([M–H]$^-$)

$^1$H-NMR (CDCl$_3$) δ: 8.21 (1H, s), 7.92 (2H, d, J=8.4 Hz), 7.79–7.84 (3H, m), 7.44–7.58 (3H, m), 7.23–7.36 (6H, m), 7.15 (1H, d, J=8.6 Hz), 4.37 (2H, t, J=6.6 Hz), 3.01 (2H, t, J=6.6 Hz), 2.79 (2H, q, J=7.6 Hz), 2.42 (3H, s), 1.34 (3H, t, J=7.6 Hz).

Example 374
2-{4-[2-ETHYL-5-(PHENYLCARBONYL)-1H-BENZIMIDAZOL-1-YL]PHENYL}ETHYL (4-METHYLPHENYL)SULFONYLCARBAMATE MONO P-TOLUENESULFONATE The title compound was prepared according to the procedure described in Example 231 from 2-{4-[2-ethyl-5-(phenylcarbonyl)-1H-benzimidazol-1-yl]phenyl}ethyl(4-methylphenyl)sulfonylcarbamate (Example 373).

m.p.: 102–107° C.

IR (KBr) v: 1747, 1654, 1517, 1448, 1033, 1008 cm$^{-1}$

Example 375
N-{[(2-{4-[2-ETHYL-5-(PHENYLCARBONYL)-1H-BENZIMIDAZOL-1-YL]PHENYL}ETHYL)AMINO] CARBONYL]-4-METHYLBENZENESULFONAMIDE Step 1. N-{[(2-{4-[2-ethyl-5-(phenylcarbonyl)-1H-benzimidazol -1-yl]phenyl}ethyl)amino]carbonyl}-4-methylbenzenesulfonamide The title compound was prepared according to the procedure described in Example 78 from {2-ethyl-1-[4-(2-hydroxyethyl)phenyl]-1H-benzimidazol-5-yl}(phenyl) methanone (Example 373, step 2).

MS (ESI) m/z: 567 (MH$^+$), 565 ([M–H]$^-$)

$^1$H-NMR (CDCl$_3$) δ: 8.20 (1H, s), 7.72–7.83 (5H, m), 7.28–7.60 (9H, m), 7.15 (1H, d, J=8.6 Hz), 6.74 (1H, br.s), 3.59 (2H, m), 2.94 (2H, t, J=7.1Hz), 2.82 (2H, q, J=7.4 Hz) 2.39 (3H, s), 1.35 (3H, t, J=7.4 Hz).

Example 376
N-{[(2-{4-[2-ETHYL-5-(PHENYLCARBONYL)-1H-BENZIMIDAZOL-1-YL]PHENYL}ETHYL)AMINO] CARBONYL}-4-METHYLBENZENESULFONAMIDE MONO P-TOLUENESULFONATE The title compound was prepared according to the procedure described in Example 231 from N-{[(2-{4-[2-ethyl-5-(phenylcarbonyl)-1H-benzimidazol-1-yl]phenyl}ethyl) amino]carbonyl}-4-methylbenzenesulfonamide (Example 375).

m.p.: 198° C.

IR (KBr) v: 1697, 1660, 1596, 1519, 1446, 1319, 1035 cm$^{-1}$

Example 377
2-{4-[2-[1-(ACETYLAMINO)-1-METHYLETHYL]-6-CHLORO-5-(TRIFLUOROMETHYL)-1H-BENZIMIDAZOL-1-YL]PHENYL}ETHYL(4-METHYLPHENYL)SULFONYLCARBAMATE Step 1. 2-{4-[6-chloro-2-(1-chloro-1-methylethyl)-5-(trifluoromethyl)-1H-benzimidazol-1-yl]phenyl}ethyl acetate To a solution of 2-{4-[6-chloro-2-(1-hydroxy-1-methylethyl)-5-(trifluoromethyl)-1H-benzimidazol-1-yl]phenyl}ethyl acetate (300 mg, 0.68 mmol) in dichloromethane (15 ml) was added thionyl chloride (0.07 ml, 1.02 mmol) and the reaction mixture was refluxed overnight. The reaction mixture was poured into water (10 ml) and the mixture was extracted with dichloromethane (30 ml). The organic layer was washed with brine (10 ml), then dried ($Na_2SO_4$). The solvent was removed to give 273 mg (87%) of the title compound as white amorphous.

MS (EI) m/z: 458 ($M^+$)

Step 2. 2-{4-[2-(1-azido-1-methylethyl)-6-chloro-5-(trifluoromethyl)-1H-benzimidazol-1-yl]phenyl}ethyl acetate A mixture of 2-{4-[6-chloro-2-(1-chloro-1-methylethyl)-5-(trifluoromethyl)-1H-benzimidazol-1-yl]phenyl}ethyl acetate (step 1, 273 mg, 0.68 mmol), sodium azide (88 mg, 1.36 mmol), KI (112 mg, 0.68 mmol) in DMF (8 ml) was stirred under nitrogen at room temperature for 5.5 h. The reaction mixture was poured into water (5 ml) and the aqueous mixture was extracted with ethyl acetate (30 ml). The organic layer was washed with water (5 ml) and brine (10 ml), then dried ($Na_2SO_4$). After removal of solvent, the crude product was purified by flash column chromatography eluting with hexane/ethyl acetate (2/1) to afford 133 mg (42%) of the title compound as yellow oil.

MS (EI) m/z: 465 ($M^+$)

$^1$H-NMR ($CDCl_3$) δ: 8.17 (1H, s), 7.46 (2H, d, J=8.4 Hz), 7.35 (2H, d, J=8.4 Hz), 7.02 (1H, s), 4.39 (2H, t, J=7.0 Hz), 3.09 (2H, t, J=7.0 Hz), 2.08 (3H, s), 1.70 (6H, s).

Step 3. 2-{4-[2-(1-amino-1-methylethyl)-6-chloro-5-(trifluoromethyl)-1H-benzimidazol-1-yl]phenyl}ethyl acetate A mixture of 2-{4-[2-(1-azido-1-methylethyl)-6-chloro-5-(trifluoromethyl)-1H-benzimidazol-1-yl]phenyl}ethyl acetate (step 2, 133 mg, 0.28 mmol) and Lindlar catalyst (13 mg) in methanol (5 ml) was stirred under $H_2$ atmosphere at room temperature for 2.5 h. The catalyst was removed by filtration through a pad of celite and the filtrates were concentrated to give the title compound as yellow oil (121 mg, 98%).

MS (EI) m/z: 439 ($M^+$)

Step 4. 2-{4-[2-[1-(acetylamino)-1-methylethyl]-6-chloro-5-(trifluoromethyl)-1H-benzimidazol-1-yl]phenyl}ethyl acetate To a solution of 2-{4-[2-(1-amino-1-methylethyl)-6-chloro-5-(trifluoromethyl)-1H-benzimidazol-1-yl]phenyl}ethyl acetate (step 3, 121 mg, 0.27 mmol) in dichloromethane (5 ml) was added acetyl chloride (0.02 ml, 0.3 mmol). The reaction mixture was stirred at room temperature for 7 h. To the reaction mixture was added water (5 ml) and the aqueous mixture was extracted with dichloromethane (30 ml). The organic layer was washed with water (5 ml) and brine (10 ml), then dried ($Na_2SO_4$). After removal of solvent, the crude product was purified by flash column chromatography eluting with $CH_2Cl_2$/methanol (10/1) to afford 76 mg (57%) of the title compound as white amorphous.

MS (EI) m/z: 481 ($M^+$)

$^1$H-NMR ($CDCl_3$) δ: 8.14 (1H, s), 7.42 (2H, d, J=8.2 Hz), 7.28 (2H, d, J=8.4 Hz), 6.91 (1H, s), 4.38 (2H, t, J=6.6 Hz), 3.07 (2H, t, J=6.6 Hz), 2.06 (3H, s), 1.75 (6H, s), 1.68 (3H, s).

Step 5. N-{1-[6-chloro-1-[4-(2-hydroxyethyl) phenyl]-5-(trifluoromethyl)-1H-benzimidazol-2-yl]-1-methylethyl}acetamide The title compound was prepared according to the procedure described in step 6 of Example 1 2-{4-[2-[1-(acetylamino)-1-methylethyl]-6-chloro-5-(trifluoromethyl)-1H-benzimidazol-1-yl]phenyl}ethyl acetate (step 4).

$^1$H-NMR ($CDCl_3$) δ: 8.13 (1H, s), 7.44 (2H, d, J=8.4 Hz), 7.27 (2H, d, J=8.4 Hz), 6.92 (1H, s), 5.95 (1H, br.s), 3.98 (2H, t, J=6.4 Hz), 2.99 (2H, t, J=6.4 Hz), 1.68–1.75 (9H, m).

Step 6. 2-{4-[2-[1-(acetylamino)-1-methylethyl]-6-chloro-5-(trifluoromethyl)-1H-benzimidazol-1-yl]phenyl}ethyl(4-methylphenyl)sulfonylcarbamate The title compound was prepared according to the procedure described in Example 3 from N-{1-[6-chloro-1-[4-(2-hydroxyethyl)phenyl]-5-(trifluoromethyl)-1H-benzimidazol-2-yl]-1-methylethyl}acetamide (step 5).

MS (ESI) m/z: 637 ($MH^+$), 635 ($[M-H]^-$)

$^1$H-NMR ($CD_3OD$) δ: 8.04 (1H, s), 7.83 (2H, d, J=8.4 Hz), 7.45 (2H, d, J=8.4 Hz), 7.34 (2H, d, J=8.5 Hz), 7.26 (2H, d, J=8.5 Hz), 6.93 (1H, s), 4.32 (2H, t, J=6.4 Hz), 3.02 (2H, t, J=6.4 Hz), 2.37 (3H, s), 1.75 (6H, s), 1.53 (3H, s).

Example 378
2-{4-[2-[1-(ACETYLAMINO)-1-METHYLETHYL]-6-CHLORO-5-(TRIFLUOROMETHYL)-1H-BENZIMIDAZOL-1-YL]PHENYL}ETHLY(4-METHYLPHENYL)SULFONYLCARBAMATE P-TOLUENESULFONATE The title compound was prepared according to the procedure described in Example 231 from N-{[(2-{4-[6-chloro-2-[1-(methyloxy)ethyl]-5-(trifluoromethyl)-1H-benzimidazol-1-yl]phenyl}ethyl)amino]carbonyl}-4-methylbenzenesulfonamide (Example 377)

IR (KBr) ν: 1751, 1508, 1450, 1340, 1161, 1122 $cm^{-1}$

Example 379
6-CHLORO-2-ETHYL-1-(4-{2-[METHYL({[(4-METHYLPHENYL)SULFONYL]AMINO}CARBONYL)AMINO]ETHYL}PHENYL)-1H-BENZIMIDAZOLE-5-CARBOXAMIDE Step 1. 2-{4-[5-(aminocarbonyl)-6-chloro-2-ethyl-1H-benzimidazol-1-yl]phenyl}ethyl methanesulfonate A mixture of 6-chloro-2-ethyl-1-[4-(2-hydroxyethyl)phenyl]-1H-benzimidazole-5-carboxamide (Example 111, step 4, 500 mg, 1.45 mmol), triethylamine (293 mg, 2.90 mmol) and methanesulfonyl chloride (322 mg, 2.9 mmol) in dichloromethane (20 ml) was stirred at room temperature for 6 h. The reaction mixture was poured into water, and extracted with dichloromethane (50 ml). The organic layer was washed with brine (50 ml), then dried ($Na_2SO_4$). After removal of solvent, the crude product was purified by TLC with hexane/ethyl acetate (1:1) to afford 304 mg (50%) of the title compound as white solids.

MS (ESI) m/z: 422 ($[M+H]^+$).

$^1$H-NMR ($CDCl_3$) δ: 7.54 (1H, s), 7.44 (2H, d, J=8.3 Hz), 7.29 (2H, d, J=8.3 Hz), 7.13 (1H, s), 3.82 (2H, t, J=7.0 Hz), 3.19 (2H, t, J=7.0 Hz), 2.82 (6H, s), 2.75 (2H, q, J=7.6 Hz), 1.35 (3H, t, J=7.6 Hz).

Step 2. 6-chloro-2-ethyl-1-{4-[2-(methylamino)ethyl]phenyl}-1H-benzimidazole-5-carboxamide A mixture of 2-{4-[5-(aminocarbonyl)-6-chloro-2-ethyl-1H-benzimidazol-1-yl]phenyl}ethyl methanesulfonate (step 1, 304 mg, 0.72 mmol), a solution of methyl amine (40% in methanol, 10 ml) and water (5 ml) in a sealed tube was heated overnight at 100° C. The reaction mixture was partitioned between dichloromethane (30 ml) and water (30 ml). The organic phase was separated and the aqueous phase was extracted with dichloromethane (50 ml). The combined organic phases were washed with brine (50 ml) and dried ($Na_2SO_4$). After removal of solvent, the crude product was purified by TLC with dichloromethane/methanol (10:1) to afford 154 mg (60%) of the title compound as yellow solids.

H-NMR ($CDCl_3$) δ: 7.54 (1H, s), 7.43 (2H, d, J=8.2 Hz), 7.29 (2H, d, J=8.2 Hz), 7.12 (1H, s), 3.62 (2H, t, J=7.0 Hz), 3.01 (2H, t, J=7.0 Hz), 2.82 (6H, s), 2.75 (2H, q, J=7.6 Hz), 1.34 (2H, t, J=7.6 Hz).

Step 3. 6-chloro-2-ethyl-1-(4-{2-[methyl({[(4-methylphenyl)sulfonyl]amino}carbonyl)amino]ethyl}phenyl)-1H-benzimidazole-5-carboxamide The reaction was carried out according to the procedure described in step 10 of Example 1 from 6-chloro-2-ethyl-1-{4-[2-(methylamino)ethyl]phenyl}-1H-benzimidazole-5-carboxamide (step2).

MS (ESI) m/z: 554 ($MH^+$), 552 ($[M-H]^-$).

$^1$H-NMR ($CDCl_3$) δ: 8.09 (1H, s), 7.97–7.94 (2H, d, J=8.4 Hz), 7.40–7.31 (4H, m), 7.16–7.13 (2H, d, J=8.4 Hz), 7.07 (1H, s), 6.36 (1H, br), 3.52 (2H, br), 2.98 (2H, br), 2.93 (3H, s), 2.78–2.69 (2H, d, J=7.6 Hz), 2.42 (3H, s), 1.34–1.28 (3H, t, J=7.6 Hz).

Example 380
6-CHLORO-2-ETHYL-1-(4-{2-[METHYL({[(4-METHYLPHENYL)SULFONYL]AMINO}CARBONYL)AMINO]ETHYL}PHENYL)-1H-BENZIMIDAZOLE-5-CARBOXAMIDE SODIUM SALT The title compound was prepared according to the procedure described in Example 2 from 6-chloro-2-ethyl-1-(4-{2-[methyl({[(4-methylphenyl)sulfonyl]amino}carbonyl)amino]ethyl}phenyl)-1H-benzimidazole-5-carboxamide (Example 379).

MS (ESI) m/z: 554 ($MH^+$), 552 ($[M-H]^-$).

What is claimed is:

1. A compound of the following formula:

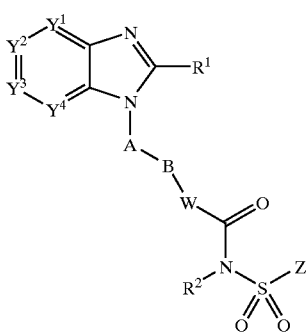

(I)

or the pharmaceutically acceptable salts thereof, wherein one of $Y^1$, $Y^2$, $Y^3$ and $Y^4$ is N and the others are independently selected from CH and C(L);

$R^1$ is H, $C_{1-8}$ alkyl, $C_{2-8}$ alkenyl, $C_{2-8}$ alkynyl, $C_{3-7}$ cycloalkyl, $C_{1-8}$ alkoxy, halo-substituted $C_{1-8}$ alkoxy, $C_{1-8}$ alkyl-S(O)m-, $Q^1$—, pyrrolidinyl, piperidyl, oxopyrrolidinyl, oxopiperidyl, amino, mono- or di-($C_{1-8}$ alkyl)amino, $C_{1-4}$ alkyl-C(=O)—N($R^3$)— or $C_{1-4}$ alkyl-S(O)m-N($R^3$)—, wherein said $C_{1-8}$ alkyl, $C_{2-8}$ alkenyl and $C_{2-8}$ alkynyl are optionally substituted with halo, $C_{1-3}$ alkyl, hydroxy, oxo, $C_{1-4}$ alkoxy-, $C_{1-4}$ alkyl-S(O)m-, $C_{3-7}$ cycloalkyl-, cyano, indanyl, 1,2,3,4-tetrahydronaphryl, 1,2-dihydronaphtyl, pyrrolidinyl, piperidyl, oxopyrrolidinyl, oxopiperidyl, $Q^1$—, $Q^1$—C(=O)—, $Q^1$—O—, $Q^1$—S(O)m-, $Q^1$—$C_{1-4}$ alkyl-O—, $Q^1$—$C_{1-4}$ alkyl-S(O)m-, $Q^1$—$C_{1-4}$ alkyl-C(O)—N($R^3$)—, $Q^1$—$C_{1-4}$ alkyl-N($R^3$)— or $C_{1-4}$ alkyl-C(O)—N($R^3$)—;

$Q^1$ is a 5–12 membered monocyclic or bicyclic aromatic ring optionally containing up to 4 heteroatoms selected from O, N and S, and is optionally substituted with halo, $C_{1-4}$ alkyl, halo-substituted $C_{1-4}$ alkyl, hydroxy, $C_{1-4}$ alkoxy, halo-substituted $C_{1-4}$ alkoxy, $C_{1-4}$ alkylthio, nitro, amino, mono- or di-($C_{1-4}$ alkyl)amino, cyano, HO—$C_{1-4}$ alkyl, $C_{1-4}$ alkoxy-$C_{1-4}$ alkyl, $C_{1-4}$ alkylsulfonyl, aminosulfonyl, $C_{1-4}$ alkylC(=O)—, HO(O=)C—, $C_{1-4}$ alkyl-O(O=)C—, $R^3N(R^4)C$(=O)—, $C_{1-4}$ alkylsulfonylamino, $C_{3-7}$ cycloalkyl, $R^3C$(=O)N($R^4$)— or $NH_2$(HN=)C—;

A is a 5–6 membered monocyclic aromatic ring optionally containing up to 3 heteroatoms selected from O, N and S, wherein said 5–6 membered monocyclic aromatic ring is optionally substituted with up to 3 substituents selected from halo, $C_{1-4}$ alkyl, halo-substituted $C_{1-4}$ alkyl, hydroxy, $C_{1-4}$ alkoxy, halo-substituted $C_{1-4}$ alkoxy, $C_{1-4}$ alkylthio, nitro, amino, mono- or di-($C_{1-4}$ alkyl)amino, cyano, HO—$C_{1-4}$ alkyl, $C_{1-4}$ alkoxy-$C_{1-4}$ alkyl, $C_{1-4}$ alkylsulfonyl, aminosulfonyl, acetyl, $R^3N(R^4)C$(=O)—, HO(O=)C—, $C_{1-4}$ alkyl-O(O=)C—, $C_{1-4}$ alkylsulfonylamino, $C_{3-7}$ cycloalkyl, $R^3C$(=O)N($R^4$)— and $NH_2$(HN=)C—;

B is halo-substituted $C_{1-6}$ alkylene, $C_{3-7}$ cycloalkylene, $C_{2-6}$ alkenylene, $C_{2-6}$ alkynylene, —O—$C_{1-5}$ alkylene; $C_{1-2}$ alkylene-O—$C_{1-2}$ alkylene or $C_{1-6}$ alkylene optionally substituted with an oxo group or $C_{1-3}$ alkyl;

W is NH, N—$C_{1-4}$ alkyl, O, S, N—$OR^5$ or a covalent bond;

$R_2$ is H, $C_{1-4}$ alkyl, OH or $C_{1-4}$ alkoxy;

Z is a 5–12 membered monocyclic or bicyclic aromatic ring optionally containing up to 3 heteroatoms selected from O, N and S, wherein said 5–12 membered monocyclic or bicyclic aromatic ring is optionally substituted with halo, $C_{1-4}$ alkyl, halo-substituted $C_{1-4}$ alkyl, $C_{1-4}$ alkenyl, $C_{1-4}$ alkynyl, hydroxy, $C_{1-4}$ alkoxy, halo-substituted $C_{1-4}$ alkoxy, $C_{1-4}$ alkylthio, nitro, amino, mono- or di-($C_{1-4}$ alkyl)amino, cyano, HO—$C_{1-4}$ alkyl, $C_{1-4}$ alkoxy-$C_{1-4}$ alkyl, $C_{1-4}$ alkylsulfonyl, aminosulfonyl, $C_{1-4}$ alkylC(=O)—, $R^3C$(=O)N($R^4$)—, HO(O=)C—, $C_{1-4}$ alkyl-O(O=)C—, $C_{1-4}$ alkylsulfonylamino, $C_{3-7}$ cycloalkyl, $NH_2$(HN=)C—, $Q^2$—S(O)m-, $Q^2$—O—, $Q^2$—N($R^3$)— or $Q^2$—;

L is halo, $C_{1-4}$ alkyl, halo-substituted $C_{1-4}$ alkyl, hydroxy, $C_{1-4}$ alkoxy, halo-substituted $C_{1-4}$ alkoxy, $C_{1-4}$ alkylthio, nitro, amino, mono- or di-($C_{1-4}$ alkyl)amino, cyano, HO—$C_{1-4}$ alkyl, $C_{1-4}$ alkoxy-$C_{1-4}$ alkyl, $C_{1-4}$ alkylsulfonyl, aminosulfonyl, $C_{1-4}$ alkylC(=O)—, HO(O=)C—, $C_{1-4}$ alkyl-O(O=)C—, $C_{1-4}$ alkylsulfonylamino, $C_{3-7}$ cycloalkyl, $R^3C$(=O)N($R^4$)—, $NH_2$(HN=)C—, $R^3N(R^4)C$(=O)—, $R^3N(R^4)S$(O)m-, $Q^2$—, $Q^2$—C(=O)—, $Q^2$—O—, $Q^2$—$C_{1-4}$ alkyl-O—, or two adjacent L groups are optionally joined together to form an alkylene chain having 3 or 4 members in which one or two (non-adjacent) carbon atoms are optionally replaced by oxygen atoms;

m is 0, 1 or 2;

$R^3$ and $R^4$ are independently selected from H and $C_{1-4}$ alkyl;

$R^5$ is H, $C_{1-4}$ alkyl, $C_{1-4}$ alkyl-(O)C— or $C_{1-4}$ alkyl-O—(O=)C—; and $Q^2$ is a 5–12 membered monocyclic or bicyclic aromatic ring, or a 5–12 membered tricyclic ring optionally containing up to 3 heteroatoms selected from O, N and S, wherein said 5–12 membered monocyclic or bicyclic aromatic ring is optionally substituted with halo, $C_{1-4}$ alkyl, halo-substituted $C_{1-4}$ alkyl, $C_{2-4}$ alkenyl, $C_{2-4}$ alkynyl, hydroxy, $C_{1-4}$ alkoxy, halo-substituted $C_{1-4}$ alkoxy, $C_{1-4}$ alkylthio, nitro, amino, mono- or di-($C_{1-4}$ alkyl)amino, cyano, HO—$C_{1-4}$ alkyl, $C_{1-4}$ alkoxy-$C_{1-4}$ alkyl, $C_{1-4}$ alkylsulfonyl, aminosulfonyl, $C_{1-4}$ alkyl-(O=)C—, $R^3(R^4)C(=O)N$—, HO(O=)C—, $C_{1-4}$ alkyl-O(O=)C—, $C_{1-4}$ alkylsulfonylamino, $C_{3-7}$ cycloalkyl, $C_{1-4}$ alkyl-C(=O)NH— or $NH_2(HN=)C$—.

2. A compound according to claim 1, wherein
one of $Y^1$, $Y^2$, $Y^3$, and $Y^4$ is N and the others are independently selected from CH and C(L);

$R^1$ is H, $C_{1-8}$ alkyl, $C_{2-8}$ alkenyl, $C_{2-8}$ alkynyl, $C_{3-7}$ cycloalkyl, $C_{1-8}$ alkoxy, halo-substituted $C_{1-8}$ alkoxy, $C_{1-8}$ alkyl-S(O)m-, $Q^1$—, pyrrolidinyl, piperidyl, oxopyrrolidinyl, oxopiperidyl, amino, mono- or di-($C_{1-8}$ alkyl)amino, $C_{1-4}$ alkyl-C(=O)—N($R^3$)— or $C_{1-4}$ alkyl-S(O)m-N($R^3$)—, wherein said $C_{1-8}$ alkyl, $C_{2-8}$ alkenyl and $C_{2-8}$ alkynyl are optionally substituted with halo, $C_{1-3}$ alkyl, hydroxy, oxo, $C_{1-4}$ alkoxy-, $C_{1-4}$ alkyl-S(O)m-, $C_{3-7}$ cycloalkyl-, cyano, indanyl, 1,2,3,4-tetrahydronaphryl, 1,2-dihydronaphtyl, pyrrolidinyl, piperidyl, oxopyrrolidinyl, oxopiperidyl, $Q^1$—, $Q^1$—C(=O)—, $Q^1$—O—, $Q^1$—S(O)m-, $Q^1$—$C_{1-4}$ alkyl-O—, $Q^1$—$C_{1-4}$ alkyl-S(O)m-, $Q^1$—$C_{1-4}$ alkyl-C(=O)—N($R^3$)—, or $C_{1-4}$ alkyl-C(O)—N($R^3$)—;

$Q^1$ is a 5–12 membered monocyclic or bicyclic aromatic ring optionally containing up to 4 heteroatoms selected from O, N and S, and is optionally substituted with halo, $C_{1-4}$ alkyl, halo-substituted $C_{1-4}$ alkyl, hydroxy, $C_{1-4}$ alkoxy, halo-substituted $C_{1-4}$ alkoxy, $C_{1-4}$ alkylthio, nitro, amino, mono- or di-($C_{1-4}$ alkyl)amino, cyano, HO—$C_{1-4}$ alkyl, $C_{1-4}$ alkoxy-$C_{1-4}$ alkyl, $C_{1-4}$ alkylsulfonyl, aminosulfonyl, $C_{1-4}$ alkylC(=O)—, HO(O=)C—, $C_{1-4}$ alkyl-O(O)C—, $R^3N(R^4)C(=O)$—, $C_{1-4}$ alkylsulfonylamino, $C_{3-7}$ cycloalkyl, $R^3C(=O)N(R^4)$— or $NH_2(HN=)C$—;

A is a 5–6 membered monocyclic aromatic ring optionally containing up to 2 heteroatoms selected from O, N, and S, wherein said 5–6 membered monocyclic aromatic ring is optionally substituted with up to 2 substituents selected from halo, $C_{1-4}$ alkyl, halo-substituted $C_{1-4}$ alkyl, hydroxy, $C_{1-4}$ alkoxy and halo-substituted $C_{1-4}$ alkoxy;

B is $C_{3-7}$ cycloalkylene or $C_{1-6}$ alkylene optionally substituted with an oxo group or $C_{1-3}$ alkyl;

W is NH, N—$C_{1-4}$ alkyl, O or N—OH;

$R^2$ is H or $C_{1-4}$ alkyl;

Z is a 5–12 membered monocyclic or bicyclic aromatic ring optionally containing up to 3 heteroatoms selected from, N and S, wherein said 5–12 membered monocyclic or bicyclic aromatic ring is optionally substituted with halo, $C_{1-4}$ alkyl, halo-substituted $C_{1-4}$ alkyl, $C_{1-4}$ alkenyl, hydroxy, $C_{1-4}$ alkoxy, nitro, amino, cyano, HO—$C_{1-4}$ alkyl, $C_{1-4}$ alkylsulfonyl, aminosulfonyl, $C_{1-4}$ alkylC(=O)—, $R^3C(=O)N(R^4)$—, HO(O=)C—, $C_{1-4}$ alkyl-O(O=)C—, $C_{1-4}$ alkylsulfonylamino, $C_{1-4}$ alkyl-C(=O)NH—, $Q^2$—S(O)m-, $Q^2$—O—, $Q^2$—N($R^3$)— or $Q^2$—;

L is halo, $C_{1-4}$ alkyl, halo-substituted $C_{1-4}$ alkyl, hydroxy, $C_{1-4}$ alkoxy, mono- or di-($C_{1-4}$ alkyl)amino, halo-substituted $C_{1-4}$ alkoxy, cyano, HO—$C_{1-4}$ alkyl, $C_{1-4}$ alkoxy-$C_{1-4}$ alkyl, $C_{1-4}$ alkylsulfonyl, aminosulfonyl, $C_{1-4}$ alkylC(=O)—, HO(O=)C—, $C_{1-4}$ alkyl-O(O=)C—, $C_{1-4}$ alkylsulfonylamino, $C_{3-7}$ cycloalkyl, $R^3C(=O)N(R^4)$—, $R^3N(R^4)C(=O)$—, $R^3N(R^4)S(O)m$-, $Q^2$—, $Q^2$—C(=O)—, $Q^2$—O—, $Q^2$—$C_{1-4}$ alkyl-O—, or two adjacent L groups are optionally joined together to form an alkylene chain having 3 or 4 members in which one or two (non-adjacent) carbon atoms are optionally replaced by oxygen atoms;

m is 0 or 2;

$R^3$ and $R^4$ are independently selected from H and $C_{1-4}$ alkyl; and $Q^2$ is a 5–12 membered monocyclic or bicyclic aromatic ring, or a 8–12 membered tricyclic ring optionally containing up to 3 heteroatoms selected from O, N and S, wherein said 5–12 membered monocyclic or bicyclic aromatic ring is optionally substituted with halo, $C_{1-4}$ alkyl, halo-substituted $C_{1-4}$ alkyl, $C_{2-4}$ alkenyl, $C_{2-4}$ alkynyl, hydroxy, $C_{1-4}$ alkoxy, halo-substituted $C_{1-4}$ alkoxy, $C_{1-4}$ alkylthio, mono- or di-($C_{1-4}$ alkyl)amino, cyano, HO—$C_{1-4}$ alkyl, $C_{1-4}$ alkoxy-$C_{1-4}$ alkyl, $C_{1-4}$ alkylsulfonyl, aminosulfonyl, $C_{1-4}$ alkyl-(O=)C—, $R^3(R^4)C(=O)N$—, HO(O=)C—, $C_{1-4}$ alkyl-O(O=)C—, $C_{1-4}$ alkylsulfonylamino, $C_{3-7}$ cycloalkyl or $C_{1-4}$ alkyl-C(=O)NH—.

3. A compound according to claim 2, wherein
one of $Y^1$, $Y^2$, $Y^3$, and $Y^4$ is N and the other are independently selected from CH and C(L);

$R^1$ is H, $C_{1-8}$ alkyl, $C_{2-8}$ alkenyl, $C_{2-8}$ alkynyl, $C_{3-7}$ cycloalkyl, $Q^1$—, pyrrolidinyl, piperidyl, oxopyrrolidinyl, oxopiperidyl, amino, mono- or di-($C_{1-8}$ alkyl)amino, wherein said $C_{1-8}$ alkyl is optionally substituted with halo, $C_{1-3}$ alkyl, hydroxy, oxo, $C_{1-4}$ alkoxy-, $C_{1-4}$ alkyl-S(O)m-, $C_{3-7}$ cycloalkyl-, cyano, indanyl, pyrrolidinyl, piperidyl, oxopyrrolidinyl, oxopiperidyl, $Q^1$—, $Q^1$—C(O)—, $Q^1$—O—, $Q^1$—S—, $Q^1$—$C_{1-4}$ alkyl-O—, or $C_{1-4}$ alkyl-C(O)—N($R^3$)—;

$Q^1$ is a 5–12 membered monocyclic aromatic ring optionally containing up to 4 heteroatoms selected from N and S, and is optionally substituted with halo, $C_{1-4}$ alkyl, $C_{1-4}$ alkylsulfonyl and $C_{1-4}$ alkylC(=O)—;

A is 5–6 membered monocyclic aromatic ring optionally substituted with halo, $C_{1-4}$ alkyl or $C_{1-4}$ alkoxy;

B is $C_{3-7}$ cycloalkylene or $C_{1-6}$ alkylene optionally substituted with an oxo group or $C_{1-3}$ alkyl;

W is NH, N—$C_{1-4}$ alkyl, O or N—OH;

$R^2$ is H or $C_{1-4}$ alkyl;

Z is 5–12 membered monocyclic or bicyclic aromatic ring optionally containing up to 3 heteroatoms selected from, N and S, wherein said 5–12 membered monocyclic or bicyclic aromatic ring is optionally substituted with halo, $C_{1-4}$ alkyl, halo-substituted $C_{1-4}$ alkyl, $C_{2-4}$ alkenyl, $C_{1-4}$ alkoxy, nitro, amino, cyano, $R^3C(O)N(R^4)$—, $C_{1-4}$ alkyl-O(O=)C—, $Q^2$—S(O)m-, $Q^2$—O—, $Q^2$—N($R^3$)— or $Q^2$—;

L is halo, $C_{1-4}$ alkyl, halo-substituted $C_{1-4}$ alkyl, hydroxy, $C_{1-4}$ alkoxy, halo-substituted $C_{1-4}$ alkoxy, mono- or di-($C_{1-4}$ alkyl)amino, cyano, HO—$C_{1-4}$ alkyl, $C_{1-4}$ alkylsulfonyl, aminosulfonyl, $C_{1-4}$ alkylC(=O)—, HO(O=)C—, $C_{1-4}$ alkyl-O(O=)C—, $C_{1-4}$ alkylsulfonylamino, $C_{3-7}$ cycloalkyl, $R^3C(=O)N(R^4)$—, $R^3N(R^4)C(=O)$—, $R^3N(R^4)S(=O)m$-, $Q^2$—, $Q^2$—C(=O)—, $Q^2$—O—, $Q^2$—$C_{1-4}$ alkyl-O—, or two adjacent L groups are optionally joined together to form an alkylene chain having 3 or 4 members in which one or two (non-adjacent) carbon atoms are optionally replaced by oxygen atoms;

m is 0 or 2;

$R^3$ and $R^4$ are independently selected from H and $C_{1-4}$ alkyl; and $Q^2$ is a 5 or 6 membered monocyclic aromatic ring, or a 8–12 membered tricyclic ring containing up to 3 heteroatoms selected from N and S, wherein said 5 or 6 membered monocyclic aromatic ring is optionally substituted with halo.

4. A compound according to claim 3, wherein one of $Y^1$, $Y^2$, $Y^3$ and $Y^4$ is N and the others are independently selected from CH and C(L);

$R^1$ is H, $C_{1-8}$ alkyl, $C_{2-8}$ alkenyl, $C_{2-8}$ alkynyl or $C_{3-7}$ cycloalkyl, wherein said $C_{1-8}$ alkyl is optionally substituted with halo, $C_{1-3}$ alkyl, hydroxy, oxo, $C_{1-4}$ alkoxy-, $C_{1-4}$ alkyl-S(O)m-, $C_{3-7}$ cycloalkyl-, cyano, indanyl, pyrrolidinyl, piperidyl, oxopyrrolidinyl, oxopiperidyl, $Q^1$—, $Q^1$—C(=O)—, $Q^1$—O—, $Q^1$—S—, $Q^1$—$C_{1-4}$ alkyl-O—, or bx;1$C_{1-4}$ alkyl-C(O)—N ($R^3$)—;

$Q^1$ is a 5 or 6 membered monocyclic aromatic ring optionally containing up to 4 heteroatoms selected from N and S;

A is 5–6 membered monocyclic aromatic ring system optionally substituted with halo or $C_{1-4}$ alkyl;

B is $C_{3-7}$ cycloalkylene or $C_{1-6}$ alkylene optionally substituted with an oxo group or $C_{1-3}$ alkyl;

W is NH, N—$C_{1-4}$ alkyl, O or N—OH;

$R^2$ is H or $C_{1-4}$ alkyl;

Z is 5–12 membered monocyclic or bicyclic aromatic ring optionally containing up to 3 heteroatoms selected from N and S, wherein said 5–12 membered monocyclic or bicyclic aromatic ring is optionally substituted with halo, $C_{1-4}$ alkyl, halo-substituted $C_{1-4}$ alkyl, $C_{2-4}$ alkenyl, $C_{1-4}$ alkoxy, nitro, amino, cyano, $R^3C(=O)N(R^4)$—, $C_{1-4}$ alkyl-O(O=)C—, $Q^2$—S(O)m-, $Q^2$—O—, $Q^2$—N($R^3$)— or $Q^2$—;

L is halo, $C_{1-4}$ alkyl, halo-substituted $C_{1-4}$ alkyl, hydroxy, $C_{1-4}$ alkoxy, halo-substituted $C_{1-4}$ alkoxy, cyano, HO—$C_{1-4}$ alkyl, $C_{1-4}$ alkylsulfonyl, aminosulfonyl, $C_{1-4}$ alkylC(=O), HO(O=)C—, $C_{1-4}$ alkyl-O(O=)C—, $C_{1-4}$ alkylsulfonylamino, $C_{3-7}$ cycloalkyl, $R^3C(=O)NR^4$—, $R^3N(R^4)C(=O)$—, $R^3N(R^4)S(O)m$-, $Q^2$—, $Q^2$—C(=O)—, $Q^2$—O—, $Q^2$—$C_{1-4}$ alkyl-O—, or two adjacent L groups are optionally joined together to form an alkylene chain having 3 or 4 members in which one or two (non-adjacent) carbon atoms are optionally replaced by oxygen atoms;

m is 0 or 2;

$R^3$ and $R^4$ are independently selected from H and $C_{1-4}$ alkyl, and $Q^2$ is 5 or 6 membered monocyclic aromatic ring or a 8–12 membered tricyclic ring optionally containing 1 sulfur atom wherein said 5 or 6 membered monocyclic aromatic ring is optionally substituted with halo.

5. A compound according to claim 4, wherein one of $Y^1$, $Y^2$, $Y^3$ and $Y^4$ is N and the others are independently selected from CH and C(L);

$R^1$ is $C_{1-5}$ alkyl or $C_{3-7}$ cycloalkyl, wherein said $C_{1-5}$ alkyl is optionally substituted with $C_{1-3}$ alkyl, hydroxy, oxo, pyrrolidinyl, piperidyl, oxopyrrolidinyl, oxopiperidyl, $Q^1$—, or $C^{1-4}$ alkyl-C(O)—N(H)—;

$Q^1$ is 5–12 membered monocyclic aromatic ring system optionally containing up to 2 heteroatoms selected from N and S, A is 5–6 membered monocyclic aromatic ring system;

B is $C_{1-3}$ alkylene optionally substituted with $C_{1-3}$ alkyl;

W is NH, N—$C_{1-2}$ alkyl or O;

$R^2$ is H;

Z is 5–12 membered monocyclic or bicyclic aromatic ring optionally containing up to 3 heteroatoms selected from N and S, wherein said 5–12 membered monocyclic aromatic ring is optionally substituted with halo, $C_{1-4}$ alkyl, nitro, $R^3C(=O)N(R^4)$— or $Q^2$—;

L is halo, $C_{1-4}$ alkyl, halo-substituted $C_{1-4}$ alkyl, hydroxy, $C_{1-4}$ alkoxy, halo-substituted $C_{1-4}$ alkoxy, cyano, HO—$C_{1-4}$ alkyl, acetyl, $R^3N(R^4)C(=O)$—, $R^3N(R^4)S(O)m$-, $Q^2$—, $Q^2C(=O)$—, or two adjacent L groups are joined together to form a methylenedioxy group;

$R^3$ and $R^4$ are independently selected from H and $C_{1-4}$ alkyl; and $Q^2$ is 5 or 6 membered monocyclic aromatic ring system.

6. A compound according to claim 5, wherein one of $Y^1$, $Y^2$, $Y^3$ and $Y^4$ is N and the others are independently selected from CH and C—L;

$R^1$ is $C_{1-5}$ alkyl optionally substituted with $C_{1-3}$ alkyl, hydroxy, oxo, 5 or 6 membered monocyclic aromatic ring, wherein said 5 or 6 membered monocyclic aromatic ring is containing 1 or 2 heteroatoms selected from N and S, or $C_{1-4}$ alkyl-C(O)—N($R^3$)—;

A is phenyl;

B is $C_{1-2}$ alkylene optionally substituted with methyl;

W is NH, N—$CH_3$ or O;

$R^2$ is H;

Z is 5–10 membered monocyclic or bicyclic aromatic ring optionally containing up to 3 heteroatoms selected from N and S, wherein said 5–10 membered monocyclic aromatic ring is optionally substituted with chloro, bromo, methyl, nitro, $CH_3C(=O)NH$—, tBuC(=O)NH— or phenyl; and L is chloro, methyl, trifluoromethyl, hydroxy, methoxy, cyano, acetyl, —C(=O)$NH_2$, trifuluoramethyloxy, methanesulfonyl, or 1-hydroxy-1-methyl-ethyl, or two adjacent L groups are joined together to form a methylenedioxy group.

7. A compound according to claim 6, wherein one of $Y^1$, $Y^2$, $Y^3$ and $Y^4$ is N and the others are independently selected from CH and C—(L);

$R^1$ is methyl, ethyl, n-propyl, isopropyl, n-butyl, isobutyl, neopentyl, thiazolylethyl methylamino, dimethylamino, pyrrolidinyl, pyridyl, or 1-acetylamino-1-methylethyl;

A is phenyl;

B is ethylene or propylene;

W is NH, N—$CH_3$ or O;

$R^2$ is H;

Z is phenyl, pyrazolyl, thiazolyl, thiadiazolyl, thienyl, naphthyl or benzothienyl, said phenyl, pyrazolyl, thiazolyl, thiadiazolyl and thienyl being optionally substituted with one to three substituents independently selected from chloro, bromo, methyl, acetylamino, pivaloylamino, nitro and phenyl; and L is chloro, methyl, trifluoromethyl, hydroxy, methoxy, cyano, acetyl, —C(=O)$NH_2$, trifuluoramethyloxy, methanesulfonyl, or 1-hydroxy-1-methyl-ethyl, or two adjacent L groups are joined together to form a methylenedioxy group.

8. A compound according to claim 7, wherein
$Y^1$, $Y^2$, $Y^3$ and $Y^4$ are selected from the group consisting of
a) $Y^1$ and $Y^3$ are C(L), $Y^2$ is CH and $Y^4$ is N;
b) $Y^1$ is CH, $Y^2$ and $Y^3$ are C(L) and $Y^4$ is N;
c) $Y^1$, $Y^2$ and $Y^3$ are C(L) and $Y^4$ is N;
d) $Y^1$ and $Y^3$ are C(L), $Y^2$ is N and $Y^4$ is CH;
k) $Y^1$ and $Y^2$ are CH, $Y^3$ is C(L) and $Y^4$ is N;
l) $Y^1$ and $Y^3$ are CH, $Y^2$ is C(L) and $Y^4$ is N;
n) $Y^1$ and $Y^2$ are C(L), $Y^3$ is CH and $Y^4$ is N;
p) $Y^1$ and $Y^2$ are C(L), $Y^3$ is N and $Y^4$ is CH;
r) $Y^1$ is C(L), $Y^2$ and $Y^3$ are CH, and $Y^4$ is N; and
s) $Y^2$ is C(L), $Y^1$ and $Y^3$ are CH, and $Y^4$ is N;
$R^1$ is methyl, ethyl, n-propyl, isopropyl, n-butyl, isobutyl, neopentyl, thiazolylethyl methylamino, dimethylamino, pyrrolidinyl, pyridyl, or 1-acetylamino-1-methylethyl;
A is phenyl;
B is ethylene or propylene;
W is NH, N—CH$_3$ or O;
$R^2$ is H;
Z is phenyl, pyrazolyl, thiazolyl, thiadiazolyl, thienyl, naphthyl or benzothienyl, said phenyl, pyrazolyl, thiazolyl, thiadiazolyl and thienyl being optionally substituted with one to three substituents independently selected from chloro, bromo, methyl, acetylamino, pivaloylamino, nitro and phenyl; and
L is chloro, methyl, trifuluoromethyl, hydroxy, methoxy, cyano, acetyl, —C(=O)NH$_2$, trifuluoromethyloxy, methanesulfonyl, or 1-hydroxy-1-methyl-ethyl, or two adjacent L groups are joined together to form a methylenedioxy group.

9. A compound according to claim 8, wherein
$Y^1$, $Y^2$, $Y^3$ and $Y^4$ are selected from the group consisting of
a) $Y^1$ and $Y^3$ are C(L), $Y^2$ is CH and $Y^4$ is N;
b) $Y^1$ is CH $Y^2$ and $Y^3$ are C(L) and $Y^4$ is N;
c) $Y^1$, $Y^2$ and $Y^3$ are C(L) and $Y^4$ is N; and
d) $Y^1$ and $Y^3$ are C(L), $Y^2$ is N and $Y^4$ is CH;
$R^1$ is methyl, ethyl, n-propyl, isopropyl, n-butyl, isobutyl, neopentyl, thiazolylethyl methylamino, dimethylamino, pyrrolidinyl, pyridyl, or 1-acetylamino-1-methylethyl;
A is phenyl;
B is ethylene or propylene;
W is NH, N—CH$_3$ or O;
$R^2$ is H;
Z is phenyl, pyrazolyl, thiazolyl, thiadiazolyl, thienyl, naphthyl or benzothienyl, said phenyl, pyrazolyl, thiazolyl, thiadiazolyl and thienyl being optionally substituted with one to three substituents independently selected from chloro, bromo, methyl, acetylamino, pivaloylamino, nitro and phenyl; and
L is chloro, methyl, trifuluoromethyl, hydroxy, methoxy, cyano, acetyl, —C(=O)NH$_2$, trifuluoromethyloxy, methanesulfonyl, or 1-hydroxy-1-methyl-ethyl, or two adjacent L groups are joined together to form a methylenedioxy group.

10. A compound according to claim 1 selected from
3-(4-{2-[({[(5-chloro-1,3-dimethyl-1h-pyrazol-4-yl)sulfonyl]amino}carbonyl)amino]ethyl}phenyl)-2-ethyl-5,7-dimethyl-3H-imidazo[4,5-b]pyridine;

3-(4-{2-[({[(2,4-dimethyl-1,3-thiazol-5-yl)sulfonyl]amino}carbonyl)amino]ethyl}phenyl)-2-ethyl-5,7-dimethyl-3H-imidazo[4,5-b]pyridine;

N-[5-({[({2-[4-(2-ethyl-5,7-dimethyl-3H-imidazo[4,5-b]pyridin-3-yl)phenyl]ethyl}amino)carbonyl]amino}sulfonyl)-1,3,4-thiadiazol-2-yl]acetamide;

2-ethyl-5,7-dimethyl-3-(4-{2-[methyl({[(4-methylphenyl)sulfonyl]amino}carbonyl)amino]ethyl}phenyl)-3H-imidazo[4,5-b]pyridine;

2-ethyl-5,7-dimethyl-3-(4-{2-[({[(4-methylphenyl)sulfonyl]amino}carbonyl)amino]propyl}phenyl)-3H-imidazo[4,5-b]pyridine;

2-[4-(2-ethyl-5,7-dimethyl-3H-imidazo[4,5-b]pyridin-3-yl)phenyl]-1-methylethyl(4-methylphenyl)sulfonylcarbamate;

5,7-dimethyl-3-(4-{2-[({[(4-methylphenyl)sulfonyl]amino}carbonyl)amino]ethyl}phenyl)-2-propyl-3H-imidazo[4,5-b]pyridine;

2-isopropyl-5,7-dimethyl-3-(4-{2-[({[(4-methylphenyl)sulfonyl]amino}carbonyl)amino]ethyl}phenyl)-3H-imidazo[4,5-b]pyridine;

2-butyl-5,7-dimethyl-3-(4-{2-[({[(4-methylphenyl)sulfonyl]amino}carbonyl)amino]ethyl}phenyl)-3H-imidazo[4,5-b]pyridine;

2-isobutyl-5,7-dimethyl-3-(4-{2-[({[(4-methylphenyl)sulfonyl]amino}carbonyl)amino]ethyl}phenyl)-3H-imidazo[4,5-b]pyridine;

5,7-dimethyl-3-(4-{2-[({[(4-methylphenyl)sulfonyl]amino}carbonyl)amino]ethyl}phenyl)-2-neopentyl-3H-imidazo[4,5-b]pyridine;

5,7-dimethyl-3-(4-{2-[({[(4-methylphenyl)sulfonyl]amino}carbonyl)amino]ethyl}phenyl)-2-[2-(1,3-thiazol-2-yl)ethyl]-3H-imidazo[4,5-b]pyridine;

3-{4-[2-({[(4-biphenylsulfonyl)amino]carbonyl}amino)ethyl]phenyl}-2-ethyl-5,7-dimethyl-3H-imidazo[4,5-b]pyridine;

2-ethyl-5,7-dimethyl-3-{4-[2-({[(1-naphthylsulfonyl)amino]carbonyl}amino)ethyl]phenyl}-3H-imidazo[4,5-b]pyridine;

2-ethyl-5,7-dimethyl-3-{4-[2-({[(2-naphthylsulfonyl)amino]carbonyl}amino)ethyl]phenyl}-3H-imidazo[4,5-b]pyridine;

2-ethyl-5,7-dimethyl-3-(4-{2-[([(2-thienyl)sulfonyl]amino}carbonyl)amino]ethyl}phenyl)-3H-imidazo[4,5-b]pyridine;

3-(4-{2-[({[(5-chloro-2-thienyl)sulfonyl]amino}carbonyl)amino]ethyl}phenyl)-2-ethyl-5,7-dimethyl-3H-imidazo[4,5-b]pyridine;

3-(4-{2-[({[(4,5-dichloro-2-thienyl)sulfonyl]amino}carbonyl)amino]ethyl}phenyl)-2-ethyl-5,7-dimethyl-3H-imidazo[4,5-b]pyridine;

3-{4-[2-({[(1-benzothien-2-ylsulfonyl)amino]carbonyl}amino)ethyl]phenyl}-2-ethyl-5,7-dimethyl-3H-imidazo[4,5-b]pyridine;

3-(4-{2-[({[(2-chlorophenyl)sulfonyl]amino}carbonyl)amino]ethyl}phenyl)-2-ethyl-5,7-dimethyl-3H-imidazo[4,5-b]pyridine;

2-ethyl-5,6-dimethyl-3-(4-{2-[({[(4-methylphenyl)sulfonyl]amino}carbonyl)amino]ethyl}phenyl)-3H-imidazo[4,5-b]pyridine;

5,6-dichloro-2-ethyl-3-(4-{2-[({[(4-methylphenyl)sulfonyl]amino}carbonyl)amino]ethyl}phenyl)-3H-imidazo[4,5-b]pyridine;

5-chloro-2-ethyl-7-methyl-3-(4-{2-[({[(4-methylphenyl)sulfonyl]amino}carbonyl)amino]ethyl}phenyl)-3H-imidazo[4,5-b]pyridine;

6-cyano-2-ethyl-5,7-dimethyl-3-(4-{2-[({[(4-methylphenyl)sulfonyl]amino}carbonyl)amino]ethyl}phenyl)-3H-imidazo[4,5-b]pyridine;

2-ethyl-4,6-dimethyl-1-(4-{2-[({[(4-methylphenyl)sulfonyl]amino}carbonyl)amino]ethyl}phenyl)-1H-imidazo[4,5-c]pyridine;

2-ethyl-3-{4-[2-({[({3-[hydroxy(oxido)amino]phenyl}sulfonyl)amino]carbonyl}amino)ethyl]phenyl}-5,7-dimethyl-3H-imidazo[4,5-b]pyridine;

3-(4-{2-[({[(4-chlorophenyl)sulfonyl]amino}carbonyl)amino]ethyl}phenyl)-2-ethyl-5,7-dimethyl-3H-imidazo[4,5-b]pyridine;

n-[4-({[({2-[4-(2-ethyl-5,7-dimethyl-3H-imidazo[4,5-b]pyridin-3-yl)phenyl]ethyl}amino)carbonyl]amino}sulfonyl)phenyl]-2,2-dimethylpropanamide;

3-(4-{2-[({[(2-chlorophenyl)sulfonyl]amino}carbonyl)amino]ethyl}phenyl)-2-ethyl-5,7-dimethyl-3H-imidazo[4,5-b]pyridine;

3-(4-{2-[({[(3-chlorophenyl)sulfonyl]amino}carbonyl)amino]ethyl}phenyl)-2-ethyl-5,7-dimethyl-3H-imidazo[4,5-b]pyridine;

3-(4-{2-[({[(5-chloro-2-thienyl)sulfonyl]amino}carbonyl)amino]ethyl}phenyl)-2-ethyl-5,7-dimethyl-3H-imidazo[4,5-b]pyridine;

3-(4-{2-[({[(5-bromo-2-thienyl)sulfonyl]amino}carbonyl)amino]ethyl}phenyl)-2-ethyl-5,7-dimethyl-3H-imidazo[4,5-b]pyridine;

3-(4-{2-[({[(2-bromophenyl)sulfonyl]amino}carbonyl)amino]ethyl}phenyl)-2-ethyl-5,7-dimethyl-3H-imidazo[4,5-b]pyridine;

3-{4-[2-({[({4-chloro-3-nitrophenyl}sulfonyl)amino]carbonyl}amino)ethyl]phenyl}-2-ethyl-5,7-dimethyl-3H-imidazo[4,5-b]pyridine;

2-[4-(2-ethyl-4,6-dimethyl-1H-imidazo[4,5-c]pyridin-1-yl)phenyl]ethyl(4-methylphenyl)sulfonylcarbamate;

2-{4-[5,7-dimethyl-2-(methylamino)-3H-imidazo[4,5-b]pyridin-3-yl]phenyl}ethyl(4-methylphenyl)sulfonylcarbamate;

N-{[(2-{4-[5,7-dimethyl-2-(methylamino)-3H-imidazo[4,5-b]pyridin-3-yl]phenyl}ethyl)amino]carbonyl}-4-methylbenzenesulfonamide;

N-[({2-[4-(2-ethyl-5,7-dimethyl-3H-imidazo[4,5-b]pyridin-3-yl )phenyl]ethyl}amino)carbonyl]-2-thiophenesulfonamide;

2-[4-(4,6-dimethyl-2-phenyl-1H-imidazo[4,5-c]pyridin-1-yl)phenyl]ethyl(4-methylphenyl)sulfonylcarbamate;

2-[4-(2-butyl-4,6-dimethyl-1H-imidazo[4,5-c]pyridin-1-yl)phenyl]ethyl(4-methylphenyl)sulfonylcarbamate;

2-{4-[4,6dimethyl-2-(3-phenylpropy)-1H-imidazo[4,5-c]pyridin-1-yl]phenyl}ethyl(4-methylphenyl)sulfonylcarbamate;

N-{[(2-{4-[5,7-dimethyl-2-(1H-pyrazol-3-yl)-3H-imidazo[3-yl]phenyl}ethyl)amino]carbonyl}-4-methylbenzenesulfonamide;

2-{4-[2-(1,1-dimethylethyl)-4,6-dimethyl-1H-imidazo[4,5-c]pyridin-1-yl]phenyl}ethyl(4-methylphenyl)sulfonylcarbamate;

salts thereof.

11. A compound according to claim 1 selected from

2-[4-(2-ethyl-5,7-dimethyl-3H-imidazo[4,5-b]pyridin-3-yl)phenyl]-1-methylethyl(4-methylphenyl)sulfonylcarbamate;

5,7-dimethyl-3-(4-{2-[({[(4-methylphenyl)sulfonyl]amino}carbonyl)amino]ethyl}phenyl)-2-[2-(1,3-thiazol-2-yl)ethyl]-3H-imidazo[4,5-b]pyridine;

2-ethyl-5,7-dimethyl-3-(4-{2-[({[(2-thienyl)sulfonyl]amino}carbonyl)amino]ethyl}phenyl)-3H-imidazo[4,5-b]pyridine;

3-(4-{2-[({[(2-chlorophenyl)sulfonyl]amino}carbonyl)amino]ethyl}phenyl)-2-ethyl-5,7-dimethyl-3H-imidazo[4,5-b]pyridine;

2-ethyl-5,6-dimethyl-3-(4-{2-[({[(4-methylphenyl)sulfonyl]amino}carbonyl)amino]ethyl}phenyl)-3H-imidazo[4,5-b]pyridine;

5,6-dichloro-2-ethyl-3-(4-{2-[({[(4-methylphenyl)sulfonyl]amino}carbonyl)amino]ethyl}phenyl)-3H-imidazo[4,5-b]pyridine;

2-ethyl-4,6-dimethyl-1-(4-{2-[({[(4-methylphenyl)sulfonyl]amino}carbonyl)amino]ethyl}phenyl)-1H-imidazo[4,5-c]pyridine;

2-[4-(2-ethyl-4,6-dimethyl-1H-imidazo[4,5-c]pyridin-1-yl)phenyl]ethyl(4-methylphenyl)sulfonylcarbamate;

2-{4-[5,7-dimethyl-2-(methylamino)-3H-imidazo[4,5-b]pyridin-3-yl]phenyl}ethyl(4-methylphenyl)sulfonylcarbamate;

N-{[(2-{4-[5,7-dimethyl-2-(methylamino)-3H-imidazo[4,5-b]pyridin-3-yl]phenyl}ethyl)amino]carbonyl}-4-methylbenzenesulfonamide;

N-[({2-[4-(2-ethyl-5,7-dimethyl-3H-imidazo[4,5-b]pyridin-3-yl)phenyl]ethyl}amino)carbonyl]-2-thiophenesulfonamide;

2-[4-(4,6-dimethyl-2-phenyl-1H-imidazo[4,5-c]pyridin-1-yl)phenyl]ethyl(4-methylphenyl)sulfonylcarbamate;

2-[4-(2-butyl-4,6-dimethyl-1H-imidazo[4,5-c]pyridin-1-yl)phenyl]ethyl(4-methylphenyl)sulfonylcarbamate;

2-{4-[4,6-dimethyl-2-(3-phenylpropyl)-1H-imidazo[4,5-c]pyridin-1-yl]phenyl}ethyl(4-methylphenyl)sulfonylcarbamate;

N-{[(2-{4-[5,7-dimethyl-2-(1H-pyrazol-3-yl)-3H-imidazo[4,5-b]pyridin-3-yl]phenyl}ethyl)amino]carbonyl}-4-methylbenzenesulfonamide;

2-{4-[2-(1,1-dimethylethyl)-4,6-dimethyl-1H-imidazo[4,5-c]pyridin-1-yl]phenyl}ethyl(4-methylphenyl)sulfonylcarbamate;

salts thereof.

12. A pharmaceutical composition for the treatment of a disorder or condition mediated by prostaglandin in a mammal including a human, which comprises an effective amount of a compound of claim 1, or a pharmaceutically acceptable salt thereof, and a pharmaceutically acceptable carrier.

13. A pharmaceutical formulation comprising a compound of claim 1, a pharmaceutically acceptable carrier and, optionally, one or more other pharmacologically active ingredients.

14. A compound of formula 2-ethyl-4,6-dimethyl-1-(4-{2-[({[(4-methyphenyl)sulfonyl]amino}carbonyl)amino]ethyl}phenyl)-1H-imidazo[4,5-C]pyridine.

15. A pharmaceutical composition for the treatment of a disorder or condition mediated by prostaglandin in mammal including a human, which comprises an effective amount of a compound of claim 14, or a pharmaceutically acceptable salt thereof, and a pharmaceutically acceptable carrier.

16. A pharmaceutical formulation comprising a compound of claim 14, a pharmaceutically acceptable carrier and optionally, one or more other pharmacologically active ingredients.

* * * * *

UNITED STATES PATENT AND TRADEMARK OFFICE
CERTIFICATE OF CORRECTION

PATENT NO. : 6,710,054 B2
DATED : March 23, 2004
INVENTOR(S) : Kazunari Nakao et al.

It is certified that error appears in the above-identified patent and that said Letters Patent is hereby corrected as shown below:

<u>Title page,</u>
Item [57], ABSTRACT,
Lines 5-6, "up to 3 heteroatoms selected form O, N and S, etc.; B is C1-6" should read
-- up to 3 heteroatoms selected from O, N and S, etc.; B is C1-6 --

<u>Column 283,</u>
Line 52, "independently selected from CH and C(L);" should read -- independently selected from N, CH and C(L); --.

<u>Column 287,</u>
Line 19, "Q1-S-, Q1-C1-4 alkyl-O-, or bx;1C1-4 alkyl-C" should read
-- Q1-S-, Q1-C1-4 alkyl-O-, or 1C1-4 alkyl-C --.

Signed and Sealed this

Seventeenth Day of May, 2005

JON W. DUDAS
*Director of the United States Patent and Trademark Office*